(12) United States Patent
Steward et al.

(10) Patent No.: US 8,685,693 B2
(45) Date of Patent: Apr. 1, 2014

(54) DEGRADABLE CLOSTRIDIAL TOXINS

(71) Applicant: Allergan, Inc., Irvine, CA (US)

(72) Inventors: Lance E. Steward, Irvine, CA (US);
Sanjiv Ghanshani, Irvine, CA (US);
Ester Fernandez-Salas, Fullerton, CA (US); Marcella A. Gilmore, Santa Ana, CA (US); Joseph Francis, Aliso Viejo, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 12 days.

(21) Appl. No.: 13/846,338

(22) Filed: Mar. 18, 2013

(65) Prior Publication Data

US 2013/0196414 A1 Aug. 1, 2013

Related U.S. Application Data

(62) Division of application No. 13/112,844, filed on May 20, 2011, now Pat. No. 8,512,992.

(60) Provisional application No. 61/346,578, filed on May 20, 2010.

(51) Int. Cl.
*C12N 9/52* (2006.01)
*C12N 9/50* (2006.01)
*C12N 9/96* (2006.01)
*C07H 21/04* (2006.01)

(52) U.S. Cl.
USPC ........... 435/220; 435/219; 435/188; 536/23.2

(58) Field of Classification Search
None
See application file for complete search history.

(56) References Cited

FOREIGN PATENT DOCUMENTS

| WO | 02-044199 | 6/2002 |
| WO | 2009-055351 A1 | 4/2009 |
| WO | WO2010-094905 | 8/2010 |

*Primary Examiner* — Iqbal H Chowdhury
(74) *Attorney, Agent, or Firm* — Kenton B. Abel; Debra Condino

(57) ABSTRACT

The specification discloses Clostridial toxins or Clostridial toxin chimeras comprising an inactivation cleavage site, polynucleotide molecules encoding such toxins or chimeras, compositions comprising such toxins or chimeras, and method of producing such toxins or chimeras.

1 Claim, 7 Drawing Sheets

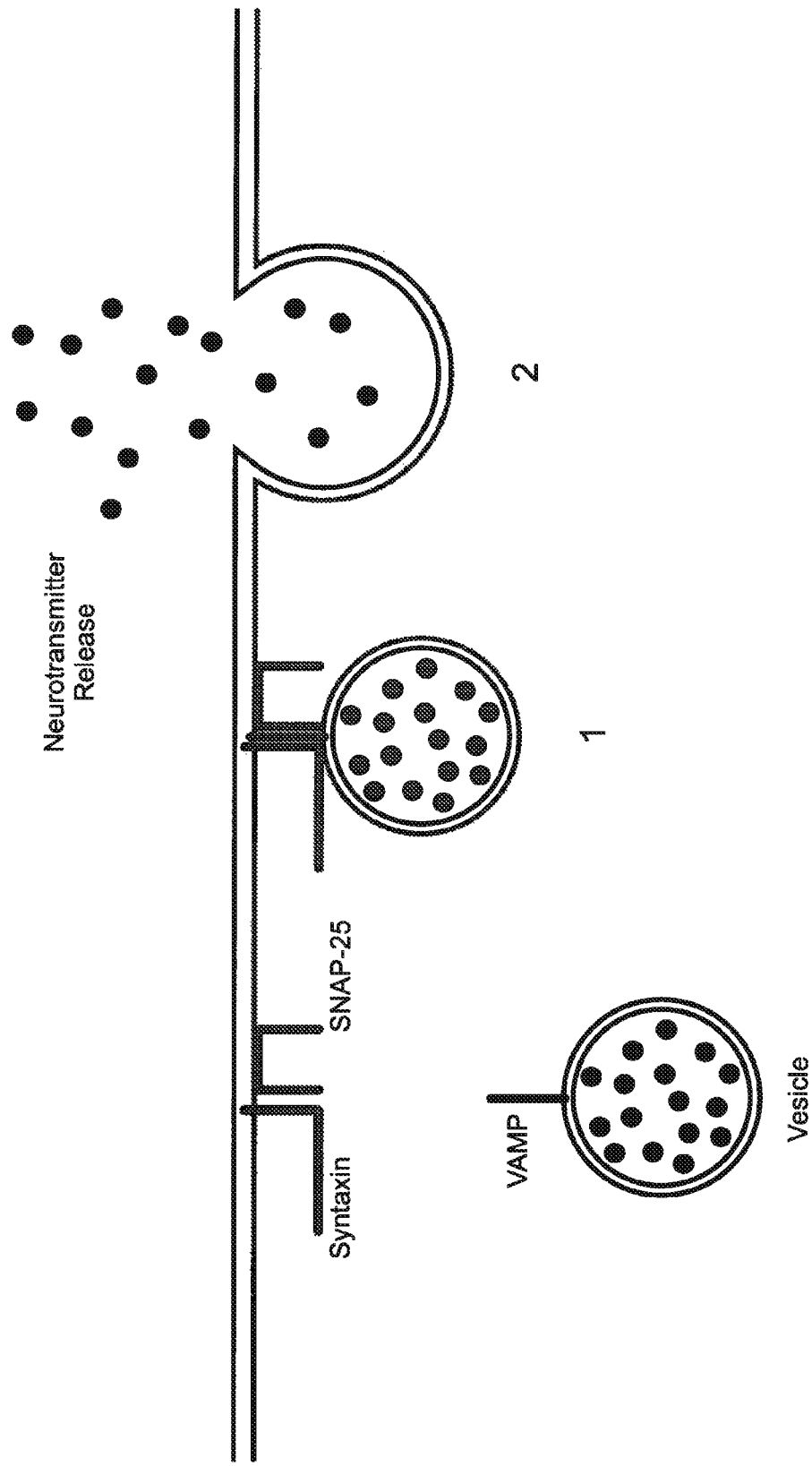

FIG. 1B.

Toxin
Heavy Chain Binding Domain
Receptor System
1
2
Heavy Chain Translocation Domain
3
ATP → ADP
H⁺
Light Chain
4

SEQUENCE LISTING

```
<160> NUMBER OF SEQ ID NOS: 537

<210> SEQ ID NO 1
<211> LENGTH: 1296
<212> TYPE: PRT
<213> ORGANISM: Clostridium botulinum A1

<400> SEQUENCE: 1

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95
```

```
Arg Ile Tyr Ser Thr Asp Leu Gly Arg Met Leu Leu Thr Ser Ile Val
                100                 105                 110
Arg Gly Ile Pro Phe Trp Gly Ser Thr Ile Asp Thr Glu Leu Lys
        115                 120                 125
Val Ile Asp Thr Asn Cys Ile Asn Val Ile Gln Pro Asp Gly Ser Tyr
    130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
            195                 200                 205
Gly Ala Gly Lys Phe Ala Thr Asp Pro Ala Val Thr Leu Ala His Glu
            210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
```

```
                515                 520                 525
   Glu Leu Met Pro Asn Ile Glu Arg Phe Pro Asn Gly Lys Lys Tyr Glu
                   530                 535                 540
   Leu Asp Lys Tyr Thr Met Phe His Tyr Leu Arg Ala Gln Glu Phe Glu
   545                 550                 555                 560
   His Gly Lys Ser Arg Ile Ala Leu Thr Asn Ser Val Asn Glu Ala Leu
                   565                 570                 575
   Leu Asn Pro Ser Arg Val Tyr Thr Phe Ser Ser Asp Tyr Val Lys
                   580                 585                 590
   Lys Val Asn Lys Ala Thr Glu Ala Met Phe Leu Gly Trp Val Glu
                   595                 600                 605
   Gln Leu Val Tyr Asp Phe Thr Asp Glu Thr Ser Glu Val Ser Thr Thr
                   610                 615                 620
   Asp Lys Ile Ala Asp Ile Thr Ile Ile Pro Tyr Ile Gly Pro Ala
   625                 630                 635                 640
   Leu Asn Ile Gly Asn Met Leu Tyr Lys Asp Asp Phe Val Gly Ala Leu
                   645                 650                 655
   Ile Phe Ser Gly Ala Val Ile Leu Leu Glu Phe Ile Pro Glu Ile Ala
                   660                 665                 670
   Ile Pro Val Leu Gly Thr Phe Ala Leu Val Ser Tyr Ile Ala Asn Lys
                   675                 680                 685
   Val Leu Thr Val Gln Thr Ile Asp Asn Ala Leu Ser Lys Arg Asn Glu
                   690                 695                 700
   Lys Trp Asp Glu Val Tyr Lys Tyr Ile Val Thr Asn Trp Leu Ala Lys
   705                 710                 715                 720
   Val Asn Thr Gln Ile Asp Leu Ile Arg Lys Lys Met Lys Glu Ala Leu
                   725                 730                 735
   Glu Asn Gln Ala Glu Ala Thr Lys Ala Ile Ile Asn Tyr Gln Tyr Asn
                   740                 745                 750
   Gln Tyr Thr Glu Glu Lys Asn Asn Ile Asn Phe Asn Ile Asp Asp
                   755                 760                 765
   Leu Ser Ser Lys Leu Asn Glu Ser Ile Asn Lys Ala Met Ile Asn Ile
   770                 775                 780
   Asn Lys Phe Leu Asn Gln Cys Ser Val Ser Tyr Leu Met Asn Ser Met
   785                 790                 795                 800
   Ile Pro Tyr Gly Val Lys Arg Leu Glu Asp Phe Asp Ala Ser Leu Lys
                   805                 810                 815
   Asp Ala Leu Leu Lys Tyr Ile Tyr Asp Asn Arg Gly Thr Leu Ile Gly
                   820                 825                 830
   Gln Val Asp Arg Leu Lys Asp Lys Val Asn Asn Thr Leu Ser Thr Asp
                   835                 840                 845
   Ile Pro Phe Gln Leu Ser Lys Tyr Val Asp Asn Gln Arg Leu Leu Ser
   850                 855                 860
   Thr Phe Thr Glu Tyr Ile Lys Asn Ile Ile Asn Thr Ser Ile Leu Asn
   865                 870                 875                 880
   Leu Arg Tyr Glu Ser Asn His Leu Ile Asp Leu Ser Arg Tyr Ala Ser
                   885                 890                 895
   Lys Ile Asn Ile Gly Ser Lys Val Asn Phe Asp Pro Ile Asp Lys Asn
                   900                 905                 910
   Gln Ile Gln Leu Phe Asn Leu Glu Ser Ser Lys Ile Glu Val Ile Leu
                   915                 920                 925
   Lys Asn Ala Ile Val Tyr Asn Ser Met Tyr Glu Asn Phe Ser Thr Ser
   930                 935                 940
```

```
Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 1296
<212> TYPE: PRT
<213> ORGANISM: Clostridium botulinum A2

<400> SEQUENCE: 2

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30
```

-continued

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
                115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
        275                 280                 285

Lys Phe Lys Asp Val Ala Ser Thr Leu Asn Lys Ala Lys Ser Ile Ile
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Asn Phe Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
                420                 425                 430

Gly Ile Ile Pro Phe Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
450                 455                 460

```
Ser Pro Ser Glu Asp Asn Phe Thr Asn Asp Leu Asp Lys Val Glu Glu
465                 470                 475                 480

Ile Thr Ala Asp Thr Asn Ile Glu Ala Ala Glu Glu Asn Ile Ser Leu
            485                 490                 495

Asp Leu Ile Gln Gln Tyr Tyr Leu Thr Phe Asp Phe Asp Asn Glu Pro
                500                 505                 510

Glu Asn Ile Ser Ile Glu Asn Leu Ser Ser Asp Ile Ile Gly Gln Leu
            515                 520                 525

Glu Pro Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
                565                 570                 575

Leu Lys Pro Asn Val Ala Tyr Thr Phe Phe Ser Ser Lys Tyr Val Lys
                580                 585                 590

Lys Ile Asn Lys Ala Val Glu Ala Phe Met Phe Leu Asn Trp Ala Glu
            595                 600                 605

Glu Leu Val Tyr Asp Phe Thr Asp Glu Thr Asn Glu Val Thr Thr Met
        610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
                645                 650                 655

Ile Phe Thr Gly Val Val Ala Met Leu Glu Phe Ile Pro Glu Tyr Ala
                660                 665                 670

Leu Pro Val Phe Gly Thr Phe Ala Ile Val Ser Tyr Ile Ala Asn Lys
            675                 680                 685

Val Leu Thr Val Gln Thr Ile Asn Asn Ala Leu Ser Lys Arg Asn Glu
        690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
            805                 810                 815

Asp Val Leu Leu Lys Tyr Ile Tyr Asp Asn Arg Gly Thr Leu Val Leu
                820                 825                 830

Gln Val Asp Arg Leu Lys Asp Glu Val Asn Asn Thr Leu Ser Ala Asp
        835                 840                 845

Ile Pro Phe Gln Leu Ser Lys Tyr Val Asp Asn Lys Lys Leu Leu Ser
            850                 855                 860

Thr Phe Thr Glu Tyr Ile Lys Asn Ile Val Asn Thr Ser Ile Leu Ser
865                 870                 875                 880

Ile Val Tyr Lys Lys Asp Asp Leu Ile Asp Leu Ser Arg Tyr Gly Ala
```

```
                885                 890                 895
Lys Ile Asn Ile Gly Asp Arg Val Tyr Tyr Asp Ser Ile Asp Lys Asn
            900                 905                 910
Gln Ile Lys Leu Ile Asn Leu Glu Ser Ser Thr Ile Glu Val Ile Leu
            915                 920                 925
Lys Asn Ala Ile Val Tyr Asn Ser Met Tyr Glu Asn Phe Ser Thr Ser
            930                 935                 940
Phe Trp Ile Lys Ile Pro Lys Tyr Phe Ser Lys Ile Asn Leu Asn Asn
945                 950                 955                 960
Glu Tyr Thr Ile Ile Asn Cys Ile Glu Asn Asn Ser Gly Trp Lys Val
            965                 970                 975
Ser Leu Asn Tyr Gly Glu Ile Ile Trp Thr Leu Gln Asp Asn Lys Gln
            980                 985                 990
Asn Ile Gln Arg Val Val Phe Lys Tyr Ser Gln Met Val Asn Ile Ser
            995                 1000                1005
Asp Tyr Ile Asn Arg Trp Ile Phe Val Thr Ile Thr Asn Asn Arg Leu
            1010                1015                1020
Thr Lys Ser Lys Ile Tyr Ile Asn Gly Arg Leu Ile Asp Gln Lys Pro
1025                1030                1035                1040
Ile Ser Asn Leu Gly Asn Ile His Ala Ser Asn Lys Ile Met Phe Lys
            1045                1050                1055
Leu Asp Gly Cys Arg Asp Pro Arg Arg Tyr Ile Met Ile Lys Tyr Phe
            1060                1065                1070
Asn Leu Phe Asp Lys Glu Leu Asn Glu Lys Glu Ile Lys Asp Leu Tyr
            1075                1080                1085
Asp Ser Gln Ser Asn Ser Gly Ile Leu Lys Asp Phe Trp Gly Asn Tyr
            1090                1095                1100
Leu Gln Tyr Asp Lys Pro Tyr Tyr Met Leu Asn Leu Phe Asp Pro Asn
1105                1110                1115                1120
Lys Tyr Val Asp Val Asn Asn Ile Gly Ile Arg Gly Tyr Met Tyr Leu
            1125                1130                1135
Lys Gly Pro Arg Gly Ser Val Val Thr Thr Asn Ile Tyr Leu Asn Ser
            1140                1145                1150
Thr Leu Tyr Glu Gly Thr Lys Phe Ile Ile Lys Lys Tyr Ala Ser Gly
            1155                1160                1165
Asn Glu Asp Asn Ile Val Arg Asn Asn Asp Arg Val Tyr Ile Asn Val
            1170                1175                1180
Val Val Lys Asn Lys Glu Tyr Arg Leu Ala Thr Asn Ala Ser Gln Ala
1185                1190                1195                1200
Gly Val Glu Lys Ile Leu Ser Ala Leu Glu Ile Pro Asp Val Gly Asn
            1205                1210                1215
Leu Ser Gln Val Val Val Met Lys Ser Lys Asp Asp Gln Gly Ile Arg
            1220                1225                1230
Asn Lys Cys Lys Met Asn Leu Gln Asp Asn Asn Gly Asn Asp Ile Gly
            1235                1240                1245
Phe Ile Gly Phe His Leu Tyr Asp Asn Ile Ala Lys Leu Val Ala Ser
            1250                1255                1260
Asn Trp Tyr Asn Arg Gln Val Gly Lys Ala Ser Arg Thr Phe Gly Cys
1265                1270                1275                1280
Ser Trp Glu Phe Ile Pro Val Asp Asp Gly Trp Gly Glu Ser Ser Leu
            1285                1290                1295

<210> SEQ ID NO 3
<211> LENGTH: 1292
```

```
<212> TYPE: PRT
<213> ORGANISM: Clostridium botulinum A3

<400> SEQUENCE: 3

Met Pro Phe Val Asn Lys Pro Phe Asn Tyr Arg Asp Pro Gly Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110

Lys Gly Ile Pro Phe Trp Gly Gly Ser Thr Ile Asp Thr Glu Leu Lys
        115                 120                 125

Val Ile Asp Thr Asn Cys Ile Asn Val Ile Glu Pro Gly Gly Ser Tyr
    130                 135                 140

Arg Ser Glu Glu Leu Asn Leu Val Ile Thr Gly Pro Ser Ala Asp Ile
145                 150                 155                 160

Ile Gln Phe Glu Cys Lys Ser Phe Gly His Asp Val Phe Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Thr Phe Ala Thr Asp Pro Ala Val Thr Leu Ala His Glu
    210                 215                 220

Leu Ile His Ala Ala His Arg Leu Tyr Gly Ile Ala Ile Asn Pro Asn
225                 230                 235                 240

Arg Val Leu Lys Val Lys Thr Asn Ala Tyr Tyr Glu Met Ser Gly Leu
                245                 250                 255

Glu Val Ser Phe Glu Glu Leu Arg Thr Phe Gly Gly Asn Asp Thr Asn
            260                 265                 270

Phe Ile Asp Ser Leu Trp Gln Lys Lys Phe Ser Arg Asp Ala Tyr Asp
        275                 280                 285

Asn Leu Gln Asn Ile Ala Arg Ile Leu Asn Glu Ala Lys Thr Ile Val
    290                 295                 300

Gly Thr Thr Thr Pro Leu Gln Tyr Met Lys Asn Ile Phe Ile Arg Lys
305                 310                 315                 320

Tyr Phe Leu Ser Glu Asp Ala Ser Gly Lys Ile Ser Val Asn Lys Ala
                325                 330                 335

Ala Phe Lys Glu Phe Tyr Arg Val Leu Thr Arg Gly Phe Thr Glu Leu
            340                 345                 350

Glu Phe Val Asn Pro Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380

Thr Ile Asn Glu Gly Phe Asn Leu Glu Gly Ala Asn Ser Asn Gly Gln
385                 390                 395                 400
```

-continued

Asn Thr Glu Ile Asn Ser Arg Asn Phe Thr Arg Leu Lys Asn Phe Thr
            405                 410                 415

Gly Leu Phe Glu Phe Tyr Lys Leu Leu Cys Val Arg Gly Ile Ile Pro
        420                 425                 430

Phe Lys Thr Lys Ser Leu Asp Glu Gly Tyr Asn Lys Ala Leu Asn Tyr
        435                 440                 445

Leu Cys Ile Lys Val Asn Asn Trp Asp Leu Phe Phe Ser Pro Ser Glu
    450                 455                 460

Asp Asn Phe Thr Asn Asp Leu Asp Lys Val Glu Glu Ile Thr Ala Asp
465                 470                 475                 480

Thr Asn Ile Glu Ala Ala Glu Glu Asn Ile Ser Ser Asp Leu Ile Gln
                485                 490                 495

Gln Tyr Tyr Leu Thr Phe Asp Phe Asp Asn Glu Pro Glu Asn Ile Ser
            500                 505                 510

Ile Glu Asn Leu Ser Ser Asp Ile Ile Gly Gln Leu Glu Pro Met Pro
            515                 520                 525

Asn Ile Glu Arg Phe Pro Asn Gly Lys Lys Tyr Glu Leu Asp Lys Tyr
        530                 535                 540

Thr Met Phe His Tyr Leu Arg Ala Gln Glu Phe Glu His Gly Asp Ser
545                 550                 555                 560

Arg Ile Ile Leu Thr Asn Ser Ala Glu Glu Ala Leu Leu Lys Pro Asn
                565                 570                 575

Val Ala Tyr Thr Phe Phe Ser Ser Lys Tyr Val Lys Lys Ile Asn Lys
            580                 585                 590

Ala Val Glu Ala Val Ile Phe Leu Ser Trp Ala Glu Gly Leu Val Tyr
        595                 600                 605

Asp Phe Thr Asp Glu Thr Asn Glu Val Thr Thr Met Asp Lys Ile Ala
    610                 615                 620

Asp Ile Thr Ile Ile Val Pro Tyr Ile Gly Pro Ala Leu Asn Ile Gly
625                 630                 635                 640

Asn Met Val Ser Lys Gly Glu Phe Val Glu Ala Ile Leu Phe Thr Gly
                645                 650                 655

Val Val Ala Leu Leu Glu Phe Ile Pro Glu Tyr Ser Leu Pro Val Phe
            660                 665                 670

Gly Thr Phe Ala Ile Val Ser Tyr Ile Ala Asn Lys Val Leu Thr Val
        675                 680                 685

Gln Thr Ile Asn Asn Ala Leu Ser Lys Arg Asn Glu Lys Trp Asp Glu
    690                 695                 700

Val Tyr Lys Tyr Thr Val Thr Asn Trp Leu Ala Lys Val Asn Thr Gln
705                 710                 715                 720

Ile Asp Leu Ile Arg Glu Lys Met Lys Lys Ala Leu Glu Asn Gln Ala
                725                 730                 735

Glu Ala Thr Arg Ala Ile Ile Asn Tyr Gln Tyr Asn Gln Tyr Thr Glu
            740                 745                 750

Glu Glu Lys Asn Asn Ile Asn Phe Asn Ile Asp Asp Leu Ser Ser Lys
        755                 760                 765

Leu Asn Arg Ser Ile Asn Arg Ala Met Ile Asn Ile Asn Lys Phe Leu
    770                 775                 780

Asp Gln Cys Ser Val Ser Tyr Leu Met Asn Ser Met Ile Pro Tyr Ala
785                 790                 795                 800

Val Lys Arg Leu Lys Asp Phe Asp Ala Ser Val Arg Asp Val Leu Leu
                805                 810                 815

Lys Tyr Ile Tyr Asp Asn Arg Gly Thr Leu Ile Leu Gln Val Asp Arg
            820                 825                 830

```
Leu Lys Asp Glu Val Asn Asn Thr Leu Ser Ala Asp Ile Pro Phe Gln
        835                 840                 845

Leu Ser Lys Tyr Val Asn Asp Lys Leu Leu Ser Thr Phe Thr Glu
    850                 855                 860

Tyr Ile Lys Asn Ile Val Asn Thr Ser Ile Leu Ser Ile Val Tyr Lys
865                 870                 875                 880

Lys Asp Asp Leu Ile Asp Leu Ser Arg Tyr Gly Ala Lys Ile Asn Ile
                885                 890                 895

Gly Asp Arg Val Tyr Tyr Asp Ser Ile Asp Lys Asn Gln Ile Lys Leu
            900                 905                 910

Ile Asn Leu Glu Ser Ser Thr Ile Glu Val Ile Leu Lys Asn Ala Ile
        915                 920                 925

Val Tyr Asn Ser Met Tyr Glu Asn Phe Ser Thr Ser Phe Trp Ile Lys
    930                 935                 940

Ile Pro Lys Tyr Phe Ser Lys Ile Asn Leu Asn Asn Glu Tyr Thr Ile
945                 950                 955                 960

Ile Asn Cys Ile Glu Asn Asn Ser Gly Trp Lys Val Ser Leu Asn Tyr
                965                 970                 975

Gly Glu Ile Ile Trp Thr Leu Gln Asp Asn Lys Gln Asn Ile Gln Arg
            980                 985                 990

Val Val Phe Lys Tyr Ser Gln Met Val Asn Ile Ser Asp Tyr Ile Asn
        995                 1000                1005

Arg Trp Met Phe Val Thr Ile Thr Asn Asn Arg Leu Thr Lys Ser Lys
    1010                1015                1020

Ile Tyr Ile Asn Gly Arg Leu Ile Asp Gln Lys Pro Ile Ser Asn Leu
1025                1030                1035                1040

Gly Asn Ile His Ala Ser Asn Lys Ile Met Phe Lys Leu Asp Gly Cys
                1045                1050                1055

Arg Asp Pro Arg Arg Tyr Ile Met Ile Lys Tyr Phe Asn Leu Phe Asp
            1060                1065                1070

Lys Glu Leu Asn Glu Lys Glu Ile Lys Asp Leu Tyr Asp Ser Gln Ser
        1075                1080                1085

Asn Pro Gly Ile Leu Lys Asp Phe Trp Gly Asn Tyr Leu Gln Tyr Asp
    1090                1095                1100

Lys Pro Tyr Tyr Met Leu Asn Leu Phe Asp Pro Asn Lys Tyr Val Asp
1105                1110                1115                1120

Val Asn Asn Ile Gly Ile Arg Gly Tyr Met Tyr Leu Lys Gly Pro Arg
                1125                1130                1135

Gly Ser Val Met Thr Thr Asn Ile Tyr Leu Asn Ser Thr Leu Tyr Met
            1140                1145                1150

Gly Thr Lys Phe Ile Ile Lys Lys Tyr Ala Ser Gly Asn Glu Asp Asn
        1155                1160                1165

Ile Val Arg Asn Asn Asp Arg Val Tyr Ile Asn Val Val Val Lys Asn
    1170                1175                1180

Lys Glu Tyr Arg Leu Ala Thr Asn Ala Ser Gln Ala Gly Val Glu Lys
1185                1190                1195                1200

Ile Leu Ser Ala Leu Glu Ile Pro Asp Val Gly Asn Leu Ser Gln Val
                1205                1210                1215

Val Val Met Lys Ser Lys Asp Asp Gln Gly Ile Arg Asn Lys Cys Lys
            1220                1225                1230

Met Asn Leu Gln Asp Asn Asn Gly Asn Asp Ile Gly Phe Val Gly Phe
        1235                1240                1245

His Leu Tyr Asp Asn Ile Ala Lys Leu Val Ala Ser Asn Trp Tyr Asn
```

```
                1250                1255                1260
Arg Gln Val Gly Lys Ala Ser Arg Thr Phe Gly Cys Ser Trp Glu Phe
1265                1270                1275                1280

Ile Pro Val Asp Asp Gly Trp Gly Glu Ser Ser Leu
                1285                1290

<210> SEQ ID NO 4
<211> LENGTH: 1296
<212> TYPE: PRT
<213> ORGANISM: Clostridium botulinum A4

<400> SEQUENCE: 4

Met Pro Leu Val Asn Gln Gln Ile Asn Tyr Tyr Asp Pro Val Asn Gly
1               5                   10                  15

Val Asp Ile Ala Tyr Ile Lys Ile Pro Asn Ala Gly Lys Met Gln Pro
                20                  25                  30

Val Lys Ala Phe Lys Ile His Asn Lys Val Trp Val Ile Pro Glu Arg
            35                  40                  45

Asp Ile Phe Thr Asn Pro Glu Glu Val Asp Leu Asn Pro Pro Glu
    50                  55                  60

Ala Lys Gln Val Pro Ile Ser Tyr Tyr Asp Ser Ala Tyr Leu Ser Thr
65                  70                  75                  80

Asp Asn Glu Lys Asp Asn Tyr Leu Lys Gly Val Ile Lys Leu Phe Glu
                85                  90                  95

Arg Ile Tyr Ser Thr Asp Leu Gly Arg Met Leu Leu Ile Ser Ile Val
            100                 105                 110

Arg Gly Ile Pro Phe Trp Gly Gly Lys Ile Asp Thr Glu Leu Lys
        115                 120                 125

Val Ile Asp Thr Asn Cys Ile Asn Ile Ile Gln Leu Asp Asp Ser Tyr
130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Val Gly Phe Glu Glu Ser Leu Glu Val Asp Thr Asn Pro Leu Leu
        195                 200                 205

Gly Ala Gly Lys Phe Ala Gln Asp Pro Ala Val Ala Leu Ala His Glu
    210                 215                 220

Leu Ile His Ala Glu His Arg Leu Tyr Gly Ile Ala Ile Asn Thr Asn
225                 230                 235                 240

Arg Val Phe Lys Val Asn Thr Asn Ala Tyr Tyr Glu Met Ala Gly Leu
                245                 250                 255

Glu Val Ser Leu Glu Glu Leu Ile Thr Phe Gly Gly Asn Asp Ala Lys
            260                 265                 270

Phe Ile Asp Ser Leu Gln Lys Lys Glu Phe Ser Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
```

-continued

```
                340                 345                 350
Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Asp Val Asn Tyr
370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Glu Gly Tyr Asn Lys
                435                 440                 445

Ala Leu Asn Glu Leu Cys Ile Lys Val Asn Asn Trp Asp Leu Phe Phe
                450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Asn Phe Asn Phe Asp Asn Glu Pro
                500                 505                 510

Glu Asn Thr Ser Ile Glu Asn Leu Ser Ser Asp Ile Ile Gly Gln Leu
                515                 520                 525

Glu Pro Met Pro Asn Ile Glu Arg Phe Pro Asn Gly Lys Lys Tyr Glu
                530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
                580                 585                 590

Ala Ile Asn Lys Ala Val Glu Ala Val Thr Phe Val Asn Trp Ile Glu
                595                 600                 605

Asn Leu Val Tyr Asp Phe Thr Asp Glu Thr Asn Glu Val Ser Thr Met
                610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
                660                 665                 670

Leu Pro Val Leu Gly Thr Phe Ala Leu Val Ser Tyr Val Ser Asn Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Ile
705                 710                 715                 720

Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Glu Lys Asn Asn Ile Asn Phe Asn Ile Asp Asp
                755                 760                 765
```

```
Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asn Arg Leu Lys Asp Lys Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Thr Asn Ala Ser Ile Leu Ser
865                 870                 875                 880

Ile Val Tyr Lys Asp Asp Leu Ile Asp Leu Ser Arg Tyr Gly Ala
                885                 890                 895

Glu Ile Tyr Asn Gly Asp Lys Val Tyr Tyr Asn Ser Ile Asp Lys Asn
            900                 905                 910

Gln Ile Arg Leu Ile Asn Leu Glu Ser Ser Thr Ile Glu Val Ile Leu
        915                 920                 925

Lys Lys Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Phe Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Ile
    1010                1015                1020

Thr Lys Ser Lys Ile Tyr Ile Asn Gly Arg Leu Ile Asp Gln Lys Pro
1025                1030                1035                1040

Ile Ser Asn Leu Gly Asn Ile His Ala Ser Asn Lys Ile Met Phe Lys
                1045                1050                1055

Leu Asp Gly Cys Arg Asp Pro His Arg Tyr Ile Val Ile Lys Tyr Phe
            1060                1065                1070

Asn Leu Phe Asp Lys Glu Leu Ser Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Ser Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Asp Asn Val Met Thr Thr Asn Ile Tyr Leu Asn Ser
            1140                1145                1150

Ser Leu Tyr Met Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200
```

```
Gly Val Glu Lys Ile Leu Ser Ala Leu Glu Ile Pro Asp Val Gly Asn
                1205                1210                1215

Leu Ser Gln Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
            1235                1240                1245

Phe Ile Gly Phe His Gln Phe Asn Asn Ile Ala Lys Leu Val Ala Ser
            1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Arg Glu Arg Pro Leu
            1285                1290                1295

<210> SEQ ID NO 5
<211> LENGTH: 1296
<212> TYPE: PRT
<213> ORGANISM: Clostridium botulinum A5

<400> SEQUENCE: 5

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Glu Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Glu His Asp Ala Lys
            260                 265                 270

Phe Ile Asp Ser Leu Gln Glu Asn Glu Phe Arg Leu Tyr Tyr Tyr Asn
        275                 280                 285
```

```
Lys Phe Lys Asp Ile Ala Ser Thr Leu Asn Lys Ala Lys Ser Ile Val
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Glu Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Glu Gly Tyr Asn Lys
        435                 440                 445
Ala Leu Asn Asp Leu Cys Ile Lys Val Asn Asn Trp Asp Leu Phe Phe
    450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
        515                 520                 525
Glu Leu Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Lys Ser Arg Ile Val Leu Thr Asn Ser Val Asn Glu Ala Leu
                565                 570                 575
Leu Asn Pro Ser Ser Val Tyr Thr Phe Phe Ser Ser Asp Tyr Val Arg
            580                 585                 590
Lys Val Asn Lys Ala Thr Glu Ala Ala Met Phe Leu Gly Trp Val Glu
        595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
        675                 680                 685
Val Leu Thr Val Gln Thr Ile Asp Asn Ala Leu Ser Lys Arg Asn Glu
    690                 695                 700
Lys Trp Gly Glu Val Tyr Lys Tyr Ile Val Thr Asn Trp Leu Ala Lys
```

```
            705                 710                 715                 720
    Val Asn Thr Gln Ile Asp Leu Ile Arg Lys Lys Met Lys Glu Ala Leu
                        725                 730                 735
    Glu Asn Gln Ala Glu Ala Thr Lys Ala Ile Ile Asn Tyr Gln Tyr Asn
                        740                 745                 750
    Gln Tyr Thr Glu Glu Lys Asn Asn Ile Asn Phe Asn Ile Gly Asp
                        755                 760                 765
    Leu Ser Ser Lys Leu Asn Asp Ser Ile Asn Lys Ala Met Ile Asn Ile
                        770                 775                 780
    Asn Lys Phe Leu Asn Gln Cys Ser Val Ser Tyr Leu Met Asn Ser Met
    785                 790                 795                 800
    Ile Pro Tyr Gly Val Lys Arg Leu Glu Asp Phe Asp Ala Ser Leu Lys
                        805                 810                 815
    Asp Ala Leu Leu Lys Tyr Ile Tyr Asp Asn Arg Gly Thr Leu Ile Gly
                        820                 825                 830
    Gln Val Asp Arg Leu Lys Asp Lys Val Asn Asn Thr Leu Ser Thr Asp
                        835                 840                 845
    Ile Pro Phe Gln Leu Ser Lys Tyr Val Asp Asn Gln Arg Leu Leu Ser
                        850                 855                 860
    Thr Phe Thr Glu Tyr Ile Lys Asn Ile Ile Asn Thr Ser Ile Leu Asn
    865                 870                 875                 880
    Leu Arg Tyr Glu Ser Asn His Leu Ile Asp Leu Ser Arg Tyr Ala Ser
                        885                 890                 895
    Glu Ile Asn Ile Gly Ser Lys Val Asn Phe Asp Pro Ile Asp Lys Asn
                        900                 905                 910
    Gln Ile Gln Leu Phe Asn Leu Glu Ser Ser Lys Ile Glu Ile Leu
                        915                 920                 925
    Lys Asn Ala Ile Val Tyr Asn Ser Met Tyr Glu Asn Phe Ser Thr Ser
    930                 935                 940
    Phe Trp Ile Lys Ile Pro Lys Tyr Phe Ser Lys Ile Asn Leu Asn Asn
    945                 950                 955                 960
    Glu Tyr Thr Ile Ile Asn Cys Ile Glu Asn Asn Ser Gly Trp Lys Val
                        965                 970                 975
    Ser Leu Asn Tyr Gly Glu Ile Ile Trp Thr Leu Gln Asp Asn Lys Gln
                        980                 985                 990
    Asn Ile Gln Arg Val Val Phe Lys Tyr Ser Gln Met Val Ala Ile Ser
                        995                 1000                1005
    Asp Tyr Ile Asn Arg Trp Ile Phe Ile Thr Ile Thr Asn Asn Arg Leu
                        1010                1015                1020
    Asn Asn Ser Lys Ile Tyr Ile Asn Gly Arg Leu Ile Asp Gln Lys Pro
    1025                1030                1035                1040
    Ile Ser Asn Leu Gly Asn Ile His Ala Ser Asn Asn Ile Met Phe Lys
                        1045                1050                1055
    Leu Asp Gly Cys Arg Asp Pro Gln Arg Tyr Ile Trp Ile Lys Tyr Phe
                        1060                1065                1070
    Asn Leu Phe Asp Lys Glu Leu Asn Glu Lys Glu Ile Lys Asp Leu Tyr
                        1075                1080                1085
    Asp Asn Gln Ser Asn Ser Gly Ile Leu Lys Asp Phe Trp Gly Asn Tyr
                        1090                1095                1100
    Leu Gln Tyr Asp Lys Pro Tyr Tyr Met Leu Asn Leu Tyr Asp Pro Asn
    1105                1110                1115                1120
    Lys Tyr Val Asp Val Asn Asn Val Gly Ile Arg Gly Tyr Met Tyr Leu
                        1125                1130                1135
```

Lys Gly Pro Arg Gly Ser Ile Val Thr Thr Asn Ile Tyr Leu Asn Ser
            1140                1145                1150

Ser Leu Tyr Met Gly Thr Lys Phe Ile Ile Lys Lys Tyr Ala Ser Gly
    1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Val Leu Glu Ile Pro Asp Val Gly Asn
            1205                1210                1215

Leu Ser Gln Val Val Met Ser Lys Asp Gln Gly Ile Arg
            1220                1225                1230

Asn Lys Cys Lys Met Asn Leu Gln Asp Asn Gly Asn Asp Ile Gly
            1235                1240                1245

Phe Ile Gly Phe His Gln Phe Asn Asn Ile Asp Lys Leu Val Ala Ser
    1250                1255                1260

Asn Trp Tyr Asn Arg Gln Ile Glu Arg Ser Ser Arg Thr Phe Gly Cys
1265                1270                1275                1280

Ser Trp Glu Phe Ile Pro Val Asp Asp Gly Trp Gly Glu Ser Pro Leu
            1285                1290                1295

<210> SEQ ID NO 6
<211> LENGTH: 1291
<212> TYPE: PRT
<213> ORGANISM: Clostridium botulinum B1

<400> SEQUENCE: 6

Met Ser Val Thr Ile Asn Asn Phe Asn Tyr Asn Asp Pro Ile Asp Asn
  1               5                  10                  15

Asp Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
 50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

-continued

```
Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
                260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
        290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Ala Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655
```

```
Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
                755                 760                 765

Asp Asn Ile Asn Asn Phe Ile Asn Gly Cys Ser Val Ser Tyr Leu Met
        770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
        850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
        900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
                980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu Ser
            1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
            1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
```

-continued

```
                    1075                1080                1085
Gly Asn Pro Leu Met Tyr Asn Lys Glu Tyr Tyr Met Phe Asn Ala Gly
            1090                1095                1100
Asn Lys Asn Ser Tyr Ile Lys Leu Lys Lys Asp Ser Pro Val Gly Glu
1105                1110                1115                1120
Ile Leu Thr Arg Ser Lys Tyr Asn Gln Asn Ser Lys Tyr Ile Asn Tyr
                1125                1130                1135
Arg Asp Leu Tyr Ile Gly Glu Lys Phe Ile Ile Arg Arg Lys Ser Asn
            1140                1145                1150
Ser Gln Ser Ile Asn Asp Asp Ile Val Arg Lys Glu Asp Tyr Ile Tyr
        1155                1160                1165
Leu Asp Phe Phe Asn Leu Asn Gln Glu Trp Arg Val Tyr Ile Tyr Lys
        1170                1175                1180
Tyr Phe Lys Lys Glu Glu Lys Leu Phe Leu Ala Pro Ile Ser Asp
1185                1190                1195                1200
Ser Asp Glu Phe Tyr Asn Thr Ile Gln Ile Lys Glu Tyr Asp Glu Gln
                1205                1210                1215
Pro Thr Tyr Ser Cys Gln Leu Leu Phe Lys Lys Asp Glu Glu Ser Thr
            1220                1225                1230
Asp Glu Ile Gly Leu Ile Gly Ile His Arg Phe Tyr Glu Ser Gly Ile
        1235                1240                1245
Val Phe Lys Glu Tyr Lys Asp Tyr Phe Cys Ile Ser Lys Trp Tyr Leu
        1250                1255                1260
Lys Glu Val Lys Arg Lys Pro Tyr Asn Ser Lys Leu Gly Cys Asn Trp
1265                1270                1275                1280
Gln Phe Ile Pro Lys Asp Glu Gly Trp Thr Glu
                1285                1290

<210> SEQ ID NO 7
<211> LENGTH: 1291
<212> TYPE: PRT
<213> ORGANISM: Clostridium botulinum B2

<400> SEQUENCE: 7

Met Pro Val Thr Ile Asn Asn Phe Asn Tyr Asn Asp Pro Ile Asp Asn
 1               5                   10                  15
Asn Asn Ile Ile Met Met Glu Pro Pro Phe Ala Arg Gly Thr Gly Arg
                20                  25                  30
Tyr Tyr Lys Ala Phe Lys Ile Thr Asp Arg Ile Trp Ile Ile Pro Glu
            35                  40                  45
Arg Tyr Thr Phe Gly Tyr Lys Pro Glu Asp Phe Asn Lys Ser Ser Gly
        50                  55                  60
Ile Phe Asn Arg Asp Val Cys Glu Tyr Tyr Asp Pro Asp Tyr Leu Asn
65                  70                  75                  80
Thr Asn Asp Lys Lys Asn Ile Phe Leu Gln Thr Met Ile Lys Leu Phe
                85                  90                  95
Asn Arg Ile Lys Ser Lys Pro Leu Gly Glu Lys Leu Leu Glu Met Ile
                100                 105                 110
Ile Asn Gly Ile Pro Tyr Leu Gly Asp Arg Arg Val Pro Leu Glu Glu
            115                 120                 125
Phe Asn Thr Asn Ile Ala Ser Val Thr Val Asn Lys Leu Ile Ser Asn
        130                 135                 140
Pro Gly Glu Val Glu Arg Lys Lys Gly Ile Phe Ala Asn Leu Ile Ile
145                 150                 155                 160
Phe Gly Pro Gly Pro Val Leu Asn Glu Asn Glu Thr Ile Asp Ile Gly
```

-continued

```
                165                 170                 175
Ile Gln Asn His Phe Ala Ser Arg Glu Gly Phe Gly Gly Ile Met Gln
                180                 185                 190
Met Lys Phe Cys Pro Glu Tyr Val Ser Val Phe Asn Asn Val Gln Glu
                195                 200                 205
Asn Lys Gly Ala Ser Ile Phe Asn Arg Arg Gly Tyr Phe Ser Asp Pro
            210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Ala Ile Gln Ala Glu Glu Leu Tyr Thr Phe
                260                 265                 270
Gly Gly Gln Asp Pro Ser Ile Ile Thr Pro Ser Thr Asp Lys Ser Ile
            275                 280                 285
Tyr Asp Lys Val Leu Gln Asn Phe Arg Gly Ile Val Asp Arg Leu Asn
            290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
            355                 360                 365
Thr Arg Ala Ser Tyr Phe Ser Asp Ser Leu Pro Pro Val Lys Ile Lys
370                 375                 380
Asn Leu Leu Asp Asn Glu Ile Tyr Thr Ile Glu Glu Gly Phe Asn Ile
385                 390                 395                 400
Ser Asp Lys Asn Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Arg Ala Pro Gly Ile Cys Ile Asp
            435                 440                 445
Val Asp Asn Glu Asp Leu Phe Phe Ile Ala Asp Lys Asn Ser Phe Ser
450                 455                 460
Asp Asp Leu Ser Lys Asn Glu Arg Ile Glu Tyr Asp Thr Gln Ser Asn
465                 470                 475                 480
Tyr Ile Glu Asn Arg Ser Ser Ile Asp Glu Leu Ile Leu Asp Thr Asn
                485                 490                 495
Leu Ile Ser Lys Ile Glu Leu Pro Ser Glu Asn Thr Glu Ser Leu Thr
            500                 505                 510
Asp Phe Asn Val Asp Val Pro Val Tyr Glu Lys Gln Pro Ala Ile Lys
            515                 520                 525
Lys Ile Phe Thr Asp Glu Asn Thr Ile Phe Gln Tyr Leu Tyr Ser Gln
530                 535                 540
Thr Phe Pro Leu Asp Ile Arg Asp Ile Ser Leu Thr Ser Ser Phe Asp
545                 550                 555                 560
Asp Ala Leu Leu Phe Ser Lys Lys Val Tyr Ser Phe Phe Ser Met Asp
                565                 570                 575
Tyr Ile Lys Thr Ala Asn Lys Val Val Glu Ala Gly Leu Phe Ala Gly
            580                 585                 590
```

-continued

Trp Val Lys Gln Ile Val Asp Asp Phe Val Ile Glu Ala Asn Lys Ser
            595                 600                 605

Ser Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asp Glu Lys Trp Ile Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Ile Ile Lys Tyr
                725                 730                 735

Lys Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Glu Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys His Leu
                820                 825                 830

Lys Thr Ile Ile Pro Phe Asp Leu Ser Lys Tyr Thr Asn Asn Thr Ile
            835                 840                 845

Leu Ile Glu Ile Phe Asn Lys Tyr Asn Ser Glu Ile Leu Asn Asn Ile
            850                 855                 860

Ile Leu Asn Leu Arg Tyr Arg Asp Asn Asn Leu Ile Asp Leu Ser Gly
865                 870                 875                 880

Tyr Gly Ala Asn Val Glu Val Tyr Asp Gly Val Glu Leu Asn Asp Lys
                885                 890                 895

Asn Gln Phe Lys Leu Thr Ser Ser Thr Asn Ser Glu Ile Arg Val Thr
                900                 905                 910

Gln Asn Gln Asn Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Ile Lys Asn Asn Ser
945                 950                 955                 960

Gly Trp Lys Ile Ser Ile Arg Gly Asn Arg Ile Ile Trp Thr Leu Thr
                965                 970                 975

Asp Ile Asn Gly Lys Thr Lys Ser Val Phe Phe Glu Tyr Ser Ile Arg
            980                 985                 990

Lys Asp Val Ser Glu Tyr Ile Asn Arg Trp Phe Phe Val Thr Ile Thr
        995                 1000                1005

Asn Asn Ser Asp Asn Ala Lys Ile Tyr Ile Asn Gly Lys Leu Glu Ser
        1010                1015                1020

Asn Ile Asp Ile Lys Asp Ile Gly Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Lys
            1060                1065                1070

Glu Ile Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Ser Val Gly Glu
1105                1110                1115                1120

Ile Leu Thr Arg Ser Lys Tyr Asn Gln Asn Ser Asn Tyr Ile Asn Tyr
                1125                1130                1135

Arg Asn Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
        1155                1160                1165

Leu Asp Phe Phe Asn Ser Asn Arg Glu Trp Arg Val Tyr Ala Tyr Lys
    1170                1175                1180

Asp Phe Lys Glu Glu Glu Lys Lys Leu Phe Leu Ala Asn Ile Tyr Asp
1185                1190                1195                1200

Ser Asn Glu Phe Tyr Lys Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Thr
        1235                1240                1245

Val Phe Lys Asn Tyr Lys Asp Tyr Phe Cys Ile Ser Lys Trp Tyr Leu
    1250                1255                1260

Lys Glu Val Lys Arg Lys Pro Tyr Asn Ser Asp Leu Gly Cys Asn Trp
1265                1270                1275                1280

Lys Phe Ile Pro Lys Asp Glu Gly Trp Thr Glu
                1285                1290

<210> SEQ ID NO 8
<211> LENGTH: 1291
<212> TYPE: PRT
<213> ORGANISM: Clostridium botulinum B3

<400> SEQUENCE: 8

Met Pro Val Thr Ile Asn Asn Phe Asn Tyr Asn Asp Pro Ile Asp Asn
 1               5                  10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

```
Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Leu Tyr Thr Phe
            260                 265                 270

Gly Gly Gln Asp Pro Arg Ile Ile Thr Pro Ser Thr Asp Lys Ser Ile
        275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
        435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asp Thr Gln Ser Asn
465                 470                 475                 480

Tyr Ile Glu Asn Arg Ser Ser Ile Asp Glu Leu Ile Leu Asp Thr Asn
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
```

```
              530                 535                 540
Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
                580                 585                 590

Trp Val Lys Gln Ile Val Asp Asp Phe Val Ile Glu Ala Asn Lys Ser
            595                 600                 605

Ser Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
675                 680                 685

Arg Asp Glu Lys Trp Ile Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Glu Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys His Leu
                820                 825                 830

Lys Thr Ile Ile Pro Phe Asp Leu Ser Met Tyr Thr Asn Asn Thr Ile
            835                 840                 845

Leu Ile Glu Ile Phe Asn Lys Tyr Asn Ser Glu Ile Leu Asn Asn Ile
850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asn Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asp Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Ile Lys Asn Asn Ser
945                 950                 955                 960
```

```
Gly Trp Lys Ile Ser Ile Arg Gly Asn Lys Ile Ile Trp Thr Leu Thr
            965                 970                 975

Asp Ile Asn Gly Lys Thr Lys Ser Val Phe Phe Glu Tyr Ser Ile Arg
            980                 985                 990

Lys Asp Val Ser Glu Tyr Ile Asn Arg Trp Phe Phe Val Thr Ile Thr
            995                1000                1005

Asn Asn Ser Asp Asn Ala Lys Ile Tyr Ile Asn Gly Lys Leu Glu Ser
           1010                1015                1020

Asn Ile Asp Ile Lys Asp Ile Gly Glu Val Ile Ala Asn Gly Glu Ile
1025                1030                1035                1040

Ile Phe Lys Leu Asp Gly Asp Ile Asp Arg Thr Gln Phe Ile Trp Met
           1045                1050                1055

Lys Tyr Phe Ser Ile Phe Asn Thr Glu Leu Ser Gln Ser Asn Ile Lys
           1060                1065                1070

Glu Ile Tyr Lys Ile Gln Ser Tyr Ser Glu Tyr Leu Lys Asp Phe Trp
           1075                1080                1085

Gly Asn Pro Leu Met Tyr Asn Lys Glu Tyr Tyr Met Phe Asn Ala Gly
           1090                1095                1100

Asn Lys Asn Ser Tyr Ile Lys Leu Lys Lys Asp Ser Val Gly Glu
1105                1110                1115                1120

Ile Leu Thr Arg Ser Lys Tyr Asn Gln Asn Ser Asn Tyr Ile Asn Tyr
           1125                1130                1135

Arg Asn Leu Tyr Ile Gly Glu Lys Phe Ile Ile Arg Arg Lys Ser Asn
           1140                1145                1150

Ser Gln Ser Ile Asn Asp Asp Ile Val Arg Lys Glu Asp Tyr Ile Tyr
           1155                1160                1165

Leu Asp Phe Phe Asn Leu Asn Gln Glu Trp Arg Val Tyr Ala Tyr Lys
           1170                1175                1180

Asp Phe Lys Lys Lys Glu Glu Lys Leu Phe Leu Ala Asn Ile Tyr Asp
1185                1190                1195                1200

Ser Asn Glu Phe Tyr Asn Thr Ile Gln Ile Lys Glu Tyr Asp Glu Gln
           1205                1210                1215

Pro Thr Tyr Ser Cys Gln Leu Leu Phe Lys Lys Asp Glu Glu Ser Thr
           1220                1225                1230

Asp Glu Ile Gly Leu Ile Gly Ile His Arg Phe Tyr Glu Ser Gly Ile
           1235                1240                1245

Val Phe Lys Asp Tyr Lys Asp Tyr Phe Cys Ile Ser Lys Trp Tyr Leu
           1250                1255                1260

Lys Glu Val Lys Arg Lys Pro Tyr Asn Pro Asn Leu Gly Cys Asn Trp
1265                1270                1275                1280

Gln Phe Ile Pro Lys Asp Glu Gly Trp Ile Glu
           1285                1290

<210> SEQ ID NO 9
<211> LENGTH: 1291
<212> TYPE: PRT
<213> ORGANISM: Clostridium botulinum Bnp

<400> SEQUENCE: 9

Met Pro Val Thr Ile Asn Asn Phe Asn Tyr Asn Asp Pro Ile Asp Asn
 1               5                  10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45
```

```
Arg Tyr Thr Phe Gly Tyr Lys Pro Glu Asp Phe Asn Lys Ser Ser Gly
 50                  55                  60

Ile Phe Asn Arg Asp Val Cys Glu Tyr Tyr Asp Pro Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
130                 135                 140

Pro Gly Glu Val Glu Gln Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Ile Met Gln
            180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
            340                 345                 350

Met Phe Gly Phe Thr Glu Ile Asn Ile Ala Glu Asn Tyr Lys Ile Lys
            355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Val Pro Gly Ile Cys Ile Asp
            435                 440                 445

Val Asp Asn Glu Asn Leu Phe Phe Ile Ala Asp Lys Asn Ser Phe Ser
    450                 455                 460

Asp Asp Leu Ser Lys Asn Glu Arg Val Glu Tyr Asn Thr Gln Asn Asn
465                 470                 475                 480
```

```
Tyr Ile Gly Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Val Phe Thr Asp Glu Asn Thr Ile Phe Gln Tyr Leu Tyr Ser Gln
        530                 535                 540

Thr Phe Pro Leu Asn Ile Arg Asp Ile Ser Leu Thr Ser Ser Phe Asp
545                 550                 555                 560

Asp Ala Leu Leu Val Ser Ser Lys Val Tyr Ser Phe Phe Ser Met Asp
                565                 570                 575

Tyr Ile Lys Thr Ala Asn Lys Val Val Glu Ala Gly Leu Phe Ala Gly
                580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
        610                 615                 620

Gly Leu Ala Leu Asn Val Gly Asp Glu Thr Ala Lys Gly Asn Phe Glu
625                 630                 635                 640

Ser Ala Phe Glu Ile Ala Gly Ser Ser Ile Leu Leu Glu Phe Ile Pro
                645                 650                 655

Glu Leu Leu Ile Pro Val Val Gly Val Phe Leu Leu Glu Ser Tyr Ile
                660                 665                 670

Asp Asn Lys Asn Lys Ile Ile Lys Thr Ile Asp Asn Ala Leu Thr Lys
            675                 680                 685

Arg Val Glu Lys Trp Ile Asp Met Tyr Gly Leu Ile Val Ala Gln Trp
        690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Glu Lys Ser Asn Ile Asn Ile Asn
                740                 745                 750

Phe Asn Asp Ile Asn Ser Lys Leu Asn Asp Gly Ile Asn Gln Ala Met
            755                 760                 765

Asp Asn Ile Asn Asp Phe Ile Asn Glu Cys Ser Val Ser Tyr Leu Met
770                 775                 780

Lys Lys Met Ile Pro Leu Ala Val Lys Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Val Glu Asp Glu Lys Ser Lys Val Asp Lys Tyr Leu
                820                 825                 830

Lys Thr Ile Ile Pro Phe Asp Leu Ser Thr Tyr Thr Asn Asn Glu Ile
        835                 840                 845

Leu Ile Lys Ile Phe Asn Lys Tyr Asn Ser Glu Ile Leu Asn Asn Ile
        850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asp Ser Lys Ile Arg Val Thr
```

```
                900                 905                 910
Gln Asn Gln Asn Ile Ile Phe Asn Ser Met Phe Leu Asp Phe Ser Val
            915                 920                 925
Ser Phe Trp Ile Arg Ile Pro Lys Tyr Arg Asn Asp Asp Ile Gln Asn
        930                 935                 940
Tyr Ile His Asn Glu Tyr Thr Ile Ile Asn Cys Met Lys Asn Asn Ser
945                 950                 955                 960
Gly Trp Lys Ile Ser Ile Arg Gly Asn Arg Ile Ile Trp Thr Leu Ile
            965                 970                 975
Asp Ile Asn Gly Lys Thr Lys Ser Val Phe Phe Glu Tyr Asn Ile Arg
        980                 985                 990
Glu Asp Ile Ser Glu Tyr Ile Asn Arg Trp Phe Phe Val Thr Ile Thr
            995                 1000                1005
Asn Asn Leu Asp Asn Ala Lys Ile Tyr Ile Asn Gly Thr Leu Glu Ser
        1010                1015                1020
Asn Met Asp Ile Lys Asp Ile Gly Glu Val Ile Val Asn Gly Glu Ile
1025                1030                1035                1040
Thr Phe Lys Leu Asp Gly Asp Val Asp Arg Thr Gln Phe Ile Trp Met
            1045                1050                1055
Lys Tyr Phe Ser Ile Phe Asn Thr Gln Leu Asn Gln Ser Asn Ile Lys
        1060                1065                1070
Glu Ile Tyr Lys Ile Gln Ser Tyr Ser Glu Tyr Leu Lys Asp Phe Trp
            1075                1080                1085
Gly Asn Pro Leu Met Tyr Asn Lys Glu Tyr Tyr Met Phe Asn Ala Gly
        1090                1095                1100
Asn Lys Asn Ser Tyr Ile Lys Leu Val Lys Asp Ser Ser Val Gly Glu
1105                1110                1115                1120
Ile Leu Ile Arg Ser Lys Tyr Asn Gln Asn Ser Asn Tyr Ile Asn Tyr
            1125                1130                1135
Arg Asn Leu Tyr Ile Gly Glu Lys Phe Ile Ile Arg Arg Lys Ser Asn
        1140                1145                1150
Ser Gln Ser Ile Asn Asp Asp Ile Val Arg Lys Glu Asp Tyr Ile His
            1155                1160                1165
Leu Asp Phe Val Asn Ser Asn Glu Glu Trp Arg Val Tyr Ala Tyr Lys
        1170                1175                1180
Asn Phe Lys Glu Gln Glu Gln Lys Leu Phe Leu Ser Ile Ile Tyr Asp
1185                1190                1195                1200
Ser Asn Glu Phe Tyr Lys Thr Ile Gln Ile Lys Glu Tyr Asp Glu Gln
            1205                1210                1215
Pro Thr Tyr Ser Cys Gln Leu Leu Phe Lys Lys Asp Glu Glu Ser Thr
        1220                1225                1230
Asp Asp Ile Gly Leu Ile Gly Ile His Arg Phe Tyr Glu Ser Gly Val
            1235                1240                1245
Leu Arg Lys Lys Tyr Lys Asp Tyr Phe Cys Ile Ser Lys Trp Tyr Leu
            1250                1255                1260
Lys Glu Val Lys Arg Lys Pro Tyr Lys Ser Asn Leu Gly Cys Asn Trp
1265                1270                1275                1280
Gln Phe Ile Pro Lys Asp Glu Gly Trp Thr Glu
            1285                1290

<210> SEQ ID NO 10
<211> LENGTH: 1291
<212> TYPE: PRT
<213> ORGANISM: Clostridium botulinum Bbv
```

<400> SEQUENCE: 10

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Met Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415
```

```
Asn Lys Gln Ala Tyr Glu Glu Ile Ser Lys Glu His Leu Ala Val Tyr
                420                 425                 430

Lys Ile Gln Met Cys Lys Ser Val Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Ala Tyr Asn Thr Gln Asn Asn
465                 470                 475                 480

Tyr Ile Glu Asn Asp Phe Ser Ile Asn Glu Leu Ile Leu Asp Thr Asp
                485                 490                 495

Leu Ile Ser Lys Ile Glu Leu Pro Ser Glu Asn Thr Gly Ser Leu Thr
            500                 505                 510

Asp Phe Asn Val Tyr Val Pro Val Tyr Lys Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
            595                 600                 605

Ser Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Glu Thr Ile Asn Ser Ala Leu Thr Lys
            675                 680                 685

Arg Asp Glu Lys Trp Ile Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Arg Ser Asn Ile Asn Ile Asp
            740                 745                 750

Phe Asn Asp Val Asn Ser Lys Leu Asn Glu Gly Ile Asn Gln Ala Ile
            755                 760                 765

Asp Asn Ile Asn Asn Phe Ile Asn Glu Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Arg Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys Tyr Leu
            820                 825                 830

Lys Thr Ser Ile Pro Phe Asp Leu Ser Thr Tyr Thr Asn Asn Thr Ile
            835                 840                 845
```

```
Leu Ile Glu Ile Phe Asn Lys Tyr Asn Ser Asp Ile Leu Asn Ile
    850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Ile
            900                 905                 910

Gln Asn Gln Asn Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
            980                 985                 990

Glu Asp Ile Ser Glu Tyr Ile Asn Arg Trp Phe Phe Val Thr Ile Thr
            995                 1000                1005

Asn Asn Ser Asp Asn Ala Lys Ile Tyr Ile Asn Gly Lys Leu Glu Ser
    1010                1015                1020

His Ile Asp Ile Arg Asp Ile Arg Glu Val Ile Ala Asn Asp Glu Ile
1025                1030                1035                1040

Ile Phe Lys Leu Asp Gly Asn Ile Asp Arg Thr Gln Phe Ile Trp Met
                1045                1050                1055

Lys Tyr Phe Ser Ile Phe Asn Thr Glu Leu Ser Gln Ser Asn Ile Glu
            1060                1065                1070

Glu Ile Tyr Lys Ile Gln Ser Tyr Ser Glu Tyr Leu Lys Asp Phe Trp
            1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Ser Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
            1155                1160                1165

Leu Asp Phe Phe Asn Leu Asn Gln Glu Trp Arg Val Tyr Met Tyr Lys
    1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
            1235                1240                1245

Val Phe Lys Glu Tyr Lys Asp Tyr Phe Cys Ile Ser Lys Trp Tyr Leu
    1250                1255                1260

Lys Glu Val Lys Arg Lys Pro Tyr Asn Ser Lys Leu Gly Cys Asn Trp
```

```
                1265                1270                1275                1280
            Gln Phe Ile Pro Lys Asp Glu Gly Trp Thr Glu
                            1285                1290

<210> SEQ ID NO 11
<211> LENGTH: 1291
<212> TYPE: PRT
<213> ORGANISM: Clostridium botulinum C1-1

<400> SEQUENCE: 11

Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
             20                  25                  30

Pro Glu Lys Ala Phe Arg Ile Thr Gly Asn Ile Trp Val Ile Pro Asp
         35                  40                  45

Arg Phe Ser Arg Asn Ser Asn Pro Asn Leu Asn Lys Pro Pro Arg Val
     50                  55                  60

Thr Ser Pro Lys Ser Gly Tyr Tyr Asp Pro Asn Tyr Leu Ser Thr Asp
 65                  70                  75                  80

Ser Asp Lys Asp Thr Phe Leu Lys Glu Ile Ile Lys Leu Phe Lys Arg
                 85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
```

```
                355                 360                 365
Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
            405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
            450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
            530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
770                 775                 780
```

-continued

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
        820                 825                 830

Lys Ala Lys Val Asn Asn Ser Phe Gln Asn Thr Ile Pro Phe Asn Ile
    835                 840                 845

Phe Ser Tyr Thr Asn Asn Ser Leu Leu Lys Asp Ile Asn Glu Tyr
850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
            885                 890                 895

Gly Asp Val Gln Leu Asn Pro Ile Phe Pro Phe Asp Phe Lys Leu Gly
        900                 905                 910

Ser Ser Gly Glu Asp Arg Gly Lys Val Ile Val Thr Gln Asn Glu Asn
    915                 920                 925

Ile Val Tyr Asn Ser Met Tyr Glu Ser Phe Ser Ile Ser Phe Trp Ile
930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ser Asn Phe
            965                 970                 975

Leu Val Phe Thr Leu Lys Gln Asn Glu Asp Ser Glu Gln Ser Ile Asn
        980                 985                 990

Phe Ser Tyr Asp Ile Ser Asn Asn Ala Pro Gly Tyr Asn Lys Trp Phe
    995                 1000                1005

Phe Val Thr Val Thr Asn Asn Met Met Gly Asn Met Lys Ile Tyr Ile
        1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
            1045                1050                1055

Gly Leu Ile Thr Ser Asp Ser Asp Asn Ile Asn Met Trp Ile Arg Asp
        1060                1065                1070

Phe Tyr Ile Phe Ala Lys Glu Leu Asp Gly Lys Asp Ile Asn Ile Leu
    1075                1080                1085

Phe Asn Ser Leu Gln Tyr Thr Asn Val Val Lys Asp Tyr Trp Gly Asn
    1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
            1125                1130                1135

Arg Asn Asn Asn Asp Phe Asn Glu Gly Tyr Lys Ile Ile Ile Lys Arg
        1140                1145                1150

Ile Arg Gly Asn Thr Asn Asp Thr Arg Val Arg Gly Gly Asp Ile Leu
    1155                1160                1165

Tyr Phe Asp Met Thr Ile Asn Asn Lys Ala Tyr Asn Leu Phe Met Lys
1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
            1205                1210                1215

```
Gln Ile Gln Pro Met Asn Asn Thr Tyr Tyr Tyr Ala Ser Gln Ile Phe
            1220                1225                1230

Lys Ser Asn Phe Asn Gly Glu Asn Ile Ser Gly Ile Cys Ser Ile Gly
        1235                1240                1245

Thr Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
                1285                1290

<210> SEQ ID NO 12
<211> LENGTH: 1280
<212> TYPE: PRT
<213> ORGANISM: Clostridium botulinum C1-2

<400> SEQUENCE: 12

Met Pro Ile Thr Ile Asn Asn Phe Asn Tyr Ser Asp Pro Val Asp Asn
 1               5                  10                  15

Lys Asn Ile Leu Tyr Leu Asp Thr His Leu Asn Thr Leu Ala Asn Glu
            20                  25                  30

Pro Glu Lys Ala Phe Arg Ile Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Thr Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Gly Arg Lys Tyr
        275                 280                 285

Phe Glu Glu Lys Ala Leu Asp Tyr Tyr Arg Ser Ile Ala Lys Arg Leu
    290                 295                 300
```

```
Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys
                340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
450                 455                 460

Phe Ile Gly Asp Ile Ser Asp Ile Lys Thr Asp Ile Phe Leu Ser Lys
465                 470                 475                 480

Asp Ile Asn Val Glu Thr Glu Val Ile Asp Tyr Pro Asp Asn Val Ser
                485                 490                 495

Val Asp Gln Val Ile Leu Ser Lys Asn Thr Ser Glu His Gly Gln Leu
                500                 505                 510

Asp Leu Leu Tyr Pro Ile Ile Glu Gly Glu Ser Gln Val Leu Pro Gly
            515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
                580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Glu Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
                660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
                690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
```

```
                725                 730                 735
Ala Ile Lys Asp Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Ile Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
            805                 810                 815

Leu Ile Asp Ser His Asn Ile Ile Leu Val Gly Glu Val Asp Arg Leu
        820                 825                 830

Lys Ala Lys Val Asn Glu Ser Phe Glu Asn Thr Ile Pro Phe Asn Ile
    835                 840                 845

Phe Ser Tyr Thr Asn Asn Ser Leu Leu Lys Asp Ile Ile Asn Glu Tyr
            850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
            885                 890                 895

Gly Asp Val Gln Val Asn Thr Ile Tyr Thr Asn Asp Phe Lys Leu Ser
        900                 905                 910

Ser Ser Gly Asp Lys Ile Ile Val Asn Leu Asn Asn Asn Ile Leu Tyr
    915                 920                 925

Ser Ala Ile Tyr Glu Asn Ser Ser Val Ser Phe Trp Ile Lys Ile Ser
930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
            965                 970                 975

Trp Ile Leu Gln Asp Ile Asn Arg Lys Tyr Lys Ser Leu Ile Phe Asp
        980                 985                 990

Tyr Ser Glu Ser Leu Ser His Thr Gly Tyr Thr Asn Lys Trp Phe Phe
    995                 1000                1005

Val Thr Ile Thr Asn Asn Ile Met Gly Tyr Met Lys Leu Tyr Ile Asn
            1010                1015                1020

Gly Glu Leu Lys Gln Ser Glu Arg Ile Glu Asp Leu Asn Glu Val Lys
1025                1030                1035                1040

Leu Asp Lys Thr Ile Val Phe Gly Ile Asp Glu Asn Ile Asp Glu Asn
            1045                1050                1055

Gln Met Leu Trp Ile Arg Asp Phe Asn Ile Phe Ser Lys Glu Leu Ser
        1060                1065                1070

Asn Glu Asp Ile Asn Ile Val Tyr Glu Gly Gln Ile Leu Arg Asn Val
    1075                1080                1085

Ile Lys Asp Tyr Trp Gly Asn Pro Leu Lys Phe Asp Thr Glu Tyr Tyr
    1090                1095                1100

Ile Ile Asn Asp Asn Tyr Ile Asp Arg Tyr Ile Ala Pro Lys Ser Asn
1105                1110                1115                1120

Ile Leu Val Leu Val Gln Tyr Pro Asp Arg Ser Lys Leu Tyr Thr Gly
            1125                1130                1135

Asn Pro Ile Thr Ile Lys Ser Val Ser Asp Lys Asn Pro Tyr Ser Arg
        1140                1145                1150
```

-continued

```
Ile Leu Asn Gly Asp Asn Ile Met Phe His Met Leu Tyr Asn Ser Gly
        1155                1160                1165
Lys Tyr Met Ile Ile Arg Asp Thr Asp Thr Ile Tyr Ala Ile Glu Gly
        1170                1175                1180
Arg Glu Cys Ser Lys Asn Cys Val Tyr Ala Leu Lys Leu Gln Ser Asn
1185                1190                1195                1200
Leu Gly Asn Tyr Gly Ile Gly Ile Phe Ser Ile Lys Asn Ile Val Ser
        1205                1210                1215
Gln Asn Lys Tyr Cys Ser Gln Ile Phe Ser Ser Phe Met Lys Asn Thr
        1220                1225                1230
Met Leu Leu Ala Asp Ile Tyr Lys Pro Trp Arg Phe Ser Phe Glu Asn
        1235                1240                1245
Ala Tyr Thr Pro Val Ala Val Thr Asn Tyr Glu Thr Lys Leu Leu Ser
        1250                1255                1260
Thr Ser Ser Phe Trp Lys Phe Ile Ser Arg Asp Pro Gly Trp Val Glu
1265                1270                1275                1280

<210> SEQ ID NO 13
<211> LENGTH: 1276
<212> TYPE: PRT
<213> ORGANISM: Clostridium botulinum D1

<400> SEQUENCE: 13

Met Thr Trp Pro Val Lys Asp Phe Asn Tyr Ser Asp Pro Val Asn Asp
  1               5                  10                  15
Asn Asp Ile Leu Tyr Leu Arg Ile Pro Gln Asn Lys Leu Ile Thr Thr
            20                  25                  30
Pro Val Lys Ala Phe Met Ile Thr Gln Asn Ile Trp Val Ile Pro Glu
        35                  40                  45
Arg Phe Ser Ser Asp Thr Asn Pro Ser Leu Ser Lys Pro Pro Arg Pro
 50                  55                  60
Thr Ser Lys Tyr Gln Ser Tyr Tyr Asp Pro Ser Tyr Leu Ser Thr Asp
 65                  70                  75                  80
Glu Gln Lys Asp Thr Phe Leu Lys Gly Ile Ile Lys Leu Phe Lys Arg
                85                  90                  95
Ile Asn Glu Arg Asp Ile Gly Lys Lys Leu Ile Asn Tyr Leu Val Val
            100                 105                 110
Gly Ser Pro Phe Met Gly Asp Ser Ser Thr Pro Glu Asp Thr Phe Asp
        115                 120                 125
Phe Thr Arg His Thr Thr Asn Ile Ala Val Glu Lys Phe Glu Asn Gly
    130                 135                 140
Ser Trp Lys Val Thr Asn Ile Ile Thr Pro Ser Val Leu Ile Phe Gly
145                 150                 155                 160
Pro Leu Pro Asn Ile Leu Asp Tyr Thr Ala Ser Leu Thr Leu Gln Gly
                165                 170                 175
Gln Gln Ser Asn Pro Ser Phe Glu Gly Phe Gly Thr Leu Ser Ile Leu
            180                 185                 190
Lys Val Ala Pro Glu Phe Leu Leu Thr Phe Ser Asp Val Thr Ser Asn
        195                 200                 205
Gln Ser Ser Ala Val Leu Gly Lys Ser Ile Phe Cys Met Asp Pro Val
    210                 215                 220
Ile Ala Leu Met His Glu Leu Thr His Ser Leu His Gln Leu Tyr Gly
225                 230                 235                 240
Ile Asn Ile Pro Ser Asp Lys Arg Ile Arg Pro Gln Val Ser Glu Gly
                245                 250                 255
```

-continued

```
Phe Phe Ser Gln Asp Gly Pro Asn Val Gln Phe Glu Leu Tyr Thr
            260                 265                 270

Phe Gly Gly Leu Asp Val Glu Ile Ile Pro Gln Ile Glu Arg Ser Gln
            275                 280                 285

Leu Arg Glu Lys Ala Leu Gly His Tyr Lys Asp Ile Ala Lys Arg Leu
            290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
            435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
            515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
            595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
    675                 680                 685
```

-continued

```
Cys Leu Glu Gln Arg Val Lys Arg Trp Lys Asp Ser Tyr Gln Trp Met
    690                 695                 700
Val Ser Asn Trp Leu Ser Arg Ile Thr Thr Gln Phe Asn His Ile Asn
705                 710                 715                 720
Tyr Gln Met Tyr Asp Ser Leu Ser Tyr Gln Ala Asp Ala Ile Lys Ala
                725                 730                 735
Lys Ile Asp Leu Glu Tyr Lys Lys Tyr Ser Gly Ser Asp Lys Glu Asn
                740                 745                 750
Ile Lys Ser Gln Val Glu Asn Leu Lys Asn Ser Leu Asp Val Lys Ile
            755                 760                 765
Ser Glu Ala Met Asn Asn Ile Asn Lys Phe Ile Arg Glu Cys Ser Val
    770                 775                 780
Thr Tyr Leu Phe Lys Asn Met Leu Pro Lys Val Ile Asp Glu Leu Asn
785                 790                 795                 800
Lys Phe Asp Leu Arg Thr Lys Thr Glu Leu Ile Asn Leu Ile Asp Ser
                805                 810                 815
His Asn Ile Ile Leu Val Gly Glu Val Asp Arg Leu Lys Ala Lys Val
                820                 825                 830
Asn Glu Ser Phe Glu Asn Thr Met Pro Phe Asn Ile Phe Ser Tyr Thr
            835                 840                 845
Asn Asn Ser Leu Leu Lys Asp Ile Ile Asn Glu Tyr Phe Asn Ser Ile
    850                 855                 860
Asn Asp Ser Lys Ile Leu Ser Leu Gln Asn Lys Lys Asn Ala Leu Val
865                 870                 875                 880
Asp Thr Ser Gly Tyr Asn Ala Glu Val Arg Val Gly Asp Asn Val Gln
                885                 890                 895
Leu Asn Thr Ile Tyr Thr Asn Asp Phe Lys Leu Ser Ser Ser Gly Asp
            900                 905                 910
Lys Ile Ile Val Asn Leu Asn Asn Asn Ile Leu Tyr Ser Ala Ile Tyr
    915                 920                 925
Glu Asn Ser Ser Val Ser Phe Trp Ile Lys Ile Ser Lys Asp Leu Thr
    930                 935                 940
Asn Ser His Asn Glu Tyr Thr Ile Ile Asn Ser Ile Glu Gln Asn Ser
945                 950                 955                 960
Gly Trp Lys Leu Cys Ile Arg Asn Gly Asn Ile Glu Trp Ile Leu Gln
                965                 970                 975
Asp Val Asn Arg Lys Tyr Lys Ser Leu Ile Phe Asp Tyr Ser Glu Ser
            980                 985                 990
Leu Ser His Thr Gly Tyr Thr Asn Lys Trp Phe Phe Val Thr Ile Thr
    995                 1000                1005
Asn Asn Ile Met Gly Tyr Met Lys Leu Tyr Ile Asn Gly Glu Leu Lys
    1010                1015                1020
Gln Ser Gln Lys Ile Glu Asp Leu Asp Glu Val Lys Leu Asp Lys Thr
1025                1030                1035                1040
Ile Val Phe Gly Ile Asp Glu Asn Ile Asp Glu Asn Gln Met Leu Trp
                1045                1050                1055
Ile Arg Asp Phe Asn Ile Phe Ser Lys Glu Leu Ser Asn Glu Asp Ile
            1060                1065                1070
Asn Ile Val Tyr Glu Gly Gln Ile Leu Arg Asn Val Ile Lys Asp Tyr
    1075                1080                1085
Trp Gly Asn Pro Leu Lys Phe Asp Thr Glu Tyr Tyr Ile Ile Asn Asp
    1090                1095                1100
Asn Tyr Ile Asp Arg Tyr Ile Ala Pro Glu Ser Asn Val Leu Val Leu
```

```
                1105                1110                1115                1120
Val Gln Tyr Pro Asp Arg Ser Lys Leu Tyr Thr Gly Asn Pro Ile Thr
                    1125                1130                1135

Ile Lys Ser Val Ser Asp Lys Asn Pro Tyr Ser Arg Ile Leu Asn Gly
                    1140                1145                1150

Asp Asn Ile Ile Leu His Met Leu Tyr Asn Ser Arg Lys Tyr Met Ile
                    1155                1160                1165

Ile Arg Asp Thr Asp Thr Ile Tyr Ala Thr Gln Gly Gly Glu Cys Ser
                    1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
                    1205                1210                1215

Cys Ser Gln Ile Phe Ser Ser Phe Arg Glu Asn Thr Met Leu Leu Ala
                    1220                1225                1230

Asp Ile Tyr Lys Pro Trp Arg Phe Ser Phe Lys Asn Ala Tyr Thr Pro
                    1235                1240                1245

Val Ala Val Thr Asn Tyr Glu Thr Lys Leu Leu Ser Thr Ser Ser Phe
                    1250                1255                1260

Trp Lys Phe Ile Ser Arg Asp Pro Gly Trp Val Glu
1265                1270                1275
```

<210> SEQ ID NO 14
<211> LENGTH: 1285
<212> TYPE: PRT
<213> ORGANISM: Clostridium botulinum D2

<400> SEQUENCE: 14

```
Met Thr Trp Pro Val Lys Asp Phe Asn Tyr Ser Asp Pro Val Asn Asp
  1               5                  10                  15

Asn Asp Ile Leu Tyr Leu Arg Ile Pro Gln Asn Lys Leu Ile Thr Thr
                 20                  25                  30

Pro Val Lys Ala Phe Met Ile Thr Gln Asn Ile Trp Val Ile Pro Glu
             35                  40                  45

Arg Phe Ser Ser Asp Thr Asn Pro Ser Leu Ser Lys Pro Pro Arg Pro
 50                  55                  60

Thr Ser Lys Tyr Gln Ser Tyr Tyr Asp Pro Ser Tyr Leu Ser Thr Asp
 65                  70                  75                  80

Glu Gln Lys Asp Thr Phe Leu Lys Gly Ile Ile Lys Leu Phe Lys Arg
                 85                  90                  95

Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
            115                 120                 125

Phe Thr Arg His Thr Thr Asn Ile Ala Val Glu Lys Phe Glu Asn Gly
130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
```

```
            210                 215                 220
Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Leu Tyr Thr
                260                 265                 270

Phe Gly Gly Ser Asp Val Glu Ile Ile Pro Gln Ile Glu Arg Leu Gln
                275                 280                 285

Leu Arg Glu Lys Ala Leu Gly His Tyr Lys Asp Ile Ala Lys Arg Leu
290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
                340                 345                 350

Asp Leu Thr Asn Val Met Ser Glu Val Val Tyr Ser Ser Gln Tyr Asn
                355                 360                 365

Val Lys Asn Arg Thr His Tyr Phe Ser Lys His Tyr Leu Pro Val Phe
370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
                420                 425                 430

Phe Thr Lys Val Cys Leu Arg Leu Thr Arg Asn Ser Arg Asp Asp Ser
                435                 440                 445

Thr Cys Ile Gln Val Lys Asn Asn Thr Leu Pro Tyr Val Ala Asp Lys
                450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
                500                 505                 510

Pro Asn Val Asn Met Glu Pro Leu Asn Val Pro Gly Glu Glu Glu Val
                515                 520                 525

Phe Tyr Asp Asp Ile Thr Lys Asp Val Asp Tyr Leu Asn Ser Tyr Tyr
                530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
                595                 600                 605

Ile Met Lys Lys Asp Thr Leu Asp Lys Ile Ser Asp Val Ser Ala Ile
                610                 615                 620

Ile Pro Tyr Ile Gly Pro Ala Leu Asn Ile Gly Asn Ser Ala Leu Arg
625                 630                 635                 640
```

-continued

```
Gly Asn Phe Lys Gln Ala Phe Ala Thr Ala Gly Val Ala Phe Leu Leu
            645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
            690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
            725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
            770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
            805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
            835                 840                 845

Asn Asn Ser Leu Leu Lys Asp Met Ile Asn Glu Tyr Phe Asn Ser Ile
            850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
            885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
            915                 920                 925

Ala Met Tyr Glu Ser Phe Ser Ile Ser Phe Trp Ile Arg Ile Asn Lys
930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
            965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr Asn Lys Trp Phe Phe Val Thr Ile
            995                1000                1005

Thr Thr Asn Met Met Gly Asn Met Met Ile Tyr Ile Asn Gly Lys Leu
            1010                1015                1020

Ile Asp Thr Ile Lys Val Lys Glu Leu Thr Gly Ile Asn Phe Ser Lys
1025                1030                1035                1040

Thr Ile Thr Phe Gln Met Asn Lys Ile Pro Asn Thr Gly Leu Ile Thr
            1045                1050                1055

Ser Asp Ser Asp Asn Ile Asn Met Trp Ile Arg Asp Phe Tyr Ile Phe
            1060                1065                1070
```

```
Ala Lys Glu Leu Asp Asp Lys Asp Ile Asn Ile Leu Phe Asn Ser Leu
        1075                1080                1085

Gln Tyr Thr Asn Val Val Lys Asp Tyr Trp Gly Asn Asp Leu Arg Tyr
    1090                1095                1100

Asp Lys Glu Tyr Tyr Met Ile Asn Val Asn Tyr Met Asn Arg Tyr Met
1105                1110                1115                1120

Ser Lys Lys Gly Asn Gly Ile Val Phe Asn Thr Arg Lys Asn Asn
        1125                1130                1135

Asp Phe Asn Glu Gly Tyr Lys Ile Ile Ile Lys Arg Ile Arg Gly Asn
                1140                1145                1150

Thr Asn Asp Thr Arg Val Arg Gly Glu Asn Val Leu Tyr Phe Asn Thr
        1155                1160                1165

Thr Ile Asp Asn Lys Gln Tyr Ser Leu Gly Met Tyr Lys Pro Ser Arg
        1170                1175                1180

Asn Leu Gly Thr Asp Leu Val Pro Leu Gly Ala Leu Asp Gln Pro Met
1185                1190                1195                1200

Asp Glu Ile Arg Lys Tyr Gly Ser Phe Ile Ile Gln Pro Cys Asn Thr
            1205                1210                1215

Phe Asp Tyr Tyr Ala Ser Gln Leu Phe Leu Ser Ser Asn Ala Thr Thr
                1220                1225                1230

Asn Arg Leu Gly Ile Leu Ser Ile Gly Ser Tyr Ser Phe Lys Leu Gly
        1235                1240                1245

Asp Asp Tyr Trp Phe Asn His Glu Tyr Leu Ile Pro Val Ile Lys Ile
    1250                1255                1260

Glu His Tyr Ala Ser Leu Leu Glu Ser Thr Ser Thr His Trp Val Phe
1265                1270                1275                1280

Val Pro Ala Ser Glu
            1285

<210> SEQ ID NO 15
<211> LENGTH: 1252
<212> TYPE: PRT
<213> ORGANISM: Clostridium botulinum E1

<400> SEQUENCE: 15

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160
```

```
Asn Ser Ser Asn Ile Ser Leu Arg Asn Tyr Met Pro Ser Asn His
            165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
        210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
        370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
        500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
        530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
```

```
                580             585             590
Val Asp Lys Ile Ala Asp Ile Ser Ile Val Pro Tyr Ile Gly Leu
            595             600             605

Ala Leu Asn Ile Gly Asn Glu Ala Gln Lys Gly Asn Phe Lys Asp Ala
        610             615             620

Glu Leu Leu Gly Ala Gly Ile Leu Glu Phe Glu Pro Glu Leu
625             630             635             640

Leu Ile Pro Thr Ile Leu Val Phe Thr Ile Lys Ser Phe Leu Gly Ser
                645             650             655

Ser Asp Asn Lys Asn Lys Val Ile Lys Ala Ile Asn Asn Ala Leu Lys
            660             665             670

Glu Arg Asp Glu Lys Trp Lys Glu Val Tyr Ser Phe Ile Val Ser Asn
            675             680             685

Trp Met Thr Lys Ile Asn Thr Gln Phe Asn Lys Arg Lys Glu Gln Met
        690             695             700

Tyr Gln Ala Leu Gln Asn Gln Val Asn Ala Ile Lys Thr Ile Ile Glu
705             710             715             720

Ser Lys Tyr Asn Ser Tyr Thr Leu Glu Glu Lys Asn Glu Leu Thr Asn
                725             730             735

Lys Tyr Asp Ile Lys Gln Ile Glu Asn Glu Leu Asn Gln Lys Val Ser
            740             745             750

Ile Ala Met Asn Asn Ile Asp Arg Phe Leu Thr Glu Ser Ser Ile Ser
            755             760             765

Tyr Leu Met Lys Leu Ile Asn Glu Val Lys Ile Asn Lys Leu Arg Glu
        770             775             780

Tyr Asp Glu Asn Val Lys Thr Tyr Leu Leu Asn Tyr Ile Ile Gln His
785             790             795             800

Gly Ser Ile Leu Gly Glu Ser Gln Gln Glu Leu Asn Ser Met Val Thr
                805             810             815

Asp Thr Leu Asn Asn Ser Ile Pro Phe Lys Leu Ser Ser Tyr Thr Asp
            820             825             830

Asp Lys Ile Leu Ile Ser Tyr Phe Asn Lys Phe Phe Lys Arg Ile Lys
            835             840             845

Ser Ser Ser Val Leu Asn Met Arg Tyr Lys Asn Asp Lys Tyr Val Asp
        850             855             860

Thr Ser Gly Tyr Asp Ser Asn Ile Asn Ile Asn Gly Asp Val Tyr Lys
865             870             875             880

Tyr Pro Thr Asn Lys Asn Gln Phe Gly Ile Tyr Asn Asp Lys Leu Ser
                885             890             895

Glu Val Asn Ile Ser Gln Asn Asp Tyr Ile Ile Tyr Asp Asn Lys Tyr
            900             905             910

Lys Asn Phe Ser Ile Ser Phe Trp Val Arg Ile Pro Asn Tyr Asp Asn
            915             920             925

Lys Ile Val Asn Val Asn Asn Glu Tyr Thr Ile Ile Asn Cys Met Arg
        930             935             940

Asp Asn Asn Ser Gly Trp Lys Val Ser Leu Asn His Asn Glu Ile Ile
945             950             955             960

Trp Thr Leu Gln Asp Asn Ala Gly Ile Asn Gln Lys Leu Ala Phe Asn
                965             970             975

Tyr Gly Asn Ala Asn Gly Ile Ser Asp Tyr Ile Asn Lys Trp Ile Phe
            980             985             990

Val Thr Ile Thr Asn Asp Arg Leu Gly Asp Ser Lys Leu Tyr Ile Asn
            995             1000            1005
```

-continued

Gly Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
                1060                1065                1070

Lys Asp Phe Trp Gly Asn Tyr Leu Leu Tyr Asp Lys Glu Tyr Tyr Leu
            1075                1080                1085

Leu Asn Val Leu Lys Pro Asn Asn Phe Ile Asp Arg Arg Lys Asp Ser
        1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
                1140                1145                1150

Val Ala Ser Lys Thr His Leu Phe Pro Leu Tyr Ala Asp Thr Ala Thr
        1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Asn Cys Thr Met Asn
1185                1190                1195                1200

Phe Lys Asn Asn Asn Gly Asn Asn Ile Gly Leu Leu Gly Phe Lys Ala
                1205                1210                1215

Asp Thr Val Val Ala Ser Thr Trp Tyr Tyr Thr His Met Arg Asp His
                1220                1225                1230

Thr Asn Ser Asn Gly Cys Phe Trp Asn Phe Ile Ser Glu Glu His Gly
            1235                1240                1245

Trp Gln Glu Lys
    1250

<210> SEQ ID NO 16
<211> LENGTH: 1252
<212> TYPE: PRT
<213> ORGANISM: Clostridium botulinum E2

<400> SEQUENCE: 16

Met Pro Lys Ile Asn Ser Phe Asn Tyr Asn Asp Pro Val Asn Asp Arg
 1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

-continued

```
Ala Ser Ala Val Glu Ile Lys Phe Ser Asn Gly Ile Gln Asp Ile Leu
        130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560
```

```
Asn Asn Val Asn Lys Pro Val Gln Ala Ala Leu Phe Val Ser Trp Ile
            565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
            595                 600                 605
Ala Leu Asn Ile Gly Asn Glu Ala Gln Lys Gly Asn Phe Lys Asp Ala
            610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
            645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
            675                 680                 685
Trp Met Thr Lys Ile Asn Thr Gln Phe Asn Lys Arg Lys Glu Gln Met
            690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
            725                 730                 735
Lys Tyr Asp Ile Lys Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
            755                 760                 765
Tyr Leu Met Lys Leu Ile Asn Glu Val Lys Ile Asn Lys Leu Arg Glu
            770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
            805                 810                 815
Asp Thr Leu Asn Asn Ser Ile Pro Phe Lys Leu Ser Ser Tyr Thr Asp
            820                 825                 830
Asp Lys Ile Leu Ile Ser Tyr Phe Asn Lys Phe Phe Lys Arg Ile Lys
            835                 840                 845
Ser Ser Ser Val Leu Asn Met Arg Tyr Lys Asn Asp Lys Tyr Val Asp
            850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
            885                 890                 895
Glu Val Asn Ile Ser Gln Asn Asp Tyr Ile Ile Tyr Asp Asn Lys Tyr
            900                 905                 910
Lys Asn Phe Ser Ile Ser Phe Trp Val Arg Ile Pro Asn Tyr Asp Asn
            915                 920                 925
Lys Ile Val Asn Val Asn Asn Glu Tyr Thr Ile Ile Asn Cys Met Arg
            930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Ala Phe Asn
            965                 970                 975
Tyr Gly Asn Ala Asn Gly Ile Ser Asp Tyr Ile Asn Lys Trp Ile Phe
```

-continued

```
                980             985             990
Val Thr Ile Thr Asn Asp Arg Leu Gly Asp Ser Lys Leu Tyr Ile Asn
            995            1000            1005

Gly Asn Leu Ile Asp Gln Lys Ser Ile Leu Asn Leu Gly Asn Ile His
        1010            1015            1020

Val Ser Asp Asn Ile Leu Phe Lys Ile Val Asn Cys Ser Tyr Thr Arg
1025            1030            1035            1040

Tyr Ile Gly Ile Arg Tyr Phe Asn Ile Phe Asp Lys Glu Leu Asp Glu
            1045            1050            1055

Thr Glu Ile Gln Thr Leu Tyr Asn Asn Glu Pro Asn Ala Asn Ile Leu
        1060            1065            1070

Lys Asp Phe Trp Gly Asn Tyr Leu Leu Tyr Asp Lys Glu Tyr Tyr Leu
            1075            1080            1085

Leu Asn Val Leu Lys Pro Asn Asn Phe Ile Asp Arg Arg Thr Asp Ser
        1090            1095            1100

Thr Leu Ser Ile Asn Asn Ile Arg Ser Thr Ile Leu Leu Ala Asn Arg
1105            1110            1115            1120

Leu Tyr Ser Gly Ile Lys Val Lys Ile Gln Arg Val Asn Asn Ser Ser
            1125            1130            1135

Thr Asn Asp Asn Leu Val Arg Lys Asn Asp Gln Val Tyr Ile Asn Phe
        1140            1145            1150

Val Ala Ser Lys Thr His Leu Phe Pro Leu Tyr Ala Asp Thr Asn Thr
            1155            1160            1165

Thr Asn Lys Glu Lys Thr Ile Lys Ser Ser Ser Gly Asn Arg Phe
        1170            1175            1180

Asn Gln Val Val Val Met Asn Ser Val Gly Asn Asn Cys Thr Met Asn
1185            1190            1195            1200

Phe Lys Asn Asn Asn Gly Asn Ile Gly Met Leu Gly Phe Lys Asp
            1205            1210            1215

Asn Thr Leu Val Ala Ser Thr Trp Tyr Tyr Thr His Met Arg Asp Asn
        1220            1225            1230

Thr Asn Ser Asn Gly Cys Phe Trp Asn Phe Ile Ser Glu Glu His Gly
            1235            1240            1245

Trp Gln Glu Lys
    1250

<210> SEQ ID NO 17
<211> LENGTH: 1252
<212> TYPE: PRT
<213> ORGANISM: Clostridium botulinum E3

<400> SEQUENCE: 17

Met Pro Lys Ile Asn Ser Phe Asn Tyr Asn Asp Pro Val Asn Asp Arg
 1               5              10              15

Thr Ile Leu Tyr Ile Lys Pro Gly Gly Cys Gln Glu Phe Tyr Lys Ser
            20              25              30

Phe Asn Ile Met Lys Asn Ile Trp Ile Ile Pro Glu Arg Asn Val Ile
        35              40              45

Gly Thr Thr Pro Gln Asp Phe His Pro Pro Thr Ser Leu Lys Asn Gly
    50              55              60

Asp Ser Tyr Tyr Asp Pro Asn Tyr Leu Gln Ser Asp Glu Glu Lys
65              70              75              80

Asp Arg Phe Leu Lys Ile Val Thr Lys Ile Phe Asn Arg Ile Asn Asn
            85              90              95

Asn Leu Ser Gly Gly Ile Leu Leu Glu Glu Leu Ser Lys Ala Asn Pro
```

```
                100             105             110
Tyr Leu Gly Asn Asp Asn Thr Pro Asp Asn Gln Phe His Ile Gly Asp
            115             120             125

Ala Ser Ala Val Glu Ile Lys Phe Ser Asn Gly Ser Gln His Ile Leu
130             135             140

Leu Pro Asn Val Ile Ile Met Gly Ala Glu Pro Asp Leu Phe Glu Thr
145             150             155             160

Asn Ser Ser Asn Ile Ser Leu Arg Asn Asn Tyr Met Pro Ser Asn His
            165             170             175

Gly Phe Gly Ser Ile Ala Ile Val Thr Phe Ser Pro Glu Tyr Ser Phe
            180             185             190

Arg Phe Asn Asp Asn Ser Ile Asn Glu Phe Ile Gln Asp Pro Ala Leu
            195             200             205

Thr Leu Met His Glu Leu Ile His Ser Leu His Gly Leu Tyr Gly Ala
            210             215             220

Lys Gly Ile Thr Thr Cys Ile Ile Thr Gln Gln Gln Asn Pro Leu
225             230             235             240

Ile Thr Asn Arg Lys Gly Ile Asn Ile Glu Glu Phe Leu Thr Phe Gly
            245             250             255

Gly Asn Asp Leu Asn Ile Ile Thr Val Ala Gln Tyr Asn Asp Ile Tyr
            260             265             270

Thr Asn Leu Leu Asn Asp Tyr Arg Lys Ile Ala Ser Lys Leu Ser Lys
            275             280             285

Val Gln Val Ser Asn Pro Gln Leu Asn Pro Tyr Lys Asp Ile Phe Gln
            290             295             300

Glu Lys Tyr Gly Leu Asp Lys Asp Ala Ser Gly Ile Tyr Ser Val Asn
305             310             315             320

Ile Asn Lys Phe Asp Asp Ile Leu Lys Lys Leu Tyr Ser Phe Thr Glu
            325             330             335

Phe Asp Leu Ala Thr Lys Phe Gln Val Lys Cys Arg Glu Thr Tyr Ile
            340             345             350

Gly Gln Tyr Lys Tyr Phe Lys Leu Ser Asn Leu Leu Asn Asp Ser Ile
            355             360             365

Tyr Asn Ile Ser Glu Gly Tyr Asn Ile Asn Asn Leu Lys Val Asn Phe
            370             375             380

Arg Gly Gln Asn Ala Asn Leu Asn Pro Arg Ile Ile Lys Pro Ile Thr
385             390             395             400

Gly Arg Gly Leu Val Lys Lys Ile Ile Arg Phe Cys Lys Asn Ile Val
            405             410             415

Ser Val Lys Gly Ile Arg Lys Ser Ile Cys Ile Glu Ile Asn Asn Gly
            420             425             430

Glu Leu Phe Phe Val Ala Ser Glu Asn Ser Tyr Asn Asp Asp Asn Ile
            435             440             445

Asn Thr Pro Lys Glu Ile Asp Asp Thr Val Thr Ser Asn Asn Asn Tyr
            450             455             460

Glu Asn Asp Leu Asp Gln Val Ile Leu Asn Phe Asn Ser Glu Ser Ala
465             470             475             480

Pro Gly Leu Ser Asp Glu Lys Leu Asn Leu Thr Ile Gln Asn Asp Ala
            485             490             495

Tyr Ile Pro Lys Tyr Asp Ser Asn Gly Thr Ser Asp Ile Glu Gln His
            500             505             510

Asp Val Asn Glu Leu Asn Val Phe Phe Tyr Leu Asp Ala Gln Lys Val
            515             520             525
```

```
Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960
```

```
Trp Thr Leu Gln Asp Asn Ala Gly Ile Asn Gln Lys Leu Ala Phe Asn
                965                 970                 975
Tyr Gly Asn Ala Asn Gly Ile Ser Asp Tyr Ile Asn Lys Trp Ile Phe
            980                 985                 990
Val Thr Ile Thr Asn Asp Arg Leu Gly Asp Ser Lys Leu Tyr Ile Asn
                995                1000                1005
Gly Asn Leu Ile Asp Gln Lys Ser Ile Leu Asn Leu Gly Asn Ile His
           1010                1015                1020
Val Ser Asp Asn Ile Leu Phe Lys Ile Val Asn Cys Ser Tyr Thr Arg
1025                1030                1035                1040
Tyr Ile Gly Ile Arg Tyr Phe Asn Ile Phe Asp Lys Glu Leu Asp Glu
                1045                1050                1055
Thr Glu Ile Gln Thr Leu Tyr Ser Asn Glu Pro Asn Thr Asn Ile Leu
                1060                1065                1070
Lys Asp Phe Trp Gly Asn Tyr Leu Leu Tyr Asp Lys Glu Tyr Tyr Leu
                1075                1080                1085
Leu Asn Val Leu Lys Pro Asn Asn Phe Ile Asp Arg Arg Lys Asp Ser
           1090                1095                1100
Thr Leu Ser Ile Asn Asn Ile Arg Ser Thr Ile Leu Leu Ala Asn Arg
1105                1110                1115                1120
Leu Tyr Ser Gly Ile Lys Val Lys Ile Gln Arg Val Asn Asn Ser Ser
                1125                1130                1135
Thr Asn Asp Asn Leu Val Arg Lys Asn Asp Gln Val Tyr Ile Asn Phe
                1140                1145                1150
Val Ala Ser Lys Thr His Leu Phe Pro Leu Tyr Ala Asp Thr Ala Thr
                1155                1160                1165
Thr Asn Lys Glu Lys Thr Ile Lys Ile Ser Ser Ser Gly Asn Arg Phe
                1170                1175                1180
Asn Gln Val Val Val Met Asn Ser Val Gly Asn Asn Cys Thr Met Asn
1185                1190                1195                1200
Phe Lys Asn Asn Asn Gly Asn Asn Ile Gly Leu Leu Gly Phe Lys Ala
                1205                1210                1215
Asp Thr Val Val Ala Ser Thr Trp Tyr Tyr Thr His Met Arg Asp His
                1220                1225                1230
Thr Asn Ser Asn Gly Cys Phe Trp Asn Phe Ile Ser Glu Glu His Gly
                1235                1240                1245
Trp Gln Glu Lys
    1250

<210> SEQ ID NO 18
<211> LENGTH: 1274
<212> TYPE: PRT
<213> ORGANISM: Clostridium botulinum F1

<400> SEQUENCE: 18

Met Pro Val Ala Ile Asn Ser Phe Asn Tyr Asn Asp Pro Val Asn Asp
 1               5                  10                  15
Asp Thr Ile Leu Tyr Met Gln Ile Pro Tyr Glu Glu Lys Ser Lys Lys
            20                  25                  30
Tyr Tyr Lys Ala Phe Glu Ile Met Arg Asn Val Trp Ile Ile Pro Glu
        35                  40                  45
Arg Asn Thr Ile Gly Thr Asn Pro Ser Asp Phe Asp Pro Pro Ala Ser
    50                  55                  60
Leu Lys Asn Gly Ser Ser Ala Tyr Tyr Asp Pro Asn Tyr Leu Thr Thr
65                  70                  75                  80
```

```
Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
```

```
                    500                 505                 510
Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
            565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
            595                 600                 605

Ser Thr Val Asp Lys Ile Ala Asp Ile Ser Leu Ile Val Pro Tyr Val
        610                 615                 620

Gly Leu Ala Leu Asn Ile Ile Glu Ala Glu Lys Gly Asn Phe Glu
625                 630                 635                 640

Glu Ala Phe Glu Leu Leu Gly Val Gly Ile Leu Leu Glu Phe Val Pro
            645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
        675                 680                 685

Leu Ile Glu Arg Glu Ala Lys Trp Lys Glu Ile Tyr Ser Trp Ile Val
        690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Leu Asn Lys Lys
            755                 760                 765

Val Ser Leu Ala Met Lys Asn Ile Glu Arg Phe Met Thr Glu Ser Ser
770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
                820                 825                 830

Val Thr Ser Thr Leu Asn Ser Ser Ile Pro Phe Glu Leu Ser Ser Tyr
        835                 840                 845

Thr Asn Asp Lys Ile Leu Ile Ile Tyr Phe Asn Arg Leu Tyr Lys Lys
        850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
            885                 890                 895

Tyr Ile Tyr Ser Thr Asn Arg Asn Gln Phe Gly Ile Tyr Asn Ser Arg
                900                 905                 910

Leu Ser Glu Val Asn Ile Ala Gln Asn Asn Asp Ile Ile Tyr Asn Ser
            915                 920                 925
```

Arg Tyr Gln Asn Phe Ser Ile Ser Phe Trp Val Arg Ile Pro Lys His
            930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
            980                 985                 990

Leu Ile Phe Arg Tyr Glu Glu Leu Asn Arg Ile Ser Asn Tyr Ile Asn
        995                 1000                1005

Lys Trp Ile Phe Val Thr Ile Thr Asn Asn Arg Leu Gly Asn Ser Arg
    1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                1045                1050                1055

Asp Asp Glu Thr Tyr Val Gly Ile Arg Tyr Phe Lys Val Phe Asn Thr
            1060                1065                1070

Glu Leu Asp Lys Thr Glu Ile Glu Thr Leu Tyr Ser Asn Glu Pro Asp
        1075                1080                1085

Pro Ser Ile Leu Lys Asn Tyr Trp Gly Asn Tyr Leu Leu Tyr Asn Lys
    1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
                1125                1130                1135

Ser Val Phe Leu Asn Tyr Lys Leu Tyr Glu Gly Val Glu Val Ile Ile
            1140                1145                1150

Arg Lys Asn Gly Pro Ile Asp Ile Ser Asn Thr Asp Asn Phe Val Arg
        1155                1160                1165

Lys Asn Asp Leu Ala Tyr Ile Asn Val Val Asp Arg Gly Val Glu Tyr
    1170                1175                1180

Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
                1205                1210                1215

Gly Asn Asn Cys Thr Met Asn Phe Gln Asn Asn Asn Gly Ser Asn Ile
            1220                1225                1230

Gly Leu Leu Gly Phe His Ser Asn Asn Leu Val Ala Ser Ser Trp Tyr
        1235                1240                1245

Tyr Asn Asn Ile Arg Arg Asn Thr Ser Ser Asn Gly Cys Phe Trp Ser
    1250                1255                1260

Ser Ile Ser Lys Glu Asn Gly Trp Lys Glu
1265                1270

<210> SEQ ID NO 19
<211> LENGTH: 1280
<212> TYPE: PRT
<213> ORGANISM: Clostridium botulinum F2

<400> SEQUENCE: 19

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

```
Tyr Tyr Lys Ala Phe Glu Ile Met Pro Asn Val Trp Ile Met Pro Glu
             35                  40                  45

Arg Asp Thr Ile Gly Thr Lys Pro Asp Glu Phe Gln Val Pro Asp Ser
 50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Met Ile Lys Leu Phe Asn
                 85                  90                  95

Arg Ile Asn Ser Asn Pro Thr Gly Lys Val Leu Leu Glu Glu Val Ser
                100                 105                 110

Asn Ala Arg Pro Tyr Leu Gly Asp Asp Thr Leu Ile Asn Glu Phe
            115                 120                 125

Leu Pro Val Asn Val Thr Thr Ser Val Asn Ile Lys Phe Ser Thr Asp
130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
            195                 200                 205

Gly Asn His Asn Ser Thr Glu Ser Phe Ile Ala Asp Pro Ala Ile Ser
210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
            275                 280                 285

Asp Leu Leu Ala Asn Tyr Glu Lys Ile Ala Thr Arg Leu Arg Glu Val
290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
            355                 360                 365

Phe Ile Lys Tyr Gly Phe Val Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
            435                 440                 445

Asn Asn Arg Glu Leu Phe Phe Val Ala Ser Glu Ser Tyr Asn Glu
450                 455                 460
```

```
Ser Asp Ile Asn Thr Pro Lys Glu Ile Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Asn Arg Thr Leu Asn Thr Leu Val Gln
                500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
                580                 585                 590

Asp Trp Ile Ser Lys Val Ile Arg Asp Phe Thr Thr Glu Ala Thr Gln
            595                 600                 605

Lys Ser Thr Val Asp Lys Ile Ala Asp Ile Ser Leu Ile Val Pro Tyr
610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
                645                 650                 655

Pro Glu Leu Thr Ile Pro Val Ile Leu Val Phe Thr Ile Lys Ser Tyr
                660                 665                 670

Ile Asp Ser Tyr Glu Asn Lys Asn Lys Ala Ile Lys Ala Ile Asn Asn
            675                 680                 685

Ser Leu Ile Glu Arg Glu Ala Lys Trp Lys Glu Ile Tyr Ser Trp Ile
            690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
                740                 745                 750

Leu Glu Ser Lys Tyr Asn Ile Asn Asn Ile Glu Glu Glu Leu Asn Lys
            755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
                805                 810                 815

Leu Tyr His Lys Leu Ile Leu Gly Glu Gln Thr Lys Glu Leu Ile Asp
            820                 825                 830

Leu Val Thr Ser Thr Leu Asn Ser Ser Ile Pro Phe Glu Leu Ser Ser
            835                 840                 845

Tyr Thr Asn Asp Lys Ile Leu Ile Ile Tyr Phe Asn Arg Leu Tyr Lys
            850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
```

```
                885                 890                 895
Val Tyr Ile Tyr Ser Thr Asn Arg Asn Gln Phe Gly Ile Tyr Ser Gly
            900                 905                 910

Arg Leu Ser Glu Val Asn Ile Ala Gln Asn Asn Asp Ile Ile Tyr Asn
            915                 920                 925

Ser Arg Tyr Gln Asn Phe Ser Ile Ser Phe Trp Val Thr Ile Pro Lys
            930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
            980                 985                 990

Lys Leu Ile Phe Arg Tyr Glu Glu Leu Ala Ser Ile Ser Asp Tyr Ile
            995                 1000                1005

Asn Lys Trp Ile Phe Val Thr Ile Thr Asn Asn Arg Leu Gly Asn Ser
            1010                1015                1020

Arg Ile Tyr Ile Asn Gly Asn Leu Ile Val Glu Lys Ser Ile Ser Asn
1025                1030                1035                1040

Leu Gly Asp Ile His Val Ser Asp Asn Ile Leu Phe Lys Ile Val Gly
                1045                1050                1055

Cys Asp Asp Glu Thr Tyr Val Gly Ile Arg Tyr Phe Lys Val Phe Asn
            1060                1065                1070

Thr Glu Leu Asp Lys Thr Glu Ile Glu Thr Leu Tyr Ser Asn Glu Pro
            1075                1080                1085

Asp Pro Ser Ile Leu Lys Asp Tyr Trp Gly Asn Tyr Leu Leu Tyr Asn
            1090                1095                1100

Lys Lys Tyr Tyr Leu Phe Asn Leu Leu Arg Lys Asp Lys Tyr Ile Thr
1105                1110                1115                1120

Arg Asn Ser Gly Ile Leu Asn Ile Asn Gln Gln Arg Gly Val Thr Gly
                1125                1130                1135

Gly Ile Ser Val Phe Leu Asn Tyr Lys Leu Tyr Glu Gly Val Glu Val
            1140                1145                1150

Ile Ile Arg Lys Asn Ala Pro Ile Asp Ile Ser Asn Thr Asp Asn Phe
            1155                1160                1165

Val Arg Lys Asn Asp Leu Ala Tyr Ile Asn Val Val Asp His Gly Val
            1170                1175                1180

Glu Tyr Arg Leu Tyr Ala Asp Ile Ser Ile Thr Lys Ser Glu Lys Ile
1185                1190                1195                1200

Ile Lys Leu Ile Arg Thr Ser Asn Pro Asn Asp Ser Leu Gly Gln Ile
                1205                1210                1215

Ile Val Met Asp Ser Ile Gly Asn Asn Cys Thr Met Asn Phe Gln Asn
            1220                1225                1230

Asn Asp Gly Ser Asn Ile Gly Leu Leu Gly Phe His Ser Asp Asp Leu
            1235                1240                1245

Val Ala Ser Ser Trp Tyr Tyr Asn His Ile Arg Arg Asn Thr Ser Ser
            1250                1255                1260

Asn Gly Cys Phe Trp Ser Phe Ile Ser Lys Glu His Gly Trp Lys Glu
1265                1270                1275                1280

<210> SEQ ID NO 20
<211> LENGTH: 1278
<212> TYPE: PRT
<213> ORGANISM: Clostridium botulinum F3
```

<400> SEQUENCE: 20

```
Met Pro Val Val Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415
```

-continued

```
Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
            435                 440                 445

Asn Asn Arg Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
                500                 505                 510

Asp Asp Ser Tyr Val Pro Arg Tyr Asp Ser Asn Gly Thr Ser Glu Ile
            515                 520                 525

Glu Glu His Asn Val Val Asp Leu Asn Val Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
            580                 585                 590

Ser Trp Ile Asn Gln Val Ile Arg Asp Phe Thr Thr Glu Ala Thr Gln
            595                 600                 605

Lys Ser Thr Phe Asp Lys Ile Ala Asp Ile Ser Leu Val Val Pro Tyr
610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
            660                 665                 670

Ile Gly Ser Ser Glu Asn Lys Asn Lys Ile Ile Lys Ala Ile Asn Asn
            675                 680                 685

Ser Leu Met Glu Arg Glu Thr Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
            740                 745                 750

Leu Glu Ser Glu Tyr Asn Ile Asn Asn Ile Arg Glu Glu Leu Asn Lys
            755                 760                 765

Lys Val Ser Leu Ala Met Glu Asn Ile Glu Arg Phe Ile Thr Glu Ser
770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
                805                 810                 815

Ser Glu His Arg Ser Ile Leu Gly Asn Ser Val Gln Glu Leu Asn Asp
            820                 825                 830

Leu Val Thr Ser Thr Leu Asn Asn Ser Ile Pro Phe Glu Leu Ser Ser
            835                 840                 845
```

```
Tyr Thr Asn Asp Lys Ile Leu Ile Leu Tyr Phe Asn Lys Leu Tyr Lys
    850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
                885                 890                 895

Val Tyr Ile Tyr Ser Thr Asn Arg Asn Gln Phe Gly Ile Tyr Ser Ser
                900                 905                 910

Lys Pro Ser Glu Val Asn Ile Ala Gln Asn Asn Asp Ile Ile Tyr Asn
                915                 920                 925

Gly Arg Tyr Gln Asn Phe Ser Ile Ser Phe Trp Val Arg Ile Pro Lys
                930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
                980                 985                 990

Phe Asn Tyr Thr Gln Met Ile Ser Ile Ser Asp Tyr Ile Asn Lys Trp
                995                 1000                1005

Ile Phe Val Thr Ile Thr Asn Asn Arg Leu Gly Asn Ser Arg Ile Tyr
    1010                1015                1020

Ile Asn Gly Asn Leu Ile Asp Glu Lys Ser Ile Ser Asn Leu Gly Asp
1025                1030                1035                1040

Ile His Val Ser Asp Asn Ile Leu Phe Lys Ile Val Gly Cys Asn Asp
                1045                1050                1055

Thr Arg Tyr Val Gly Ile Arg Tyr Phe Lys Val Phe Asp Thr Glu Leu
                1060                1065                1070

Gly Lys Thr Glu Ile Glu Thr Leu Tyr Ser Asp Glu Pro Asp Pro Ser
                1075                1080                1085

Ile Leu Lys Asp Phe Trp Gly Asn Tyr Leu Leu Tyr Asn Lys Arg Tyr
                1090                1095                1100

Tyr Leu Leu Asn Leu Leu Arg Thr Asp Lys Ser Ile Thr Gln Asn Ser
1105                1110                1115                1120

Asn Phe Leu Asn Ile Asn Gln Gln Arg Gly Val Tyr Gln Lys Pro Asn
                1125                1130                1135

Ile Phe Ser Asn Thr Arg Leu Tyr Thr Gly Val Glu Val Ile Ile Arg
                1140                1145                1150

Lys Asn Gly Ser Thr Asp Ile Ser Asn Thr Asp Asn Phe Val Arg Lys
                1155                1160                1165

Asn Asp Leu Ala Tyr Ile Asn Val Val Asp Arg Asp Val Glu Tyr Arg
                1170                1175                1180

Leu Tyr Ala Asp Ile Ser Ile Ala Lys Pro Glu Lys Ile Ile Lys Leu
1185                1190                1195                1200

Ile Arg Thr Ser Asn Ser Asn Asn Ser Leu Gly Gln Ile Ile Val Met
                1205                1210                1215

Asp Ser Ile Gly Asn Asn Cys Thr Met Asn Phe Gln Asn Asn Asn Gly
                1220                1225                1230

Gly Asn Ile Gly Leu Leu Gly Phe His Ser Asn Leu Val Ala Ser
                1235                1240                1245

Ser Trp Tyr Tyr Asn Asn Ile Arg Lys Asn Thr Ser Ser Asn Gly Cys
    1250                1255                1260

Phe Trp Ser Phe Ile Ser Lys Glu His Gly Trp Gln Glu Asn
```

<210> SEQ ID NO 21
<211> LENGTH: 1297
<212> TYPE: PRT
<213> ORGANISM: Clostridium botulinum G
<220> FEATURE:
<221> NAME/KEY: VARIANT
<222> LOCATION: 7
<223> OTHER INFORMATION: Identity of Xaa at position 7 is unknown

<400> SEQUENCE: 21

```
Met Pro Val Asn Ile Lys Xaa Phe Asn Tyr Asn Asp Pro Ile Asn Asn
  1               5                  10                  15

Asp Asp Ile Ile Met Met Glu Pro Phe Asn Asp Pro Gly Pro Gly Thr
             20                  25                  30

Tyr Tyr Lys Ala Phe Arg Ile Ile Asp Arg Ile Trp Ile Val Pro Glu
         35                  40                  45

Arg Phe Thr Tyr Gly Phe Gln Pro Asp Gln Phe Asn Ala Ser Thr Gly
     50                  55                  60

Val Phe Ser Lys Asp Val Tyr Glu Tyr Tyr Asp Pro Thr Tyr Leu Lys
 65                  70                  75                  80

Thr Asp Ala Glu Lys Asp Lys Phe Leu Lys Thr Met Ile Lys Leu Phe
                 85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350
```

```
Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Ile Ser Leu Glu His Leu Val Ile Tyr Arg
                420                 425                 430

Ile Ala Met Cys Lys Pro Val Met Tyr Lys Asn Thr Gly Lys Ser Glu
                435                 440                 445

Gln Cys Ile Ile Val Asn Asn Glu Asp Leu Phe Phe Ile Ala Asn Lys
450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
                515                 520                 525

Gln Ser Ala Leu Lys Lys Ile Phe Val Asp Gly Asp Ser Leu Phe Glu
530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
                580                 585                 590

Ser Leu Phe Val Asn Trp Val Lys Gly Val Ile Asp Asp Phe Thr Ser
                595                 600                 605

Glu Ser Thr Gln Lys Ser Thr Ile Asp Lys Val Ser Asp Val Ser Ile
610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
                660                 665                 670

Leu Glu Ser Tyr Val Gly Asn Lys Gly His Ile Ile Met Thr Ile Ser
                675                 680                 685

Asn Ala Leu Lys Lys Arg Asp Gln Lys Trp Thr Asp Met Tyr Gly Leu
                690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750

Asn Ile Asn Ile Asp Phe Asn Asp Ile Asp Phe Lys Leu Asn Gln Ser
                755                 760                 765

Ile Asn Leu Ala Ile Asn Asn Ile Asp Asp Phe Ile Asn Gln Cys Ser
770                 775                 780
```

```
Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
                900                 905                 910

Asn Ser Asn Ile Thr Ala His Gln Ser Lys Phe Val Val Tyr Asp Ser
            915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
                980                 985                 990

Phe Phe Glu Tyr Ser Ile Lys Asp Asn Ile Ser Asp Tyr Ile Asn Lys
            995                 1000                1005

Trp Phe Ser Ile Thr Ile Thr Asn Asp Arg Leu Gly Asn Ala Asn Ile
    1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
                1045                1050                1055

Asp Thr Thr Lys Phe Val Trp Ile Lys Asp Phe Asn Ile Phe Gly Arg
                1060                1065                1070

Glu Leu Asn Ala Thr Glu Val Ser Ser Leu Tyr Trp Ile Gln Ser Ser
            1075                1080                1085

Thr Asn Thr Leu Lys Asp Phe Trp Gly Asn Pro Leu Arg Tyr Asp Thr
    1090                1095                1100

Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
                1125                1130                1135

Asn Ala Ala Ile Asn Tyr Gln Asn Leu Tyr Leu Gly Leu Arg Phe Ile
                1140                1145                1150

Ile Lys Lys Ala Ser Asn Ser Arg Asn Ile Asn Asn Asp Asn Ile Val
            1155                1160                1165

Arg Glu Gly Asp Tyr Ile Tyr Leu Asn Ile Asp Asn Ile Ser Asp Glu
    1170                1175                1180

Ser Tyr Arg Val Tyr Val Leu Val Asn Ser Lys Glu Ile Gln Thr Gln
1185                1190                1195                1200

Leu Phe Leu Ala Pro Ile Asn Asp Asp Pro Thr Phe Tyr Asp Val Leu
```

-continued

```
                 1205                 1210                 1215
Gln Ile Lys Lys Tyr Tyr Glu Lys Thr Thr Tyr Asn Cys Gln Ile Leu
             1220                 1225                 1230

Cys Glu Lys Asp Thr Lys Thr Phe Gly Leu Phe Gly Ile Gly Lys Phe
             1235                 1240                 1245

Val Lys Asp Tyr Gly Tyr Val Trp Asp Thr Tyr Asp Asn Tyr Phe Cys
             1250                 1255                 1260

Ile Ser Gln Trp Tyr Leu Arg Arg Ile Ser Glu Asn Ile Asn Lys Leu
1265                 1270                 1275                 1280

Arg Leu Gly Cys Asn Trp Gln Phe Ile Pro Val Asp Glu Gly Trp Thr
             1285                 1290                 1295

Glu

<210> SEQ ID NO 22
<211> LENGTH: 1315
<212> TYPE: PRT
<213> ORGANISM: Clostridium tetani

<400> SEQUENCE: 22

Met Pro Ile Thr Ile Asn Asn Phe Arg Tyr Ser Asp Pro Val Asn Asn
  1               5                  10                  15

Asp Thr Ile Ile Met Met Glu Pro Pro Tyr Cys Lys Gly Leu Asp Ile
                 20                  25                  30

Tyr Tyr Lys Ala Phe Lys Ile Thr Asp Arg Ile Trp Ile Val Pro Glu
             35                  40                  45

Arg Tyr Glu Phe Gly Thr Lys Pro Glu Asp Phe Asn Pro Pro Ser Ser
 50                  55                  60

Leu Ile Glu Gly Ala Ser Glu Tyr Tyr Asp Pro Asn Tyr Leu Arg Thr
 65                  70                  75                  80

Asp Ser Asp Lys Asp Arg Phe Leu Gln Thr Met Val Lys Leu Phe Asn
                 85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
             115                 120                 125

Asp Thr Asn Ser Asn Ser Val Ser Phe Asn Leu Leu Glu Gln Asp Pro
130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
             180                 185                 190

Ile Met Gln Met Ala Phe Cys Pro Glu Tyr Val Pro Thr Phe Asp Asn
             195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
             260                 265                 270

Phe Thr Phe Gly Gly Gln Asp Ala Asn Leu Ile Ser Ile Asp Ile Lys
             275                 280                 285
```

```
Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
```

```
                705                 710                 715                 720
Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
                740                 745                 750

Lys Lys Ile Ile Asp Tyr Glu Tyr Lys Ile Tyr Ser Gly Pro Asp Lys
                755                 760                 765

Glu Gln Ile Ala Asp Glu Ile Asn Asn Leu Lys Asn Lys Leu Glu Glu
                770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
                820                 825                 830

Lys Ala Asn Ser Lys Phe Ile Gly Ile Thr Glu Leu Lys Lys Leu Glu
                835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
                900                 905                 910

Gln Leu Val Pro Gly Ile Asn Gly Lys Ala Ile His Leu Val Asn Asn
                915                 920                 925

Glu Ser Ser Glu Val Ile Val His Lys Ala Met Asp Ile Glu Tyr Asn
                930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
                980                 985                 990

Val Ser Leu Lys Gly Asn Asn Leu Ile Trp Thr Leu Lys Asp Ser Ala
                995                 1000                1005

Gly Glu Val Arg Gln Ile Thr Phe Arg Asp Leu Pro Asp Lys Phe Asn
                1010                1015                1020

Ala Tyr Leu Ala Asn Lys Trp Val Phe Ile Thr Ile Thr Asn Asp Arg
1025                1030                1035                1040

Leu Ser Ser Ala Asn Leu Tyr Ile Asn Gly Val Leu Met Gly Ser Ala
                1045                1050                1055

Glu Ile Thr Gly Leu Gly Ala Ile Arg Glu Asp Asn Asn Ile Thr Leu
                1060                1065                1070

Lys Leu Asp Arg Cys Asn Asn Asn Asn Gln Tyr Val Ser Ile Asp Lys
                1075                1080                1085

Phe Arg Ile Phe Cys Lys Ala Leu Asn Pro Lys Glu Ile Glu Lys Leu
                1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
                1125                1130                1135
```

```
Ser Lys Asp Val Gln Leu Lys Asn Ile Thr Asp Tyr Met Tyr Leu Thr
        1140                1145                1150

Asn Ala Pro Ser Tyr Thr Asn Gly Lys Leu Asn Ile Tyr Tyr Arg Arg
        1155                1160                1165

Leu Tyr Asn Gly Leu Lys Phe Ile Ile Lys Arg Tyr Thr Pro Asn Asn
        1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
        1205                1210                1215

Ala Phe Asn Asn Leu Asp Arg Ile Leu Arg Val Gly Tyr Asn Ala Pro
        1220                1225                1230

Gly Ile Pro Leu Tyr Lys Lys Met Glu Ala Val Lys Leu Arg Asp Leu
        1235                1240                1245

Lys Thr Tyr Ser Val Gln Leu Lys Leu Tyr Asp Asp Lys Asn Ala Ser
        1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
        1285                1290                1295

Lys Ile Leu Gly Cys Asp Trp Tyr Phe Val Pro Thr Asp Glu Gly Trp
        1300                1305                1310

Thr Asn Asp
        1315

<210> SEQ ID NO 23
<211> LENGTH: 1268
<212> TYPE: PRT
<213> ORGANISM: Clostridium baratii

<400> SEQUENCE: 23

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190
```

```
Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
                260                 265                 270

Ser Thr Asn Gln Lys Ile Tyr Val Ile Leu Leu Ser Asn Tyr Thr Ala
        275                 280                 285

Ile Ala Ser Arg Leu Ser Gln Val Asn Arg Asn Asn Ser Ala Leu Asn
290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
                340                 345                 350

Gln Val Lys Asn Arg Ser Asn Tyr Leu Phe His Phe Lys Pro Phe Arg
        355                 360                 365

Leu Leu Asp Leu Leu Asp Asp Asn Ile Tyr Ser Ile Ser Glu Gly Phe
370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Gly Thr Lys Asn
                420                 425                 430

Ser Leu Cys Ile Lys Val Asn Asn Arg Asp Leu Phe Phe Val Ala Ser
        435                 440                 445

Glu Ser Ser Tyr Asn Glu Asn Gly Ile Asn Ser Pro Lys Glu Ile Asp
450                 455                 460

Asp Thr Thr Ile Thr Asn Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Thr Thr Ala Gln Asn Asp Ser Tyr Val Pro Lys Tyr Asp Ser
                500                 505                 510

Asn Gly Thr Ser Glu Ile Lys Glu Tyr Thr Val Asp Lys Leu Asn Val
        515                 520                 525

Phe Phe Tyr Leu Tyr Ala Gln Lys Ala Pro Glu Gly Glu Ser Ala Ile
530                 535                 540

Ser Leu Thr Ser Ser Val Asn Thr Ala Leu Leu Asp Ala Ser Lys Val
545                 550                 555                 560

Tyr Thr Phe Phe Ser Ser Asp Phe Ile Asn Thr Val Asn Lys Pro Val
                565                 570                 575

Gln Ala Ala Leu Phe Ile Ser Trp Ile Gln Gln Val Ile Asn Asp Phe
                580                 585                 590

Thr Thr Glu Ala Thr Gln Lys Ser Thr Ile Asp Lys Ile Ala Asp Ile
        595                 600                 605

Ser Leu Ile Val Pro Tyr Val Gly Leu Ala Leu Asn Ile Gly Asn Glu
610                 615                 620
```

```
Val Gln Lys Gly Asn Phe Lys Glu Ala Ile Glu Leu Leu Gly Ala Gly
625                 630                 635                 640

Ile Leu Leu Glu Phe Val Pro Glu Leu Leu Ile Pro Thr Ile Leu Val
                645                 650                 655

Phe Thr Ile Lys Ser Phe Ile Asn Ser Asp Asp Ser Lys Asn Lys Ile
            660                 665                 670

Ile Lys Ala Ile Asn Asn Ala Leu Arg Glu Arg Glu Leu Lys Trp Lys
        675                 680                 685

Glu Val Tyr Ser Trp Ile Val Ser Asn Trp Leu Thr Arg Ile Asn Thr
    690                 695                 700

Gln Phe Asn Lys Arg Lys Glu Gln Met Tyr Gln Ala Leu Gln Asn Gln
705                 710                 715                 720

Val Asp Gly Ile Lys Lys Ile Ile Glu Tyr Lys Tyr Asn Asn Tyr Thr
                725                 730                 735

Leu Asp Glu Lys Asn Arg Leu Arg Ala Glu Tyr Asn Ile Tyr Ser Ile
            740                 745                 750

Lys Glu Glu Leu Asn Lys Lys Val Ser Leu Ala Met Gln Asn Ile Asp
        755                 760                 765

Arg Phe Leu Thr Glu Ser Ser Ile Ser Tyr Leu Met Lys Leu Ile Asn
    770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Pro Glu Leu Asn Asn Leu Val Ser Asn Thr Leu Asn Asn Ser
            820                 825                 830

Ile Pro Phe Glu Leu Ser Glu Tyr Thr Asn Asp Lys Ile Leu Ile His
        835                 840                 845

Ile Leu Ile Arg Phe Tyr Lys Arg Ile Asp Ser Ser Ile Leu Asn
    850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
            900                 905                 910

Asn Asn Thr Ile Ile Tyr Asn Ser Arg Tyr Gln Asn Phe Ser Val Ser
        915                 920                 925

Phe Trp Val Arg Ile Pro Lys Tyr Asn Asn Leu Lys Asn Leu Asn Asn
    930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
            980                 985                 990

Ser Asp Tyr Ile Asn Lys Trp Thr Phe Val Thr Ile Thr Asn Asn Arg
        995                 1000                1005

Leu Gly His Ser Lys Leu Tyr Ile Asn Gly Asn Leu Thr Asp Gln Lys
    1010                1015                1020

Ser Ile Leu Asn Leu Gly Asn Ile His Val Asp Asp Asn Ile Leu Phe
1025                1030                1035                1040

Lys Ile Val Gly Cys Asn Asp Thr Arg Tyr Val Gly Ile Arg Tyr Phe
```

```
                    1045                1050                1055
Lys Ile Phe Asn Met Glu Leu Asp Lys Thr Glu Ile Glu Thr Leu Tyr
                1060                1065                1070

His Ser Glu Pro Asp Ser Thr Ile Leu Lys Asp Phe Trp Gly Asn Tyr
                1075                1080                1085

Leu Leu Tyr Asn Lys Lys Tyr Tyr Leu Leu Asn Leu Leu Lys Pro Asn
                1090                1095                1100

Met Ser Val Thr Lys Asn Ser Asp Ile Leu Asn Ile Asn Arg Gln Arg
1105                1110                1115                1120

Gly Ile Tyr Ser Lys Thr Asn Ile Phe Ser Asn Ala Arg Leu Tyr Thr
                1125                1130                1135

Gly Val Glu Val Ile Ile Arg Lys Val Gly Ser Thr Asp Thr Ser Asn
                1140                1145                1150

Thr Asp Asn Phe Val Arg Lys Asn Asp Thr Val Tyr Ile Asn Val Val
                1155                1160                1165

Asp Gly Asn Ser Glu Tyr Gln Leu Tyr Ala Asp Val Ser Thr Ser Ala
                1170                1175                1180

Val Glu Lys Thr Ile Lys Leu Arg Arg Ile Ser Asn Ser Asn Tyr Asn
1185                1190                1195                1200

Ser Asn Gln Met Ile Ile Met Asp Ser Ile Gly Asp Asn Cys Thr Met
                1205                1210                1215

Asn Phe Lys Thr Asn Asn Gly Asn Asp Ile Gly Leu Leu Gly Phe His
                1220                1225                1230

Leu Asn Asn Leu Val Ala Ser Ser Trp Tyr Tyr Lys Asn Ile Arg Asn
                1235                1240                1245

Asn Thr Arg Asn Asn Gly Cys Phe Trp Ser Phe Ile Ser Lys Glu His
                1250                1255                1260

Gly Trp Gln Glu
1265

<210> SEQ ID NO 24
<211> LENGTH: 1251
<212> TYPE: PRT
<213> ORGANISM: Clostridium butyricum 1

<400> SEQUENCE: 24

Met Pro Thr Ile Asn Ser Phe Asn Tyr Asn Asp Pro Val Asn Asn Arg
1               5                   10                  15

Thr Ile Leu Tyr Ile Lys Pro Gly Gly Cys Gln Gln Phe Tyr Lys Ser
                20                  25                  30

Phe Asn Ile Met Lys Asn Ile Trp Ile Ile Pro Glu Arg Asn Val Ile
            35                  40                  45

Gly Thr Ile Pro Gln Asp Phe Leu Pro Pro Thr Ser Leu Lys Asn Gly
        50                  55                  60

Asp Ser Ser Tyr Tyr Asp Pro Asn Tyr Leu Gln Ser Asp Gln Glu Lys
65              70                  75                  80

Asp Lys Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
```

```
                145                 150                 155                 160
Asn Ser Ser Asn Ile Ser Leu Arg Asn Tyr Met Pro Ser Asn His
                    165                 170                 175
Gly Phe Gly Ser Ile Ala Ile Val Thr Phe Ser Pro Glu Tyr Ser Phe
                    180                 185                 190
Arg Phe Lys Asp Asn Ser Met Asn Glu Phe Ile Gln Asp Pro Ala Leu
                    195                 200                 205
Thr Leu Met His Glu Leu Ile His Ser Leu His Gly Leu Tyr Gly Ala
            210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                    245                 250                 255
Gly Thr Asp Leu Asn Ile Ile Thr Ser Ala Gln Ser Asn Asp Ile Tyr
                260                 265                 270
Thr Asn Leu Leu Ala Asp Tyr Lys Lys Ile Ala Ser Lys Leu Ser Lys
            275                 280                 285
Val Gln Val Ser Asn Pro Leu Leu Asn Pro Tyr Lys Asp Val Phe Glu
        290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                    325                 330                 335
Phe Asp Leu Ala Thr Lys Phe Gln Val Lys Cys Arg Gln Thr Tyr Ile
                340                 345                 350
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Asn Asn Leu Lys Val Asn Phe
        370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                    405                 410                 415
Ser Val Lys Gly Ile Arg Lys Ser Ile Cys Ile Glu Ile Asn Asn Gly
                420                 425                 430
Glu Leu Phe Phe Val Ala Ser Glu Asn Ser Tyr Asn Asp Asp Asn Ile
            435                 440                 445
Asn Thr Pro Lys Glu Ile Asp Asp Thr Val Thr Ser Asn Asn Asn Tyr
        450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                    485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
            515                 520                 525
Pro Glu Gly Glu Asn Asn Val Asn Leu Thr Ser Ser Ile Asp Thr Ala
        530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Gly Trp Ile
                    565                 570                 575
```

-continued

```
Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
    595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Leu Lys Ala Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Glu Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ser Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005
```

Gly Asn Leu Ile Asp Lys Lys Ser Ile Leu Asn Leu Gly Asn Ile His
            1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
            1045                1050                1055

Thr Glu Ile Gln Thr Leu Tyr Asn Asn Glu Pro Asn Ala Asn Ile Leu
            1060                1065                1070

Lys Asp Phe Trp Gly Asn Tyr Leu Leu Tyr Asp Lys Glu Tyr Tyr Leu
            1075                1080                1085

Leu Asn Val Leu Lys Pro Asn Asn Phe Ile Asn Arg Arg Thr Asp Ser
            1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
            1125                1130                1135

Thr Asn Asp Asn Leu Val Arg Lys Asn Asp Gln Val Tyr Ile Asn Phe
            1140                1145                1150

Val Ala Ser Lys Thr His Leu Leu Pro Leu Tyr Ala Asp Thr Ala Thr
            1155                1160                1165

Thr Asn Lys Glu Lys Thr Ile Lys Ile Ser Ser Gly Asn Arg Phe
            1170                1175                1180

Asn Gln Val Val Val Met Asn Ser Val Gly Asn Cys Thr Met Asn Phe
1185                1190                1195                1200

Lys Asn Asn Gly Asn Asn Ile Gly Leu Leu Gly Phe Lys Ala Asp
            1205                1210                1215

Thr Val Val Ala Ser Thr Trp Tyr Tyr Thr His Met Arg Asp Asn Thr
            1220                1225                1230

Asn Ser Asn Gly Phe Phe Trp Asn Phe Ile Ser Glu Glu His Gly Trp
            1235                1240                1245

Gln Glu Lys
    1250

<210> SEQ ID NO 25
<211> LENGTH: 1251
<212> TYPE: PRT
<213> ORGANISM: Clostridium butyricum 2

<400> SEQUENCE: 25

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Pro Glu Arg Asn Val Ile
        35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
            115                 120                 125

```
Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
```

```
                545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
                580                 585                 590
Val Asp Lys Ile Ala Asp Ile Ser Ile Val Val Pro Tyr Ile Gly Leu
                595                 600                 605
Ala Leu Asn Ile Gly Asn Glu Ala Gln Lys Gly Asn Phe Lys Asp Ala
                610                 615                 620
Leu Glu Leu Leu Gly Ala Gly Ile Leu Leu Glu Phe Val Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
                675                 680                 685
Trp Met Thr Lys Ile Asn Thr Gln Phe Asn Lys Arg Lys Glu Gln Met
                690                 695                 700
Tyr Gln Ala Leu Gln Asn Gln Val Asn Ala Leu Lys Thr Ile Ile Glu
705                 710                 715                 720
Phe Lys Tyr Asn Ser Tyr Thr Leu Glu Glu Lys Lys Glu Leu Lys Asn
                725                 730                 735
Asn Tyr Asp Ile Glu Gln Ile Glu Asn Glu Leu Asn Gln Lys Val Ser
                740                 745                 750
Ile Ala Met Asn Asn Ile Asp Arg Phe Leu Thr Glu Ser Ser Ile Ser
                755                 760                 765
Tyr Leu Met Lys Leu Ile Asn Glu Val Lys Ile Asn Lys Leu Arg Glu
                770                 775                 780
Tyr Asp Glu Asn Val Lys Thr Tyr Leu Leu Asp Tyr Ile Ile Gln His
785                 790                 795                 800
Gly Ser Ile Leu Gly Glu Ser Gln Gln Glu Leu Asn Ser Met Val Ile
                805                 810                 815
Asp Thr Leu Asn Asn Ser Ile Pro Phe Lys Leu Ser Ser Tyr Thr Asp
                820                 825                 830
Asp Lys Ile Leu Ile Ser Tyr Phe Asn Lys Phe Phe Lys Arg Ile Lys
                835                 840                 845
Ser Ser Ser Val Leu Asn Met Arg Tyr Lys Asn Asp Lys Tyr Val Asp
                850                 855                 860
Thr Ser Gly Tyr Asp Ser Asn Ile Asn Ile Asn Gly Glu Ile Phe Ile
865                 870                 875                 880
Tyr Pro Thr Asn Lys Asn Gln Phe Thr Ile Phe Asn Ser Lys Pro Ser
                885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
                915                 920                 925
Lys Ile Val Asn Ile Asn Asn Glu Tyr Thr Ile Ile Asn Cys Met Arg
                930                 935                 940
Asp Asn Asn Ser Gly Trp Lys Val Ser Leu Asn His Asn Glu Ile Ile
945                 950                 955                 960
Trp Thr Leu Gln Asp Asn Ala Arg Ile Asn Gln Lys Leu Val Phe Lys
                965                 970                 975
```

```
Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
            995                1000                1005

Gly His Leu Ile Asp Gln Lys Ser Ile Leu Asn Leu Gly Asn Ile His
           1010                1015                1020

Val Ser Asp Asn Ile Leu Phe Lys Ile Val Asn Cys Ser Tyr Thr Arg
           1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
           1060                1065                1070

Lys Asp Phe Trp Gly Asn Tyr Leu Leu Tyr Asp Lys Gly Tyr Tyr Leu
           1075                1080                1085

Leu Asn Val Leu Lys Pro Asn Asn Phe Ile Asp Arg Arg Lys Asp Ser
           1090                1095                1100

Thr Leu Ser Ile Asn Asn Ile Arg Ser Thr Ile Leu Leu Ala Asn Arg
           1105                1110                1115                1120

Leu Tyr Ser Gly Ile Lys Val Lys Ile Gln Arg Val Asn Asp Ser Ser
                1125                1130                1135

Thr Asn Asp Arg Phe Val Arg Lys Asn Asp Gln Val Tyr Ile Asn Tyr
           1140                1145                1150

Ile Ser Asn Ser Ser Ser Tyr Ser Leu Tyr Ala Asp Thr Asn Thr Thr
           1155                1160                1165

Asp Lys Glu Lys Thr Ile Lys Ser Ser Ser Gly Asn Arg Phe Asn
           1170                1175                1180

Gln Val Val Met Asn Ser Val Gly Asn Asn Cys Thr Met Asn Phe
1185                1190                1195                1200

Lys Asn Asn Asn Gly Asn Asn Ile Gly Leu Leu Gly Phe Lys Ala Asp
                1205                1210                1215

Thr Val Val Ala Ser Thr Trp Tyr Tyr Thr His Met Arg Asp His Thr
                1220                1225                1230

Asn Ser Asn Gly Cys Phe Trp Asn Phe Ile Ser Glu Glu His Gly Trp
           1235                1240                1245

Gln Glu Lys
    1250

<210> SEQ ID NO 26
<211> LENGTH: 5
<212> TYPE: PRT
<213> ORGANISM: Homo sapiens

<400> SEQUENCE: 26

Tyr Gly Gly Phe Leu
1               5

<210> SEQ ID NO 27
<211> LENGTH: 5
<212> TYPE: PRT
<213> ORGANISM: Homo sapiens

<400> SEQUENCE: 27

Tyr Gly Gly Phe Met
1               5

<210> SEQ ID NO 28
<211> LENGTH: 8
<212> TYPE: PRT
```

```
<213> ORGANISM: Homo sapiens

<400> SEQUENCE: 28

Tyr Gly Gly Phe Met Arg Gly Leu
1               5

<210> SEQ ID NO 29
<211> LENGTH: 7
<212> TYPE: PRT
<213> ORGANISM: Homo sapiens

<400> SEQUENCE: 29

Tyr Gly Gly Phe Met Arg Phe
1               5

<210> SEQ ID NO 30
<211> LENGTH: 22
<212> TYPE: PRT
<213> ORGANISM: Homo sapiens

<400> SEQUENCE: 30

Tyr Gly Gly Phe Met Arg Arg Val Gly Arg Pro Glu Trp Trp Met Asp
1               5                   10                  15

Tyr Gln Lys Arg Tyr Gly
            20

<210> SEQ ID NO 31
<211> LENGTH: 22
<212> TYPE: PRT
<213> ORGANISM: Necturus maculosus

<400> SEQUENCE: 31

Tyr Gly Gly Phe Met Arg Arg Val Gly Arg Pro Glu Trp Trp Leu Asp
1               5                   10                  15

Tyr Gln Lys Arg Tyr Gly
            20

<210> SEQ ID NO 32
<211> LENGTH: 22
<212> TYPE: PRT
<213> ORGANISM: Bombina orientalis

<400> SEQUENCE: 32

Tyr Gly Gly Phe Met Arg Arg Val Gly Arg Pro Glu Trp Trp Gln Asp
1               5                   10                  15

Tyr Gln Lys Arg Tyr Gly
            20

<210> SEQ ID NO 33
<211> LENGTH: 22
<212> TYPE: PRT
<213> ORGANISM: Xenopus laevis

<400> SEQUENCE: 33

Tyr Gly Gly Phe Met Arg Arg Val Gly Arg Pro Glu Trp Trp Glu Asp
1               5                   10                  15

Tyr Gln Lys Arg Tyr Gly
            20

<210> SEQ ID NO 34
<211> LENGTH: 22
<212> TYPE: PRT
<213> ORGANISM: Neoceratodus forsteri
```

-continued

```
<400> SEQUENCE: 34

Tyr Gly Gly Phe Met Arg Arg Val Gly Arg Pro Glu Trp Lys Leu Asp
1               5                   10                  15

Asn Gln Lys Arg Tyr Gly
            20

<210> SEQ ID NO 35
<211> LENGTH: 21
<212> TYPE: PRT
<213> ORGANISM: Danio rerio

<400> SEQUENCE: 35

Tyr Gly Gly Phe Met Arg Arg Val Gly Arg Pro Asp Trp Trp Gln Glu
1               5                   10                  15

Ser Lys Arg Tyr Gly
            20

<210> SEQ ID NO 36
<211> LENGTH: 4
<212> TYPE: PRT
<213> ORGANISM: Homo sapiens

<400> SEQUENCE: 36

Tyr Pro Trp Phe
1

<210> SEQ ID NO 37
<211> LENGTH: 4
<212> TYPE: PRT
<213> ORGANISM: Homo sapiens

<400> SEQUENCE: 37

Tyr Pro Phe Phe
1

<210> SEQ ID NO 38
<211> LENGTH: 16
<212> TYPE: PRT
<213> ORGANISM: Homo sapiens

<400> SEQUENCE: 38

Tyr Gly Gly Phe Met Thr Ser Glu Lys Ser Gln Thr Pro Leu Val Thr
1               5                   10                  15

<210> SEQ ID NO 39
<211> LENGTH: 10
<212> TYPE: PRT
<213> ORGANISM: Homo sapiens

<400> SEQUENCE: 39

Tyr Gly Gly Phe Leu Arg Lys Tyr Pro Lys
1               5                   10

<210> SEQ ID NO 40
<211> LENGTH: 31
<212> TYPE: PRT
<213> ORGANISM: Homo sapiens

<400> SEQUENCE: 40

Tyr Gly Gly Phe Met Thr Ser Glu Lys Ser Gln Thr Pro Leu Val Thr
1               5                   10                  15

Leu Phe Lys Asn Ala Ile Ile Asn Ala Tyr Lys Lys Gly Glu
            20                  25                  30
```

```
<210> SEQ ID NO 41
<211> LENGTH: 31
<212> TYPE: PRT
<213> ORGANISM: Homo sapiens

<400> SEQUENCE: 41

Tyr Gly Gly Phe Met Ser Ser Glu Lys Ser Gln Thr Pro Leu Val Thr
1               5                   10                  15

Leu Phe Lys Asn Ala Ile Ile Lys Asn Ala His Lys Lys Gly Gln
            20                  25                  30

<210> SEQ ID NO 42
<211> LENGTH: 9
<212> TYPE: PRT
<213> ORGANISM: Homo sapiens

<400> SEQUENCE: 42

Tyr Gly Gly Phe Leu Arg Lys Tyr Pro
1               5

<210> SEQ ID NO 43
<211> LENGTH: 16
<212> TYPE: PRT
<213> ORGANISM: Homo sapiens

<400> SEQUENCE: 43

Tyr Gly Gly Phe Met Thr Ser Glu Lys Ser Gln Thr Pro Leu Val Thr
1               5                   10                  15

<210> SEQ ID NO 44
<211> LENGTH: 16
<212> TYPE: PRT
<213> ORGANISM: Homo sapiens

<400> SEQUENCE: 44

Tyr Gly Gly Phe Leu Arg Arg Ile Arg Pro Lys Leu Lys Trp Asp Asn
1               5                   10                  15

<210> SEQ ID NO 45
<211> LENGTH: 13
<212> TYPE: PRT
<213> ORGANISM: Homo sapiens

<400> SEQUENCE: 45

Tyr Gly Gly Phe Leu Arg Arg Ile Arg Pro Lys Leu Lys
1               5                   10

<210> SEQ ID NO 46
<211> LENGTH: 16
<212> TYPE: PRT
<213> ORGANISM: Homo sapiens

<400> SEQUENCE: 46

Gly Gly Phe Leu Arg Arg Ile Arg Pro Lys Leu Lys Trp Asp Asn Gln
1               5                   10                  15

<210> SEQ ID NO 47
<211> LENGTH: 12
<212> TYPE: PRT
<213> ORGANISM: Homo sapiens

<400> SEQUENCE: 47

Gly Gly Phe Leu Arg Arg Ile Arg Pro Lys Leu Lys
1               5                   10
```

<210> SEQ ID NO 48
<211> LENGTH: 17
<212> TYPE: PRT
<213> ORGANISM: Xenopus laevis

<400> SEQUENCE: 48

Tyr Gly Gly Phe Leu Arg Arg Ile Arg Pro Lys Leu Arg Trp Asp Asn
1               5                   10                  15

Gln

<210> SEQ ID NO 49
<211> LENGTH: 17
<212> TYPE: PRT
<213> ORGANISM: Xenopus laevis

<400> SEQUENCE: 49

Tyr Gly Gly Phe Leu Arg Arg Ile Arg Pro Arg Leu Arg Trp Asp Asn
1               5                   10                  15

Gln

<210> SEQ ID NO 50
<211> LENGTH: 17
<212> TYPE: PRT
<213> ORGANISM: Protopterus annectens

<400> SEQUENCE: 50

Tyr Gly Gly Phe Met Arg Arg Ile Arg Pro Lys Ile Arg Trp Asp Asn
1               5                   10                  15

Gln

<210> SEQ ID NO 51
<211> LENGTH: 17
<212> TYPE: PRT
<213> ORGANISM: Danio rerio

<400> SEQUENCE: 51

Tyr Gly Gly Phe Met Arg Arg Ile Arg Pro Lys Leu Arg Trp Asp Asn
1               5                   10                  15

Gln

<210> SEQ ID NO 52
<211> LENGTH: 17
<212> TYPE: PRT
<213> ORGANISM: Anguilla rostrata

<400> SEQUENCE: 52

Tyr Gly Gly Phe Met Arg Arg Ile Arg Pro Lys Leu Lys Trp Asp Ser
1               5                   10                  15

Gln

<210> SEQ ID NO 53
<211> LENGTH: 29
<212> TYPE: PRT
<213> ORGANISM: Homo sapiens

<400> SEQUENCE: 53

Tyr Gly Gly Phe Leu Arg Arg Gln Phe Lys Val Val Thr Arg Ser Gln
1               5                   10                  15

Glu Asp Pro Asn Ala Tyr Ser Gly Glu Leu Phe Asp Ala
            20                  25

```
<210> SEQ ID NO 54
<211> LENGTH: 28
<212> TYPE: PRT
<213> ORGANISM: Rattus norvegicus

<400> SEQUENCE: 54

Tyr Gly Gly Phe Leu Arg Arg Gln Phe Lys Val Val Thr Arg Ser Gln
 1               5                  10                  15

Glu Asn Pro Asn Thr Tyr Ser Glu Asp Leu Asp Val
             20                  25

<210> SEQ ID NO 55
<211> LENGTH: 28
<212> TYPE: PRT
<213> ORGANISM: Mus musculus

<400> SEQUENCE: 55

Tyr Gly Gly Phe Leu Arg Arg Gln Phe Lys Val Val Thr Arg Ser Gln
 1               5                  10                  15

Glu Ser Pro Asn Thr Tyr Ser Glu Asp Leu Asp Val
             20                  25

<210> SEQ ID NO 56
<211> LENGTH: 29
<212> TYPE: PRT
<213> ORGANISM: Cavia porcellus

<400> SEQUENCE: 56

Tyr Gly Gly Phe Leu Arg Arg Gln Phe Lys Val Val Thr Arg Ser Gln
 1               5                  10                  15

Glu Asp Pro Asn Ala Tyr Ser Glu Glu Phe Phe Asp Val
             20                  25

<210> SEQ ID NO 57
<211> LENGTH: 29
<212> TYPE: PRT
<213> ORGANISM: Sus scrofa

<400> SEQUENCE: 57

Tyr Gly Gly Phe Leu Arg Arg Gln Phe Lys Val Val Thr Arg Ser Gln
 1               5                  10                  15

Glu Asp Pro Asn Ala Tyr Tyr Glu Glu Leu Phe Asp Val
             20                  25

<210> SEQ ID NO 58
<211> LENGTH: 29
<212> TYPE: PRT
<213> ORGANISM: Canis familiaris

<400> SEQUENCE: 58

Tyr Gly Gly Phe Leu Arg Arg Gln Phe Lys Val Val Thr Arg Ser Gln
 1               5                  10                  15

Glu Asp Pro Asn Ala Tyr Ser Gly Glu Leu Leu Asp Gly
             20                  25

<210> SEQ ID NO 59
<211> LENGTH: 29
<212> TYPE: PRT
<213> ORGANISM: Bos taurus

<400> SEQUENCE: 59

Tyr Gly Gly Phe Leu Arg Arg Gln Phe Lys Val Val Thr Arg Ser Gln
 1               5                  10                  15
```

Glu Asp Pro Ser Ala Tyr Tyr Glu Glu Leu Phe Asp Val
            20                  25

<210> SEQ ID NO 60
<211> LENGTH: 29
<212> TYPE: PRT
<213> ORGANISM: Bufo marinus

<400> SEQUENCE: 60

Tyr Gly Gly Phe Leu Arg Arg Gln Phe Lys Val Thr Thr Arg Ser Glu
1               5                   10                  15

Glu Asp Pro Ser Thr Phe Ser Gly Glu Leu Ser Asn Leu
            20                  25

<210> SEQ ID NO 61
<211> LENGTH: 29
<212> TYPE: PRT
<213> ORGANISM: Bombina orientalis

<400> SEQUENCE: 61

Tyr Gly Gly Phe Leu Arg Arg Gln Phe Lys Val Thr Thr Arg Ser Glu
1               5                   10                  15

Glu Glu Pro Gly Ser Phe Ser Gly Glu Ile Ser Asn Leu
            20                  25

<210> SEQ ID NO 62
<211> LENGTH: 29
<212> TYPE: PRT
<213> ORGANISM: Xenopus laevis

<400> SEQUENCE: 62

Tyr Gly Gly Phe Leu Arg Arg Gln Phe Lys Val Asn Ala Arg Ser Glu
1               5                   10                  15

Glu Asp Pro Thr Met Phe Ser Asp Glu Leu Ser Tyr Leu
            20                  25

<210> SEQ ID NO 63
<211> LENGTH: 29
<212> TYPE: PRT
<213> ORGANISM: Xenopus laevis

<400> SEQUENCE: 63

Tyr Gly Gly Phe Leu Arg Arg Gln Phe Lys Val Asn Ala Arg Ser Glu
1               5                   10                  15

Glu Asp Pro Thr Met Phe Ser Gly Glu Leu Ser Tyr Leu
            20                  25

<210> SEQ ID NO 64
<211> LENGTH: 29
<212> TYPE: PRT
<213> ORGANISM: Polypterus senegalus

<400> SEQUENCE: 64

Tyr Gly Gly Phe Leu Arg Arg His Phe Lys Ile Ser Val Arg Ser Asp
1               5                   10                  15

Glu Glu Pro Ser Ser Tyr Ser Asp Glu Val Leu Glu Leu
            20                  25

<210> SEQ ID NO 65
<211> LENGTH: 27
<212> TYPE: PRT
<213> ORGANISM: Danio rerio

<400> SEQUENCE: 65

```
Tyr Gly Gly Phe Leu Arg Arg His Phe Lys Ile Ser Val Arg Ser Asp
1               5                   10                  15

Glu Glu Pro Ser Ser Tyr Glu Asp Tyr Ala Leu
            20                  25

<210> SEQ ID NO 66
<211> LENGTH: 27
<212> TYPE: PRT
<213> ORGANISM: Anguilla rostrata

<400> SEQUENCE: 66

Tyr Gly Gly Phe Leu Arg Arg His Phe Lys Ile Ser Val Arg Ser Asp
1               5                   10                  15

Glu Glu Pro Gly Ser Tyr Asp Val Ile Gly Leu
            20                  25

<210> SEQ ID NO 67
<211> LENGTH: 29
<212> TYPE: PRT
<213> ORGANISM: Neoceratodus forsteri

<400> SEQUENCE: 67

Tyr Gly Gly Phe Leu Arg Arg His Phe Lys Ile Thr Val Arg Ser Asp
1               5                   10                  15

Glu Asp Pro Ser Pro Tyr Leu Asp Glu Phe Ser Asp Leu
            20                  25

<210> SEQ ID NO 68
<211> LENGTH: 27
<212> TYPE: PRT
<213> ORGANISM: Oncorhynchus masou

<400> SEQUENCE: 68

Tyr Gly Gly Phe Leu Arg Arg His Tyr Lys Leu Ser Val Arg Ser Asp
1               5                   10                  15

Glu Glu Pro Ser Ser Tyr Asp Asp Phe Gly Leu
            20                  25

<210> SEQ ID NO 69
<211> LENGTH: 13
<212> TYPE: PRT
<213> ORGANISM: Homo sapiens

<400> SEQUENCE: 69

Tyr Gly Gly Phe Leu Arg Arg Gln Phe Lys Val Val Thr
1               5                   10

<210> SEQ ID NO 70
<211> LENGTH: 13
<212> TYPE: PRT
<213> ORGANISM: Bufo marinus

<400> SEQUENCE: 70

Tyr Gly Gly Phe Leu Arg Arg Gln Phe Lys Val Thr Thr
1               5                   10

<210> SEQ ID NO 71
<211> LENGTH: 13
<212> TYPE: PRT
<213> ORGANISM: Xenopus laevis

<400> SEQUENCE: 71

Tyr Gly Gly Phe Leu Arg Arg Gln Phe Lys Val Asn Ala
```

<210> SEQ ID NO 72
<211> LENGTH: 13
<212> TYPE: PRT
<213> ORGANISM: Polypterus senegalus

<400> SEQUENCE: 72

Tyr Gly Gly Phe Leu Arg Arg His Phe Lys Ile Ser Val
1               5                   10

<210> SEQ ID NO 73
<211> LENGTH: 13
<212> TYPE: PRT
<213> ORGANISM: Neoceratodus forsteri

<400> SEQUENCE: 73

Tyr Gly Gly Phe Leu Arg Arg His Phe Lys Ile Thr Val
1               5                   10

<210> SEQ ID NO 74
<211> LENGTH: 13
<212> TYPE: PRT
<213> ORGANISM: Oncorhynchus masou

<400> SEQUENCE: 74

Tyr Gly Gly Phe Leu Arg Arg His Tyr Lys Leu Ser Val
1               5                   10

<210> SEQ ID NO 75
<211> LENGTH: 17
<212> TYPE: PRT
<213> ORGANISM: Homo sapiens

<400> SEQUENCE: 75

Phe Gly Gly Phe Thr Gly Ala Arg Lys Ser Ala Arg Lys Arg Lys Asn
1               5                   10                  15

Gln

<210> SEQ ID NO 76
<211> LENGTH: 17
<212> TYPE: PRT
<213> ORGANISM: Homo sapiens

<400> SEQUENCE: 76

Phe Gly Gly Phe Thr Gly Ala Arg Lys Ser Ala Arg Lys Leu Ala Asn
1               5                   10                  15

Gln

<210> SEQ ID NO 77
<211> LENGTH: 17
<212> TYPE: PRT
<213> ORGANISM: Homo sapiens

<400> SEQUENCE: 77

Phe Gly Gly Phe Thr Gly Ala Arg Lys Ser Ala Arg Lys Tyr Ala Asn
1               5                   10                  15

Gln

<210> SEQ ID NO 78
<211> LENGTH: 11
<212> TYPE: PRT
<213> ORGANISM: Homo sapiens

<400> SEQUENCE: 78

Phe Gly Gly Phe Thr Gly Ala Arg Lys Ser Ala
1               5                   10

<210> SEQ ID NO 79
<211> LENGTH: 11
<212> TYPE: PRT
<213> ORGANISM: Homo sapiens

<400> SEQUENCE: 79

Phe Gly Gly Phe Thr Gly Ala Arg Lys Tyr Ala
1               5                   10

<210> SEQ ID NO 80
<211> LENGTH: 11
<212> TYPE: PRT
<213> ORGANISM: Homo sapiens

<400> SEQUENCE: 80

Phe Gly Gly Phe Thr Gly Ala Arg Lys Ser Tyr
1               5                   10

<210> SEQ ID NO 81
<211> LENGTH: 13
<212> TYPE: PRT
<213> ORGANISM: Homo sapiens

<400> SEQUENCE: 81

Phe Gly Gly Phe Thr Gly Ala Arg Lys Ser Ala Arg Lys
1               5                   10

<210> SEQ ID NO 82
<211> LENGTH: 30
<212> TYPE: PRT
<213> ORGANISM: Homo sapiens

<400> SEQUENCE: 82

Met Pro Arg Val Arg Ser Leu Phe Gln Glu Gln Glu Pro Glu Pro
1               5                   10                  15

Gly Met Glu Glu Ala Gly Glu Met Glu Gln Lys Gln Leu Gln
            20                  25                  30

<210> SEQ ID NO 83
<211> LENGTH: 17
<212> TYPE: PRT
<213> ORGANISM: Homo sapiens

<400> SEQUENCE: 83

Phe Ser Glu Phe Met Arg Gln Tyr Leu Val Leu Ser Met Gln Ser Ser
1               5                   10                  15

Gln

<210> SEQ ID NO 84
<211> LENGTH: 8
<212> TYPE: PRT
<213> ORGANISM: Homo sapiens

<400> SEQUENCE: 84

Thr Leu His Gln Asn Gly Asn Val
1               5

<210> SEQ ID NO 85
<211> LENGTH: 10
<212> TYPE: PRT

<213> ORGANISM: Homo sapiens

<400> SEQUENCE: 85

Leu Val Val Tyr Pro Trp Thr Gln Arg Phe
 1               5                  10

<210> SEQ ID NO 86
<211> LENGTH: 9
<212> TYPE: PRT
<213> ORGANISM: Homo sapiens

<400> SEQUENCE: 86

Val Val Tyr Pro Trp Thr Gln Arg Phe
 1               5

<210> SEQ ID NO 87
<211> LENGTH: 8
<212> TYPE: PRT
<213> ORGANISM: Homo sapiens

<400> SEQUENCE: 87

Val Tyr Pro Trp Thr Gln Arg Phe
 1               5

<210> SEQ ID NO 88
<211> LENGTH: 7
<212> TYPE: PRT
<213> ORGANISM: Homo sapiens

<400> SEQUENCE: 88

Tyr Pro Trp Thr Gln Arg Phe
 1               5

<210> SEQ ID NO 89
<211> LENGTH: 9
<212> TYPE: PRT
<213> ORGANISM: Homo sapiens

<400> SEQUENCE: 89

Leu Val Val Tyr Pro Trp Thr Gln Arg
 1               5

<210> SEQ ID NO 90
<211> LENGTH: 8
<212> TYPE: PRT
<213> ORGANISM: Homo sapiens

<400> SEQUENCE: 90

Leu Val Val Tyr Pro Trp Thr Gln
 1               5

<210> SEQ ID NO 91
<211> LENGTH: 7
<212> TYPE: PRT
<213> ORGANISM: Homo sapiens

<400> SEQUENCE: 91

Val Val Tyr Pro Trp Thr Gln
 1               5

<210> SEQ ID NO 92
<211> LENGTH: 7
<212> TYPE: PRT
<213> ORGANISM: Homo sapiens

<400> SEQUENCE: 92

```
Leu Val Val Tyr Pro Trp Thr
 1               5

<210> SEQ ID NO 93
<211> LENGTH: 6
<212> TYPE: PRT
<213> ORGANISM: Homo sapiens

<400> SEQUENCE: 93

Leu Val Val Tyr Pro Trp
 1               5

<210> SEQ ID NO 94
<211> LENGTH: 30
<212> TYPE: PRT
<213> ORGANISM: Homo sapiens

<400> SEQUENCE: 94

Gly Trp Thr Leu Asn Ser Ala Gly Tyr Leu Leu Gly Pro His Ala Val
 1               5                  10                  15

Gly Asn His Arg Ser Phe Ser Asp Lys Asn Gly Leu Thr Ser
            20                  25                  30

<210> SEQ ID NO 95
<211> LENGTH: 59
<212> TYPE: PRT
<213> ORGANISM: Homo sapiens

<400> SEQUENCE: 95

Glu Leu Arg Pro Glu Asp Asp Met Lys Pro Gly Ser Phe Asp Arg Ser
 1               5                  10                  15

Ile Pro Glu Asn Asn Ile Met Arg Thr Ile Ile Glu Phe Leu Ser Phe
            20                  25                  30

Leu His Leu Lys Glu Ala Gly Ala Leu Asp Arg Leu Leu Asp Leu Pro
        35                  40                  45

Ala Ala Ala Ser Ser Glu Asp Ile Glu Arg Ser
    50                  55

<210> SEQ ID NO 96
<211> LENGTH: 11
<212> TYPE: PRT
<213> ORGANISM: Homo sapiens

<400> SEQUENCE: 96

Arg Pro Lys Pro Gln Gln Phe Phe Gly Leu Met
 1               5                  10

<210> SEQ ID NO 97
<211> LENGTH: 12
<212> TYPE: PRT
<213> ORGANISM: Homo sapiens

<400> SEQUENCE: 97

Arg Pro Lys Pro Gln Gln Phe Phe Gly Leu Met Gly
 1               5                  10

<210> SEQ ID NO 98
<211> LENGTH: 13
<212> TYPE: PRT
<213> ORGANISM: Homo sapiens

<400> SEQUENCE: 98

Arg Pro Lys Pro Gln Gln Phe Phe Gly Leu Met Gly Lys
```

<210> SEQ ID NO 99
<211> LENGTH: 14
<212> TYPE: PRT
<213> ORGANISM: Homo sapiens

<400> SEQUENCE: 99

Arg Pro Lys Pro Gln Gln Phe Phe Gly Leu Met Gly Lys Arg
1               5                   10

<210> SEQ ID NO 100
<211> LENGTH: 36
<212> TYPE: PRT
<213> ORGANISM: Homo sapiens

<400> SEQUENCE: 100

Asp Ala Asp Ser Ser Ile Glu Lys Gln Val Ala Leu Leu Lys Ala Leu
1               5                   10                  15

Tyr Gly His Gly Gln Ile Ser His Lys Arg His Lys Thr Asp Ser Phe
            20                  25                  30

Val Gly Leu Met
        35

<210> SEQ ID NO 101
<211> LENGTH: 19
<212> TYPE: PRT
<213> ORGANISM: Homo sapiens

<400> SEQUENCE: 101

Gly His Gly Gln Ile Ser His Lys Arg His Lys Thr Asp Ser Phe Val
1               5                   10                  15

Gly Leu Met

<210> SEQ ID NO 102
<211> LENGTH: 10
<212> TYPE: PRT
<213> ORGANISM: Homo sapiens

<400> SEQUENCE: 102

His Lys Thr Asp Ser Phe Val Gly Leu Met
1               5                   10

<210> SEQ ID NO 103
<211> LENGTH: 10
<212> TYPE: PRT
<213> ORGANISM: Rattus norvegicus

<400> SEQUENCE: 103

Asp Met His Asp Phe Phe Val Gly Leu Met
1               5                   10

<210> SEQ ID NO 104
<211> LENGTH: 10
<212> TYPE: PRT
<213> ORGANISM: Homo sapiens

<400> SEQUENCE: 104

Ser Arg Thr Arg Gln Phe Tyr Gly Leu Met
1               5                   10

<210> SEQ ID NO 105
<211> LENGTH: 10
<212> TYPE: PRT

<213> ORGANISM: Homo sapiens

<400> SEQUENCE: 105

Gly Lys Ala Ser Gln Phe Phe Gly Leu Met
1               5                   10

<210> SEQ ID NO 106
<211> LENGTH: 14
<212> TYPE: PRT
<213> ORGANISM: Homo sapiens

<400> SEQUENCE: 106

Lys Lys Ala Tyr Gln Leu Glu His Thr Phe Gln Gly Leu Leu
1               5                   10

<210> SEQ ID NO 107
<211> LENGTH: 14
<212> TYPE: PRT
<213> ORGANISM: Homo sapiens

<400> SEQUENCE: 107

Val Gly Ala Tyr Gln Leu Glu His Thr Phe Gln Gly Leu Leu
1               5                   10

<210> SEQ ID NO 108
<211> LENGTH: 36
<212> TYPE: PRT
<213> ORGANISM: Homo sapiens

<400> SEQUENCE: 108

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 109
<211> LENGTH: 36
<212> TYPE: PRT
<213> ORGANISM: Homo sapiens

<400> SEQUENCE: 109

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 110
<211> LENGTH: 33
<212> TYPE: PRT
<213> ORGANISM: Homo sapiens

<400> SEQUENCE: 110

Glu Pro Val Tyr Pro Gly Asp Asn Ala Thr Pro Glu Gln Met Ala Gln
1               5                   10                  15

Tyr Ala Ala Asp Leu Arg Arg Tyr Ile Asn Met Leu Thr Arg Pro Arg
            20                  25                  30

Tyr

```
<210> SEQ ID NO 111
<211> LENGTH: 36
<212> TYPE: PRT
<213> ORGANISM: Homo sapiens

<400> SEQUENCE: 111

Ala Pro Leu Glu Pro Val Tyr Pro Gly Asp Asn Ala Thr Pro Glu Gln
 1               5                  10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 112
<211> LENGTH: 20
<212> TYPE: PRT
<213> ORGANISM: Homo sapiens

<400> SEQUENCE: 112

His Lys Glu Asp Thr Leu Ala Phe Ser Glu Trp Gly Ser Pro His Ala
 1               5                  10                  15

Ala Val Pro Arg
            20

<210> SEQ ID NO 113
<211> LENGTH: 8
<212> TYPE: PRT
<213> ORGANISM: Artificial Sequence
<220> FEATURE:
<223> OTHER INFORMATION: Consensus sequence for Thrombin cleavage site
<220> FEATURE:
<221> NAME/KEY: VARIANT
<222> LOCATION: 1
<223> OTHER INFORMATION: Position 1 is S, T, N, Q, H, K, R, F, W, Y, G,
      P, A, V, L, I or M
<220> FEATURE:
<221> NAME/KEY: VARIANT
<222> LOCATION: 2, 6, 7, 8
<223> OTHER INFORMATION: Position 2, 6, 7, and 8, are independently any
      amino acid
<220> FEATURE:
<221> NAME/KEY: VARIANT
<222> LOCATION: 3
<223> OTHER INFORMATION: Position 3 is F, S, T, an amidic amino acid
      like N or Q, or an aliphatic hydrophobic amino acid like,
      G, P, A, V, L, I, and M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 5
<223> OTHER INFORMATION: Position 5 is S, T, a positive amino acid like
      H, K, and R, or an aliphatic hydrophobic amino acid
      like, G, P, A, V, L, I, and M

<400> SEQUENCE: 113

Xaa Xaa Xaa Xaa Xaa Xaa Xaa Xaa
 1               5

<210> SEQ ID NO 114
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 114

Leu Val Pro Arg Gly Ser
```

-continued

```
<210> SEQ ID NO 115
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 115

Leu Val Pro Lys Gly Ser
1               5

<210> SEQ ID NO 116
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 116

Phe Ile Pro Arg Thr Phe
1               5

<210> SEQ ID NO 117
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 117

Val Leu Pro Arg Ser Phe
1               5

<210> SEQ ID NO 118
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 118

Ile Val Pro Arg Ser Phe
1               5

<210> SEQ ID NO 119
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 119

Ile Val Pro Arg Gly Tyr
1               5

<210> SEQ ID NO 120
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 120

Val Val Pro Arg Gly Val
1               5
```

```
<210> SEQ ID NO 121
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 121

Val Leu Pro Arg Leu Ile
 1               5

<210> SEQ ID NO 122
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 122

Val Met Pro Arg Ser Leu
 1               5

<210> SEQ ID NO 123
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 123

Met Phe Pro Arg Ser Leu
 1               5

<210> SEQ ID NO 124
<211> LENGTH: 8
<212> TYPE: PRT
<213> ORGANISM: Artificial Sequence
<220> FEATURE:
<223> OTHER INFORMATION: Consensus sequence for Coagulation Factor VIIa
      cleavage site
<220> FEATURE:
<221> NAME/KEY: VARIANT
<222> LOCATION: 1
<223> OTHER INFORMATION: Position 1 is an acidic amino acid like D and
      E, an amidic amino acid like N and Q, a basic amino
      acid like K and R, or an aliphatic hydrophobic
      amino acid like, G, P, A, V, L, I, and M
<220> FEATURE:
<221> NAME/KEY: VARIANT
<222> LOCATION: 2
<223> OTHER INFORMATION: Position 2 is Q, S, T, an aromatic hydrophobic
      amino acid like F, W and Y, or an aliphatic
      hydrophobic amino acid like, G, P, A, V, L, I, and
      M
<220> FEATURE:
<221> NAME/KEY: VARIANT
<222> LOCATION: 3
<223> OTHER INFORMATION: Position 3 is Q, S, T, or an aliphatic
      hydrophobic amino acid like, G, P, A, V, L, I, and M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 5, 6, 7  8
<223> OTHER INFORMATION: Position 5, 6, 7, and 8 are independently any
      amino acid

<400> SEQUENCE: 124

Xaa Xaa Xaa Xaa Xaa Xaa Xaa Xaa
 1               5
```

<210> SEQ ID NO 125
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 125

Lys Leu Thr Arg Ala Glu Thr Val
 1               5

<210> SEQ ID NO 126
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 126

Asp Phe Thr Arg Val Val Gly Gly
 1               5

<210> SEQ ID NO 127
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 127

Leu Ser Pro Arg Thr Phe His Pro
 1               5

<210> SEQ ID NO 128
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 128

Leu Ile Gln Arg Asn Leu Ser Pro
 1               5

<210> SEQ ID NO 129
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 129

Met Ala Thr Arg Lys Met His Asp
 1               5

<210> SEQ ID NO 130
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 130

Leu Gly Ile Arg Ser Phe Arg Asn
 1               5

```
<210> SEQ ID NO 131
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 131

Pro Gln Gly Arg Ile Val Gly Gly
 1               5

<210> SEQ ID NO 132
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 132

Asn Leu Thr Arg Ile Val Gly Gly
 1               5

<210> SEQ ID NO 133
<211> LENGTH: 8
<212> TYPE: PRT
<213> ORGANISM: Artificial Sequence
<220> FEATURE:
<223> OTHER INFORMATION: Coagulation Factor VIIa cleavage site

<400> SEQUENCE: 133

Gln Val Val Arg Ile Val Gly Gly
 1               5

<210> SEQ ID NO 134
<211> LENGTH: 8
<212> TYPE: PRT
<213> ORGANISM: Artificial Sequence
<220> FEATURE:
<223> OTHER INFORMATION: Consenus sequence for Coagulation Factor IXa
      cleavage site
<220> FEATURE:
<221> NAME/KEY: VARIANT
<222> LOCATION: 1
<223> OTHER INFORMATION: Position 1 is an acidic amino acid like D and
      E, an amidic amino acid like N and Q, or an aliphatic
      hydrophobic amino acid like, G, P, A, V, L, I, and
      M
<220> FEATURE:
<221> NAME/KEY: VARIANT
<222> LOCATION: 2
<223> OTHER INFORMATION: Position 2 is an acidic amino acid like D and
      E, an amidic amino acid like N and Q, or an aliphatic
      hydrophobic amino acid like, G, P, A, V, L, I, and
      M
<220> FEATURE:
<221> NAME/KEY: VARIANT
<222> LOCATION: 3
<223> OTHER INFORMATION: Position 3 is, S, T, an aromatic hydrophobic
      amino acid like F, W and Y, or an aliphatic hydrophobic
      amino acid like, G, P, A, V, L, I, and M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 5, 6, 7, 8
<223> OTHER INFORMATION: Positions 5, 6, 7, and 8 are independently  any
      amino acid

<400> SEQUENCE: 134

Xaa Xaa Xaa Xaa Xaa Xaa Xaa Xaa
 1               5
```

```
<210> SEQ ID NO 135
<211> LENGTH: 8
<212> TYPE: PRT
<213> ORGANISM: Artificial Sequence
<220> FEATURE:
<223> OTHER INFORMATION: Coagulation Factor IXa cleavage site

<400> SEQUENCE: 135

Pro Gln Gly Arg Ile Val Gly Gly
 1               5

<210> SEQ ID NO 136
<211> LENGTH: 8
<212> TYPE: PRT
<213> ORGANISM: Artificial Sequence
<220> FEATURE:
<223> OTHER INFORMATION: Coagulation Factor IXa cleavage site

<400> SEQUENCE: 136

Pro Gln Leu Arg Met Lys Asn Asn
 1               5

<210> SEQ ID NO 137
<211> LENGTH: 8
<212> TYPE: PRT
<213> ORGANISM: Artificial Sequence
<220> FEATURE:
<223> OTHER INFORMATION: Coagulation Factor IXa cleavage site

<400> SEQUENCE: 137

Asn Leu Thr Arg Ile Val Gly Gly
 1               5

<210> SEQ ID NO 138
<211> LENGTH: 8
<212> TYPE: PRT
<213> ORGANISM: Artificial Sequence
<220> FEATURE:
<223> OTHER INFORMATION: Coagulation Factor IXa cleavage site

<400> SEQUENCE: 138

Gln Val Val Arg Ile Val Gly Gly
 1               5

<210> SEQ ID NO 139
<211> LENGTH: 8
<212> TYPE: PRT
<213> ORGANISM: Artificial Sequence
<220> FEATURE:
<223> OTHER INFORMATION: Consensus sequence for Coagulation Factor Xa
      cleavage site
<220> FEATURE:
<221> NAME/KEY: VARIANT
<222> LOCATION: 1, 6, 7, 8
<223> OTHER INFORMATION: Positions 1, 6, 7, and 8 are independently any
      amino acid
<220> FEATURE:
<221> NAME/KEY: VARIANT
<222> LOCATION: 2
<223> OTHER INFORMATION: Position 2 is G, A, S, an acidic amino acid
      like D and E, an amidic amino acid like Q and N, or an
      aromatic hydrophobic amino acid like F, W and Y
<220> FEATURE:
<221> NAME/KEY: VARIANT
<222> LOCATION: 3
<223> OTHER INFORMATION: Position 3 is an aromatic hydrophobic amino
      acid like F, W and Y, or an aliphatic hydrophobic amino
      acid like, G, P, A, V, L, I, and M
<220> FEATURE:
<221> NAME/KEY: VARIANT
```

```
<222> LOCATION: 4
<223> OTHER INFORMATION: Position 4 is K or R
<220> FEATURE:
<221> NAME/KEY: VARIANT
<222> LOCATION: 5
<223> OTHER INFORMATION: Position 5 is an amidic amino acid like N and
      Q, an uncharged amino acid like C, S, and T, or an
      aliphatic hydrophobic amino acid like, G, P, A, V,
      L, I, and M

<400> SEQUENCE: 139

Xaa Xaa Xaa Xaa Xaa Xaa Xaa Xaa
 1               5

<210> SEQ ID NO 140
<211> LENGTH: 4
<212> TYPE: PRT
<213> ORGANISM: Artificial Sequence
<220> FEATURE:
<223> OTHER INFORMATION: Coagulation Factor Xa cleavage site

<400> SEQUENCE: 140

Ile Asp Gly Arg
 1

<210> SEQ ID NO 141
<211> LENGTH: 4
<212> TYPE: PRT
<213> ORGANISM: Artificial Sequence
<220> FEATURE:
<223> OTHER INFORMATION: Coagulation Factor Xa cleavage site

<400> SEQUENCE: 141

Ile Glu Gly Arg
 1

<210> SEQ ID NO 142
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 142

Ile Asp Gly Arg Ser Val Gly Gly
 1               5

<210> SEQ ID NO 143
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 143

Ile Asp Gly Arg Thr Val Gly Gly
 1               5

<210> SEQ ID NO 144
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 144

Ile Asp Gly Arg Ile Val Gly Gly
 1               5
```

```
<210> SEQ ID NO 145
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 145

Ile Glu Gly Arg Ser Val Gly Gly
 1               5

<210> SEQ ID NO 146
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 146

Ile Glu Gly Arg Thr Val Gly Gly
 1               5

<210> SEQ ID NO 147
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 147

Ile Glu Gly Arg Ile Val Gly Gly
 1               5

<210> SEQ ID NO 148
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 148

Pro Gln Gly Arg Ile Val Gly Gly
 1               5

<210> SEQ ID NO 149
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 149

Ile Glu Gly Arg Thr Ser Glu Asp
 1               5

<210> SEQ ID NO 150
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 150

Ile Glu Gly Arg Ile Val Glu Gly
 1               5

<210> SEQ ID NO 151
```

```
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 151

Ile Asp Gly Arg Ile Val Glu Gly
 1               5

<210> SEQ ID NO 152
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 152

Phe Asn Pro Arg Thr Phe Gly Ser
 1               5

<210> SEQ ID NO 153
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 153

Phe Asp Glu Arg Thr Phe Gly Leu
 1               5

<210> SEQ ID NO 154
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 154

Ile Asp Glu Arg Ile Val Gly Gly
 1               5

<210> SEQ ID NO 155
<211> LENGTH: 8
<212> TYPE: PRT
<213> ORGANISM: Artificial Sequence
<220> FEATURE:
<223> OTHER INFORMATION: Coagulation Factor Xa cleavage site

<400> SEQUENCE: 155

Phe Asn Glu Lys Thr Phe Gly Leu
 1               5

<210> SEQ ID NO 156
<211> LENGTH: 8
<212> TYPE: PRT
<213> ORGANISM: Artificial Sequence
<220> FEATURE:
<223> OTHER INFORMATION: Consensus sequence for Coagulation Factor XIa
      cleavage site
<220> FEATURE:
<221> NAME/KEY: VARIANT
<222> LOCATION: 1
<223> OTHER INFORMATION: Position 1 is an acidic amino acid like D or E,
      a basic amino acid like K and R, or an aliphatic
      hydrophobic amino acid like, G, P, A, V, L, I, and M
<220> FEATURE:
<221> NAME/KEY: VARIANT
<222> LOCATION: 2
```

```
<223> OTHER INFORMATION: Position 2 is D, E, Q, N, K, R, F, W, Y, G, P,
      A, V, L, I, or M
<220> FEATURE:
<221> NAME/KEY: VARIANT
<222> LOCATION: 3
<223> OTHER INFORMATION: Position 3 is H, C, S, T, F, W, Y, G, P, A, V,
      L, I, or M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 5, 8
<223> OTHER INFORMATION: Positions 5 and 6 are independently H, an
      uncharged amino acid like C, S, and T, or an
      aliphatic hydrophobic amino acid like, G, P, A, V,
      L, I, and M
<220> FEATURE:
<221> NAME/KEY: VARIANT
<222> LOCATION: (6)...(6)
<223> OTHER INFORMATION: Position 6 is an acidic amino acid like D and
      E, or an aliphatic hydrophobic amino acid like, G, P,
      A, V, L, I, and M
<220> FEATURE:
<221> NAME/KEY: VARIANT
<222> LOCATION: (7)...(7)
<223> OTHER INFORMATION: Position 7 is Q, N, C, S, T, F, W, Y, G, P,
      A, V, L, I, or M

<400> SEQUENCE: 156

Xaa Xaa Xaa Xaa Xaa Xaa Xaa Xaa
1               5

<210> SEQ ID NO 157
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 157

Ala Phe Trp Lys Thr Asp Ala Ser
1               5

<210> SEQ ID NO 158
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 158

Lys Leu Thr Arg Ala Glu Thr Val
1               5

<210> SEQ ID NO 159
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 159

Lys Leu Thr Arg Ala Glu Thr Ile
1               5

<210> SEQ ID NO 160
<211> LENGTH: 8
<212> TYPE: PRT
<213> ORGANISM: Artificial Sequence
<220> FEATURE:
```

```
<223> OTHER INFORMATION: Coagulation Factor XIa cleavage site

<400> SEQUENCE: 160

Asp Phe Thr Arg Val Val Gly Gly
 1               5

<210> SEQ ID NO 161
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 161

Glu Phe Ser Arg Val Val Gly Gly
 1               5

<210> SEQ ID NO 162
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 162

Lys Leu Thr Arg Ala Glu Thr Val
 1               5

<210> SEQ ID NO 163
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 163

Asp Phe Thr Arg Val Val Gly Gly
 1               5

<210> SEQ ID NO 164
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 164

Ile Lys Pro Arg Ile Val Gly Gly
 1               5

<210> SEQ ID NO 165
<211> LENGTH: 8
<212> TYPE: PRT
<213> ORGANISM: Artificial Sequence
<220> FEATURE:
<223> OTHER INFORMATION: Coagulation Factor XIa cleavage site

<400> SEQUENCE: 165

Asp Leu His Arg His Ile Phe Trp
 1               5

<210> SEQ ID NO 166
<211> LENGTH: 8
<212> TYPE: PRT
<213> ORGANISM: Artificial Sequence
<220> FEATURE:
<223> OTHER INFORMATION: Coagulation Factor XIa cleavage site
```

```
<400> SEQUENCE: 166

Lys Gln Leu Arg Val Val Asn Gly
1               5

<210> SEQ ID NO 167
<211> LENGTH: 8
<212> TYPE: PRT
<213> ORGANISM: Artificial Sequence
<220> FEATURE:
<223> OTHER INFORMATION: Consensus sequence for Coagulation Factor XIIa
      cleavage site
<220> FEATURE:
<221> NAME/KEY: VARIANT
<222> LOCATION: 1, 6
<223> OTHER INFORMATION: Positions 1 and 6 are independently an
      uncharged amino acid like C, S, and T, or an aliphatic
      hydrophobic amino acid like, G, P, A, V, L, I, and
      M
<220> FEATURE:
<221> NAME/KEY: VARIANT
<222> LOCATION: 2
<223> OTHER INFORMATION: Position 2 is an acidic amino acid like D and
      E, a basic amino acid like K and R, an uncharged amino
      acid like C, S, and T, or an aliphatic hydrophobic
      amino acid like, G, P, A, V, L, I, and M
<220> FEATURE:
<221> NAME/KEY: VARIANT
<222> LOCATION: 3
<223> OTHER INFORMATION: Position 3 is a basic amino acid like K and R,
      an uncharged amino acid like C, S, and T, or an
      aliphatic hydrophobic amino acid like, G, P, A, V,
      L, I, and M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 5, 7, 8
<223> OTHER INFORMATION: Positions 5, 7 and 8 are independently an
      aliphatic hydrophobic amino acid like, G, P, A, V,
      L, I, and M

<400> SEQUENCE: 167

Xaa Xaa Xaa Xaa Xaa Xaa Xaa Xaa
1               5

<210> SEQ ID NO 168
<211> LENGTH: 8
<212> TYPE: PRT
<213> ORGANISM: Artificial Sequence
<220> FEATURE:
<223> OTHER INFORMATION: Coagulation Factor XIIa cleavage site

<400> SEQUENCE: 168

Pro Gln Gly Arg Ile Val Gly Gly
1               5

<210> SEQ ID NO 169
<211> LENGTH: 8
<212> TYPE: PRT
<213> ORGANISM: Artificial Sequence
<220> FEATURE:
<223> OTHER INFORMATION: Coagulation Factor XIIa cleavage site

<400> SEQUENCE: 169

Ile Lys Pro Arg Ile Val Gly Gly
1               5

<210> SEQ ID NO 170
<211> LENGTH: 8
<212> TYPE: PRT
```

<213> ORGANISM: Artificial Sequence
<220> FEATURE:
<223> OTHER INFORMATION: Coagulation Factor XIIa cleavage site

<400> SEQUENCE: 170

Ser Met Thr Arg Val Val Gly Gly
 1               5

<210> SEQ ID NO 171
<211> LENGTH: 8
<212> TYPE: PRT
<213> ORGANISM: Artificial Sequence
<220> FEATURE:
<223> OTHER INFORMATION: Coagulation Factor XIIa cleavage site

<400> SEQUENCE: 171

Thr Ser Thr Arg Ile Val Gly Gly
 1               5

<210> SEQ ID NO 172
<211> LENGTH: 8
<212> TYPE: PRT
<213> ORGANISM: Artificial Sequence
<220> FEATURE:
<223> OTHER INFORMATION: Coagulation Factor XIIa cleavage site

<400> SEQUENCE: 172

Pro Met Lys Arg Leu Thr Leu Gly
 1               5

<210> SEQ ID NO 173
<211> LENGTH: 8
<212> TYPE: PRT
<213> ORGANISM: Artificial Sequence
<220> FEATURE:
<223> OTHER INFORMATION: Consensus sequence for Kallikrein 1 cleavage
      site
<220> FEATURE:
<221> NAME/KEY: VARIANT
<222> LOCATION: 1
<223> OTHER INFORMATION: Position 1 is D, E, Q, N, C, S, T, G, P, A, V,
      L, I or M
<220> FEATURE:
<221> NAME/KEY: VARIANT
<222> LOCATION: 2, 3, 6, 7, 8
<223> OTHER INFORMATION: Positions 2, 3, 6, 7 and 8 are independently
      any amino acid
<220> FEATURE:
<221> NAME/KEY: VARIANT
<222> LOCATION: 4
<223> OTHER INFORMATION: Position 4 is a positive amino acid like H, K,
      and R, a large non-polar amino acid like F, I, L, M
      and V, or an aromatic hydrophobic amino acid like
      F, W and Y
<220> FEATURE:
<221> NAME/KEY: VARIANT
<222> LOCATION: 5
<223> OTHER INFORMATION: Position 5 is S, K, or R

<400> SEQUENCE: 173

Xaa Xaa Xaa Xaa Xaa Xaa Xaa Xaa
 1               5

<210> SEQ ID NO 174
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 174

```
Ser Met Thr Arg Val Val Gly Gly
1               5

<210> SEQ ID NO 175
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 175

Ser Pro Phe Arg Ser Ser Asp Ile
1               5

<210> SEQ ID NO 176
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 176

Ser Leu Met Lys Arg Pro Pro Gly
1               5

<210> SEQ ID NO 177
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 177

Tyr Asp Trp Arg Thr Pro Tyr Leu
1               5

<210> SEQ ID NO 178
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 178

Ser Pro Phe Arg Ser Val Gln Val
1               5

<210> SEQ ID NO 179
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 179

Ser Pro Phe Arg Thr Pro Tyr Leu
1               5

<210> SEQ ID NO 180
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 180

Thr Phe His Lys Ala Glu Tyr Arg
1               5
```

```
<210> SEQ ID NO 181
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 181

Pro Arg Phe Lys Ile Ile Gly Gly
 1               5

<210> SEQ ID NO 182
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 182

Ile Ser Leu Met Lys Arg Pro Pro
 1               5

<210> SEQ ID NO 183
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 183

Leu Glu Ala Arg Ser Ala Tyr His
 1               5

<210> SEQ ID NO 184
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 184

Glu Ala Lys Arg Ser Tyr His Ser
 1               5

<210> SEQ ID NO 185
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 185

Pro Asn Arg Trp Ser Thr Gly Ala
 1               5

<210> SEQ ID NO 186
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 186

Glu Ala Phe Tyr Ser Gln Phe Gly
 1               5
```

```
<210> SEQ ID NO 187
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 187

Asn Ala Ala Arg Ser Thr Gly Ala
 1               5

<210> SEQ ID NO 188
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 188

Ser Ser Glu Trp Ser Met Pro Tyr
 1               5

<210> SEQ ID NO 189
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 189

Gly Thr Leu Phe Arg Ser Gly Asn
 1               5

<210> SEQ ID NO 190
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 190

Ala Arg Leu Tyr Ser Arg Gly Ala
 1               5

<210> SEQ ID NO 191
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 191

Glu Ala Ser Arg Ser Ala Thr Leu
 1               5

<210> SEQ ID NO 192
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 192

Glu Ala Ser Tyr Arg Arg Lys Gln
 1               5

<210> SEQ ID NO 193
<211> LENGTH: 8
```

```
<212> TYPE: PRT
<213> ORGANISM: Artificial Sequence
<220> FEATURE:
<223> OTHER INFORMATION: Kallikrein 1 cleavage site

<400> SEQUENCE: 193

Thr Thr Phe Tyr Arg Arg Gly Ala
 1               5

<210> SEQ ID NO 194
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 194

Ala Ala Trp Tyr Arg Thr Ser Arg
 1               5

<210> SEQ ID NO 195
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 195

Ser Phe His Tyr Arg Met Val Gly
 1               5

<210> SEQ ID NO 196
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 196

Ala Ser Ser Tyr Arg Thr Ser Arg
 1               5

<210> SEQ ID NO 197
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 197

Thr Arg Phe Tyr Ser Arg Gly Arg
 1               5

<210> SEQ ID NO 198
<211> LENGTH: 8
<212> TYPE: PRT
<213> ORGANISM: Artificial Sequence
<220> FEATURE:
<223> OTHER INFORMATION: Kallikrein 1 cleavage site

<400> SEQUENCE: 198

Ile Lys Phe Phe Ser Ala Gln Thr
 1               5

<210> SEQ ID NO 199
<211> LENGTH: 8
<212> TYPE: PRT
<213> ORGANISM: Artificial Sequence
```

```
<220> FEATURE:
<223> OTHER INFORMATION: Consensus sequence for Protein C cleavage site
<220> FEATURE:
<221> NAME/KEY: VARIANT
<222> LOCATION: 1
<223> OTHER INFORMATION: Position 1 is a basic amino acid like K and R,
      or an aliphatic hydrophobic amino acid like, G, P, A,
      V, L, I, and M
<220> FEATURE:
<221> NAME/KEY: VARIANT
<222> LOCATION: 2
<223> OTHER INFORMATION: Position 2 is an acidic amino acid like D and
      E, an amidic amino acid like Q and N, a basic amino
      acid like K and R, or an aliphatic hydrophobic
      amino acid like, G, P, A, V, L, I, and M
<220> FEATURE:
<221> NAME/KEY: VARIANT
<222> LOCATION: 3, 5
<223> OTHER INFORMATION: Positions 3 and 5 is Q, N, K, R, C, S, T, G, P,
      A, V, L, I or M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 6
<223> OTHER INFORMATION: Position 6 is Q, N, K, R, F, W, Y, G, P, A, V,
      L, I or M
<220> FEATURE:
<221> NAME/KEY: VARIANT
<222> LOCATION: (7)...(7)
<223> OTHER INFORMATION: Position 7 is an amidic amino acid like Q and
      N, a positive amino acid like H, K, and R, an uncharged
      amino acid like C, S, and T, or an aromatic
      hydrophobic amino acid like F, W and Y
<220> FEATURE:
<221> NAME/KEY: VARIANT
<222> LOCATION: (8)...(8)
<223> OTHER INFORMATION: Position 8 is D, E, Q, N, K, R, C, S, T, G, P,
      A, V, L, I or M

<400> SEQUENCE: 199

Xaa Xaa Xaa Xaa Xaa Xaa Xaa Xaa
 1               5

<210> SEQ ID NO 200
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 200

Lys Lys Thr Arg Asn Leu Lys Lys
 1               5

<210> SEQ ID NO 201
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 201

Leu Asp Arg Arg Gly Leu Gln Arg
 1               5

<210> SEQ ID NO 202
<211> LENGTH: 8
<212> TYPE: PRT
<213> ORGANISM: Artificial Sequence
<220> FEATURE:
<223> OTHER INFORMATION: Protein C cleavage site
```

```
<400> SEQUENCE: 202

Met Ala Thr Arg Lys Met His Asp
1               5

<210> SEQ ID NO 203
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 203

Arg Leu Lys Lys Ser Gln Phe Leu
1               5

<210> SEQ ID NO 204
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 204

Pro Gln Leu Arg Met Lys Asn Asn
1               5

<210> SEQ ID NO 205
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 205

Val Asp Gln Arg Gly Asn Gln Ile
1               5

<210> SEQ ID NO 206
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 206

Ile Glu Pro Arg Ser Pro Ser Gln
1               5

<210> SEQ ID NO 207
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 207

Lys Lys Thr Arg Ser Pro Lys Thr
1               5

<210> SEQ ID NO 208
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 208
```

```
Leu Asp Gln Arg Gly Val Gln Arg
1               5

<210> SEQ ID NO 209
<211> LENGTH: 8
<212> TYPE: PRT
<213> ORGANISM: Artificial Sequence
<220> FEATURE:
<223> OTHER INFORMATION: Protein C cleavage site

<400> SEQUENCE: 209

Pro Asp Pro Arg Ser Lys Asn Asn
1               5

<210> SEQ ID NO 210
<211> LENGTH: 8
<212> TYPE: PRT
<213> ORGANISM: Artificial Sequence
<220> FEATURE:
<223> OTHER INFORMATION: Consensus sequence for Plasminogen cleavage
      site
<220> FEATURE:
<221> NAME/KEY: VARIANT
<222> LOCATION: 1, 5, 6
<223> OTHER INFORMATION: Positions 1, 5, and 6 are independently H, K R,
      C, S, T, G, P, A, V, L, I or M
<220> FEATURE:
<221> NAME/KEY: VARIANT
<222> LOCATION: 2
<223> OTHER INFORMATION: Position 3 is N, Q, H, K, R, C, S, T, G, P, A,
      V, L, I or M
<220> FEATURE:
<221> NAME/KEY: VARIANT
<222> LOCATION: 3
<223> OTHER INFORMATION: Position 3 is N, Q, C, S, T, F, W, Y, G, P, A,
      V, L, I or M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 7
<223> OTHER INFORMATION: Position 7 is any amino acid
<220> FEATURE:
<221> NAME/KEY: VARIANT
<222> LOCATION: (8)...(8)
<223> OTHER INFORMATION: Position 8 is H, F, Y, R, an uncharged amino
      acid like C, S, and T, an aliphatic hydrophobic amino
      acid like, G, P, A, V, L, I, and M

<400> SEQUENCE: 210

Xaa Xaa Xaa Xaa Xaa Xaa Xaa Xaa
1               5

<210> SEQ ID NO 211
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 211

Gly Glu Ala Arg Gly Ser Val Ile
1               5

<210> SEQ ID NO 212
<211> LENGTH: 8
<212> TYPE: PRT
<213> ORGANISM: Artificial Sequence
<220> FEATURE:
<223> OTHER INFORMATION: Plasminogen cleavage site
```

```
<400> SEQUENCE: 212

Gly His Ala Arg Leu Val His Val
1               5

<210> SEQ ID NO 213
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 213

Ala Glu Phe Arg His Asp Ser Gly
1               5

<210> SEQ ID NO 214
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 214

His His Gln Lys Leu Val Phe Phe
1               5

<210> SEQ ID NO 215
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 215

Gly Ser Asn Lys Gly Ala Leu Leu
1               5

<210> SEQ ID NO 216
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 216

Arg Ala Gln Arg Ser Ala Gly Ala
1               5

<210> SEQ ID NO 217
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 217

Ala Phe Trp Lys Thr Asp Ala Ser
1               5

<210> SEQ ID NO 218
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 218
```

```
Met Ser Met Arg Val Arg Arg His
1               5
```

<210> SEQ ID NO 219
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 219

```
Arg Gly Val Arg Arg Thr Ala Ser
1               5
```

<210> SEQ ID NO 220
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 220

```
Arg Ala Ala Arg Ser Gln Cys Thr
1               5
```

<210> SEQ ID NO 221
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 221

```
Pro Gln Ser Arg Ser Val Pro Pro
1               5
```

<210> SEQ ID NO 222
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 222

```
Pro Tyr Leu Lys Val Phe Asn Pro
1               5
```

<210> SEQ ID NO 223
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 223

```
Leu Ser Phe Arg Ala Arg Ala Tyr
1               5
```

<210> SEQ ID NO 224
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 224

```
Pro Gln Leu Arg Arg Gly Trp Arg
```

```
<210> SEQ ID NO 225
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 225

Glu Asp Asn Arg Asp Ser Ser Met
1               5

<210> SEQ ID NO 226
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 226

Leu Ser Phe Arg Ala Arg Ala Tyr
1               5

<210> SEQ ID NO 227
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 227

Phe Arg Ala Arg Ala Tyr Gly Phe
1               5

<210> SEQ ID NO 228
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 228

Tyr Gly Phe Arg Gly Pro Gly Pro
1               5

<210> SEQ ID NO 229
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 229

Ile Thr Phe Arg Met Asn Val Ala
1               5

<210> SEQ ID NO 230
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 230

Thr His Glu Lys Gly Arg Gln Ser
1               5
```

```
<210> SEQ ID NO 231
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 231

Pro Arg Leu Lys Ala Arg Ala Gly
 1               5

<210> SEQ ID NO 232
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 232

Pro Lys Ala Lys Ser His Ala Pro
 1               5

<210> SEQ ID NO 233
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 233

Pro Ser His Lys Glu Gly Pro Gln
 1               5

<210> SEQ ID NO 234
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 234

Leu Phe Glu Lys Lys Val Tyr Leu
 1               5

<210> SEQ ID NO 235
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 235

Ala Asp Gly Lys Lys Pro Ser Ser
 1               5

<210> SEQ ID NO 236
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 236

Pro Arg Phe Lys Ile Ile Gly Gly
 1               5

<210> SEQ ID NO 237
```

```
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 237

Pro Gln Phe Arg Ile Lys Gly Gly
1               5

<210> SEQ ID NO 238
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 238

Pro Arg Cys Arg His Arg Pro His
1               5

<210> SEQ ID NO 239
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 239

Lys Gly Tyr Arg Ser Gln Arg Gly
1               5

<210> SEQ ID NO 240
<211> LENGTH: 8
<212> TYPE: PRT
<213> ORGANISM: Artificial Sequence
<220> FEATURE:
<223> OTHER INFORMATION: Plasminogen cleavage site

<400> SEQUENCE: 240

Asp Val Ala Gln Phe Val Leu Thr
1               5

<210> SEQ ID NO 241
<211> LENGTH: 8
<212> TYPE: PRT
<213> ORGANISM: Artificial Sequence
<220> FEATURE:
<223> OTHER INFORMATION: Consensus sequence for MMP-2 cleavage site
<220> FEATURE:
<221> NAME/KEY: VARIANT
<222> LOCATION: 1, 3, 4, 6, 7, 8
<223> OTHER INFORMATION: Positions 1, 3, 4, 6, 7, 8 are independently
      any amino acid
<220> FEATURE:
<221> NAME/KEY: VARIANT
<222> LOCATION: 2
<223> OTHER INFORMATION: Position 2 is P, A, V, L, or I
<220> FEATURE:
<221> NAME/KEY: VARIANT
<222> LOCATION: 5
<223> OTHER INFORMATION: Position 5 is V, L, I, F, or Q

<400> SEQUENCE: 241

Xaa Xaa Xaa Xaa Xaa Xaa Xaa Xaa
1               5

<210> SEQ ID NO 242
<211> LENGTH: 8
<212> TYPE: PRT
```

```
<213> ORGANISM: Artificial Sequence
<220> FEATURE:
<223> OTHER INFORMATION: MMP-2 cleavage site

<400> SEQUENCE: 242

Gln Pro Val Ser Val Lys Val Gly
 1               5

<210> SEQ ID NO 243
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 243

Arg Gly Val Gly Ile Lys Ser Thr
 1               5

<210> SEQ ID NO 244
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 244

Phe Val Asp Cys Leu Ile Glu Gln
 1               5

<210> SEQ ID NO 245
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 245

Val Pro Ala Gly Asn Trp Val Leu
 1               5

<210> SEQ ID NO 246
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 246

Tyr His Ala Asp Ile Tyr Asp Lys
 1               5

<210> SEQ ID NO 247
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 247

Arg Ala Cys Arg Leu Ala Lys Ala
 1               5

<210> SEQ ID NO 248
<211> LENGTH: 8
<212> TYPE: PRT
<213> ORGANISM: Artificial Sequence
<220> FEATURE:
```

<223> OTHER INFORMATION: MMP-2 cleavage site

<400> SEQUENCE: 248

Gln Gly Ala Tyr Gln Glu Ala Phe
1               5

<210> SEQ ID NO 249
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 249

Asp Val Leu Ser Leu Leu Glu Lys
1               5

<210> SEQ ID NO 250
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 250

Thr Leu Asp Asp Leu Ile Met Ala
1               5

<210> SEQ ID NO 251
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 251

His Ile Ser Ser Leu Ile Lys Leu
1               5

<210> SEQ ID NO 252
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 252

Asp Pro Asn Asn Leu Leu Asn Asp
1               5

<210> SEQ ID NO 253
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 253

Pro Val Gln Pro Gln Gln Ser Pro
1               5

<210> SEQ ID NO 254
<211> LENGTH: 8
<212> TYPE: PRT
<213> ORGANISM: Artificial Sequence
<220> FEATURE:
<223> OTHER INFORMATION: MMP-2 cleavage site

```
<400> SEQUENCE: 254

Lys Pro Lys Thr Ile Thr Gly Pro
 1               5

<210> SEQ ID NO 255
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 255

Val Val His Pro Leu Val Leu Leu
 1               5

<210> SEQ ID NO 256
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 256

His Pro Leu Val Leu Leu Ser Val
 1               5

<210> SEQ ID NO 257
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 257

Ala Val Ala Leu Leu Ile Gly Pro
 1               5

<210> SEQ ID NO 258
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 258

Gln Pro Leu Gln Leu Leu Asp Ala
 1               5

<210> SEQ ID NO 259
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 259

Tyr Ile Gln Gly Ile Asn Leu Val
 1               5

<210> SEQ ID NO 260
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 260
```

```
Leu Pro Gln Glu Ile Lys Ala Asn
1               5

<210> SEQ ID NO 261
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 261

Asn Ile Ser Asp Leu Thr Ala Ala
1               5

<210> SEQ ID NO 262
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 262

Lys Pro Arg Ala Leu Thr Ala Leu
1               5

<210> SEQ ID NO 263
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 263

Ala Pro Ser Trp Leu Leu Thr Ala
1               5

<210> SEQ ID NO 264
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 264

Ala Val Arg Trp Leu Leu Thr Ala
1               5

<210> SEQ ID NO 265
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 265

Ala Val Ser Trp Leu Leu Thr Ala
1               5

<210> SEQ ID NO 266
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 266

Ser Leu Arg Arg Leu Thr Ala Ala
1               5
```

```
<210> SEQ ID NO 267
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 267

Ser Leu Ser Arg Leu Thr Ala Leu
 1               5

<210> SEQ ID NO 268
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 268

Arg Tyr Ser Ser Leu Thr Ala Ala
 1               5

<210> SEQ ID NO 269
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 269

Ser Leu Ala Tyr Tyr Thr Ala Leu
 1               5

<210> SEQ ID NO 270
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 270

Ser Leu Arg Tyr Tyr Thr Ala Ala
 1               5

<210> SEQ ID NO 271
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 271

Ser Pro Ala Tyr Tyr Thr Ala Leu
 1               5

<210> SEQ ID NO 272
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 272

Met His Lys Ala Leu Thr Ala Ala
 1               5
```

```
<210> SEQ ID NO 273
<211> LENGTH: 8
<212> TYPE: PRT
<213> ORGANISM: Artificial Sequence
<220> FEATURE:
<223> OTHER INFORMATION: MMP-2 cleavage site

<400> SEQUENCE: 273

Leu Arg Leu Ala Ile Thr Ala Leu
 1               5

<210> SEQ ID NO 274
<211> LENGTH: 8
<212> TYPE: PRT
<213> ORGANISM: Artificial Sequence
<220> FEATURE:
<223> OTHER INFORMATION: Consensus sequence for MMP-9 cleavage site
<220> FEATURE:
<221> NAME/KEY: VARIANT
<222> LOCATION: 1
<223> OTHER INFORMATION: Position 1 is F, D, E, N, Q, H, K, R, C, S, T,
      G, P, A, V, L, I or M
<220> FEATURE:
<221> NAME/KEY: VARIANT
<222> LOCATION: 2
<223> OTHER INFORMATION: Position 2 is F, Y, S, T, D, E, N, Q, H, K, R,
      G, P, A, V, L, I or M
<220> FEATURE:
<221> NAME/KEY: VARIANT
<222> LOCATION: 3, 8
<223> OTHER INFORMATION: Positions 3 and 8 are independently F, Y, D, E,
      N, Q, H, K, R, C, S, T, G, P, A, V, L, I or M
<220> FEATURE:
<221> NAME/KEY: VARIANT
<222> LOCATION: 4, 6, 7
<223> OTHER INFORMATION: Positions 4, 6 and 7 are independently any
      amino acid
<220> FEATURE:
<221> NAME/KEY: VARIANT
<222> LOCATION: 5
<223> OTHER INFORMATION: Position 5 is S, T, D, E, N, Q, H, K, R, F, W,
      Y, G, P, A, V, L, I or M

<400> SEQUENCE: 274

Xaa Xaa Xaa Xaa Xaa Xaa Xaa Xaa
 1               5

<210> SEQ ID NO 275
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 275

Ile Pro Glu Asn Phe Phe Gly Val
 1               5

<210> SEQ ID NO 276
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 276

Met Asp Ile Ala Ile His His Pro
 1               5

<210> SEQ ID NO 277
<211> LENGTH: 8
<212> TYPE: PRT
```

<213> ORGANISM: Artificial Sequence
<220> FEATURE:
<223> OTHER INFORMATION: MMP-9 cleavage site

<400> SEQUENCE: 277

Ser Pro Ser Arg Leu Phe Asp Gln
1               5

<210> SEQ ID NO 278
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 278

Ser Glu Met Arg Leu Glu Lys Asp
1               5

<210> SEQ ID NO 279
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 279

Phe Ser Val Asn Leu Asp Val Lys
1               5

<210> SEQ ID NO 280
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 280

Arg Leu Phe Asp Gln Phe Phe Gly
1               5

<210> SEQ ID NO 281
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 281

Phe Phe Gly Glu His Leu Leu Glu
1               5

<210> SEQ ID NO 282
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 282

Gly Leu Ser Glu Met Arg Leu Glu
1               5

<210> SEQ ID NO 283
<211> LENGTH: 8
<212> TYPE: PRT
<213> ORGANISM: Artificial Sequence
<220> FEATURE:

```
<223> OTHER INFORMATION: MMP-9 cleavage site

<400> SEQUENCE: 283

Ser Pro Glu Glu Leu Lys Val Lys
 1               5

<210> SEQ ID NO 284
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 284

Asp Val Ile Glu Val His Gly Lys
 1               5

<210> SEQ ID NO 285
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 285

Glu Val His Gly Lys His Glu Glu
 1               5

<210> SEQ ID NO 286
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 286

Asp Glu His Gly Phe Ile Ser Arg
 1               5

<210> SEQ ID NO 287
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 287

Gly Glu His Leu Leu Glu Ser Asp
 1               5

<210> SEQ ID NO 288
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 288

Phe His Arg Lys Tyr Arg Ile Pro
 1               5

<210> SEQ ID NO 289
<211> LENGTH: 8
<212> TYPE: PRT
<213> ORGANISM: Artificial Sequence
<220> FEATURE:
<223> OTHER INFORMATION: MMP-9 cleavage site
```

```
<400> SEQUENCE: 289

Gly Pro Arg Lys Gln Val Ser Gly
  1               5

<210> SEQ ID NO 290
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 290

Leu Ser Pro Phe Tyr Leu Arg Pro
  1               5

<210> SEQ ID NO 291
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 291

Pro Pro Ser Phe Leu Arg Ala Pro
  1               5

<210> SEQ ID NO 292
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 292

Asn Pro Leu Glu Asn Ser Gly Phe
  1               5

<210> SEQ ID NO 293
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 293

Val Pro Tyr Gly Leu Gly Ser Pro
  1               5

<210> SEQ ID NO 294
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 294

Pro Pro Leu Lys Leu Met His Ser
  1               5

<210> SEQ ID NO 295
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 295
```

```
Gly Pro Glu Gly Leu Arg Val Gly
1               5

<210> SEQ ID NO 296
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 296

Phe Met Lys Gly Leu Ser Lys Ala
1               5

<210> SEQ ID NO 297
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 297

Val Val Thr Gly Val Thr Ala Val
1               5

<210> SEQ ID NO 298
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 298

Ala Ile Ile Gly Leu Met Val Gly
1               5

<210> SEQ ID NO 299
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 299

Ser Asp Leu Gly Leu Thr Gly Ile
1               5

<210> SEQ ID NO 300
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 300

Val Pro Tyr Gly Leu Gly Ser Pro
1               5

<210> SEQ ID NO 301
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 301

Gly Ala Ala Gly Val Lys Gly Asp
1               5
```

```
<210> SEQ ID NO 302
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 302

Gly Pro Thr Gly Lys Gln Gly Asp
1               5

<210> SEQ ID NO 303
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 303

Gly Pro Ser Gly Asp Gln Gly Ala
1               5

<210> SEQ ID NO 304
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 304

Gly Pro Ser Gly Phe Pro Phe Pro
1               5

<210> SEQ ID NO 305
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 305

Gly Ala Pro Gly Phe Pro Gly Pro
1               5

<210> SEQ ID NO 306
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 306

Gly Ala Pro Gly Asn Arg Gly Phe
1               5

<210> SEQ ID NO 307
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 307

Gly Leu Arg Gly Glu Arg Gly Glu
1               5
```

```
<210> SEQ ID NO 308
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 308

Gly Pro Pro Gly Ser Gln Gly Asn
 1               5

<210> SEQ ID NO 309
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 309

Gly Pro Ala Gly Gln Gln Gly Ala
 1               5

<210> SEQ ID NO 310
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 310

Gly Pro Pro Gly Lys Asp Gly Thr
 1               5

<210> SEQ ID NO 311
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 311

Gly Gln Pro Gly Ser Pro Gly Ser
 1               5

<210> SEQ ID NO 312
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 312

Gly Ser Pro Gly Tyr Gln Gly Pro
 1               5

<210> SEQ ID NO 313
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 313

Gly Pro Val Ser Ala Val Leu Thr
 1               5

<210> SEQ ID NO 314
<211> LENGTH: 8
```

```
<212> TYPE: PRT
<213> ORGANISM: Artificial Sequence
<220> FEATURE:
<223> OTHER INFORMATION: MMP-9 cleavage site

<400> SEQUENCE: 314

Gly Pro Leu Gly Met Leu Ser Gln
 1               5

<210> SEQ ID NO 315
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 315

Gly Pro Leu Gly Met Trp Ala Gln
 1               5

<210> SEQ ID NO 316
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 316

Gly Pro Gln Gly Ile Phe Gly Gln
 1               5

<210> SEQ ID NO 317
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 317

Leu Pro Arg Ser Ala Lys Glu Leu
 1               5

<210> SEQ ID NO 318
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 318

Asn Ser Phe Gly Leu Arg Phe Gly
 1               5

<210> SEQ ID NO 319
<211> LENGTH: 8
<212> TYPE: PRT
<213> ORGANISM: Artificial Sequence
<220> FEATURE:
<223> OTHER INFORMATION: MMP-9 cleavage site

<400> SEQUENCE: 319

Arg Ala Ile His Ile Asn Ala Glu
 1               5

<210> SEQ ID NO 320
<211> LENGTH: 8
<212> TYPE: PRT
<213> ORGANISM: Artificial Sequence
```

```
<220> FEATURE:
<223> OTHER INFORMATION: Consensus sequence for Furin cleavage site
<220> FEATURE:
<221> NAME/KEY: VARIANT
<222> LOCATION: 1
<223> OTHER INFORMATION: Position 1 is R, I, or A
<220> FEATURE:
<221> NAME/KEY: VARIANT
<222> LOCATION: 2, 5, 6, 7, 8
<223> OTHER INFORMATION: Positions 2, 5, 6, 7, and 8 are independently
      any amino acid
<220> FEATURE:
<221> NAME/KEY: VARIANT
<222> LOCATION: 3
<223> OTHER INFORMATION: Position 3 is R, K, A, or P
<220> FEATURE:
<221> NAME/KEY: VARIANT
<222> LOCATION: (0)...(0)

<400> SEQUENCE: 320

Xaa Xaa Xaa Arg Xaa Xaa Xaa Xaa
 1               5

<210> SEQ ID NO 321
<211> LENGTH: 8
<212> TYPE: PRT
<213> ORGANISM: Artificial Sequence
<220> FEATURE:
<223> OTHER INFORMATION: Furin cleavage site

<400> SEQUENCE: 321

Arg Pro Arg Arg Ala Lys Arg Phe
 1               5

<210> SEQ ID NO 322
<211> LENGTH: 8
<212> TYPE: PRT
<213> ORGANISM: Artificial Sequence
<220> FEATURE:
<223> OTHER INFORMATION: Furin cleavage site

<400> SEQUENCE: 322

Arg Lys Lys Arg Gly Leu Tyr Ala
 1               5

<210> SEQ ID NO 323
<211> LENGTH: 8
<212> TYPE: PRT
<213> ORGANISM: Artificial Sequence
<220> FEATURE:
<223> OTHER INFORMATION: Furin cleavage site

<400> SEQUENCE: 323

Arg Glu Arg Arg Arg Lys Lys Arg
 1               5

<210> SEQ ID NO 324
<211> LENGTH: 8
<212> TYPE: PRT
<213> ORGANISM: Artificial Sequence
<220> FEATURE:
<223> OTHER INFORMATION: Furin cleavage site

<400> SEQUENCE: 324

Arg Lys Lys Arg Gly Leu Tyr Ala
 1               5

<210> SEQ ID NO 325
<211> LENGTH: 8
<212> TYPE: PRT
```

```
<213> ORGANISM: Artificial Sequence
<220> FEATURE:
<223> OTHER INFORMATION: Furin cleavage site

<400> SEQUENCE: 325

Arg Lys Lys Arg Thr Thr Ser Ala
1               5

<210> SEQ ID NO 326
<211> LENGTH: 8
<212> TYPE: PRT
<213> ORGANISM: Artificial Sequence
<220> FEATURE:
<223> OTHER INFORMATION: Furin cleavage site

<400> SEQUENCE: 326

Arg His Lys Arg Glu Thr Leu Lys
1               5

<210> SEQ ID NO 327
<211> LENGTH: 8
<212> TYPE: PRT
<213> ORGANISM: Artificial Sequence
<220> FEATURE:
<223> OTHER INFORMATION: Furin cleavage site

<400> SEQUENCE: 327

Arg Leu Lys Arg Asp Val Val Thr
1               5

<210> SEQ ID NO 328
<211> LENGTH: 8
<212> TYPE: PRT
<213> ORGANISM: Artificial Sequence
<220> FEATURE:
<223> OTHER INFORMATION: Furin cleavage site

<400> SEQUENCE: 328

Arg Met Lys Arg Glu Asp Leu Asn
1               5

<210> SEQ ID NO 329
<211> LENGTH: 8
<212> TYPE: PRT
<213> ORGANISM: Artificial Sequence
<220> FEATURE:
<223> OTHER INFORMATION: Furin cleavage site

<400> SEQUENCE: 329

Arg Ala Lys Arg Phe Ala Ser Leu
1               5

<210> SEQ ID NO 330
<211> LENGTH: 8
<212> TYPE: PRT
<213> ORGANISM: Artificial Sequence
<220> FEATURE:
<223> OTHER INFORMATION: Furin cleavage site

<400> SEQUENCE: 330

Arg Lys Lys Arg Phe Val Ser Ser
1               5

<210> SEQ ID NO 331
<211> LENGTH: 8
<212> TYPE: PRT
<213> ORGANISM: Artificial Sequence
<220> FEATURE:
```

<223> OTHER INFORMATION: Furin cleavage site

<400> SEQUENCE: 331

Arg Thr Lys Arg Phe Leu Ser Tyr
1               5

<210> SEQ ID NO 332
<211> LENGTH: 8
<212> TYPE: PRT
<213> ORGANISM: Artificial Sequence
<220> FEATURE:
<223> OTHER INFORMATION: Furin cleavage site

<400> SEQUENCE: 332

Arg Arg Ala Arg Ser Val Asp Gly
1 5

<210> SEQ ID NO 333
<211> LENGTH: 8
<212> TYPE: PRT
<213> ORGANISM: Artificial Sequence
<220> FEATURE:
<223> OTHER INFORMATION: Furin cleavage site

<400> SEQUENCE: 333

Val Phe Arg Arg Asp Ala His Lys
1 5

<210> SEQ ID NO 334
<211> LENGTH: 8
<212> TYPE: PRT
<213> ORGANISM: Artificial Sequence
<220> FEATURE:
<223> OTHER INFORMATION: Furin cleavage site

<400> SEQUENCE: 334

Val Phe Arg Arg Glu Ala His Lys
1 5

<210> SEQ ID NO 335
<211> LENGTH: 8
<212> TYPE: PRT
<213> ORGANISM: Artificial Sequence
<220> FEATURE:
<223> OTHER INFORMATION: Furin cleavage site

<400> SEQUENCE: 335

Arg Val Ala Arg Asp Ile Thr Met
1 5

<210> SEQ ID NO 336
<211> LENGTH: 8
<212> TYPE: PRT
<213> ORGANISM: Artificial Sequence
<220> FEATURE:
<223> OTHER INFORMATION: Furin cleavage site

<400> SEQUENCE: 336

Arg Ile Ser Arg Ser Leu Pro Gln
1 5

<210> SEQ ID NO 337
<211> LENGTH: 8
<212> TYPE: PRT
<213> ORGANISM: Artificial Sequence
<220> FEATURE:
<223> OTHER INFORMATION: Furin cleavage site

<400> SEQUENCE: 337

Arg Ser Arg Arg Ala Thr Ser
1               5

<210> SEQ ID NO 338
<211> LENGTH: 8
<212> TYPE: PRT
<213> ORGANISM: Artificial Sequence
<220> FEATURE:
<223> OTHER INFORMATION: Furin cleavage site

<400> SEQUENCE: 338

Arg Ala Lys Arg Ser Pro Lys His
1               5

<210> SEQ ID NO 339
<211> LENGTH: 8
<212> TYPE: PRT
<213> ORGANISM: Artificial Sequence
<220> FEATURE:
<223> OTHER INFORMATION: Furin cleavage site

<400> SEQUENCE: 339

Phe Trp His Arg Gly Val Thr Lys
1               5

<210> SEQ ID NO 340
<211> LENGTH: 8
<212> TYPE: PRT
<213> ORGANISM: Artificial Sequence
<220> FEATURE:
<223> OTHER INFORMATION: Furin cleavage site

<400> SEQUENCE: 340

Ala Lys Arg Arg Thr Lys Arg Asp
1               5

<210> SEQ ID NO 341
<211> LENGTH: 8
<212> TYPE: PRT
<213> ORGANISM: Artificial Sequence
<220> FEATURE:
<223> OTHER INFORMATION: Furin cleavage site

<400> SEQUENCE: 341

Ala Lys Arg Arg Ala Lys Arg Asp
1               5

<210> SEQ ID NO 342
<211> LENGTH: 8
<212> TYPE: PRT
<213> ORGANISM: Artificial Sequence
<220> FEATURE:
<223> OTHER INFORMATION: Furin cleavage site

<400> SEQUENCE: 342

Ala Lys Gln Arg Ala Lys Arg Asp
1               5

<210> SEQ ID NO 343
<211> LENGTH: 8
<212> TYPE: PRT
<213> ORGANISM: Artificial Sequence
<220> FEATURE:
<223> OTHER INFORMATION: Furin cleavage site

<400> SEQUENCE: 343

```
Arg Asp Val Arg Gly Phe Ala Ser
 1               5

<210> SEQ ID NO 344
<211> LENGTH: 8
<212> TYPE: PRT
<213> ORGANISM: Artificial Sequence
<220> FEATURE:
<223> OTHER INFORMATION: Furin cleavage site

<400> SEQUENCE: 344

Arg Lys Arg Arg Ser Val Asn Pro
 1               5

<210> SEQ ID NO 345
<211> LENGTH: 8
<212> TYPE: PRT
<213> ORGANISM: Artificial Sequence
<220> FEATURE:
<223> OTHER INFORMATION: Furin cleavage site

<400> SEQUENCE: 345

Arg Gln Lys Arg Phe Val Leu Ser
 1               5

<210> SEQ ID NO 346
<211> LENGTH: 8
<212> TYPE: PRT
<213> ORGANISM: Artificial Sequence
<220> FEATURE:
<223> OTHER INFORMATION: Furin cleavage site

<400> SEQUENCE: 346

Arg Ser Lys Arg Ser Leu Ser Cys
 1               5

<210> SEQ ID NO 347
<211> LENGTH: 8
<212> TYPE: PRT
<213> ORGANISM: Artificial Sequence
<220> FEATURE:
<223> OTHER INFORMATION: Consensus sequence for u-PA cleavage site
<220> FEATURE:
<221> NAME/KEY: VARIANT
<222> LOCATION: 1, 5, 8
<223> OTHER INFORMATION: Positions 1, 5, and 8 are independently any
      amino acid
<220> FEATURE:
<221> NAME/KEY: VARIANT
<222> LOCATION: 2, 7
<223> OTHER INFORMATION: Positions 2 and 7 are independently an
      uncharged amino acid like C, S, and T, an aromatic amino
      acid like F, W, and Y, or an aliphatic hydrophobic
      amino acid like, G, P, A, V, L, I, and M
<220> FEATURE:
<221> NAME/KEY: VARIANT
<222> LOCATION: 3
<223> OTHER INFORMATION: Position 3 is an amidic amino acid like N and
      Q, an uncharged amino acid like C, S, and T, or an
      aliphatic hydrophobic amino acid like, G, P, A, V,
      L, I, and M
<220> FEATURE:
<221> NAME/KEY: VARIANT
<222> LOCATION: 4
<223> OTHER INFORMATION: Position 4 is K or R
<220> FEATURE:
<221> NAME/KEY: VARIANT
<222> LOCATION: 6
<223> OTHER INFORMATION: Position 6 is a basic amino acid like K and R,
      an aromatic amino acid like F, W, and Y, or an
      aliphatic hydrophobic amino acid like, G, P, A, V,
      L, I, and M
```

```
<400> SEQUENCE: 347

Xaa Xaa Xaa Xaa Xaa Xaa Xaa Xaa
 1               5

<210> SEQ ID NO 348
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 348

Gly Ser Gly Lys Ser Ala Thr Leu
 1               5

<210> SEQ ID NO 349
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 349

Gln Arg Gly Arg Ser Ala Thr Leu
 1               5

<210> SEQ ID NO 350
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 350

Arg Gly Ser Val Ile Leu Thr Val
 1               5

<210> SEQ ID NO 351
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 351

Pro Ser Ser Arg Arg Arg Val Asn
 1               5

<210> SEQ ID NO 352
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 352

Cys Pro Gly Arg Val Val Gly Gly
 1               5

<210> SEQ ID NO 353
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 353
```

```
Pro Gly Ala Arg Gly Arg Ala Phe
1               5

<210> SEQ ID NO 354
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 354

Ser Ser Ser Arg Gly Pro Thr His
1               5

<210> SEQ ID NO 355
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 355

Val Ser Asn Lys Tyr Phe Ser Asn
1               5

<210> SEQ ID NO 356
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 356

Asn Ser Gly Arg Ala Val Thr Tyr
1               5

<210> SEQ ID NO 357
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 357

Thr Tyr Ser Arg Ser Arg Tyr Leu
1               5

<210> SEQ ID NO 358
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 358

Asn Ser Gly Arg Ala Val Thr Tyr
1               5

<210> SEQ ID NO 359
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 359

Pro Ser Gly Arg Gly Arg Thr Leu
1               5
```

<210> SEQ ID NO 360
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 360

Ala Gly Ser Arg Ala Val Tyr Tyr
1               5

<210> SEQ ID NO 361
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 361

Thr Tyr Gly Arg Ser Arg Thr Asn
1               5

<210> SEQ ID NO 362
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 362

Asn Ser Ser Arg Gly Val Tyr Leu
1               5

<210> SEQ ID NO 363
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 363

Pro Ser Ser Arg Ser Val Tyr Asn
1               5

<210> SEQ ID NO 364
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 364

Ala Ser Gly Arg Gly Arg Thr Tyr
1               5

<210> SEQ ID NO 365
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 365

Thr Ser Ser Arg Ala Val Tyr Leu
1               5

```
<210> SEQ ID NO 366
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 366

Asn Ser Gly Arg Ser Arg Thr Leu
 1               5

<210> SEQ ID NO 367
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 367

Val Ser Gly Arg Ile Arg Thr Gly
 1               5

<210> SEQ ID NO 368
<211> LENGTH: 8
<212> TYPE: PRT
<213> ORGANISM: Artificial Sequence
<220> FEATURE:
<223> OTHER INFORMATION: u-PA cleavage site

<400> SEQUENCE: 368

Ser Ser Gly Arg Ile Arg Thr Val
 1               5

<210> SEQ ID NO 369
<211> LENGTH: 8
<212> TYPE: PRT
<213> ORGANISM: Artificial Sequence
<220> FEATURE:
<223> OTHER INFORMATION: Consensus sequence for t-PA cleavage site
<220> FEATURE:
<221> NAME/KEY: VARIANT
<222> LOCATION: 1, 2, 3, 5, 6, 7, 8
<223> OTHER INFORMATION: Positions 1, 2, 3, 5, 6, 7, and 8 are
      independently any amino acid
<220> FEATURE:
<221> NAME/KEY: VARIANT
<222> LOCATION: 4
<223> OTHER INFORMATION: Position 4 is K or R

<400> SEQUENCE: 369

Xaa Xaa Xaa Xaa Xaa Xaa Xaa Xaa
 1               5

<210> SEQ ID NO 370
<211> LENGTH: 8
<212> TYPE: PRT
<213> ORGANISM: Artificial Sequence
<220> FEATURE:
<223> OTHER INFORMATION: t-PA cleavage site

<400> SEQUENCE: 370

Asn Ala Leu Arg Tyr Ala Pro Asp
 1               5

<210> SEQ ID NO 371
<211> LENGTH: 8
<212> TYPE: PRT
<213> ORGANISM: Artificial Sequence
<220> FEATURE:
<223> OTHER INFORMATION: t-PA cleavage site
```

<400> SEQUENCE: 371

Cys Pro Gly Arg Val Val Gly Gly
 1               5

<210> SEQ ID NO 372
<211> LENGTH: 8
<212> TYPE: PRT
<213> ORGANISM: Artificial Sequence
<220> FEATURE:
<223> OTHER INFORMATION: t-PA cleavage site

<400> SEQUENCE: 372

Pro Gln Phe Arg Ile Lys Gly Gly
 1               5

<210> SEQ ID NO 373
<211> LENGTH: 8
<212> TYPE: PRT
<213> ORGANISM: Artificial Sequence
<220> FEATURE:
<223> OTHER INFORMATION: t-PA cleavage site

<400> SEQUENCE: 373

Ala Leu Ser Arg Met Ala Val Leu
 1               5

<210> SEQ ID NO 374
<211> LENGTH: 6
<212> TYPE: PRT
<213> ORGANISM: Artificial Sequence
<220> FEATURE:
<223> OTHER INFORMATION: Consensus sequence for Tryptase-epsilon
      cleavage site
<220> FEATURE:
<221> NAME/KEY: VARIANT
<222> LOCATION: 1
<223> OTHER INFORMATION: Position 1 is K or R
<220> FEATURE:
<221> NAME/KEY: VARIANT
<222> LOCATION: 2, 3, 4, 5
<223> OTHER INFORMATION: Positions 2, 3, 4, and 5 are independently an
      aliphatic hydrophobic amino acid like, G, P, A, V,
      L, I, and M
<220> FEATURE:
<221> NAME/KEY: VARIANT
<222> LOCATION: 6
<223> OTHER INFORMATION: Position 6 is D or E

<400> SEQUENCE: 374

Xaa Xaa Xaa Xaa Xaa Xaa
 1               5

<210> SEQ ID NO 375
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 375

Arg Val Val Gly Gly Glu
 1               5

<210> SEQ ID NO 376
<211> LENGTH: 6
<212> TYPE: PRT
<213> ORGANISM: Artificial Sequence
<220> FEATURE:
<223> OTHER INFORMATION: Tryptase-epsilon cleavage site

```
<400> SEQUENCE: 376

Arg Ile Val Gly Gly Glu
 1               5

<210> SEQ ID NO 377
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 377

Arg Ile Ile Gly Gly Glu
 1               5

<210> SEQ ID NO 378
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 378

Arg Val Val Gly Gly Asp
 1               5

<210> SEQ ID NO 379
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 379

Arg Ile Val Gly Gly Asp
 1               5

<210> SEQ ID NO 380
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 380

Arg Ile Ile Gly Gly Asp
 1               5

<210> SEQ ID NO 381
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 381

Lys Val Val Gly Gly Glu
 1               5

<210> SEQ ID NO 382
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 382
```

Lys Ile Val Gly Gly Glu
1               5

<210> SEQ ID NO 383
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 383

Lys Ile Ile Gly Gly Glu
1               5

<210> SEQ ID NO 384
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 384

Lys Val Val Gly Gly Asp
1               5

<210> SEQ ID NO 385
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 385

Lys Ile Val Gly Gly Asp
1               5

<210> SEQ ID NO 386
<211> LENGTH: 6
<212> TYPE: PRT
<213> ORGANISM: Artificial Sequence
<220> FEATURE:
<223> OTHER INFORMATION: Tryptase-epsilon cleavage site

<400> SEQUENCE: 386

Lys Ile Ile Gly Gly Asp
1               5

<210> SEQ ID NO 387
<211> LENGTH: 8
<212> TYPE: PRT
<213> ORGANISM: Artificial Sequence
<220> FEATURE:
<223> OTHER INFORMATION: Consensus sequence for mMCP-7 cleavage site
<220> FEATURE:
<221> NAME/KEY: VARIANT
<222> LOCATION: 1, 5, 6, 7, 8
<223> OTHER INFORMATION: Positions 1, 5, 6, 7, and 8 are independently
      any amino acid
<220> FEATURE:
<221> NAME/KEY: VARIANT
<222> LOCATION: 2
<223> OTHER INFORMATION: Potition 2 is an amidic amino acid like N or Q,
      or an aliphatic hydrophobic amino acid like, G, P, A,
      V, L, I, and M
<220> FEATURE:
<221> NAME/KEY: VARIANT
<222> LOCATION: 3
<223> OTHER INFORMATION: Position 3 is an aliphatic hydrophobic amino
      acid like, G, P, A, V, L, I, and M
<220> FEATURE:

```
<221> NAME/KEY: VARIANT
<222> LOCATION: 4
<223> OTHER INFORMATION: Position 4 is K or R

<400> SEQUENCE: 387

Xaa Xaa Xaa Xaa Xaa Xaa Xaa Xaa
 1               5

<210> SEQ ID NO 388
<211> LENGTH: 8
<212> TYPE: PRT
<213> ORGANISM: Artificial Sequence
<220> FEATURE:
<223> OTHER INFORMATION: mMCP-7 cleavage site

<400> SEQUENCE: 388

Leu Ser Ser Arg Gln Ser Pro Gly
 1               5

<210> SEQ ID NO 389
<211> LENGTH: 8
<212> TYPE: PRT
<213> ORGANISM: Artificial Sequence
<220> FEATURE:
<223> OTHER INFORMATION: mMCP-7 cleavage site

<400> SEQUENCE: 389

Leu Gln Ala Arg Gly Ala Ser Leu
 1               5

<210> SEQ ID NO 390
<211> LENGTH: 8
<212> TYPE: PRT
<213> ORGANISM: Artificial Sequence
<220> FEATURE:
<223> OTHER INFORMATION: mMCP-7 cleavage site

<400> SEQUENCE: 390

Leu Gly Pro Lys Ala Ile Thr Met
 1               5

<210> SEQ ID NO 391
<211> LENGTH: 8
<212> TYPE: PRT
<213> ORGANISM: Artificial Sequence
<220> FEATURE:
<223> OTHER INFORMATION: mMCP-7 cleavage site

<400> SEQUENCE: 391

Leu Gly Pro Arg Ser Ala Val Tyr
 1               5

<210> SEQ ID NO 392
<211> LENGTH: 8
<212> TYPE: PRT
<213> ORGANISM: Artificial Sequence
<220> FEATURE:
<223> OTHER INFORMATION: Consensus sequence for ECE-1 cleavage site
<220> FEATURE:
<221> NAME/KEY: VARIANT
<222> LOCATION: 1, 2, 3, 4, 6, 7, 8
<223> OTHER INFORMATION: Positions 1, 2, 3, 4, 6, 7, and 8 are
      independently any amino acid
<220> FEATURE:
<221> NAME/KEY: VARIANT
<222> LOCATION: 5
<223> OTHER INFORMATION: Position 5 is F, L, I, V, or Y

<400> SEQUENCE: 392
```

```
Xaa Xaa Xaa Xaa Xaa Xaa Xaa Xaa
 1               5

<210> SEQ ID NO 393
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 393

His Gln Lys Leu Val Phe Phe Ala
 1               5

<210> SEQ ID NO 394
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 394

His His Gln Lys Leu Val Phe Phe
 1               5

<210> SEQ ID NO 395
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 395

Lys Leu Val Phe Phe Ala Glu Asp
 1               5

<210> SEQ ID NO 396
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 396

Asp Arg Val Tyr Ile His Pro Phe
 1               5

<210> SEQ ID NO 397
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 397

Tyr Ile His Pro Phe His Leu Val
 1               5

<210> SEQ ID NO 398
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 398

Tyr Gly Leu Gly Ser Pro Arg Ser
 1               5
```

```
<210> SEQ ID NO 399
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 399

Thr Pro Glu His Val Val Pro Tyr
1               5

<210> SEQ ID NO 400
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 400

Asp Ile Ile Trp Val Asn Thr Pro
1               5

<210> SEQ ID NO 401
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 401

Asp Ile Ile Trp Ile Asn Thr Pro
1               5

<210> SEQ ID NO 402
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 402

Cys His Leu Asp Ile Ile Trp Val
1               5

<210> SEQ ID NO 403
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 403

His Leu Asp Ile Ile Trp Val Asn
1               5

<210> SEQ ID NO 404
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 404

Cys Val Tyr Phe Cys His Leu Asp
1               5
```

```
<210> SEQ ID NO 405
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 405

Ser Cys Ser Ser Leu Met Asp Lys
1               5

<210> SEQ ID NO 406
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 406

Glu Cys Val Tyr Phe Cys His Leu
1               5

<210> SEQ ID NO 407
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 407

Arg Ser Lys Arg Cys Ser Cys Ser
1               5

<210> SEQ ID NO 408
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 408

Arg Ser Lys Arg Ala Leu Glu Asn
1               5

<210> SEQ ID NO 409
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 409

Gly Phe Ser Pro Phe Arg Ser Ser
1               5

<210> SEQ ID NO 410
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 410

Pro Arg Arg Pro Tyr Ile Leu Pro
1               5

<210> SEQ ID NO 411
<211> LENGTH: 8
```

```
<212> TYPE: PRT
<213> ORGANISM: Artificial Sequence
<220> FEATURE:
<223> OTHER INFORMATION: ECE-1 cleavage site

<400> SEQUENCE: 411

Lys Pro Gln Gln Phe Phe Gly Leu
 1               5

<210> SEQ ID NO 412
<211> LENGTH: 8
<212> TYPE: PRT
<213> ORGANISM: Artificial Sequence
<220> FEATURE:
<223> OTHER INFORMATION: ECE-1 cleavage site

<400> SEQUENCE: 412

Pro Gln Gln Phe Phe Gly Leu Met
 1               5

<210> SEQ ID NO 413
<211> LENGTH: 8
<212> TYPE: PRT
<213> ORGANISM: Artificial Sequence
<220> FEATURE:
<223> OTHER INFORMATION: Consensus sequence for KBGP cleavage site
<220> FEATURE:
<221> NAME/KEY: VARIANT
<222> LOCATION: 1
<223> OTHER INFORMATION: Position 1 is an acidic amino acid like D and E
<220> FEATURE:
<221> NAME/KEY: VARIANT
<222> LOCATION: 2, 5
<223> OTHER INFORMATION: Positions 2 and 5 are independently T or an
      aliphatic hydrophobic amino acid like, G, P, A, V,
      L, I, and M
<220> FEATURE:
<221> NAME/KEY: VARIANT
<222> LOCATION: 3, 8
<223> OTHER INFORMATION: Positions 3 and 8 are independently an
      aliphatic hydrophobic amino acid like, G, P, A, V, L, I, and
      M
<220> FEATURE:
<221> NAME/KEY: VARIANT
<222> LOCATION: 4
<223> OTHER INFORMATION: Position 4 is an aromatic amino acid like F, W
<220> FEATURE:
<221> NAME/KEY: VARIANT
<222> LOCATION: 6
<223> OTHER INFORMATION: Position 6 is an amidic amino acid like N and Q
<220> FEATURE:
<221> NAME/KEY: VARIANT
<222> LOCATION: (7)...(7)
<223> OTHER INFORMATION: Position 7 is an uncharged amino acid like C,
      S, and T, or a C-beta branched amino acid like I, V,
      or T

<400> SEQUENCE: 413

Xaa Xaa Xaa Xaa Xaa Xaa Xaa Xaa
 1               5

<210> SEQ ID NO 414
<211> LENGTH: 8
<212> TYPE: PRT
<213> ORGANISM: Artificial Sequence
<220> FEATURE:
<223> OTHER INFORMATION: KBGP cleavage site

<400> SEQUENCE: 414

Asp Ile Ile Trp Val Asn Thr Pro
 1               5
```

```
<210> SEQ ID NO 415
<211> LENGTH: 8
<212> TYPE: PRT
<213> ORGANISM: Artificial Sequence
<220> FEATURE:
<223> OTHER INFORMATION: KBGP cleavage site

<400> SEQUENCE: 415

Asp Ile Ile Trp Ile Asn Thr Pro
 1               5

<210> SEQ ID NO 416
<211> LENGTH: 8
<212> TYPE: PRT
<213> ORGANISM: Artificial Sequence
<220> FEATURE:
<223> OTHER INFORMATION: Consensus sequence for Cathepsin L cleavage
      site
<220> FEATURE:
<221> NAME/KEY: VARIANT
<222> LOCATION: 1
<223> OTHER INFORMATION: Position 1 is W, D, E, N, Q, H, K, R, C, S, T,
      G, P, A, V, L, I or M
<220> FEATURE:
<221> NAME/KEY: VARIANT
<222> LOCATION: 2, 4, 5, 6, 7, 8
<223> OTHER INFORMATION: Positions 2, 4, 5, 6, 7, 8  are independently
      any amino acid
<220> FEATURE:
<221> NAME/KEY: VARIANT
<222> LOCATION: 3
<223> OTHER INFORMATION: Position 3 is L, V, F or Y

<400> SEQUENCE: 416

Xaa Xaa Xaa Xaa Xaa Xaa Xaa Xaa
 1               5

<210> SEQ ID NO 417
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 417

Met Phe Leu Glu Ala Ile Pro Met
 1               5

<210> SEQ ID NO 418
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 418

Lys Val Phe Gln Glu Pro Leu Phe
 1               5

<210> SEQ ID NO 419
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 419

Ala Thr Leu Thr Phe Asp His Ser
 1               5
```

```
<210> SEQ ID NO 420
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 420

Pro Leu Phe Tyr Glu Ala Pro Arg
 1               5

<210> SEQ ID NO 421
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 421

Thr Gly Leu Arg Asp Pro Phe Asn
 1               5

<210> SEQ ID NO 422
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 422

Lys Ile Leu His Leu Pro Thr Ser
 1               5

<210> SEQ ID NO 423
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 423

Ala His Leu Lys Asn Ser Gln Glu
 1               5

<210> SEQ ID NO 424
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 424

Ala Pro Leu Thr Ala Glu Ile Gln
 1               5

<210> SEQ ID NO 425
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 425

Glu Ala Leu Phe Ala Glu Arg Lys
 1               5

<210> SEQ ID NO 426
<211> LENGTH: 8
```

```
<212> TYPE: PRT
<213> ORGANISM: Artificial Sequence
<220> FEATURE:
<223> OTHER INFORMATION: Cathepsin L cleavage site

<400> SEQUENCE: 426

Glu Pro Leu Ala Ala Glu Arg Lys
  1               5

<210> SEQ ID NO 427
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 427

Gly Thr Phe Thr Ser Asp Tyr Ser
  1               5

<210> SEQ ID NO 428
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 428

Lys Tyr Leu Asp Ser Arg Arg Ala
  1               5

<210> SEQ ID NO 429
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 429

Gln Asp Phe Val Gln Trp Leu Met
  1               5

<210> SEQ ID NO 430
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 430

Lys Gln Leu Ala Thr Lys Ala Ala
  1               5

<210> SEQ ID NO 431
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 431

Ser Thr Phe Glu Glu Arg Ser Tyr
  1               5

<210> SEQ ID NO 432
<211> LENGTH: 8
<212> TYPE: PRT
<213> ORGANISM: Artificial Sequence
```

```
<220> FEATURE:
<223> OTHER INFORMATION: Cathepsin L cleavage site

<400> SEQUENCE: 432

Leu Arg Leu Glu Trp Pro Tyr Gln
1               5

<210> SEQ ID NO 433
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 433

Arg Gly Phe Phe Tyr Thr Pro Lys
1               5

<210> SEQ ID NO 434
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 434

Gly Phe Phe Tyr Thr Pro Lys Ala
1               5

<210> SEQ ID NO 435
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 435

His Phe Phe Lys Asn Ile Val Thr
1               5

<210> SEQ ID NO 436
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 436

Arg Gly Leu Ser Leu Ser Arg Phe
1               5

<210> SEQ ID NO 437
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 437

Gln Trp Leu Gly Ala Pro Val Pro
1               5

<210> SEQ ID NO 438
<211> LENGTH: 8
<212> TYPE: PRT
<213> ORGANISM: Artificial Sequence
<220> FEATURE:
<223> OTHER INFORMATION: Cathepsin L cleavage site
```

```
<400> SEQUENCE: 438

Asn Met Leu Lys Arg Gly Leu Pro
1               5

<210> SEQ ID NO 439
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 439

Leu Ser Leu Ala His Thr His Gln
1               5

<210> SEQ ID NO 440
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 440

Thr Pro Phe Ala Ala Thr Ser Ser
1               5

<210> SEQ ID NO 441
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 441

Lys Leu Leu Ala Val Ser Gly Pro
1               5

<210> SEQ ID NO 442
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 442

Gln Leu Phe Arg Arg Ala Val Leu
1               5

<210> SEQ ID NO 443
<211> LENGTH: 8
<212> TYPE: PRT
<213> ORGANISM: Artificial Sequence
<220> FEATURE:
<223> OTHER INFORMATION: Cathepsin L cleavage site

<400> SEQUENCE: 443

Pro Arg Phe Lys Ile Ile Gly Gly
1               5

<210> SEQ ID NO 444
<211> LENGTH: 6
<212> TYPE: PRT
<213> ORGANISM: Artificial Sequence
<220> FEATURE:
<223> OTHER INFORMATION: Consensus sequence for PAR1 cleavage site
<220> FEATURE:
<221> NAME/KEY: VARIANT
```

```
<222> LOCATION: 1
<223> OTHER INFORMATION: Position 1 is a small non-polar amino acid like
      A, C G, S, and T
<220> FEATURE:
<221> NAME/KEY: VARIANT
<222> LOCATION: 2, 3
<223> OTHER INFORMATION: Positions 2 and 3 are independently a large
      non-polar amino acid like F, I, L, M, V, or an
      aromatic amino acid like F, H, W, or Y
<220> FEATURE:
<221> NAME/KEY: VARIANT
<222> LOCATION: 4
<223> OTHER INFORMATION: Position 4 is an aliphatic hydrophobic amino
      acid like, G, P, A, V, L, I, and M
<220> FEATURE:
<221> NAME/KEY: VARIANT
<222> LOCATION: 5
<223> OTHER INFORMATION: Position 5 is K or R
<220> FEATURE:
<221> NAME/KEY: VARIANT
<222> LOCATION: 6
<223> OTHER INFORMATION: Position 6 is an amidic amino acid like N and
      Q, or an aromatic hydrophobic amino acid like F, W,
      or Y

<400> SEQUENCE: 444

Xaa Xaa Xaa Xaa Xaa Xaa
 1               5

<210> SEQ ID NO 445
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 445

Ser Phe Leu Leu Arg Asn
 1               5

<210> SEQ ID NO 446
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 446

Ser Phe Phe Leu Arg Asn
 1               5

<210> SEQ ID NO 447
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 447

Ser Phe Phe Leu Lys Asn
 1               5

<210> SEQ ID NO 448
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 448

Thr Phe Leu Leu Arg Asn
```

<210> SEQ ID NO 449
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 449

Gly Phe Pro Gly Lys Phe
1               5

<210> SEQ ID NO 450
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 450

Gly Tyr Pro Ala Lys Phe
1               5

<210> SEQ ID NO 451
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 451

Gly Tyr Pro Leu Lys Phe
1               5

<210> SEQ ID NO 452
<211> LENGTH: 6
<212> TYPE: PRT
<213> ORGANISM: Artificial Sequence
<220> FEATURE:
<223> OTHER INFORMATION: PAR1 cleavage site

<400> SEQUENCE: 452

Gly Tyr Pro Ile Lys Phe
1               5

<210> SEQ ID NO 453
<211> LENGTH: 6
<212> TYPE: PRT
<213> ORGANISM: Artificial Sequence
<220> FEATURE:
<223> OTHER INFORMATION: Consensus sequence for PAR2 cleavage site
<220> FEATURE:
<221> NAME/KEY: VARIANT
<222> LOCATION: 1
<223> OTHER INFORMATION: Position 1 is a small non-polar amino acid like
      A, C G, S, and T
<220> FEATURE:
<221> NAME/KEY: VARIANT
<222> LOCATION: 2, 3, 6
<223> OTHER INFORMATION: Positions 2, 3, and 6 are independently a large
      non-polar amino acid like F, I, L, M, V
<220> FEATURE:
<221> NAME/KEY: VARIANT
<222> LOCATION: 4
<223> OTHER INFORMATION: Position 4 is an aliphatic hydrophobic amino
      acid like, G, P, A, V, L, I, and M
<220> FEATURE:
<221> NAME/KEY: VARIANT
<222> LOCATION: 5
<223> OTHER INFORMATION: Position 5 is K or R

```
<400> SEQUENCE: 453

Xaa Xaa Xaa Xaa Xaa Xaa
 1               5

<210> SEQ ID NO 454
<211> LENGTH: 6
<212> TYPE: PRT
<213> ORGANISM: Artificial Sequence
<220> FEATURE:
<223> OTHER INFORMATION: PAR2 cleavage site

<400> SEQUENCE: 454

Ser Leu Ile Gly Lys Val
 1               5

<210> SEQ ID NO 455
<211> LENGTH: 6
<212> TYPE: PRT
<213> ORGANISM: Artificial Sequence
<220> FEATURE:
<223> OTHER INFORMATION: PAR2 cleavage site

<400> SEQUENCE: 455

Ser Leu Ile Gly Arg Leu
 1               5

<210> SEQ ID NO 456
<211> LENGTH: 6
<212> TYPE: PRT
<213> ORGANISM: Artificial Sequence
<220> FEATURE:
<223> OTHER INFORMATION: Consensus sequence for PAR3 cleavage site
<220> FEATURE:
<221> NAME/KEY: VARIANT
<222> LOCATION: 1, 4
<223> OTHER INFORMATION: Positions 1 and 4 are independently a small
      non-polar amino acid like A, C G, S, and T
<220> FEATURE:
<221> NAME/KEY: VARIANT
<222> LOCATION: 2
<223> OTHER INFORMATION: Position 2 is a large non-polar amino acid like
      F, I, L, M, V
<220> FEATURE:
<221> NAME/KEY: VARIANT
<222> LOCATION: 3
<223> OTHER INFORMATION: Position 3 is an amidic amino acid like N and
      Q, or a basic amino acid like K and R
<220> FEATURE:
<221> NAME/KEY: VARIANT
<222> LOCATION: 5
<223> OTHER INFORMATION: Position 5 is a small non-polar amino acid like
      A, C G, S, and T, or a small polar amino acid like D,
      N, or P
<220> FEATURE:
<221> NAME/KEY: VARIANT
<222> LOCATION: 6
<223> OTHER INFORMATION: Position 6 is an acidic amino acid like D and
      E, or a small polar amino acid like D, N, or P

<400> SEQUENCE: 456

Xaa Xaa Xaa Xaa Xaa Xaa
 1               5

<210> SEQ ID NO 457
<211> LENGTH: 6
<212> TYPE: PRT
<213> ORGANISM: Artificial Sequence
<220> FEATURE:
<223> OTHER INFORMATION: PAR3 cleavage site

<400> SEQUENCE: 457
```

```
Thr Phe Arg Gly Ala Pro
1               5

<210> SEQ ID NO 458
<211> LENGTH: 6
<212> TYPE: PRT
<213> ORGANISM: Artificial Sequence
<220> FEATURE:
<223> OTHER INFORMATION: PAR3 cleavage site

<400> SEQUENCE: 458

Ser Phe Asn Gly Gly Pro
1               5

<210> SEQ ID NO 459
<211> LENGTH: 6
<212> TYPE: PRT
<213> ORGANISM: Artificial Sequence
<220> FEATURE:
<223> OTHER INFORMATION: PAR3 cleavage site

<400> SEQUENCE: 459

Ser Phe Asn Gly Asn Glu
1               5

<210> SEQ ID NO 460
<211> LENGTH: 6
<212> TYPE: PRT
<213> ORGANISM: Artificial Sequence
<220> FEATURE:
<223> OTHER INFORMATION: Consensus sequence for PAR4 cleavage site
<220> FEATURE:
<221> NAME/KEY: VARIANT
<222> LOCATION: 1
<223> OTHER INFORMATION: Position 1 is a small non-polar amino acid like
      A, C G, S, and T
<220> FEATURE:
<221> NAME/KEY: VARIANT
<222> LOCATION: 2
<223> OTHER INFORMATION: Position 2 is a large non-polar amino acid like
      F, I, L, M, V, or an aromatic amino acid like F, H,
      W, or Y
<220> FEATURE:
<221> NAME/KEY: VARIANT
<222> LOCATION: 3, 4
<223> OTHER INFORMATION: Positions 3 and 4 are independently an
      aliphatic hydrophobic amino acid like, G, P, A, V, L, I, and
      M
<220> FEATURE:
<221> NAME/KEY: VARIANT
<222> LOCATION: 5
<223> OTHER INFORMATION: Position 5 is K or R
<220> FEATURE:
<221> NAME/KEY: VARIANT
<222> LOCATION: 6
<223> OTHER INFORMATION: Position 6 is a basic amino acid like K and R,
      an aromatic hydrophobic amino acid like F, W, or Y,
      or an aliphatic hydrophobic amino acid like, G, P,
      A, V, L, I, and M

<400> SEQUENCE: 460

Xaa Xaa Xaa Xaa Xaa Xaa
1               5

<210> SEQ ID NO 461
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 461
```

```
Gly Tyr Pro Gly Gln Val
1               5

<210> SEQ ID NO 462
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 462

Ala Tyr Pro Gly Lys Phe
1               5

<210> SEQ ID NO 463
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 463

Thr Tyr Pro Gly Lys Phe
1               5

<210> SEQ ID NO 464
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 464

Gly Tyr Pro Gly Lys Tyr
1               5

<210> SEQ ID NO 465
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 465

Gly Tyr Pro Gly Lys Trp
1               5

<210> SEQ ID NO 466
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 466

Gly Tyr Pro Gly Lys Lys
1               5

<210> SEQ ID NO 467
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 467

Gly Tyr Pro Gly Lys Phe
```

<210> SEQ ID NO 468
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 468

Gly Tyr Pro Gly Arg Phe
1               5

<210> SEQ ID NO 469
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 469

Gly Tyr Pro Gly Phe Lys
1               5

<210> SEQ ID NO 470
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 470

Gly Tyr Pro Ala Lys Phe
1               5

<210> SEQ ID NO 471
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 471

Gly Phe Pro Gly Lys Phe
1               5

<210> SEQ ID NO 472
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 472

Gly Phe Pro Gly Lys Pro
1               5

<210> SEQ ID NO 473
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 473

Ser Tyr Pro Gly Lys Phe
1               5

<210> SEQ ID NO 474
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 474

Ser Tyr Pro Ala Lys Phe
 1               5

<210> SEQ ID NO 475
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 475

Ser Tyr Pro Gly Arg Phe
 1               5

<210> SEQ ID NO 476
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 476

Ser Tyr Ala Gly Lys Phe
 1               5

<210> SEQ ID NO 477
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 477

Ser Phe Pro Gly Gln Pro
 1               5

<210> SEQ ID NO 478
<211> LENGTH: 6
<212> TYPE: PRT
<213> ORGANISM: Artificial Sequence
<220> FEATURE:
<223> OTHER INFORMATION: PAR4 cleavage site

<400> SEQUENCE: 478

Ser Phe Pro Gly Gln Ala
 1               5

<210> SEQ ID NO 479
<211> LENGTH: 8
<212> TYPE: PRT
<213> ORGANISM: Artificial Sequence
<220> FEATURE:
<223> OTHER INFORMATION: ADAMTS13 cleavage site

<400> SEQUENCE: 479

Asn Leu Val Tyr Met Val Thr Gly
 1               5

<210> SEQ ID NO 480

```
<211> LENGTH: 5
<212> TYPE: PRT
<213> ORGANISM: Artificial Sequence
<220> FEATURE:
<223> OTHER INFORMATION: Bovine enterokinase protease cleavage site

<400> SEQUENCE: 480

Asp Asp Asp Asp Lys
1               5

<210> SEQ ID NO 481
<211> LENGTH: 7
<212> TYPE: PRT
<213> ORGANISM: Artificial Sequence
<220> FEATURE:
<223> OTHER INFORMATION: Consensus sequence for TEV protease cleavage
      site
<220> FEATURE:
<221> NAME/KEY: VARIANT
<222> LOCATION: 2, 3, 5
<223> OTHER INFORMATION: Positions 2, 3, and 5 are independently any
      amino amino acid

<400> SEQUENCE: 481

Glu Xaa Xaa Tyr Xaa Gln Gly
1               5

<210> SEQ ID NO 482
<211> LENGTH: 7
<212> TYPE: PRT
<213> ORGANISM: Artificial Sequence
<220> FEATURE:
<223> OTHER INFORMATION: Consensus sequence for TEV protease cleavage
      site
<220> FEATURE:
<221> NAME/KEY: VARIANT
<222> LOCATION: 2, 3, 5
<223> OTHER INFORMATION: Positions 2, 3, and 5 are independently any
      amino acid

<400> SEQUENCE: 482

Glu Xaa Xaa Tyr Xaa Gln Ser
1               5

<210> SEQ ID NO 483
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 483

Glu Asn Leu Tyr Phe Gln Gly
1               5

<210> SEQ ID NO 484
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 484

Glu Asn Leu Tyr Phe Gln Ser
1               5

<210> SEQ ID NO 485
<211> LENGTH: 7
<212> TYPE: PRT
<213> ORGANISM: Artificial Sequence
```

```
<220> FEATURE:
<223> OTHER INFORMATION: TEV protease cleavage site

<400> SEQUENCE: 485

Glu Asn Ile Tyr Thr Gln Gly
  1               5

<210> SEQ ID NO 486
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 486

Glu Asn Ile Tyr Thr Gln Ser
  1               5

<210> SEQ ID NO 487
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 487

Glu Asn Ile Tyr Leu Gln Gly
  1               5

<210> SEQ ID NO 488
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 488

Glu Asn Ile Tyr Leu Gln Ser
  1               5

<210> SEQ ID NO 489
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 489

Glu Asn Val Tyr Phe Gln Gly
  1               5

<210> SEQ ID NO 490
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 490

Glu Asn Val Tyr Ser Gln Ser
  1               5

<210> SEQ ID NO 491
<211> LENGTH: 7
<212> TYPE: PRT
<213> ORGANISM: Artificial Sequence
<220> FEATURE:
<223> OTHER INFORMATION: TEV protease cleavage site
```

<400> SEQUENCE: 491

Glu Asn Val Tyr Ser Gln Gly
1               5

<210> SEQ ID NO 492
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 492

Glu Asn Val Tyr Ser Gln Ser
1               5

<210> SEQ ID NO 493
<211> LENGTH: 7
<212> TYPE: PRT
<213> ORGANISM: Artificial Sequence
<220> FEATURE:
<223> OTHER INFORMATION: Consensus sequence for TVMV protease cleavage
      site
<220> FEATURE:
<221> NAME/KEY: VARIANT
<222> LOCATION: 1, 2
<223> OTHER INFORMATION: Positions 1 and 2 are independently any amino
      acid

<400> SEQUENCE: 493

Xaa Xaa Val Arg Phe Gln Gly
1               5

<210> SEQ ID NO 494
<211> LENGTH: 7
<212> TYPE: PRT
<213> ORGANISM: Artificial Sequence
<220> FEATURE:
<223> OTHER INFORMATION: Consensus sequence for TVMV protease cleavage
      site
<220> FEATURE:
<221> NAME/KEY: VARIANT
<222> LOCATION: 1, 2
<223> OTHER INFORMATION: Positions 1 and 2 are independently any amino
      acid

<400> SEQUENCE: 494

Xaa Xaa Val Arg Phe Gln Ser
1               5

<210> SEQ ID NO 495
<211> LENGTH: 7
<212> TYPE: PRT
<213> ORGANISM: Artificial Sequence
<220> FEATURE:
<223> OTHER INFORMATION: TVMV protease cleavage site

<400> SEQUENCE: 495

Glu Thr Val Arg Phe Gln Gly
1               5

<210> SEQ ID NO 496
<211> LENGTH: 7
<212> TYPE: PRT
<213> ORGANISM: Artificial Sequence
<220> FEATURE:
<223> OTHER INFORMATION: TVMV protease cleavage site

<400> SEQUENCE: 496

```
Glu Thr Val Arg Phe Gln Ser
  1               5

<210> SEQ ID NO 497
<211> LENGTH: 7
<212> TYPE: PRT
<213> ORGANISM: Artificial Sequence
<220> FEATURE:
<223> OTHER INFORMATION: TVMV protease cleavage site

<400> SEQUENCE: 497

Asn Asn Val Arg Phe Gln Gly
  1               5

<210> SEQ ID NO 498
<211> LENGTH: 7
<212> TYPE: PRT
<213> ORGANISM: Artificial Sequence
<220> FEATURE:
<223> OTHER INFORMATION: TVMV protease cleavage site

<400> SEQUENCE: 498

Asn Asn Val Arg Phe Gln Ser
  1               5

<210> SEQ ID NO 499
<211> LENGTH: 7
<212> TYPE: PRT
<213> ORGANISM: Artificial Sequence
<220> FEATURE:
<223> OTHER INFORMATION: Consensus sequence for HR3C protease cleavage
      site
<220> FEATURE:
<221> NAME/KEY: VARIANT
<222> LOCATION: 1
<223> OTHER INFORMATION: Position 1 can be amino acid, with D or E
      preferred
<220> FEATURE:
<221> NAME/KEY: VARIANT
<222> LOCATION: 2
<223> OTHER INFORMATION: Position 2 is S, T, and an aliphatic
      hydrophobic amino acid like G, P, A, V, L, I, and M

<400> SEQUENCE: 499

Xaa Xaa Leu Phe Gln Gly Pro
  1               5

<210> SEQ ID NO 500
<211> LENGTH: 7
<212> TYPE: PRT
<213> ORGANISM: Artificial Sequence
<220> FEATURE:
<223> OTHER INFORMATION: HR3C protease cleavage site

<400> SEQUENCE: 500

Glu Ala Leu Phe Gln Gly Pro
  1               5

<210> SEQ ID NO 501
<211> LENGTH: 7
<212> TYPE: PRT
<213> ORGANISM: Artificial Sequence
<220> FEATURE:
<223> OTHER INFORMATION: HR3C protease cleavage site

<400> SEQUENCE: 501

Glu Val Leu Phe Gln Gly Pro
  1               5
```

```
<210> SEQ ID NO 502
<211> LENGTH: 7
<212> TYPE: PRT
<213> ORGANISM: Artificial Sequence
<220> FEATURE:
<223> OTHER INFORMATION: HR3C protease cleavage site

<400> SEQUENCE: 502

Glu Leu Leu Phe Gln Gly Pro
 1               5

<210> SEQ ID NO 503
<211> LENGTH: 7
<212> TYPE: PRT
<213> ORGANISM: Artificial Sequence
<220> FEATURE:
<223> OTHER INFORMATION: HR3C protease cleavage site

<400> SEQUENCE: 503

Asp Ala Leu Phe Gln Gly Pro
 1               5

<210> SEQ ID NO 504
<211> LENGTH: 7
<212> TYPE: PRT
<213> ORGANISM: Artificial Sequence
<220> FEATURE:
<223> OTHER INFORMATION: HR3C protease cleavage site

<400> SEQUENCE: 504

Asp Val Leu Phe Gln Gly Pro
 1               5

<210> SEQ ID NO 505
<211> LENGTH: 7
<212> TYPE: PRT
<213> ORGANISM: Artificial Sequence
<220> FEATURE:
<223> OTHER INFORMATION: HR3C protease cleavage site

<400> SEQUENCE: 505

Asp Leu Leu Phe Gln Gly Pro
 1               5

<210> SEQ ID NO 506
<211> LENGTH: 6
<212> TYPE: PRT
<213> ORGANISM: Artificial Sequence
<220> FEATURE:
<223> OTHER INFORMATION: Consensus sequence for Subtilisin protease
      cleavage site
<220> FEATURE:
<221> NAME/KEY: VARIANT
<222> LOCATION: 1, 2, 3, 4
<223> OTHER INFORMATION: Positions 1, 2, 3, and 4 are independently any
      amino acid

<400> SEQUENCE: 506

Xaa Xaa Xaa Xaa His Tyr
 1               5

<210> SEQ ID NO 507
<211> LENGTH: 6
<212> TYPE: PRT
<213> ORGANISM: Artificial Sequence
<220> FEATURE:
<223> OTHER INFORMATION: Consensus sequence for Subtilisin protease
      cleavage site
<220> FEATURE:
<221> NAME/KEY: VARIANT
```

-continued

```
<222> LOCATION: 1, 2, 3, 4
<223> OTHER INFORMATION: Positions 1, 2, 3, and 4 are independently any
      amino acid

<400> SEQUENCE: 507

Xaa Xaa Xaa Xaa Tyr His
 1               5

<210> SEQ ID NO 508
<211> LENGTH: 2
<212> TYPE: PRT
<213> ORGANISM: Artificial Sequence
<220> FEATURE:
<223> OTHER INFORMATION: Subtilisin protease cleavage site

<400> SEQUENCE: 508

His Tyr
 1

<210> SEQ ID NO 509
<211> LENGTH: 2
<212> TYPE: PRT
<213> ORGANISM: Artificial Sequence
<220> FEATURE:
<223> OTHER INFORMATION: Subtilisin protease cleavage site

<400> SEQUENCE: 509

Tyr His
 1

<210> SEQ ID NO 510
<211> LENGTH: 6
<212> TYPE: PRT
<213> ORGANISM: Artificial Sequence
<220> FEATURE:
<223> OTHER INFORMATION: Subtilisin protease cleavage site

<400> SEQUENCE: 510

Pro Gly Ala Ala His Tyr
 1               5

<210> SEQ ID NO 511
<211> LENGTH: 6
<212> TYPE: PRT
<213> ORGANISM: Artificial Sequence
<220> FEATURE:
<223> OTHER INFORMATION: Hydroxylamine cleavage site

<400> SEQUENCE: 511

Asn Gly Asn Gly Asn Gly
 1               5

<210> SEQ ID NO 512
<211> LENGTH: 2
<212> TYPE: PRT
<213> ORGANISM: Artificial Sequence
<220> FEATURE:
<223> OTHER INFORMATION: Hydroxylamine cleavage site

<400> SEQUENCE: 512

Asn Gly
 1

<210> SEQ ID NO 513
<211> LENGTH: 5
<212> TYPE: PRT
<213> ORGANISM: Artificial Sequence
<220> FEATURE:
```

<223> OTHER INFORMATION: Consensus sequence for SUMO/ULP-1 protease
      cleavage site
<220> FEATURE:
<221> NAME/KEY: VARIANT
<222> LOCATION: 3, 4, 5
<223> OTHER INFORMATION: Positions 3, 4, and 5 are independently any
      amino acid

<400> SEQUENCE: 513

Gly Gly Xaa Xaa Xaa
 1               5

<210> SEQ ID NO 514
<211> LENGTH: 98
<212> TYPE: PRT
<213> ORGANISM: Artificial Sequence
<220> FEATURE:
<223> OTHER INFORMATION: SUMO/ULP-1 protease cleavage site

<400> SEQUENCE: 514

Met Ala Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
             20                  25                  30

Ser Glu Ile Phe Phe Lys Ile Lys Lys Thr Thr Pro Leu Arg Arg Leu
         35                  40                  45

Met Glu Ala Phe Ala Lys Arg Gln Gly Lys Glu Met Asp Ser Leu Arg
     50                  55                  60

Phe Leu Tyr Asp Gly Ile Arg Ile Gln Ala Asp Gln Thr Pro Glu Asp
 65                  70                  75                  80

Leu Asp Met Glu Asp Asn Asp Ile Ile Glu Ala His Arg Glu Gln Ile
                 85                  90                  95

Gly Gly

<210> SEQ ID NO 515
<211> LENGTH: 5
<212> TYPE: PRT
<213> ORGANISM: Artificial Sequence
<220> FEATURE:
<223> OTHER INFORMATION: Consensus sequence for Caspase 3 protease
      cleavage site
<220> FEATURE:
<221> NAME/KEY: VARIANT
<222> LOCATION: 2
<223> OTHER INFORMATION: Position 2 can be any amino acid with E
      preferred
<220> FEATURE:
<221> NAME/KEY: VARIANT
<222> LOCATION: 3
<223> OTHER INFORMATION: Position 3 is any amino acid
<220> FEATURE:
<221> NAME/KEY: VARIANT
<222> LOCATION: 5
<223> OTHER INFORMATION: Position 5 can be any amino acid with G or S
      preferred

<400> SEQUENCE: 515

Asp Xaa Xaa Asp Xaa
 1               5

<210> SEQ ID NO 516
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 516

```
Asp Glu Val Asp Gly
 1               5

<210> SEQ ID NO 517
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 517

Asp Glu Val Asp Ser
 1               5

<210> SEQ ID NO 518
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 518

Asp Glu Pro Asp Gly
 1               5

<210> SEQ ID NO 519
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 519

Asp Glu Pro Asp Ser
 1               5

<210> SEQ ID NO 520
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 520

Asp Glu Leu Asp Gly
 1               5

<210> SEQ ID NO 521
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 521

Asp Glu Leu Asp Ser
 1               5

<210> SEQ ID NO 522
<211> LENGTH: 4
<212> TYPE: PRT
<213> ORGANISM: Artificial Sequence
<220> FEATURE:
<223> OTHER INFORMATION: Flexible G-spacer

<400> SEQUENCE: 522

Gly Gly Gly Gly
```

1

<210> SEQ ID NO 523
<211> LENGTH: 5
<212> TYPE: PRT
<213> ORGANISM: Artificial Sequence
<220> FEATURE:
<223> OTHER INFORMATION: Flexible G-spacer

<400> SEQUENCE: 523

Gly Gly Gly Gly Ser
1 5

<210> SEQ ID NO 524
<211> LENGTH: 4
<212> TYPE: PRT
<213> ORGANISM: Artificial Sequence
<220> FEATURE:
<223> OTHER INFORMATION: Flexible A-spacer

<400> SEQUENCE: 524

Ala Ala Ala Ala
1

<210> SEQ ID NO 525
<211> LENGTH: 5
<212> TYPE: PRT
<213> ORGANISM: Artificial Sequence
<220> FEATURE:
<223> OTHER INFORMATION: Flexible A-spacer

<400> SEQUENCE: 525

Ala Ala Ala Ala Val
1 5

<210> SEQ ID NO 526
<211> LENGTH: 3939
<212> TYPE: DNA
<213> ORGANISM: Artificial Sequence
<220> FEATURE:
<223> OTHER INFORMATION: DNA encoding a BoNT/A with a HIS tag

<400> SEQUENCE: 526
atgccgttcg taaacaaaca gttcaactat aaagacccag tcaacggcgt ggacattgcc 60
tatatcaaaa tcccgaatgc gggtcaaatg cagcccgtga aagcatttaa aatccataac 120
aaaatttggg tgatcccgga gcgcgatacg ttcacgaacc cggaagaagg agatttaaac 180
ccaccgcctg aggctaaaca ggtcccggtg tcttactatg atagcacata cctgagtacc 240
gacaatgaaa aggacaacta cctgaaaggt gttaccaaac tgttcgagcg catttattcg 300
acagatctcg gtcgcatgtt gctgacttct attgtgcgcg gcattccgtt ttggggtggt 360
agcaccatcg atacagaact caaagtgatt gacaccaact gcatcaatgt gattcagcct 420
gatgggagct accggtccga agagcttaac ctcgtaatca ttggcccgag cgcggatatt 480
atccaattcg aatgtaaatc ttttgggcat gaagtcctga atctgacgcg gaatggctat 540
ggatcgacgc agtatattcg tttttctcca gatttcacat ttggatttga agaaagcctc 600
gaagttgata cgaaccctct tttaggcgcg ggaaaattcg cgacggaccc agcggtgacc 660
ttggcacatg aacttattca tgccgggcat cgcttgtatg gaatcgccat taacccgaac 720
cgtgttttca aggtgaatac gaacgcgtat tacgagatgt cgggcttaga agtgtccttt 780
gaagaactgc gcacgtttgg cggtcatgat gcaaaattta ttgatagtct gcaagaaaac 840
gaatttcggc tgtactatta caataaattc aaagacattg catcaacctt aaacaaggcg 900

```
aaaagcattg tgggtaccac ggctagctta caatatatga aaaacgtttt caaagaaaaa    960
tacctcctta gcgaagacac ttccggcaaa ttctctgtcg ataaactgaa atttgataaa   1020
ctgtataaaa tgctcaccga gatctacaca gaggataact ttgtcaaatt cttcaaggtc   1080
ttgaatcgga aaacctatct gaacttcgat aaagccgtct ttaagatcaa catcgtaccg   1140
aaagttaact acaccatcta tgatggcttt aatctgcgca atacgaatct ggcggcgaac   1200
tttaacggcc agaacaccga atcaacaac atgaacttta ctaaactgaa aaattttacc   1260
ggcttgtttg aattttataa gctcctgtgt gtccgcggta ttatcaccag caaaaccaaa   1320
tccttggata agggctataa caaggcgctc aatgattat gcatcaaggt gaacaactgg    1380
gacttgtttt tctctccatc tgaagataat tttactaacg acttgaacaa aggagaggaa   1440
attacttccg ataccaacat cgaagcagcg aagagaata ttagcctgga tcttattcaa    1500
caatattacc tgacctttaa ttttgataac gagcctgaga catttccat tgagaatctc     1560 agctctgaca tcatcggcca gctggaactg atgccgaata tcgaacgctt tcctaatgga   1620
aagaaatatg aattggacaa atacaccatg ttccactatc tccgcgcgca ggagtttgag   1680
cacggcaagt ctcgtattgc tctgaccaat tcggtaaacg aagccctttt aaatccttcg   1740
cgtgtgtaca ccttttttctc aagcgattat gttaaaaaag tgaacaaggc gaccgaagcg   1800
gcgatgtttt tgggatgggt ggaacaactg gtatatgact ttacgatgaa acttctgaa    1860 gtctcgacca ccgacaaaat tgccgatatt accattatca ttccctatat tggccctgca   1920
ctgaacattg gtaacatgct gtataaagat gattttgtgg gcgccctgat cttttcaggc   1980
gctgttatcc tgctggaatt tatcccggaa atcgccattc cagtactcgg tacctttgcg   2040
ctggtgtcct atatcgcaaa caaagtttg actgtccaga cgatcgacaa cgcgctcagt   2100
aaacgtaacg aaaaatggga tgaggtgtat aagtatattg ttaccaactg gctcgctaaa   2160
gtaaacaccc agattgacct gattcgcaag aagatgaaag aagcgctgga aaaccaagca   2220
gaagcgacca aagctattat caactatcaa tataaccagt acacagagga agaaaagaat   2280
aacatcaact tcaacatcga cgacttatct tcaaagctga tgaatctat taacaaagcg    2340 atgattaata ttaacaagtt cttgaaccaa tgtagtgtca gctatctgat gaactcgatg   2400
atcccttacg gtgtgaaacg tctggaagac ttcgatgcaa gccttaaaga tgcccttctg   2460
aagtatattt acgataatcg cggaactctt attggccaag tggatcgctt aaaagataaa   2520
gtcaacaaca cgctgagtac agacatccct tttcagctgt ctaaatatgt ggacaatcag   2580
cgcctgctgt ccacgtttac ggaatacatc aaaaacatca tcaacactag tattctgaac   2640
ttgcgttacg agagtaacca tctgattgat ctgagccgtt acgcatctaa aatcaacatc   2700
ggctcgaagg tgaacttcga tcctatcgac aaaaaccaga ttcaattgtt caacttagaa   2760
tcgtcaaaga ttgaagttat cttaaaaaat gcgattgtat ataattcaat gtacgaaaat   2820
ttctctacga gcttttggat tcgtattccg aaatatttca acagtatctc tttaaacaac   2880
gagtatacta tcatcaattg tatggagaat aacagcgggt ggaaagtgag ccttaactat   2940
ggtgaaatca tctggactct gcaggacact caagaaatta acaacgcgt ggtgtttaaa     3000 tactcacaga tgattaacat ctcggattat attaatcgct ggattttgt gacaattact    3060 aacaaccggc tgaacaacag caaaatttac attaacggtc gcctgatcga tcagaaacca   3120
atcagtaatc tcggtaacat tcacgcatcg aataatatca tgttcaaact ggatggttgt   3180
cgcgacacgc accgttacat ttggatcaaa tacttcaatt tattcgacaa agaactcaac   3240
gaaaaggaga ttaaggatct ttatgacaat cagtctaatt cgggtattct gaaagacttt   3300
```

```
tggggtgatt accttcagta cgataaaccg tattatatgt taaacttata tgatccgaat   3360
aaatacgttg acgtcaacaa cgttggcatt cgtggctata tgtatctgaa agggccgcgt   3420
ggcagcgtga tgaccactaa catttactta aactcctccc tctatcgcgg tactaaattt   3480
attatcaaga aatatgcctc tggcaacaag gacaatatcg tacgcaataa cgatcgcgtc   3540
tacattaacg tggtggtgaa gaataaagaa tatcgtctgg cgaccaatgc tagtcaggcg   3600
ggcgtggaga aaattctgtc tgcacttgaa atcccggatg tgggtaattt atcccaggtg   3660
gttgtgatga aaagtaaaaa tgaccaaggg atcaccaata aatgcaaaat gaatctgcaa   3720
gataacaacg gcaacgacat tggttttatc ggcttccacc aattcaataa tatcgcgaaa   3780
ctggtggcct caaattggta caaccgtcag attgagcgca gctcccgcac tttaggctgt   3840
agctgggagt tcattccggt agatgacggt tggggagaac gcccattgaa agtcgacaag   3900
cttgcggccg cactcgagca ccaccaccac caccactga                         3939
```

<210> SEQ ID NO 527
<211> LENGTH: 1312
<212> TYPE: PRT
<213> ORGANISM: Artificial Sequence
<220> FEATURE:
<223> OTHER INFORMATION: BoNT/A with a HIS tag

<400> SEQUENCE: 527

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

```
Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
            450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
```

```
            675                 680                 685
Val Leu Thr Val Gln Thr Ile Asp Asn Ala Leu Ser Lys Arg Asn Glu
690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Met Lys Glu Ala Leu
                    725                 730                 735
Glu Asn Gln Ala Glu Ala Thr Lys Ala Ile Ile Asn Tyr Gln Tyr Asn
                740                 745                 750
Gln Tyr Thr Glu Glu Lys Asn Asn Ile Asn Phe Asn Ile Asp Asp
            755                 760                 765
Leu Ser Ser Lys Leu Asn Glu Ser Ile Asn Lys Ala Met Ile Asn Ile
            770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                    805                 810                 815
Asp Ala Leu Leu Lys Tyr Ile Tyr Asp Asn Arg Gly Thr Leu Ile Gly
                820                 825                 830
Gln Val Asp Arg Leu Lys Asp Lys Val Asn Asn Thr Leu Ser Thr Asp
            835                 840                 845
Ile Pro Phe Gln Leu Ser Lys Tyr Val Asp Asn Gln Arg Leu Leu Ser
850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                    885                 890                 895
Lys Ile Asn Ile Gly Ser Lys Val Asn Phe Asp Pro Ile Asp Lys Asn
                900                 905                 910
Gln Ile Gln Leu Phe Asn Leu Glu Ser Ser Lys Ile Glu Val Ile Leu
            915                 920                 925
Lys Asn Ala Ile Val Tyr Asn Ser Met Tyr Glu Asn Phe Ser Thr Ser
930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                    965                 970                 975
Ser Leu Asn Tyr Gly Glu Ile Ile Trp Thr Leu Gln Asp Thr Gln Glu
                980                 985                 990
Ile Lys Gln Arg Val Val Phe Lys Tyr Ser Gln Met Ile Asn Ile Ser
            995                 1000                1005
Asp Tyr Ile Asn Arg Trp Ile Phe Val Thr Ile Thr Asn Asn Arg Leu
            1010                1015                1020
Asn Asn Ser Lys Ile Tyr Ile Asn Gly Arg Leu Ile Asp Gln Lys Pro
1025                1030                1035                1040
Ile Ser Asn Leu Gly Asn Ile His Ala Ser Asn Asn Ile Met Phe Lys
                    1045                1050                1055
Leu Asp Gly Cys Arg Asp Thr His Arg Tyr Ile Trp Ile Lys Tyr Phe
                1060                1065                1070
Asn Leu Phe Asp Lys Glu Leu Asn Glu Lys Glu Ile Lys Asp Leu Tyr
            1075                1080                1085
Asp Asn Gln Ser Asn Ser Gly Ile Leu Lys Asp Phe Trp Gly Asp Tyr
            1090                1095                1100
```

```
Leu Gln Tyr Asp Lys Pro Tyr Met Leu Asn Leu Tyr Asp Pro Asn
1105                1110                1115                1120

Lys Tyr Val Asp Val Asn Asn Val Gly Ile Arg Gly Tyr Met Tyr Leu
            1125                1130                1135

Lys Gly Pro Arg Gly Ser Val Met Thr Thr Asn Ile Tyr Leu Asn Ser
        1140                1145                1150

Ser Leu Tyr Arg Gly Thr Lys Phe Ile Ile Lys Lys Tyr Ala Ser Gly
    1155                1160                1165

Asn Lys Asp Asn Ile Val Arg Asn Asn Asp Arg Val Tyr Ile Asn Val
1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
            1205                1210                1215

Leu Ser Gln Val Val Val Met Lys Ser Lys Asn Asp Gln Gly Ile Thr
        1220                1225                1230

Asn Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala Ser
1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
            1285                1290                1295

Lys Val Asp Lys Leu Ala Ala Ala Leu Glu His His His His His His
        1300                1305                1310

<210> SEQ ID NO 528
<211> LENGTH: 3921
<212> TYPE: DNA
<213> ORGANISM: Artificial Sequence
<220> FEATURE:
<223> OTHER INFORMATION: DNA encoding a BoNT/A-TEV with a HIS tag

<400> SEQUENCE: 528
atgccgttcg taaacaaaca gttcaactat aaagacccag tcaacggcgt ggacattgcc      60
tatatcaaaa tcccgaatgc gggtcaaatg cagcccgtga agcatttaa aatccataac     120 aaaatttggg tgatcccgga gcgcgatacg ttcacgaacc cggaagaagg agatttaaac     180 ccaccgccctg aggctaaaca ggtcccggtg tcttactatg atagcacata cctgagtacc     240
gacaatgaaa aggacaacta cctgaaaggt gttaccaaac tgttcgagcg catttattcg     300
acagatctcg gtcgcatgtt gctgacttct attgtgcgcg gcattccgtt ttggggtggt     360
agcaccatcg atacagaact caaagtgatt gacaccaact gcatcaatgt gattcagcct     420
gatgggagct accggtccga agagcttaac ctcgtaatca ttggcccgag cgcggatatt     480
atccaattcg aatgtaaatc ttttgggcat gaagtcctga tctgacgcg aatggctat      540 ggatcgacgc agtatatcg ttttctcca gatttcacat ttggatttga agaaagcctc      600
gaagttgata cgaaccctct tttaggcgcg ggaaaattcg cgacggaccc agcggtgacc      660
ttggcacatg aacttattca tgccgggcat cgcttgtatg aatcgccat taacccgaac      720 cgtgttttca ggtgaatac gaacgcgtat tacgagatgt cgggcttaga agtgtccttt      780
gaagaactgc gcacgtttgg cggtcatgat gcaaaattta tgatagtct gcaagaaaac      840 gaatttcggc tgtactatta caataaaattc aagacattg catcaacctt aaacaaggcg      900
aaaagcattg tgggtaccac ggctagctta caatatatga aaaacgttt caaagaaaaa     960
```

```
tacctcctta gcgaagacac ttccggcaaa ttctctgtcg ataaactgaa atttgataaa    1020
ctgtataaaa tgctcaccga gatctacaca gaggataact ttgtcaaatt cttcaaggtc    1080
ttgaatcgga aaacctatct gaacttcgat aaagccgtct ttaagatcaa catcgtaccg    1140
aaagttaact acaccatcta tgatggcttt aatctgcgca atacgaatct ggcggcgaac    1200
tttaacggcc agaacaccga aatcaacaac atgaacttta ctaaactgaa aaattttacc    1260
ggcttgtttg aattctataa gctcctgtgt gtccgcggta ttatcaccag caaaggcggt    1320
ggttctggcg gtggtgaaaa cctgtacttc cagggcggtg gctccggtgg tggtgcgctc    1380
aatgatttat gcatcaaggt gaacaactgg gacttgtttt tctctccatc tgaagataat    1440
tttactaacg acttgaacaa aggagaggaa attacttccg ataccaacat cgaagcagcg    1500
gaagagaata ttagtctaga tcttattcaa caatattacc tgacctttaa ttttgataac    1560
gagcctgaga acatttccat tgagaatctc agctctgaca tcatcggcca gctggaactg    1620
atgccgaata tcgaacgctt tcctaatgga aagaaatatg aattggacaa atacaccatg    1680
ttccactatc tccgcgcgca ggagtttgag cacggcaagt ctcgtattgc tctgaccaat    1740
tcggtaaacg aagccctttt aaatccttcg cgtgtgtaca cctttttctc aagcgattat    1800
gttaaaaaag tgaacaaggc gaccgaagcg gcgatgtttt gggatgggt ggaacaactg    1860 gtatatgact ttacgatga aacttctgaa gtctcgacca ccgacaaaat tgccgatatt    1920
accattatca ttccctatat tggccctgca ctgaacattg gtaacatgct gtataaagat    1980
gattttgtgg gcgccctgat cttttcaggc gctgttatcc tgctggaatt tatcccggaa    2040
atcgccattc cagtactcgg tacctttgcg ctggtgtcct atatcgcaaa caaagttttg    2100
actgtccaga cgatcgacaa cgcgctcagt aaacgtaacg aaaaatggga tgaggtgtat    2160
aagtatattg ttaccaactg gctcgctaaa gtaaacaccc agattgaccT gattcgcaag    2220
aagatgaaag aagcgctgga aaaccaagca gaagcgacca agctattat caactatcaa    2280 tataaccagt acacagagga agaaaagaat aacatcaact tcaacatcga cgacttatct    2340
tcaaagctga tgaatctat taacaaagcg atgattaata ttaacaagtt cttgaaccaa    2400
tgtagtgtca gctatctgat gaactcgatg atcccttacg gtgtgaaacg tctggaagac    2460
ttcgatgcaa gccttaaaga tgcccttctg aagtatattt acgataatcg cggaactctt    2520
attggccaag tggatcgctt aaaagataaa gtcaacaaca cgctgagtac agacatccct    2580
tttcagctgt ctaaatatgt ggacaatcag cgcctgctgt ccacgtttac ggaatacatc    2640
aaaaacatca tcaacactag tattctgaac ttgcgttacg agagtaacca tctgattgat    2700
ctgagccgtt acgcatctaa aatcaacatc ggatccaagg tgaacttcga tcctatcgac    2760
aaaaaccaga ttcaattgtt caacttagaa tcgtcaaaga ttgaagttat cttaaaaaat    2820
gcgattgtat ataattcaat gtacgaaaat ttctctacga gcttttggat tcgtattccg    2880
aaatatttca acagtatctc tttaaacaac gagtatacta tcatcaattg tatggagaat    2940
aacagcgggt ggaaagtgag ccttaactat ggtgaaatca tctggactct gcaggacact    3000
caagaaatta acaacgcgt ggtgtttaaa tactcacaga tgattaacat ctcggattat    3060
attaatcgct ggattttgt gacaattact aacaaccggc tgaacaacag caaaatttac    3120
attaacggtc gcctgatcga tcagaaacca atcagtaatc tcggtaacat tcacgcatcg    3180
aataatatca tgttcaaact ggatggttgt cgcgacacgc accgttacat ttggatcaaa    3240
tacttcaatt tattcgacaa agaactcaac gaaaaggaga ttaaggatct ttatgacaat    3300
cagtctaatt cgggtattct gaaagacttt tggggtgatt accttcagta cgataaaccg    3360
```

```
tattatatgt taaacttata tgatccgaat aaatacgttg acgtcaacaa cgttggcatt    3420
cgtggctata tgtatctgaa agggccgcgt ggcagcgtga tgaccactaa catttactta    3480
aactcctccc tctatcgcgg tactaaattt attatcaaga aatatgcctc tggcaacaag    3540
gacaatatcg tacgcaataa cgatcgcgtc tacattaacg tggtggtgaa gaataaagaa    3600
tatcgtctgg cgaccaatgc tagtcaggcg ggcgtggaga aaattctgtc tgcacttgaa    3660
atcccggatg tgggtaattt atcccaggtg gttgtgatga aaagtaaaaa tgaccaaggg    3720
atcaccaata aatgcaaaat gaatctgcaa gataacaacg gcaacgacat tggttttatc    3780
ggcttccacc aattcaataa tatcgcgaaa ctggtggcct caaattggta caaccgtcag    3840
attgagcgca gctcccgcac tttaggctgt agctgggagt tcattccggt agatgacggt    3900
tggggagaac gcccattgta a                                              3921
```

<210> SEQ ID NO 529
<211> LENGTH: 1306
<212> TYPE: PRT
<213> ORGANISM: Artificial Sequence
<220> FEATURE:
<223> OTHER INFORMATION: BoNT/A-TEV with a HIS tag

<400> SEQUENCE: 529

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
```

```
                260                 265                 270
Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Gly Gly Ser Gly Gly Glu Asn Leu
                435                 440                 445

Tyr Phe Gln Gly Gly Gly Ser Gly Gly Gly Ala Leu Asn Asp Leu Cys
                450                 455                 460

Ile Lys Val Asn Asn Trp Asp Leu Phe Phe Ser Pro Ser Glu Asp Asn
465                 470                 475                 480

Phe Thr Asn Asp Leu Asn Lys Gly Glu Glu Ile Thr Ser Asp Thr Asn
                485                 490                 495

Ile Glu Ala Ala Glu Glu Asn Ile Ser Leu Asp Leu Ile Gln Gln Tyr
                500                 505                 510

Tyr Leu Thr Phe Asn Phe Asp Asn Glu Pro Glu Asn Ile Ser Ile Glu
                515                 520                 525

Asn Leu Ser Ser Asp Ile Ile Gly Gln Leu Glu Leu Met Pro Asn Ile
                530                 535                 540

Glu Arg Phe Pro Asn Gly Lys Lys Tyr Glu Leu Asp Lys Tyr Thr Met
545                 550                 555                 560

Phe His Tyr Leu Arg Ala Gln Glu Phe Glu His Gly Lys Ser Arg Ile
                565                 570                 575

Ala Leu Thr Asn Ser Val Asn Glu Ala Leu Leu Asn Pro Ser Arg Val
                580                 585                 590

Tyr Thr Phe Phe Ser Ser Asp Tyr Val Lys Lys Val Asn Lys Ala Thr
                595                 600                 605

Glu Ala Ala Met Phe Leu Gly Trp Val Glu Gln Leu Val Tyr Asp Phe
                610                 615                 620

Thr Asp Glu Thr Ser Glu Val Ser Thr Thr Asp Lys Ile Ala Asp Ile
625                 630                 635                 640

Thr Ile Ile Ile Pro Tyr Ile Gly Pro Ala Leu Asn Ile Gly Asn Met
                645                 650                 655

Leu Tyr Lys Asp Asp Phe Val Gly Ala Leu Ile Phe Ser Gly Ala Val
                660                 665                 670

Ile Leu Leu Glu Phe Ile Pro Glu Ile Ala Ile Pro Val Leu Gly Thr
                675                 680                 685
```

-continued

Phe Ala Leu Val Ser Tyr Ile Ala Asn Lys Val Leu Thr Val Gln Thr
690                 695                 700

Ile Asp Asn Ala Leu Ser Lys Arg Asn Glu Lys Trp Asp Glu Val Tyr
705                 710                 715                 720

Lys Tyr Ile Val Thr Asn Trp Leu Ala Lys Val Asn Thr Gln Ile Asp
            725                 730                 735

Leu Ile Arg Lys Lys Met Lys Glu Ala Leu Glu Asn Gln Ala Glu Ala
        740                 745                 750

Thr Lys Ala Ile Ile Asn Tyr Gln Tyr Asn Gln Tyr Thr Glu Glu Glu
    755                 760                 765

Lys Asn Asn Ile Asn Phe Asn Ile Asp Asp Leu Ser Ser Lys Leu Asn
770                 775                 780

Glu Ser Ile Asn Lys Ala Met Ile Asn Ile Asn Lys Phe Leu Asn Gln
785                 790                 795                 800

Cys Ser Val Ser Tyr Leu Met Asn Ser Met Ile Pro Tyr Gly Val Lys
            805                 810                 815

Arg Leu Glu Asp Phe Asp Ala Ser Leu Lys Asp Ala Leu Leu Lys Tyr
        820                 825                 830

Ile Tyr Asp Asn Arg Gly Thr Leu Ile Gly Gln Val Asp Arg Leu Lys
    835                 840                 845

Asp Lys Val Asn Asn Thr Leu Ser Thr Asp Ile Pro Phe Gln Leu Ser
850                 855                 860

Lys Tyr Val Asp Asn Gln Arg Leu Leu Ser Thr Phe Thr Glu Tyr Ile
865                 870                 875                 880

Lys Asn Ile Ile Asn Thr Ser Ile Leu Asn Leu Arg Tyr Glu Ser Asn
            885                 890                 895

His Leu Ile Asp Leu Ser Arg Tyr Ala Ser Lys Ile Asn Ile Gly Ser
        900                 905                 910

Lys Val Asn Phe Asp Pro Ile Asp Lys Asn Gln Ile Gln Leu Phe Asn
    915                 920                 925

Leu Glu Ser Ser Lys Ile Glu Val Ile Leu Lys Asn Ala Ile Val Tyr
930                 935                 940

Asn Ser Met Tyr Glu Asn Phe Ser Thr Ser Phe Trp Ile Arg Ile Pro
945                 950                 955                 960

Lys Tyr Phe Asn Ser Ile Ser Leu Asn Asn Glu Tyr Thr Ile Ile Asn
            965                 970                 975

Cys Met Glu Asn Asn Ser Gly Trp Lys Val Ser Leu Asn Tyr Gly Glu
        980                 985                 990

Ile Ile Trp Thr Leu Gln Asp Thr Gln Glu Ile Lys Gln Arg Val Val
    995                 1000                1005

Phe Lys Tyr Ser Gln Met Ile Asn Ile Ser Asp Tyr Ile Asn Arg Trp
1010                1015                1020

Ile Phe Val Thr Ile Thr Asn Asn Arg Leu Asn Asn Ser Lys Ile Tyr
1025                1030                1035                1040

Ile Asn Gly Arg Leu Ile Asp Gln Lys Pro Ile Ser Asn Leu Gly Asn
            1045                1050                1055

Ile His Ala Ser Asn Asn Ile Met Phe Lys Leu Asp Gly Cys Arg Asp
        1060                1065                1070

Thr His Arg Tyr Ile Trp Ile Lys Tyr Phe Asn Leu Phe Asp Lys Glu
    1075                1080                1085

Leu Asn Glu Lys Glu Ile Lys Asp Leu Tyr Asp Asn Gln Ser Asn Ser
1090                1095                1100

Gly Ile Leu Lys Asp Phe Trp Gly Asp Tyr Leu Gln Tyr Asp Lys Pro
1105                1110                1115                1120

```
Tyr Tyr Met Leu Asn Leu Tyr Asp Pro Asn Lys Tyr Val Asp Val Asn
                1125                1130                1135

Asn Val Gly Ile Arg Gly Tyr Met Tyr Leu Lys Gly Pro Arg Gly Ser
            1140                1145                1150

Val Met Thr Thr Asn Ile Tyr Leu Asn Ser Ser Leu Tyr Arg Gly Thr
        1155                1160                1165

Lys Phe Ile Ile Lys Lys Tyr Ala Ser Gly Asn Lys Asp Asn Ile Val
    1170                1175                1180

Arg Asn Asn Asp Arg Val Tyr Ile Asn Val Val Val Lys Asn Lys Glu
1185                1190                1195                1200

Tyr Arg Leu Ala Thr Asn Ala Ser Gln Ala Gly Val Glu Lys Ile Leu
                1205                1210                1215

Ser Ala Leu Glu Ile Pro Asp Val Gly Asn Leu Ser Gln Val Val Val
            1220                1225                1230

Met Lys Ser Lys Asn Asp Gln Gly Ile Thr Asn Lys Cys Lys Met Asn
        1235                1240                1245

Leu Gln Asp Asn Asn Gly Asn Asp Ile Gly Phe Ile Gly Phe His Gln
    1250                1255                1260

Phe Asn Asn Ile Ala Lys Leu Val Ala Ser Asn Trp Tyr Asn Arg Gln
1265                1270                1275                1280

Ile Glu Arg Ser Ser Arg Thr Leu Gly Cys Ser Trp Glu Phe Ile Pro
                1285                1290                1295

Val Asp Asp Gly Trp Gly Glu Arg Pro Leu
            1300                1305
```

<210> SEQ ID NO 530
<211> LENGTH: 3945
<212> TYPE: DNA
<213> ORGANISM: Artificial Sequence
<220> FEATURE:
<223> OTHER INFORMATION: DNA encoding a BoNT/A comprising Thrombin (N880) and Thrombin (D890)

<400> SEQUENCE: 530

```
atgccgttcg taaacaaaca gttcaactat aaagacccag tcaacggcgt ggacattgcc     60
tatatcaaaa tcccgaatgc gggtcaaatg cagcccgtga aagcatttaa aatccataac    120
aaaatttggg tgatcccgga gcgcgatacg ttcacgaacc cggaagaagg agatttaaac    180
ccaccgcctg aggctaaaca ggtcccggtg tcttactatg atagcacata cctgagtacc    240
gacaatgaaa aggacaacta cctgaaaggt gttaccaaac tgttcgagcg catttattcg    300
acagatctcg gtcgcatgtt gctgacttct attgtgcgcg gcattccgtt ttggggtggt    360
agcaccatcg atacagaact caaagtgatt gacaccaact gcatcaatgt gattcagcct    420
gatgggagct accggtccga agagcttaac ctcgtaatca ttggcccgag cgcggatatt    480
atccaattcg aatgtaaatc ttttgggcat gaagtcctga atctgacgcg gaatggctat    540
ggatcgacgc agtatattcg tttttctcca gatttcacat ttggatttga agaaagcctc    600
gaagttgata cgaaccctct tttaggcgcg ggaaaattcg cgacggaccc agcggtgacc    660
ttggcacatg aacttattca tgccgggcat cgcttgtatg gaatcgccat taacccgaac    720
cgtgttttca aggtgaatac gaacgcgtat tacgagatgt cgggcttaga agtgtccttt    780
gaagaactgc gcacgtttgg cggtcatgat gcaaaattta ttgatagtct gcaagaaaac    840
gaatttcggc tgtactatta caataaattc aaagacattg catcaacctt aaacaaggcg    900
aaaagcattg tgggtaccac ggctagctta caatatatga aaaacgtttt caaagaaaaa    960
```

```
tacctcctta gcgaagacac ttccggcaaa ttctctgtcg ataaactgaa atttgataaa    1020
ctgtataaaa tgctcaccga gatctacaca gaggataact ttgtcaaatt cttcaaggtc    1080
ttgaatcgga aaacctatct gaacttcgat aaagccgtct ttaagatcaa catcgtaccg    1140
aaagttaact acaccatcta tgatggcttt aatctgcgca atacgaatct ggcggcgaac    1200
tttaacggcc agaacaccga aatcaacaac atgaacttta ctaaactgaa aaattttacc    1260
ggcttgtttg aattctataa gctcctgtgt gtccgcggta ttatcaccag caaaggcggt    1320
ggttctggcg gtggtgaaaa cctgtacttc cagggcggtg gctccggtgg tggtgcgctc    1380
aatgatttat gcatcaaggt gaacaactgg gacttgtttt tctctccatc tgaagataat    1440
tttactaacg acttgaacaa aggagaggaa attacttccg ataccaacat cgaagcagcg    1500
gaagagaata ttagtctaga tcttattcaa caatattacc tgacctttaa ttttgataac    1560
gagcctgaga acatttccat tgagaatctc agctctgaca tcatcggcca gctggaactg    1620
atgccgaata tcgaacgctt tcctaatgga agaaatatg aattggacaa atacaccatg    1680
ttccactatc tccgcgcgca ggagtttgag cacggcaagt ctcgtattgc tctgaccaat    1740
tcggtaaacg aagcccttttt aaatccttcg cgtgtgtaca ccttttttctc aagcgattat    1800 gttaaaaaag tgaacaaggc gaccgaagcg gcgatgtttt gggatgggt ggaacaactg    1860 gtatatgact ttacggatga aacttctgaa gtctcgacca ccgacaaaat tgccgatatt    1920
accattatca ttccctatat tggccctgca ctgaacattg taacatgct gtataaagat    1980 gattttgtgg gcgccctgat cttttcaggc gctgttatcc tgctggaatt tatcccggaa    2040
atcgccattc cagtactcgg tacctttgcg ctggtgtcct atatcgcaaa caaagttttg    2100
actgtccaga cgatcgacaa cgcgctcagt aaacgtaacg aaaaatggga tgaggtgtat    2160
aagtatattg ttaccaactg gctcgctaaa gtaaacaccc agattgacct gattcgcaag    2220
aagatgaaag aagcgctgga aaaccaagca gaagcgacca agctattat caactatcaa    2280 tataaccagt acacagagga agaaaagaat aacatcaact tcaacatcga cgacttatct    2340
tcaaagctga tgaatctat taacaaagcg atgattaata ttaacaagtt cttgaaccaa    2400
tgtagtgtca gctatctgat gaactcgatg atcccttacg gtgtgaaacg tctggaagac    2460
ttcgatgcaa gccttaaaga tgcccttctg aagtatattt acgataatcg cggaactctt    2520
attggccaag tggatcgctt aaaagataaa gtcaacaaca cgctgagtac agacatccct    2580
tttcagctgt ctaaatatgt ggacaatcag cgcctgctgt ccacgtttac ggaatacatc    2640
aaaaacatca tcaacactag tattctgaac ctggtgccgc gtggctccta cgagagtaac    2700
catctgattg atctggtgcc gcgtggcagc cgttacgcat ctaaaatcaa catcggatcc    2760
aaggtgaact tcgatcctat cgacaaaaac cagattcaat tgttcaactt agaatcgtca    2820
aagattgaag ttatcttaaa aaatgcgatt gtatataatt caatgtacga aaatttctct    2880
acgagctttt ggattcgtat tccgaaatat ttcaacagta tctctttaaa caacgagtat    2940
actatcatca attgtatgga gaataacagc gggtggaaag tgagccttaa ctatggtgaa    3000
atcatctgga ctctgcagga cactcaagaa attaaacaac gcgtggtgtt taaatactca    3060
cagatgatta acatctcgga ttatattaat cgctggattt ttgtgacaat tactaacaac    3120
cggctgaaca acagcaaaat ttacattaac ggtcgcctga tcgatcagaa accaatcagt    3180
aatctcggta acattcacgc atcgaataat atcatgttca aactggatgg ttgtcgcgac    3240
acgcaccgtt acatttggat caaatacttc aatttattcg acaaagaact caacgaaaag    3300
gagattaagg atctttatga caatcagtct aattcgggta ttctgaaaga cttttgggt    3360
```

```
gattaccttc agtacgataa accgtattat atgttaaact tatatgatcc gaataaatac   3420
gttgacgtca acaacgttgg cattcgcggc tatatgtatc tgaaagggcc gcgtggcagc   3480
gtgatgacca ctaacattta cttaaactcc tccctctatc gcggtactaa atttattatc   3540
aagaaatatg cctctggcaa caaggacaat atcgtacgca ataacgatcg cgtctacatt   3600
aacgtggtgg tgaagaataa agaatatcgt ctggcgacca atgctagtca ggcgggcgtg   3660
gagaaaattc tgtctgcact tgaaatcccg gatgtgggta atttatccca ggtggttgtg   3720
atgaaaagta aaaatgacca agggatcacc aataaatgca aaatgaatct gcaagataac   3780
aacggcaacg acattggttt tatcggcttc caccaattca ataatatcgc gaagcttgtg   3840
gcctcaaatt ggtacaaccg tcagattgag cgcagctccc gcactttagg ctgtagctgg   3900
gagttcattc cggtagatga cggttgggga gaacgcccat tgtaa                   3945
```

<210> SEQ ID NO 531
<211> LENGTH: 1314
<212> TYPE: PRT
<213> ORGANISM: Artificial Sequence
<220> FEATURE:
<223> OTHER INFORMATION: BoNT/A comprising Thrombin (N880) and Thrombin (D890)

<400> SEQUENCE: 531

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
```

-continued

```
                260                 265                 270
Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Gly Gly Ser Gly Gly Glu Asn Leu
                435                 440                 445

Tyr Phe Gln Gly Gly Gly Ser Gly Gly Gly Ala Leu Asn Asp Leu Cys
        450                 455                 460

Ile Lys Val Asn Asn Trp Asp Leu Phe Phe Ser Pro Ser Glu Asp Asn
465                 470                 475                 480

Phe Thr Asn Asp Leu Asn Lys Gly Glu Glu Ile Thr Ser Asp Thr Asn
                485                 490                 495

Ile Glu Ala Ala Glu Glu Asn Ile Ser Leu Asp Leu Ile Gln Gln Tyr
        500                 505                 510

Tyr Leu Thr Phe Asn Phe Asp Asn Glu Pro Glu Asn Ile Ser Ile Glu
        515                 520                 525

Asn Leu Ser Ser Asp Ile Ile Gly Gln Leu Glu Leu Met Pro Asn Ile
        530                 535                 540

Glu Arg Phe Pro Asn Gly Lys Lys Tyr Glu Leu Asp Lys Tyr Thr Met
545                 550                 555                 560

Phe His Tyr Leu Arg Ala Gln Glu Phe Glu His Gly Lys Ser Arg Ile
                565                 570                 575

Ala Leu Thr Asn Ser Val Asn Glu Ala Leu Leu Asn Pro Ser Arg Val
                580                 585                 590

Tyr Thr Phe Phe Ser Ser Asp Tyr Val Lys Lys Val Asn Lys Ala Thr
        595                 600                 605

Glu Ala Ala Met Phe Leu Gly Trp Val Glu Gln Leu Val Tyr Asp Phe
        610                 615                 620

Thr Asp Glu Thr Ser Glu Val Ser Thr Thr Asp Lys Ile Ala Asp Ile
625                 630                 635                 640

Thr Ile Ile Ile Pro Tyr Ile Gly Pro Ala Leu Asn Ile Gly Asn Met
                645                 650                 655

Leu Tyr Lys Asp Asp Phe Val Gly Ala Leu Ile Phe Ser Gly Ala Val
                660                 665                 670

Ile Leu Leu Glu Phe Ile Pro Glu Ile Ala Ile Pro Val Leu Gly Thr
                675                 680                 685
```

-continued

```
Phe Ala Leu Val Ser Tyr Ile Ala Asn Lys Val Leu Thr Val Gln Thr
    690                 695                 700

Ile Asp Asn Ala Leu Ser Lys Arg Asn Glu Lys Trp Asp Glu Val Tyr
705                 710                 715                 720

Lys Tyr Ile Val Thr Asn Trp Leu Ala Lys Val Asn Thr Gln Ile Asp
                725                 730                 735

Leu Ile Arg Lys Lys Met Lys Glu Ala Leu Glu Asn Gln Ala Glu Ala
            740                 745                 750

Thr Lys Ala Ile Ile Asn Tyr Gln Tyr Asn Gln Tyr Thr Glu Glu Glu
        755                 760                 765

Lys Asn Asn Ile Asn Phe Asn Ile Asp Asp Leu Ser Ser Lys Leu Asn
770                 775                 780

Glu Ser Ile Asn Lys Ala Met Ile Asn Ile Asn Lys Phe Leu Asn Gln
785                 790                 795                 800

Cys Ser Val Ser Tyr Leu Met Asn Ser Met Ile Pro Tyr Gly Val Lys
                805                 810                 815

Arg Leu Glu Asp Phe Asp Ala Ser Leu Lys Asp Ala Leu Leu Lys Tyr
            820                 825                 830

Ile Tyr Asp Asn Arg Gly Thr Leu Ile Gly Gln Val Asp Arg Leu Lys
        835                 840                 845

Asp Lys Val Asn Asn Thr Leu Ser Thr Asp Ile Pro Phe Gln Leu Ser
850                 855                 860

Lys Tyr Val Asp Asn Gln Arg Leu Leu Ser Thr Phe Thr Glu Tyr Ile
865                 870                 875                 880

Lys Asn Ile Ile Asn Thr Ser Ile Leu Asn Leu Val Pro Arg Gly Ser
                885                 890                 895

Tyr Glu Ser Asn His Leu Ile Asp Leu Val Pro Arg Gly Ser Arg Tyr
            900                 905                 910

Ala Ser Lys Ile Asn Ile Gly Ser Lys Val Asn Phe Asp Pro Ile Asp
        915                 920                 925

Lys Asn Gln Ile Gln Leu Phe Asn Leu Glu Ser Ser Lys Ile Glu Val
930                 935                 940

Ile Leu Lys Asn Ala Ile Val Tyr Asn Ser Met Tyr Glu Asn Phe Ser
945                 950                 955                 960

Thr Ser Phe Trp Ile Arg Ile Pro Lys Tyr Phe Asn Ser Ile Ser Leu
                965                 970                 975

Asn Asn Glu Tyr Thr Ile Ile Asn Cys Met Glu Asn Asn Ser Gly Trp
            980                 985                 990

Lys Val Ser Leu Asn Tyr Gly Glu Ile Ile Trp Thr Leu Gln Asp Thr
        995                 1000                1005

Gln Glu Ile Lys Gln Arg Val Val Phe Lys Tyr Ser Gln Met Ile Asn
    1010                1015                1020

Ile Ser Asp Tyr Ile Asn Arg Trp Ile Phe Val Thr Ile Thr Asn Asn
1025                1030                1035                1040

Arg Leu Asn Asn Ser Lys Ile Tyr Ile Asn Gly Arg Leu Ile Asp Gln
                1045                1050                1055

Lys Pro Ile Ser Asn Leu Gly Asn Ile His Ala Ser Asn Asn Ile Met
            1060                1065                1070

Phe Lys Leu Asp Gly Cys Arg Asp Thr His Arg Tyr Ile Trp Ile Lys
        1075                1080                1085

Tyr Phe Asn Leu Phe Asp Lys Glu Leu Asn Glu Lys Glu Ile Lys Asp
1090                1095                1100

Leu Tyr Asp Asn Gln Ser Asn Ser Gly Ile Leu Lys Asp Phe Trp Gly
1105                1110                1115                1120
```

Asp Tyr Leu Gln Tyr Asp Lys Pro Tyr Met Leu Asn Leu Tyr Asp
                1125                1130                1135

Pro Asn Lys Tyr Val Asp Val Asn Asn Val Gly Ile Arg Gly Tyr Met
            1140                1145                1150

Tyr Leu Lys Gly Pro Arg Gly Ser Val Met Thr Thr Asn Ile Tyr Leu
        1155                1160                1165

Asn Ser Ser Leu Tyr Arg Gly Thr Lys Phe Ile Ile Lys Lys Tyr Ala
    1170                1175                1180

Ser Gly Asn Lys Asp Asn Ile Val Arg Asn Asn Asp Arg Val Tyr Ile
1185                1190                1195                1200

Asn Val Val Val Lys Asn Lys Glu Tyr Arg Leu Ala Thr Asn Ala Ser
                1205                1210                1215

Gln Ala Gly Val Glu Lys Ile Leu Ser Ala Leu Glu Ile Pro Asp Val
            1220                1225                1230

Gly Asn Leu Ser Gln Val Val Val Met Lys Ser Lys Asn Asp Gln Gly
        1235                1240                1245

Ile Thr Asn Lys Cys Lys Met Asn Leu Gln Asp Asn Asn Gly Asn Asp
    1250                1255                1260

Ile Gly Phe Ile Gly Phe His Gln Phe Asn Asn Ile Ala Lys Leu Val
1265                1270                1275                1280

Ala Ser Asn Trp Tyr Asn Arg Gln Ile Glu Arg Ser Ser Arg Thr Leu
                1285                1290                1295

Gly Cys Ser Trp Glu Phe Ile Pro Val Asp Asp Gly Trp Gly Glu Arg
            1300                1305                1310

Pro Leu

<210> SEQ ID NO 532
<211> LENGTH: 3945
<212> TYPE: DNA
<213> ORGANISM: Artificial Sequence
<220> FEATURE:
<223> OTHER INFORMATION: DNA encoding a BoNT/A comprising FXa (N872) and
      Thrombin (E884)

<400> SEQUENCE: 532

```
atgccgttcg taaacaaaca gttcaactat aaagacccag tcaacggcgt ggacattgcc      60
tatatcaaaa tcccgaatgc gggtcaaatg cagcccgtga agcatttaa atccataac      120
aaaatttggg tgatcccgga gcgcgatacg ttcacgaacc cggaagaagg agatttaaac      180
ccaccgcctg aggctaaaca ggtcccggtg tcttactatg atagcacata cctgagtacc      240
gacaatgaaa aggacaacta cctgaaaggt gttaccaaac tgttcgagcg catttattcg      300
acagatctcg gtcgcatgtt gctgacttct attgtgcgcg gcattccgtt ttggggtggt      360
agcaccatcg atacagaact caaagtgatt gacaccaact gcatcaatgt gattcagcct      420
gatgggagct accggtccga agagcttaac ctcgtaatca ttggcccgag cgcggatatt      480
atccaattcg aatgtaaatc ttttgggcat gaagtcctga atctgacgcg aatggctat      540
ggatcgacgc agtatattcg tttttctcca gatttcacat ttggatttga agaaagcctc      600
gaagttgata cgaaccctct tttaggcgcg ggaaaattcg cgacggaccc agcggtgacc      660
ttggcacatg aacttattca tgccgggcat cgcttgtatg aatcgccat taacccgaac      720
cgtgttttca aggtgaatac gaacgcgtat tacgagatgt cgggcttaga agtgtccttt      780
gaagaactgc gcacgtttgg cggtcatgat gcaaaattta ttgatagtct gcaagaaaac      840
gaatttcggc tgtactatta caataaattc aaagacattg catcaaccct aaacaaggcg      900
```

```
aaaagcattg tgggtaccac ggctagctta caatatatga aaaacgtttt caaagaaaaa    960
tacctcctta gcgaagacac ttccggcaaa ttctctgtcg ataaactgaa atttgataaa   1020
ctgtataaaa tgctcaccga gatctacaca gaggataact tgtcaaatt cttcaaggtc    1080
ttgaatcgga aaacctatct gaacttcgat aaagccgtct ttaagatcaa catcgtaccg   1140
aaagttaact acaccatcta tgatggcttt aatctgcgca atacgaatct ggcggcgaac   1200
tttaacggcc agaacaccga aatcaacaac atgaacttta ctaaactgaa aaattttacc   1260
ggcttgtttg aattctataa gctcctgtgt gtccgcggta ttatcaccag caaaggcggt   1320
ggttctggcg gtggtgaaaa cctgtacttc cagggcggtg gctccggtgg tggtgcgctc   1380
aatgatttat gcatcaaggt gaacaactgg gacttgtttt tctctccatc tgaagataat   1440
tttactaacg acttgaacaa aggagaggaa attacttccg ataccaacat cgaagcagcg   1500
gaagagaata ttagtctaga tcttattcaa caatattacc tgacctttaa ttttgataac   1560
gagcctgaga acatttccat tgagaatctc agctctgaca tcatcggcca gctggaactg   1620
atgccgaata tcgaacgctt tcctaatgga aagaaatatg aattggacaa atacaccatg   1680
ttccactatc tccgcgcgca ggagtttgag cacggcaagt ctcgtattgc tctgaccaat   1740
tcggtaaacg aagccctttt aaatccttcg cgtgtgtaca cctttttctc aagcgattat   1800
gttaaaaaag tgaacaaggc gaccgaagcg gcgatgtttt tgggatgggt ggaacaactg   1860
gtatatgact ttacggatga aacttctgaa gtctcgacca ccgacaaaat tgccgatatt   1920
accattatca ttccctatat tggccctgca ctgaacattg gtaacatgct gtataaagat   1980
gattttgtgg gcgccctgat cttttcaggc gctgttatcc tgctggaatt tatcccggaa   2040
atcgccattc cagtactcgg tacctttgcg ctggtgtcct atatcgcaaa caaagttttg   2100
actgtccaga cgatcgacaa cgcgctcagt aaacgtaacg aaaaatggga tgaggtgtat   2160
aagtatattg ttaccaactg gctcgctaaa gtaaacaccc agattgacct gattcgcaag   2220
aagatgaaag aagcgctgga aaaccaagca gaagcgacca aagctattat caactatcaa   2280
tataaccagt acacagagga agaaaagaat aacatcaact tcaacatcga cgacttatct   2340
tcaaagctga atgaatctat taacaaagcg atgattaata ttaacaagtt cttgaaccaa   2400
tgtagtgtca gctatctgat gaactcgatg atcccttacg gtgtgaaacg tctggaagac   2460
ttcgatgcaa gccttaaaga tgcccttctg aagtatattt acgataatcg cggaactctt   2520
attggccaag tggatcgctt aaaagataaa gtcaacaaca cgctgagtac agacatccct   2580
tttcagctgt ctaaatatgt ggacaatcag cgcctgctgt ccacgtttac ggaatacatc   2640
aaaaacattg agggccgtat caacactagt attctgaact tgcgttacga gttggtgcca   2700
cgcggttcta accatctgat tgatctgagc cgttacgcat ctaaaatcaa catcggatcc   2760
aaggtgaact tcgatcctat cgacaaaaac cagattcaat tgttcaactt agaatcgtca   2820
aagattgaag ttatcttaaa aaatgcgatt gtatataatt caatgtacga aaatttctct   2880
acgagctttt ggattcgtat tccgaaatat ttcaacagta tctctttaaa caacgagtat   2940
actatcatca attgtatgga gaataacagc gggtggaaag tgagccttaa ctatggtgaa   3000
atcatctgga ctctgcagga cactcaagaa attaaacaac gcgtggtgtt taaatactca   3060
cagatgatta acatctcgga ttatattaat cgctggattt ttgtgacaat tactaacaac   3120
cggctgaaca acagcaaaat ttacattaac ggtcgcctga tcgatcagaa accaatcagt   3180
aatctcggta acattcacgc atcgaataat atcatgttca aactggatgg ttgtcgcgac   3240
acgcaccgtt acatttggat caaatacttc aatttattcg acaaagaact caacgaaaag   3300
```

-continued

```
gagattaagg atctttatga caatcagtct aattcgggta ttctgaaaga cttttgggt   3360
gattaccttc agtacgataa accgtattat atgttaaact tatatgatcc gaataaatac  3420
gttgacgtca acaacgttgg cattcgcggc tatatgtatc tgaaagggcc gcgtggcagc  3480
gtgatgacca ctaacattta cttaaactcc tccctctatc gcggtactaa atttattatc  3540
aagaaatatg cctctggcaa caaggacaat atcgtacgca ataacgatcg cgtctacatt  3600
aacgtggtgg tgaagaataa agaatatcgt ctggcgacca atgctagtca ggcgggcgtg  3660
gagaaaattc tgtctgcact tgaaatcccg gatgtgggta atttatccca ggtggttgtg  3720
atgaaaagta aaaatgacca agggatcacc aataaatgca aatgaatct gcaagataac   3780
aacggcaacg acattggttt tatcggcttc caccaattca ataatatcgc gaagcttgtg  3840
gcctcaaatt ggtacaaccg tcagattgag cgcagctccc gcactttagg ctgtagctgg  3900
gagttcattc cggtagatga cggttgggga gaacgcccat tgtaa                  3945
```

<210> SEQ ID NO 533
<211> LENGTH: 1314
<212> TYPE: PRT
<213> ORGANISM: Artificial Sequence
<220> FEATURE:
<223> OTHER INFORMATION: BoNT/A comprising FXa -continued Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
        340                 345                 350

Asn Phe Val Lys Phe Phe Lys Val Leu Asn Arg Lys Thr Tyr Leu Asn
    355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
        420                 425                 430

Gly Ile Ile Thr Ser Lys Gly Gly Ser Gly Gly Gly Glu Asn Leu
    435                 440                 445

Tyr Phe Gln Gly Gly Ser Gly Gly Gly Ala Leu Asn Asp Leu Cys
450                 455                 460

Ile Lys Val Asn Asn Trp Asp Leu Phe Phe Ser Pro Ser Glu Asp Asn
465                 470                 475                 480

Phe Thr Asn Asp Leu Asn Lys Gly Glu Glu Ile Thr Ser Asp Thr Asn
            485                 490                 495

Ile Glu Ala Ala Glu Glu Asn Ile Ser Leu Asp Leu Ile Gln Gln Tyr
        500                 505                 510

Tyr Leu Thr Phe Asn Phe Asp Asn Glu Pro Glu Asn Ile Ser Ile Glu
    515                 520                 525

Asn Leu Ser Ser Asp Ile Ile Gly Gln Leu Glu Leu Met Pro Asn Ile
530                 535                 540

Glu Arg Phe Pro Asn Gly Lys Lys Tyr Glu Leu Asp Lys Tyr Thr Met
545                 550                 555                 560

Phe His Tyr Leu Arg Ala Gln Glu Phe Glu His Gly Lys Ser Arg Ile
            565                 570                 575

Ala Leu Thr Asn Ser Val Asn Glu Ala Leu Leu Asn Pro Ser Arg Val
        580                 585                 590

Tyr Thr Phe Phe Ser Ser Asp Tyr Val Lys Lys Val Asn Lys Ala Thr
    595                 600                 605

Glu Ala Ala Met Phe Leu Gly Trp Val Glu Gln Leu Val Tyr Asp Phe
610                 615                 620

Thr Asp Glu Thr Ser Glu Val Ser Thr Thr Asp Lys Ile Ala Asp Ile
625                 630                 635                 640

Thr Ile Ile Ile Pro Tyr Ile Gly Pro Ala Leu Asn Ile Gly Asn Met
            645                 650                 655

Leu Tyr Lys Asp Asp Phe Val Gly Ala Leu Ile Phe Ser Gly Ala Val
        660                 665                 670

Ile Leu Leu Glu Phe Ile Pro Glu Ile Ala Ile Pro Val Leu Gly Thr

-continued

```
            675                 680                 685
Phe Ala Leu Val Ser Tyr Ile Ala Asn Lys Val Leu Thr Val Gln Thr
690                 695                 700
Ile Asp Asn Ala Leu Ser Lys Arg Asn Glu Lys Trp Asp Glu Val Tyr
705                 710                 715                 720
Lys Tyr Ile Val Thr Asn Trp Leu Ala Lys Val Asn Thr Gln Ile Asp
                    725                 730                 735
Leu Ile Arg Lys Lys Met Lys Glu Ala Leu Glu Asn Gln Ala Glu Ala
                740                 745                 750
Thr Lys Ala Ile Ile Asn Tyr Gln Tyr Asn Gln Tyr Thr Glu Glu Glu
            755                 760                 765
Lys Asn Asn Ile Asn Phe Asn Ile Asp Asp Leu Ser Ser Lys Leu Asn
770                 775                 780
Glu Ser Ile Asn Lys Ala Met Ile Asn Ile Asn Lys Phe Leu Asn Gln
785                 790                 795                 800
Cys Ser Val Ser Tyr Leu Met Asn Ser Met Ile Pro Tyr Gly Val Lys
                    805                 810                 815
Arg Leu Glu Asp Phe Asp Ala Ser Leu Lys Asp Ala Leu Leu Lys Tyr
                820                 825                 830
Ile Tyr Asp Asn Arg Gly Thr Leu Ile Gly Gln Val Asp Arg Leu Lys
            835                 840                 845
Asp Lys Val Asn Asn Thr Leu Ser Thr Asp Ile Pro Phe Gln Leu Ser
850                 855                 860
Lys Tyr Val Asp Asn Gln Arg Leu Leu Ser Thr Phe Thr Glu Tyr Ile
865                 870                 875                 880
Lys Asn Ile Glu Gly Arg Ile Asn Thr Ser Ile Leu Asn Leu Arg Tyr
                    885                 890                 895
Glu Leu Val Pro Arg Gly Ser Asn His Leu Ile Asp Leu Ser Arg Tyr
                900                 905                 910
Ala Ser Lys Ile Asn Ile Gly Ser Lys Val Asn Phe Asp Pro Ile Asp
            915                 920                 925
Lys Asn Gln Ile Gln Leu Phe Asn Leu Glu Ser Ser Lys Ile Glu Val
930                 935                 940
Ile Leu Lys Asn Ala Ile Val Tyr Asn Ser Met Tyr Glu Asn Phe Ser
945                 950                 955                 960
Thr Ser Phe Trp Ile Arg Ile Pro Lys Tyr Phe Asn Ser Ile Ser Leu
                    965                 970                 975
Asn Asn Glu Tyr Thr Ile Ile Asn Cys Met Glu Asn Asn Ser Gly Trp
                980                 985                 990
Lys Val Ser Leu Asn Tyr Gly Glu Ile Ile Trp Thr Leu Gln Asp Thr
            995                 1000                1005
Gln Glu Ile Lys Gln Arg Val Val Phe Lys Tyr Ser Gln Met Ile Asn
1010                1015                1020
Ile Ser Asp Tyr Ile Asn Arg Trp Ile Phe Val Thr Ile Thr Asn Asn
1025                1030                1035                1040
Arg Leu Asn Asn Ser Lys Ile Tyr Ile Asn Gly Arg Leu Ile Asp Gln
                    1045                1050                1055
Lys Pro Ile Ser Asn Leu Gly Asn Ile His Ala Ser Asn Asn Ile Met
                1060                1065                1070
Phe Lys Leu Asp Gly Cys Arg Asp Thr His Arg Tyr Ile Trp Ile Lys
            1075                1080                1085
Tyr Phe Asn Leu Phe Asp Lys Glu Leu Asn Glu Lys Glu Ile Lys Asp
1090                1095                1100
```

-continued

```
Leu Tyr Asp Asn Gln Ser Asn Ser Gly Ile Leu Lys Asp Phe Trp Gly
1105                1110                1115                1120

Asp Tyr Leu Gln Tyr Asp Lys Pro Tyr Tyr Met Leu Asn Leu Tyr Asp
            1125                1130                1135

Pro Asn Lys Tyr Val Asp Val Asn Asn Val Gly Ile Arg Gly Tyr Met
        1140                1145                1150

Tyr Leu Lys Gly Pro Arg Gly Ser Val Met Thr Thr Asn Ile Tyr Leu
    1155                1160                1165

Asn Ser Ser Leu Tyr Arg Gly Thr Lys Phe Ile Ile Lys Lys Tyr Ala
1170                1175                1180

Ser Gly Asn Lys Asp Asn Ile Val Arg Asn Asn Asp Arg Val Tyr Ile
1185                1190                1195                1200

Asn Val Val Val Lys Asn Lys Glu Tyr Arg Leu Ala Thr Asn Ala Ser
                1205                1210                1215

Gln Ala Gly Val Glu Lys Ile Leu Ser Ala Leu Glu Ile Pro Asp Val
            1220                1225                1230

Gly Asn Leu Ser Gln Val Val Val Met Lys Ser Lys Asn Asp Gln Gly
        1235                1240                1245

Ile Thr Asn Lys Cys Lys Met Asn Leu Gln Asp Asn Asn Gly Asn Asp
    1250                1255                1260

Ile Gly Phe Ile Gly Phe His Gln Phe Asn Asn Ile Ala Lys Leu Val
1265                1270                1275                1280

Ala Ser Asn Trp Tyr Asn Arg Gln Ile Glu Arg Ser Ser Arg Thr Leu
                1285                1290                1295

Gly Cys Ser Trp Glu Phe Ile Pro Val Asp Asp Gly Trp Gly Glu Arg
            1300                1305                1310

Pro Leu

<210> SEQ ID NO 534
<211> LENGTH: 3921
<212> TYPE: DNA
<213> ORGANISM: Artificial Sequence
<220> FEATURE:
<223> OTHER INFORMATION: DNA encoding a BoNT/A comprising MMP-9 (I870)

<400> SEQUENCE: 534
atgccgttcg taaacaaaca gttcaactat aaagacccag tcaacggcgt ggacattgcc      60
tatatcaaaa tcccgaatgc gggtcaaatg cagcccgtga agcatttaa atccataac     120 aaaatttggg tgatcccgga gcgcgatacg ttcacgaacc cggaagaagg agatttaaac     180
ccaccgcctg aggctaaaca ggtcccggtg tcttactatg atagcacata cctgagtacc     240
gacaatgaaa aggacaacta cctgaaaggt gttaccaaac tgttcgagcg catttattcg     300
acagatctcg gtcgcatgtt gctgacttct attgtgcgcg gcattccgtt ttggggtggt     360
agcaccatcg atacagaact caaagtgatt gacaccaact gcatcaatgt gattcagcct     420
gatgggagct accggtccga agagcttaac ctcgtaatca ttggcccgag cgcggatatt     480
atccaattcg aatgtaaatc ttttgggcat gaagtcctga atctgacgcg gaatggctat     540
ggatcgacgc agtatattcg tttttctcca gatttcacat tggatttga agaaagcctc     600 gaagttgata cgaaccctct tttaggcgcg ggaaaattcg cgacggaccc agcggtgacc     660
ttggcacatg aacttattca tgccgggcat cgcttgtatg gatcgccat taacccgaac     720 cgtgtttca ggtgaatac gaacgcgtat tacgagatgt cgggcttaga agtgtccttt     780
gaagaactgc gcacgtttgg cggtcatgat gcaaaattta ttgatagtct gcaagaaaac     840
gaatttcggc tgtactatta caataaattc aaagacattg catcaacctt aaacaaggcg     900
```

```
aaaagcattg tgggtaccac ggctagctta caatatatga aaaacgtttt caaagaaaaa    960
tacctcctta gcgaagacac ttccggcaaa ttctctgtcg ataaactgaa atttgataaa   1020
ctgtataaaa tgctcaccga gatctacaca gaggataact ttgtcaaatt cttcaaggtc   1080
ttgaatcgga aaacctatct gaacttcgat aaagccgtct ttaagatcaa catcgtaccg   1140
aaagttaact acaccatcta tgatggcttt aatctgcgca atacgaatct ggcggcgaac   1200
tttaacggcc agaacaccga atcaacaac atgaacttta ctaaactgaa aaattttacc    1260
ggcttgtttg aattctataa gctcctgtgt gtccgcggta ttatcaccag caaaggcggt   1320
ggttctggcg gtggtgaaaa cctgtacttc cagggcggtg gctccggtgg tggtgcgctc   1380
aatgatttat gcatcaaggt gaacaactgg gacttgtttt tctctccatc tgaagataat   1440
tttactaacg acttgaacaa aggagaggaa attacttccg ataccaacat cgaagcagcg   1500
gaagagaata ttagtctaga tcttattcaa caatattacc tgacctttaa ttttgataac   1560
gagcctgaga acatttccat tgagaatctc agctctgaca tcatcggcca gctggaactg   1620
atgccgaata tcgaacgctt tcctaatgga agaaatatg aattggacaa atacaccatg     1680
ttccactatc tccgcgcgca ggagtttgag cacggcaagt ctcgtattgc tctgaccaat   1740
tcggtaaacg aagccctttt aaatccttcg cgtgtgtaca ccttttctc aagcgattat    1800 gttaaaaaag tgaacaaggc gaccgaagcg gcgatgtttt tgggatgggt ggaacaactg   1860
gtatatgact ttacggatga aacttctgaa gtctcgacca ccgacaaaat tgccgatatt   1920
accattatca ttccctatat tggccctgca ctgaacattg gtaacatgct gtataaagat   1980
gattttgtgg gcgccctgat cttttcaggc gctgttatcc tgctggaatt tatcccggaa   2040
atcgccattc cagtactcgg tacctttgcg ctggtgtcct atatcgcaaa caaagttttg   2100
actgtccaga cgatcgacaa cgcgctcagt aaacgtaacg aaaaatggga tgaggtgtat   2160
aagtatattg ttaccaactg gctcgctaaa gtaaacaccc agattgacct gattcgcaag   2220
aagatgaaag aagcgctgga aaaccaagca gaagcgacca agctattat caactatcaa    2280 tataaccagt acacagagga agaaaagaat aacatcaact tcaacatcga cgacttatct   2340
tcaaagctga atgaatctat taacaaagcg atgattaata ttaacaagtt cttgaaccaa   2400
tgtagtgtca gctatctgat gaactcgatg atcccttacg gtgtgaaacg tctgaagac    2460 ttcgatgcaa gccttaaaga tgcccttctg aagtatattt acgataatcg cggaactctt   2520
attggccaag tggatcgctt aaaagataaa gtcaacaaca cgctgagtac agacatccct   2580
tttcagctgt ctaaatatgt ggacaatcag cgcctgctgt ccacgtttac ggaatacatc   2640
ggtccactgg gtctgtgggc acagctgaac ttgcgttacg agagtaacca tctgattgat   2700
ctgagccgtt acgcatctaa aatcaacatc ggatccaagg tgaacttcga tcctatcgac   2760
aaaaaccaga ttcaattgtt caacttagaa tcgtcaaaga ttgaagttat cttaaaaaat   2820
gcgattgtat ataattcaat gtacgaaaat ttctctacga gcttttggat tcgtattccg   2880
aaatatttca acagtatctc tttaaacaac gagtatacta tcatcaattg tatggagaat   2940
aacagcgggt ggaaagtgag ccttaactat ggtgaaatca tctggactct gcaggacact   3000
caagaaatta acaacgcgt ggtgtttaaa tactcacaga tgattaacat ctcggattat    3060
attaatcgct ggattttgt gacaattact aacaaccggc tgaacaacag caaaatttac    3120
attaacggtc gcctgatcga tcagaaacca atcagtaatc tcggtaacat tcacgcatcg   3180
aataatatca tgttcaaact ggatggttgt cgcgacacgc accgttacat ttggatcaaa   3240
tacttcaatt tattcgacaa agaactcaac gaaaaggaga ttaaggatct ttatgacaat   3300
```

```
cagtctaatt cgggtattct gaaagacttt tggggtgatt accttcagta cgataaaccg   3360
tattatatgt taaacttata tgatccgaat aaatacgttg acgtcaacaa cgttggcatt   3420
cgcggctata tgtatctgaa agggccgcgt ggcagcgtga tgaccactaa catttactta   3480
aactcctccc tctatcgcgg tactaaattt attatcaaga aatatgcctc tggcaacaag   3540
gacaatatcg tacgcaataa cgatcgcgtc tacattaacg tggtggtgaa gaataaagaa   3600
tatcgtctgg cgaccaatgc tagtcaggcg ggcgtggaga aaattctgtc tgcacttgaa   3660
atcccggatg tgggtaattt atcccaggtg gttgtgatga aaagtaaaaa tgaccaaggg   3720
atcaccaata aatgcaaaat gaatctgcaa gataacaacg gcaacgacat tggttttatc   3780
ggcttccacc aattcaataa tatcgcgaag cttgtggcct caaattggta caaccgtcag   3840
attgagcgca gctcccgcac tttaggctgt agctgggagt tcattccggt agatgacggt   3900
tggggagaac gcccattgta a                                             3921
```

<210> SEQ ID NO 535
<211> LENGTH: 1306
<212> TYPE: PRT
<213> ORGANISM: Artificial Sequence
<220> FEATURE:
<223> OTHER INFORMATION: BoNT/A comprising MMP-9 (I870)

<400> SEQUENCE: 535

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

```
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
        290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Gly Gly Ser Gly Gly Gly Glu Asn Leu
        435                 440                 445
Tyr Phe Gln Gly Gly Ser Gly Gly Gly Ala Leu Asn Asp Leu Cys
    450                 455                 460
Ile Lys Val Asn Asn Trp Asp Leu Phe Phe Ser Pro Ser Glu Asp Asn
465                 470                 475                 480
Phe Thr Asn Asp Leu Asn Lys Gly Glu Glu Ile Thr Ser Asp Thr Asn
                485                 490                 495
Ile Glu Ala Ala Glu Glu Asn Ile Ser Leu Asp Leu Ile Gln Gln Tyr
            500                 505                 510
Tyr Leu Thr Phe Asn Phe Asp Asn Glu Pro Glu Asn Ile Ser Ile Glu
        515                 520                 525
Asn Leu Ser Ser Asp Ile Ile Gly Gln Leu Glu Leu Met Pro Asn Ile
    530                 535                 540
Glu Arg Phe Pro Asn Gly Lys Lys Tyr Glu Leu Asp Lys Tyr Thr Met
545                 550                 555                 560
Phe His Tyr Leu Arg Ala Gln Glu Phe Glu His Gly Lys Ser Arg Ile
                565                 570                 575
Ala Leu Thr Asn Ser Val Asn Glu Ala Leu Leu Asn Pro Ser Arg Val
            580                 585                 590
Tyr Thr Phe Phe Ser Ser Asp Tyr Val Lys Lys Val Asn Lys Ala Thr
        595                 600                 605
Glu Ala Ala Met Phe Leu Gly Trp Val Glu Gln Leu Val Tyr Asp Phe
    610                 615                 620
Thr Asp Glu Thr Ser Glu Val Ser Thr Thr Asp Lys Ile Ala Asp Ile
625                 630                 635                 640
Thr Ile Ile Ile Pro Tyr Ile Gly Pro Ala Leu Asn Ile Gly Asn Met
                645                 650                 655
Leu Tyr Lys Asp Asp Phe Val Gly Ala Leu Ile Phe Ser Gly Ala Val
            660                 665                 670
Ile Leu Leu Glu Phe Ile Pro Glu Ile Ala Ile Pro Val Leu Gly Thr
```

```
            675                 680                 685
Phe Ala Leu Val Ser Tyr Ile Ala Asn Lys Val Leu Thr Val Gln Thr
    690                 695                 700
Ile Asp Asn Ala Leu Ser Lys Arg Asn Glu Lys Trp Asp Glu Val Tyr
705                 710                 715                 720
Lys Tyr Ile Val Thr Asn Trp Leu Ala Lys Val Asn Thr Gln Ile Asp
                725                 730                 735
Leu Ile Arg Lys Lys Met Lys Glu Ala Leu Glu Asn Gln Ala Glu Ala
                740                 745                 750
Thr Lys Ala Ile Ile Asn Tyr Gln Tyr Asn Gln Tyr Thr Glu Glu Glu
                755                 760                 765
Lys Asn Asn Ile Asn Phe Asn Ile Asp Asp Leu Ser Ser Lys Leu Asn
770                 775                 780
Glu Ser Ile Asn Lys Ala Met Ile Asn Ile Asn Lys Phe Leu Asn Gln
785                 790                 795                 800
Cys Ser Val Ser Tyr Leu Met Asn Ser Met Ile Pro Tyr Gly Val Lys
                805                 810                 815
Arg Leu Glu Asp Phe Asp Ala Ser Leu Lys Asp Ala Leu Leu Lys Tyr
                820                 825                 830
Ile Tyr Asp Asn Arg Gly Thr Leu Ile Gly Gln Val Asp Arg Leu Lys
                835                 840                 845
Asp Lys Val Asn Asn Thr Leu Ser Thr Asp Ile Pro Phe Gln Leu Ser
850                 855                 860
Lys Tyr Val Asp Asn Gln Arg Leu Leu Ser Thr Phe Thr Glu Tyr Ile
865                 870                 875                 880
Gly Pro Leu Gly Leu Trp Ala Gln Leu Asn Leu Arg Tyr Glu Ser Asn
                885                 890                 895
His Leu Ile Asp Leu Ser Arg Tyr Ala Ser Lys Ile Asn Ile Gly Ser
                900                 905                 910
Lys Val Asn Phe Asp Pro Ile Asp Lys Asn Gln Ile Gln Leu Phe Asn
                915                 920                 925
Leu Glu Ser Ser Lys Ile Glu Val Ile Leu Lys Asn Ala Ile Val Tyr
                930                 935                 940
Asn Ser Met Tyr Glu Asn Phe Ser Thr Ser Phe Trp Ile Arg Ile Pro
945                 950                 955                 960
Lys Tyr Phe Asn Ser Ile Ser Leu Asn Asn Glu Tyr Thr Ile Ile Asn
                965                 970                 975
Cys Met Glu Asn Asn Ser Gly Trp Lys Val Ser Leu Asn Tyr Gly Glu
                980                 985                 990
Ile Ile Trp Thr Leu Gln Asp Thr Gln Glu Ile Lys Gln Arg Val Val
                995                 1000                1005
Phe Lys Tyr Ser Gln Met Ile Asn Ile Ser Asp Tyr Ile Asn Arg Trp
                1010                1015                1020
Ile Phe Val Thr Ile Thr Asn Asn Arg Leu Asn Asn Ser Lys Ile Tyr
1025                1030                1035                1040
Ile Asn Gly Arg Leu Ile Asp Gln Lys Pro Ile Ser Asn Leu Gly Asn
                1045                1050                1055
Ile His Ala Ser Asn Asn Ile Met Phe Lys Leu Asp Gly Cys Arg Asp
                1060                1065                1070
Thr His Arg Tyr Ile Trp Ile Lys Tyr Phe Asn Leu Phe Asp Lys Glu
                1075                1080                1085
Leu Asn Glu Lys Glu Ile Lys Asp Leu Tyr Asp Asn Gln Ser Asn Ser
                1090                1095                1100
```

-continued

```
Gly Ile Leu Lys Asp Phe Trp Gly Asp Tyr Leu Gln Tyr Asp Lys Pro
1105                1110                1115                1120

Tyr Tyr Met Leu Asn Leu Tyr Asp Pro Asn Lys Tyr Val Asp Val Asn
            1125                1130                1135

Asn Val Gly Ile Arg Gly Tyr Met Tyr Leu Lys Gly Pro Arg Gly Ser
        1140                1145                1150

Val Met Thr Thr Asn Ile Tyr Leu Asn Ser Ser Leu Tyr Arg Gly Thr
    1155                1160                1165

Lys Phe Ile Ile Lys Lys Tyr Ala Ser Gly Asn Lys Asp Asn Ile Val
1170                1175                1180

Arg Asn Asn Asp Arg Val Tyr Ile Asn Val Val Leu Asn Lys Glu
1185                1190                1195                1200

Tyr Arg Leu Ala Thr Asn Ala Ser Gln Ala Gly Val Glu Lys Ile Leu
            1205                1210                1215

Ser Ala Leu Glu Ile Pro Asp Val Gly Asn Leu Ser Gln Val Val Val
        1220                1225                1230

Met Lys Ser Lys Asn Asp Gln Gly Ile Thr Asn Lys Cys Lys Met Asn
    1235                1240                1245

Leu Gln Asp Asn Asn Gly Asn Asp Ile Gly Phe Ile Gly Phe His Gln
1250                1255                1260

Phe Asn Asn Ile Ala Lys Leu Val Ala Ser Asn Trp Tyr Asn Arg Gln
1265                1270                1275                1280

Ile Glu Arg Ser Ser Arg Thr Leu Gly Cys Ser Trp Glu Phe Ile Pro
            1285                1290                1295

Val Asp Asp Gly Trp Gly Glu Arg Pro Leu
        1300                1305

<210> SEQ ID NO 536
<211> LENGTH: 3916
<212> TYPE: DNA
<213> ORGANISM: Artificial Sequence
<220> FEATURE:
<223> OTHER INFORMATION: DNA encoding a BoNT/A comprising Fxa (N872)

<400> SEQUENCE: 536
atgccgttcg taaacaaaca gttcaactat aaagacccag tcaacggcgt ggacattgcc      60
tatatcaaaa tcccgaatgc gggtcaaatg cagcccgtga agcatttaa aatccataac     120 aaaatttggg tgatcccgga gcgcgatacg ttcacgaacc cggaagaagg agatttaaac     180
ccaccgcctg aggctaaaca ggtcccggtg tcttactatg atagcacata cctgagtacc     240
gacaatgaaa aggacaacta cctgaaaggt gttaccaaac tgttcgagcg catttattcg     300
acagatctcg gtcgcatgtt gctgacttct attgtgcgcg gcattccgtt ttggggtggt     360
agcaccatcg atacagaact caaagtgatt gacaccaact gcatcaatgt gattcagcct     420
gatgggagct accggtccga agagcttaac ctcgtaatca ttggcccgag cgcggatatt     480
atccaattcg aatgtaaatc ttttgggcat gaagtcctga atctgacgcg aatggctat     540 ggatcgacgc agtatattcg ttttctcca gatttcacat ttggattga agaaagcctc     600 gaagttgata cgaaccctct tttaggcgcg ggaaaattcg cgacggaccc agcggtgacc     660
ttggcacatg aacttattca tgccgggcat cgcttgtatg aatcgccat taacccgaac     720 cgtgttttca ggtgaatac gaacgcgtat tacgagatgt cgggcttaga agtgtccttt     780
gaagaactgc gcacgtttgg cggtcatgat gcaaaattta ttgatagtct gcaagaaaac     840
gaatttcggc tgtactatta caataaaattc aagacattg catcaacctt aaacaaggcg     900
aaaagcattg tgggtaccac ggctagctta caatatatga aaaacgtttt caaagaaaaa     960
```

```
tacctcctta gcgaagacac ttccggcaaa ttctctgtcg ataaactgaa atttgataaa    1020
ctgtataaaa tgctcaccga gatctacaca gaggataact tgtcaaatt cttcaaggtc    1080 ttgaatcgga aaacctatct gaacttcgat aaagccgtct ttaagatcaa catcgtaccg    1140
aaagttaact acaccatcta tgatggcttt aatctgcgca atacgaatct ggcggcgaac    1200
tttaacggcc agaacaccga aatcaacaac atgaacttta ctaaactgaa aaattttacc    1260
ggcttgtttg aattctataa gctcctgtgt gtccgcggta ttatcaccag caaaggcggt    1320
ggttctggcg gtggtgaaaa cctgtacttc cagggcggtg gctccggtgg tggtgcgctc    1380
aatgatttat gcatcaaggt gaacaactgg gacttgtttt tctctccatc tgaagataat    1440
tttactaacg acttgaacaa aggagaggaa attacttccg ataccaacat cgaagcagcg    1500
gaagagaata ttagtctaga tcttattcaa caatattacc tgacctttaa ttttgataac    1560
gagcctgaga acatttccat tgagaatctc agctctgaca tcatcggcca gctggaactg    1620
atgccgaata tcgaacgctt tcctaatgga aagaaatatg aattggacaa atacaccatg    1680
ttccactatc tccgcgcgca ggagtttgag cacggcaagt ctcgtattgc tctgaccaat    1740
tcggtaaacg aagccctttt aaatccttcg cgtgtgtaca ccttttttctc aagcgattat    1800 gttaaaaaag tgaacaaggc gaccgaagcg gcgatgtttt gggatgggt ggaacaactg    1860 gtatatgact ttacgatgga aacttctgaa gtctcgacca ccgacaaaat tgccgatatt    1920
accattatca ttccctatat tggccctgca ctgaacattg taacatgct gtataaagat    1980 gattttgtgg gcgccctgat cttttcaggc gctgttatcc tgctggaatt tatcccggaa    2040
atcgccattc cagtactcgg taccttttgcg ctggtgtcct atatcgcaaa caaagttttg    2100
actgtccaga cgatcgacaa cgcgctcagt aaacgtaacg aaaaatggga tgaggtgtat    2160
aagtatattg ttaccaactg gctcgctaaa gtaaacaccc agattgacct gattcgcaag    2220
aagatgaaag aagcgctgga aaaccaagca gaagcgacca aagctattat caactatcaa    2280
tataaccagt acacagagga agaaaagaat aacatcaact tcaacatcga cgacttatct    2340
tcaaagctga tgaatctat taacaaagcg atgattaata ttaacaagtt cttgaaccaa    2400
tgtagtgtca gctatctgat gaactcgatg atcccttacg gtgtgaaacg tctggaagac    2460
ttcgatgcaa gccttaaaga tgcccttctg aagtatattt acgataatcg cggaactctt    2520
attggccaag tggatcgctt aaaagataaa gtcaacaaca cgctgagtac agacatccct    2580
tttcagctgt ctaaatatgt ggacaatcag cgcctgctgt ccacgtttac ggaatacatc    2640
aaaaacattg agggccgtat caacactagt attctgatct aaccatctga ttgatctgag    2700
ccgttacgca tctaaaatca acatcggatc caaggtgaac ttcgatccta tcgacaaaaa    2760
ccagattcaa ttgttcaact tagaatcgtc aaagattgaa gttatcttaa aaaatgcgat    2820
tgtatataat tcaatgtacg aaaatttctc tacgagcttt tggattcgta ttccgaaata    2880
tttcaacagt atctctttaa acaacgagta tactatcatc aattgtatgg agaataacag    2940
cgggtggaaa gtgagcctta actatggtga atcatctgg actctgcagg acactcaaga    3000
aattaaacaa cgcgtggtgt ttaaatactc acagatgatt aacatctcgg attatattaa    3060
tcgctggatt tttgtgacaa ttactaacaa ccggctgaac aacagcaaaa tttacattaa    3120
cggtcgcctg atcgatcaga aaccaatcag taatctcggt aacattcacg catcgaataa    3180
tatcatgttc aaactggatg gttgtcgcga cacgcaccgt tacatttgga tcaaatactt    3240
caatttattc gacaaagaac tcaacgaaaa ggagattaag gatctttatg acaatcagtc    3300
taattcgggt attctgaaag acttttgggg tgattacctt cagtacgata aaccgtatta    3360
```

-continued

```
tatgttaaac ttatatgatc cgaataaata cgttgacgtc aacaacgttg gcattcgcgg    3420
ctatatgtat ctgaaagggc cgcgtggcag cgtgatgacc actaacattt acttaaactc    3480
ctccctctat cgcggtacta aatttattat caagaaatat gcctctggca acaaggacaa    3540
tatcgtacgc aataacgatc gcgtctacat taacgtggtg gtgaagaata agaatatcg     3600 tctggcgacc aatgctagtc aggcgggcgt ggagaaaatt ctgtctgcac ttgaaatccc    3660
ggatgtgggt aatttatccc aggtggttgt gatgaaaagt aaaaatgacc aagggatcac    3720
caataaatgc aaaatgaatc tgcaagataa caacggcaac gacattggtt ttatcggctt    3780
ccaccaattc aataatatcg cgaagcttgt ggcctcaaat tggtacaacc gtcagattga    3840
gcgcagctcc cgcactttag gctgtagctg ggagttcatt ccggtagatg acggttgggg    3900
agaacgccca ttgtaa                                                    3916
```

<210> SEQ ID NO 537
<211> LENGTH: 1309
<212> TYPE: PRT
<213> ORGANISM: Artificial Sequence
<220> FEATURE:
<223> OTHER INFORMATION: BoNT/A comprising Fxa (N872)

<400> SEQUENCE: 537

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
```

-continued

```
                260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
                370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Gly Gly Ser Gly Gly Glu Asn Leu
                435                 440                 445
Tyr Phe Gln Gly Gly Gly Ser Gly Gly Gly Ala Leu Asn Asp Leu Cys
                450                 455                 460
Ile Lys Val Asn Asn Trp Asp Leu Phe Phe Ser Pro Ser Glu Asp Asn
465                 470                 475                 480
Phe Thr Asn Asp Leu Asn Lys Gly Glu Glu Ile Thr Ser Asp Thr Asn
                485                 490                 495
Ile Glu Ala Ala Glu Asn Ile Ser Leu Asp Leu Ile Gln Gln Tyr
                500                 505                 510
Tyr Leu Thr Phe Asn Phe Asp Asn Glu Pro Glu Asn Ile Ser Ile Glu
                515                 520                 525
Asn Leu Ser Ser Asp Ile Ile Gly Gln Leu Glu Leu Met Pro Asn Ile
                530                 535                 540
Glu Arg Phe Pro Asn Gly Lys Lys Tyr Glu Leu Asp Lys Tyr Thr Met
545                 550                 555                 560
Phe His Tyr Leu Arg Ala Gln Glu Phe Glu His Gly Lys Ser Arg Ile
                565                 570                 575
Ala Leu Thr Asn Ser Val Asn Glu Ala Leu Leu Asn Pro Ser Arg Val
                580                 585                 590
Tyr Thr Phe Phe Ser Ser Asp Tyr Val Lys Lys Val Asn Lys Ala Thr
                595                 600                 605
Glu Ala Ala Met Phe Leu Gly Trp Val Glu Gln Leu Val Tyr Asp Phe
610                 615                 620
Thr Asp Glu Thr Ser Glu Val Ser Thr Thr Asp Lys Ile Ala Asp Ile
625                 630                 635                 640
Thr Ile Ile Ile Pro Tyr Ile Gly Pro Ala Leu Asn Ile Gly Asn Met
                645                 650                 655
Leu Tyr Lys Asp Asp Phe Val Gly Ala Leu Ile Phe Ser Gly Ala Val
                660                 665                 670
Ile Leu Leu Glu Phe Ile Pro Glu Ile Ala Ile Pro Val Leu Gly Thr
                675                 680                 685
```

-continued

```
Phe Ala Leu Val Ser Tyr Ile Ala Asn Lys Val Leu Thr Val Gln Thr
            690                 695                 700

Ile Asp Asn Ala Leu Ser Lys Arg Asn Glu Lys Trp Asp Glu Val Tyr
705                 710                 715                 720

Lys Tyr Ile Val Thr Asn Trp Leu Ala Lys Val Asn Thr Gln Ile Asp
                725                 730                 735

Leu Ile Arg Lys Lys Met Lys Glu Ala Leu Glu Asn Gln Ala Glu Ala
            740                 745                 750

Thr Lys Ala Ile Ile Asn Tyr Gln Tyr Asn Gln Tyr Thr Glu Glu Glu
        755                 760                 765

Lys Asn Asn Ile Asn Phe Asn Ile Asp Asp Leu Ser Ser Lys Leu Asn
770                 775                 780

Glu Ser Ile Asn Lys Ala Met Ile Asn Ile Asn Lys Phe Leu Asn Gln
785                 790                 795                 800

Cys Ser Val Ser Tyr Leu Met Asn Ser Met Ile Pro Tyr Gly Val Lys
                805                 810                 815

Arg Leu Glu Asp Phe Asp Ala Ser Leu Lys Asp Ala Leu Leu Lys Tyr
            820                 825                 830

Ile Tyr Asp Asn Arg Gly Thr Leu Ile Gly Gln Val Asp Arg Leu Lys
        835                 840                 845

Asp Lys Val Asn Asn Thr Leu Ser Thr Asp Ile Pro Phe Gln Leu Ser
850                 855                 860

Lys Tyr Val Asp Asn Gln Arg Leu Leu Ser Thr Phe Thr Glu Tyr Ile
865                 870                 875                 880

Lys Asn Ile Glu Gly Arg Ile Asn Thr Ser Ile Leu Asn Leu Arg Tyr
                885                 890                 895

Glu Ser Asn His Leu Ile Asp Leu Ser Arg Tyr Ala Ser Lys Ile Asn
            900                 905                 910

Ile Gly Ser Lys Val Asn Phe Asp Pro Ile Asp Lys Asn Gln Ile Gln
        915                 920                 925

Leu Phe Asn Leu Glu Ser Ser Lys Ile Glu Val Ile Leu Lys Asn Ala
930                 935                 940

Ile Val Tyr Asn Ser Met Tyr Glu Asn Phe Ser Thr Ser Phe Trp Ile
945                 950                 955                 960

Arg Ile Pro Lys Tyr Phe Asn Ser Ile Ser Leu Asn Asn Glu Tyr Thr
                965                 970                 975

Ile Ile Asn Cys Met Glu Asn Asn Ser Gly Trp Lys Val Ser Leu Asn
            980                 985                 990

Tyr Gly Glu Ile Ile Trp Thr Leu Gln Asp Thr Gln Glu Ile Lys Gln
        995                 1000                1005

Arg Val Val Phe Lys Tyr Ser Gln Met Ile Asn Ile Ser Asp Tyr Ile
    1010                1015                1020

Asn Arg Trp Ile Phe Val Thr Ile Thr Asn Asn Arg Leu Asn Asn Ser
1025                1030                1035                1040

Lys Ile Tyr Ile Asn Gly Arg Leu Ile Asp Gln Lys Pro Ile Ser Asn
                1045                1050                1055

Leu Gly Asn Ile His Ala Ser Asn Asn Ile Met Phe Lys Leu Asp Gly
            1060                1065                1070

Cys Arg Asp Thr His Arg Tyr Ile Trp Ile Lys Tyr Phe Asn Leu Phe
        1075                1080                1085

Asp Lys Glu Leu Asn Glu Lys Glu Ile Lys Asp Leu Tyr Asp Asn Gln
1090                1095                1100

Ser Asn Ser Gly Ile Leu Lys Asp Phe Trp Gly Asp Tyr Leu Gln Tyr
1105                1110                1115                1120
```

```
Asp Lys Pro Tyr Tyr Met Leu Asn Leu Tyr Asp Pro Asn Lys Tyr Val
                1125                1130                1135

Asp Val Asn Asn Val Gly Ile Arg Gly Tyr Met Tyr Leu Lys Gly Pro
        1140                1145                1150

Arg Gly Ser Val Met Thr Thr Asn Ile Tyr Leu Asn Ser Ser Leu Tyr
            1155                1160                1165

Arg Gly Thr Lys Phe Ile Ile Lys Lys Tyr Ala Ser Gly Asn Lys Asp
        1170                1175                1180

Asn Ile Val Arg Asn Asn Asp Arg Val Tyr Ile Asn Val Val Val Lys
1185                1190                1195                1200

Asn Lys Glu Tyr Arg Leu Ala Thr Asn Ala Ser Gln Ala Gly Val Glu
                1205                1210                1215

Lys Ile Leu Ser Ala Leu Glu Ile Pro Asp Val Gly Asn Leu Ser Gln
            1220                1225                1230

Val Val Val Met Lys Ser Lys Asn Asp Gln Gly Ile Thr Asn Lys Cys
        1235                1240                1245

Lys Met Asn Leu Gln Asp Asn Asn Gly Asn Asp Ile Gly Phe Ile Gly
        1250                1255                1260

Phe His Gln Phe Asn Asn Ile Ala Lys Leu Val Ala Ser Asn Trp Tyr
1265                1270                1275                1280

Asn Arg Gln Ile Glu Arg Ser Ser Arg Thr Leu Gly Cys Ser Trp Glu
                1285                1290                1295

Phe Ile Pro Val Asp Asp Gly Trp Gly Glu Arg Pro Leu
                1300                1305
```

DEGRADABLE CLOSTRIDIAL TOXINS

This application is a divisional and claims priority pursuant to 35 U.S.C. §120 to U.S. patent application Ser. No. 13/112,844, filed May 20, 2011, now U.S. Pat. No. 8,512,992, which claims priority pursuant to 35 U.S.C. §119(e) to U.S. Provisional Patent Application Ser. No. 61/346,578, filed on May 20, 2010, both incorporated entirely by reference.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Beaufour Ipsen, Porton Down, England), NEURONOX® (Medy-Tox, Inc., Ochang-myeon, South Korea) BTX-A (Lanzhou Institute Biological Products, China) and XEOMIN® (Merz Pharmaceuticals, GmbH., Frankfurt, Germany); and BoNT/B preparations, such as, e.g., MYOBLOC™/NEUROBLOC™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

A Clostridial toxin treatment inhibits neurotransmitter release by disrupting the exocytotic process used to secrete the neurotransmitter into the synaptic cleft. There is a great desire by the pharmaceutical industry to expand the use of Clostridial toxin therapies beyond its current myo-relaxant applications to treat sensory nerve-based ailments, such as, e.g., various kinds of chronic pain, neurogenic inflammation and urogenital disorders, as well as other disorders, such as, e.g., pancreatitis. One approach that is currently being exploited to expand Clostridial toxin-based therapies involves modifying a Clostridial toxin so that the modified toxin has an altered cell targeting capability for a non-Clostridial toxin target cell. This re-targeted capability is achieved by replacing a naturally-occurring targeting domain of a Clostridial toxin with a targeting domain showing a preferential binding activity for a non-Clostridial toxin receptor present in a non-Clostridial toxin target cell. Such modifications to a targeting domain result in a Clostridial toxin chimeric called a Targeted Vesicular Exocytosis Modulating Protein (TVEMP) that is able to selectively bind to a non-Clostridial toxin receptor (target receptor) present on a non-Clostridial toxin target cell (re-targeted). A Clostridial toxin chimeric with a targeting activity for a non-Clostridial toxin target cell can bind to a receptor present on the non-Clostridial toxin target cell, translocate into the cytoplasm, and exert its proteolytic effect on the SNARE complex of the non-Clostridial toxin target cell.

Clostridial toxin and Clostridial toxin chimeric therapies are successfully used for many indications. Generally, administration of a Clostridial toxin or Clostridial toxin chimeric is well tolerated. However, administration in some applications can be challenging because of the larger doses required to achieve a beneficial effect. Larger doses can increase the likelihood that the toxin or Clostridial toxin chimeric may move through the interstitial fluids and the circulatory systems, such as, e.g., the cardiovascular system and the lymphatic system, of the body, resulting in the undesirable dispersal of the toxin or Clostridial toxin chimeric to areas not targeted for treatment. Such dispersal can lead to undesirable side effects, such as, e.g., inhibition of neurotransmitter release in neurons not targeted for toxin treatment or paralysis of a muscle not targeted for treatment. For example, a patient administered a therapeutically effective amount of a BoNT/A treatment into the neck muscles for torticollis may develop dysphagia because of dispersal of the toxin into the oropharynx. Thus, there remains a need for improved Clostridial toxins and/or Clostridial toxin chimeras that are effective at the site of treatment, but have negligible to minimal effects in areas not targeted for toxin treatment.

The growing clinical, therapeutic, and cosmetic use of Clostridial toxins and Clostridial toxin chimeras in therapies requiring larger doses necessitates the pharmaceutical industry to develop modified Clostridial toxins and Clostridial toxin chimeras that are effective at the target site of application, but reduce or prevent the possible side-effects associated with the dispersal of the toxins to an unwanted location. The present specification provides novel modified Clostridial toxins and Clostridial toxin chimeras that reduce or prevent unwanted side-effects associated with toxin dispersal into non-targeted areas. These and related advantages are useful for various clinical, therapeutic and cosmetic applications, such as, e.g., the treatment of neuromuscular disorders, neuropathic disorders, eye disorders, pain, muscle injuries, headache, cardiovascular diseases, neuropsychiatric disorders, endocrine disorders, cancers, otic disorders and hyperkinetic facial lines, as well as, other disorders where a Clostridial toxin or a Clostridial toxin chimeric administration to a mammal can produce a beneficial effect.

BRIEF DESCRIPTION OF THE DRAWINGS

FIGS. 1A and 1B show a schematic of the current paradigm of neurotransmitter release and Clostridial toxin intoxication in a central and peripheral neuron. FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed. FIG. 1B shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including, e.g., changes in the internal pH of the vesicle, formation of a channel pore comprising the $H_N$ domain of the Clostridial toxin heavy chain, separation of the Clostridial toxin light chain from the heavy chain, and release of the active light chain and 4) enzymatic target modification, where the activate light chain of Clostridial toxin proteolytically cleaves its target SNARE substrate, such as, e.g., SNAP-25, VAMP or Syntaxin, thereby preventing vesicle docking and neurotransmitter release.

FIG. 3A depicts the single-chain polypeptide form of a toxin or chimera with an amino to carboxyl linear organization comprising a binding element, a translocation element, a di-chain loop region comprising an exogenous protease cleavage site (P), and a therapeutic element. Upon proteolytic cleavage with a P protease, the single-chain form of the toxin or chimera is converted to the di-chain form. FIG. 3B depicts the single polypeptide form of a toxin or chimera with an amino to carboxyl linear organization comprising a binding element, a therapeutic element, a di-chain loop region comprising an exogenous protease cleavage site (P), and a translocation element. Upon proteolytic cleavage with a P protease, the single-chain form of the toxin or chimera is converted to the di-chain form.

FIG. 4A depicts the single polypeptide form of a toxin or chimera with an amino to carboxyl linear organization comprising a therapeutic element, a di-chain loop region comprising an exogenous protease cleavage site (P), a binding element, and a translocation element. Upon proteolytic cleavage with a P protease, the single-chain form of the toxin or chimera is converted to the di-chain form. FIG. 4B depicts the single polypeptide form of a toxin or chimera with an amino to carboxyl linear organization comprising a translocation element, a di-chain loop region comprising an exogenous protease cleavage site (P), a binding element, and a therapeutic element. Upon proteolytic cleavage with a P protease, the single-chain form of the toxin or chimera is converted to the di-chain form. FIG. 4C depicts the single polypeptide form of a toxin or chimera with an amino to carboxyl linear organization comprising a therapeutic element, a binding element, a di-chain loop region comprising an exogenous protease cleavage site (P), and a translocation element. Upon proteolytic cleavage with a P protease, the single-chain form of the toxin or chimera is converted to the di-chain form. FIG. 4D depicts the single polypeptide form of a toxin or chimera with an amino to carboxyl linear organization comprising a translocation element, a binding element, a di-chain loop region comprising an exogenous protease cleavage site (P), and a therapeutic element. Upon proteolytic cleavage with a P protease, the single-chain form of the toxin or chimera is converted to the di-chain form.

FIG. 5A depicts the single polypeptide form of a toxin or chimera with an amino to carboxyl linear organization comprising a therapeutic element, a di-chain loop region comprising an exogenous protease cleavage site (P), a translocation element, and a binding element. Upon proteolytic cleavage with a P protease, the single-chain form of the toxin is converted to the di-chain form. FIG. 5B depicts the single polypeptide form of a toxin or chimera with an amino to carboxyl linear organization comprising a translocation element, a di-chain loop region comprising an exogenous protease cleavage site (P), a therapeutic element, and a binding element. Upon proteolytic cleavage with a P protease, the single-chain form of the toxin or chimera is converted to the di-chain form.

DETAILED DESCRIPTION

Figure 2:
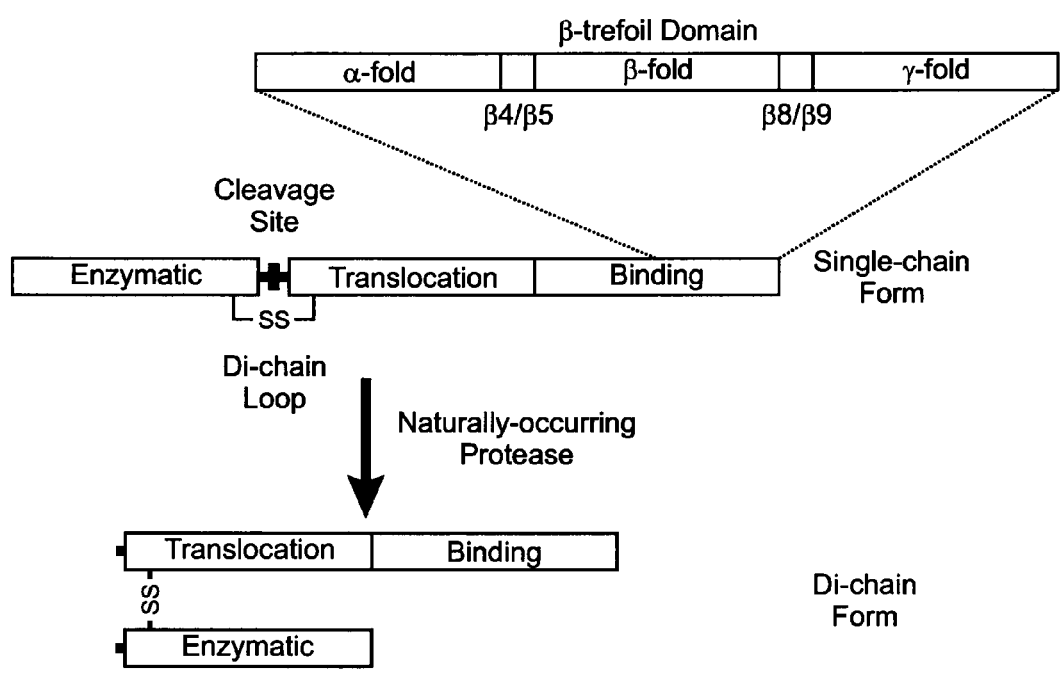
FIG. 2 shows the domain organization of naturally-occurring Clostridial toxins. The single-chain form depicts the amino to carboxyl linear organization comprising an enzymatic domain, a translocation domain, and a binding domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single-chain form of the toxin into the di-chain form. Above the single-chain form, the $H_{CC}$ region of the Clostridial toxin binding domain is depicted. This region comprises the β-trefoil domain which comprises in an amino to carboxyl linear organization an α-fold, a β4/β5 hairpin turn, a β-fold, a β8/β9 hairpin turn, and a γ-fold.

The present specification discloses modified Clostridial toxins and modified Clostridial toxin chimeras that can be rapidly inactivated from an unwanted location or locations by exploiting the presence of proteases present in interstitial fluids and circulatory systems, such as, e.g., the cardiovascular system and the lymphatic system. This is because the modified Clostridial toxins and modified Clostridial toxin chimeras disclosed in the present specification comprise a protease cleavage site for a protease present in an interstitial fluid and/or a circulatory system. The presence of such a protease cleavage site makes the modified Clostridial toxin or modified Clostridial toxin chimeric susceptible to proteolytic cleavage by its cognate protease, which renders such modified toxins inactive. For example, in situations where a Clostridial toxin or Clostridial toxin chimeric modified to comprise a cleavage site for an extracellular matrix protease has diffused into the interstitial fluid, this modified toxin or modified Clostridial toxin chimeric can be effectively cleaved by the cognate extracellular matrix protease. As another example, in situations where a Clostridial toxin or Clostridial toxin chimeric modified to comprise a cleavage site for a blood protease has diffused into the cardiovascular system, this modified toxin or modified Clostridial toxin chimeric can be effectively cleaved by the cognate blood protease. As yet another example, in situations where a Clostridial toxin or Clostridial toxin chimeric modified to comprise a cleavage site for a lymphatic protease has diffused into the lymphatic system, this modified toxin or modified Clostridial toxin chimeric can be effectively cleaved by the cognate lymphatic protease. Thus utilizing a Clostridial toxin or Clostridial toxin chimeric comprising a cleavage site(s) for proteases present the interstitial fluid and/or circulatory system will lessen or remove such Clostridial toxin or Clostridial toxin chimeric from an unwanted location, thereby reducing or preventing the undesirable side-effects associated with the diffusion of a Clostridial toxin or Clostridial toxin chimeric to an unwanted location.

Thus, aspects of the present specification provide a Clostridial toxin comprising an inactivation cleavage site located within an inactivation cleavage site region, wherein the inactivation cleavage site region is located in the translocation domain or the $H_{CN}$ binding subdomain. Such disclosed toxins can comprise a Clostridial toxin enzymatic domain, a Clostridial toxin translocation domain, a Clostridial toxin binding domain, a di-chain loop region comprising an exogenous protease cleavage site, and an inactivation cleavage site located within an inactivation cleavage site region. Non-limiting examples of inactivation cleavage sites include Thrombin cleavage sites, Plasmin cleavage sites, Coagulation Factor VIIa cleavage sites, Coagulation Factor IXa cleavage sites, Coagulation Factor Xa cleavage sites, Coagulation Factor XIa cleavage sites, Coagulation Factor XIIa cleavage sites, plasma kallikrein cleavage sites, protease-activated G protein-coupled receptor-1 (PAR1) cleavage sites, PAR2 cleavage sites, PAR3 cleavage sites, PAR4 cleavage sites, Matrix Metalloproteinase-2 (MMP-2) cleavage sites, Matrix Metalloproteinase-9 (MMP-9) cleavage sites, Furin cleavage sites, urokinase-type Plasminogen activator (uPA) cleavage sites, tissue-type Plasminogen activator (tPA) cleavage sites, Tryptase-ε cleavage sites, Mouse mast cell protease-7 (mMCP-7) cleavage sites, endothelin-converting enzyme-1 (ECE-1) cleavage sites, Kell blood group cleavage sites, DPPIV cleavage sites, ADAM metallopeptidase with thrombospondin type 1 motif-13 (ADAMTS13) cleavage sites, and Cathepsin L cleavage sites. The addition of the inactivation cleavage site increases the safety margin of the Clostridial toxin or Clostridial toxin chimeric relative to the same or similar Clostridial toxin or Clostridial toxin chimeric, but without the additional inactivation cleavage site.

Other aspects of the present specification provide a Clostridial toxin chimeric comprising a Clostridial toxin enzymatic domain, a Clostridial toxin translocation domain, a non-Clostridial toxin binding domain, and an inactivation cleavage site located within an inactivation cleavage site region, wherein the inactivation cleavage site region is located in the translocation domain or the $H_{CN}$ binding subdomain. Such disclosed toxins can comprise a Clostridial toxin enzymatic domain, a Clostridial toxin translocation domain, a non-Clostridial toxin binding domain, a di-chain loop region comprising an exogenous protease cleavage site, and an inactivation cleavage site located within an inactivation cleavage site region. Non-limiting examples of inactivation cleavage sites include Thrombin cleavage sites, Plasmin cleavage sites, Coagulation Factor VIIa cleavage sites, Coagulation Factor IXa cleavage sites, Coagulation Factor Xa cleavage sites, Coagulation Factor XIa cleavage sites, Coagulation Factor XIIa cleavage sites, plasma kallikrein cleavage sites, protease-activated G protein-coupled receptor-1 (PAR1) cleavage sites, PAR 2 cleavage sites, PAR3 cleavage sites, PAR4 cleavage sites, Matrix Metalloproteinase-2 (MMP-2) cleavage sites, Matrix Metalloproteinase-9 (MMP-9) cleavage sites, Furin cleavage sites, urokinase-type Plasminogen activator (uPA) cleavage sites, tissue-type Plasminogen activator (tPA) cleavage sites, Tryptase-ε cleavage sites, Mouse mast cell protease-7 (mMCP-7) cleavage sites, endothelin-converting enzyme-1 (ECE-1) cleavage sites, Kell blood group cleavage sites, DPPIV cleavage sites, ADAM metallopeptidase with thrombospondin type 1 motif-13 (ADAMTS13) cleavage sites, and Cathepsin L cleavage sites. The addition of the inactivation cleavage site increases the safety margin of the Clostridial toxin or Clostridial toxin chimeric relative to the same or similar Clostridial toxin or Clostridial toxin chimeric, but without the additional inactivation cleavage site.

Other aspects of the present specification provide polynucleotide molecules encoding a Clostridial toxin or a Clostridial toxin chimeric disclosed in the present specification. A polynucleotide molecule encoding such a Clostridial toxin or a Clostridial toxin chimeric can further comprise an expression vector.

Other aspects of the present specification provide a composition comprising a Clostridial toxin or a Clostridial toxin chimeric disclosed in the present specification. A composition comprising such a Clostridial toxin or a Clostridial toxin chimeric can be a pharmaceutical composition. Such a pharmaceutical composition can comprise, in addition to a modified Clostridial toxin disclosed in the present specification a pharmaceutical carrier, a pharmaceutical component, or both.

Other aspects of the present specification provide a method of producing a Clostridial toxin or Clostridial toxin chimeric disclosed in the present specification, the method comprising the step of expressing in a cell a polynucleotide molecule encoding a Clostridial toxin or Clostridial toxin chimeric disclosed in the present specification, wherein expression from the polynucleotide molecule produces the encoded Clostridial toxin or Clostridial toxin chimeric. In other aspects, the method comprises the steps of introducing into a cell a polynucleotide molecule encoding a Clostridial toxin or Clostridial toxin chimeric disclosed in the present specification, and expressing the polynucleotide molecule, wherein expression from the polynucleotide molecule produces the encoded Clostridial toxin or Clostridial toxin chimeric.

Clostridia toxins produced by *Clostridium botulinum*, *Clostridium tetani*, *Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes which differ somewhat in their amino acid sequence, and also in the nucleic acids encoding these proteins. For example, there are presently five BoNT/A subtypes, BoNT/A1, BoNT/A2, BoNT/A3, BoNT/A4, and BoNT/A5, with specific subtypes showing about 84% to 93% amino acid identity when compared to the BoNT/A subtype of SEQ ID NO: 1. As another example, there are presently five BoNT/B subtypes, BoNT/B1, BoNT/B2, BoNT/B3, BoNT/Bnp, and BoNT/Bbv, with specific subtypes showing about 93% to 96% amino acid identity when compared to the BoNT/B subtype of SEQ ID NO: 6. As yet another example, there are presently three BoNT/E subtypes, BoNT/E1, BoNT/E2, and BoNT/E3, with specific subtypes showing about 95% to 99% amino acid identity when compared to the BoNT/E subtype of SEQ ID NO: 15. While all seven BoNT serotypes have similar structure and pharmacological properties, each also displays heterogeneous bacteriological characteristics. In contrast, tetanus toxin (TeNT) is produced by a uniform group of *C. tetani*. Two other Clostridia species, *C. baratii* and *C. butyricum*, produce toxins, BaNT and BuNT, which are similar to BoNT/F and BoNT/E, respectively.

Clostridial toxins are each translated as a single chain polypeptide of approximately 150 kDa that is subsequently cleaved by proteolytic scission within a disulfide loop by a naturally-occurring protease (FIG. 1). This cleavage occurs within the discrete di-chain loop region created between two cysteine residues that form a disulfide bridge. This posttranslational processing yields a di-chain molecule comprising an approximately 50 kDa light chain (LC) and an approximately 100 kDa heavy chain (HC) held together by the single disulfide bond and non-covalent interactions between the two chains. The naturally-occurring protease used to convert the single chain molecule into the di-chain is currently not known. In some serotypes, such as, e.g., BoNT/A, the naturally-occurring protease is produced endogenously by the bacteria serotype and cleavage occurs within the cell before the toxin is released into the environment. However, in other serotypes, such as, e.g., BoNT/E, the bacterial strain appears not to produce an endogenous protease capable of converting the single chain form of the toxin into the di-chain form. In these situations, the toxin is released from the cell as a single-chain toxin which is subsequently converted into the di-chain form by a naturally-occurring protease found in the environment.

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC($H_N$) that facilitates release of the LC from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell. D. B. Lacy and R. C. Stevens, Sequence Homology and Structural Analysis of the Clostridial Neurotoxins, J. Mol. Biol. 291: 1091-1104 (1999). The $H_C$ domain comprises two distinct structural features of roughly equal size, separated by an α-helix, designated the $H_{CN}$ and $H_{CC}$ subdomains. Table 1 gives approximate boundary regions for each domain and subdomain found in exemplary Clostridial toxins.

TABLE 1

Clostridial Toxin Reference Sequences and Regions

| Toxin | SEQ ID NO: | LC | Di-Chain Loop | $H_N$ | $H_{CN}$ | α-Linker | $H_{CC}$ |
|---|---|---|---|---|---|---|---|
| BoNT/A | 1 | M1/P2-L429 | C430-C454 | I455-I873 | I874-N1080 | E1081-Q1091 | S1092-L1296 |
| BoNT/B | 6 | M1/P2-M436 | C437-C446 | I447-I860 | L861-S1067 | Q1068-Q1078 | S1079-E1291 |
| BoNT/C1 | 11 | M1/P2-F436 | C437-C453 | R454-I868 | N869-D1081 | G1082-L1092 | Q1093-E1291 |
| BoNT/D | 13 | M1/T2-V436 | C437-C450 | I451-I864 | N865-S1069 | N1069-Q1079 | I1080-E1276 |
| BoNT/E | 15 | M1/P2-F411 | C412-C426 | I427-I847 | K848-D1055 | E1056-E1066 | P1067-K1252 |
| BoNT/F | 18 | M1/P2-F428 | C429-C445 | I446-I865 | K866-D1075 | K1076-E1086 | P1087-K1274 |
| BoNT/G | 21 | M1/P2-M435 | C436-C450 | I451-I865 | S866-N1075 | A1076-Q1086 | S1087-E1297 |
| TeNT | 22 | M1/P2-L438 | C439-C467 | I468-L881 | K882-N1097 | P1098-Y1108 | L1109-D1315 |
| BaNT | 23 | M1/P2-L420 | C421-C435 | I436-I857 | I858-D1064 | K1065-E1075 | P1076-E1268 |
| BuNT | 24 | M1/P2-F411 | C412-C426 | I427-I847 | K848-D1055 | E1056-E1066 | P1067-K1251 |

The binding, translocation, and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (FIG. 3). The process is initiated when the $H_C$ domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it appears to specifically target one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); Giovanna Lalli et al., *The Journey of Tetanus and Botulinum Neurotoxins in Neurons*, 11(9) Trends Microbiol. 431-437, (2003).

The three-dimensional crystal structures of BoNT/A, BoNT/B and the $H_C$ domain of TeNT indicate that the three functional domains of Clostridial neurotoxins are structurally distinct domains that are shared by all Clostridial toxins. The HEXXH consensus motif of the light chain forms the tetrahedral zinc binding pocket of the catalytic site located in a deep cleft on the protein surface that is accessible by a channel. The structure of the $H_N$ and $H_C$ domains consists primarily of β-sheet topologies that are linked by a single α-helix. The cylindrical-shaped $H_N$ domain comprises two long amphipathic α-helices that resemble the coiled-coil motif found in some viral proteins. The $H_N$ domain also forms a long unstructured loop called the 'translocation belt,' which wraps around a large negatively charged cleft of the light chain that blocks access of the zinc atom to the catalytic-binding pocket of active site. The $H_C$ domain comprises two distinct structural features of roughly equal size that indicate function. The first, designated the $H_{CN}$ domain, is located in the amino half of the $H_C$ domain. The $H_{CN}$ domain forms a β-barrel, jelly-roll fold. The $H_{CC}$ domain is the second domain that comprises the $H_C$ domain. This carboxyl-terminal domain comprises a modified β-trefoil domain which forms three distinct carbohydrate binding regions that resembles the carbohydrate binding moiety found in many sugar-binding proteins, such as, e.g., serum amyloid P, sialidase, cryia, insecticidal δ-endotoxin and lectins. Biochemical studies indicate that the β-trefoil domain structure of the $H_{CC}$ domain appears to mediate the binding to specific carbohydrate containing components of the Clostridial toxin receptor on the cell surface, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site*, 482(1-2) FEBS Lett. 119-124 (2000). The $H_C$ domain tilts away from the $H_N$ domain exposing the surface loops and making them accessible for binding. No contacts occur between the light chain and the $H_C$ domain.

Aspects of the present specification provide, in part, a Clostridial toxin. As used herein, the term "Clostridial toxin" refers to any neurotoxin produced by a Clostridial toxin strain that can execute the overall cellular mechanism whereby a Clostridial toxin intoxicates a cell and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate. A Clostridial toxin comprises a Clostridial toxin enzymatic domain, a Clostridial toxin translocation domain, and a Clostridial toxin binding domain. Exemplary Clostridial toxins include those produced by a *Clostridium botulinum*, a *Clostridium tetani*, a *Clostridium baratii* and a *Clostridium butyricum*.

A Clostridial toxin includes, without limitation, naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, and active Clostridial toxin fragments thereof, or any combination thereof. As used herein, the term "Clostridial toxin variant," whether naturally-occurring or non-naturally-occurring, refers to a Clostridial toxin that has at least one amino acid change from the corresponding region of the disclosed reference sequences (Table 1) and can be described in percent identity to the corresponding region of that reference sequence. As non-limiting examples, a BoNT/A variant of SEQ ID NO: 1 will have at least one amino acid difference, such as, e.g., an amino acid substitution, deletion or addition, as compared to the corresponding position(s) of SEQ ID NO: 1; a BoNT/B variant of SEQ ID NO: 6 will have at least one amino acid difference, such as, e.g., an amino acid substitution, deletion or addition, as compared to the corresponding position(s) of SEQ ID NO: 6; a BoNT/C1 variant of SEQ ID NO: 11 will have at least one amino acid difference, such as, e.g., an amino acid substitution, deletion or addition, as compared to the corresponding position(s) of SEQ ID NO: 11; a BoNT/D variant of SEQ ID NO: 13 will have at least one amino acid difference, such as, e.g., an amino acid substitution, deletion or addition, as compared to the corresponding position(s) of SEQ ID NO: 13; a BoNT/E variant of SEQ ID NO: 15 will have at least one amino acid difference, such as, e.g., an amino acid substitution, deletion or addition, as compared to the corresponding position(s) of SEQ ID NO: 15; a BoNT/F variant of SEQ ID NO: 18 will have at least one amino acid difference, such as, e.g., an amino acid substitution, deletion or addition, as compared to the corresponding position(s) of SEQ ID NO: 18; a BoNT/G variant of SEQ ID NO: 21 will have at least one amino acid difference, such as, e.g., an amino acid substitution, deletion or addition, as compared to the corresponding position(s) of SEQ ID NO: 21; a TeNT variant c of SEQ ID NO: 22 will have at least one amino acid difference, such as, e.g., an amino acid substitution, deletion or addition, as compared to the corresponding position(s) of SEQ ID NO: 22; a BaNT variant of SEQ ID NO: 23 will have at least one amino acid difference, such as, e.g., an amino acid substitution, deletion or addition, as compared to the corresponding position(s) of SEQ ID NO: 23; and a BuNT variant of SEQ ID NO: 24 will have at least one amino acid difference, such as, e.g., an amino acid substitution, deletion or addition, as compared to the corresponding position(s) of SEQ ID NO: 24.

As used herein, the term "naturally occurring Clostridial toxin variant" refers to any Clostridial toxin produced without the aid of any human manipulation, including, without limitation, Clostridial toxin isoforms produced from alternatively-spliced transcripts, Clostridial toxin isoforms produced by spontaneous mutation and Clostridial toxin subtypes. Non-limiting examples of a Clostridial toxin isoform include, e.g., BoNT/A isoforms, BoNT/B isoforms, BoNT/C1 isoforms, BoNT/D isoforms, BoNT/E isoforms, BoNT/F isoforms, BoNT/G isoforms, TeNT isoforms, BaNT isoforms and BuNT isoforms. Non-limiting examples of a Clostridial toxin subtype include, e.g., BoNT/A subtypes BoNT/A1, BoNT/A2, BoNT/A3, BoNT/A4, and BoNT/A5; BoNT/B subtypes BoNT/B1, BoNT/B2, BoNT/B3, BoNT/B bivalent and BoNT/B nonproteolytic; BoNT/C1 subtypes BoNT/C1-1 and BoNT/C1-2; BoNT/E subtypes BoNT/E1, BoNT/E2, and BoNT/E3; BoNT/F subtypes BoNT/F1, BoNT/F2, and BoNT/F3; and BuNT subtypes BuNT-1, and BuNT-2. Other non-limiting examples of a Clostridial toxin subtype include, e.g., BoNT/A subtypes SEQ ID NO: 1, SEQ ID NO: 2, SEQ ID NO: 3, SEQ ID NO: 4, and SEQ ID NO: 5; BoNT/B subtypes SEQ ID NO: 6, SEQ ID NO: 7, SEQ ID NO: 8, SEQ ID NO: 9, and SEQ ID NO: 10; BoNT/C1 subtypes SEQ ID NO: 11 and SEQ ID NO: 12; BoNT/E subtypes SEQ ID NO: 15, SEQ ID NO: 16, and SEQ ID NO: 17; BoNT/F subtypes SEQ ID NO: 18, SEQ ID NO: 19, and SEQ ID NO: 20; and BuNT subtypes SEQ ID NO: 24 and SEQ ID NO: 25.

As used herein, the term "non-naturally occurring Clostridial toxin variant" refers to any Clostridial toxin produced with the aid of human manipulation, including, without limitation, Clostridial toxins produced by genetic engineering using random mutagenesis or rational design and Clostridial toxins produced by chemical synthesis. Non-limiting examples of non-naturally occurring Clostridial toxin variants include, e.g., conservative Clostridial toxin variants, non-conservative Clostridial toxin variants, and active Clostridial toxin fragments.

As used herein, the term "conservative Clostridial toxin variant" refers to a Clostridial toxin that has at least one amino acid substituted by another amino acid or an amino acid analog that has at least one property similar to that of the original amino acid from the reference Clostridial toxin sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin variant can function in substantially the same manner as the reference Clostridial toxin on which the conservative Clostridial toxin variant is based, and can be substituted for the reference Clostridial toxin in any aspect of the present specification. A conservative Clostridial toxin variant may substitute 1, 2, 3, 4, 5, 10, 20, 30, 40, 50, 75, 100, 200, 300, 400, or 500 or more amino acids from the reference Clostridial toxin on which the conservative Clostridial toxin variant is based. A conservative Clostridial toxin variant can also substitute at least 5, 10, 15, 20, or 25 contiguous amino acids from the reference Clostridial toxin on which the conservative Clostridial toxin variant is based. Non-limiting examples of a conservative Clostridial toxin variant include, e.g., conservative BoNT/A variants, conservative BoNT/B variants, conservative BoNT/C1 variants, conservative BoNT/D variants, conservative BoNT/E variants, conservative BoNT/F variants, conservative BoNT/G variants, conservative TeNT variants, conservative BaNT variants and conservative BuNT variants.

As used herein, the term "non-conservative Clostridial toxin variant" refers to a Clostridial toxin in which 1) at least one amino acid is deleted from the reference Clostridial toxin on which the non-conservative Clostridial toxin variant is based; 2) at least one amino acid added to the reference Clostridial toxin on which the non-conservative Clostridial toxin is based; or 3) at least one amino acid is substituted by another amino acid or an amino acid analog that does not share any property similar to that of the original amino acid from the reference Clostridial toxin sequence (Table 1). A non-conservative Clostridial toxin variant can function in substantially the same manner as the reference Clostridial toxin on which the non-conservative Clostridial toxin variant is based, and can be substituted for the reference Clostridial toxin in any aspect of the present specification. A non-conservative Clostridial toxin variant can delete one or more amino acids, two or more amino acids, three or more amino acids, four or more amino acids, five or more amino acids, and ten or more amino acids from the reference Clostridial toxin on which the non-conservative Clostridial toxin variant is based. A non-conservative Clostridial toxin variant can add one or more amino acids, two or more amino acids, three or more amino acids, four or more amino acids, five or more amino acids, and ten or more amino acids to the reference Clostridial toxin on which the non-conservative Clostridial toxin variant is based. A non-conservative Clostridial toxin variant may substitute 1, 2, 3, 4, 5, 10, 20, 30, 40, 50, 75, 100, 200, 300, 400, or 500 or more amino acids from the reference Clostridial toxin on which the non-conservative Clostridial toxin variant is based. A non-conservative Clostridial toxin variant can also substitute at least 5, 10, 15, 20, or 25 contiguous amino acids from the reference Clostridial toxin on which the non-conservative Clostridial toxin variant is based. Non-limiting examples of a non-conservative Clostridial toxin variant include, e.g., non-conservative BoNT/A variants, non-conservative BoNT/B variants, non-conservative BoNT/C1 variants, non-conservative BoNT/D variants, non-conservative BoNT/E variants, non-conservative BoNT/F variants, non-conservative BoNT/G variants, non-conservative TeNT variants, non-conservative BaNT variants and non-conservative BuNT variants.

It is also envisioned that any of a variety of Clostridial toxin fragments can be useful in aspects of the present specification with the proviso that these active fragments can execute the overall cellular mechanism whereby a Clostridial toxin proteolytically cleaves a substrate. Thus, aspects of this embodiment can include Clostridial toxin fragments having a length of, e.g., at least 600, 700, 800, 900, 1000, 1100, or at least 1200 amino acids. Other aspects of this embodiment, can include Clostridial toxin fragments having a length of, e.g., at most 600, 700, 800, 900, 1000, 1100, or at most 1200 amino acids.

It is also envisioned that any of a variety of Clostridial toxin fragments comprising the light chain can be useful in aspects of the present specification with the proviso that these light chain fragments can specifically target the core components of the neurotransmitter release apparatus and thus participate in executing the overall cellular mechanism whereby a Clostridial toxin proteolytically cleaves a substrate. The light chains of Clostridial toxins are approximately 420-460 amino acids in length and comprise a Clostridial toxin enzymatic domain (Table 1). Research has shown that the entire length of a Clostridial toxin light chain is not necessary for the enzymatic activity of the Clostridial toxin enzymatic domain. As a non-limiting example, the first eight amino acids of a BoNT/A light chain are not required for enzymatic activity. As another non-limiting example, the first eight amino acids of the TeNT light chain are not required for enzymatic activity. Likewise, the carboxyl-terminus of the light chain is not necessary for activity. As a non-limiting example, the last 32 amino acids of the BoNT/A light chain are not required for enzymatic activity. As another non-limiting example, the last 31 amino acids of the TeNT light chain are not required for enzymatic activity. Thus, aspects of this embodiment include a Clostridial toxin light chain comprising a Clostridial toxin enzymatic domain having a length of, e.g., at least 350, 375, 400, 425, or 450 amino acids. Other aspects of this embodiment include a Clostridial toxin light chain comprising a Clostridial toxin enzymatic domain having a length of, e.g., at most 350, 375, 400, 425, or 450 amino acids.

It is also envisioned that any of a variety of Clostridial toxin $H_N$ regions comprising a Clostridial toxin translocation domain can be useful in aspects of the present specification with the proviso that these active fragments can facilitate the release of the LC from intracellular vesicles into the cytoplasm of the target cell and thus participate in executing the overall cellular mechanism whereby a Clostridial toxin proteolytically cleaves a substrate. The $H_N$ regions from the heavy chains of Clostridial toxins are approximately 410-430 amino acids in length and comprise a Clostridial toxin translocation domain (Table 1). Research has shown that the entire length of a $H_N$ region from a Clostridial toxin heavy chain is not necessary for the translocating activity of the Clostridial toxin translocation domain. Thus, aspects of this embodiment can include Clostridial toxin $H_N$ regions comprising a Clostridial toxin translocation domain having a length of, e.g., at least 350, 375, 400, or 425 amino acids. Other aspects of this embodiment can include Clostridial toxin $H_N$ regions comprising Clostridial toxin translocation domain having a length of, e.g., at most 350, 375, 400, or 425 amino acids.

It is also envisioned that any of a variety of Clostridial toxin $H_C$ regions comprising a Clostridial toxin binding domain can be useful in aspects of the present specification with the proviso that these active fragments can determine the binding activity and binding specificity of the toxin to the receptor complex located at the surface of the target cell and facilitate the overall cellular mechanism whereby a Clostridial toxin proteolytically cleaves a substrate. The $H_C$ regions from the heavy chains of Clostridial toxins are approximately 400-440 amino acids in length and comprise a binding domain (Table 1). Research has shown that the entire length of a $H_C$ region from a Clostridial toxin heavy chain is not necessary for the binding activity of the Clostridial toxin binding domain. Thus, aspects of this embodiment can include Clostridial toxin $H_C$ regions comprising a binding domain having a length of, e.g., at least 350, 375, 400, or 425 amino acids. Other aspects of this embodiment can include Clostridial toxin $H_C$ regions comprising a binding domain having a length of, e.g., at most 350, 375, 400, or 425 amino acids.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264 (4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics,: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

The present specification describes various polypeptide variants where one amino acid is substituted for another, such as, e.g., Clostridial toxin variants, Clostridial toxin enzymatic domain variants, Clostridial toxin translocation domain variants, Clostridial toxin binding domain variants, non-Clostridial toxin binding domain variants, and protease cleavage site variants. A substitution can be assessed by a variety of factors, such as, e.g., the physical properties of the amino acid being substituted (Table 2) or how the original amino acid would tolerate a substitution (Table 3). The selections of which amino acid can be substituted for another amino acid in a polypeptide are known to a person of ordinary skill in the art.

TABLE 2

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 3

Amino Acid Substitutions

| Amino Acid | Favored Substitution | Neutral Substitutions | Disfavored substitution |
| --- | --- | --- | --- |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert B. Russell, Amino Acid Properties and Consequences of Substitutions, pp. 289-316, *In Bioinformatics for Geneticists*, (eds Michael R. Barnes, Ian C. Gray, Wiley, 2003).

Thus, in an embodiment, a Clostridial toxin comprises a Clostridial toxin enzymatic domain, a Clostridial toxin translocation domain, and a Clostridial toxin binding domain. In an aspect of this embodiment, a Clostridial toxin comprises a naturally occurring Clostridial toxin variant, such as, e.g., a Clostridial toxin isoform or a Clostridial toxin subtype. In another aspect of this embodiment, a Clostridial toxin comprises a non-naturally occurring Clostridial toxin variant, such as, e.g., a conservative Clostridial toxin variant, a non-conservative Clostridial toxin variant or an active Clostridial toxin fragment, or any combination thereof. In another aspect of this embodiment, a Clostridial toxin comprises a Clostridial toxin enzymatic domain or an active fragment thereof, a Clostridial toxin translocation domain or an active fragment thereof, a Clostridial toxin binding domain or an active fragment thereof, or any combination thereof. In other aspects of this embodiment, a Clostridial toxin can comprise a BoNT/A, a BoNT/B, a BoNT/C1, a BoNT/D, a BoNT/E, a BoNT/F, a BoNT/G, a TeNT, a BaNT, or a BuNT.

In another embodiment, a hydrophobic amino acid at one particular position in the polypeptide chain of the Clostridial toxin can be substituted with another hydrophobic amino acid. Examples of hydrophobic amino acids include, e.g., C, F, I, L, M, V and W. In another aspect of this embodiment, an aliphatic amino acid at one particular position in the polypeptide chain of the Clostridial toxin can be substituted with another aliphatic amino acid. Examples of aliphatic amino acids include, e.g., A, I, L, P, and V. In yet another aspect of this embodiment, an aromatic amino acid at one particular position in the polypeptide chain of the Clostridial toxin can be substituted with another aromatic amino acid. Examples of aromatic amino acids include, e.g., F, H, W and Y. In still another aspect of this embodiment, a stacking amino acid at one particular position in the polypeptide chain of the Clostridial toxin can be substituted with another stacking amino acid. Examples of stacking amino acids include, e.g., F, H, W and Y. In a further aspect of this embodiment, a polar amino acid at one particular position in the polypeptide chain of the Clostridial toxin can be substituted with another polar amino acid. Examples of polar amino acids include, e.g., D, E, K, N, Q, and R. In a further aspect of this embodiment, a less polar or indifferent amino acid at one particular position in the polypeptide chain of the Clostridial toxin can be substituted with another less polar or indifferent amino acid. Examples of less polar or indifferent amino acids include, e.g., A, H, G, P, S, T, and Y. In a yet further aspect of this embodiment, a positive charged amino acid at one particular position in the polypeptide chain of the Clostridial toxin can be substituted with another positive charged amino acid. Examples of positive charged amino acids include, e.g., K, R, and H. In a still further aspect of this embodiment, a negative charged amino acid at one particular position in the polypeptide chain of the Clostridial toxin can be substituted with another negative charged amino acid. Examples of negative charged amino acids include, e.g., D and E. In another aspect of this embodiment, a small amino acid at one particular position in the polypeptide chain of the Clostridial toxin can be substituted with another small amino acid. Examples of small amino acids include, e.g., A, D, G, N, P, S, and T. In yet another aspect of this embodiment, a C-beta branched amino acid at one particular position in the polypeptide chain of the Clostridial toxin can be substituted with another C-beta branched amino acid. Examples of C-beta branched amino acids include, e.g., I, T and V.

In another embodiment, a Clostridial toxin comprises a BoNT/A. In an aspect of this embodiment, a BoNT/A comprises a BoNT/A enzymatic domain, a BoNT/A translocation domain, and a BoNT/A binding domain. In another aspect of this embodiment, a BoNT/A comprises SEQ ID NO: 1, SEQ ID NO: 2, SEQ ID NO: 3, SEQ ID NO: 4, or SEQ ID NO: 5. In another aspect of this embodiment, a BoNT/A comprises a naturally occurring BoNT/A variant, such as, e.g., a BoNT/A isoform or a BoNT/A subtype. In another aspect of this embodiment, a BoNT/A comprises a naturally occurring BoNT/A variant of SEQ ID NO: 1, SEQ ID NO: 2, SEQ ID NO: 3, SEQ ID NO: 4, or SEQ ID NO: 5, such as, e.g., a BoNT/A isoform or a BoNT/A subtype. In still another aspect of this embodiment, a BoNT/A comprises a non-naturally occurring BoNT/A variant, such as, e.g., a conservative BoNT/A variant, a non-conservative BoNT/A variant or an active BoNT/A fragment, or any combination thereof. In still another aspect of this embodiment, a BoNT/A comprises a non-naturally occurring BoNT/A variant of SEQ ID NO: 1, SEQ ID NO: 2, SEQ ID NO: 3, SEQ ID NO: 4, or SEQ ID NO: 5, such as, e.g., a conservative BoNT/A variant, a non-conservative BoNT/A variant, an active BoNT/A fragment, or any combination thereof. In yet another aspect of this embodiment, a BoNT/A comprises a BoNT/A enzymatic domain or an active fragment thereof, a BoNT/A translocation domain or an active fragment thereof, a BoNT/A binding domain or an active fragment thereof, or any combination thereof. In yet another aspect of this embodiment, a BoNT/A comprising a BoNT/A enzymatic domain SEQ ID NO: 1, SEQ ID NO: 2, SEQ ID NO: 3, SEQ ID NO: 4, or SEQ ID NO: 5, or an active fragment thereof, a BoNT/A translocation domain of SEQ ID NO: 1, SEQ ID NO: 2, SEQ ID NO: 3, SEQ ID NO: 4, or SEQ ID NO: 5, or an active fragment thereof, a BoNT/A binding domain of SEQ ID NO: 1, SEQ ID NO: 2, SEQ ID NO: 3, SEQ ID NO: 4, or SEQ ID NO: 5, or an active fragment thereof, or any combination thereof.

In other aspects of this embodiment, a BoNT/A comprises a polypeptide having an amino acid identity of, e.g., at least 70%, at least 75%, at least 80%, at least 85%, at least 90%, or at least 95% to SEQ ID NO: 1, SEQ ID NO: 2, SEQ ID NO: 3, SEQ ID NO: 4, or SEQ ID NO: 5; or at most 70%, at most 75%, at most 80%, at most 85%, at most 90%, or at most 95% to SEQ ID NO: 1, SEQ ID NO: 2, SEQ ID NO: 3, SEQ ID NO: 4, or SEQ ID NO: 5. In yet other aspects of this embodiment, a BoNT/A comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 1, SEQ ID NO: 2, SEQ ID NO: 3, SEQ ID NO: 4, or SEQ ID NO: 5; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 1, SEQ ID NO: 2, SEQ ID NO: 3, SEQ ID NO: 4, or SEQ ID NO: 5. In still other aspects of this embodiment, a BoNT/A comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 1, SEQ ID NO: 2, SEQ ID NO: 3, SEQ ID NO: 4, or SEQ ID NO: 5; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 1, SEQ ID NO: 2, SEQ ID NO: 3, SEQ ID NO: 4, or SEQ ID NO: 5.

In another embodiment, a Clostridial toxin comprises a BoNT/B. In an aspect of this embodiment, a BoNT/B comprises a BoNT/B enzymatic domain, a BoNT/B translocation domain, and a BoNT/B binding domain. In another aspect of this embodiment, a BoNT/B comprises SEQ ID NO: 6, SEQ ID NO: 7, SEQ ID NO: 8, SEQ ID NO: 9, or SEQ ID NO: 10. In another aspect of this embodiment, a BoNT/B comprises a naturally occurring BoNT/B variant, such as, e.g., a BoNT/B isoform or a BoNT/B subtype. In another aspect of this embodiment, a BoNT/B comprises a naturally occurring BoNT/B variant of SEQ ID NO: 6, SEQ ID NO: 7, SEQ ID NO: 8, SEQ ID NO: 9, or SEQ ID NO: 10, such as, e.g., a BoNT/B isoform or a BoNT/B subtype. In still another aspect of this embodiment, a BoNT/B comprises a non-naturally occurring BoNT/B variant, such as, e.g., a conservative BoNT/B variant, a non-conservative BoNT/B variant, an active BoNT/B fragment, or any combination thereof. In still another aspect of this embodiment, a BoNT/B comprises a non-naturally occurring BoNT/B variant of SEQ ID NO: 6, SEQ ID NO: 7, SEQ ID NO: 8, SEQ ID NO: 9, or SEQ ID NO: 10, such as, e.g., a conservative BoNT/B variant, a non-conservative BoNT/B variant, an active BoNT/B fragment, or any combination thereof. In yet another aspect of this embodiment, a BoNT/B comprises a BoNT/B enzymatic domain or an active fragment thereof, a BoNT/B translocation domain or active fragment thereof, a BoNT/B binding domain or active fragment thereof, or any combination thereof. In yet another aspect of this embodiment, a BoNT/B comprises a BoNT/B enzymatic domain of SEQ ID NO: 6, SEQ ID NO: 7, SEQ ID NO: 8, SEQ ID NO: 9, or SEQ ID NO: 10, or active fragment thereof, a BoNT/B translocation domain of SEQ ID NO: 6, SEQ ID NO: 7, SEQ ID NO: 8, SEQ ID NO: 9, or SEQ ID NO: 10, or active fragment thereof, a BoNT/B binding domain of SEQ ID NO: 6, SEQ ID NO: 7, SEQ ID NO: 8, SEQ ID NO: 9, or SEQ ID NO: 10, or active fragment thereof, or any combination thereof.

In other aspects of this embodiment, a BoNT/B comprises a polypeptide having an amino acid identity of, e.g., at least 70%, at least 75%, at least 80%, at least 85%, at least 90%, or at least 95% to SEQ ID NO: 6, SEQ ID NO: 7, SEQ ID NO: 8, SEQ ID NO: 9, or SEQ ID NO: 102; or at most 70%, at most 75%, at most 80%, at most 85%, at most 90%, or at most 95% to SEQ ID NO: 6, SEQ ID NO: 7, SEQ ID NO: 8, SEQ ID NO: 9, or SEQ ID NO: 10. In yet other aspects of this embodiment, a BoNT/B comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 6, SEQ ID NO: 7, SEQ ID NO: 8, SEQ ID NO: 9, or SEQ ID NO: 10; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 6, SEQ ID NO: 7, SEQ ID NO: 8, SEQ ID NO: 9, or SEQ ID NO: 10. In still other aspects of this embodiment, a BoNT/B comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 6, SEQ ID NO: 7, SEQ ID NO: 8, SEQ ID NO: 9, or SEQ ID NO: 10; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 6, SEQ ID NO: 7, SEQ ID NO: 8, SEQ ID NO: 9, or SEQ ID NO: 10.

In another embodiment, a Clostridial toxin comprises a BoNT/C1. In an aspect of this embodiment, a BoNT/C1 comprises a BoNT/C1 enzymatic domain, a BoNT/C1 translocation domain, and a BoNT/C1 binding domain. In another aspect of this embodiment, a BoNT/C1 comprises SEQ ID NO: 11 or SEQ ID NO: 12. In another aspect of this embodiment, a BoNT/C1 comprises a naturally occurring BoNT/C1 variant, such as, e.g., a BoNT/C1 isoform or a BoNT/C1 subtype. In another aspect of this embodiment, a BoNT/C1 comprises a naturally occurring BoNT/C1 variant of SEQ ID NO: 11 or SEQ ID NO: 12, such as, e.g., a BoNT/C1 isoform or a BoNT/C1 subtype. In still another aspect of this embodiment, a BoNT/C1 comprises a non-naturally occurring BoNT/C1 variant, such as, e.g., a conservative BoNT/C1 variant, a non-conservative BoNT/C1 variant, an active BoNT/C1 fragment, or any combination thereof. In still another aspect of this embodiment, a BoNT/C1 comprises a non-naturally occurring BoNT/C1 variant of SEQ ID NO: 11 or SEQ ID NO: 12, such as, e.g., a conservative BoNT/C1 variant, a non-conservative BoNT/C1 variant, an active BoNT/C1 fragment, or any combination thereof. In yet another aspect of this embodiment, a BoNT/C1 comprises a BoNT/C1 enzymatic domain or active fragment thereof, a BoNT/C1 translocation domain or active fragment thereof, a BoNT/C1 binding domain, active fragment thereof, or any combination thereof. In yet another aspect of this embodiment, a BoNT/C1 comprises a BoNT/C1 enzymatic domain of SEQ ID NO: 11 or SEQ ID NO: 12, or active fragment thereof, a BoNT/C1 translocation domain of SEQ ID NO: 11 or SEQ ID NO: 12, or active fragment thereof, a BoNT/C1 binding domain of SEQ ID NO: 11 or SEQ ID NO: 12, or active fragment thereof, or any combination thereof.

In other aspects of this embodiment, a BoNT/C1 comprises a polypeptide having an amino acid identity of, e.g., at least 70%, at least 75%, at least 80%, at least 85%, at least 90%, or at least 95% to SEQ ID NO: 11 or SEQ ID NO: 12; or at most 70%, at most 75%, at most 80%, at most 85%, at most 90%, or at most 95% to SEQ ID NO: 11 or SEQ ID NO: 12. In yet other aspects of this embodiment, a BoNT/C1 comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 11 or SEQ ID NO: 12; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 11 or SEQ ID NO: 12. In still other aspects of this embodiment, a BoNT/C1 comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 3; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 11 or SEQ ID NO: 12.

In another embodiment, a Clostridial toxin comprises a BoNT/D. In an aspect of this embodiment, a BoNT/D comprises a BoNT/D enzymatic domain, a BoNT/D translocation domain, and a BoNT/D binding domain. In another aspect of this embodiment, a BoNT/D comprises SEQ ID NO: 13 or SEQ ID NO: 14. In another aspect of this embodiment, a BoNT/D comprises a naturally occurring BoNT/D variant, such as, e.g., a BoNT/D isoform or a BoNT/D subtype. In another aspect of this embodiment, a BoNT/D comprises a naturally occurring BoNT/D variant of SEQ ID NO: 13 or SEQ ID NO: 14, such as, e.g., a BoNT/D isoform or a BoNT/D subtype. In still another aspect of this embodiment, a BoNT/D comprises a non-naturally occurring BoNT/D variant, such as, e.g., a conservative BoNT/D variant, a non-conservative BoNT/D variant, an active BoNT/D fragment, or any combination thereof. In still another aspect of this embodiment, a BoNT/D comprises a non-naturally occurring BoNT/D variant of SEQ ID NO: 13 or SEQ ID NO: 14, such as, e.g., a conservative BoNT/D variant, a non-conservative BoNT/D variant, an active BoNT/D fragment, or any combination thereof. In yet another aspect of this embodiment, a BoNT/D comprises a BoNT/D enzymatic domain or an active fragment thereof, a BoNT/D translocation domain or an active fragment thereof, a BoNT/D binding domain or an active fragment thereof, or any combination thereof. In yet another aspect of this embodiment, a BoNT/D comprises a BoNT/D enzymatic domain of SEQ ID NO: 13 or SEQ ID NO: 14, or an active fragment thereof, a BoNT/D translocation domain of SEQ ID NO: 13 or SEQ ID NO: 14, or an active fragment thereof, a BoNT/D binding domain of SEQ ID NO: 13 or SEQ ID NO: 14, or an active fragment thereof, or any combination thereof.

In other aspects of this embodiment, a BoNT/D comprises a polypeptide having an amino acid identity of, e.g., at least 70%, at least 75%, at least 80%, at least 85%, at least 90%, or at least 95% to SEQ ID NO: 13 or SEQ ID NO: 14; or at most 70%, at most 75%, at most 80%, at most 85%, at most 90%, or at most 95% to SEQ ID NO: 13 or SEQ ID NO: 14. In yet other aspects of this embodiment, a BoNT/D comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 13 or SEQ ID NO: 14; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 13 or SEQ ID NO: 14. In still other aspects of this embodiment, a BoNT/D comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 13 or SEQ ID NO: 14; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 13 or SEQ ID NO: 14.

In another embodiment, a Clostridial toxin comprises a BoNT/E. In an aspect of this embodiment, a BoNT/E comprises a BoNT/E enzymatic domain, a BoNT/E translocation domain, and a BoNT/E binding domain. In another aspect of this embodiment, a BoNT/E comprises SEQ ID NO: 15, SEQ ID NO: 16, or SEQ ID NO: 17. In another aspect of this embodiment, a BoNT/E comprises a naturally occurring BoNT/E variant, such as, e.g., a BoNT/E isoform or a BoNT/E subtype. In another aspect of this embodiment, a BoNT/E comprises a naturally occurring BoNT/E variant of SEQ ID NO: 15, SEQ ID NO: 16, or SEQ ID NO: 17, such as, e.g., a BoNT/E isoform or a BoNT/E subtype. In still another aspect of this embodiment, a BoNT/E comprises a non-naturally occurring BoNT/E variant, such as, e.g., a conservative BoNT/E variant, a non-conservative BoNT/E variant, an active BoNT/E fragment, or any combination thereof. In still another aspect of this embodiment, a BoNT/E comprises a non-naturally occurring BoNT/E variant of SEQ ID NO: 15, SEQ ID NO: 16, or SEQ ID NO: 17, such as, e.g., a conservative BoNT/E variant, a non-conservative BoNT/E variant, an active BoNT/E fragment, or any combination thereof. In yet another aspect of this embodiment, a BoNT/E comprises a BoNT/E enzymatic domain or an active fragment thereof, a BoNT/E translocation domain or active fragment thereof, a BoNT/E binding domain or active fragment thereof, or any combination thereof. In yet another aspect of this embodiment, a BoNT/E comprises a BoNT/E enzymatic domain of SEQ ID NO: 15, SEQ ID NO: 16, or SEQ ID NO: 17, or active fragment thereof, a BoNT/E translocation domain of SEQ ID NO: 15, SEQ ID NO: 16, or SEQ ID NO: 17, or active fragment thereof, a BoNT/E binding domain of SEQ ID NO: 15, SEQ ID NO: 16, or SEQ ID NO: 17, or active fragment thereof, or any combination thereof.

In other aspects of this embodiment, a BoNT/E comprises a polypeptide having an amino acid identity of, e.g., at least 70%, at least 75%, at least 80%, at least 85%, at least 90%, or at least 95% to SEQ ID NO: 15, SEQ ID NO: 16, or SEQ ID NO: 17; or at most 70%, at most 75%, at most 80%, at most 85%, at most 90%, or at most 95% to SEQ ID NO: 15, SEQ ID NO: 16, or SEQ ID NO: 17. In yet other aspects of this embodiment, a BoNT/E comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 15, SEQ ID NO: 16, or SEQ ID NO: 17; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 15, SEQ ID NO: 16, or SEQ ID NO: 17. In still other aspects of this embodiment, a BoNT/E comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 15, SEQ ID NO: 16, or SEQ ID NO: 17; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 15, SEQ ID NO: 16, or SEQ ID NO: 17.

In another embodiment, a Clostridial toxin comprises a BoNT/F. In an aspect of this embodiment, a BoNT/F comprises a BoNT/F enzymatic domain, a BoNT/F translocation domain, and a BoNT/F binding domain. In another aspect of this embodiment, a BoNT/F comprises SEQ ID NO: 18, SEQ ID NO: 19, or SEQ ID NO: 20. In another aspect of this embodiment, a BoNT/F comprises a naturally occurring BoNT/F variant, such as, e.g., a BoNT/F isoform or a BoNT/F subtype. In another aspect of this embodiment, a BoNT/F comprises a naturally occurring BoNT/F variant of SEQ ID NO: 18, SEQ ID NO: 19, or SEQ ID NO: 20, such as, e.g., a BoNT/F isoform or a BoNT/F subtype. In still another aspect of this embodiment, a BoNT/F comprises a non-naturally occurring BoNT/F variant, such as, e.g., a conservative BoNT/F variant, a non-conservative BoNT/F variant, an active BoNT/F fragment, or any combination thereof. In still another aspect of this embodiment, a BoNT/F comprises a non-naturally occurring BoNT/F variant of SEQ ID NO: 18, SEQ ID NO: 19, or SEQ ID NO: 20, such as, e.g., a conservative BoNT/F variant, a non-conservative BoNT/F variant, an active BoNT/F fragment, or any combination thereof. In yet another aspect of this embodiment, a BoNT/F comprises a BoNT/F enzymatic domain or active fragment thereof, a BoNT/F translocation domain or active fragment thereof, a BoNT/F binding domain or active fragment thereof, or any combination thereof. In yet another aspect of this embodiment, a BoNT/F comprises a BoNT/F enzymatic domain of SEQ ID NO: 18, SEQ ID NO: 19, or SEQ ID NO: 20, or active fragment thereof, a BoNT/F translocation domain of SEQ ID NO: 18, SEQ ID NO: 19, or SEQ ID NO: 20, or active fragment thereof, a BoNT/F binding domain of SEQ ID NO: 18, SEQ ID NO: 19, or SEQ ID NO: 20, or active fragment thereof, or any combination thereof.

In other aspects of this embodiment, a BoNT/F comprises a polypeptide having an amino acid identity of, e.g., at least 70%, at least 75%, at least 80%, at least 85%, at least 90%, or at least 95% to SEQ ID NO: 18, SEQ ID NO: 19, or SEQ ID NO: 20; or at most 70%, at most 75%, at most 80%, at most 85%, at most 90%, or at most 95% to SEQ ID NO: 18, SEQ ID NO: 19, or SEQ ID NO: 20. In yet other aspects of this embodiment, a BoNT/F comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 18, SEQ ID NO: 19, or SEQ ID NO: 20; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 18, SEQ ID NO: 19, or SEQ ID NO: 20. In still other aspects of this embodiment, a BoNT/F comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 18, SEQ ID NO: 19, or SEQ ID NO: 20; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 18, SEQ ID NO: 19, or SEQ ID NO: 20.

In another embodiment, a Clostridial toxin comprises a BoNT/G. In an aspect of this embodiment, a BoNT/G comprises a BoNT/G enzymatic domain, a BoNT/G translocation domain, and a BoNT/G binding domain. In another aspect of this embodiment, a BoNT/G comprises SEQ ID NO: 21. In another aspect of this embodiment, a BoNT/G comprises a naturally occurring BoNT/G variant, such as, e.g., a BoNT/G isoform or a BoNT/G subtype. In another aspect of this embodiment, a BoNT/G comprises a naturally occurring BoNT/G variant of SEQ ID NO: 21, such as, e.g., a BoNT/G isoform or a BoNT/G subtype of SEQ ID NO: 21. In still another aspect of this embodiment, a BoNT/G comprises a non-naturally occurring BoNT/G variant, such as, e.g., a conservative BoNT/G variant, a non-conservative BoNT/G variant or an active BoNT/G fragment, or any combination thereof. In still another aspect of this embodiment, a BoNT/D comprises a non-naturally occurring BoNT/G variant of SEQ ID NO: 21, such as, e.g., a conservative BoNT/G variant, a non-conservative BoNT/G variant, an active BoNT/G fragment, or any combination thereof. In yet another aspect of this embodiment, a BoNT/G comprises a BoNT/G enzymatic domain or an active fragment thereof, a BoNT/G translocation domain or an active fragment thereof, a BoNT/G binding domain or an active fragment thereof, or any combination thereof. In yet another aspect of this embodiment, a BoNT/G comprises a BoNT/G enzymatic domain of SEQ ID NO: 21 or an active fragment thereof, a BoNT/G translocation domain of SEQ ID NO: 21 or an active fragment thereof, a BoNT/G binding domain of SEQ ID NO: 21 or an active fragment thereof, or any combination thereof.

In other aspects of this embodiment, a BoNT/G comprises a polypeptide having an amino acid identity of, e.g., at least 70%, at least 75%, at least 80%, at least 85%, at least 90%, or at least 95% to SEQ ID NO: 21; or at most 70%, at most 75%, at most 80%, at most 85%, at most 90%, or at most 95% to SEQ ID NO: 21. In yet other aspects of this embodiment, a BoNT/G comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 21; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 21. In still other aspects of this embodiment, a BoNT/G comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 21; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 21.

In another embodiment, a Clostridial toxin comprises a TeNT. In an aspect of this embodiment, a TeNT comprises a TeNT enzymatic domain, a TeNT translocation domain, and a TeNT binding domain. In an aspect of this embodiment, a TeNT comprises SEQ ID NO: 22. In another aspect of this embodiment, a TeNT comprises a naturally occurring TeNT variant, such as, e.g., a TeNT isoform or a TeNT subtype. In another aspect of this embodiment, a TeNT comprises a naturally occurring TeNT variant of SEQ ID NO: 22, such as, e.g., a TeNT isoform or a TeNT subtype. In still another aspect of this embodiment, a TeNT comprises a non-naturally occurring TeNT variant, such as, e.g., a conservative TeNT variant, a non-conservative TeNT variant, an active TeNT fragment, or any combination thereof. In still another aspect of this embodiment, a TeNT comprises a non-naturally occurring TeNT variant of SEQ ID NO: 22, such as, e.g., a conservative TeNT variant, a non-conservative TeNT variant, an active TeNT fragment, or any combination thereof. In yet another aspect of this embodiment, a TeNT comprises a TeNT enzymatic domain or an active fragment thereof, a TeNT translocation domain or active fragment thereof, a TeNT binding domain or active fragment thereof, or any combination thereof. In yet another aspect of this embodiment, a TeNT comprises a TeNT enzymatic domain of SEQ ID NO: 22 or active fragment thereof, a TeNT translocation domain of SEQ ID NO: 22 or active fragment thereof, a TeNT binding domain of SEQ ID NO: 22 or active fragment thereof, or any combination thereof.

In other aspects of this embodiment, a TeNT comprises a polypeptide having an amino acid identity of, e.g., at least 70%, at least 75%, at least 80%, at least 85%, at least 90%, or at least 95% to SEQ ID NO: 22; or at most 70%, at most 75%, at most 80%, at most 85%, at most 90%, or at most 95% to SEQ ID NO: 22. In yet other aspects of this embodiment, a TeNT comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 22; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 22. In still other aspects of this embodiment, a TeNT comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 22; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 22.

In another embodiment, a Clostridial toxin comprises a BaNT. In an aspect of this embodiment, a BaNT comprises a BaNT enzymatic domain, a BaNT translocation domain, and a BaNT binding domain. In another aspect of this embodiment, a BaNT comprises SEQ ID NO: 23. In another aspect of this embodiment, a BaNT comprises a naturally occurring BaNT variant, such as, e.g., a BaNT isoform or a BaNT subtype. In another aspect of this embodiment, a BaNT comprises a naturally occurring BaNT variant of SEQ ID NO: 23, such as, e.g., a BaNT isoform or a BaNT subtype. In still another aspect of this embodiment, a BaNT comprises a non-naturally occurring BaNT variant, such as, e.g., a conservative BaNT variant, a non-conservative BaNT variant or an active BaNT fragment, or any combination thereof. In still another aspect of this embodiment, a BaNT comprises a non-naturally occurring BaNT variant of SEQ ID NO: 23, such as, e.g., a conservative BaNT variant, a non-conservative BaNT variant, an active BaNT fragment, or any combination thereof. In yet another aspect of this embodiment, a BaNT comprises a BaNT enzymatic domain or an active fragment thereof, a BaNT translocation domain or an active fragment thereof, a BaNT binding domain or an active fragment thereof, or any combination thereof. In yet another aspect of this embodiment, a BaNT comprises a BaNT enzymatic domain of SEQ ID NO: 23 or an active fragment thereof, a BaNT translocation domain of SEQ ID NO: 23 or an active fragment thereof, a BaNT binding domain of SEQ ID NO: 23 or an active fragment thereof, or any combination thereof.

In other aspects of this embodiment, a BaNT comprises a polypeptide having an amino acid identity of, e.g., at least 70%, at least 75%, at least 80%, at least 85%, at least 90%, or at least 95% to SEQ ID NO: 23; or at most 70%, at most 75%, at most 80%, at most 85%, at most 90%, or at most 95% to SEQ ID NO: 23. In yet other aspects of this embodiment, a BaNT comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 23; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 23. In still other aspects of this embodiment, a BaNT comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 23; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 23.

In another embodiment, a Clostridial toxin comprises a BuNT. In an aspect of this embodiment, a BuNT comprises a BuNT enzymatic domain, a BuNT translocation domain, and a BuNT binding domain. In another aspect of this embodiment, a BuNT comprises SEQ ID NO: 24 or SEQ ID NO: 25. In another aspect of this embodiment, a BuNT comprises a naturally occurring BuNT variant, such as, e.g., a BuNT isoform or a BuNT subtype. In another aspect of this embodiment, a BuNT comprises a naturally occurring BuNT variant of SEQ ID NO: 24 or SEQ ID NO: 25, such as, e.g., a BuNT isoform or a BuNT subtype. In still another aspect of this embodiment, a BuNT comprises a non-naturally occurring BuNT variant, such as, e.g., a conservative BuNT variant, a non-conservative BuNT variant, an active BuNT fragment, or any combination thereof. In still another aspect of this embodiment, a BuNT comprises a non-naturally occurring BuNT variant of SEQ ID NO: 24 or SEQ ID NO: 25, such as, e.g., a conservative BuNT variant, a non-conservative BuNT variant, an active BuNT fragment, or any combination thereof. In yet another aspect of this embodiment, a BuNT comprises a BuNT enzymatic domain or an active fragment thereof, a BuNT translocation domain or an active fragment thereof, a BuNT binding domain, an active fragment thereof, or any combination thereof. In yet another aspect of this embodiment, a BuNT comprises a BuNT enzymatic domain of SEQ ID NO: 24 or SEQ ID NO: 25, or an active fragment thereof, a BuNT translocation domain of SEQ ID NO: 24 or SEQ ID NO: 25, or an active fragment thereof, a BuNT binding domain of SEQ ID NO: 24 or SEQ ID NO: 25, or an active fragment thereof, or any combination thereof.

In other aspects of this embodiment, a BuNT comprises a polypeptide having an amino acid identity of, e.g., at least 70%, at least 75%, at least 80%, at least 85%, at least 90%, or at least 95% to SEQ ID NO: 24 or SEQ ID NO: 25; or at most 70%, at most 75%, at most 80%, at most 85%, at most 90%, or at most 95% to SEQ ID NO: 24 or SEQ ID NO: 25. In yet other aspects of this embodiment, a BuNT comprises a polypeptide having, e.g., at least 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 24 or SEQ ID NO: 25; at most 1, 2, 3, 4, 5, 6, 7, 8, 9, 10, 20, 30, 40, 50, 100, 200, 300, 400, or 500 non-contiguous amino acid deletions, additions, and/or substitutions relative to SEQ ID NO: 24 or SEQ ID NO: 25. In still other aspects of this embodiment, a BuNT comprises a polypeptide having, e.g., at least 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 24 or SEQ ID NO: 25; at most 1, 2, 3, 4, 5, 6, 7, 8, 9, 10, 20, 30, 40, 50, 100, 200, 300, 400, or 500 contiguous amino acid deletions, additions, and/or substitutions relative to SEQ ID NO: 24 or SEQ ID NO: 25.

As used herein, the term "Clostridial toxin chimeric" or "Clostridial toxin chimeras" refers to a molecule comprising at least a portion from one Clostridial toxin and a portion from at least one other protein to form a toxin with at least one property different from the reference Clostridial toxins of Table 1. Non-limiting examples of Clostridial toxin chimeras include a Clostridial toxin comprising a non-Clostridial toxin enzymatic domain, a Clostridial toxin comprising a non-Clostridial toxin translocation domain, a Clostridial toxin comprising a non-Clostridial toxin binding domain, or any combination thereof. Other non-limiting example of a Clostridial toxin chimeras include a Clostridial toxin comprising a enzymatic domain from a different Clostridial toxin, a Clostridial toxin comprising a translocation domain from a different Clostridial toxin, a Clostridial toxin comprising a binding domain from a different Clostridial toxin, or any combination thereof.

One class of Clostridial toxin chimeric comprises a modified Clostridial toxin were the enzymatic domain or portion thereof, translocation domain or portion thereof, and/or binding domain or portion thereof of a naturally-occurring Clostridial toxin is either modified or replaced with an enzymatic domain or portion thereof, translocation domain or portion thereof, and/or binding domain or portion thereof of a different Clostridial toxin. As non-limiting example, the binding domain of BoNT/A can be replaced with the binding domain of BoNT/B producing a Clostridial toxin chimeric comprising a BoNT/A enzymatic domain, a BoNT/A translocation domain, and a BoNT/B binding domain. Such Clostridial toxin chimeras are described in, e.g., J. Oliver Dolly et al., Activatable Recombinant Neurotoxins, U.S. Pat. No. 7,132,259, which is incorporated by reference in its entirety. As another non-limiting example, the leucine motif from BoNT/A can be inserted into the light chain of a BoNT/E in order to increase biological persistence. Such Clostridial toxin chimeras are described in, e.g., Lance E. Steward et al., Leucine-based Motif and Clostridial Toxins, U.S. Patent Publication 2003/0027752 (Feb. 6, 2003); Lance E. Steward et al., Clostridial Neurotoxin Compositions and Modified Clostridial Neurotoxins, U.S. Patent Publication 2003/0219462 (Nov. 27, 2003); and Lance E. Steward et al., Clostridial Neurotoxin Compositions and Modified Clostridial Neurotoxins, U.S. Patent Publication 2004/0220386 (Nov. 4, 2004), each of which is incorporated by reference in its entirety.

Another class of Clostridial toxin chimeric comprises a Clostridial toxin where the binding domain of a naturally-occurring Clostridial toxin is either modified or replaced with a binding domain of a non-Clostridial toxin. Such Clostridial toxin chimeras possesses an altered cell binding activity because the modified toxin can either, e.g., 1) use the same receptor present on the surface of a naturally occurring Clostridial toxin target cell as that used by the naturally-occurring Clostridial toxin, referred to as an enhanced cell binding activity for a naturally-occurring Clostridial toxin target cell; 2) use a different receptor present on the surface of a naturally occurring Clostridial toxin target cell, referred to as an altered cell binding activity for a naturally-occurring Clostridial toxin target cell; or 3) use a different receptor present on the surface of the non-Clostridial toxin target cell, referred to as an altered cell binding activity for a non-naturally-occurring Clostridial toxin target cell, a re-targeted toxin or a TVEMP.

A Clostridial toxin chimeric can be a Clostridial toxin with an enhanced cell binding activity capable of intoxicating a naturally occurring Clostridial toxin target cell, e.g., a motor neuron. One way this enhanced binding activity is achieved by modifying the endogenous binding domain of a naturally-occurring Clostridial toxin in order to enhance a cell binding activity of the toxin for its naturally-occurring receptor. Such modifications to a targeting domain result in, e.g., a enhanced cell binding activity that increases binding affinity for an endogenous Clostridial toxin receptor present on a naturally-occurring Clostridial toxin target cell; an enhanced cell binding activity that increases binding specificity for a subgroup of endogenous Clostridial toxin receptors present on a naturally-occurring Clostridial toxin target cell; or an enhanced cell binding activity that increases both binding affinity and binding specificity. Non-limiting examples of modified Clostridial toxins an enhanced cell binding activity for a naturally-occurring Clostridial toxin receptor are described in, e.g., Lance E. Steward et al., Modified Clostridial Toxins with Enhanced Targeting Capabilities For Endogenous Clostridial Toxin Receptor Systems, U.S. Patent Publication 2008/0096248; Lance E. Steward, Modified Clostridial Toxins with Enhanced Translocation Capabilities and Enhanced Targeting Activity for Clostridial Toxin Target Cells, International Patent Publication 2008/105901; each of which is hereby incorporated by reference in its entirety.

A Clostridial toxin chimeric can be a Clostridial toxin with an altered cell binding activity capable of intoxicating a naturally occurring Clostridial toxin target cell, e.g., a motor neuron. One way this altered capability is achieved by replacing the endogenous binding domain of a naturally-occurring Clostridial toxin with a binding domain of another molecule that preferentially binds to a different receptor present on the surface of a Clostridial toxin target cell. Such a modification to a binding domain results in a modified toxin that is able to preferentially bind to a non-Clostridial toxin receptor present on a Clostridial toxin target cell. This enhanced binding activity for a naturally occurring Clostridial toxin target cell allows for lower effective doses of a modified Clostridial toxin to be administered to an individual because more toxin will be delivered to the target cell. Thus, modified Clostridial toxins with an enhanced binding activity will reduce the undesirable dispersal of the toxin to areas not targeted for treatment, thereby reducing or preventing the undesirable side-effects associated with diffusion of a Clostridial toxin to an unwanted location. Non-limiting examples of modified Clostridial toxins with an altered cell binding capability for a Clostridial toxin target cell are described in, e.g., Lance E. Steward et al., Multivalent Clostridial Toxin Derivatives and Methods of Their Use, U.S. Pat. No. 7,514,088; Lance E. Steward et al., Modified Clostridial Toxins with Altered Targeting Capabilities For Clostridial Toxin Target Cells, U.S. Patent Publication 2008/0161543; Lance E. Steward, Modified Clostridial Toxins with Enhanced Translocation Capabilities and Altered Targeting Activity for Clostridial Toxin Target Cells, U.S. Patent Publication 2008/0241881; Lance E. Steward et al., Multivalent Clostridial Toxin Derivatives and Methods of Their Use, U.S. Patent Publication 2009/0048431; Lance E. Steward et al., Modified Clostridial Toxins with Altered Targeting Capabilities For Clostridial Toxin Target Cells, International Patent Publication WO 2007/106115; each of which is hereby incorporated by reference in its entirety.

A Clostridial toxin chimeric can be a Clostridial toxin with an altered cell binding activity capable of intoxicating a cell other than a Clostridial toxin target cell, e.g., a cell other than a motor neuron. Called TVEMPs, these molecules achieve this intoxication by using a target receptor present on non-Clostridial toxin target cell. This re-targeted capability is achieved by replacing a naturally-occurring binding domain of a Clostridial toxin with a binding domain showing a preferential binding activity for a non-Clostridial toxin receptor present in a non-Clostridial toxin target cell. Such modifications to a binding domain result in a modified toxin that is able to preferentially bind to a non-Clostridial toxin receptor present on a non-Clostridial toxin target cell. A Clostridial toxin chimeric with an altered targeting activity for a non-Clostridial toxin target cell can bind to a target receptor, translocate into the cytoplasm, and exert its proteolytic effect on the SNARE complex of the non-Clostridial toxin target cell. Non-limiting examples of Clostridial toxin chimeras with an altered targeting activity for a non-Clostridial toxin target cell are described in, e.g., Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods and Compositions for the Treatment of Pancreatitis, U.S. Pat. No. 6,843,998; J. Oliver Dolly et al., Activatable Recombinant Neurotoxins, U.S. Pat. No. 7,132,259; Stephan Donovan, Clostridial Toxin Derivatives and Methods For Treating Pain, U.S. Pat. No. 7,244,437; Stephan Donovan, Clostridial Toxin Derivatives and Methods For Treating Pain, U.S. Pat. No. 7,413,742; Stephan Donovan, Clostridial Toxin Derivatives and Methods For Treating Pain, U.S. Pat. No. 7,415,338; Lance E. Steward et al., Multivalent Clostridial Toxin Derivatives and Methods of Their Use, U.S. Pat. No. 7,514,088; Keith A. Foster et al., Inhibition of Secretion from Non-neural Cells, U.S. Patent Publication 2006/0216283; Keith A. Foster, Fusion Proteins, U.S. Patent Publication 2008/0064092; Keith A. Foster, Fusion Proteins, U.S. Patent Publication 2009/0035822; Lance E. Steward et al., Multivalent Clostridial Toxin Derivatives and Methods of Their Use, U.S. Patent Publication 2009/0048431; Keith A. Foster, Non-Cytotoxic Protein Conjugates, U.S. Patent Publication 2009/0162341; Keith A. Foster et al., Re-targeted Toxin Conjugates, International Patent Publication WO 2005/023309; and Lance E. Steward, Modified Clostridial Toxins with Enhanced Translocation Capabilities and Altered Targeting Capabilities for Non-Clostridial Toxin Target Cells, International Patent Application WO 2008/008805; each of which is hereby incorporated by reference in its entirety.

Aspects of the present specification provide, in part, a Clostridial toxin enzymatic domain. As used herein, the term "Clostridial toxin enzymatic domain" refers to any Clostridial toxin polypeptide that can execute the enzymatic target modification step of the intoxication process. Thus, a Clostridial toxin enzymatic domain specifically targets a Clostridial toxin substrate and encompasses the proteolytic cleavage of a Clostridial toxin substrate, such as, e.g., SNARE proteins like a SNAP-25 substrate, a VAMP substrate, and a Syntaxin substrate. Non-limiting examples of a Clostridial toxin enzymatic domain include, e.g., a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, and a BuNT enzymatic domain.

A Clostridial toxin enzymatic domain includes, without limitation, naturally occurring Clostridial toxin enzymatic domain variants, such as, e.g., Clostridial toxin enzymatic domain isoforms and Clostridial toxin enzymatic domain subtypes; and non-naturally occurring Clostridial toxin enzymatic domain variants, such as, e.g., conservative Clostridial toxin enzymatic domain variants, non-conservative Clostridial toxin enzymatic domain variants, active Clostridial toxin enzymatic domain fragments thereof, or any combination thereof.

As used herein, the term "Clostridial toxin enzymatic domain variant," whether naturally-occurring or non-naturally-occurring, refers to a Clostridial toxin enzymatic domain that has at least one amino acid change from the corresponding region of the disclosed reference sequences (Table 1) and can be described in percent identity to the corresponding region of that reference sequence. Unless expressly indicated, Clostridial toxin enzymatic domain variants useful to practice disclosed embodiments are variants that execute the enzymatic target modification step of the intoxication process. As non-limiting examples, a BoNT/A enzymatic domain variant will have at least one amino acid difference, such as, e.g., an amino acid substitution, deletion or addition, as compared to amino acids 1/2-429 of SEQ ID NO: 1; a BoNT/B enzymatic domain variant will have at least one amino acid difference, such as, e.g., an amino acid substitution, deletion or addition, as compared to amino acids 1/2-436 of SEQ ID NO: 6; a BoNT/C1 enzymatic domain variant will have at least one amino acid difference, such as, e.g., an amino acid substitution, deletion or addition, as compared to amino acids 1/2-436 of SEQ ID NO: 11; a BoNT/D enzymatic domain variant will have at least one amino acid difference, such as, e.g., an amino acid substitution, deletion or addition, as compared to amino acids 1/2-436 of SEQ ID NO: 13; a BoNT/E enzymatic domain variant will have at least one amino acid difference, such as, e.g., an amino acid substitution, deletion or addition, as compared to amino acids 1/2-411 of SEQ ID NO: 15; a BoNT/F enzymatic domain variant will have at least one amino acid difference, such as, e.g., an amino acid substitution, deletion or addition, as compared to amino acids 1/2-428 of SEQ ID NO: 18; a BoNT/G enzymatic domain variant will have at least one amino acid difference, such as, e.g., an amino acid substitution, deletion or addition, as compared to amino acids 1/2-438 of SEQ ID NO: 21; a TeNT enzymatic domain variant will have at least one amino acid difference, such as, e.g., an amino acid substitution, deletion or addition, as compared to amino acids 1/2-438 of SEQ ID NO: 22; a BaNT enzymatic domain variant will have at least one amino acid difference, such as, e.g., an amino acid substitution, deletion or addition, as compared to amino acids 1/2-420 of SEQ ID NO: 23; and a BuNT enzymatic domain variant will have at least one amino acid difference, such as, e.g., an amino acid substitution, deletion or addition, as compared to amino acids 1/2-411 of SEQ ID NO: 24.

It is recognized by those of skill in the art that within each serotype of Clostridial toxin there can be naturally occurring Clostridial toxin enzymatic domain variants that differ somewhat in their amino acid sequence, and also in the nucleic acids encoding these proteins. For example, there are presently five BoNT/A subtypes, BoNT/A1, BoNT/A2, BoNT/A3, BoNT/A4, and BoNT/A5, with specific enzymatic domain subtypes showing about 80% to 95% amino acid identity when compared to the BoNT/A enzymatic domain of SEQ ID NO: 1. As used herein, the term "naturally occurring Clostridial toxin enzymatic domain variant" refers to any Clostridial toxin enzymatic domain produced by a naturally-occurring process, including, without limitation, Clostridial toxin enzymatic domain isoforms produced from alternatively-spliced transcripts, Clostridial toxin enzymatic domain isoforms produced by spontaneous mutation and Clostridial toxin enzymatic domain subtypes. A naturally occurring Clostridial toxin enzymatic domain variant can function in substantially the same manner as the reference Clostridial toxin enzymatic domain on which the naturally occurring Clostridial toxin enzymatic domain variant is based, and can be substituted for the reference Clostridial toxin enzymatic domain in any aspect of the present specification.

A non-limiting examples of a naturally occurring Clostridial toxin enzymatic domain variant is a Clostridial toxin enzymatic domain isoform such as, e.g., a BoNT/A enzymatic domain isoform, a BoNT/B enzymatic domain isoform, a BoNT/C1 enzymatic domain isoform, a BoNT/D enzymatic domain isoform, a BoNT/E enzymatic domain isoform, a BoNT/F enzymatic domain isoform, a BoNT/G enzymatic domain isoform, a TeNT enzymatic domain isoform, a BaNT enzymatic domain isoform, and a BuNT enzymatic domain isoform. Another non-limiting examples of a naturally occurring Clostridial toxin enzymatic domain variant is a Clostridial toxin enzymatic domain subtype such as, e.g., an enzymatic domain from subtype BoNT/A1, BoNT/A2, BoNT/A3, BoNT/A4, or BoNT/A5; an enzymatic domain from subtype BoNT/B1, BoNT/B2, BoNT/Bbv, or BoNT/Bnp; an enzymatic domain from subtype BoNT/C1-1 or BoNT/C1-2; an enzymatic domain from subtype BoNT/E1, BoNT/E2 and BoNT/E3; an enzymatic domain from subtype BoNT/F1, BoNT/F2, or BoNT/F3; and an enzymatic domain from subtype BuNT-1 or BuNT-2.

As used herein, the term "non-naturally occurring Clostridial toxin enzymatic domain variant" refers to any Clostridial toxin enzymatic domain produced with the aid of human manipulation, including, without limitation, Clostridial toxin enzymatic domains produced by genetic engineering using random mutagenesis or rational design and Clostridial toxin enzymatic domains produced by chemical synthesis. Non-limiting examples of non-naturally occurring Clostridial toxin enzymatic domain variants include, e.g., conservative Clostridial toxin enzymatic domain variants, non-conservative Clostridial toxin enzymatic domain variants, Clostridial toxin enzymatic domain chimeric variants, and active Clostridial toxin enzymatic domain fragments.

As used herein, the term "conservative Clostridial toxin enzymatic domain variant" refers to a Clostridial toxin enzymatic domain that has at least one amino acid substituted by another amino acid or an amino acid analog that has at least one property similar to that of the original amino acid from the reference Clostridial toxin enzymatic domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin enzymatic domain variant can function in substantially the same manner as the reference Clostridial toxin enzymatic domain on which the conservative Clostridial toxin enzymatic domain variant is based, and can be substituted for the reference Clostridial toxin enzymatic domain in any aspect of the present specification. Non-limiting examples of a conservative Clostridial toxin enzymatic domain variant include, e.g., conservative BoNT/A enzymatic domain variants, conservative BoNT/B enzymatic domain variants, conservative BoNT/C1 enzymatic domain variants, conservative BoNT/D enzymatic domain variants, conservative BoNT/E enzymatic domain variants, conservative BoNT/F enzymatic domain variants, conservative BoNT/G enzymatic domain variants, conservative TeNT enzymatic domain variants, conservative BaNT enzymatic domain variants, and conservative BuNT enzymatic domain variants.

As used herein, the term "non-conservative Clostridial toxin enzymatic domain variant" refers to a Clostridial toxin enzymatic domain in which 1) at least one amino acid is deleted from the reference Clostridial toxin enzymatic domain on which the non-conservative Clostridial toxin enzymatic domain variant is based; 2) at least one amino acid added to the reference Clostridial toxin enzymatic domain on which the non-conservative Clostridial toxin enzymatic domain is based; or 3) at least one amino acid is substituted by another amino acid or an amino acid analog that does not share any property similar to that of the original amino acid from the reference Clostridial toxin enzymatic domain sequence (Table 1). A non-conservative Clostridial toxin enzymatic domain variant can function in substantially the same manner as the reference Clostridial toxin enzymatic domain on which the non-conservative Clostridial toxin enzymatic domain variant is based, and can be substituted for the reference Clostridial toxin enzymatic domain in any aspect of the present specification. Non-limiting examples of a non-conservative Clostridial toxin enzymatic domain variant include, e.g., non-conservative BoNT/A enzymatic domain variants, non-conservative BoNT/B enzymatic domain variants, non-conservative BoNT/C1 enzymatic domain variants, non-conservative BoNT/D enzymatic domain variants, non-conservative BoNT/E enzymatic domain variants, non-conservative BoNT/F enzymatic domain variants, non-conservative BoNT/G enzymatic domain variants, and non-conservative TeNT enzymatic domain variants, non-conservative BaNT enzymatic domain variants, and non-conservative BuNT enzymatic domain variants.

As used herein, the term "active Clostridial toxin enzymatic domain fragment" refers to any of a variety of Clostridial toxin fragments comprising the enzymatic domain can be useful in aspects of the present specification with the proviso that these enzymatic domain fragments can specifically target the core components of the neurotransmitter release apparatus and thus participate in executing the overall cellular mechanism whereby a Clostridial toxin proteolytically cleaves a substrate. The enzymatic domains of Clostridial toxins are approximately 420-460 amino acids in length and comprise an enzymatic domain (Table 1). Research has shown that the entire length of a Clostridial toxin enzymatic domain is not necessary for the enzymatic activity of the enzymatic domain. As a non-limiting example, the first eight amino acids of the BoNT/A enzymatic domain are not required for enzymatic activity. As another non-limiting example, the first eight amino acids of the TeNT enzymatic domain are not required for enzymatic activity. Likewise, the carboxyl-terminus of the enzymatic domain is not necessary for activity. As a non-limiting example, the last 32 amino acids of the BoNT/A enzymatic domain are not required for enzymatic activity. As another non-limiting example, the last 31 amino acids of the TeNT enzymatic domain are not required for enzymatic activity. Thus, aspects of this embodiment include Clostridial toxin enzymatic domains comprising an enzymatic domain having a length of, e.g., at least 350, 375, 400, 425, or 450 amino acids. Other aspects of this embodiment include Clostridial toxin enzymatic domains comprising an enzymatic domain having a length of, e.g., at most 350, 375, 400, 425, or 450 amino acids.

Any of a variety of sequence alignment methods can be used to determine percent identity of naturally-occurring Clostridial toxin enzymatic domain variants and non-naturally-occurring Clostridial toxin enzymatic domain variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises a Clostridial toxin enzymatic domain. In an aspect of this embodiment, a Clostridial toxin enzymatic domain comprises a naturally occurring Clostridial toxin enzymatic domain variant, such as, e.g., a Clostridial toxin enzymatic domain isoform or a Clostridial toxin enzymatic domain subtype. In another aspect of this embodiment, a Clostridial toxin enzymatic domain comprises a non-naturally occurring Clostridial toxin enzymatic domain variant, such as, e.g., a conservative Clostridial toxin enzymatic domain variant, a non-conservative Clostridial toxin enzymatic domain variant, an active Clostridial toxin enzymatic domain fragment, or any combination thereof.

In another embodiment, a hydrophobic amino acid at one particular position in the polypeptide chain of the Clostridial toxin enzymatic domain can be substituted with another hydrophobic amino acid. Examples of hydrophobic amino acids include, e.g., C, F, I, L, M, V and W. In another aspect of this embodiment, an aliphatic amino acid at one particular position in the polypeptide chain of the Clostridial toxin enzymatic domain can be substituted with another aliphatic amino acid. Examples of aliphatic amino acids include, e.g., A, I, L, P, and V. In yet another aspect of this embodiment, an aromatic amino acid at one particular position in the polypeptide chain of the Clostridial toxin enzymatic domain can be substituted with another aromatic amino acid. Examples of aromatic amino acids include, e.g., F, H, W and Y. In still another aspect of this embodiment, a stacking amino acid at one particular position in the polypeptide chain of the Clostridial toxin enzymatic domain can be substituted with another stacking amino acid. Examples of stacking amino acids include, e.g., F, H, W and Y. In a further aspect of this embodiment, a polar amino acid at one particular position in the polypeptide chain of the Clostridial toxin enzymatic domain can be substituted with another polar amino acid. Examples of polar amino acids include, e.g., D, E, K, N, Q, and R. In a further aspect of this embodiment, a less polar or indifferent amino acid at one particular position in the polypeptide chain of the Clostridial toxin enzymatic domain can be substituted with another less polar or indifferent amino acid. Examples of less polar or indifferent amino acids include, e.g., A, H, G, P, S, T, and Y. In a yet further aspect of this embodiment, a positive charged amino acid at one particular position in the polypeptide chain of the Clostridial toxin enzymatic domain can be substituted with another positive charged amino acid. Examples of positive charged amino acids include, e.g., K, R, and H. In a still further aspect of this embodiment, a negative charged amino acid at one particular position in the polypeptide chain of the Clostridial toxin enzymatic domain can be substituted with another negative charged amino acid. Examples of negative charged amino acids include, e.g., D and E. In another aspect of this embodiment, a small amino acid at one particular position in the polypeptide chain of the Clostridial toxin enzymatic domain can be substituted with another small amino acid. Examples of small amino acids include, e.g., A, D, G, N, P, S, and T. In yet another aspect of this embodiment, a C-beta branching amino acid at one particular position in the polypeptide chain of the Clostridial toxin enzymatic domain can be substituted with another C-beta branching amino acid. Examples of C-beta branching amino acids include, e.g., I, T and V.

In another embodiment, a Clostridial toxin enzymatic domain comprises a BoNT/A enzymatic domain. In an aspect of this embodiment, a BoNT/A enzymatic domain comprises the enzymatic domains of SEQ ID NO: 1, SEQ ID NO: 2, SEQ ID NO: 3, SEQ ID NO: 4, or SEQ ID NO: 5. In other aspects of this embodiment, a BoNT/A enzymatic domain comprises amino acids 1/2-429 of SEQ ID NO: 1. In another aspect of this embodiment, a BoNT/A enzymatic domain comprises a naturally occurring BoNT/A enzymatic domain variant, such as, e.g., an enzymatic domain from a BoNT/A isoform or an enzymatic domain from a BoNT/A subtype. In another aspect of this embodiment, a BoNT/A enzymatic domain comprises a naturally occurring BoNT/A enzymatic domain variant of SEQ ID NO: 1, SEQ ID NO: 2, SEQ ID NO: 3, SEQ ID NO: 4, or SEQ ID NO: 5, such as, e.g., a BoNT/A isoform enzymatic domain or a BoNT/A subtype enzymatic domain. In another aspect of this embodiment, a BoNT/A enzymatic domain comprises amino acids 1/2-429 of a naturally occurring BoNT/A enzymatic domain variant of SEQ ID NO: 1, such as, e.g., a BoNT/A isoform enzymatic domain or a BoNT/A subtype enzymatic domain. In still another aspect of this embodiment, a BoNT/A enzymatic domain comprises a non-naturally occurring BoNT/A enzymatic domain variant, such as, e.g., a conservative BoNT/A enzymatic domain variant, a non-conservative BoNT/A enzymatic domain variant, an active BoNT/A enzymatic domain fragment, or any combination thereof. In still another aspect of this embodiment, a BoNT/A enzymatic domain comprises the enzymatic domain of a non-naturally occurring BoNT/A enzymatic domain variant of SEQ ID NO: 1, SEQ ID NO: 2, SEQ ID NO: 3, SEQ ID NO: 4, or SEQ ID NO: 5, such as, e.g., a conservative BoNT/A enzymatic domain variant, a non-conservative BoNT/A enzymatic domain variant, an active BoNT/A enzymatic domain fragment, or any combination thereof. In still another aspect of this embodiment, a BoNT/A enzymatic domain comprises amino acids 1/2-429 of a non-naturally occurring BoNT/A enzymatic domain variant of SEQ ID NO: 1, such as, e.g., a conservative BoNT/A enzymatic domain variant, a non-conservative BoNT/A enzymatic domain variant, an active BoNT/A enzymatic domain fragment, or any combination thereof.

In other aspects of this embodiment, a BoNT/A enzymatic domain comprises a polypeptide having an amino acid identity of, e.g., at least 70%, at least 75%, at least 80%, at least 85%, at least 90%, or at least 95% to the enzymatic domain of SEQ ID NO: 1, SEQ ID NO: 2, SEQ ID NO: 3, SEQ ID NO: 4, or SEQ ID NO: 5; or at most 70%, at most 75%, at most 80%, at most 85%, at most 90%, or at most 95% to the enzymatic domain of SEQ ID NO: 1, SEQ ID NO: 2, SEQ ID NO: 3, SEQ ID NO: 4, or SEQ ID NO: 5. In yet other aspects of this embodiment, a BoNT/A enzymatic domain comprises a polypeptide having an amino acid identity of, e.g., at least 70%, at least 75%, at least 80%, at least 85%, at least 90%, or at least 95% to amino acids 1/2-429 of SEQ ID NO: 1; or at most 70%, at most 75%, at most 80%, at most 85%, at most 90%, or at most 95% to amino acids 1/2-429 of SEQ ID NO: 1.

In other aspects of this embodiment, a BoNT/A enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 1, SEQ ID NO: 2, SEQ ID NO: 3, SEQ ID NO: 4, or SEQ ID NO: 5; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 1, SEQ ID NO: 2, SEQ ID NO: 3, SEQ ID NO: 4, or SEQ ID NO: 5. In yet other aspects of this embodiment, a BoNT/A enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-429 of SEQ ID NO: 1; or at most 1, 2, 3, 4, 5, 6, 7, 8, 9, 10, 20, 30, 40, 50, or 100 non-contiguous amino acid deletions, additions, and/or substitutions relative to amino acids 1/2-429 of SEQ ID NO: 1. In still other aspects of this embodiment, a BoNT/A enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 1, SEQ ID NO: 2, SEQ ID NO: 3, SEQ ID NO: 4, or SEQ ID NO: 5; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 1, SEQ ID NO: 2, SEQ ID NO: 3, SEQ ID NO: 4, or SEQ ID NO: 5. In further other aspects of this embodiment, a BoNT/A enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-429 of SEQ ID NO: 1; or at most 1, 2, 3, 4, 5, 6, 7, 8, 9, 10, 20, 30, 40, 50, or 100 contiguous amino acid deletions, additions, and/or substitutions relative to amino acids 1/2-429 of SEQ ID NO: 1.

In another embodiment, a Clostridial toxin enzymatic domain comprises a BoNT/B enzymatic domain. In an aspect of this embodiment, a BoNT/B enzymatic domain comprises the enzymatic domains of SEQ ID NO: 6, SEQ ID NO: 7, SEQ ID NO: 8, SEQ ID NO: 9, or SEQ ID NO: 10. In other aspects of this embodiment, a BoNT/B enzymatic domain comprises amino acids 1/2-436 of SEQ ID NO: 6. In another aspect of this embodiment, a BoNT/B enzymatic domain comprises a naturally occurring BoNT/B enzymatic domain variant, such as, e.g., an enzymatic domain from a BoNT/B isoform or an enzymatic domain from a BoNT/B subtype. In another aspect of this embodiment, a BoNT/B enzymatic domain comprises a naturally occurring BoNT/B enzymatic domain variant of SEQ ID NO: 6, SEQ ID NO: 7, SEQ ID NO: 8, SEQ ID NO: 9, or SEQ ID NO: 10, such as, e.g., a BoNT/B isoform enzymatic domain or a BoNT/B subtype enzymatic domain. In another aspect of this embodiment, a BoNT/B enzymatic domain comprises amino acids 1/2-436 of a naturally occurring BoNT/B enzymatic domain variant of SEQ ID NO: 6, such as, e.g., a BoNT/B isoform enzymatic domain or a BoNT/B subtype enzymatic domain. In still another aspect of this embodiment, a BoNT/B enzymatic domain comprises a non-naturally occurring BoNT/B enzymatic domain variant, such as, e.g., a conservative BoNT/B enzymatic domain variant, a non-conservative BoNT/B enzymatic domain variant, an active BoNT/B enzymatic domain fragment, or any combination thereof. In still another aspect of this embodiment, a BoNT/B enzymatic domain comprises the enzymatic domain of a non-naturally occurring BoNT/B enzymatic domain variant of SEQ ID NO: 6, SEQ ID NO: 7, SEQ ID NO: 8, SEQ ID NO: 9, or SEQ ID NO: 10, such as, e.g., a conservative BoNT/B enzymatic domain variant, a non-conservative BoNT/B enzymatic domain variant, an active BoNT/B enzymatic domain fragment, or any combination thereof. In still another aspect of this embodiment, a BoNT/B enzymatic domain comprises amino acids 1/2-436 of a non-naturally occurring BoNT/B enzymatic domain variant of SEQ ID NO: 6, such as, e.g., a conservative BoNT/B enzymatic domain variant, a non-conservative BoNT/B enzymatic domain variant, an active BoNT/B enzymatic domain fragment, or any combination thereof.

In other aspects of this embodiment, a BoNT/B enzymatic domain comprises a polypeptide having an amino acid identity of, e.g., at least 70%, at least 75%, at least 80%, at least 85%, at least 90%, or at least 95% to the enzymatic domain of SEQ ID NO: 6, SEQ ID NO: 7, SEQ ID NO: 8, SEQ ID NO: 9, or SEQ ID NO: 10; or at most 70%, at most 75%, at most 80%, at most 85%, at most 90%, or at most 95% to the enzymatic domain of SEQ ID NO: 6, SEQ ID NO: 7, SEQ ID NO: 8, SEQ ID NO: 9, or SEQ ID NO: 10. In yet other aspects of this embodiment, a BoNT/B enzymatic domain comprises a polypeptide having an amino acid identity of, e.g., at least 70%, at least 75%, at least 80%, at least 85%, at least 90%, or at least 95% to amino acids 1/2-436 of SEQ ID NO: 6; or at most 70%, at most 75%, at most 80%, at most 85%, at most 90%, or at most 95% to amino acids 1/2-436 of SEQ ID NO: 6.

In other aspects of this embodiment, a BoNT/B enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 6, SEQ ID NO: 7, SEQ ID NO: 8, SEQ ID NO: 9, or SEQ ID NO: 10; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 6, SEQ ID NO: 7, SEQ ID NO: 8, SEQ ID NO: 9, or SEQ ID NO: 10. In yet other aspects of this embodiment, a BoNT/B enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-436 of SEQ ID NO: 6; or at most 1, 2, 3, 4, 5, 6, 7, 8, 9, 10, 20, 30, 40, 50, or 100 non-contiguous amino acid deletions, additions, and/or substitutions relative to amino acids 1/2-436 of SEQ ID NO: 6. In still other aspects of this embodiment, a BoNT/B enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 6, SEQ ID NO: 7, SEQ ID NO: 8, SEQ ID NO: 9, or SEQ ID NO: 10; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 6, SEQ ID NO: 7, SEQ ID NO: 8, SEQ ID NO: 9, or SEQ ID NO: 10. In further other aspects of this embodiment, a BoNT/B enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-436 of SEQ ID NO: 6; or at most 1, 2, 3, 4, 5, 6, 7, 8, 9, 10, 20, 30, 40, 50, or 100 contiguous amino acid deletions, additions, and/or substitutions relative to amino acids 1/2-436 of SEQ ID NO: 6.

In another embodiment, a Clostridial toxin enzymatic domain comprises a BoNT/C1 enzymatic domain. In an aspect of this embodiment, a BoNT/C1 enzymatic domain comprises the enzymatic domains of SEQ ID NO: 11 or SEQ ID NO: 12. In other aspects of this embodiment, a BoNT/C1 enzymatic domain comprises amino acids 1/2-436 of SEQ ID NO: 11. In another aspect of this embodiment, a BoNT/C1 enzymatic domain comprises a naturally occurring BoNT/C1 enzymatic domain variant, such as, e.g., an enzymatic domain from a BoNT/C1 isoform or an enzymatic domain from a BoNT/C1 subtype. In another aspect of this embodiment, a BoNT/C1 enzymatic domain comprises a naturally occurring BoNT/C1 enzymatic domain variant of SEQ ID NO: 11 or SEQ ID NO: 12, such as, e.g., a BoNT/C1 isoform enzymatic domain or a BoNT/C1 subtype enzymatic domain. In another aspect of this embodiment, a BoNT/C1 enzymatic domain comprises amino acids 1/2-436 of a naturally occurring BoNT/C1 enzymatic domain variant of SEQ ID NO: 11, such as, e.g., a BoNT/C1 isoform enzymatic domain or a BoNT/C1 subtype enzymatic domain. In still another aspect of this embodiment, a BoNT/C1 enzymatic domain comprises a non-naturally occurring BoNT/C1 enzymatic domain variant, such as, e.g., a conservative BoNT/C1 enzymatic domain variant, a non-conservative BoNT/C1 enzymatic domain variant, an active BoNT/C1 enzymatic domain fragment, or any combination thereof. In still another aspect of this embodiment, a BoNT/C1 enzymatic domain comprises the enzymatic domain of a non-naturally occurring BoNT/C1 enzymatic domain variant of SEQ ID NO: 11 or SEQ ID NO: 12, such as, e.g., a conservative BoNT/C1 enzymatic domain variant, a non-conservative BoNT/C1 enzymatic domain variant, an active BoNT/C1 enzymatic domain fragment, or any combination thereof. In still another aspect of this embodiment, a BoNT/C1 enzymatic domain comprises amino acids 1/2-436 of a non-naturally occurring BoNT/C1 enzymatic domain variant of SEQ ID NO: 11, such as, e.g., a conservative BoNT/C1 enzymatic domain variant, a non-conservative BoNT/C1 enzymatic domain variant, an active BoNT/C1 enzymatic domain fragment, or any combination thereof.

In other aspects of this embodiment, a BoNT/C1 enzymatic domain comprises a polypeptide having an amino acid identity of, e.g., at least 70%, at least 75%, at least 80%, at least 85%, at least 90%, or at least 95% to the enzymatic domain of SEQ ID NO: 11 or SEQ ID NO: 12; or at most 70%, at most 75%, at most 80%, at most 85%, at most 90%, or at most 95% to the enzymatic domain of SEQ ID NO: 11 or SEQ ID NO: 12. In yet other aspects of this embodiment, a BoNT/C1 enzymatic domain comprises a polypeptide having an amino acid identity of, e.g., at least 70%, at least 75%, at least 80%, at least 85%, at least 90%, or at least 95% to amino acids 1/2-436 of SEQ ID NO: 11; or at most 70%, at most 75%, at most 80%, at most 85%, at most 90%, or at most 95% to amino acids 1/2-436 of SEQ ID NO: 11.

In other aspects of this embodiment, a BoNT/C1 enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 11 or SEQ ID NO: 12; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 11 or SEQ ID NO: 12. In yet other aspects of this embodiment, a BoNT/C1 enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-436 of SEQ ID NO: 11; or at most 1, 2, 3, 4, 5, 6, 7, 8, 9, 10, 20, 30, 40, 50, or 100 non-contiguous amino acid deletions, additions, and/or substitutions relative to amino acids 1/2-436 of SEQ ID NO: 11. In still other aspects of this embodiment, a BoNT/C1 enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 11 or SEQ ID NO: 12; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 11 or SEQ ID NO: 12. In further other aspects of this embodiment, a BoNT/C1 enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-436 of SEQ ID NO: 11; or at most 1, 2, 3, 4, 5, 6, 7, 8, 9, 10, 20, 30, 40, 50, or 100 contiguous amino acid deletions, additions, and/or substitutions relative to amino acids 1/2-436 of SEQ ID NO: 11.

In another embodiment, a Clostridial toxin enzymatic domain comprises a BoNT/D enzymatic domain. In an aspect of this embodiment, a BoNT/D enzymatic domain comprises the enzymatic domains of SEQ ID NO: 13 or SEQ ID NO: 14. In other aspects of this embodiment, a BoNT/D enzymatic domain comprises amino acids 1/2-436 of SEQ ID NO: 13. In another aspect of this embodiment, a BoNT/D enzymatic domain comprises a naturally occurring BoNT/D enzymatic domain variant, such as, e.g., an enzymatic domain from a BoNT/D isoform or an enzymatic domain from a BoNT/D subtype. In another aspect of this embodiment, a BoNT/D enzymatic domain comprises a naturally occurring BoNT/D enzymatic domain variant of SEQ ID NO: 13 or SEQ ID NO: 14, such as, e.g., a BoNT/D isoform enzymatic domain or a BoNT/D subtype enzymatic domain. In another aspect of this embodiment, a BoNT/D enzymatic domain comprises amino acids 1/2-436 of a naturally occurring BoNT/D enzymatic domain variant of SEQ ID NO: 13, such as, e.g., a BoNT/D isoform enzymatic domain or a BoNT/D subtype enzymatic domain. In still another aspect of this embodiment, a BoNT/D enzymatic domain comprises a non-naturally occurring BoNT/D enzymatic domain variant, such as, e.g., a conservative BoNT/D enzymatic domain variant, a non-conservative BoNT/D enzymatic domain variant, an active BoNT/D enzymatic domain fragment, or any combination thereof. In still another aspect of this embodiment, a BoNT/D enzymatic domain comprises the enzymatic domain of a non-naturally occurring BoNT/D enzymatic domain variant of SEQ ID NO: 13 or SEQ ID NO: 14, such as, e.g., a conservative BoNT/D enzymatic domain variant, a non-conservative BoNT/D enzymatic domain variant, an active BoNT/D enzymatic domain fragment, or any combination thereof. In still another aspect of this embodiment, a BoNT/D enzymatic domain comprises amino acids 1/2-436 of a non-naturally occurring BoNT/D enzymatic domain variant of SEQ ID NO: 13, such as, e.g., a conservative BoNT/D enzymatic domain variant, a non-conservative BoNT/D enzymatic domain variant, an active BoNT/D enzymatic domain fragment, or any combination thereof.

In other aspects of this embodiment, a BoNT/D enzymatic domain comprises a polypeptide having an amino acid identity of, e.g., at least 70%, at least 75%, at least 80%, at least 85%, at least 90%, or at least 95% to the enzymatic domain of SEQ ID NO: 13 or SEQ ID NO: 14; or at most 70%, at most 75%, at most 80%, at most 85%, at most 90%, or at most 95% to the enzymatic domain of SEQ ID NO: 13 or SEQ ID NO: 14. In yet other aspects of this embodiment, a BoNT/D enzymatic domain comprises a polypeptide having an amino acid identity of, e.g., at least 70%, at least 75%, at least 80%, at least 85%, at least 90%, or at least 95% to amino acids 1/2-436 of SEQ ID NO: 13; or at most 70%, at most 75%, at most 80%, at most 85%, at most 90%, or at most 95% to amino acids 1/2-436 of SEQ ID NO: 13.

In other aspects of this embodiment, a BoNT/D enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 13 or SEQ ID NO: 14; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 13 or SEQ ID NO: 14. In yet other aspects of this embodiment, a BoNT/D enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-436 of SEQ ID NO: 13; or at most 1, 2, 3, 4, 5, 6, 7, 8, 9, 10, 20, 30, 40, 50, or 100 non-contiguous amino acid deletions, additions, and/or substitutions relative to amino acids 1/2-436 of SEQ ID NO: 13. In still other aspects of this embodiment, a BoNT/D enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 13 or SEQ ID NO: 14; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 13 or SEQ ID NO: 14. In further other aspects of this embodiment, a BoNT/D enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-436 of SEQ ID NO: 13; or at most 1, 2, 3, 4, 5, 6, 7, 8, 9, 10, 20, 30, 40, 50, or 100 contiguous amino acid deletions, additions, and/or substitutions relative to amino acids 1/2-436 of SEQ ID NO: 13.

In another embodiment, a Clostridial toxin enzymatic domain comprises a BoNT/E enzymatic domain. In an aspect of this embodiment, a BoNT/E enzymatic domain comprises the enzymatic domains of SEQ ID NO: 15, SEQ ID NO: 16, or SEQ ID NO: 17. In other aspects of this embodiment, a BoNT/E enzymatic domain comprises amino acids 1/2-411 of SEQ ID NO: 15. In another aspect of this embodiment, a BoNT/E enzymatic domain comprises a naturally occurring BoNT/E enzymatic domain variant, such as, e.g., an enzymatic domain from a BoNT/E isoform or an enzymatic domain from a BoNT/E subtype. In another aspect of this embodiment, a BoNT/E enzymatic domain comprises a naturally occurring BoNT/E enzymatic domain variant of SEQ ID NO: 15, SEQ ID NO: 16, or SEQ ID NO: 17, such as, e.g., a BoNT/E isoform enzymatic domain or a BoNT/E subtype enzymatic domain. In another aspect of this embodiment, a BoNT/E enzymatic domain comprises amino acids 1/2-411 of a naturally occurring BoNT/E enzymatic domain variant of SEQ ID NO: 15, such as, e.g., a BoNT/E isoform enzymatic domain or a BoNT/E subtype enzymatic domain. In still another aspect of this embodiment, a BoNT/E enzymatic domain comprises a non-naturally occurring BoNT/E enzymatic domain variant, such as, e.g., a conservative BoNT/E enzymatic domain variant, a non-conservative BoNT/E enzymatic domain variant, an active BoNT/E enzymatic domain fragment, or any combination thereof. In still another aspect of this embodiment, a BoNT/E enzymatic domain comprises the enzymatic domain of a non-naturally occurring BoNT/E enzymatic domain variant of SEQ ID NO: 15, SEQ ID NO: 16, or SEQ ID NO: 17, such as, e.g., a conservative BoNT/E enzymatic domain variant, a non-conservative BoNT/E enzymatic domain variant, an active BoNT/E enzymatic domain fragment, or any combination thereof. In still another aspect of this embodiment, a BoNT/E enzymatic domain comprises amino acids 1/2-411 of a non-naturally occurring BoNT/E enzymatic domain variant of SEQ ID NO: 15, such as, e.g., a conservative BoNT/E enzymatic domain variant, a non-conservative BoNT/E enzymatic domain variant, an active BoNT/E enzymatic domain fragment, or any combination thereof.

In other aspects of this embodiment, a BoNT/E enzymatic domain comprises a polypeptide having an amino acid identity of, e.g., at least 70%, at least 75%, at least 80%, at least 85%, at least 90%, or at least 95% to the enzymatic domain of SEQ ID NO: 15, SEQ ID NO: 16, or SEQ ID NO: 17; or at most 70%, at most 75%, at most 80%, at most 85%, at most 90%, or at most 95% to the enzymatic domain of SEQ ID NO: 15, SEQ ID NO: 16, or SEQ ID NO: 17. In yet other aspects of this embodiment, a BoNT/E enzymatic domain comprises a polypeptide having an amino acid identity of, e.g., at least 70%, at least 75%, at least 80%, at least 85%, at least 90%, or at least 95% to amino acids 1/2-411 of SEQ ID NO: 15; or at most 70%, at most 75%, at most 80%, at most 85%, at most 90%, or at most 95% to amino acids 1/2-411 of SEQ ID NO: 15.

In other aspects of this embodiment, a BoNT/E enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 15, SEQ ID NO: 16, or SEQ ID NO: 17; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 15, SEQ ID NO: 16, or SEQ ID NO: 17. In yet other aspects of this embodiment, a BoNT/E enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-411 of SEQ ID NO: 15; or at most 1, 2, 3, 4, 5, 6, 7, 8, 9, 10, 20, 30, 40, 50, or 100 non-contiguous amino acid deletions, additions, and/or substitutions relative to amino acids 1/2-411 of SEQ ID NO: 15. In still other aspects of this embodiment, a BoNT/E enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 15, SEQ ID NO: 16, or SEQ ID NO: 17; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 15, SEQ ID NO: 16, or SEQ ID NO: 17. In further other aspects of this embodiment, a BoNT/E enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-411 of SEQ ID NO: 15; or at most 1, 2, 3, 4, 5, 6, 7, 8, 9, 10, 20, 30, 40, 50, or 100 contiguous amino acid deletions, additions, and/or substitutions relative to amino acids 1/2-411 of SEQ ID NO: 15.

In another embodiment, a Clostridial toxin enzymatic domain comprises a BoNT/F enzymatic domain. In an aspect of this embodiment, a BoNT/F enzymatic domain comprises the enzymatic domains of SEQ ID NO: 18, SEQ ID NO: 19, or SEQ ID NO: 20. In other aspects of this embodiment, a BoNT/F enzymatic domain comprises amino acids 1/2-428 of SEQ ID NO: 18. In another aspect of this embodiment, a BoNT/F enzymatic domain comprises a naturally occurring BoNT/F enzymatic domain variant, such as, e.g., an enzymatic domain from a BoNT/F isoform or an enzymatic domain from a BoNT/F subtype. In another aspect of this embodiment, a BoNT/F enzymatic domain comprises a naturally occurring BoNT/F enzymatic domain variant of SEQ ID NO: 18, SEQ ID NO: 19, or SEQ ID NO: 20, such as, e.g., a BoNT/F isoform enzymatic domain or a BoNT/F subtype enzymatic domain. In another aspect of this embodiment, a BoNT/F enzymatic domain comprises amino acids 1/2-428 of a naturally occurring BoNT/F enzymatic domain variant of SEQ ID NO: 18, such as, e.g., a BoNT/F isoform enzymatic domain or a BoNT/F subtype enzymatic domain. In still another aspect of this embodiment, a BoNT/F enzymatic domain comprises a non-naturally occurring BoNT/F enzymatic domain variant, such as, e.g., a conservative BoNT/F enzymatic domain variant, a non-conservative BoNT/F enzymatic domain variant, an active BoNT/F enzymatic domain fragment, or any combination thereof. In still another aspect of this embodiment, a BoNT/F enzymatic domain comprises the enzymatic domain of a non-naturally occurring BoNT/F enzymatic domain variant of SEQ ID NO: 18, SEQ ID NO: 19, or SEQ ID NO: 20, such as, e.g., a conservative BoNT/F enzymatic domain variant, a non-conservative BoNT/F enzymatic domain variant, an active BoNT/F enzymatic domain fragment, or any combination thereof. In still another aspect of this embodiment, a BoNT/F enzymatic domain comprises amino acids 1/2-428 of a non-naturally occurring BoNT/F enzymatic domain variant of SEQ ID NO: 18, such as, e.g., a conservative BoNT/F enzymatic domain variant, a non-conservative BoNT/F enzymatic domain variant, an active BoNT/F enzymatic domain fragment, or any combination thereof.

In other aspects of this embodiment, a BoNT/F enzymatic domain comprises a polypeptide having an amino acid identity of, e.g., at least 70%, at least 75%, at least 80%, at least 85%, at least 90%, or at least 95% to the enzymatic domain of SEQ ID NO: 18, SEQ ID NO: 19, or SEQ ID NO: 20; or at most 70%, at most 75%, at most 80%, at most 85%, at most 90%, or at most 95% to the enzymatic domain of SEQ ID NO: 18, SEQ ID NO: 19, or SEQ ID NO: 20. In yet other aspects of this embodiment, a BoNT/F enzymatic domain comprises a polypeptide having an amino acid identity of, e.g., at least 70%, at least 75%, at least 80%, at least 85%, at least 90%, or at least 95% to amino acids 1/2-428 of SEQ ID NO: 18; or at most 70%, at most 75%, at most 80%, at most 85%, at most 90%, or at most 95% to amino acids 1/2-428 of SEQ ID NO: 18.

In other aspects of this embodiment, a BoNT/F enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 18, SEQ ID NO: 19, or SEQ ID NO: 20; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 18, SEQ ID NO: 19, or SEQ ID NO: 20. In yet other aspects of this embodiment, a BoNT/F enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-428 of SEQ ID NO: 18; or at most 1, 2, 3, 4, 5, 6, 7, 8, 9, 10, 20, 30, 40, 50, or 100 non-contiguous amino acid deletions, additions, and/or substitutions relative to amino acids 1/2-428 of SEQ ID NO: 18. In still other aspects of this embodiment, a BoNT/F enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 18, SEQ ID NO: 19, or SEQ ID NO: 20; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 18, SEQ ID NO: 19, or SEQ ID NO: 20. In further other aspects of this embodiment, a BoNT/F enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-428 of SEQ ID NO: 18; or at most 1, 2, 3, 4, 5, 6, 7, 8, 9, 10, 20, 30, 40, 50, or 100 contiguous amino acid deletions, additions, and/or substitutions relative to amino acids 1/2-428 of SEQ ID NO: 18.

In another embodiment, a Clostridial toxin enzymatic domain comprises a BoNT/G enzymatic domain. In an aspect of this embodiment, a BoNT/G enzymatic domain comprises the enzymatic domains of SEQ ID NO: 21. In other aspects of this embodiment, a BoNT/G enzymatic domain comprises amino acids 1/2-4435 of SEQ ID NO: 21. In another aspect of this embodiment, a BoNT/G enzymatic domain comprises a naturally occurring BoNT/G enzymatic domain variant, such as, e.g., an enzymatic domain from a BoNT/G isoform or an enzymatic domain from a BoNT/G subtype. In another aspect of this embodiment, a BoNT/G enzymatic domain comprises a naturally occurring BoNT/G enzymatic domain variant of SEQ ID NO: 21, such as, e.g., a BoNT/G isoform enzymatic domain or a BoNT/G subtype enzymatic domain. In another aspect of this embodiment, a BoNT/G enzymatic domain comprises amino acids 1/2-4435 of a naturally occurring BoNT/G enzymatic domain variant of SEQ ID NO: 21, such as, e.g., a BoNT/G isoform enzymatic domain or a BoNT/G subtype enzymatic domain. In still another aspect of this embodiment, a BoNT/G enzymatic domain comprises a non-naturally occurring BoNT/G enzymatic domain variant, such as, e.g., a conservative BoNT/G enzymatic domain variant, a non-conservative BoNT/G enzymatic domain variant, an active BoNT/G enzymatic domain fragment, or any combination thereof. In still another aspect of this embodiment, a BoNT/G enzymatic domain comprises the enzymatic domain of a non-naturally occurring BoNT/G enzymatic domain variant of SEQ ID NO: 21, such as, e.g., a conservative BoNT/G enzymatic domain variant, a non-conservative BoNT/G enzymatic domain variant, an active BoNT/G enzymatic domain fragment, or any combination thereof. In still another aspect of this embodiment, a BoNT/G enzymatic domain comprises amino acids 1/2-4435 of a non-naturally occurring BoNT/G enzymatic domain variant of SEQ ID NO: 21, such as, e.g., a conservative BoNT/G enzymatic domain variant, a non-conservative BoNT/G enzymatic domain variant, an active BoNT/G enzymatic domain fragment, or any combination thereof.

In other aspects of this embodiment, a BoNT/G enzymatic domain comprises a polypeptide having an amino acid identity of, e.g., at least 70%, at least 75%, at least 80%, at least 85%, at least 90%, or at least 95% to the enzymatic domain of SEQ ID NO: 21; or at most 70%, at most 75%, at most 80%, at most 85%, at most 90%, or at most 95% to the enzymatic domain of SEQ ID NO: 21. In yet other aspects of this embodiment, a BoNT/G enzymatic domain comprises a polypeptide having an amino acid identity of, e.g., at least 70%, at least 75%, at least 80%, at least 85%, at least 90%, or at least 95% to amino acids 1/2-4435 of SEQ ID NO: 21; or at most 70%, at most 75%, at most 80%, at most 85%, at most 90%, or at most 95% to amino acids 1/2-4435 of SEQ ID NO: 21.

In other aspects of this embodiment, a BoNT/G enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 21; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 21. In yet other aspects of this embodiment, a BoNT/G enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-4435 of SEQ ID NO: 21; or at most 1, 2, 3, 4, 5, 6, 7, 8, 9, 10, 20, 30, 40, 50, or 100 non-contiguous amino acid deletions, additions, and/or substitutions relative to amino acids 1/2-4435 of SEQ ID NO: 21. In still other aspects of this embodiment, a BoNT/G enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 21; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 21. In further other aspects of this embodiment, a BoNT/G enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-4435 of SEQ ID NO: 21; or at most 1, 2, 3, 4, 5, 6, 7, 8, 9, 10, 20, 30, 40, 50, or 100 contiguous amino acid deletions, additions, and/or substitutions relative to amino acids 1/2-4435 of SEQ ID NO: 21.

In another embodiment, a Clostridial toxin enzymatic domain comprises a TeNT enzymatic domain. In an aspect of this embodiment, a TeNT enzymatic domain comprises the enzymatic domains of SEQ ID NO: 22. In other aspects of this embodiment, a TeNT enzymatic domain comprises amino acids 1/2-438 of SEQ ID NO: 22. In another aspect of this embodiment, a TeNT enzymatic domain comprises a naturally occurring TeNT enzymatic domain variant, such as, e.g., an enzymatic domain from a TeNT isoform or an enzymatic domain from a TeNT subtype. In another aspect of this embodiment, a TeNT enzymatic domain comprises a naturally occurring TeNT enzymatic domain variant of SEQ ID NO: 22, such as, e.g., a TeNT isoform enzymatic domain or a TeNT subtype enzymatic domain. In another aspect of this embodiment, a TeNT enzymatic domain comprises amino acids 1/2-438 of a naturally occurring TeNT enzymatic domain variant of SEQ ID NO: 22, such as, e.g., a TeNT isoform enzymatic domain or a TeNT subtype enzymatic domain. In still another aspect of this embodiment, a TeNT enzymatic domain comprises a non-naturally occurring TeNT enzymatic domain variant, such as, e.g., a conservative TeNT enzymatic domain variant, a non-conservative TeNT enzymatic domain variant, an active TeNT enzymatic domain fragment, or any combination thereof. In still another aspect of this embodiment, a TeNT enzymatic domain comprises the enzymatic domain of a non-naturally occurring TeNT enzymatic domain variant of SEQ ID NO: 22, such as, e.g., a conservative TeNT enzymatic domain variant, a non-conservative TeNT enzymatic domain variant, an active TeNT enzymatic domain fragment, or any combination thereof. In still another aspect of this embodiment, a TeNT enzymatic domain comprises amino acids 1/2-438 of a non-naturally occurring TeNT enzymatic domain variant of SEQ ID NO: 22, such as, e.g., a conservative TeNT enzymatic domain variant, a non-conservative TeNT enzymatic domain variant, an active TeNT enzymatic domain fragment, or any combination thereof.

In other aspects of this embodiment, a TeNT enzymatic domain comprises a polypeptide having an amino acid identity of, e.g., at least 70%, at least 75%, at least 80%, at least 85%, at least 90%, or at least 95% to the enzymatic domain of SEQ ID NO: 22; or at most 70%, at most 75%, at most 80%, at most 85%, at most 90%, or at most 95% to the enzymatic domain of SEQ ID NO: 22. In yet other aspects of this embodiment, a TeNT enzymatic domain comprises a polypeptide having an amino acid identity of, e.g., at least 70%, at least 75%, at least 80%, at least 85%, at least 90%, or at least 95% to amino acids 1/2-438 of SEQ ID NO: 22; or at most 70%, at most 75%, at most 80%, at most 85%, at most 90%, or at most 95% to amino acids 1/2-438 of SEQ ID NO: 22.

In other aspects of this embodiment, a TeNT enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 22; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 22. In yet other aspects of this embodiment, a TeNT enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-438 of SEQ ID NO: 22; or at most 1, 2, 3, 4, 5, 6, 7, 8, 9, 10, 20, 30, 40, 50, or 100 non-contiguous amino acid deletions, additions, and/or substitutions relative to amino acids 1/2-438 of SEQ ID NO: 22. In still other aspects of this embodiment, a TeNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 22; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 22. In further other aspects of this embodiment, a TeNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-438 of SEQ ID NO: 22; or at most 1, 2, 3, 4, 5, 6, 7, 8, 9, 10, 20, 30, 40, 50, or 100 contiguous amino acid deletions, additions, and/or substitutions relative to amino acids 1/2-438 of SEQ ID NO: 22.

In another embodiment, a Clostridial toxin enzymatic domain comprises a BaNT enzymatic domain. In an aspect of this embodiment, a BaNT enzymatic domain comprises the enzymatic domains of SEQ ID NO: 23. In other aspects of this embodiment, a BaNT enzymatic domain comprises amino acids 1/2-420 of SEQ ID NO: 23. In another aspect of this embodiment, a BaNT enzymatic domain comprises a naturally occurring BaNT enzymatic domain variant, such as, e.g., an enzymatic domain from a BaNT isoform or an enzymatic domain from a BaNT subtype. In another aspect of this embodiment, a BaNT enzymatic domain comprises a naturally occurring BaNT enzymatic domain variant of SEQ ID NO: 23, such as, e.g., a BaNT isoform enzymatic domain or a BaNT subtype enzymatic domain. In another aspect of this embodiment, a BaNT enzymatic domain comprises amino acids 1/2-420 of a naturally occurring BaNT enzymatic domain variant of SEQ ID NO: 23, such as, e.g., a BaNT isoform enzymatic domain or a BaNT subtype enzymatic domain. In still another aspect of this embodiment, a BaNT enzymatic domain comprises a non-naturally occurring BaNT enzymatic domain variant, such as, e.g., a conservative BaNT enzymatic domain variant, a non-conservative BaNT enzymatic domain variant, an active BaNT enzymatic domain fragment, or any combination thereof. In still another aspect of this embodiment, a BaNT enzymatic domain comprises the enzymatic domain of a non-naturally occurring BaNT enzymatic domain variant of SEQ ID NO: 23, such as, e.g., a conservative BaNT enzymatic domain variant, a non-conservative BaNT enzymatic domain variant, an active BaNT enzymatic domain fragment, or any combination thereof. In still another aspect of this embodiment, a BaNT enzymatic domain comprises amino acids 1/2-420 of a non-naturally occurring BaNT enzymatic domain variant of SEQ ID NO: 23, such as, e.g., a conservative BaNT enzymatic domain variant, a non-conservative BaNT enzymatic domain variant, an active BaNT enzymatic domain fragment, or any combination thereof.

In other aspects of this embodiment, a BaNT enzymatic domain comprises a polypeptide having an amino acid identity of, e.g., at least 70%, at least 75%, at least 80%, at least 85%, at least 90%, or at least 95% to the enzymatic domain of SEQ ID NO: 23; or at most 70%, at most 75%, at most 80%, at most 85%, at most 90%, or at most 95% to the enzymatic domain of SEQ ID NO: 23. In yet other aspects of this embodiment, a BaNT enzymatic domain comprises a polypeptide having an amino acid identity of, e.g., at least 70%, at least 75%, at least 80%, at least 85%, at least 90%, or at least 95% to amino acids 1/2-420 of SEQ ID NO: 23; or at most 70%, at most 75%, at most 80%, at most 85%, at most 90%, or at most 95% to amino acids 1/2-420 of SEQ ID NO: 23.

In other aspects of this embodiment, a BaNT enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 23; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 23. In yet other aspects of this embodiment, a BaNT enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-420 of SEQ ID NO: 23; or at most 1, 2, 3, 4, 5, 6, 7, 8, 9, 10, 20, 30, 40, 50, or 100 non-contiguous amino acid deletions, additions, and/or substitutions relative to amino acids 1/2-420 of SEQ ID NO: 23. In still other aspects of this embodiment, a BaNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 23; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 23. In further other aspects of this embodiment, a BaNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-420 of SEQ ID NO: 23; or at most 1, 2, 3, 4, 5, 6, 7, 8, 9, 10, 20, 30, 40, 50, or 100 contiguous amino acid deletions, additions, and/or substitutions relative to amino acids 1/2-420 of SEQ ID NO: 23.

In another embodiment, a Clostridial toxin enzymatic domain comprises a BuNT enzymatic domain. In an aspect of this embodiment, a BuNT enzymatic domain comprises the enzymatic domains of SEQ ID NO: 24 or SEQ ID NO: 25. In other aspects of this embodiment, a BuNT enzymatic domain comprises amino acids 1/2-411 of SEQ ID NO: 24. In another aspect of this embodiment, a BuNT enzymatic domain comprises a naturally occurring BuNT enzymatic domain variant, such as, e.g., an enzymatic domain from a BuNT isoform or an enzymatic domain from a BuNT subtype. In another aspect of this embodiment, a BuNT enzymatic domain comprises a naturally occurring BuNT enzymatic domain variant of SEQ ID NO: 24 or SEQ ID NO: 25, such as, e.g., a BuNT isoform enzymatic domain or a BuNT subtype enzymatic domain. In another aspect of this embodiment, a BuNT enzymatic domain comprises amino acids 1/2-411 of a naturally occurring BuNT enzymatic domain variant of SEQ ID NO: 24, such as, e.g., a BuNT isoform enzymatic domain or a BuNT subtype enzymatic domain. In still another aspect of this embodiment, a BuNT enzymatic domain comprises a non-naturally occurring BuNT enzymatic domain variant, such as, e.g., a conservative BuNT enzymatic domain variant, a non-conservative BuNT enzymatic domain variant, an active BuNT enzymatic domain fragment, or any combination thereof. In still another aspect of this embodiment, a BuNT enzymatic domain comprises the enzymatic domain of a non-naturally occurring BuNT enzymatic domain variant of SEQ ID NO: 24 or SEQ ID NO: 25, such as, e.g., a conservative BuNT enzymatic domain variant, a non-conservative BuNT enzymatic domain variant, an active BuNT enzymatic domain fragment, or any combination thereof. In still another aspect of this embodiment, a BuNT enzymatic domain comprises amino acids 1/2-411 of a non-naturally occurring BuNT enzymatic domain variant of SEQ ID NO: 24, such as, e.g., a conservative BuNT enzymatic domain variant, a non-conservative BuNT enzymatic domain variant, an active BuNT enzymatic domain fragment, or any combination thereof.

In other aspects of this embodiment, a BuNT enzymatic domain comprises a polypeptide having an amino acid identity of, e.g., at least 70%, at least 75%, at least 80%, at least 85%, at least 90%, or at least 95% to the enzymatic domain of SEQ ID NO: 24 or SEQ ID NO: 25; or at most 70%, at most 75%, at most 80%, at most 85%, at most 90%, or at most 95% to the enzymatic domain of SEQ ID NO: 24 or SEQ ID NO: 25. In yet other aspects of this embodiment, a BuNT enzymatic domain comprises a polypeptide having an amino acid identity of, e.g., at least 70%, at least 75%, at least 80%, at least 85%, at least 90%, or at least 95% to amino acids 1/2-411 of SEQ ID NO: 24 or SEQ ID NO: 25; or at most 70%, at most 75%, at most 80%, at most 85%, at most 90%, or at most 95% to amino acids 1/2-411 of SEQ ID NO: 24 or SEQ ID NO: 25.

In other aspects of this embodiment, a BuNT enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 24 or SEQ ID NO: 25; or at most 1, 2, 3, 4, 5, 6, 7, 8, 9, 10, 20, 30, 40, 50, or 100 non-contiguous amino acid deletions, additions, and/or substitutions relative to the enzymatic domain of SEQ ID NO: 240R SEQ ID NO: 25. In yet other aspects of this embodiment, a BuNT enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1/2-411 of SEQ ID NO: 24 or SEQ ID NO: 25; or at most 1, 2, 3, 4, 5, 6, 7, 8, 9, 10, 20, 30, 40, 50, or 100 non-contiguous amino acid deletions, additions, and/or substitutions relative to amino acids 1/2-411 of SEQ ID NO: 24 or SEQ ID NO: 25. In still other aspects of this embodiment, a BuNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 24 or SEQ ID NO: 25; or at most 1, 2, 3, 4, 5, 6, 7, 8, 9, 10, 20, 30, 40, 50, or 100 contiguous amino acid deletions, additions, and/or substitutions relative to the enzymatic domain of SEQ ID NO: 24 or SEQ ID NO: 25. In further other aspects of this embodiment, a BuNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1/2-411 of SEQ ID NO: 24 or SEQ ID NO: 25; or at most 1, 2, 3, 4, 5, 6, 7, 8, 9, 10, 20, 30, 40, 50, or 100 contiguous amino acid deletions, additions, and/or substitutions relative to amino acids 1/2-411 of SEQ ID NO: 24 or SEQ ID NO: 25.

The "translocation domain" comprises a portion of a Clostridial neurotoxin heavy chain having a translocation activity. By "translocation" is meant the ability to facilitate the transport of a polypeptide through a vesicular membrane, thereby exposing some or all of the polypeptide to the cytoplasm. In the various botulinum neurotoxins translocation is thought to involve an allosteric conformational change of the heavy chain caused by a decrease in pH within the endosome. This conformational change appears to involve and be mediated by the N terminal half of the heavy chain and to result in the formation of pores in the vesicular membrane; this change permits the movement of the proteolytic light chain from within the endosomal vesicle into the cytoplasm. See e.g., Lacy, et al., *Nature Struct. Biol.* 5:898-902 (October 1998).

The amino acid sequence of the translocation-mediating portion of the botulinum neurotoxin heavy chain is known to those of skill in the art; additionally, those amino acid residues within this portion that are known to be essential for conferring the translocation activity are also known. It would therefore be well within the ability of one of ordinary skill in the art, for example, to employ the naturally occurring N-terminal peptide half of the heavy chain of any of the various *Clostridium tetanus* or *Clostridium botulinum* neurotoxin subtypes as a translocation domain, or to design an analogous translocation domain by aligning the primary sequences of the N-terminal halves of the various heavy chains and selecting a consensus primary translocation sequence based on conserved amino acid, polarity, steric and hydrophobicity characteristics between the sequences.

Aspects of the present specification provide, in part, a Clostridial toxin translocation domain. As used herein, the term "Clostridial toxin translocation domain" refers to any Clostridial toxin polypeptide that can execute the translocation step of the intoxication process that mediates Clostridial toxin light chain translocation. Thus, a Clostridial toxin translocation domain facilitates the movement of a Clostridial toxin light chain across a membrane and encompasses the movement of a Clostridial toxin light chain through the membrane an intracellular vesicle into the cytoplasm of a cell. Non-limiting examples of a Clostridial toxin translocation domain include, e.g., a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, and a BuNT translocation domain.

A Clostridial toxin translocation domain includes, without limitation, naturally occurring Clostridial toxin translocation domain variants, such as, e.g., Clostridial toxin translocation domain isoforms and Clostridial toxin translocation domain subtypes; non-naturally occurring Clostridial toxin translocation domain variants, such as, e.g., conservative Clostridial toxin translocation domain variants, non-conservative Clostridial toxin translocation domain variants, active Clostridial toxin translocation domain fragments thereof, or any combination thereof.

As used herein, the term "Clostridial toxin translocation domain variant," whether naturally-occurring or non-naturally-occurring, refers to a Clostridial toxin translocation domain that has at least one amino acid change from the corresponding region of the disclosed reference sequences (Table 1) and can be described in percent identity to the corresponding region of that reference sequence. Unless expressly indicated, Clostridial toxin translocation domain variants useful to practice disclosed embodiments are variants that execute the translocation step of the intoxication process that mediates Clostridial toxin light chain translocation. As non-limiting examples, a BoNT/A translocation domain variant will have at least one amino acid difference, such as, e.g., an amino acid substitution, deletion or addition, as compared to amino acids 455-873 of SEQ ID NO: 1; a BoNT/B translocation domain variant will have at least one amino acid difference, such as, e.g., an amino acid substitution, deletion or addition, as compared to amino acids 447-860 of SEQ ID NO: 6; a BoNT/C1 translocation domain variant will have at least one amino acid difference, such as, e.g., an amino acid substitution, deletion or addition, as compared to amino acids 454-868 of SEQ ID NO: 11; a BoNT/D translocation domain variant will have at least one amino acid difference, such as, e.g., an amino acid substitution, deletion or addition, as compared to amino acids 451-864 of SEQ ID NO: 13; a BoNT/E translocation domain variant will have at least one amino acid difference, such as, e.g., an amino acid substitution, deletion or addition, as compared to amino acids 427-847 of SEQ ID NO: 15; a BoNT/F translocation domain variant will have at least one amino acid difference, such as, e.g., an amino acid substitution, deletion or addition, as compared to amino acids 446-865 of SEQ ID NO: 18; a BoNT/G translocation domain variant will have at least one amino acid difference, such as, e.g., an amino acid substitution, deletion or addition, as compared to amino acids 451-865 of SEQ ID NO: 21; a TeNT translocation domain variant will have at least one amino acid difference, such as, e.g., an amino acid substitution, deletion or addition, as compared to amino acids 468-881 of SEQ ID NO: 22; a BaNT translocation domain variant will have at least one amino acid difference, such as, e.g., an amino acid substitution, deletion or addition, as compared to amino acids 436-857 of SEQ ID NO: 23; and a BuNT translocation domain variant will have at least one amino acid difference, such as, e.g., an amino acid substitution, deletion or addition, as compared to amino acids 427-847 of SEQ ID NO: 24.

It is recognized by those of skill in the art that within each serotype of Clostridial toxin there can be naturally occurring Clostridial toxin translocation domain variants that differ somewhat in their amino acid sequence, and also in the nucleic acids encoding these proteins. For example, there are presently five BoNT/A subtypes, BoNT/A1, BoNT/A2, BoNT/A3, BoNT/A4, and BoNT/A5, with specific translocation domain subtypes showing about 85-87% amino acid identity when compared to the BoNT/A translocation domain subtype of SEQ ID NO: 1. As used herein, the term "naturally occurring Clostridial toxin translocation domain variant" refers to any Clostridial toxin translocation domain produced by a naturally-occurring process, including, without limitation, Clostridial toxin translocation domain isoforms produced from alternatively-spliced transcripts, Clostridial toxin translocation domain isoforms produced by spontaneous mutation and Clostridial toxin translocation domain subtypes. A naturally occurring Clostridial toxin translocation domain variant can function in substantially the same manner as the reference Clostridial toxin translocation domain on which the naturally occurring Clostridial toxin translocation domain variant is based, and can be substituted for the reference Clostridial toxin translocation domain in any aspect of the present specification.

A non-limiting examples of a naturally occurring Clostridial toxin translocation domain variant is a Clostridial toxin translocation domain isoform such as, e.g., a BoNT/A translocation domain isoform, a BoNT/B translocation domain isoform, a BoNT/C1 translocation domain isoform, a BoNT/D translocation domain isoform, a BoNT/E translocation domain isoform, a BoNT/F translocation domain isoform, a BoNT/G translocation domain isoform, a TeNT translocation domain isoform, a BaNT translocation domain isoform, and a BuNT translocation domain isoform. Another non-limiting examples of a naturally occurring Clostridial toxin translocation domain variant is a Clostridial toxin translocation domain subtype such as, e.g., a translocation domain from subtype BoNT/A1, BoNT/A2, BoNT/A3, BoNT/A4, and BoNT/A5; a translocation domain from subtype BoNT/B1, BoNT/B2, BoNT/B bivalent and BoNT/B nonproteolytic; a translocation domain from subtype BoNT/C1-1 and BoNT/C1-2; a translocation domain from subtype BoNT/E1, BoNT/E2 and BoNT/E3; a translocation domain from subtype BoNT/F1, BoNT/F2, BoNT/F3; and a translocation domain from subtype BuNT-1 and BuNT-2.

As used herein, the term "non-naturally occurring Clostridial toxin translocation domain variant" refers to any Clostridial toxin translocation domain produced with the aid of human manipulation, including, without limitation, Clostridial toxin translocation domains produced by genetic engineering using random mutagenesis or rational design and Clostridial toxin translocation domains produced by chemical synthesis. Non-limiting examples of non-naturally occurring Clostridial toxin translocation domain variants include, e.g., conservative Clostridial toxin translocation domain variants, non-conservative Clostridial toxin translocation domain variants, and active Clostridial toxin translocation domain fragments.

As used herein, the term "conservative Clostridial toxin translocation domain variant" refers to a Clostridial toxin translocation domain that has at least one amino acid substituted by another amino acid or an amino acid analog that has at least one property similar to that of the original amino acid from the reference Clostridial toxin translocation domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin translocation domain variant can function in substantially the same manner as the reference Clostridial toxin translocation domain on which the conservative Clostridial toxin translocation domain variant is based, and can be substituted for the reference Clostridial toxin translocation domain in any aspect of the present specification. Non-limiting examples of a conservative Clostridial toxin translocation domain variant include, e.g., conservative BoNT/A translocation domain variants, conservative BoNT/B translocation domain variants, conservative BoNT/C1 translocation domain variants, conservative BoNT/D translocation domain variants, conservative BoNT/E translocation domain variants, conservative BoNT/F translocation domain variants, conservative BoNT/G translocation domain variants, conservative TeNT translocation domain variants, conservative BaNT translocation domain variants, and conservative BuNT translocation domain variants.

As used herein, the term "non-conservative Clostridial toxin translocation domain variant" refers to a Clostridial toxin translocation domain in which 1) at least one amino acid is deleted from the reference Clostridial toxin translocation domain on which the non-conservative Clostridial toxin translocation domain variant is based; 2) at least one amino acid added to the reference Clostridial toxin translocation domain on which the non-conservative Clostridial toxin translocation domain is based; or 3) at least one amino acid is substituted by another amino acid or an amino acid analog that does not share any property similar to that of the original amino acid from the reference Clostridial toxin translocation domain sequence (Table 1). A non-conservative Clostridial toxin translocation domain variant can function in substantially the same manner as the reference Clostridial toxin translocation domain on which the non-conservative Clostridial toxin translocation domain variant is based, and can be substituted for the reference Clostridial toxin translocation domain in any aspect of the present specification. Non-limiting examples of a non-conservative Clostridial toxin translocation domain variant include, e.g., non-conservative BoNT/A translocation domain variants, non-conservative BoNT/B translocation domain variants, non-conservative BoNT/C1 translocation domain variants, non-conservative BoNT/D translocation domain variants, non-conservative BoNT/E translocation domain variants, non-conservative BoNT/F translocation domain variants, non-conservative BoNT/G translocation domain variants, and non-conservative TeNT translocation domain variants, non-conservative BaNT translocation domain variants, and non-conservative BuNT translocation domain variants.

As used herein, the term "active Clostridial toxin translocation domain fragment" refers to any of a variety of Clostridial toxin fragments comprising the translocation domain can be useful in aspects of the present specification with the proviso that these active fragments can facilitate the release of the LC from intracellular vesicles into the cytoplasm of the target cell and thus participate in executing the overall cellular mechanism whereby a Clostridial toxin proteolytically cleaves a substrate. The translocation domains from the heavy chains of Clostridial toxins are approximately 410-430 amino acids in length and comprise a translocation domain (Table 1). Research has shown that the entire length of a translocation domain from a Clostridial toxin heavy chain is not necessary for the translocating activity of the translocation domain. Thus, aspects of this embodiment include a Clostridial toxin translocation domain having a length of, e.g., at least 350, 375, 400, or 425 amino acids. Other aspects of this embodiment include a Clostridial toxin translocation domain having a length of, e.g., at most 350, 375, 400, or 425 amino acids.

Any of a variety of sequence alignment methods can be used to determine percent identity of naturally-occurring Clostridial toxin translocation domain variants and non-naturally-occurring Clostridial toxin translocation domain variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises a Clostridial toxin translocation domain. In an aspect of this embodiment, a Clostridial toxin translocation domain comprises a naturally occurring Clostridial toxin translocation domain variant, such as, e.g., a Clostridial toxin translocation domain isoform or a Clostridial toxin translocation domain subtype. In another aspect of this embodiment, a Clostridial toxin translocation domain comprises a non-naturally occurring Clostridial toxin translocation domain variant, such as, e.g., a conservative Clostridial toxin translocation domain variant, a non-conservative Clostridial toxin translocation domain variant, an active Clostridial toxin translocation domain fragment, or any combination thereof.

In another embodiment, a hydrophobic amino acid at one particular position in the polypeptide chain of the Clostridial toxin translocation domain can be substituted with another hydrophobic amino acid. Examples of hydrophobic amino acids include, e.g., C, F, I, L, M, V and W. In another aspect of this embodiment, an aliphatic amino acid at one particular position in the polypeptide chain of the Clostridial toxin translocation domain can be substituted with another aliphatic amino acid. Examples of aliphatic amino acids include, e.g., A, I, L, P, and V. In yet another aspect of this embodiment, an aromatic amino acid at one particular position in the polypeptide chain of the Clostridial toxin translocation domain can be substituted with another aromatic amino acid. Examples of aromatic amino acids include, e.g., F, H, W and Y. In still another aspect of this embodiment, a stacking amino acid at one particular position in the polypeptide chain of the Clostridial toxin translocation domain can be substituted with another stacking amino acid. Examples of stacking amino acids include, e.g., F, H, W and Y. In a further aspect of this embodiment, a polar amino acid at one particular position in the polypeptide chain of the Clostridial toxin translocation domain can be substituted with another polar amino acid. Examples of polar amino acids include, e.g., D, E, K, N, Q, and R. In a further aspect of this embodiment, a less polar or indifferent amino acid at one particular position in the polypeptide chain of the Clostridial toxin translocation domain can be substituted with another less polar or indifferent amino acid. Examples of less polar or indifferent amino acids include, e.g., A, H, G, P, S, T, and Y. In a yet further aspect of this embodiment, a positive charged amino acid at one particular position in the polypeptide chain of the Clostridial toxin translocation domain can be substituted with another positive charged amino acid. Examples of positive charged amino acids include, e.g., K, R, and H. In a still further aspect of this embodiment, a negative charged amino acid at one particular position in the polypeptide chain of the Clostridial toxin translocation domain can be substituted with another negative charged amino acid. Examples of negative charged amino acids include, e.g., D and E. In another aspect of this embodiment, a small amino acid at one particular position in the polypeptide chain of the Clostridial toxin translocation domain can be substituted with another small amino acid. Examples of small amino acids include, e.g., A, D, G, N, P, S, and T. In yet another aspect of this embodiment, a C-beta branching amino acid at one particular position in the polypeptide chain of the Clostridial toxin translocation domain can be substituted with another C-beta branching amino acid. Examples of C-beta branching amino acids include, e.g., I, T and V.

In another embodiment, a Clostridial toxin translocation domain comprises a BoNT/A translocation domain. In an aspect of this embodiment, a BoNT/A translocation domain comprises the translocation domains of SEQ ID NO: 1, SEQ ID NO: 2, SEQ ID NO: 3, SEQ ID NO: 4, or SEQ ID NO: 5. In other aspects of this embodiment, a BoNT/A translocation domain comprises amino acids 455-873 of SEQ ID NO: 1. In another aspect of this embodiment, a BoNT/A translocation domain comprises a naturally occurring BoNT/A translocation domain variant, such as, e.g., an translocation domain from a BoNT/A isoform or an translocation domain from a BoNT/A subtype. In another aspect of this embodiment, a BoNT/A translocation domain comprises a naturally occurring BoNT/A translocation domain variant of SEQ ID NO: 1, SEQ ID NO: 2, SEQ ID NO: 3, SEQ ID NO: 4, or SEQ ID NO: 5, such as, e.g., a BoNT/A isoform translocation domain or a BoNT/A subtype translocation domain. In another aspect of this embodiment, a BoNT/A translocation domain comprises amino acids 455-873 of a naturally occurring BoNT/A translocation domain variant of SEQ ID NO: 1, such as, e.g., a BoNT/A isoform translocation domain or a BoNT/A subtype translocation domain. In still another aspect of this embodiment, a BoNT/A translocation domain comprises a non-naturally occurring BoNT/A translocation domain variant, such as, e.g., a conservative BoNT/A translocation domain variant, a non-conservative BoNT/A translocation domain variant, an active BoNT/A translocation domain fragment, or any combination thereof. In still another aspect of this embodiment, a BoNT/A translocation domain comprises the translocation domain of a non-naturally occurring BoNT/A translocation domain variant of SEQ ID NO: 1, SEQ ID NO: 2, SEQ ID NO: 3, SEQ ID NO: 4, or SEQ ID NO: 5, such as, e.g., a conservative BoNT/A translocation domain variant, a non-conservative BoNT/A translocation domain variant, an active BoNT/A translocation domain fragment, or any combination thereof. In still another aspect of this embodiment, a BoNT/A translocation domain comprises amino acids 455-873 of a non-naturally occurring BoNT/A translocation domain variant of SEQ ID NO: 1, such as, e.g., a conservative BoNT/A translocation domain variant, a non-conservative BoNT/A translocation domain variant, an active BoNT/A translocation domain fragment, or any combination thereof.

In other aspects of this embodiment, a BoNT/A translocation domain comprises a polypeptide having an amino acid identity of, e.g., at least 70%, at least 75%, at least 80%, at least 85%, at least 90%, or at least 95% to the translocation domain of SEQ ID NO: 1, SEQ ID NO: 2, SEQ ID NO: 3, SEQ ID NO: 4, or SEQ ID NO: 5; or at most 70%, at most 75%, at most 80%, at most 85%, at most 90%, or at most 95% to the translocation domain of SEQ ID NO: 1, SEQ ID NO: 2, SEQ ID NO: 3, SEQ ID NO: 4, or SEQ ID NO: 5. In yet other aspects of this embodiment, a BoNT/A translocation domain comprises a polypeptide having an amino acid identity of, e.g., at least 70%, at least 75%, at least 80%, at least 85%, at least 90%, or at least 95% to amino acids 455-873 of SEQ ID NO: 1; or at most 70%, at most 75%, at most 80%, at most 85%, at most 90%, or at most 95% to amino acids 455-873 of SEQ ID NO: 1.

In other aspects of this embodiment, a BoNT/A translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 1, SEQ ID NO: 2, SEQ ID NO: 3, SEQ ID NO: 4, or SEQ ID NO: 5; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 1, SEQ ID NO: 2, SEQ ID NO: 3, SEQ ID NO: 4, or SEQ ID NO: 5. In yet other aspects of this embodiment, a BoNT/A translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 455-873 of SEQ ID NO: 1; or at most 1, 2, 3, 4, 5, 6, 7, 8, 9, 10, 20, 30, 40, 50, or 100 non-contiguous amino acid deletions, additions, and/or substitutions relative to amino acids 455-873 of SEQ ID NO: 1. In still other aspects of this embodiment, a BoNT/A translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 1, SEQ ID NO: 2, SEQ ID NO: 3, SEQ ID NO: 4, or SEQ ID NO: 5; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 1, SEQ ID NO: 2, SEQ ID NO: 3, SEQ ID NO: 4, or SEQ ID NO: 5. In further other aspects of this embodiment, a BoNT/A translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 455-873 of SEQ ID NO: 1; or at most 1, 2, 3, 4, 5, 6, 7, 8, 9, 10, 20, 30, 40, 50, or 100 contiguous amino acid deletions, additions, and/or substitutions relative to amino acids 455-873 of SEQ ID NO: 1.

In another embodiment, a Clostridial toxin translocation domain comprises a BoNT/B translocation domain. In an aspect of this embodiment, a BoNT/B translocation domain comprises the translocation domains of SEQ ID NO: 6, SEQ ID NO: 7, SEQ ID NO: 8, SEQ ID NO: 9, or SEQ ID NO: 10. In other aspects of this embodiment, a BoNT/B translocation domain comprises amino acids 447-860 of SEQ ID NO: 6. In another aspect of this embodiment, a BoNT/B translocation domain comprises a naturally occurring BoNT/B translocation domain variant, such as, e.g., an translocation domain from a BoNT/B isoform or an translocation domain from a BoNT/B subtype. In another aspect of this embodiment, a BoNT/B translocation domain comprises a naturally occurring BoNT/B translocation domain variant of SEQ ID NO: 6, SEQ ID NO: 7, SEQ ID NO: 8, SEQ ID NO: 9, or SEQ ID NO: 10, such as, e.g., a BoNT/B isoform translocation domain or a BoNT/B subtype translocation domain. In another aspect of this embodiment, a BoNT/B translocation domain comprises amino acids 447-860 of a naturally occurring BoNT/B translocation domain variant of SEQ ID NO: 6, such as, e.g., a BoNT/B isoform translocation domain or a BoNT/B subtype translocation domain. In still another aspect of this embodiment, a BoNT/B translocation domain comprises a non-naturally occurring BoNT/B translocation domain variant, such as, e.g., a conservative BoNT/B translocation domain variant, a non-conservative BoNT/B translocation domain variant, an active BoNT/B translocation domain fragment, or any combination thereof. In still another aspect of this embodiment, a BoNT/B translocation domain comprises the translocation domain of a non-naturally occurring BoNT/B translocation domain variant of SEQ ID NO: 6, SEQ ID NO: 7, SEQ ID NO: 8, SEQ ID NO: 9, or SEQ ID NO: 10, such as, e.g., a conservative BoNT/B translocation domain variant, a non-conservative BoNT/B translocation domain variant, an active BoNT/B translocation domain fragment, or any combination thereof. In still another aspect of this embodiment, a BoNT/B translocation domain comprises amino acids 447-860 of a non-naturally occurring BoNT/B translocation domain variant of SEQ ID NO: 6, such as, e.g., a conservative BoNT/B translocation domain variant, a non-conservative BoNT/B translocation domain variant, an active BoNT/B translocation domain fragment, or any combination thereof.

In other aspects of this embodiment, a BoNT/B translocation domain comprises a polypeptide having an amino acid identity of, e.g., at least 70%, at least 75%, at least 80%, at least 85%, at least 90%, or at least 95% to the translocation domain of SEQ ID NO: 6, SEQ ID NO: 7, SEQ ID NO: 8, SEQ ID NO: 9, or SEQ ID NO: 10; or at most 70%, at most 75%, at most 80%, at most 85%, at most 90%, or at most 95% to the translocation domain of SEQ ID NO: 6, SEQ ID NO: 7, SEQ ID NO: 8, SEQ ID NO: 9, or SEQ ID NO: 10. In yet other aspects of this embodiment, a BoNT/B translocation domain comprises a polypeptide having an amino acid identity of, e.g., at least 70%, at least 75%, at least 80%, at least 85%, at least 90%, or at least 95% to amino acids 447-860 of SEQ ID NO: 6; or at most 70%, at most 75%, at most 80%, at most 85%, at most 90%, or at most 95% to amino acids 447-860 of SEQ ID NO: 6.

In other aspects of this embodiment, a BoNT/B translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 6, SEQ ID NO: 7, SEQ ID NO: 8, SEQ ID NO: 9, or SEQ ID NO: 10; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 6, SEQ ID NO: 7, SEQ ID NO: 8, SEQ ID NO: 9, or SEQ ID NO: 10. In yet other aspects of this embodiment, a BoNT/B translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 447-860 of SEQ ID NO: 6; or at most 1, 2, 3, 4, 5, 6, 7, 8, 9, 10, 20, 30, 40, 50, or 100 non-contiguous amino acid deletions, additions, and/or substitutions relative to amino acids 447-860 of SEQ ID NO: 6. In still other aspects of this embodiment, a BoNT/B translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 6, SEQ ID NO: 7, SEQ ID NO: 8, SEQ ID NO: 9, or SEQ ID NO: 10; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 6, SEQ ID NO: 7, SEQ ID NO: 8, SEQ ID NO: 9, or SEQ ID NO: 10. In further other aspects of this embodiment, a BoNT/B translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 447-860 of SEQ ID NO: 6; or at most 1, 2, 3, 4, 5, 6, 7, 8, 9, 10, 20, 30, 40, 50, or 100 contiguous amino acid deletions, additions, and/or substitutions relative to amino acids 447-860 of SEQ ID NO: 6.

In another embodiment, a Clostridial toxin translocation domain comprises a BoNT/C1 translocation domain. In an aspect of this embodiment, a BoNT/C1 translocation domain comprises the translocation domains of SEQ ID NO: 11 or SEQ ID NO: 12. In other aspects of this embodiment, a BoNT/C1 translocation domain comprises amino acids 454-868 of SEQ ID NO: 11. In another aspect of this embodiment, a BoNT/C1 translocation domain comprises a naturally occurring BoNT/C1 translocation domain variant, such as, e.g., an translocation domain from a BoNT/C1 isoform or an translocation domain from a BoNT/C1 subtype. In another aspect of this embodiment, a BoNT/C1 translocation domain comprises a naturally occurring BoNT/C1 translocation domain variant of SEQ ID NO: 11 or SEQ ID NO: 12, such as, e.g., a BoNT/C1 isoform translocation domain or a BoNT/C1 subtype translocation domain. In another aspect of this embodiment, a BoNT/C1 translocation domain comprises amino acids 454-868 of a naturally occurring BoNT/C1 translocation domain variant of SEQ ID NO: 11, such as, e.g., a BoNT/C1 isoform translocation domain or a BoNT/C1 subtype translocation domain. In still another aspect of this embodiment, a BoNT/C1 translocation domain comprises a non-naturally occurring BoNT/C1 translocation domain variant, such as, e.g., a conservative BoNT/C1 translocation domain variant, a non-conservative BoNT/C1 translocation domain variant, an active BoNT/C1 translocation domain fragment, or any combination thereof. In still another aspect of this embodiment, a BoNT/C1 translocation domain comprises the translocation domain of a non-naturally occurring BoNT/C1 translocation domain variant of SEQ ID NO: 11 or SEQ ID NO: 12, such as, e.g., a conservative BoNT/C1 translocation domain variant, a non-conservative BoNT/C1 translocation domain variant, an active BoNT/C1 translocation domain fragment, or any combination thereof. In still another aspect of this embodiment, a BoNT/C1 translocation domain comprises amino acids 454-868 of a non-naturally occurring BoNT/C1 translocation domain variant of SEQ ID NO: 11, such as, e.g., a conservative BoNT/C1 translocation domain variant, a non-conservative BoNT/C1 translocation domain variant, an active BoNT/C1 translocation domain fragment, or any combination thereof.

In other aspects of this embodiment, a BoNT/C1 translocation domain comprises a polypeptide having an amino acid identity of, e.g., at least 70%, at least 75%, at least 80%, at least 85%, at least 90%, or at least 95% to the translocation domain of SEQ ID NO: 11 or SEQ ID NO: 12; or at most 70%, at most 75%, at most 80%, at most 85%, at most 90%, or at most 95% to the translocation domain of SEQ ID NO: 11 or SEQ ID NO: 12. In yet other aspects of this embodiment, a BoNT/C1 translocation domain comprises a polypeptide having an amino acid identity of, e.g., at least 70%, at least 75%, at least 80%, at least 85%, at least 90%, or at least 95% to amino acids 454-868 of SEQ ID NO: 11; or at most 70%, at most 75%, at most 80%, at most 85%, at most 90%, or at most 95% to amino acids 454-868 of SEQ ID NO: 11.

In other aspects of this embodiment, a BoNT/C1 translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 11 or SEQ ID NO: 12; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 11 or SEQ ID NO: 12. In yet other aspects of this embodiment, a BoNT/C1 translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 454-868 of SEQ ID NO: 11; or at most 1, 2, 3, 4, 5, 6, 7, 8, 9, 10, 20, 30, 40, 50, or 100 non-contiguous amino acid deletions, additions, and/or substitutions relative to amino acids 454-868 of SEQ ID NO: 11. In still other aspects of this embodiment, a BoNT/C1 translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 11 or SEQ ID NO: 12; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 11 or SEQ ID NO: 12. In further other aspects of this embodiment, a BoNT/C1 translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 454-868 of SEQ ID NO: 11; or at most 1, 2, 3, 4, 5, 6, 7, 8, 9, 10, 20, 30, 40, 50, or 100 contiguous amino acid deletions, additions, and/or substitutions relative to amino acids 454-868 of SEQ ID NO: 11.

In another embodiment, a Clostridial toxin translocation domain comprises a BoNT/D translocation domain. In an aspect of this embodiment, a BoNT/D translocation domain comprises the translocation domains of SEQ ID NO: 13 or SEQ ID NO: 14. In other aspects of this embodiment, a BoNT/D translocation domain comprises amino acids 451-864 of SEQ ID NO: 13. In another aspect of this embodiment, a BoNT/D translocation domain comprises a naturally occurring BoNT/D translocation domain variant, such as, e.g., an translocation domain from a BoNT/D isoform or an translocation domain from a BoNT/D subtype. In another aspect of this embodiment, a BoNT/D translocation domain comprises a naturally occurring BoNT/D translocation domain variant of SEQ ID NO: 13 or SEQ ID NO: 14, such as, e.g., a BoNT/D isoform translocation domain or a BoNT/D subtype translocation domain. In another aspect of this embodiment, a BoNT/D translocation domain comprises amino acids 451-864 of a naturally occurring BoNT/D translocation domain variant of SEQ ID NO: 13, such as, e.g., a BoNT/D isoform translocation domain or a BoNT/D subtype translocation domain. In still another aspect of this embodiment, a BoNT/D translocation domain comprises a non-naturally occurring BoNT/D translocation domain variant, such as, e.g., a conservative BoNT/D translocation domain variant, a non-conservative BoNT/D translocation domain variant, an active BoNT/D translocation domain fragment, or any combination thereof. In still another aspect of this embodiment, a BoNT/D translocation domain comprises the translocation domain of a non-naturally occurring BoNT/D translocation domain variant of SEQ ID NO: 13 or SEQ ID NO: 14, such as, e.g., a conservative BoNT/D translocation domain variant, a non-conservative BoNT/D translocation domain variant, an active BoNT/D translocation domain fragment, or any combination thereof. In still another aspect of this embodiment, a BoNT/D translocation domain comprises amino acids 451-864 of a non-naturally occurring BoNT/D translocation domain variant of SEQ ID NO: 13, such as, e.g., a conservative BoNT/D translocation domain variant, a non-conservative BoNT/D translocation domain variant, an active BoNT/D translocation domain fragment, or any combination thereof.

In other aspects of this embodiment, a BoNT/D translocation domain comprises a polypeptide having an amino acid identity of, e.g., at least 70%, at least 75%, at least 80%, at least 85%, at least 90%, or at least 95% to the translocation domain of SEQ ID NO: 13 or SEQ ID NO: 14; or at most 70%, at most 75%, at most 80%, at most 85%, at most 90%, or at most 95% to the translocation domain of SEQ ID NO: 13 or SEQ ID NO: 14. In yet other aspects of this embodiment, a BoNT/D translocation domain comprises a polypeptide having an amino acid identity of, e.g., at least 70%, at least 75%, at least 80%, at least 85%, at least 90%, or at least 95% to amino acids 451-864 of SEQ ID NO: 13; or at most 70%, at most 75%, at most 80%, at most 85%, at most 90%, or at most 95% to amino acids 451-864 of SEQ ID NO: 13.

In other aspects of this embodiment, a BoNT/D translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 13 or SEQ ID NO: 14; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 13 or SEQ ID NO: 14. In yet other aspects of this embodiment, a BoNT/D translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 451-864 of SEQ ID NO: 13; or at most 1, 2, 3, 4, 5, 6, 7, 8, 9, 10, 20, 30, 40, 50, or 100 non-contiguous amino acid deletions, additions, and/or substitutions relative to amino acids 451-864 of SEQ ID NO: 13. In still other aspects of this embodiment, a BoNT/D translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 13 or SEQ ID NO: 14; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 13 or SEQ ID NO: 14. In further other aspects of this embodiment, a BoNT/D translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 451-864 of SEQ ID NO: 13; or at most 1, 2, 3, 4, 5, 6, 7, 8, 9, 10, 20, 30, 40, 50, or 100 contiguous amino acid deletions, additions, and/or substitutions relative to amino acids 451-864 of SEQ ID NO: 13.

In another embodiment, a Clostridial toxin translocation domain comprises a BoNT/E translocation domain. In an aspect of this embodiment, a BoNT/E translocation domain comprises the translocation domains of SEQ ID NO: 15, SEQ ID NO: 16, or SEQ ID NO: 17. In other aspects of this embodiment, a BoNT/E translocation domain comprises amino acids 427-847 of SEQ ID NO: 15. In another aspect of this embodiment, a BoNT/E translocation domain comprises a naturally occurring BoNT/E translocation domain variant, such as, e.g., an translocation domain from a BoNT/E isoform or an translocation domain from a BoNT/E subtype. In another aspect of this embodiment, a BoNT/E translocation domain comprises a naturally occurring BoNT/E translocation domain variant of SEQ ID NO: 15, SEQ ID NO: 16, or SEQ ID NO: 17, such as, e.g., a BoNT/E isoform translocation domain or a BoNT/E subtype translocation domain. In another aspect of this embodiment, a BoNT/E translocation domain comprises amino acids 427-847 of a naturally occurring BoNT/E translocation domain variant of SEQ ID NO: 15, such as, e.g., a BoNT/E isoform translocation domain or a BoNT/E subtype translocation domain. In still another aspect of this embodiment, a BoNT/E translocation domain comprises a non-naturally occurring BoNT/E translocation domain variant, such as, e.g., a conservative BoNT/E translocation domain variant, a non-conservative BoNT/E translocation domain variant, an active BoNT/E translocation domain fragment, or any combination thereof. In still another aspect of this embodiment, a BoNT/E translocation domain comprises the translocation domain of a non-naturally occurring BoNT/E translocation domain variant of SEQ ID NO: 15, SEQ ID NO: 16, or SEQ ID NO: 17, such as, e.g., a conservative BoNT/E translocation domain variant, a non-conservative BoNT/E translocation domain variant, an active BoNT/E translocation domain fragment, or any combination thereof. In still another aspect of this embodiment, a BoNT/E translocation domain comprises amino acids 427-847 of a non-naturally occurring BoNT/E translocation domain variant of SEQ ID NO: 15, such as, e.g., a conservative BoNT/E translocation domain variant, a non-conservative BoNT/E translocation domain variant, an active BoNT/E translocation domain fragment, or any combination thereof.

In other aspects of this embodiment, a BoNT/E translocation domain comprises a polypeptide having an amino acid identity of, e.g., at least 70%, at least 75%, at least 80%, at least 85%, at least 90%, or at least 95% to the translocation domain of SEQ ID NO: 15, SEQ ID NO: 16, or SEQ ID NO: 17; or at most 70%, at most 75%, at most 80%, at most 85%, at most 90%, or at most 95% to the translocation domain of SEQ ID NO: 15, SEQ ID NO: 16, or SEQ ID NO: 17. In yet other aspects of this embodiment, a BoNT/E translocation domain comprises a polypeptide having an amino acid identity of, e.g., at least 70%, at least 75%, at least 80%, at least 85%, at least 90%, or at least 95% to amino acids 427-847 of SEQ ID NO: 15; or at most 70%, at most 75%, at most 80%, at most 85%, at most 90%, or at most 95% to amino acids 427-847 of SEQ ID NO: 15.

In other aspects of this embodiment, a BoNT/E translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 15, SEQ ID NO: 16, or SEQ ID NO: 17; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 15, SEQ ID NO: 16, or SEQ ID NO: 17. In yet other aspects of this embodiment, a BoNT/E translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 427-847 of SEQ ID NO: 15; or at most 1, 2, 3, 4, 5, 6, 7, 8, 9, 10, 20, 30, 40, 50, or 100 non-contiguous amino acid deletions, additions, and/or substitutions relative to amino acids 427-847 of SEQ ID NO: 15. In still other aspects of this embodiment, a BoNT/E translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 15, SEQ ID NO: 16, or SEQ ID NO: 17; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 15, SEQ ID NO: 16, or SEQ ID NO: 17. In further other aspects of this embodiment, a BoNT/E translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 427-847 of SEQ ID NO: 15; or at most 1, 2, 3, 4, 5, 6, 7, 8, 9, 10, 20, 30, 40, 50, or 100 contiguous amino acid deletions, additions, and/or substitutions relative to amino acids 427-847 of SEQ ID NO: 15.

In another embodiment, a Clostridial toxin translocation domain comprises a BoNT/F translocation domain. In an aspect of this embodiment, a BoNT/F translocation domain comprises the translocation domains of SEQ ID NO: 18, SEQ ID NO: 19, or SEQ ID NO: 20. In other aspects of this embodiment, a BoNT/F translocation domain comprises amino acids 446-865 of SEQ ID NO: 18. In another aspect of this embodiment, a BoNT/F translocation domain comprises a naturally occurring BoNT/F translocation domain variant, such as, e.g., an translocation domain from a BoNT/F isoform or an translocation domain from a BoNT/F subtype. In another aspect of this embodiment, a BoNT/F translocation domain comprises a naturally occurring BoNT/F translocation domain variant of SEQ ID NO: 18, SEQ ID NO: 19, or SEQ ID NO: 20, such as, e.g., a BoNT/F isoform translocation domain or a BoNT/F subtype translocation domain. In another aspect of this embodiment, a BoNT/F translocation domain comprises amino acids 446-865 of a naturally occurring BoNT/F translocation domain variant of SEQ ID NO: 18, such as, e.g., a BoNT/F isoform translocation domain or a BoNT/F subtype translocation domain. In still another aspect of this embodiment, a BoNT/F translocation domain comprises a non-naturally occurring BoNT/F translocation domain variant, such as, e.g., a conservative BoNT/F translocation domain variant, a non-conservative BoNT/F translocation domain variant, an active BoNT/F translocation domain fragment, or any combination thereof. In still another aspect of this embodiment, a BoNT/F translocation domain comprises the translocation domain of a non-naturally occurring BoNT/F translocation domain variant of SEQ ID NO: 18, SEQ ID NO: 19, or SEQ ID NO: 20, such as, e.g., a conservative BoNT/F translocation domain variant, a non-conservative BoNT/F translocation domain variant, an active BoNT/F translocation domain fragment, or any combination thereof. In still another aspect of this embodiment, a BoNT/F translocation domain comprises amino acids 446-865 of a non-naturally occurring BoNT/F translocation domain variant of SEQ ID NO: 18, such as, e.g., a conservative BoNT/F translocation domain variant, a non-conservative BoNT/F translocation domain variant, an active BoNT/F translocation domain fragment, or any combination thereof.

In other aspects of this embodiment, a BoNT/F translocation domain comprises a polypeptide having an amino acid identity of, e.g., at least 70%, at least 75%, at least 80%, at least 85%, at least 90%, or at least 95% to the translocation domain of SEQ ID NO: 18, SEQ ID NO: 19, or SEQ ID NO: 20; or at most 70%, at most 75%, at most 80%, at most 85%, at most 90%, or at most 95% to the translocation domain of SEQ ID NO: 18, SEQ ID NO: 19, or SEQ ID NO: 20. In yet other aspects of this embodiment, a BoNT/F translocation domain comprises a polypeptide having an amino acid identity of, e.g., at least 70%, at least 75%, at least 80%, at least 85%, at least 90%, or at least 95% to amino acids 446-865 of SEQ ID NO: 18; or at most 70%, at most 75%, at most 80%, at most 85%, at most 90%, or at most 95% to amino acids 446-865 of SEQ ID NO: 18.

In other aspects of this embodiment, a BoNT/F translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 18, SEQ ID NO: 19, or SEQ ID NO: 20; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 18, SEQ ID NO: 19, or SEQ ID NO: 20. In yet other aspects of this embodiment, a BoNT/F translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 446-865 of SEQ ID NO: 18; or at most 1, 2, 3, 4, 5, 6, 7, 8, 9, 10, 20, 30, 40, 50, or 100 non-contiguous amino acid deletions, additions, and/or substitutions relative to amino acids 446-865 of SEQ ID NO: 18. In still other aspects of this embodiment, a BoNT/F translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 18, SEQ ID NO: 19, or SEQ ID NO: 20; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 18, SEQ ID NO: 19, or SEQ ID NO: 20. In further other aspects of this embodiment, a BoNT/F translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 446-865 of SEQ ID NO: 18; or at most 1, 2, 3, 4, 5, 6, 7, 8, 9, 10, 20, 30, 40, 50, or 100 contiguous amino acid deletions, additions, and/or substitutions relative to amino acids 446-865 of SEQ ID NO: 18.

In another embodiment, a Clostridial toxin translocation domain comprises a BoNT/G translocation domain. In an aspect of this embodiment, a BoNT/G translocation domain comprises the translocation domains of SEQ ID NO: 21. In other aspects of this embodiment, a BoNT/G translocation domain comprises amino acids 451-865 of SEQ ID NO: 21. In another aspect of this embodiment, a BoNT/G translocation domain comprises a naturally occurring BoNT/G translocation domain variant, such as, e.g., an translocation domain from a BoNT/G isoform or an translocation domain from a BoNT/G subtype. In another aspect of this embodiment, a BoNT/G translocation domain comprises a naturally occurring BoNT/G translocation domain variant of SEQ ID NO: 21, such as, e.g., a BoNT/G isoform translocation domain or a BoNT/G subtype translocation domain. In another aspect of this embodiment, a BoNT/G translocation domain comprises amino acids 451-865 of a naturally occurring BoNT/G translocation domain variant of SEQ ID NO: 21, such as, e.g., a BoNT/G isoform translocation domain or a BoNT/G subtype translocation domain. In still another aspect of this embodiment, a BoNT/G translocation domain comprises a non-naturally occurring BoNT/G translocation domain variant, such as, e.g., a conservative BoNT/G translocation domain variant, a non-conservative BoNT/G translocation domain variant, an active BoNT/G translocation domain fragment, or any combination thereof. In still another aspect of this embodiment, a BoNT/G translocation domain comprises the translocation domain of a non-naturally occurring BoNT/G translocation domain variant of SEQ ID NO: 21, such as, e.g., a conservative BoNT/G translocation domain variant, a non-conservative BoNT/G translocation domain variant, an active BoNT/G translocation domain fragment, or any combination thereof. In still another aspect of this embodiment, a BoNT/G translocation domain comprises amino acids 451-865 of a non-naturally occurring BoNT/G translocation domain variant of SEQ ID NO: 21, such as, e.g., a conservative BoNT/G translocation domain variant, a non-conservative BoNT/G translocation domain variant, an active BoNT/G translocation domain fragment, or any combination thereof.

In other aspects of this embodiment, a BoNT/G translocation domain comprises a polypeptide having an amino acid identity of, e.g., at least 70%, at least 75%, at least 80%, at least 85%, at least 90%, or at least 95% to the translocation domain of SEQ ID NO: 21; or at most 70%, at most 75%, at most 80%, at most 85%, at most 90%, or at most 95% to the translocation domain of SEQ ID NO: 21. In yet other aspects of this embodiment, a BoNT/G translocation domain comprises a polypeptide having an amino acid identity of, e.g., at least 70%, at least 75%, at least 80%, at least 85%, at least 90%, or at least 95% to amino acids 451-865 of SEQ ID NO: 21; or at most 70%, at most 75%, at most 80%, at most 85%, at most 90%, or at most 95% to amino acids 451-865 of SEQ ID NO: 21.

In other aspects of this embodiment, a BoNT/G translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 21; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 21. In yet other aspects of this embodiment, a BoNT/G translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 451-865 of SEQ ID NO: 21; or at most 1, 2, 3, 4, 5, 6, 7, 8, 9, 10, 20, 30, 40, 50, or 100 non-contiguous amino acid deletions, additions, and/or substitutions relative to amino acids 451-865 of SEQ ID NO: 21. In still other aspects of this embodiment, a BoNT/G translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 21; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 21. In further other aspects of this embodiment, a BoNT/G translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 451-865 of SEQ ID NO: 21; or at most 1, 2, 3, 4, 5, 6, 7, 8, 9, 10, 20, 30, 40, 50, or 100 contiguous amino acid deletions, additions, and/or substitutions relative to amino acids 451-865 of SEQ ID NO: 21.

In another embodiment, a Clostridial toxin translocation domain comprises a TeNT translocation domain. In an aspect of this embodiment, a TeNT translocation domain comprises the translocation domains of SEQ ID NO: 22. In other aspects of this embodiment, a TeNT translocation domain comprises amino acids 468-881 of SEQ ID NO: 22. In another aspect of this embodiment, a TeNT translocation domain comprises a naturally occurring TeNT translocation domain variant, such as, e.g., an translocation domain from a TeNT isoform or an translocation domain from a TeNT subtype. In another aspect of this embodiment, a TeNT translocation domain comprises a naturally occurring TeNT translocation domain variant of SEQ ID NO: 22, such as, e.g., a TeNT isoform translocation domain or a TeNT subtype translocation domain. In another aspect of this embodiment, a TeNT translocation domain comprises amino acids 468-881 of a naturally occurring TeNT translocation domain variant of SEQ ID NO: 22, such as, e.g., a TeNT isoform translocation domain or a TeNT subtype translocation domain. In still another aspect of this embodiment, a TeNT translocation domain comprises a non-naturally occurring TeNT translocation domain variant, such as, e.g., a conservative TeNT translocation domain variant, a non-conservative TeNT translocation domain variant, an active TeNT translocation domain fragment, or any combination thereof. In still another aspect of this embodiment, a TeNT translocation domain comprises the translocation domain of a non-naturally occurring TeNT translocation domain variant of SEQ ID NO: 22, such as, e.g., a conservative TeNT translocation domain variant, a non-conservative TeNT translocation domain variant, an active TeNT translocation domain fragment, or any combination thereof. In still another aspect of this embodiment, a TeNT translocation domain comprises amino acids 468-881 of a non-naturally occurring TeNT translocation domain variant of SEQ ID NO: 22, such as, e.g., a conservative TeNT translocation domain variant, a non-conservative TeNT translocation domain variant, an active TeNT translocation domain fragment, or any combination thereof.

In other aspects of this embodiment, a TeNT translocation domain comprises a polypeptide having an amino acid identity of, e.g., at least 70%, at least 75%, at least 80%, at least 85%, at least 90%, or at least 95% to the translocation domain of SEQ ID NO: 22; or at most 70%, at most 75%, at most 80%, at most 85%, at most 90%, or at most 95% to the translocation domain of SEQ ID NO: 22. In yet other aspects of this embodiment, a TeNT translocation domain comprises a polypeptide having an amino acid identity of, e.g., at least 70%, at least 75%, at least 80%, at least 85%, at least 90%, or at least 95% to amino acids 468-881 of SEQ ID NO: 22; or at most 70%, at most 75%, at most 80%, at most 85%, at most 90%, or at most 95% to amino acids 468-881 of SEQ ID NO: 22.

In other aspects of this embodiment, a TeNT translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 22; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 22. In yet other aspects of this embodiment, a TeNT translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 468-881 of SEQ ID NO: 22; or at most 1, 2, 3, 4, 5, 6, 7, 8, 9, 10, 20, 30, 40, 50, or 100 non-contiguous amino acid deletions, additions, and/or substitutions relative to amino acids 468-881 of SEQ ID NO: 22. In still other aspects of this embodiment, a TeNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 22; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 22. In further other aspects of this embodiment, a TeNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 468-881 of SEQ ID NO: 22; or at most 1, 2, 3, 4, 5, 6, 7, 8, 9, 10, 20, 30, 40, 50, or 100 contiguous amino acid deletions, additions, and/or substitutions relative to amino acids 468-881 of SEQ ID NO: 22.

In another embodiment, a Clostridial toxin translocation domain comprises a BaNT translocation domain. In an aspect of this embodiment, a BaNT translocation domain comprises the translocation domains of SEQ ID NO: 23. In other aspects of this embodiment, a BaNT translocation domain comprises amino acids 436-857 of SEQ ID NO: 23. In another aspect of this embodiment, a BaNT translocation domain comprises a naturally occurring BaNT translocation domain variant, such as, e.g., an translocation domain from a BaNT isoform or an translocation domain from a BaNT subtype. In another aspect of this embodiment, a BaNT translocation domain comprises a naturally occurring BaNT translocation domain variant of SEQ ID NO: 23, such as, e.g., a BaNT isoform translocation domain or a BaNT subtype translocation domain. In another aspect of this embodiment, a BaNT translocation domain comprises amino acids 436-857 of a naturally occurring BaNT translocation domain variant of SEQ ID NO: 23, such as, e.g., a BaNT isoform translocation domain or a BaNT subtype translocation domain. In still another aspect of this embodiment, a BaNT translocation domain comprises a non-naturally occurring BaNT translocation domain variant, such as, e.g., a conservative BaNT translocation domain variant, a non-conservative BaNT translocation domain variant, an active BaNT translocation domain fragment, or any combination thereof. In still another aspect of this embodiment, a BaNT translocation domain comprises the translocation domain of a non-naturally occurring BaNT translocation domain variant of SEQ ID NO: 23, such as, e.g., a conservative BaNT translocation domain variant, a non-conservative BaNT translocation domain variant, an active BaNT translocation domain fragment, or any combination thereof. In still another aspect of this embodiment, a BaNT translocation domain comprises amino acids 436-857 of a non-naturally occurring BaNT translocation domain variant of SEQ ID NO: 23, such as, e.g., a conservative BaNT translocation domain variant, a non-conservative BaNT translocation domain variant, an active BaNT translocation domain fragment, or any combination thereof.

In other aspects of this embodiment, a BaNT translocation domain comprises a polypeptide having an amino acid identity of, e.g., at least 70%, at least 75%, at least 80%, at least 85%, at least 90%, or at least 95% to the translocation domain of SEQ ID NO: 23; or at most 70%, at most 75%, at most 80%, at most 85%, at most 90%, or at most 95% to the translocation domain of SEQ ID NO: 23. In yet other aspects of this embodiment, a BaNT translocation domain comprises a polypeptide having an amino acid identity of, e.g., at least 70%, at least 75%, at least 80%, at least 85%, at least 90%, or at least 95% to amino acids 436-857 of SEQ ID NO: 23; or at most 70%, at most 75%, at most 80%, at most 85%, at most 90%, or at most 95% to amino acids 436-857 of SEQ ID NO: 23.

In other aspects of this embodiment, a BaNT translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 23; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 23. In yet other aspects of this embodiment, a BaNT translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 436-857 of SEQ ID NO: 23; or at most 1, 2, 3, 4, 5, 6, 7, 8, 9, 10, 20, 30, 40, 50, or 100 non-contiguous amino acid deletions, additions, and/or substitutions relative to amino acids 436-857 of SEQ ID NO: 23. In still other aspects of this embodiment, a BaNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 23; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 23. In further other aspects of this embodiment, a BaNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 436-857 of SEQ ID NO: 23; or at most 1, 2, 3, 4, 5, 6, 7, 8, 9, 10, 20, 30, 40, 50, or 100 contiguous amino acid deletions, additions, and/or substitutions relative to amino acids 436-857 of SEQ ID NO: 23.

In another embodiment, a Clostridial toxin translocation domain comprises a BuNT translocation domain. In an aspect of this embodiment, a BuNT translocation domain comprises the translocation domains of SEQ ID NO: 24 or SEQ ID NO: 25. In other aspects of this embodiment, a BuNT translocation domain comprises amino acids 427-847 of SEQ ID NO: 24. In another aspect of this embodiment, a BuNT translocation domain comprises a naturally occurring BuNT translocation domain variant, such as, e.g., an translocation domain from a BuNT isoform or an translocation domain from a BuNT subtype. In another aspect of this embodiment, a BuNT translocation domain comprises a naturally occurring BuNT translocation domain variant of SEQ ID NO: 24 or SEQ ID NO: 25, such as, e.g., a BuNT isoform translocation domain or a BuNT subtype translocation domain. In another aspect of this embodiment, a BuNT translocation domain comprises amino acids 427-847 of a naturally occurring BuNT translocation domain variant of SEQ ID NO: 24, such as, e.g., a BuNT isoform translocation domain or a BuNT subtype translocation domain. In still another aspect of this embodiment, a BuNT translocation domain comprises a non-naturally occurring BuNT translocation domain variant, such as, e.g., a conservative BuNT translocation domain variant, a non-conservative BuNT translocation domain variant, an active BuNT translocation domain fragment, or any combination thereof. In still another aspect of this embodiment, a BuNT translocation domain comprises the translocation domain of a non-naturally occurring BuNT translocation domain variant of SEQ ID NO: 24 or SEQ ID NO: 25, such as, e.g., a conservative BuNT translocation domain variant, a non-conservative BuNT translocation domain variant, an active BuNT translocation domain fragment, or any combination thereof. In still another aspect of this embodiment, a BuNT translocation domain comprises amino acids 427-847 of a non-naturally occurring BuNT translocation domain variant of SEQ ID NO: 24, such as, e.g., a conservative BuNT translocation domain variant, a non-conservative BuNT translocation domain variant, an active BuNT translocation domain fragment, or any combination thereof.

In other aspects of this embodiment, a BuNT translocation domain comprises a polypeptide having an amino acid identity of, e.g., at least 70%, at least 75%, at least 80%, at least 85%, at least 90%, or at least 95% to the translocation domain of SEQ ID NO: 24 or SEQ ID NO: 25; or at most 70%, at most 75%, at most 80%, at most 85%, at most 90%, or at most 95% to the translocation domain of SEQ ID NO: 24 or SEQ ID NO: 25. In yet other aspects of this embodiment, a BuNT translocation domain comprises a polypeptide having an amino acid identity of, e.g., at least 70%, at least 75%, at least 80%, at least 85%, at least 90%, or at least 95% to amino acids 427-847 of SEQ ID NO: 24 or SEQ ID NO: 25; or at most 70%, at most 75%, at most 80%, at most 85%, at most 90%, or at most 95% to amino acids 427-847 of SEQ ID NO: 24 or SEQ ID NO: 25.

In other aspects of this embodiment, a BuNT translocation domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 24 or SEQ ID NO: 25; or at most 1, 2, 3, 4, 5, 6, 7, 8, 9, 10, 20, 30, 40, 50, or 100 non-contiguous amino acid deletions, additions, and/or substitutions relative to the translocation domain of SEQ ID NO: 240R SEQ ID NO: 25. In yet other aspects of this embodiment, a BuNT translocation domain comprises a polypeptide having, e.g., at most 1, 2, 3, 4, 5, 6, 7, 8, 9, 10, 20, 30, 40, 50, or 100 non-contiguous amino acid deletions, additions, and/ or substitutions relative to amino acids 427-847 of SEQ ID NO: 24 or SEQ ID NO: 25; or at most 1, 2, 3, 4, 5, 6, 7, 8, 9, 10, 20, 30, 40, 50, or 100 non-contiguous amino acid deletions, additions, and/or substitutions relative to amino acids 427-847 of SEQ ID NO: 24 or SEQ ID NO: 25. In still other aspects of this embodiment, a BuNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the translocation domain of SEQ ID NO: 24 or SEQ ID NO: 25; or at most 1, 2, 3, 4, 5, 6, 7, 8, 9, 10, 20, 30, 40, 50, or 100 contiguous amino acid deletions, additions, and/or substitutions relative to the translocation domain of SEQ ID NO: 24 or SEQ ID NO: 25. In further other aspects of this embodiment, a BuNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 427-847 of SEQ ID NO: 24 or SEQ ID NO: 25; or at most 1, 2, 3, 4, 5, 6, 7, 8, 9, 10, 20, 30, 40, 50, or 100 contiguous amino acid deletions, additions, and/or substitutions relative to amino acids 427-847 of SEQ ID NO: 24 or SEQ ID NO: 25.

Aspects of the present specification provide, in part, a binding domain. As used herein, the term "binding domain" is synonymous with "ligand" or "targeting moiety" and refers to any molecule that can preferentially interact with another molecule present on the surface of a cell under physiological conditions. The cell surface molecule may comprise a polypeptide, a polysaccharide, a lipid, or may have structural characteristics of more than one of these. As used herein, the term "preferentially interacts" refers to molecule is able to bind its target receptor under physiological conditions, or in vitro conditions substantially approximating physiological conditions, to a statistically significantly greater degree relative to other, non-target receptor. With reference to a Clostridial toxin binding domain disclosed in the present specification, there is a discriminatory binding of the Clostridial toxin binding domain to its cognate receptor relative to other receptors. With reference to a non-Clostridial toxin binding domain disclosed in the present specification, there is a discriminatory binding of the non-Clostridial toxin binding domain to it cognate receptor relative to other receptors.

Thus, in an embodiment, a binding domain that selectively binds a target receptor has a dissociation equilibrium constant ($K_D$) that is greater for the target receptor relative to a non-target receptor by, e.g., at least one-fold, at least two-fold, at least three-fold, at least four fold, at least five-fold, at least 10 fold, at least 50 fold, at least 100 fold, at least 1000 fold, at least 10,000, or at least 100,000 fold.

Aspects of the present specification provide, in part, a Clostridial toxin binding domain. As used herein, the term "Clostridial toxin binding domain" refers to any Clostridial toxin polypeptide that can execute the binding step of the intoxication process that initiates the overall internalization mechanism whereby the modified Clostridial toxin disclosed in the present specification intoxicates a target cell. Non-limiting examples of a Clostridial toxin binding domain include, e.g., a BoNT/A binding domain, a BoNT/B binding domain, a BoNT/C1 binding domain, a BoNT/D binding domain, a BoNT/E binding domain, a BoNT/F binding domain, a BoNT/G binding domain, a TeNT binding domain, a BaNT binding domain, and a BuNT binding domain. Other non-limiting examples of a Clostridial toxin binding domain include, e.g., amino acids 874-1296 of SEQ ID NO: 1, amino acids 861-1291 of SEQ ID NO: 2, amino acids 869-1291 of SEQ ID NO: 3, amino acids 865-1291 of SEQ ID NO: 4, amino acids 848-1252 of SEQ ID NO: 5, amino acids 866-1274 of SEQ ID NO: 6, amino acids 866-1297 of SEQ ID NO: 7, amino acids 882-1315 of SEQ ID NO: 8, amino acids 858-1268 of SEQ ID NO: 9, and amino acids 848-1251 of SEQ ID NO: 10.

A Clostridial toxin binding domain includes, without limitation, naturally occurring Clostridial toxin binding domain variants, such as, e.g., Clostridial toxin binding domain isoforms and Clostridial toxin binding domain subtypes; non-naturally occurring Clostridial toxin binding domain variants, such as, e.g., conservative Clostridial toxin binding domain variants, non-conservative Clostridial toxin binding domain variants, active Clostridial toxin binding domain fragments thereof, or any combination thereof.

As used herein, the term "Clostridial toxin binding domain variant," whether naturally-occurring or non-naturally-occurring, refers to a Clostridial toxin binding domain that has at least one amino acid change from the corresponding region of the disclosed reference sequences (Table 1) and can be described in percent identity to the corresponding region of that reference sequence. Unless expressly indicated, Clostridial toxin binding domain variants useful to practice disclosed embodiments are variants that execute the translocation step of the intoxication process that mediates Clostridial toxin light chain translocation. As non-limiting examples, a BoNT/A binding domain variant will have at least one amino acid difference, such as, e.g., an amino acid substitution, deletion or addition, as compared to amino acids 874-1296 of SEQ ID NO: 1; a BoNT/B binding domain variant will have at least one amino acid difference, such as, e.g., an amino acid substitution, deletion or addition, as compared to amino acids 861-1291 of SEQ ID NO: 6; a BoNT/C1 binding domain variant will have at least one amino acid difference, such as, e.g., an amino acid substitution, deletion or addition, as compared to amino acids 869-1291 of SEQ ID NO: 11; a BoNT/D binding domain variant will have at least one amino acid difference, such as, e.g., an amino acid substitution, deletion or addition, as compared to amino acids 865-1291 of SEQ ID NO: 13; a BoNT/E binding domain variant will have at least one amino acid difference, such as, e.g., an amino acid substitution, deletion or addition, as compared to amino acids 848-1252 of SEQ ID NO: 15; a BoNT/F binding domain variant will have at least one amino acid difference, such as, e.g., an amino acid substitution, deletion or addition, as compared to amino acids 866-1274 of SEQ ID NO: 18; a BoNT/G binding domain variant will have at least one amino acid difference, such as, e.g., an amino acid substitution, deletion or addition, as compared to amino acids 866-1297 of SEQ ID NO: 21; a TeNT binding domain variant will have at least one amino acid difference, such as, e.g., an amino acid substitution, deletion or addition, as compared to amino acids 882-1315 of SEQ ID NO: 22; a BaNT binding domain variant will have at least one amino acid difference, such as, e.g., an amino acid substitution, deletion or addition, as compared to amino acids 858-1268 of SEQ ID NO: 23; and a BuNT binding domain variant will have at least one amino acid difference, such as, e.g., an amino acid substitution, deletion or addition, as compared to amino acids 848-1251 of SEQ ID NO: 24.

It is recognized by those of skill in the art that within each serotype of Clostridial toxin there can be naturally occurring Clostridial toxin binding domain variants that differ somewhat in their amino acid sequence, and also in the nucleic acids encoding these proteins. For example, there are presently five BoNT/A subtypes, BoNT/A1, BoNT/A2, BoNT/A3, BoNT/A4, and BoNT/A5, with specific binding domain subtypes showing about 83-97% amino acid identity when compared to the BoNT/A binding domain subtype of SEQ ID NO: 1. As another example, there are presently five BoNT/A subtypes, BoNT/A1, BoNT/A2, BoNT/A3, BoNT/A4, and BoNT/A5, with specific binding domain subtypes showing about 83-97% amino acid identity when compared to the BoNT/A binding domain subtype of SEQ ID NO: 1. As used herein, the term "naturally occurring Clostridial toxin binding domain variant" refers to any Clostridial toxin binding domain produced by a naturally-occurring process, including, without limitation, Clostridial toxin binding domain isoforms produced from alternatively-spliced transcripts, Clostridial toxin binding domain isoforms produced by spontaneous mutation and Clostridial toxin binding domain subtypes. A naturally occurring Clostridial toxin binding domain variant can function in substantially the same manner as the reference Clostridial toxin binding domain on which the naturally occurring Clostridial toxin binding domain variant is based, and can be substituted for the reference Clostridial toxin binding domain in any aspect of the present specification.

A non-limiting examples of a naturally occurring Clostridial toxin binding domain variant is a Clostridial toxin binding domain isoform such as, e.g., a BoNT/A binding domain isoform, a BoNT/B binding domain isoform, a BoNT/C1 binding domain isoform, a BoNT/D binding domain isoform, a BoNT/E binding domain isoform, a BoNT/F binding domain isoform, a BoNT/G binding domain isoform, a TeNT binding domain isoform, a BaNT binding domain isoform, and a BuNT binding domain isoform. Another non-limiting examples of a naturally occurring Clostridial toxin binding domain variant is a Clostridial toxin binding domain subtype such as, e.g., a binding domain from subtype BoNT/A1, BoNT/A2, BoNT/A3, BoNT/A4, and BoNT/A5; a binding domain from subtype BoNT/B1, BoNT/B2, BoNT/B bivalent and BoNT/B nonproteolytic; a binding domain from subtype BoNT/C1-1 and BoNT/C1-2; a binding domain from subtype BoNT/E1, BoNT/E2 and BoNT/E3; and a binding domain from subtype BoNT/F1, BoNT/F2, and BoNT/F3; and a binding domain from subtype BuNT-1 and BuNT-2.

As used herein, the term "non-naturally occurring Clostridial toxin binding domain variant" refers to any Clostridial toxin binding domain produced with the aid of human manipulation, including, without limitation, Clostridial toxin binding domains produced by genetic engineering using random mutagenesis or rational design and Clostridial toxin binding domains produced by chemical synthesis. Non-limiting examples of non-naturally occurring Clostridial toxin binding domain variants include, e.g., conservative Clostridial toxin binding domain variants, non-conservative Clostridial toxin binding domain variants, Clostridial toxin binding domain chimeric variants and active Clostridial toxin binding domain fragments.

As used herein, the term "conservative Clostridial toxin binding domain variant" refers to a Clostridial toxin binding domain that has at least one amino acid substituted by another amino acid or an amino acid analog that has at least one property similar to that of the original amino acid from the reference Clostridial toxin binding domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin binding domain variant can function in substantially the same manner as the reference Clostridial toxin binding domain on which the conservative Clostridial toxin binding domain variant is based, and can be substituted for the reference Clostridial toxin binding domain in any aspect of the present specification. Non-limiting examples of a conservative Clostridial toxin binding domain variant include, e.g., conservative BoNT/A binding domain variants, conservative BoNT/B binding domain variants, conservative BoNT/C1 binding domain variants, conservative BoNT/D binding domain variants, conservative BoNT/E binding domain variants, conservative BoNT/F binding domain variants, conservative BoNT/G binding domain variants, conservative TeNT binding domain variants, conservative BaNT binding domain variants, and conservative BuNT binding domain variants.

As used herein, the term "non-conservative Clostridial toxin binding domain variant" refers to a Clostridial toxin binding domain in which 1) at least one amino acid is deleted from the reference Clostridial toxin binding domain on which the non-conservative Clostridial toxin binding domain variant is based; 2) at least one amino acid added to the reference Clostridial toxin binding domain on which the non-conservative Clostridial toxin binding domain is based; or 3) at least one amino acid is substituted by another amino acid or an amino acid analog that does not share any property similar to that of the original amino acid from the reference Clostridial toxin binding domain sequence (Table 1). A non-conservative Clostridial toxin binding domain variant can function in substantially the same manner as the reference Clostridial toxin binding domain on which the non-conservative Clostridial toxin binding domain variant is based, and can be substituted for the reference Clostridial toxin binding domain in any aspect of the present specification. Non-limiting examples of a non-conservative Clostridial toxin binding domain variant include, e.g., non-conservative BoNT/A binding domain variants, non-conservative BoNT/B binding domain variants, non-conservative BoNT/C1 binding domain variants, non-conservative BoNT/D binding domain variants, non-conservative BoNT/E binding domain variants, non-conservative BoNT/F binding domain variants, non-conservative BoNT/G binding domain variants, and non-conservative TeNT binding domain variants, non-conservative BaNT binding domain variants, and non-conservative BuNT binding domain variants.

As used herein, the term "active Clostridial toxin binding domain fragment" refers to any of a variety of Clostridial toxin fragments comprising the binding domain can be useful in aspects of the present specification with the proviso that these active fragments can facilitate the release of the LC from intracellular vesicles into the cytoplasm of the target cell and thus participate in executing the overall cellular mechanism whereby a Clostridial toxin proteolytically cleaves a substrate. The binding domains from the heavy chains of Clostridial toxins are approximately 400-440 amino acids in length and comprise a binding domain (Table 1). Research has shown that the entire length of a binding domain from a Clostridial toxin heavy chain is not necessary for the translocating activity of the binding domain. Thus, aspects of this embodiment include a Clostridial toxin binding domain having a length of, e.g., at least 350, 375, 400, or 425 amino acids. Other aspects of this embodiment include a Clostridial toxin binding domain having a length of, e.g., at most 350, 375, 400, or 425 amino acids.

Any of a variety of sequence alignment methods can be used to determine percent identity of naturally-occurring Clostridial toxin binding domain variants and non-naturally-occurring Clostridial toxin binding domain variants, including, without limitation, global methods, local methods, and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises a Clostridial toxin binding domain. In an aspect of this embodiment, a Clostridial toxin binding domain comprises a naturally occurring Clostridial toxin binding domain variant, such as, e.g., a Clostridial toxin binding domain isoform or a Clostridial toxin binding domain subtype. In another aspect of this embodiment, a Clostridial toxin binding domain comprises a non-naturally occurring Clostridial toxin binding domain variant, such as, e.g., a conservative Clostridial toxin binding domain variant, a non-conservative Clostridial toxin binding domain variant, an active Clostridial toxin binding domain fragment, or any combination thereof.

In another embodiment, a hydrophobic amino acid at one particular position in the polypeptide chain of the Clostridial toxin binding domain can be substituted with another hydrophobic amino acid. Examples of hydrophobic amino acids include, e.g., C, F, I, L, M, V and W. In another aspect of this embodiment, an aliphatic amino acid at one particular position in the polypeptide chain of the Clostridial toxin binding domain can be substituted with another aliphatic amino acid. Examples of aliphatic amino acids include, e.g., A, I, L, P, and V. In yet another aspect of this embodiment, an aromatic amino acid at one particular position in the polypeptide chain of the Clostridial toxin binding domain can be substituted with another aromatic amino acid. Examples of aromatic amino acids include, e.g., F, H, W and Y. In still another aspect of this embodiment, a stacking amino acid at one particular position in the polypeptide chain of the Clostridial toxin binding domain can be substituted with another stacking amino acid. Examples of stacking amino acids include, e.g., F, H, W and Y. In a further aspect of this embodiment, a polar amino acid at one particular position in the polypeptide chain of the Clostridial toxin binding domain can be substituted with another polar amino acid. Examples of polar amino acids include, e.g., D, E, K, N, Q, and R. In a further aspect of this embodiment, a less polar or indifferent amino acid at one particular position in the polypeptide chain of the Clostridial toxin binding domain can be substituted with another less polar or indifferent amino acid. Examples of less polar or indifferent amino acids include, e.g., A, H, G, P, S, T, and Y. In a yet further aspect of this embodiment, a positive charged amino acid at one particular position in the polypeptide chain of the Clostridial toxin binding domain can be substituted with another positive charged amino acid. Examples of positive charged amino acids include, e.g., K, R, and H. In a still further aspect of this embodiment, a negative charged amino acid at one particular position in the polypeptide chain of the Clostridial toxin binding domain can be substituted with another negative charged amino acid. Examples of negative charged amino acids include, e.g., D and E. In another aspect of this embodiment, a small amino acid at one particular position in the polypeptide chain of the Clostridial toxin binding domain can be substituted with another small amino acid. Examples of small amino acids include, e.g., A, D, G, N, P, S, and T. In yet another aspect of this embodiment, a C-beta branching amino acid at one particular position in the polypeptide chain of the Clostridial toxin binding domain can be substituted with another C-beta branching amino acid. Examples of C-beta branching amino acids include, e.g., I, T and V.

In another embodiment, a Clostridial toxin binding domain comprises a BoNT/A binding domain. In an aspect of this embodiment, a BoNT/A binding domain comprises the binding domains of SEQ ID NO: 1, SEQ ID NO: 2, SEQ ID NO: 3, SEQ ID NO: 4, or SEQ ID NO: 5. In other aspects of this embodiment, a BoNT/A binding domain comprises amino acids 874-1296 of SEQ ID NO: 1. In another aspect of this embodiment, a BoNT/A binding domain comprises a naturally occurring BoNT/A binding domain variant, such as, e.g., an binding domain from a BoNT/A isoform or an binding domain from a BoNT/A subtype. In another aspect of this embodiment, a BoNT/A binding domain comprises a naturally occurring BoNT/A binding domain variant of SEQ ID NO: 1, SEQ ID NO: 2, SEQ ID NO: 3, SEQ ID NO: 4, or SEQ ID NO: 5, such as, e.g., a BoNT/A isoform binding domain or a BoNT/A subtype binding domain. In another aspect of this embodiment, a BoNT/A binding domain comprises amino acids 874-1296 of a naturally occurring BoNT/A binding domain variant of SEQ ID NO: 1, such as, e.g., a BoNT/A isoform binding domain or a BoNT/A subtype binding domain. In still another aspect of this embodiment, a BoNT/A binding domain comprises a non-naturally occurring BoNT/A binding domain variant, such as, e.g., a conservative BoNT/A binding domain variant, a non-conservative BoNT/A binding domain variant, an active BoNT/A binding domain fragment, or any combination thereof. In still another aspect of this embodiment, a BoNT/A binding domain comprises the binding domain of a non-naturally occurring BoNT/A binding domain variant of SEQ ID NO: 1, SEQ ID NO: 2, SEQ ID NO: 3, SEQ ID NO: 4, or SEQ ID NO: 5, such as, e.g., a conservative BoNT/A binding domain variant, a non-conservative BoNT/A binding domain variant, an active BoNT/A binding domain fragment, or any combination thereof. In still another aspect of this embodiment, a BoNT/A binding domain comprises amino acids 874-1296 of a non-naturally occurring BoNT/A binding domain variant of SEQ ID NO: 1, such as, e.g., a conservative BoNT/A binding domain variant, a non-conservative BoNT/A binding domain variant, an active BoNT/A binding domain fragment, or any combination thereof.

In other aspects of this embodiment, a BoNT/A binding domain comprises a polypeptide having an amino acid identity of, e.g., at least 70%, at least 75%, at least 80%, at least 85%, at least 90%, or at least 95% to the binding domain of SEQ ID NO: 1, SEQ ID NO: 2, SEQ ID NO: 3, SEQ ID NO: 4, or SEQ ID NO: 5; or at most 70%, at most 75%, at most 80%, at most 85%, at most 90%, or at most 95% to the binding domain of SEQ ID NO: 1, SEQ ID NO: 2, SEQ ID NO: 3, SEQ ID NO: 4, or SEQ ID NO: 5. In yet other aspects of this embodiment, a BoNT/A binding domain comprises a polypeptide having an amino acid identity of, e.g., at least 70%, at least 75%, at least 80%, at least 85%, at least 90%, or at least 95% to amino acids 874-1296 of SEQ ID NO: 1; or at most 70%, at most 75%, at most 80%, at most 85%, at most 90%, or at most 95% to amino acids 874-1296 of SEQ ID NO: 1.

In other aspects of this embodiment, a BoNT/A binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 1, SEQ ID NO: 2, SEQ ID NO: 3, SEQ ID NO: 4, or SEQ ID NO: 5; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 1, SEQ ID NO: 2, SEQ ID NO: 3, SEQ ID NO: 4, or SEQ ID NO: 5. In yet other aspects of this embodiment, a BoNT/A binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 874-1296 of SEQ ID NO: 1; or at most 1, 2, 3, 4, 5, 6, 7, 8, 9, 10, 20, 30, 40, 50, or 100 non-contiguous amino acid deletions, additions, and/or substitutions relative to amino acids 874-1296 of SEQ ID NO: 1. In still other aspects of this embodiment, a BoNT/A binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 1, SEQ ID NO: 2, SEQ ID NO: 3, SEQ ID NO: 4, or SEQ ID NO: 5; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 1, SEQ ID NO: 2, SEQ ID NO: 3, SEQ ID NO: 4, or SEQ ID NO: 5. In further other aspects of this embodiment, a BoNT/A binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 874-1296 of SEQ ID NO: 1; or at most 1, 2, 3, 4, 5, 6, 7, 8, 9, 10, 20, 30, 40, 50, or 100 contiguous amino acid deletions, additions, and/or substitutions relative to amino acids 874-1296 of SEQ ID NO: 1.

In another embodiment, a Clostridial toxin binding domain comprises a BoNT/B binding domain. In an aspect of this embodiment, a BoNT/B binding domain comprises the binding domains of SEQ ID NO: 6, SEQ ID NO: 7, SEQ ID NO: 8, SEQ ID NO: 9, or SEQ ID NO: 10. In other aspects of this embodiment, a BoNT/B binding domain comprises amino acids 861-1291 of SEQ ID NO: 6. In another aspect of this embodiment, a BoNT/B binding domain comprises a naturally occurring BoNT/B binding domain variant, such as, e.g., an binding domain from a BoNT/B isoform or an binding domain from a BoNT/B subtype. In another aspect of this embodiment, a BoNT/B binding domain comprises a naturally occurring BoNT/B binding domain variant of SEQ ID NO: 6, SEQ ID NO: 7, SEQ ID NO: 8, SEQ ID NO: 9, or SEQ ID NO: 10, such as, e.g., a BoNT/B isoform binding domain or a BoNT/B subtype binding domain. In another aspect of this embodiment, a BoNT/B binding domain comprises amino acids 861-1291 of a naturally occurring BoNT/B binding domain variant of SEQ ID NO: 6, such as, e.g., a BoNT/B isoform binding domain or a BoNT/B subtype binding domain. In still another aspect of this embodiment, a BoNT/B binding domain comprises a non-naturally occurring BoNT/B binding domain variant, such as, e.g., a conservative BoNT/B binding domain variant, a non-conservative BoNT/B binding domain variant, an active BoNT/B binding domain fragment, or any combination thereof. In still another aspect of this embodiment, a BoNT/B binding domain comprises the binding domain of a non-naturally occurring BoNT/B binding domain variant of SEQ ID NO: 6, SEQ ID NO: 7, SEQ ID NO: 8, SEQ ID NO: 9, or SEQ ID NO: 10, such as, e.g., a conservative BoNT/B binding domain variant, a non-conservative BoNT/B binding domain variant, an active BoNT/B binding domain fragment, or any combination thereof. In still another aspect of this embodiment, a BoNT/B binding domain comprises amino acids 861-1291 of a non-naturally occurring BoNT/B binding domain variant of SEQ ID NO: 6, such as, e.g., a conservative BoNT/B binding domain variant, a non-conservative BoNT/B binding domain variant, an active BoNT/B binding domain fragment, or any combination thereof.

In other aspects of this embodiment, a BoNT/B binding domain comprises a polypeptide having an amino acid identity of, e.g., at least 70%, at least 75%, at least 80%, at least 85%, at least 90%, or at least 95% to the binding domain of SEQ ID NO: 6, SEQ ID NO: 7, SEQ ID NO: 8, SEQ ID NO: 9, or SEQ ID NO: 10; or at most 70%, at most 75%, at most 80%, at most 85%, at most 90%, or at most 95% to the binding domain of SEQ ID NO: 6, SEQ ID NO: 7, SEQ ID NO: 8, SEQ ID NO: 9, or SEQ ID NO: 10. In yet other aspects of this embodiment, a BoNT/B binding domain comprises a polypeptide having an amino acid identity of, e.g., at least 70%, at least 75%, at least 80%, at least 85%, at least 90%, or at least 95% to amino acids 861-1291 of SEQ ID NO: 6; or at most 70%, at most 75%, at most 80%, at most 85%, at most 90%, or at most 95% to amino acids 861-1291 of SEQ ID NO: 6.

In other aspects of this embodiment, a BoNT/B binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 6, SEQ ID NO: 7, SEQ ID NO: 8, SEQ ID NO: 9, or SEQ ID NO: 10; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 6, SEQ ID NO: 7, SEQ ID NO: 8, SEQ ID NO: 9, or SEQ ID NO: 10. In yet other aspects of this embodiment, a BoNT/B binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 861-1291 of SEQ ID NO: 6; or at most 1, 2, 3, 4, 5, 6, 7, 8, 9, 10, 20, 30, 40, 50, or 100 non-contiguous amino acid deletions, additions, and/or substitutions relative to amino acids 861-1291 of SEQ ID NO: 6. In still other aspects of this embodiment, a BoNT/B binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 6, SEQ ID NO: 7, SEQ ID NO: 8, SEQ ID NO: 9, or SEQ ID NO: 10; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 6, SEQ ID NO: 7, SEQ ID NO: 8, SEQ ID NO: 9, or SEQ ID NO: 10. In further other aspects of this embodiment, a BoNT/B binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 861-1291 of SEQ ID NO: 6; or at most 1, 2, 3, 4, 5, 6, 7, 8, 9, 10, 20, 30, 40, 50, or 100 contiguous amino acid deletions, additions, and/or substitutions relative to amino acids 861-1291 of SEQ ID NO: 6.

In another embodiment, a Clostridial toxin binding domain comprises a BoNT/C1 binding domain. In an aspect of this embodiment, a BoNT/C1 binding domain comprises the binding domains of SEQ ID NO: 11 or SEQ ID NO: 12. In other aspects of this embodiment, a BoNT/C1 binding domain comprises amino acids 869-1291 of SEQ ID NO: 11. In another aspect of this embodiment, a BoNT/C1 binding domain comprises a naturally occurring BoNT/C1 binding domain variant, such as, e.g., an binding domain from a BoNT/C1 isoform or an binding domain from a BoNT/C1 subtype. In another aspect of this embodiment, a BoNT/C1 binding domain comprises a naturally occurring BoNT/C1 binding domain variant of SEQ ID NO: 11 or SEQ ID NO: 12, such as, e.g., a BoNT/C1 isoform binding domain or a BoNT/C1 subtype binding domain. In another aspect of this embodiment, a BoNT/C1 binding domain comprises amino acids 869-1291 of a naturally occurring BoNT/C1 binding domain variant of SEQ ID NO: 11, such as, e.g., a BoNT/C1 isoform binding domain or a BoNT/C1 subtype binding domain. In still another aspect of this embodiment, a BoNT/C1 binding domain comprises a non-naturally occurring BoNT/C1 binding domain variant, such as, e.g., a conservative BoNT/C1 binding domain variant, a non-conservative BoNT/C1 binding domain variant, an active BoNT/C1 binding domain fragment, or any combination thereof. In still another aspect of this embodiment, a BoNT/C1 binding domain comprises the binding domain of a non-naturally occurring BoNT/C1 binding domain variant of SEQ ID NO: 11 or SEQ ID NO: 12, such as, e.g., a conservative BoNT/C1 binding domain variant, a non-conservative BoNT/C1 binding domain variant, an active BoNT/C1 binding domain fragment, or any combination thereof. In still another aspect of this embodiment, a BoNT/C1 binding domain comprises amino acids 869-1291 of a non-naturally occurring BoNT/C1 binding domain variant of SEQ ID NO: 11, such as, e.g., a conservative BoNT/C1 binding domain variant, a non-conservative BoNT/C1 binding domain variant, an active BoNT/C1 binding domain fragment, or any combination thereof.

In other aspects of this embodiment, a BoNT/C1 binding domain comprises a polypeptide having an amino acid identity of, e.g., at least 70%, at least 75%, at least 80%, at least 85%, at least 90%, or at least 95% to the binding domain of SEQ ID NO: 11 or SEQ ID NO: 12; or at most 70%, at most 75%, at most 80%, at most 85%, at most 90%, or at most 95% to the binding domain of SEQ ID NO: 11 or SEQ ID NO: 12. In yet other aspects of this embodiment, a BoNT/C1 binding domain comprises a polypeptide having an amino acid identity of, e.g., at least 70%, at least 75%, at least 80%, at least 85%, at least 90%, or at least 95% to amino acids 869-1291 of SEQ ID NO: 11; or at most 70%, at most 75%, at most 80%, at most 85%, at most 90%, or at most 95% to amino acids 869-1291 of SEQ ID NO: 11.

In other aspects of this embodiment, a BoNT/C1 binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 11 or SEQ ID NO: 12; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 11 or SEQ ID NO: 12. In yet other aspects of this embodiment, a BoNT/C1 binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 869-1291 of SEQ ID NO: 11; or at most 1, 2, 3, 4, 5, 6, 7, 8, 9, 10, 20, 30, 40, 50, or 100 non-contiguous amino acid deletions, additions, and/or substitutions relative to amino acids 869-1291 of SEQ ID NO: 11. In still other aspects of this embodiment, a BoNT/C1 binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 11 or SEQ ID NO: 12; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 11 or SEQ ID NO: 12. In further other aspects of this embodiment, a BoNT/C1 binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 869-1291 of SEQ ID NO: 11; or at most 1, 2, 3, 4, 5, 6, 7, 8, 9, 10, 20, 30, 40, 50, or 100 contiguous amino acid deletions, additions, and/or substitutions relative to amino acids 869-1291 of SEQ ID NO: 11.

In another embodiment, a Clostridial toxin binding domain comprises a BoNT/D binding domain. In an aspect of this embodiment, a BoNT/D binding domain comprises the binding domains of SEQ ID NO: 13 or SEQ ID NO: 14. In other aspects of this embodiment, a BoNT/D binding domain comprises amino acids 865-1291 of SEQ ID NO: 13. In another aspect of this embodiment, a BoNT/D binding domain comprises a naturally occurring BoNT/D binding domain variant, such as, e.g., an binding domain from a BoNT/D isoform or an binding domain from a BoNT/D subtype. In another aspect of this embodiment, a BoNT/D binding domain comprises a naturally occurring BoNT/D binding domain variant of SEQ ID NO: 13 or SEQ ID NO: 14, such as, e.g., a BoNT/D isoform binding domain or a BoNT/D subtype binding domain. In another aspect of this embodiment, a BoNT/D binding domain comprises amino acids 865-1291 of a naturally occurring BoNT/D binding domain variant of SEQ ID NO: 13, such as, e.g., a BoNT/D isoform binding domain or a BoNT/D subtype binding domain. In still another aspect of this embodiment, a BoNT/D binding domain comprises a non-naturally occurring BoNT/D binding domain variant, such as, e.g., a conservative BoNT/D binding domain variant, a non-conservative BoNT/D binding domain variant, an active BoNT/D binding domain fragment, or any combination thereof. In still another aspect of this embodiment, a BoNT/D binding domain comprises the binding domain of a non-naturally occurring BoNT/D binding domain variant of SEQ ID NO: 13 or SEQ ID NO: 14, such as, e.g., a conservative BoNT/D binding domain variant, a non-conservative BoNT/D binding domain variant, an active BoNT/D binding domain fragment, or any combination thereof. In still another aspect of this embodiment, a BoNT/D binding domain comprises amino acids 865-1291 of a non-naturally occurring BoNT/D binding domain variant of SEQ ID NO: 13, such as, e.g., a conservative BoNT/D binding domain variant, a non-conservative BoNT/D binding domain variant, an active BoNT/D binding domain fragment, or any combination thereof.

In other aspects of this embodiment, a BoNT/D binding domain comprises a polypeptide having an amino acid identity of, e.g., at least 70%, at least 75%, at least 80%, at least 85%, at least 90%, or at least 95% to the binding domain of SEQ ID NO: 13 or SEQ ID NO: 14; or at most 70%, at most 75%, at most 80%, at most 85%, at most 90%, or at most 95% to the binding domain of SEQ ID NO: 13 or SEQ ID NO: 14. In yet other aspects of this embodiment, a BoNT/D binding domain comprises a polypeptide having an amino acid identity of, e.g., at least 70%, at least 75%, at least 80%, at least 85%, at least 90%, or at least 95% to amino acids 865-1291 of SEQ ID NO: 13; or at most 70%, at most 75%, at most 80%, at most 85%, at most 90%, or at most 95% to amino acids 865-1291 of SEQ ID NO: 13.

In other aspects of this embodiment, a BoNT/D binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 13 or SEQ ID NO: 14; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 13 or SEQ ID NO: 14. In yet other aspects of this embodiment, a BoNT/D binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 865-1291 of SEQ ID NO: 13; or at most 1, 2, 3, 4, 5, 6, 7, 8, 9, 10, 20, 30, 40, 50, or 100 non-contiguous amino acid deletions, additions, and/or substitutions relative to amino acids 865-1291 of SEQ ID NO: 13. In still other aspects of this embodiment, a BoNT/D binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 13 or SEQ ID NO: 14; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 13 or SEQ ID NO: 14. In further other aspects of this embodiment, a BoNT/D binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 865-1291 of SEQ ID NO: 13; or at most 1, 2, 3, 4, 5, 6, 7, 8, 9, 10, 20, 30, 40, 50, or 100 contiguous amino acid deletions, additions, and/or substitutions relative to amino acids 865-1291 of SEQ ID NO: 13.

In another embodiment, a Clostridial toxin binding domain comprises a BoNT/E binding domain. In an aspect of this embodiment, a BoNT/E binding domain comprises the binding domains of SEQ ID NO: 15, SEQ ID NO: 16, or SEQ ID NO: 17. In other aspects of this embodiment, a BoNT/E binding domain comprises amino acids 848-1252 of SEQ ID NO: 15. In another aspect of this embodiment, a BoNT/E binding domain comprises a naturally occurring BoNT/E binding domain variant, such as, e.g., an binding domain from a BoNT/E isoform or an binding domain from a BoNT/E subtype. In another aspect of this embodiment, a BoNT/E binding domain comprises a naturally occurring BoNT/E binding domain variant of SEQ ID NO: 15, SEQ ID NO: 16, or SEQ ID NO: 17, such as, e.g., a BoNT/E isoform binding domain or a BoNT/E subtype binding domain. In another aspect of this embodiment, a BoNT/E binding domain comprises amino acids 848-1252 of a naturally occurring BoNT/E binding domain variant of SEQ ID NO: 15, such as, e.g., a BoNT/E isoform binding domain or a BoNT/E subtype binding domain. In still another aspect of this embodiment, a BoNT/E binding domain comprises a non-naturally occurring BoNT/E binding domain variant, such as, e.g., a conservative BoNT/E binding domain variant, a non-conservative BoNT/E binding domain variant, an active BoNT/E binding domain fragment, or any combination thereof. In still another aspect of this embodiment, a BoNT/E binding domain comprises the binding domain of a non-naturally occurring BoNT/E binding domain variant of SEQ ID NO: 15, SEQ ID NO: 16, or SEQ ID NO: 17, such as, e.g., a conservative BoNT/E binding domain variant, a non-conservative BoNT/E binding domain variant, an active BoNT/E binding domain fragment, or any combination thereof. In still another aspect of this embodiment, a BoNT/E binding domain comprises amino acids 848-1252 of a non-naturally occurring BoNT/E binding domain variant of SEQ ID NO: 15, such as, e.g., a conservative BoNT/E binding domain variant, a non-conservative BoNT/E binding domain variant, an active BoNT/E binding domain fragment, or any combination thereof.

In other aspects of this embodiment, a BoNT/E binding domain comprises a polypeptide having an amino acid identity of, e.g., at least 70%, at least 75%, at least 80%, at least 85%, at least 90%, or at least 95% to the binding domain of SEQ ID NO: 15, SEQ ID NO: 16, or SEQ ID NO: 17; or at most 70%, at most 75%, at most 80%, at most 85%, at most 90%, or at most 95% to the binding domain of SEQ ID NO: 15, SEQ ID NO: 16, or SEQ ID NO: 17. In yet other aspects of this embodiment, a BoNT/E binding domain comprises a polypeptide having an amino acid identity of, e.g., at least 70%, at least 75%, at least 80%, at least 85%, at least 90%, or at least 95% to amino acids 848-1252 of SEQ ID NO: 15; or at most 70%, at most 75%, at most 80%, at most 85%, at most 90%, or at most 95% to amino acids 848-1252 of SEQ ID NO: 15.

In other aspects of this embodiment, a BoNT/E binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 15, SEQ ID NO: 16, or SEQ ID NO: 17; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 15, SEQ ID NO: 16, or SEQ ID NO: 17. In yet other aspects of this embodiment, a BoNT/E binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 848-1252 of SEQ ID NO: 15; or at most 1, 2, 3, 4, 5, 6, 7, 8, 9, 10, 20, 30, 40, 50, or 100 non-contiguous amino acid deletions, additions, and/or substitutions relative to amino acids 848-1252 of SEQ ID NO: 15. In still other aspects of this embodiment, a BoNT/E binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 15, SEQ ID NO: 16, or SEQ ID NO: 17; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 15, SEQ ID NO: 16, or SEQ ID NO: 17. In further other aspects of this embodiment, a BoNT/E binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 848-1252 of SEQ ID NO: 15; or at most 1, 2, 3, 4, 5, 6, 7, 8, 9, 10, 20, 30, 40, 50, or 100 contiguous amino acid deletions, additions, and/or substitutions relative to amino acids 848-1252 of SEQ ID NO: 15.

In another embodiment, a Clostridial toxin binding domain comprises a BoNT/F binding domain. In an aspect of this embodiment, a BoNT/F binding domain comprises the binding domains of SEQ ID NO: 18, SEQ ID NO: 19, or SEQ ID NO: 20. In other aspects of this embodiment, a BoNT/F binding domain comprises amino acids 866-1274 of SEQ ID NO: 18. In another aspect of this embodiment, a BoNT/F binding domain comprises a naturally occurring BoNT/F binding domain variant, such as, e.g., an binding domain from a BoNT/F isoform or an binding domain from a BoNT/F subtype. In another aspect of this embodiment, a BoNT/F binding domain comprises a naturally occurring BoNT/F binding domain variant of SEQ ID NO: 18, SEQ ID NO: 19, or SEQ ID NO: 20, such as, e.g., a BoNT/F isoform binding domain or a BoNT/F subtype binding domain. In another aspect of this embodiment, a BoNT/F binding domain comprises amino acids 866-1274 of a naturally occurring BoNT/F binding domain variant of SEQ ID NO: 18, such as, e.g., a BoNT/F isoform binding domain or a BoNT/F subtype binding domain. In still another aspect of this embodiment, a BoNT/F binding domain comprises a non-naturally occurring BoNT/F binding domain variant, such as, e.g., a conservative BoNT/F binding domain variant, a non-conservative BoNT/F binding domain variant, an active BoNT/F binding domain fragment, or any combination thereof. In still another aspect of this embodiment, a BoNT/F binding domain comprises the binding domain of a non-naturally occurring BoNT/F binding domain variant of SEQ ID NO: 18, SEQ ID NO: 19, or SEQ ID NO: 20, such as, e.g., a conservative BoNT/F binding domain variant, a non-conservative BoNT/F binding domain variant, an active BoNT/F binding domain fragment, or any combination thereof. In still another aspect of this embodiment, a BoNT/F binding domain comprises amino acids 866-1274 of a non-naturally occurring BoNT/F binding domain variant of SEQ ID NO: 18, such as, e.g., a conservative BoNT/F binding domain variant, a non-conservative BoNT/F binding domain variant, an active BoNT/F binding domain fragment, or any combination thereof.

In other aspects of this embodiment, a BoNT/F binding domain comprises a polypeptide having an amino acid identity of, e.g., at least 70%, at least 75%, at least 80%, at least 85%, at least 90%, or at least 95% to the binding domain of SEQ ID NO: 18, SEQ ID NO: 19, or SEQ ID NO: 20; or at most 70%, at most 75%, at most 80%, at most 85%, at most 90%, or at most 95% to the binding domain of SEQ ID NO: 18, SEQ ID NO: 19, or SEQ ID NO: 20. In yet other aspects of this embodiment, a BoNT/F binding domain comprises a polypeptide having an amino acid identity of, e.g., at least 70%, at least 75%, at least 80%, at least 85%, at least 90%, or at least 95% to amino acids 866-1274 of SEQ ID NO: 18; or at most 70%, at most 75%, at most 80%, at most 85%, at most 90%, or at most 95% to amino acids 866-1274 of SEQ ID NO: 18.

In other aspects of this embodiment, a BoNT/F binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 18, SEQ ID NO: 19, or SEQ ID NO: 20; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 18, SEQ ID NO: 19, or SEQ ID NO: 20. In yet other aspects of this embodiment, a BoNT/F binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 866-1274 of SEQ ID NO: 18; or at most 1, 2, 3, 4, 5, 6, 7, 8, 9, 10, 20, 30, 40, 50, or 100 non-contiguous amino acid deletions, additions, and/or substitutions relative to amino acids 866-1274 of SEQ ID NO: 18. In still other aspects of this embodiment, a BoNT/F binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 18, SEQ ID NO: 19, or SEQ ID NO: 20; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 18, SEQ ID NO: 19, or SEQ ID NO: 20. In further other aspects of this embodiment, a BoNT/F binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 866-1274 of SEQ ID NO: 18; or at most 1, 2, 3, 4, 5, 6, 7, 8, 9, 10, 20, 30, 40, 50, or 100 contiguous amino acid deletions, additions, and/or substitutions relative to amino acids 866-1274 of SEQ ID NO: 18.

In another embodiment, a Clostridial toxin binding domain comprises a BoNT/G binding domain. In an aspect of this embodiment, a BoNT/G binding domain comprises the binding domains of SEQ ID NO: 21. In other aspects of this embodiment, a BoNT/G binding domain comprises amino acids 866-1297 of SEQ ID NO: 21. In another aspect of this embodiment, a BoNT/G binding domain comprises a naturally occurring BoNT/G binding domain variant, such as, e.g., an binding domain from a BoNT/G isoform or an binding domain from a BoNT/G subtype. In another aspect of this embodiment, a BoNT/G binding domain comprises a naturally occurring BoNT/G binding domain variant of SEQ ID NO: 21, such as, e.g., a BoNT/G isoform binding domain or a BoNT/G subtype binding domain. In another aspect of this embodiment, a BoNT/G binding domain comprises amino acids 866-1297 of a naturally occurring BoNT/G binding domain variant of SEQ ID NO: 21, such as, e.g., a BoNT/G isoform binding domain or a BoNT/G subtype binding domain. In still another aspect of this embodiment, a BoNT/G binding domain comprises a non-naturally occurring BoNT/G binding domain variant, such as, e.g., a conservative BoNT/G binding domain variant, a non-conservative BoNT/G binding domain variant, an active BoNT/G binding domain fragment, or any combination thereof. In still another aspect of this embodiment, a BoNT/G binding domain comprises the binding domain of a non-naturally occurring BoNT/G binding domain variant of SEQ ID NO: 21, such as, e.g., a conservative BoNT/G binding domain variant, a non-conservative BoNT/G binding domain variant, an active BoNT/G binding domain fragment, or any combination thereof. In still another aspect of this embodiment, a BoNT/G binding domain comprises amino acids 866-1297 of a non-naturally occurring BoNT/G binding domain variant of SEQ ID NO: 21, such as, e.g., a conservative BoNT/G binding domain variant, a non-conservative BoNT/G binding domain variant, an active BoNT/G binding domain fragment, or any combination thereof.

In other aspects of this embodiment, a BoNT/G binding domain comprises a polypeptide having an amino acid identity of, e.g., at least 70%, at least 75%, at least 80%, at least 85%, at least 90%, or at least 95% to the binding domain of SEQ ID NO: 21; or at most 70%, at most 75%, at most 80%, at most 85%, at most 90%, or at most 95% to the binding domain of SEQ ID NO: 21. In yet other aspects of this embodiment, a BoNT/G binding domain comprises a polypeptide having an amino acid identity of, e.g., at least 70%, at least 75%, at least 80%, at least 85%, at least 90%, or at least 95% to amino acids 866-1297 of SEQ ID NO: 21; or at most 70%, at most 75%, at most 80%, at most 85%, at most 90%, or at most 95% to amino acids 866-1297 of SEQ ID NO: 21.

In other aspects of this embodiment, a BoNT/G binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 21; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 21. In yet other aspects of this embodiment, a BoNT/G binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 866-1297 of SEQ ID NO: 21; or at most 1, 2, 3, 4, 5, 6, 7, 8, 9, 10, 20, 30, 40, 50, or 100 non-contiguous amino acid deletions, additions, and/or substitutions relative to amino acids 866-1297 of SEQ ID NO: 21. In still other aspects of this embodiment, a BoNT/G binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 21; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 21. In further other aspects of this embodiment, a BoNT/G binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 866-1297 of SEQ ID NO: 21; or at most 1, 2, 3, 4, 5, 6, 7, 8, 9, 10, 20, 30, 40, 50, or 100 contiguous amino acid deletions, additions, and/or substitutions relative to amino acids 866-1297 of SEQ ID NO: 21.

In another embodiment, a Clostridial toxin binding domain comprises a TeNT binding domain. In an aspect of this embodiment, a TeNT binding domain comprises the binding domains of SEQ ID NO: 22. In other aspects of this embodiment, a TeNT binding domain comprises amino acids 882-1315 of SEQ ID NO: 22. In another aspect of this embodiment, a TeNT binding domain comprises a naturally occurring TeNT binding domain variant, such as, e.g., an binding domain from a TeNT isoform or an binding domain from a TeNT subtype. In another aspect of this embodiment, a TeNT binding domain comprises a naturally occurring TeNT binding domain variant of SEQ ID NO: 22, such as, e.g., a TeNT isoform binding domain or a TeNT subtype binding domain. In another aspect of this embodiment, a TeNT binding domain comprises amino acids 882-1315 of a naturally occurring TeNT binding domain variant of SEQ ID NO: 22, such as, e.g., a TeNT isoform binding domain or a TeNT subtype binding domain. In still another aspect of this embodiment, a TeNT binding domain comprises a non-naturally occurring TeNT binding domain variant, such as, e.g., a conservative TeNT binding domain variant, a non-conservative TeNT binding domain variant, an active TeNT binding domain fragment, or any combination thereof. In still another aspect of this embodiment, a TeNT binding domain comprises the binding domain of a non-naturally occurring TeNT binding domain variant of SEQ ID NO: 22, such as, e.g., a conservative TeNT binding domain variant, a non-conservative TeNT binding domain variant, an active TeNT binding domain fragment, or any combination thereof. In still another aspect of this embodiment, a TeNT binding domain comprises amino acids 882-1315 of a non-naturally occurring TeNT binding domain variant of SEQ ID NO: 22, such as, e.g., a conservative TeNT binding domain variant, a non-conservative TeNT binding domain variant, an active TeNT binding domain fragment, or any combination thereof.

In other aspects of this embodiment, a TeNT binding domain comprises a polypeptide having an amino acid identity of, e.g., at least 70%, at least 75%, at least 80%, at least 85%, at least 90%, or at least 95% to the binding domain of SEQ ID NO: 22; or at most 70%, at most 75%, at most 80%, at most 85%, at most 90%, or at most 95% to the binding domain of SEQ ID NO: 22. In yet other aspects of this embodiment, a TeNT binding domain comprises a polypeptide having an amino acid identity of, e.g., at least 70%, at least 75%, at least 80%, at least 85%, at least 90%, or at least 95% to amino acids 882-1315 of SEQ ID NO: 22; or at most 70%, at most 75%, at most 80%, at most 85%, at most 90%, or at most 95% to amino acids 882-1315 of SEQ ID NO: 22.

In other aspects of this embodiment, a TeNT binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 22; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 22. In yet other aspects of this embodiment, a TeNT binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 882-1315 of SEQ ID NO: 22; or at most 1, 2, 3, 4, 5, 6, 7, 8, 9, 10, 20, 30, 40, 50, or 100 non-contiguous amino acid deletions, additions, and/or substitutions relative to amino acids 882-1315 of SEQ ID NO: 22.

In still other aspects of this embodiment, a TeNT binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 22; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 22. In further other aspects of this embodiment, a TeNT binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 882-1315 of SEQ ID NO: 22; or at most 1, 2, 3, 4, 5, 6, 7, 8, 9, 10, 20, 30, 40, 50, or 100 contiguous amino acid deletions, additions, and/or substitutions relative to amino acids 882-1315 of SEQ ID NO: 22.

In another embodiment, a Clostridial toxin binding domain comprises a BaNT binding domain. In an aspect of this embodiment, a BaNT binding domain comprises the binding domains of SEQ ID NO: 23. In other aspects of this embodiment, a BaNT binding domain comprises amino acids 858-1268 of SEQ ID NO: 23. In another aspect of this embodiment, a BaNT binding domain comprises a naturally occurring BaNT binding domain variant, such as, e.g., an binding domain from a BaNT isoform or an binding domain from a BaNT subtype. In another aspect of this embodiment, a BaNT binding domain comprises a naturally occurring BaNT binding domain variant of SEQ ID NO: 23, such as, e.g., a BaNT isoform binding domain or a BaNT subtype binding domain. In another aspect of this embodiment, a BaNT binding domain comprises amino acids 858-1268 of a naturally occurring BaNT binding domain variant of SEQ ID NO: 23, such as, e.g., a BaNT isoform binding domain or a BaNT subtype binding domain. In still another aspect of this embodiment, a BaNT binding domain comprises a non-naturally occurring BaNT binding domain variant, such as, e.g., a conservative BaNT binding domain variant, a non-conservative BaNT binding domain variant, an active BaNT binding domain fragment, or any combination thereof. In still another aspect of this embodiment, a BaNT binding domain comprises the binding domain of a non-naturally occurring BaNT binding domain variant of SEQ ID NO: 23, such as, e.g., a conservative BaNT binding domain variant, a non-conservative BaNT binding domain variant, an active BaNT binding domain fragment, or any combination thereof. In still another aspect of this embodiment, a BaNT binding domain comprises amino acids 858-1268 of a non-naturally occurring BaNT binding domain variant of SEQ ID NO: 23, such as, e.g., a conservative BaNT binding domain variant, a non-conservative BaNT binding domain variant, an active BaNT binding domain fragment, or any combination thereof.

In other aspects of this embodiment, a BaNT binding domain comprises a polypeptide having an amino acid identity of, e.g., at least 70%, at least 75%, at least 80%, at least 85%, at least 90%, or at least 95% to the binding domain of SEQ ID NO: 23; or at most 70%, at most 75%, at most 80%, at most 85%, at most 90%, or at most 95% to the binding domain of SEQ ID NO: 23. In yet other aspects of this embodiment, a BaNT binding domain comprises a polypeptide having an amino acid identity of, e.g., at least 70%, at least 75%, at least 80%, at least 85%, at least 90%, or at least 95% to amino acids 858-1268 of SEQ ID NO: 23; or at most 70%, at most 75%, at most 80%, at most 85%, at most 90%, or at most 95% to amino acids 858-1268 of SEQ ID NO: 23.

In other aspects of this embodiment, a BaNT binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 23; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 23. In yet other aspects of this embodiment, a BaNT binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 858-1268 of SEQ ID NO: 23; or at most 1, 2, 3, 4, 5, 6, 7, 8, 9, 10, 20, 30, 40, 50, or 100 non-contiguous amino acid deletions, additions, and/or substitutions relative to amino acids 858-1268 of SEQ ID NO: 23. In still other aspects of this embodiment, a BaNT binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 23; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 23. In further other aspects of this embodiment, a BaNT binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 858-1268 of SEQ ID NO: 23; or at most 1, 2, 3, 4, 5, 6, 7, 8, 9, 10, 20, 30, 40, 50, or 100 contiguous amino acid deletions, additions, and/or substitutions relative to amino acids 858-1268 of SEQ ID NO: 23.

In another embodiment, a Clostridial toxin binding domain comprises a BuNT binding domain. In an aspect of this embodiment, a BuNT binding domain comprises the binding domains of SEQ ID NO: 24 or SEQ ID NO: 25. In other aspects of this embodiment, a BuNT binding domain comprises amino acids 848-1251 of SEQ ID NO: 24. In another aspect of this embodiment, a BuNT binding domain comprises a naturally occurring BuNT binding domain variant, such as, e.g., an binding domain from a BuNT isoform or an binding domain from a BuNT subtype. In another aspect of this embodiment, a BuNT binding domain comprises a naturally occurring BuNT binding domain variant of SEQ ID NO: 24 or SEQ ID NO: 25, such as, e.g., a BuNT isoform binding domain or a BuNT subtype binding domain. In another aspect of this embodiment, a BuNT binding domain comprises amino acids 848-1251 of a naturally occurring BuNT binding domain variant of SEQ ID NO: 24, such as, e.g., a BuNT isoform binding domain or a BuNT subtype binding domain. In still another aspect of this embodiment, a BuNT binding domain comprises a non-naturally occurring BuNT binding domain variant, such as, e.g., a conservative BuNT binding domain variant, a non-conservative BuNT binding domain variant, an active BuNT binding domain fragment, or any combination thereof. In still another aspect of this embodiment, a BuNT binding domain comprises the binding domain of a non-naturally occurring BuNT binding domain variant of SEQ ID NO: 24 or SEQ ID NO: 25, such as, e.g., a conservative BuNT binding domain variant, a non-conservative BuNT binding domain variant, an active BuNT binding domain fragment, or any combination thereof. In still another aspect of this embodiment, a BuNT binding domain comprises amino acids 848-1251 of a non-naturally occurring BuNT binding domain variant of SEQ ID NO: 24, such as, e.g., a conservative BuNT binding domain variant, a non-conservative BuNT binding domain variant, an active BuNT binding domain fragment, or any combination thereof.

In other aspects of this embodiment, a BuNT binding domain comprises a polypeptide having an amino acid identity of, e.g., at least 70%, at least 75%, at least 80%, at least 85%, at least 90%, or at least 95% to the binding domain of SEQ ID NO: 24 or SEQ ID NO: 25; or at most 70%, at most 75%, at most 80%, at most 85%, at most 90%, or at most 95% to the binding domain of SEQ ID NO: 24 or SEQ ID NO: 25. In yet other aspects of this embodiment, a BuNT binding domain comprises a polypeptide having an amino acid identity of, e.g., at least 70%, at least 75%, at least 80%, at least 85%, at least 90%, or at least 95% to amino acids 848-1251 of SEQ ID NO: 24 or SEQ ID NO: 25; or at most 70%, at most 75%, at most 80%, at most 85%, at most 90%, or at most 95% to amino acids 848-1251 of SEQ ID NO: 24 or SEQ ID NO: 25.

In other aspects of this embodiment, a BuNT binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 24 or SEQ ID NO: 25; or at most 1, 2, 3, 4, 5, 6, 7, 8, 9, 10, 20, 30, 40, 50, or 100 non-contiguous amino acid deletions, additions, and/or substitutions relative to the binding domain of SEQ ID NO: 24 OR SEQ ID NO: 25. In yet other aspects of this embodiment, a BuNT binding domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 848-1251 of SEQ ID NO: 24 or SEQ ID NO: 25; or at most 1, 2, 3, 4, 5, 6, 7, 8, 9, 10, 20, 30, 40, 50, or 100 non-contiguous amino acid deletions, additions, and/or substitutions relative to amino acids 848-1251 of SEQ ID NO: 24 or SEQ ID NO: 25. In still other aspects of this embodiment, a BuNT binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to the binding domain of SEQ ID NO: 24 or SEQ ID NO: 25; or at most 1, 2, 3, 4, 5, 6, 7, 8, 9, 10, 20, 30, 40, 50, or 100 contiguous amino acid deletions, additions, and/or substitutions relative to the binding domain of SEQ ID NO: 24 or SEQ ID NO: 25. In further other aspects of this embodiment, a BuNT binding domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 848-1251 of SEQ ID NO: 24 or SEQ ID NO: 25; or at most 1, 2, 3, 4, 5, 6, 7, 8, 9, 10, 20, 30, 40, 50, or 100 contiguous amino acid deletions, additions, and/or substitutions relative to amino acids 848-1251 of SEQ ID NO: 24 or SEQ ID NO: 25.

Aspects of the present specification provide, in part, a non-Clostridial toxin binding domain. As used herein, the term "non-Clostridial toxin binding domain" refers to any polypeptide that can execute the binding step of the intoxication process that initiates the overall internalization mechanism whereby the modified Clostridial toxin disclosed in the present specification intoxicates a target cell. Examples of binding domains are described in, e.g., Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; J. Oliver Dolly et al., Activatable Recombinant Neurotoxins, U.S. Pat. No. 7,132,259; Stephan Donovan, Clostridial Toxin Derivatives and Methods For Treating Pain, U.S. Patent Publication 2002/0037833; Keith A. Foster et al., Inhibition of Secretion from Non-neural Cells, U.S. Patent Publication 2003/0180289; Lance E. Steward et al., Multivalent Clostridial Toxin Derivatives and Methods of Their Use, U.S. Patent Publication 2006/0211619; Keith A. Foster et al., Non-Cytotoxic Protein Conjugates, U.S. Patent Publication 2008/0187960; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Keith A. Foster et al., Re-targeted Toxin Conjugates, U.S. patent application Ser. No. 11/792,210; each of which is incorporated by reference in its entirety.

A non-Clostridial toxin binding domain includes, without limitation, naturally occurring non-Clostridial toxin binding domain variants, such as, e.g., non-Clostridial toxin binding domain isoforms and non-Clostridial toxin binding domain subtypes; and non-naturally occurring non-Clostridial toxin binding domain variants, such as, e.g., conservative non-Clostridial toxin binding domain variants, non-conservative non-Clostridial toxin binding domain variants, non-Clostridial toxin binding domain chimeras, active non-Clostridial toxin binding domain fragments thereof, or any combination thereof.

As used herein, the term "non-Clostridial toxin binding domain variant," whether naturally-occurring or non-naturally-occurring, refers to a non-Clostridial toxin binding domain that has at least one amino acid change from the corresponding region of a reference sequence and can be described in percent identity to the corresponding region of that reference sequence. Unless expressly indicated, non-Clostridial toxin binding domain variants useful to practice the disclosed embodiments are variants that execute the binding step of the intoxication process.

It is recognized by those of skill in the art that within each non-Clostridial toxin binding domain there can be naturally occurring variants that differ somewhat in their amino acid sequence, and also in the nucleic acids encoding these proteins. As used herein, the term "naturally occurring non-Clostridial toxin binding domain variant" refers to any non-Clostridial toxin binding domain produced by a naturally-occurring process, including, without limitation, non-Clostridial toxin binding domain isoforms produced from alternatively-spliced transcripts and non-Clostridial toxin binding domain isoforms produced by spontaneous mutation. A naturally occurring non-Clostridial toxin binding domain variant can function in substantially the same manner as the reference non-Clostridial toxin binding domain on which the naturally occurring non-Clostridial toxin binding domain variant is based, and can be substituted for the reference non-Clostridial toxin binding domain in any aspect of the present specification. A non-limiting examples of a naturally occurring non-Clostridial toxin binding domain variant is a non-Clostridial toxin binding domain isoform. Non-limiting examples of a non-Clostridial toxin binding domain isoform include, e.g., opioid binding domain isoforms, tachykinin binding domain isoforms, melanocortin binding domain isoforms, galanin binding domain isoforms, granin binding domain isoforms, Neuropeptide Y related peptide binding domain isoforms, neurohormone binding domain isoforms, neuroregulatory cytokine binding domain isoforms, kinin peptide binding domain isoforms, growth factor binding domain isoforms, and glucagon like hormone binding domain isoforms.

As used herein, the term "non-naturally occurring non-Clostridial toxin binding domain variant" refers to any non-Clostridial toxin binding domain produced with the aid of human manipulation, including, without limitation, non-Clostridial toxin binding domains produced by genetic engineering using random mutagenesis or rational design and non-Clostridial toxin binding domains produced by chemical synthesis. Non-limiting examples of non-naturally occurring non-Clostridial toxin binding domain variants include, e.g., conservative non-Clostridial toxin binding domain variants, non-conservative non-Clostridial toxin binding domain variants, non-Clostridial toxin binding domain chimeric variants and active non-Clostridial toxin binding domain fragments.

As used herein, the term "conservative non-Clostridial toxin binding domain variant" refers to a non-Clostridial toxin binding domain that has at least one amino acid substituted by another amino acid or an amino acid analog that has at least one property similar to that of the original amino acid from a reference non-Clostridial toxin binding domain sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative non-Clostridial toxin binding domain variant can function in substantially the same manner as the reference non-Clostridial toxin binding domain on which the conservative non-Clostridial toxin binding domain variant is based, and can be substituted for the reference non-Clostridial toxin binding domain in any aspect of the present specification. Non-limiting examples of a conservative non-Clostridial toxin binding domain variant include, e.g., conservative opioid binding domain variants, conservative tachykinin binding domain variants, conservative melanocortin binding domain variants, conservative galanin binding domain variants, conservative granin binding domain variants, conservative Neuropeptide Y related peptide binding domain variants, conservative neurohormone binding domain variants, conservative neuroregulatory cytokine binding domain variants, conservative kinin peptide binding domain variants, conservative growth factor binding domain variants, and conservative glucagon like hormone binding domain variants.

As used herein, the term "non-conservative non-Clostridial toxin binding domain variant" refers to a non-Clostridial toxin binding domain in which 1) at least one amino acid is deleted from the reference non-Clostridial toxin binding domain on which the non-conservative non-Clostridial toxin binding domain variant is based; 2) at least one amino acid added to the reference non-Clostridial toxin binding domain on which the non-conservative non-Clostridial toxin binding domain is based; or 3) at least one amino acid is substituted by another amino acid or an amino acid analog that does not share any property similar to that of the original amino acid from a reference non-Clostridial toxin binding domain sequence. A non-conservative non-Clostridial toxin binding domain variant can function in substantially the same manner as the reference non-Clostridial toxin binding domain on which the non-conservative non-Clostridial toxin binding domain variant is based, and can be substituted for the reference non-Clostridial toxin binding domain in any aspect of the present specification. Non-limiting examples of a non-conservative non-Clostridial toxin binding domain variant include, e.g., non-conservative opioid binding domain variants, non-conservative tachykinin binding domain variants, non-conservative melanocortin binding domain variants, non-conservative galanin binding domain variants, non-conservative granin binding domain variants, non-conservative Neuropeptide Y related peptide binding domain variants, non-conservative neurohormone binding domain variants, non-conservative neuroregulatory cytokine binding domain variants, non-conservative kinin peptide binding domain variants, non-conservative growth factor binding domain variants, and non-conservative glucagon like hormone binding domain variants.

As used herein, the term "active non-Clostridial toxin binding domain fragment" refers to any of a variety of Clostridial toxin fragments comprising the binding domain can be useful in aspects of the present specification with the proviso that these biding domain fragments can preferentially interact with the cognate receptor, and thus participate in executing the overall cellular mechanism whereby a Clostridial toxin proteolytically cleaves a substrate.

Any of a variety of sequence alignment methods can be used to determine percent identity of naturally-occurring Clostridial toxin binding domain variants and non-naturally-occurring Clostridial toxin binding domain variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises a non-Clostridial toxin binding domain. In an aspect of this embodiment, a non-Clostridial toxin binding domain comprises a naturally occurring non-Clostridial toxin binding domain variant, such as, e.g., a non-Clostridial toxin binding domain isoform. In another aspect of this embodiment, a non-Clostridial toxin binding domain comprises a non-naturally occurring non-Clostridial toxin binding domain variant, such as, e.g., a conservative non-Clostridial toxin binding domain variant, a non-conservative non-Clostridial toxin binding domain variant, an active non-Clostridial toxin binding domain fragment, or any combination thereof.

In another embodiment, a hydrophobic amino acid at one particular position in the polypeptide chain of the non-Clostridial toxin binding domain can be substituted with another hydrophobic amino acid. Examples of hydrophobic amino acids include, e.g., C, F, I, L, M, V and W. In another aspect of this embodiment, an aliphatic amino acid at one particular position in the polypeptide chain of the non-Clostridial toxin binding domain can be substituted with another aliphatic amino acid. Examples of aliphatic amino acids include, e.g., A, I, L, P, and V. In yet another aspect of this embodiment, an aromatic amino acid at one particular position in the polypeptide chain of the non-Clostridial toxin binding domain can be substituted with another aromatic amino acid. Examples of aromatic amino acids include, e.g., F, H, W and Y. In still another aspect of this embodiment, a stacking amino acid at one particular position in the polypeptide chain of the non-Clostridial toxin binding domain can be substituted with another stacking amino acid. Examples of stacking amino acids include, e.g., F, H, W and Y. In a further aspect of this embodiment, a polar amino acid at one particular position in the polypeptide chain of the non-Clostridial toxin binding domain can be substituted with another polar amino acid. Examples of polar amino acids include, e.g., D, E, K, N, Q, and R. In a further aspect of this embodiment, a less polar or indifferent amino acid at one particular position in the polypeptide chain of the non-Clostridial toxin binding domain can be substituted with another less polar or indifferent amino acid. Examples of less polar or indifferent amino acids include, e.g., A, H, G, P, S, T, and Y. In a yet further aspect of this embodiment, a positive charged amino acid at one particular position in the polypeptide chain of the non-Clostridial toxin binding domain can be substituted with another positive charged amino acid. Examples of positive charged amino acids include, e.g., K, R, and H. In a still further aspect of this embodiment, a negative charged amino acid at one particular position in the polypeptide chain of the non-Clostridial toxin binding domain can be substituted with another negative charged amino acid. Examples of negative charged amino acids include, e.g., D and E. In another aspect of this embodiment, a small amino acid at one particular position in the polypeptide chain of the non-Clostridial toxin binding domain can be substituted with another small amino acid. Examples of small amino acids include, e.g., A, D, G, N, P, S, and T. In yet another aspect of this embodiment, a C-beta branching amino acid at one particular position in the polypeptide chain of the non-Clostridial toxin binding domain can be substituted with another C-beta branching amino acid. Examples of C-beta branching amino acids include, e.g., I, T and V.

In another embodiment, a non-Clostridial toxin binding domain comprises an opioid binding domain, such as, e.g., an enkephalin, an endomorphin, an endorphin, a dynorphin, a nociceptin or a hemorphin. In yet another aspect of this embodiment, a non-Clostridial toxin binding domain comprises a tachykinin binding domain, such as, e.g., a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. In still another aspect of this embodiment, a non-Clostridial toxin comprises a melanocortin binding domain, such as, e.g., a melanocyte stimulating hormone, adrenocorticotropin, or a lipotropin. In still another aspect of this embodiment, a non-Clostridial toxin binding domain comprises a galanin binding domain, such as, e.g., a galanin or a galanin message-associated peptide. In a further aspect of this embodiment, a non-Clostridial toxin binding domain comprises a granin binding domain, such as, e.g., a Chromogranin A, a Chromogranin B, or a Chromogranin C. In another aspect of this embodiment, a non-Clostridial toxin binding domain comprises a Neuropeptide Y related peptide binding domain, such as, e.g., a Neuropeptide Y, a Peptide YY, Pancreatic peptide or a Pancreatic icosapeptide. In yet another aspect of this embodiment, a non-Clostridial toxin binding domain comprises a neurohormone binding domain, such as, e.g., a corticotropin-releasing hormone, a parathyroid hormone, a thyrotropin-releasing hormone, or a somatostatin. In still another aspect of this embodiment, a non-Clostridial toxin binding domain comprises a neuroregulatory cytokine binding domain, such as, e.g., a ciliary neurotrophic factor, a glycophorin-A, a leukemia inhibitory factor, a cholinergic differentiation factor, an interleukin, an oncostatin M, a cardiotrophin-1, a cardiotrophin-like cytokine, or a neuroleukin. In a further aspect of this embodiment, a non-Clostridial toxin binding domain comprises a kinin peptide binding domain, such as, e.g., a bradykinin, a kallidin, a desArg9 bradykinin, or a desArg10 bradykinin. In another aspect of this embodiment, a non-Clostridial toxin binding domain comprises a growth factor binding domain, such as, e.g., a fibroblast growth factor binding domain, a nerve growth factor binding domain, an insulin growth factor binding domain, an epidermal growth factor binding domain, a vascular endothelial growth factor binding domain, a brain derived neurotrophic factor binding domain, a growth derived neurotrophic factor binding domain, a neurotrophin binding domain, such as, e.g., a neurotrophin-3, a neurotrophin-4/5, a head activator peptide binding domain, a neurturin binding domain, a persephin binding domain, an artemin binding domain, a transformation growth factor β binding domain, such as, e.g., a TGFβ1, a TGFβ2, a TGFβ3 or a TGFβ4, a bone morphogenic protein binding domain, such as, e.g., a BMP2, a BMP3, a BMP4, a BMP5, a BMP6, a BMP7, a BMP8 or a BMP10, a growth differentiation factor binding domain, such as, e.g., a GDF1, a GDF2, a GDF3, a GDF5, a GDF6, a GDF7, a GDF8, a GDF10, a GDF11 or a GDF15, or an activin binding domain, such as, e.g., an activin A, an activin B, an activin C, an activin E or an inhibin A. In another aspect of this embodiment, a non-Clostridial toxin binding domain comprises a glucagon like hormone binding domain, such as, e.g., a secretin, a glucagon-like peptide, like a GLP-1 and a GLP-2, a pituitary adenylate cyclase activating peptide binding domain, a growth hormone-releasing hormone binding domain, vasoactive intestinal peptide binding domain like a VIP1 or a VIP2, a gastric inhibitory polypeptide binding domain, a calcitonin-related peptide, visceral gut peptide binding domain like a gastrin, a gastrin-releasing peptide or a cholecystokinin, or a PAR peptide binding domain like a PAR1 peptide, a PAR2 peptide, a PAR3 peptide or a PAR4 peptide.

In another embodiment, an opioid peptide comprises an enkephalin peptide. In aspects of this embodiment, an enkephalin peptide comprises a Leu-enkephalin, a Met-enkephalin, a Met-enkephalin MRGL or a Met-enkephalin MRF. In other aspects of this embodiment, an enkephalin peptide comprises SEQ ID NO: 26, SEQ ID NO: 27, SEQ ID NO: 28 or SEQ ID NO: 29.

In other aspects of this embodiment, an enkephalin comprises a polypeptide having an amino acid identity of, e.g., at least 70%, at least 75%, at least 80%, at least 85%, at least 90%, or at least 95% to SEQ ID NO: 26, SEQ ID NO: 27, SEQ ID NO: 28 or SEQ ID NO: 29; or at most 70%, at most 75%, at most 80%, at most 85%, at most 90%, or at most 95% to SEQ ID NO: 26, SEQ ID NO: 27, SEQ ID NO: 28 or SEQ ID NO: 29. In yet other aspects of this embodiment, an enkephalin comprises a polypeptide having, e.g., at least 1, 2, or 3 non-contiguous amino acid deletions, additions, and/or substitutions relative to SEQ ID NO: 26, SEQ ID NO: 27, SEQ ID NO: 28 or SEQ ID NO: 29; or at most 1, 2, or 3 non-contiguous amino acid deletions, additions, and/or substitutions relative to SEQ ID NO: 26, SEQ ID NO: 27, SEQ ID NO: 28 or SEQ ID NO: 29. In still other aspects of this embodiment, an enkephalin comprises a polypeptide having, e.g., at least 1, 2, or 3 contiguous amino acid deletions, additions, and/or substitutions relative to SEQ ID NO: 26, SEQ ID NO: 27, SEQ ID NO: 28 or SEQ ID NO: 29; or at most 1, 2, or 3 contiguous amino acid deletions, additions, and/or substitutions relative to SEQ ID NO: 26, SEQ ID NO: 27, SEQ ID NO: 28 or SEQ ID NO: 29.

In another embodiment, an opioid peptide comprises a bovine adrenomedullary-22 (BAM22) peptide. In aspects of this embodiment, a BAM22 peptide comprises a BAM22 peptide (1-12), a BAM22 peptide (6-22), a BAM22 peptide (8-22) or a BAM22 peptide (1-22). In other aspects of this embodiment, a BAM22 peptide comprises amino acids 1-12, amino acids 6-22, amino acids 8-22 or amino acids 1-22 of SEQ ID NO: 30; amino acids 1-12, amino acids 6-22, amino acids 8-22 or amino acids 1-22 of SEQ ID NO: 31; amino acids 1-12, amino acids 6-22, amino acids 8-22 or amino acids 1-22 of SEQ ID NO: 32; amino acids 1-12, amino acids 6-22, amino acids 8-22 or amino acids 1-22 of SEQ ID NO: 33; amino acids 1-12, amino acids 6-22, amino acids 8-22 or amino acids 1-22 of SEQ ID NO: 34 or amino acids 1-12, amino acids 6-22, amino acids 8-22 or amino acids 1-22 of SEQ ID NO: 35.

In other aspects of this embodiment, a BAM22 peptide comprises a polypeptide having an amino acid identity of, e.g., at least 70%, at least 75%, at least 80%, at least 85%, at least 90%, or at least 95% to amino acids 1-12, amino acids 6-22, amino acids 8-22 or amino acids 1-22 of SEQ ID NO: 30; amino acids 1-12, amino acids 6-22, amino acids 8-22 or amino acids 1-22 of SEQ ID NO: 31; amino acids 1-12, amino acids 6-22, amino acids 8-22 or amino acids 1-22 of SEQ ID NO: 32; amino acids 1-12, amino acids 6-22, amino acids 8-22 or amino acids 1-22 of SEQ ID NO: 33; amino acids 1-12, amino acids 6-22, amino acids 8-22 or amino acids 1-22 of SEQ ID NO: 34 or amino acids 1-12, amino acids 6-22, amino acids 8-22 or amino acids 1-22 of SEQ ID NO: 35; or at most 70%, at most 75%, at most 80%, at most 85%, at most 90%, or at most 95% to amino acids 1-12, amino acids 6-22, amino acids 8-22 or amino acids 1-22 of SEQ ID NO: 30; amino acids 1-12, amino acids 6-22, amino acids 8-22 or amino acids 1-22 of SEQ ID NO: 31; amino acids 1-12, amino acids 6-22, amino acids 8-22 or amino acids 1-22 of SEQ ID NO: 32; amino acids 1-12, amino acids 6-22, amino acids 8-22 or amino acids 1-22 of SEQ ID NO: 33; amino acids 1-12, amino acids 6-22, amino acids 8-22 or amino acids 1-22 of SEQ ID NO: 34 or amino acids 1-12, amino acids 6-22, amino acids 8-22 or amino acids 1-22 of SEQ ID NO: 35.

In yet other aspects of this embodiment, a BAM22 peptide comprises a polypeptide having, e.g., at least 1, 2, 3, 4, or 5 non-contiguous amino acid deletions, additions, and/or substitutions relative to amino acids 1-12, amino acids 6-22, amino acids 8-22 or amino acids 1-22 of SEQ ID NO: 30; amino acids 1-12, amino acids 6-22, amino acids 8-22 or amino acids 1-22 of SEQ ID NO: 31; amino acids 1-12, amino acids 6-22, amino acids 8-22 or amino acids 1-22 of SEQ ID NO: 32; amino acids 1-12, amino acids 6-22, amino acids 8-22 or amino acids 1-22 of SEQ ID NO: 33; amino acids 1-12, amino acids 6-22, amino acids 8-22 or amino acids 1-22 of SEQ ID NO: 34 or amino acids 1-12, amino acids 6-22, amino acids 8-22 or amino acids 1-22 of SEQ ID NO: 35; or at most 1, 2, 3, 4, or 5 non-contiguous amino acid deletions, additions, and/or substitutions relative to amino acids 1-12, amino acids 6-22, amino acids 8-22 or amino acids 1-22 of SEQ ID NO: 30; amino acids 1-12, amino acids 6-22, amino acids 8-22 or amino acids 1-22 of SEQ ID NO: 31; amino acids 1-12, amino acids 6-22, amino acids 8-22 or amino acids 1-22 of SEQ ID NO: 32; amino acids 1-12, amino acids 6-22, amino acids 8-22 or amino acids 1-22 of SEQ ID NO:

33; amino acids 1-12, amino acids 6-22, amino acids 8-22 or amino acids 1-22 of SEQ ID NO: 34 or amino acids 1-12, amino acids 6-22, amino acids 8-22 or amino acids 1-22 of SEQ ID NO: 35.

In still other aspects of this embodiment, a BAM22 peptide comprises a polypeptide having, e.g., at least 1, 2, 3, 4, or 5 contiguous amino acid deletions, additions, and/or substitutions relative to amino acids 1-12, amino acids 6-22, amino acids 8-22 or amino acids 1-22 of SEQ ID NO: 30; amino acids 1-12, amino acids 6-22, amino acids 8-22 or amino acids 1-22 of SEQ ID NO: 31; amino acids 1-12, amino acids 6-22, amino acids 8-22 or amino acids 1-22 of SEQ ID NO: 32; amino acids 1-12, amino acids 6-22, amino acids 8-22 or amino acids 1-22 of SEQ ID NO: 33; amino acids 1-12, amino acids 6-22, amino acids 8-22 or amino acids 1-22 of SEQ ID NO: 34 or amino acids 1-12, amino acids 6-22, amino acids 8-22 or amino acids 1-22 of SEQ ID NO: 35; or at most 1, 2, 3, 4, or 5 contiguous amino acid deletions, additions, and/or substitutions relative to amino acids 1-12, amino acids 6-22, amino acids 8-22 or amino acids 1-22 of SEQ ID NO: 30; amino acids 1-12, amino acids 6-22, amino acids 8-22 or amino acids 1-22 of SEQ ID NO: 71; amino acids 1-12, amino acids 6-22, amino acids 8-22 or amino acids 1-22 of SEQ ID NO: 32; amino acids 1-12, amino acids 6-22, amino acids 8-22 or amino acids 1-22 of SEQ ID NO: 33; amino acids 1-12, amino acids 6-22, amino acids 8-22 or amino acids 1-22 of SEQ ID NO: 34 or amino acids 1-12, amino acids 6-22, amino acids 8-22 or amino acids 1-22 of SEQ ID NO: 35.

In another embodiment, an opioid peptide comprises an endomorphin peptide. In aspects of this embodiment, an endomorphin peptide comprises an endomorphin-1 or an endomorphin-2. In other aspects of this embodiment, an endomorphin peptide comprises SEQ ID NO: 36 or SEQ ID NO: 37.

In other aspects of this embodiment, an endomorphin comprises a polypeptide having an amino acid identity of, e.g., at least 70%, at least 75%, at least 80%, at least 85%, at least 90%, or at least 95% to SEQ ID NO: 36 or SEQ ID NO: 37; or at most 70%, at most 75%, at most 80%, at most 85%, at most 90%, or at most 95% to SEQ ID NO: 36 or SEQ ID NO: 37. In yet other aspects of this embodiment, an endomorphin comprises a polypeptide having, e.g., at least 1, 2, or 3 non-contiguous amino acid deletions, additions, and/or substitutions relative to SEQ ID NO: 36 or SEQ ID NO: 37; or at most 1, 2, or 3 non-contiguous amino acid deletions, additions, and/or substitutions relative to SEQ ID NO: 36 or SEQ ID NO: 37. In still other aspects of this embodiment, an endomorphin comprises a polypeptide having, e.g., at least 1, 2, or 3 contiguous amino acid deletions, additions, and/or substitutions relative to SEQ ID NO: 36 or SEQ ID NO: 37; or at most 1, 2, or 3 contiguous amino acid deletions, additions, and/or substitutions relative to SEQ ID NO: 36 or SEQ ID NO: 37.

In another embodiment, an opioid peptide comprises an endorphin peptide. In aspects of this embodiment, an endorphin peptide comprises an endorphin-α, a neoendorphin-α, an endorphin-β, a neoendorphin-β or an endorphin-γ. In other aspects of this embodiment, an endorphin peptide comprises SEQ ID NO: 38, SEQ ID NO: 39, SEQ ID NO: 40, SEQ ID NO: 41, SEQ ID NO: 42, or SEQ ID NO: 43. In other aspects of this embodiment, an endorphin comprises a polypeptide having an amino acid identity of, e.g., at least 70%, at least 75%, at least 80%, at least 85%, at least 90%, or at least 95% to SEQ ID NO: 38, SEQ ID NO: 39, SEQ ID NO: 40, SEQ ID NO: 41, SEQ ID NO: 42, or SEQ ID NO: 43; or at most 70%, at most 75%, at most 80%, at most 85%, at most 90%, or at most 95% to SEQ ID NO: 38, SEQ ID NO: 39, SEQ ID NO: 40, SEQ ID NO: 41, SEQ ID NO: 42, or SEQ ID NO: 43. In yet other aspects of this embodiment, an endorphin comprises a polypeptide having, e.g., at least 1, 2, 3, 4, or 5 non-contiguous amino acid deletions, additions, and/or substitutions relative to SEQ ID NO: 38, SEQ ID NO: 39, SEQ ID NO: 40, SEQ ID NO: 41, SEQ ID NO: 42, or SEQ ID NO: 43; or at most 1, 2, 3, 4, or 5 non-contiguous amino acid deletions, additions, and/or substitutions relative to SEQ ID NO: 38, SEQ ID NO: 39, SEQ ID NO: 40, SEQ ID NO: 41, SEQ ID NO: 42, or SEQ ID NO: 43. In still other aspects of this embodiment, an endorphin comprises a polypeptide having, e.g., at least 1, 2, 3, 4, or 5 contiguous amino acid deletions, additions, and/or substitutions relative to SEQ ID NO: 38, SEQ ID NO: 39, SEQ ID NO: 40, SEQ ID NO: 41, SEQ ID NO: 42, or SEQ ID NO: 43; or at most 1, 2, 3, 4, or 5 contiguous amino acid deletions, additions, and/or substitutions relative to SEQ ID NO: 38, SEQ ID NO: 39, SEQ ID NO: 40, SEQ ID NO: 41, SEQ ID NO: 42, or SEQ ID NO: 43.

In another embodiment, an opioid peptide comprises a dynorphin peptide. In aspects of this embodiment, a dynorphin peptide comprises a dynorphin A, a dynorphin B (leumorphin) or a rimorphin. In other aspects of this embodiment, a dynorphin peptide comprises SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, or SEQ ID NO: 74.

In other aspects of this embodiment, a dynorphin comprises a polypeptide having an amino acid identity of, e.g., at least 70%, at least 75%, at least 80%, at least 85%, at least 90%, or at least 95% to SEQ ID NO: 44, SEQ ID NO: 45, SEQ ID NO: 46, SEQ ID NO: 47, SEQ ID NO: 53, or SEQ ID NO: 69; or at most 70%, at most 75%, at most 80%, at most 85%, at most 90%, or at most 95% to SEQ ID NO: 44, SEQ ID NO: 45, SEQ ID NO: 46, SEQ ID NO: 47, SEQ ID NO: 53, or SEQ ID NO: 69. In yet other aspects of this embodiment, a dynorphin comprises a polypeptide having, e.g., at least 1, 2, 3, 4, 5, 6, 7, 8, 9, or 10 non-contiguous amino acid deletions, additions, and/or substitutions relative to SEQ ID NO: 44, SEQ ID NO: 45, SEQ ID NO: 46, SEQ ID NO: 47, SEQ ID NO: 53, or SEQ ID NO: 69; or at most 1, 2, 3, 4, 5, 6, 7, 8, 9, or 10 non-contiguous amino acid deletions, additions, and/or substitutions relative to SEQ ID NO: 44, SEQ ID NO: 45, SEQ ID NO: 46, SEQ ID NO: 47, SEQ ID NO: 53, or SEQ ID NO: 69. In still other aspects of this embodiment, a dynorphin comprises a polypeptide having, e.g., at least 1, 2, 3, 4, 5, 6, 7, 8, 9, or 10 contiguous amino acid deletions, additions, and/or substitutions relative to SEQ ID NO: 44, SEQ ID NO: 45, SEQ ID NO: 46, SEQ ID NO: 47, SEQ ID NO: 53, or SEQ ID NO: 69; or at most 1, 2, 3, 4, 5, 6, 7, 8, 9, or 10 contiguous amino acid deletions, additions, and/or substitutions relative to SEQ ID NO: 44, SEQ ID NO: 45, SEQ ID NO: 46, SEQ ID NO: 47, SEQ ID NO: 53, or SEQ ID NO: 69.

In another embodiment, an opioid peptide comprises a nociceptin peptide. In aspects of this embodiment, a nociceptin peptide comprises a nociceptin RK, a nociceptin, a neuropeptide 1, a neuropeptide 2, or a neuropeptide 3. In other aspects of this embodiment, a nociceptin peptide comprises SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84.

In other aspects of this embodiment, a nociceptin comprises a polypeptide having an amino acid identity of, e.g., at least 70%, at least 75%, at least 80%, at least 85%, at least 90%, or at least 95% to SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84; or at most 70%, at most 75%, at most 80%, at most 85%, at most 90%, or at most 95% to SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84. In yet other aspects of this embodiment, a nociceptin comprises a polypeptide having, e.g., at least 1, 2, 3, 4, 5, 6, 7, 8, 9, or 10 non-contiguous amino acid deletions, additions, and/or substitutions relative to SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84; or at most 1, 2, 3, 4, 5, 6, 7, 8, 9, or 10 non-contiguous amino acid deletions, additions, and/or substitutions relative to SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84. In still other aspects of this embodiment, a nociceptin comprises a polypeptide having, e.g., at least 1, 2, 3, 4, 5, 6, 7, 8, 9, or 10 contiguous amino acid deletions, additions, and/or substitutions relative to SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84; or at most 1, 2, 3, 4, 5, 6, 7, 8, 9, or 10 contiguous amino acid deletions, additions, and/or substitutions relative to SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84.

In another embodiment, an opioid peptide comprises a hemorphin peptide. In aspects of this embodiment, a hemorphin peptide comprises a LVVH7, a VVH7, a VH7, a H7, a LVVH6, a LVVH5, VVH5, a LVVH4, and a LVVH3. In other aspects of this embodiment, a hemorphin peptide comprises SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93.

In other aspects of this embodiment, a hemorphin comprises a polypeptide having an amino acid identity of, e.g., at least 70%, at least 75%, at least 80%, at least 85%, at least 90%, or at least 95% to SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93; or at most 70%, at most 75%, at most 80%, at most 85%, at most 90%, or at most 95% to SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93. In yet other aspects of this embodiment, a nociceptin comprises a polypeptide having, e.g., at least 1, 2, or 3 non-contiguous amino acid deletions, additions, and/or substitutions relative to SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93; or at most 1, 2, or 3 non-contiguous amino acid deletions, additions, and/or substitutions relative to SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93. In still other aspects of this embodiment, a nociceptin comprises a polypeptide having, e.g., at least 1, 2, or 3 contiguous amino acid deletions, additions, and/or substitutions relative to SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93; or at most 1, 2, or 3 contiguous amino acid deletions, additions, and/or substitutions relative to SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93.

In yet another embodiment, a non-Clostridial toxin binding domain comprises a galanin peptide binding domain. In aspects of this embodiment, a galanin peptide binding domain comprises a galanin or a galanin message-associated peptide (GMAP). In other aspects of this embodiment, a galanin peptide binding domain comprises SEQ ID NO: 94 or SEQ ID NO: 95.

In other aspects of this embodiment, a galanin binding domain comprises a polypeptide having an amino acid identity of, e.g., at least 70%, at least 75%, at least 80%, at least 85%, at least 90%, or at least 95% to SEQ ID NO: 94 or SEQ ID NO: 95; or at most 70%, at most 75%, at most 80%, at most 85%, at most 90%, or at most 95% to SEQ ID NO: 94 or SEQ ID NO: 95. In yet other aspects of this embodiment, a galanin binding domain comprises a polypeptide having, e.g., at least 1, 2, 3, 4, 5, 6, 7, 8, 9, or 10 non-contiguous amino acid deletions, additions, and/or substitutions relative to SEQ ID NO: 94 or SEQ ID NO: 95; or at most 1, 2, 3, 4, 5, 6, 7, 8, 9, or 10 non-contiguous amino acid deletions, additions, and/or substitutions relative to SEQ ID NO: 94 or SEQ ID NO: 95. In still other aspects of this embodiment, a galanin binding domain comprises a polypeptide having, e.g., at least 1, 2, 3, 4, 5, 6, 7, 8, 9, or 10 contiguous amino acid deletions, additions, and/or substitutions relative to SEQ ID NO: 94 or SEQ ID NO: 95; or at most 1, 2, 3, 4, 5, 6, 7, 8, 9, or 10 contiguous amino acid deletions, additions, and/or substitutions relative to SEQ ID NO: 94 or SEQ ID NO: 95.

In still another embodiment, a non-Clostridial toxin binding domain comprises a tachykinin peptide binding domain. In aspects of this embodiment, a tachykinin peptide binding domain comprises a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. In other aspects of this embodiment, a tachykinin peptide binding domain comprises SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In other aspects of this embodiment, a tachykinin peptide binding domain comprises a polypeptide having an amino acid identity of, e.g., at least 70%, at least 75%, at least 80%, at least 85%, at least 90%, or at least 95% to SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107; or at most 70%, at most 75%, at most 80%, at most 85%, at most 90%, or at most 95% to SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107. In yet other aspects of this embodiment, a tachykinin peptide binding domain comprises a polypeptide having, e.g., at least 1, 2, 3, 4, or 5 non-contiguous amino acid deletions, additions, and/or substitutions relative to SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107; or at most 1, 2, 3, 4, or 5 non-contiguous amino acid deletions, additions, and/or substitutions relative to SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107. In still other aspects of this embodiment, a tachykinin peptide binding domain comprises a polypeptide having, e.g., at least 1, 2, 3, 4, or 5 contiguous amino acid deletions, additions, and/or substitutions relative to SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107; or at most 1, 2, 3, 4, or 5 contiguous amino acid deletions, additions, and/or substitutions relative to SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In still another embodiment, a non-Clostridial toxin binding domain comprises a Neuropeptide Y related peptide binding domain. In aspects of this embodiment, a Neuropeptide Y related peptide binding domain comprises a Neuropeptide Y (NPY), a Peptide YY (PYY), Pancreatic peptide (PP) or a Pancreatic icosapeptide (PIP). In other aspects of this embodiment, a Neuropeptide Y related peptide binding domain comprises SEQ ID NO: 108, SEQ ID NO: 109, SEQ ID NO: 110, SEQ ID NO: 111, or SEQ ID NO: 112.

In other aspects of this embodiment, a Neuropeptide Y related peptide binding domain comprises a polypeptide having an amino acid identity of, e.g., at least 70%, at least 75%, at least 80%, at least 85%, at least 90%, or at least 95% to SEQ ID NO: 108, SEQ ID NO: 109, SEQ ID NO: 110, SEQ ID NO: 111, or SEQ ID NO: 112; or at most 70%, at most 75%, at most 80%, at most 85%, at most 90%, or at most 95% to SEQ ID NO: 108, SEQ ID NO: 109, SEQ ID NO: 110, SEQ ID NO: 111, or SEQ ID NO: 112. In yet other aspects of this embodiment, a Neuropeptide Y related peptide binding domain comprises a polypeptide having, e.g., at least 1, 2, 3, 4, 5, 6, 7, 8, 9, or 10 non-contiguous amino acid deletions, additions, and/or substitutions relative to SEQ ID NO: 108, SEQ ID NO: 109, SEQ ID NO: 110, SEQ ID NO: 111, or SEQ ID NO: 112; or at most 1, 2, 3, 4, 5, 6, 7, 8, 9, or 10 non-contiguous amino acid deletions, additions, and/or substitutions relative to SEQ ID NO: 108, SEQ ID NO: 109, SEQ ID NO: 110, SEQ ID NO: 111, or SEQ ID NO: 112. In still other aspects of this embodiment, a Neuropeptide Y related peptide binding domain comprises a polypeptide having, e.g., at least 1, 2, 3, 4, 5, 6, 7, 8, 9, or 10 contiguous amino acid deletions, additions, and/or substitutions relative to SEQ ID NO: 108, SEQ ID NO: 109, SEQ ID NO: 110, SEQ ID NO: 111, or SEQ ID NO: 112; or at most 1, 2, 3, 4, 5, 6, 7, 8, 9, or 10 contiguous amino acid deletions, additions, and/or substitutions relative to SEQ ID NO: 108, SEQ ID NO: 109, SEQ ID NO: 110, SEQ ID NO: 111, or SEQ ID NO: 112.

It is envisioned that a Clostridial toxin chimeric disclosed in the present specification can comprise a non-Clostridial binding domain in any and all locations with the proviso that a Clostridial toxin chimeric can perform the intoxication process. Non-limiting examples include, locating a non-Clostridial binding domain at the amino terminus of a modified Clostridial toxin; locating a non-Clostridial binding domain between a Clostridial toxin enzymatic domain and a translocation domain of a modified Clostridial toxin; and locating a non-Clostridial binding domain at the carboxyl terminus of a modified Clostridial toxin. Other non-limiting examples include, locating a non-Clostridial binding domain between a Clostridial toxin enzymatic domain and a Clostridial toxin translocation domain of a modified Clostridial toxin. The enzymatic domain of naturally-occurring Clostridial toxins contains the native start methionine. Thus, in domain organizations where the enzymatic domain is not in the amino-terminal location an amino acid sequence comprising the start methionine should be placed in front of the amino-terminal domain. Likewise, where a non-Clostridial binding domain is in the amino-terminal position, an amino acid sequence comprising a start methionine and a protease cleavage site may be operably-linked in situations in which a non-Clostridial binding domain requires a free amino terminus, see, e.g., Shengwen Li et al., Degradable Clostridial Toxins, U.S. patent application Ser. No. 11/572,512 (Jan. 23, 2007), which is hereby incorporated by reference in its entirety. In addition, it is known in the art that when adding a polypeptide that is operably-linked to the amino terminus of another polypeptide comprising the start methionine that the original methionine residue can be deleted.

Figure 3A:
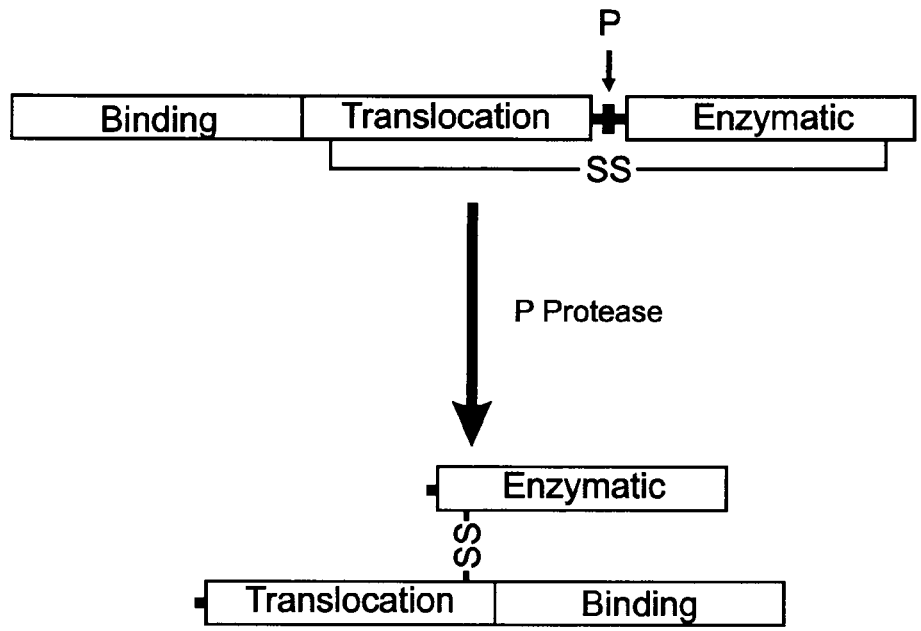
FIGS. 3A and 3B show Clostridial toxins or Clostridial toxin chimeras with a binding domain located at the amino terminus of the toxin.

Thus, in an embodiment, a modified Clostridial toxin can comprise an amino to carboxyl single polypeptide linear order comprising a non-Clostridial binding domain, a translocation domain, an exogenous protease cleavage site and an enzymatic domain (FIG. 3A). In an aspect of this embodiment, a modified Clostridial toxin can comprise an amino to carboxyl single polypeptide linear order comprising a non-Clostridial binding domain, a Clostridial toxin translocation domain, an exogenous protease cleavage site and a Clostridial toxin enzymatic domain.

Figure 3B:
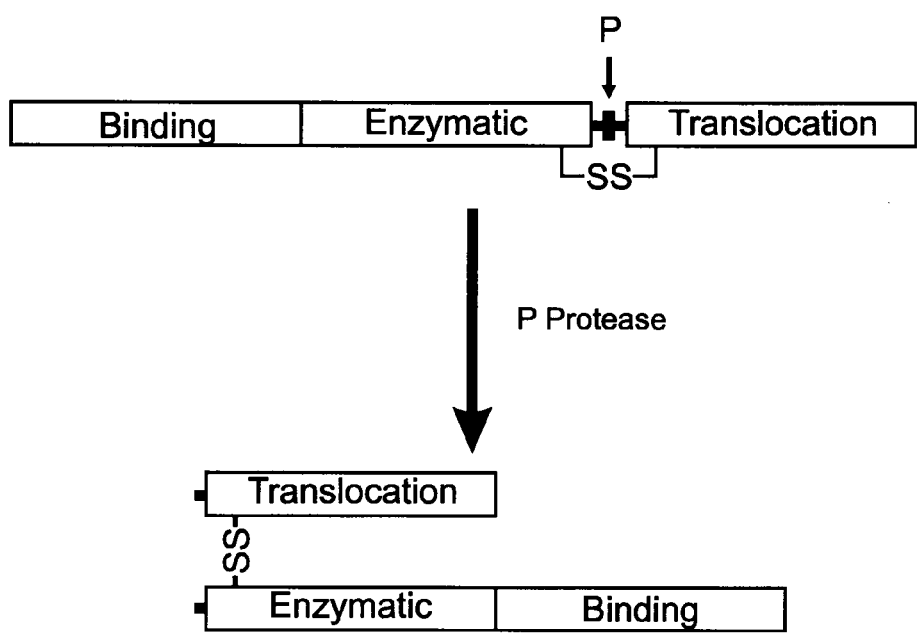

In another embodiment, a modified Clostridial toxin can comprise an amino to carboxyl single polypeptide linear order comprising a non-Clostridial binding domain, an enzymatic domain, an exogenous protease cleavage site, and a translocation domain (FIG. 3B). In an aspect of this embodiment, a modified Clostridial toxin can comprise an amino to carboxyl single polypeptide linear order comprising a non-Clostridial binding domain, a Clostridial toxin enzymatic domain, an exogenous protease cleavage site, a Clostridial toxin translocation domain.

Figure 4A:
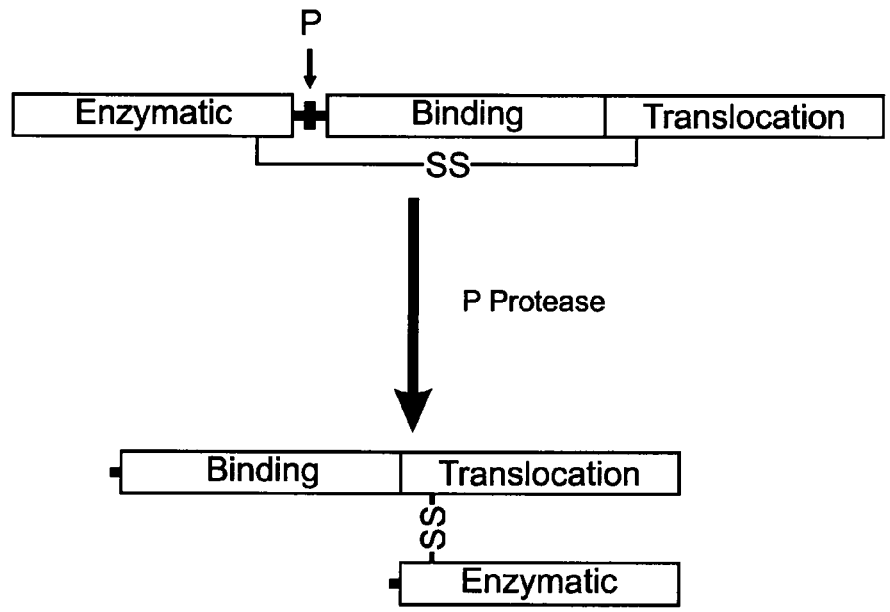
FIGS. 4A, 4B, 4C and 4D show Clostridial toxins or Clostridial toxin chimeras with a binding domain located at the amino terminus of the toxin.

In yet another embodiment, a modified Clostridial toxin can comprise an amino to carboxyl single polypeptide linear order comprising an enzymatic domain, an exogenous protease cleavage site, a non-Clostridial binding domain, and a translocation domain (FIG. 4A). In an aspect of this embodiment, a modified Clostridial toxin can comprise an amino to carboxyl single polypeptide linear order comprising a Clostridial toxin enzymatic domain, an exogenous protease cleavage site, a non-Clostridial binding domain, and a Clostridial toxin translocation domain.

Figure 4B:
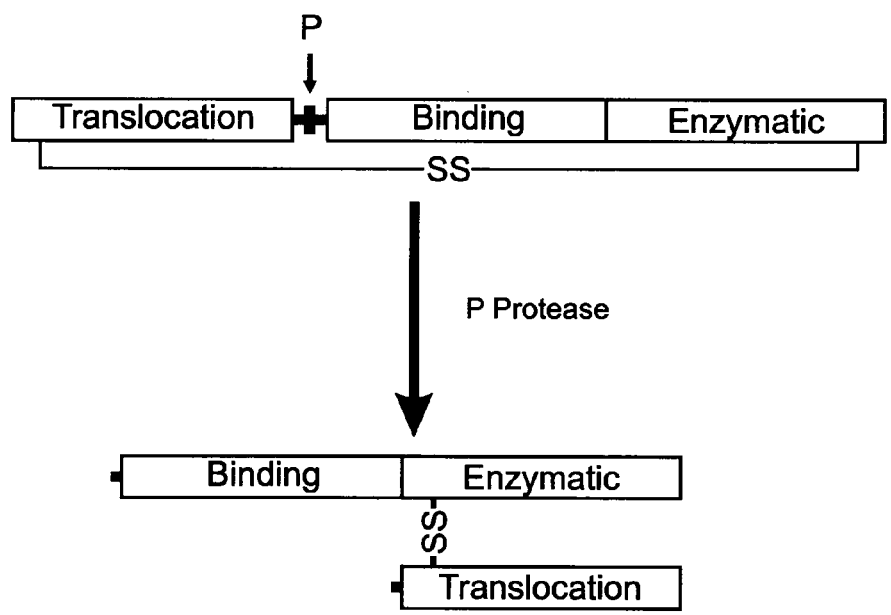

In yet another embodiment, a modified Clostridial toxin can comprise an amino to carboxyl single polypeptide linear order comprising a translocation domain, an exogenous protease cleavage site, a non-Clostridial binding domain, and an enzymatic domain (FIG. 4B). In an aspect of this embodiment, a modified Clostridial toxin can comprise an amino to carboxyl single polypeptide linear order comprising a Clostridial toxin translocation domain, a non-Clostridial binding domain, an exogenous protease cleavage site and a Clostridial toxin enzymatic domain.

Figure 4C:
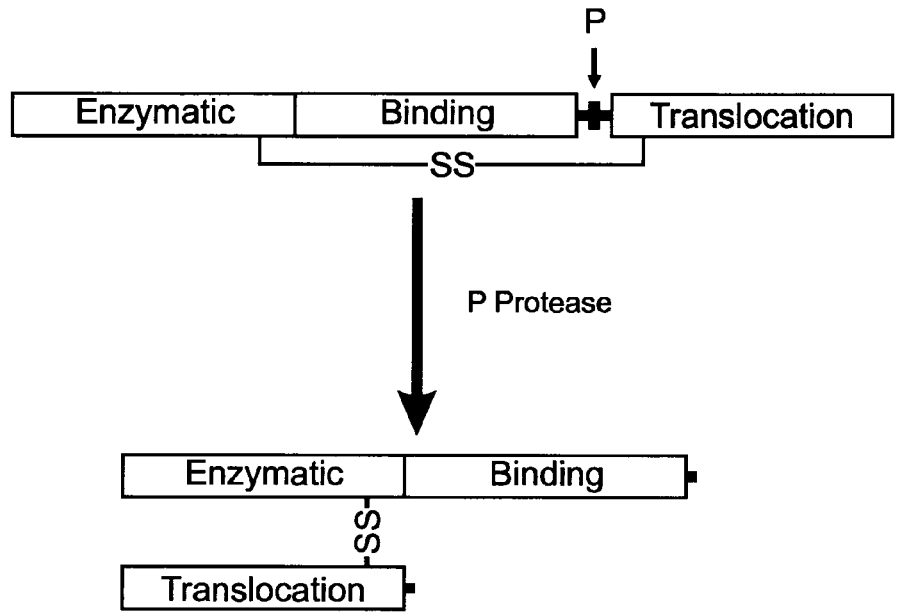

In another embodiment, a modified Clostridial toxin can comprise an amino to carboxyl single polypeptide linear order comprising an enzymatic domain, a non-Clostridial binding domain, an exogenous protease cleavage site, and a translocation domain (FIG. 4C). In an aspect of this embodiment, a modified Clostridial toxin can comprise an amino to carboxyl single polypeptide linear order comprising a Clostridial toxin enzymatic domain, a non-Clostridial binding domain, an exogenous protease cleavage site, a Clostridial toxin translocation domain.

Figure 4D:
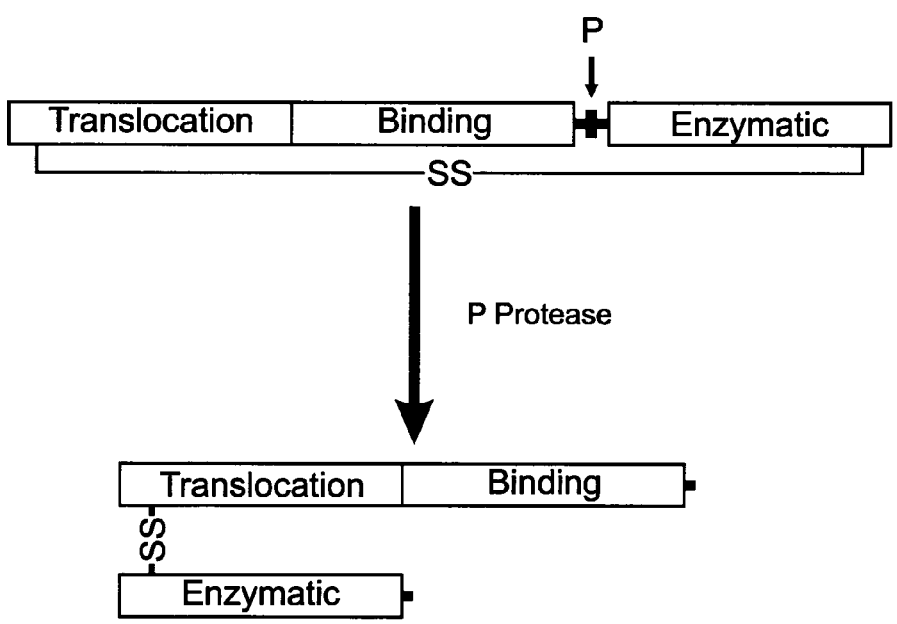

In yet another embodiment, a modified Clostridial toxin can comprise an amino to carboxyl single polypeptide linear order comprising a translocation domain, a non-Clostridial binding domain, an exogenous protease cleavage site and an enzymatic domain (FIG. 4D). In an aspect of this embodiment, a modified Clostridial toxin can comprise an amino to carboxyl single polypeptide linear order comprising a Clostridial toxin translocation domain, a non-Clostridial binding domain, an exogenous protease cleavage site and a Clostridial toxin enzymatic domain.

Figure 5A:
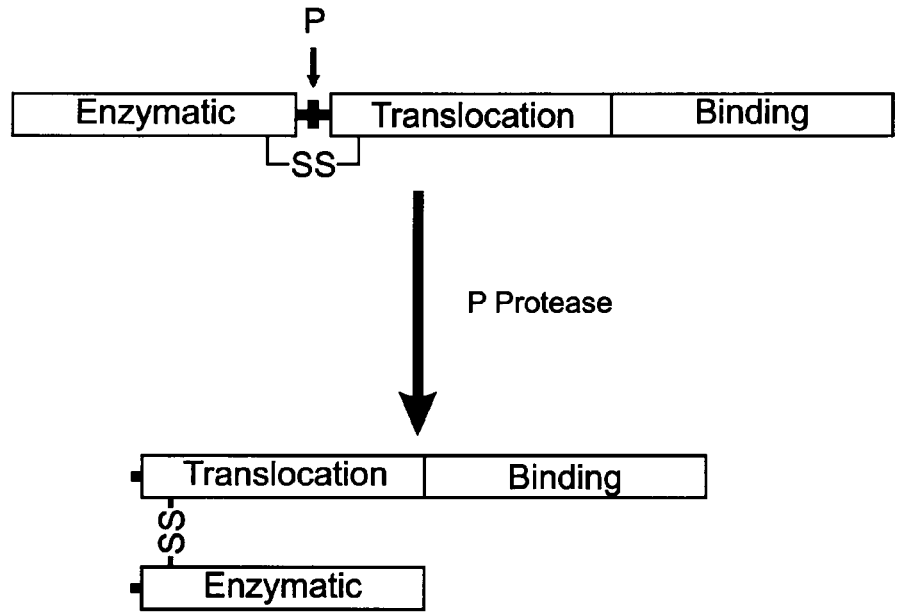
FIGS. 5A and 5B show Clostridial toxins or Clostridial toxin chimeras with a binding domain located at the amino terminus of the toxin.

In still another embodiment, a modified Clostridial toxin can comprise an amino to carboxyl single polypeptide linear order comprising an enzymatic domain, an exogenous protease cleavage site, a translocation domain, and a non-Clostridial binding domain (FIG. 5A). In an aspect of this embodiment, a modified Clostridial toxin can comprise an amino to carboxyl single polypeptide linear order comprising a Clostridial toxin enzymatic domain, an exogenous protease cleavage site, a Clostridial toxin translocation domain, and a non-Clostridial binding domain.

Figure 5B:
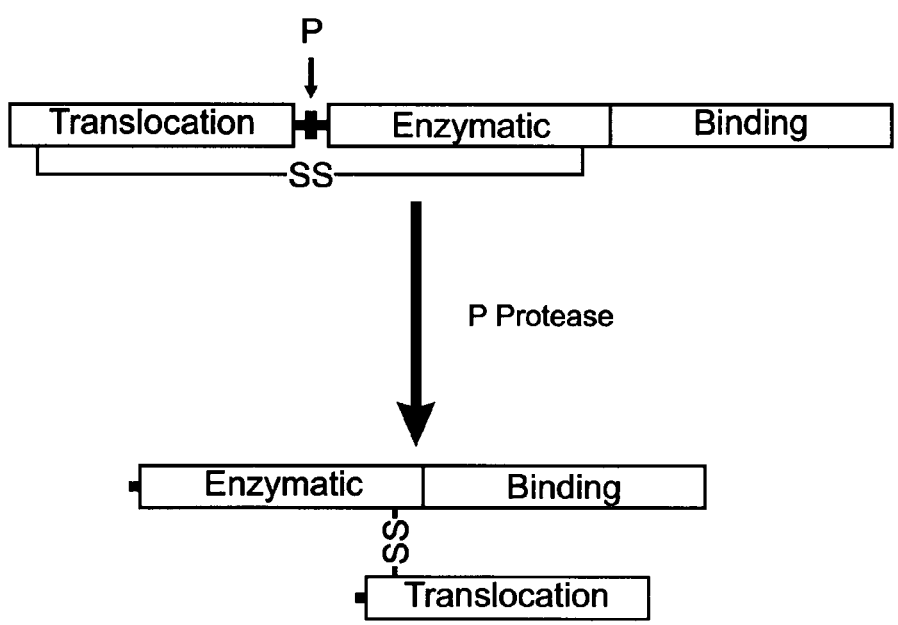

In still another embodiment, a modified Clostridial toxin can comprise an amino to carboxyl single polypeptide linear order comprising a translocation domain, an exogenous protease cleavage site, an enzymatic domain and a non-Clostridial binding domain, (FIG. 5B). In an aspect of this embodiment, a modified Clostridial toxin can comprise an amino to carboxyl single polypeptide linear order comprising a Clostridial toxin translocation domain, a non-Clostridial binding domain, an exogenous protease cleavage site and a Clostridial toxin enzymatic domain.

Aspects of the present specification provide, in part, an inactivation cleavage site. As used herein, the term "inactivation cleavage site" refers to a scissile bond together with adjacent or non-adjacent recognition elements, or both, sufficient for selective proteolysis at the scissile bond by a protease present in interstitial fluids or circulatory systems, such as, e.g., the cardiovascular system or the lymphatic system. Such an inactivation cleavage site is operably-linked as a fusion protein to a Clostridial toxin or Clostridial toxin chimeric disclosed in the present specification. By definition, an inactivation cleavage site is susceptible to selective cleavage by at least one protease present in interstitial fluids or circulatory systems. Non-limiting examples of inactivation cleavage sites include Thrombin cleavage sites, Plasmin cleavage sites, Coagulation Factor VIIa cleavage sites, Coagulation Factor IXa cleavage sites, Coagulation Factor Xa cleavage sites, Coagulation Factor XIa cleavage sites, Coagulation Factor XIIa cleavage sites, plasma kallikrein cleavage sites, protease-activated G protein-coupled receptor-1 (PAR1) cleavage sites, PAR 2 cleavage sites, PAR3 cleavage sites, PAR4 cleavage sites, Matrix Metalloproteinase-2 (MMP-2) cleavage sites, Matrix Metalloproteinase-9 (MMP-9) cleavage sites, Furin cleavage sites, urokinase-type Plasminogen activator (uPA) cleavage sites, tissue-type Plasminogen activator (tPA) cleavage sites, Tryptase-ε cleavage sites, Mouse mast cell protease-7 (mMCP-7) cleavage sites, endothelin-converting enzyme-1 (ECE-1) cleavage sites, Kell blood group cleavage sites, DPPIV cleavage sites, ADAM metallopeptidase with thrombospondin type 1 motif-13 (AD-AMTS13) cleavage sites, and Cathepsin L cleavage sites (Table 4).

TABLE 4

Inactivation Cleavage Sites

| Protease Cleavage Site | Reference Sequences | SEQ ID NO: |
|---|---|---|
| Thrombin | LVPR*GS | 114 |
|  | LVPK*GS | 115 |
|  | FIPR*TF | 116 |
|  | VLPR*SF | 117 |
|  | IVPR*SF | 118 |
|  | IVPR*GY | 119 |
|  | VVPR*GV | 120 |
|  | VLPR*LI | 121 |
|  | VMPR*SL | 122 |
|  | MFPR*SL | 123 |
| Coagulation Factor VIIa (FVIIA) | KLTR*AETV | 125 |
|  | DFTR*VVGG | 126 |
|  | LSPR*TFHP | 127 |
|  | LIQR*NLSP | 128 |
|  | MATR*KMHD | 129 |
|  | LGIR*SFRN | 130 |
|  | PQGR*IVGG | 131 |
|  | NLTR*IVGG | 132 |
|  | QVVR*IVGG | 133 |
| Coagulation Factor IXa (FIXa) | PQGR*IVGG | 135 |
|  | PQLR*MKNN | 136 |
|  | NLTR*IVGG | 137 |
|  | QVVR*IVGG | 138 |
| Coagulation Factor Xa (FXa) | IDGR* | 140 |
|  | IEGR* | 141 |
|  | IDGR*SVGG | 142 |
|  | IDGR*TVGG | 143 |
|  | IDGR*IVGG | 144 |
|  | IEGR*SVGG | 145 |
|  | IEGR*TVGG | 146 |
|  | IEGR*IVGG | 147 |
|  | PQGR*IVGG | 148 |
|  | IEGR*TSED | 149 |
|  | IEGR*IVEG | 150 |
|  | IDGR*IVEG | 151 |
|  | FNPR*TFGS | 152 |
|  | FDER*TFGL | 153 |
|  | IDER*IVGG | 154 |
|  | FNEK*TFGL | 155 |
| Coagulation Factor XIa (FXIa) | AFWK*TDAS | 157 |
|  | KLTR*AETV | 158 |
|  | KLTR*AETI | 159 |
|  | DFTR*VVGG | 160 |
|  | EFSR*VVGG | 161 |
|  | KLTR*AETV | 162 |
|  | DFTR*VVGG | 163 |
|  | IKPR*IVGG | 164 |
|  | DLHR*HIFW | 165 |
|  | KQLR*VVNG | 166 |
| Coagulation Factor XIIa (FXIIa) | PQGR*IVGG | 168 |
|  | IKPR*IVGG | 169 |
|  | SMTR*VVGG | 170 |
|  | TSTR*IVGG | 171 |
|  | PMKR*LTLG | 172 |
| Kallikrein 1 | SMTR*VVGG | 174 |
|  | SPFR*SSDI | 175 |
|  | SLMK*RPPG | 176 |
|  | YDWR*TPYL | 177 |
|  | SPFR*SVQV | 178 |
|  | SPFR*TPYL | 179 |
|  | TFHK*AEYR | 180 |
|  | PRFK*IIGG | 181 |
|  | ISLM*KRPP | 182 |
|  | LEAR*SAYH | 183 |
|  | EAKR*SYHS | 184 |
|  | PNRW*STGA | 185 |
|  | EAFY*SQFG | 186 |
|  | NAAR*STGA | 187 |
|  | SSEW*SMPY | 188 |
|  | GTLF*RSGN | 189 |
|  | ARLY*SRGA | 190 |
|  | EASR*SATL | 191 |
|  | EASY*RRKQ | 192 |
|  | TTFY*RRGA | 193 |

TABLE 4-continued

Inactivation Cleavage Sites

| Protease Cleavage Site | Reference Sequences | SEQ ID NO: |
|---|---|---|
| | AAWY*RTSR | 194 |
| | SFHY*RMVG | 195 |
| | ASSY*RTSR | 196 |
| | TRFY*SRGR | 197 |
| | IKFF*SAQT | 198 |
| Protein C | KKTR*NLKK | 200 |
| | LDRR*GLQR | 201 |
| | MATR*KMHD | 202 |
| | RLKK*SQFL | 203 |
| | PQLR*MKNN | 204 |
| | VDQR*GNQI | 205 |
| | IEPR*SPSQ | 206 |
| | KKTR*SPKT | 207 |
| | LDQR*GVQR | 208 |
| | PDPR*SKNN | 209 |
| Plasminogen | GEAR*GSVI | 211 |
| | GHAR*LVHV | 212 |
| | AEFR*HDSG | 213 |
| | HHQK*LVFF | 214 |
| | GSNK*GALL | 215 |
| | RAQR*SAGA | 216 |
| | AFWK*TDAS | 217 |
| | MSMR*VRRH | 218 |
| | RGVR*RTAS | 219 |
| | RAAR*SQCT | 220 |
| | PQSR*SVPP | 221 |
| | PYLK*VFNP | 222 |
| | LSFR*ARAY | 223 |
| | PQLR*RGWR | 224 |
| | EDNR*DSSM | 225 |
| | LSFR*ARAY | 226 |
| | FRAR*AYGF | 227 |
| | YGFR*GPGP | 228 |
| | ITFR*MNVA | 229 |
| | THEK*GRQS | 230 |
| | PRLK*ARAG | 231 |
| | PKAK*SHAP | 232 |
| | PSHK*EGPQ | 233 |
| | LFEK*KVYL | 234 |
| | ADGK*KPSS | 235 |
| | PRFK*IIGG | 236 |
| | PQFR*IKGG | 237 |
| | PRCR*HRPH | 238 |
| | KGYR*SQRG | 239 |
| | DVAQ*FVLT | 240 |
| Matrix Metalloproteinase-2 (MMP-2) | QPVS*VKVG | 242 |
| | RGVG*IKST | 243 |
| | FVDC*LIEQ | 244 |
| | VPAG*NWVL | 245 |
| | YHAD*IYDK | 246 |
| | RACR*LAKA | 247 |
| | QGAY*QEAF | 248 |
| | DVLS*LLEK | 249 |
| | TLDD*LIMA | 250 |
| | HISS*LIKL | 251 |
| | DPNN*LLND | 252 |
| | PVQP*QQSP | 253 |
| | KPKT*ITGP | 254 |
| | VVHP*LVLL | 255 |
| | HPLV*LLSV | 256 |
| | AVAL*LIGP | 257 |
| | QPLQ*LLDA | 258 |
| | YIQG*INLV | 259 |
| | LPQE*IKAN | 260 |
| | NISD*LTAA | 261 |
| | KPRA*LTAL | 262 |
| | APSW*LLTA | 263 |
| | AVRW*LLTA | 264 |
| | AVSW*LLTA | 265 |
| | SLRR*LTAA | 266 |
| | SLSR*LTAL | 267 |
| | RYSS*LTAA | 268 |
| | SLAY*YTAL | 269 |
| | SLRY*YTAA | 270 |
| | SPAY*YTAL | 271 |
| | MHKA*LTAA | 272 |
| | LRLA*ITAL | 273 |
| Matrix Metalloproteinase-9 (MMP-9) | IPEN*FFGV | 275 |
| | MDIA*IHHP | 276 |
| | SPSR*LFDQ | 277 |
| | SEMR*LEKD | 278 |
| | FSVN*LDVK | 279 |
| | RLFD*QFFG | 280 |
| | FFGE*HLLE | 281 |
| | GLSE*MRLE | 282 |
| | SPEE*LKVK | 283 |
| | DVIE*VHGK | 284 |
| | EVHG*KHEE | 285 |
| | DEHG*FISR | 286 |
| | GEHL*LESD | 287 |
| | FHRK*YRIP | 288 |
| | GPRK*QVSG | 289 |
| | LSPF*YLRP | 290 |
| | PPSF*LRAP | 291 |
| | NPLE*NSGF | 292 |
| | VPYG*LGSP | 293 |
| | PPLK*LMHS | 294 |
| | GPEG*LRVG | 295 |
| | FMKG*LSKA | 296 |
| | VVTG*VTAV | 297 |
| | AIIG*LMVG | 298 |
| | SDLG*LTGI | 299 |
| | VPYG*LGSP | 300 |
| | GAAG*VKGD | 301 |
| | GPTG*KQGD | 302 |
| | GPSG*DQGA | 303 |
| | GPSG*FPFP | 304 |
| | GAPG*FPGP | 305 |
| | GAPG*NRGF | 306 |
| | GLRG*ERGE | 307 |
| | GPPG*SQGN | 308 |
| | GPAG*QQGA | 309 |
| | GPPG*KDGT | 310 |
| | GQPG*SPGS | 311 |
| | GSPG*YQGP | 312 |
| | GPVS*AVLT | 313 |
| | GPLG*MLSQ | 314 |
| | GPLG*MWAQ | 315 |
| | GPQG*IFGQ | 316 |
| | LPRS*AKEL | 317 |
| | NSFG*LRFG | 318 |
| | RAIH*INAE | 319 |
| Furin | RPRR*AKRF | 321 |
| | RKKR*GLYA | 322 |
| | RERR*RKKR | 323 |
| | RKKR*GLYA | 324 |
| | RKKR*TTSA | 325 |
| | RHKR*ETLK | 326 |
| | RLKR*DVVT | 327 |
| | RMKR*EDLN | 328 |
| | RAKR*FASL | 329 |
| | RKKR*FVSS | 330 |
| | RTKR*FLSY | 331 |
| | RRAR*SVDG | 332 |
| | VFRR*DAHK | 333 |
| | VFRR*EAHK | 334 |
| | RVAR*DITM | 335 |
| | RISR*SLPQ | 336 |
| | RSRR*AATS | 337 |
| | RAKR*SPKH | 338 |
| | FWHR*GVTK | 339 |
| | AKRR*TKRD | 340 |
| | AKRR*AKRD | 341 |
| | AKQR*AKRD | 342 |
| | RDVR*GFAS | 343 |

TABLE 4-continued

Inactivation Cleavage Sites

| Protease Cleavage Site | Reference Sequences | SEQ ID NO: |
|---|---|---|
| | RKRR*SVNP | 344 |
| | RQKR*FVLS | 345 |
| | RSKR*SLSC | 346 |
| u-Plasminogen Activator (u-PA) | GSGK*SATL | 348 |
| | QRGR*SATL | 349 |
| | RGSV*ILTV | 350 |
| | PSSR*RRVN | 351 |
| | CPGR*VVGG | 352 |
| | PGAR*GRAF | 353 |
| | SSSR*GPTH | 354 |
| | VSNK*YFSN | 355 |
| | NSGR*AVTY | 356 |
| | TYSR*SRYL | 357 |
| | NSGR*AVTY | 358 |
| | PSGR*GRTL | 359 |
| | AGSR*AVYY | 360 |
| | TYGR*SRTN | 361 |
| | NSSR*GVYL | 362 |
| | PSSR*SVYN | 363 |
| | ASGR*GRTY | 364 |
| | TSSR*AVYL | 365 |
| | NSGR*SRTL | 366 |
| | VSGR*IRTG | 367 |
| | SSGR*IRTV | 368 |
| t-Plasminogen Activator (t-PA) | NALR*YAPD | 370 |
| | CPGR*VVGG | 371 |
| | PQFR*IKGG | 372 |
| | ALSR*MAVL | 373 |
| Tryptase-ε (Prosemin) | *RVVGGE | 375 |
| | *RIVGGE | 376 |
| | *RIIGGE | 377 |
| | *RVVGGD | 378 |
| | *RIVGGD | 379 |
| | *RIIGGD | 380 |
| | *KVVGGE | 381 |
| | *KIVGGE | 382 |
| | *KIIGGE | 383 |
| | *KVVGGD | 384 |
| | *KIVGGD | 385 |
| | *KIIGGD | 386 |
| Mouse mast cell protease-7 (mMCP-7) | LSSR*QSPG | 388 |
| | LQAR*GASL | 389 |
| | LGPK*AITM | 390 |
| | LGPR*SAVY | 391 |
| Endothelin-converting enzyme-1 (ECE-1) | HQKL*VFFA | 393 |
| | HHQK*LVFF | 394 |
| | KLVF*FAED | 395 |
| | DRVY*IHPF | 396 |
| | YIHP*FHLV | 397 |
| | YGLG*SPRS | 398 |
| | TPEH*VVPY | 399 |
| | DIIW*VNTP | 400 |
| | DIIW*INTP | 401 |
| | CHLD*IIWV | 402 |
| | HLDI*IWVN | 403 |
| | CVYF*CHLD | 404 |
| | SCSS*LMDK | 405 |
| | ECVY*FCHL | 406 |
| | RSKR*CSCS | 407 |
| | RSKR*ALEN | 408 |
| | GFSP*FRSS | 409 |
| | PRRP*YILP | 410 |
| | KPQQ*FFGL | 411 |
| | PQQF*FGLM | 412 |
| Kell blood-group protein (KBGP) | DIIW*VNTP | 414 |
| | DIIW*INTP | 415 |
| Cathepsin L | MFLE*AIPM | 417 |
| | KVFQ*EPLF | 418 |
| | ATLT*FDHS | 419 |
| | PLFY*EAPR | 420 |
| | TGLR*DPFN | 421 |
| | KILH*LPTS | 422 |
| | AHLK*NSQE | 423 |
| | APLT*AEIQ | 424 |
| | EALF*AERK | 425 |
| | EPLA*AERK | 426 |
| | GTFT*SDYS | 427 |
| | KYLD*SRRA | 428 |
| | QDFV*QWLM | 429 |
| | KQLA*TKAA | 430 |
| | STFE*ERSY | 431 |
| | LRLE*WPYQ | 432 |
| | RGFF*YTPK | 433 |
| | GFFY*TPKA | 434 |
| | HFFK*NIVT | 435 |
| | RGLS*LSRF | 436 |
| | QWLG*APVP | 437 |
| | NMLK*RGLP | 438 |
| | LSLA*HTHQ | 439 |
| | TPFA*ATSS | 440 |
| | KLLA*VSGP | 441 |
| | QLFR*RAVL | 442 |
| | PRFK*IIGG | 443 |
| PAR1 | *SFLLRN | 445 |
| | *SFFLRN | 446 |
| | *SFFLKN | 447 |
| | *TFLLRN | 448 |
| | *GFPGKF | 449 |
| | *GYPAKF | 450 |
| | *GYPLKF | 451 |
| | *GYPIKF | 452 |
| PAR2 | *SLIGKV | 454 |
| | *SLIGRL | 455 |
| PAR3 | *TFRGAP | 457 |
| | *SFNGGP | 458 |
| | *SFNGNE | 459 |
| PAR4 | *GYPGQV | 461 |
| | *AYPGKF | 462 |
| | *TYPGKF | 463 |
| | *GYPGKY | 464 |
| | *GYPGKW | 465 |
| | *GYPGKK | 466 |
| | *GYPLKF | 467 |
| | *GYPGRF | 468 |
| | *GYPGFK | 469 |
| | *GYPAKF | 470 |
| | *GFPGKF | 471 |
| | *GFPGKP | 472 |
| | *SYPGKF | 473 |
| | *SYPAKF | 474 |
| | *SYPGRF | 475 |
| | *SYAGKF | 476 |
| | *SFPGQP | 477 |
| | *SFPGQA | 478 |
| ADAMTS13 | NLVY*MVTG | 479 |

An asterisks (*) indicates the peptide bond of the $P_1$-$P_1$ cleavage site that is cleaved by the indicated protease.

It is envisioned that an inactivation cleavage site of any and all lengths can be useful in aspects of the present specification with the proviso that the inactivation cleavage site is capable of being cleaved by a interstitial fluid or circulatory system protease. Thus, in aspects of this embodiment, an inactivation cleavage site can be, e.g., at least 3, 4, 5, 6, 7, 8, 9, 10, 15, or 20 amino acids in length. In other aspects of this embodiment, an inactivation cleavage site can be, e.g., at most 3, 4, 5, 6, 7, 8, 9, 10, 15, or 20 amino acids in length.

An inactivation cleavage site useful in aspects of the specification includes, without limitation, naturally occurring inactivation cleavage site; naturally occurring inactivation cleavage site variants; and non-naturally-occurring inactivation cleavage site variants, such as, e.g., conservative inactivation cleavage site variants, non-conservative inactivation cleavage site variants and inactivation cleavage site peptidomimetics. As used herein, the term "inactivation cleavage site variant," whether naturally-occurring or non-naturally-occurring, refers to an inactivation cleavage site that has at least one amino acid change from the corresponding region of the disclosed reference sequences and can be described in percent identity to the corresponding region of that reference sequence. Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

As used herein, the term "naturally occurring inactivation cleavage site variant" refers to any inactivation cleavage site produced without the aid of any human manipulation. Non-limiting examples of inactivation cleavage sites include Thrombin cleavage site variants, Plasmin cleavage site variants, Coagulation Factor V cleavage site variants, Coagulation Factor VII cleavage site variants, Coagulation Factor VIII cleavage site variants, Coagulation Factor IXa cleavage site variants, Coagulation Factor Xa cleavage site variants, Coagulation Factor XIa cleavage site variants, Coagulation Factor XIIa cleavage site variants, plasma kallikrein cleavage site variants, MMP-2 cleavage site variants, MMP-9 cleavage site variants, Furin cleavage site variants, u-Plasminogen activator cleavage site variants, t-Plasminogen activator cleavage site variants, Tryptase-ε cleavage site variants, mMCP-7 cleavage site variants, ECE-1 cleavage site variants, KBGP cleavage site variants, Cathepsin L cleavage site variants, PAR1 cleavage site variants, PAR2 cleavage site variants, PAR3 cleavage site variants, PAR4 cleavage site variants, and ADAM-TS13 cleavage site variants.

As used herein, the term "non-naturally occurring inactivation cleavage site variant" refers to any inactivation cleavage site produced with the aid of human manipulation, including, without limitation, inactivation cleavage site variants produced by genetic engineering using random mutagenesis or rational design and inactivation cleavage site variants produced by chemical synthesis. Non-limiting examples of non-naturally occurring inactivation cleavage site variants include, e.g., conservative inactivation cleavage site variants, non-conservative inactivation cleavage site variants, and inactivation cleavage site peptidomimetics.

As used herein, the term "conservative inactivation cleavage site variant" refers to an inactivation cleavage site that has at least one amino acid substituted by another amino acid or an amino acid analog that has at least one property similar to that of the original amino acid from the reference inactivation cleavage site sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative inactivation cleavage site variant can function in substantially the same manner as the reference inactivation cleavage site on which the conservative inactivation cleavage site variant is based, and can be substituted for the reference inactivation cleavage site in any aspect of the present specification. Non-limiting examples of a conservative inactivation cleavage site variant include, e.g., conservative Thrombin cleavage site variants, conservative Plasmin cleavage site variants, conservative Coagulation Factor V cleavage site variants, conservative Coagulation Factor VII cleavage site variants, conservative Coagulation Factor VIII cleavage site variants, conservative Coagulation Factor IXa cleavage site variants, conservative Coagulation Factor Xa cleavage site variants, conservative Coagulation Factor XIa cleavage site variants, conservative Coagulation Factor XIIa cleavage site variants, conservative plasma kallikrein cleavage site variants, conservative MMP-2 cleavage site variants, conservative MMP-9 cleavage site variants, conservative Furin cleavage site variants, conservative u-Plasminogen activator cleavage site variants, conservative t-Plasminogen activator cleavage site variants, conservative Tryptase-ε cleavage site variants, conservative mMCP-7 cleavage site variants, conservative ECE-1 cleavage site variants, conservative KBGP cleavage site variants, conservative Cathepsin L cleavage site variants, conservative PAR1 cleavage site variants, conservative PAR2 cleavage site variants, conservative PAR3 cleavage site variants, conservative PAR4 cleavage site variants, and conservative ADAM-TS13 cleavage site variants.

As used herein, the term "non-conservative inactivation cleavage site variant" refers to an inactivation cleavage site in which 1) at least one amino acid is deleted from the reference inactivation cleavage site on which the non-conservative inactivation cleavage site variant is based; 2) at least one amino acid added to the reference inactivation cleavage site on which the non-conservative inactivation cleavage site is based; or 3) at least one amino acid is substituted by another amino acid or an amino acid analog that does not share any property similar to that of the original amino acid from the reference inactivation cleavage site sequence (Table 4). A non-conservative inactivation cleavage site variant can function in substantially the same manner as the reference inactivation cleavage site on which the non-conservative inactivation cleavage site is based, and can be substituted for the reference inactivation cleavage site in any aspect of the present specification. Non-limiting examples of a non-conservative inactivation cleavage site variant include, e.g., non-conservative Thrombin cleavage site variants, non-conservative Plasmin cleavage site variants, non-conservative Coagulation Factor V cleavage site variants, non-conservative Coagulation Factor VII cleavage site variants, non-conservative Coagulation Factor VIII cleavage site variants, non-conservative Coagulation Factor IXa cleavage site variants, non-conservative Coagulation Factor Xa cleavage site variants, non-conservative Coagulation Factor XIa cleavage site variants, non-conservative Coagulation Factor XIIa cleavage site variants, non-conservative plasma kallikrein cleavage site variants, non-conservative MMP-2 cleavage site variants, non-conservative MMP-9 cleavage site variants, non-conservative Furin cleavage site variants, non-conservative u-Plasminogen activator cleavage site variants, non-conservative t-Plasminogen activator cleavage site variants, non-conservative Tryptase-ε cleavage site variants, non-conservative mMCP-7 cleavage site variants, non-conservative ECE-1 cleavage site variants, non-conservative KBGP cleavage site variants, non-conservative Cathepsin L cleavage site variants, non-conservative PAR1 cleavage site variants, non-conservative PAR2 cleavage site variants, non-conservative PAR3 cleavage site variants, non-conservative PAR4 cleavage site variants, and non-conservative ADAM-TS13 cleavage site variants.

As used herein, the term "inactivation cleavage site peptidomimetic" refers to an inactivation cleavage site that has at least one amino acid substituted by a non-natural oligomer that has at least one property similar to that of the first amino acid. Examples of properties include, without limitation, topography of a peptide primary structural element, functionality of a peptide primary structural element, topology of a peptide secondary structural element, functionality of a peptide secondary structural element, of the like, or any combination thereof. An inactivation cleavage site peptidomimetic can function in substantially the same manner as the reference inactivation cleavage site on which the inactivation cleavage site peptidomimetic is based, and can be substituted for the reference inactivation cleavage site in any aspect of the present specification. For examples of peptidomimetic methods see, e.g., Amy S. Ripka & Daniel H. Rich, Peptidomimetic design, 2(4) CURR. OPIN. CHEM. BIOL. 441-452 (1998); and M. Angels Estiarte & Daniel H. Rich, *Peptidomimetics for Drug Design*, 803-861 (BURGER'S MEDICINAL CHEMISTRY AND DRUG DISCOVERY VOL. 1 PRINCIPLE AND PRACTICE, Donald J. Abraham ed., Wiley-Interscience, 6$^{th}$ ed 2003). Non-limiting examples of an inactivation cleavage site peptidomimetic include, e.g., Thrombin cleavage site peptidomimetics, Plasmin cleavage site peptidomimetics, Coagulation Factor V cleavage site peptidomimetics, Coagulation Factor VII cleavage site peptidomimetics, Coagulation Factor VIII cleavage site peptidomimetics, Coagulation Factor IXa cleavage site peptidomimetics, Coagulation Factor Xa cleavage site peptidomimetics, Coagulation Factor XIa cleavage site peptidomimetics, Coagulation Factor XIIa cleavage site peptidomimetics, plasma kallikrein cleavage site peptidomimetics, MMP-2 cleavage site peptidomimetics, MMP-9 cleavage site peptidomimetics, Furin cleavage site peptidomimetics, u-Plasminogen activator cleavage site peptidomimetics, t-Plasminogen activator cleavage site peptidomimetics, Tryptase-ε cleavage site peptidomimetics, mMCP-7 cleavage site variants, ECE-1 cleavage site peptidomimetics, KBGP cleavage site peptidomimetics, Cathepsin L cleavage site peptidomimetics, PAR1 cleavage site peptidomimetics, PAR2 cleavage site peptidomimetics, PAR3 cleavage site peptidomimetics, PAR4 cleavage site peptidomimetics, and ADAM-TS13 cleavage site peptidomimetics.

Thus, in an embodiment, a Clostridial toxin comprises an inactivation cleavage site. In an aspect of this embodiment, a Clostridial toxin comprises a Clostridial toxin enzymatic domain, a Clostridial toxin translocation domain, a Clostridial toxin binding domain, and an inactivation cleavage site. In another aspect of this embodiment, a Clostridial toxin comprises a naturally occurring inactivation cleavage site variant, such as, e.g., an inactivation cleavage site isoform. In another aspect of this embodiment, a Clostridial toxin comprises a non-naturally occurring inactivation cleavage site variant, such as, e.g., a conservative inactivation cleavage site variant, a non-conservative inactivation cleavage site variant or an active inactivation cleavage site fragment, or any combination thereof.

In another embodiment, a Clostridial toxin chimeric comprises an inactivation cleavage site. In an aspect of this embodiment, a Clostridial toxin chimeric comprises a Clostridial toxin enzymatic domain, a Clostridial toxin translocation domain, a non-Clostridial toxin binding domain, and an inactivation cleavage site. In another aspect of this embodiment, a Clostridial toxin chimeric comprises a naturally occurring inactivation cleavage site variant, such as, e.g., an inactivation cleavage site isoform. In another aspect of this embodiment, a Clostridial toxin chimeric comprises a non-naturally occurring inactivation cleavage site variant, such as, e.g., a conservative inactivation cleavage site variant, a non-conservative inactivation cleavage site variant or an active inactivation cleavage site fragment, or any combination thereof.

In another embodiment, a hydrophobic amino acid at one particular position in the inactivation cleavage site can be substituted with another hydrophobic amino acid. Examples of hydrophobic amino acids include, e.g., C, F, I, L, M, V and W. In another aspect of this embodiment, an aliphatic amino acid at one particular position in the inactivation cleavage site can be substituted with another aliphatic amino acid. Examples of aliphatic amino acids include, e.g., A, I, L, P, and V. In yet another aspect of this embodiment, an aromatic amino acid at one particular position in the inactivation cleavage site can be substituted with another aromatic amino acid. Examples of aromatic amino acids include, e.g., F, H, W and Y. In still another aspect of this embodiment, a stacking amino acid at one particular position in the inactivation cleavage site can be substituted with another stacking amino acid. Examples of stacking amino acids include, e.g., F, H, W and Y. In a further aspect of this embodiment, a polar amino acid at one particular position in the inactivation cleavage site can be substituted with another polar amino acid. Examples of polar amino acids include, e.g., D, E, K, N, Q, and R. In a further aspect of this embodiment, a less polar or indifferent amino acid at one particular position in the inactivation cleavage site can be substituted with another less polar or indifferent amino acid. Examples of less polar or indifferent amino acids include, e.g., A, H, G, P, S, T, and Y. In a yet further aspect of this embodiment, a positive charged amino acid at one particular position in the inactivation cleavage site can be substituted with another positive charged amino acid. Examples of positive charged amino acids include, e.g., K, R, and H. In a still further aspect of this embodiment, a negative charged amino acid at one particular position in the inactivation cleavage site can be substituted with another negative charged amino acid. Examples of negative charged amino acids include, e.g., D and E. In another aspect of this embodiment, a small amino acid at one particular position in the inactivation cleavage site can be substituted with another small amino acid. Examples of small amino acids include, e.g., A, D, G, N, P, S, and T. In yet another aspect of this embodiment, a C-beta branching amino acid at one particular position in the inactivation cleavage site can be substituted with another C-beta branching amino acid. Examples of C-beta branching amino acids include, e.g., I, T and V.

Aspects of the present specification disclose, in part, a Thrombin cleavage site as an inactivation cleavage site. As used herein, the term "Thrombin cleavage site" refers to a scissile bond together with adjacent or non-adjacent recognition elements, or both, sufficient for detectable proteolysis at the scissile bond by Thrombin under conditions suitable for Thrombin protease activity. It is envisioned that any amino acid sequence cleaved by Thrombin can be useful in aspects of the present specification. Although exceptions are known, a generalized consensus sequence for a Thrombin cleavage site is $X_1X_2X_3(R/K)^*X_4X_5X_6X_7$ (SEQ ID NO: 113), where $X_1$ is preferentially S, T, an amidic amino acid like N and Q, a positive amino acid like H, K, and R, an aromatic hydrophobic amino acid like F, W, and Y, an aliphatic hydrophobic amino acid like, G, P, A, V, L, I, and M; $X_2$ is any amino acid; $X_3$ is preferentially F, S, T, an amidic amino acid like N or Q, or an aliphatic hydrophobic amino acid like, G, P, A, V, L, I, and M; $X_4$ is preferentially S, T, a positive amino acid like H, K, and R, or an aliphatic hydrophobic amino acid like, G, P, A, V, L, I, and M; and $X_5$, $X_6$, and $X_7$, are independently any amino acid. Table 4 lists exemplary reference cleavage sites for Thrombin (SEQ ID NO: 114-123). Additional Thrombin cleavage sites are well known in the art or can be defined by routine methods. See, e.g., O. Schilling and C. M. Overall, *Proteome-Derived, Database-Searchable Peptide Libraries* for Identifying Protease Cleavage Sites, Nat. Biotechnol. 26: 685-694 (2008); Neil D. Rawlings, et al., MEROPS: The Peptidase Database, Nucleic Acids Res. 36(Database issue): D320-D325 (2008); Neil D. Rawlings, et al., MEROPS: The Peptidase Database, Nucleic Acids Res. 38(Database issue): D227-D233 (2010); Neil D. Rawlings, et al., A Large and Accurate Collection of Peptidase Cleavages in the MEROPS Database, Database in press (2010), each of which is incorporated by reference in its entirety.

Thus, in an embodiment, a Clostridial toxin or Clostridial toxin chimeric comprises a Thrombin cleavage site. In an aspect of this embodiment, a Thrombin cleavage site comprises the consensus sequence SEQ ID NO: 113, where $X_1$ is S, T, an amidic amino acid like N and Q, a positive amino acid like H, K, and R, an aromatic hydrophobic amino acid like F, W, and Y, an aliphatic hydrophobic amino acid like, G, P, A, V, L, I, and M; $X_2$ is any amino acid; $X_3$ is F, S, T, an amidic amino acid like N or Q, or an aliphatic hydrophobic amino acid like, G, P, A, V, L, I, and M; $X_4$ is S, T, a positive amino acid like H, K, and R, or an aliphatic hydrophobic amino acid like, G, P, A, V, L, I, and M; and $X_5$, $X_6$, and $X_7$, are independently any amino acid. In another aspect of this embodiment, a Thrombin cleavage site comprises the consensus sequence SEQ ID NO: 113, where $X_1$ is S, Q, K, or an aliphatic hydrophobic amino acid like, G, P, A, V, L, I, and M; $X_2$ is an acidic amino acid like D and E, an amidic amino acid like N and Q, a basic amino acid like K and R, an uncharged amino acid like C, S, and T, or an aliphatic hydrophobic amino acid like, G, P, A, V, L, I, and M; $X_3$ is N, Q, G, P, A, V, L, or I; $X_4$ is S, T, H, G, A, L, or I; $X_5$ is S, T, Q, K, R, F, Y, or an aliphatic hydrophobic amino acid like, G, P, A, V, L, I, and M; $X_6$ is S, T, Q, K, R, G, P, A, V, L, or I; and $X_7$ is S, T, Q, K, R, G, P, A, V, L, or I. In another aspect of this embodiment, a Thrombin cleavage site comprises the consensus sequence SEQ ID NO: 113, where $X_1$ is Q, G, P, A, V, L, I, or M; $X_2$ is S, T, D, E, G, A, V, or I; $X_3$ is G, P, A, V, or L; $X_4$ is S, G, A, or L; $X_5$ is Q, K, F, A, V, or L; $X_6$ is S, Q, K, R, G, P, V, or L; and $X_7$ is S, T, K, G, V, L, or I. In other aspects of this embodiment, a Thrombin cleavage site comprises, e.g., SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123.

Aspects of the present specification disclose, in part, a Plasmin cleavage site as an inactivation cleavage site. As used herein, the term "Plasmin cleavage site" refers to a scissile bond together with adjacent or non-adjacent recognition elements, or both, sufficient for detectable proteolysis at the scissile bond by Plasmin under conditions suitable for Plasmin protease activity. It is envisioned that any amino acid sequence cleaved by Plasmin can be useful in aspects of the present specification. Plasmin catalyzes cleavage of Lys| and Arg| bonds, with a specificity similar to that of Trypsin. However, Plasmin is a much less efficient enzyme than Trypsin, and cleaves only some of these bonds in proteins. Trypsin cleaves peptide chains mainly at the carboxyl side of the amino acids lysine or arginine, except when either is followed by proline.

Aspects of the present specification disclose, in part, a Coagulation Factor VIIa cleavage site as an inactivation cleavage site. As used herein, the term "Coagulation Factor VIIa cleavage site" or "FVIIa cleavage site" refers to a scissile bond together with adjacent or non-adjacent recognition elements, or both, sufficient for detectable proteolysis at the scissile bond by FVIIa under conditions suitable for FVIIa protease activity. It is envisioned that any amino acid sequence cleaved by FVIIa can be useful in aspects of the present specification. Although exceptions are known, a generalized consensus sequence for a FVIIa cleavage site is $X_1X_2X_3$(R/K)*$X_4X_5X_6X_7$ (SEQ ID NO: 124), where $X_1$ is preferentially an acidic amino acid like D and E, an amidic amino acid like N and Q, a basic amino acid like K and R, or an aliphatic hydrophobic amino acid like, G, P, A, V, L, I, and M; $X_2$ is Q, S, T, an aromatic hydrophobic amino acid like F, W and Y, or an aliphatic hydrophobic amino acid like, G, P, A, V, L, I, and M; $X_3$ is preferentially Q, S, T, or an aliphatic hydrophobic amino acid like, G, P, A, V, L, I, and M; $X_4$, $X_5$, $X_6$, and $X_7$, are independently any amino acid. Table 4 lists exemplary reference cleavage sites for FVIIa (SEQ ID NO: 125-133). Additional FVIIa cleavage sites are well known in the art or can be defined by routine methods. See, e.g., J. H. Morrissey, Coagulation Factor VIIa. In HANDBOOK OF PROTEOLYTIC ENZYMES, pp. 1659-1662 (A. J. Barrett, N. D. Rawlings, and J. F. Woessner, eds; Elsevier, London, 2d, 2004); O, Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Coagulation Factor VIIa cleavage site. In an aspect of this embodiment, a Coagulation Factor VIIa cleavage site comprises the consensus sequence SEQ ID NO: 124, where $X_1$ is an acidic amino acid like D and E, an amidic amino acid like N and Q, a basic amino acid like K and R, or an aliphatic hydrophobic amino acid like, G, P, A, V, L, I, and M; $X_2$ is Q, S, T, an aromatic hydrophobic amino acid like F, W and Y, or an aliphatic hydrophobic amino acid like, G, P, A, V, L, I, and M; $X_3$ is Q, S, T, or an aliphatic hydrophobic amino acid like, G, P, A, V, L, I, and M; and $X_4$, $X_5$, $X_6$, and $X_7$, are independently any amino acid. In other aspects of this embodiment, a Coagulation Factor VIIa cleavage site comprises, e.g., SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, or SEQ ID NO: 133

Aspects of the present specification disclose, in part, a Coagulation Factor IXa cleavage site as an inactivation cleavage site. As used herein, the term "Coagulation Factor IXa cleavage site" or "FIXa cleavage site" refers to a scissile bond together with adjacent or non-adjacent recognition elements, or both, sufficient for detectable proteolysis at the scissile bond by FIXa under conditions suitable for FIXa protease activity. It is envisioned that any amino acid sequence cleaved by FIXa can be useful in aspects of the present specification. Although exceptions are known, a generalized consensus sequence for a FIXa cleavage site is $X_1X_2X_3$(R/K)*$X_4X_5X_6X_7$ (SEQ ID NO: 134), where $X_1$ is preferentially an acidic amino acid like D and E, an amidic amino acid like N and Q, or an aliphatic hydrophobic amino acid like, G, P, A, V, L, I, and M; $X_2$ is preferentially an acidic amino acid like D and E, an amidic amino acid like N and Q, or an aliphatic hydrophobic amino acid like, G, P, A, V, L, I, and M; $X_3$ is preferentially, S, T, an aromatic hydrophobic amino acid like F, W and Y, or an aliphatic hydrophobic amino acid like, G, P, A, V, L, I, and M; and $X_4$, $X_5$, $X_6$, and $X_7$, are independently any amino acid. Table 4 lists exemplary reference cleavage sites for FIXa (SEQ ID NO: 135-138). Additional FIXa cleavage sites are well known in the art or can be defined by routine methods. See, e.g., A. T. Thompson, *Molecular*

*Biology of Factor IX.* In HEMOSTASIS AND THROMBOSIS, BASIC PRINCIPLES AND CLINICAL PRACTICE, pp. 128-129 (R. W. Colman, J. Hirsh, V. J. Marder, A. W Clowes, J. N. George, eds; Lippincott Williams & Wilkins, Philadelphia, Pa., 2d, 2001); S. Kawabata and S. Iwanaga, *Russellysin*. In HANDBOOK OF PROTEOLYTIC ENZYMES, pp. 683-684 (A. J. Barrett, N. D. Rawlings, and J. F. Woessner, eds; Elsevier, London, 2d, 2004); A. E. Schmidt and S. P. Bajaj, *Coagulation factor IXa*. In HANDBOOK OF PROTEOLYTIC ENZYMES, pp. 1655-1659 (A. J. Barrett, N. D. Rawlings, and J. F. Woessner, eds; Elsevier, London, 2d, 2004); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages* in the MEROPS Database, Database in press (2010), each of which is incorporated by reference in its entirety.

Thus, in an embodiment, a Clostridial toxin or Clostridial toxin chimeric comprises a Coagulation Factor IXa cleavage site. In an aspect of this embodiment, a Coagulation Factor IXa cleavage site comprises the consensus sequence SEQ ID NO: 134, where $X_1$ is an acidic amino acid like D and E, an amidic amino acid like N and Q, or an aliphatic hydrophobic amino acid like, G, P, A, V, L, I, and M; $X_2$ is an acidic amino acid like D and E, an amidic amino acid like N and Q, or an aliphatic hydrophobic amino acid like, G, P, A, V, L, I, and M; $X_3$ is, S, T, an aromatic hydrophobic amino acid like F, W and Y, or an aliphatic hydrophobic amino acid like, G, P, A, V, L, I, and M; and $X_4$, $X_5$, $X_6$, and $X_7$, are independently any amino acid. In another aspect of this embodiment, a Coagulation Factor IXa cleavage site comprises the consensus sequence SEQ ID NO: 134, where $X_1$ is an acidic amino acid like D and E, an amidic amino acid like N and Q, or an aliphatic hydrophobic amino acid like, G, P, A, V, L, I, and M; $X_2$ is an acidic amino acid like D and E, an amidic amino acid like N and Q, or an aliphatic hydrophobic amino acid like, G, P, A, V, L, I, and M; $X_3$ is, S, T, an aromatic hydrophobic amino acid like F, W and Y, or an aliphatic hydrophobic amino acid like, G, P, A, V, L, I, and M; $X_4$, $X_5$, $X_6$, and $X_7$, are independently an acidic amino acid like D and E, an amidic amino acid like N and Q, or an aliphatic hydrophobic amino acid like, G, P, A, V, L, I, and M. In other aspects of this embodiment, a Coagulation Factor IXa cleavage site comprises, e.g., SEQ ID NO: 135, SEQ ID NO: 136, SEQ ID NO: 137, or SEQ ID NO: 138.

Aspects of the present specification disclose, in part, a Coagulation Factor Xa cleavage site as an inactivation cleavage site. As used herein, the term "Coagulation Factor Xa cleavage site" or "FXa cleavage site" refers to a scissile bond together with adjacent or non-adjacent recognition elements, or both, sufficient for detectable proteolysis at the scissile bond by FXa under conditions suitable for FXa protease activity. It is envisioned that any amino acid sequence cleaved by FXa can be useful in aspects of the present specification. Although exceptions are known, a generalized consensus sequence for a FXa cleavage site is $X_1X_2X_3$(R/K)*$X_4X_5X_6X_7$ (SEQ ID NO: 139), where $X_1$ is any amino acid, $X_2$ is preferentially G, A, S, an acidic amino acid like D and E, an amidic amino acid like Q and N, or an aromatic hydrophobic amino acid like F, W and Y, $X_3$ is preferentially an aromatic hydrophobic amino acid like F, W and Y, or an aliphatic hydrophobic amino acid like, G, P, A, V, L, I, and M; $X_4$ is preferentially an amidic amino acid like N and Q, an uncharged amino acid like C, S, and T, or an aliphatic hydrophobic amino acid like, G, P, A, V, L, I, and M; $X_5$, $X_6$, and $X_7$, are independently any amino acid. Table 4 lists exemplary reference cleavage sites for FXa (SEQ ID NO: 140-155). Additional FXa cleavage sites are well known in the art or can be defined by routine methods. See, e.g., D. L. Greenberg and E. W. Davie, Blood Coagulation Factors: Their Complementary DNAs, Genes, and Expression. In HEMOSTASIS AND THROMBOSIS, BASIC PRINCIPLES AND CLINICAL PRACTICE, pp. 34-35 (R. W. Colman, J. Hirsh, V. J. Marder, A. W Clowes, J. N. George, eds; Lippincott Williams & Wilkins, Philadelphia, Pa., 2d, 2001); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Coagulation Factor Xa cleavage site. In an aspect of this embodiment, a Coagulation Factor Xa cleavage site comprises the consensus sequence SEQ ID NO: 139, where $X_1$ is any amino acid, $X_2$ is G, A, S, an acidic amino acid like D and E, an amidic amino acid like Q and N, or an aromatic hydrophobic amino acid like F, W and Y, $X_3$ is an aromatic hydrophobic amino acid like F, W and Y, or an aliphatic hydrophobic amino acid like, G, P, A, V, L, I, and M; $X_4$ is an amidic amino acid like N and Q, an uncharged amino acid like C, S, and T, or an aliphatic hydrophobic amino acid like, G, P, A, V, L, I, and M; $X_5$, $X_6$, and $X_7$, are independently any amino acid. In another aspect of this embodiment, a Coagulation Factor Xa cleavage site comprises the consensus sequence SEQ ID NO: 139, where $X_1$ is E, F, P, A, L, or I; $X_2$ is S, Q, D, E, F, G, or A; $X_3$ is F, G, or P; $X_4$ is S, T, L, or I; $X_5$ is S, F, A, or V; $X_6$ is S, T, E, N, H, G, A, or M; and $X_7$ is S, N, D, Q, K, R, or G. In another aspect of this embodiment, a Coagulation Factor Xa cleavage site comprises the consensus sequence SEQ ID NO: 139, where $X_1$ is I or A; $X_2$ is E or F; $X_3$ is F, G, or P; is S, T, or I; $X_5$ is S, F, or V; $X_6$ is E or G; and $X_7$ is S or G. In other aspects of this embodiment, a Coagulation Factor Xa cleavage site comprises, e.g., the amino acid sequence SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, or SEQ ID NO: 155.

Aspects of the present specification disclose, in part, a Coagulation Factor XIa cleavage site as an inactivation cleavage site. As used herein, the term "Coagulation Factor XIa cleavage site" or "FXIa cleavage site" refers to a scissile bond together with adjacent or non-adjacent recognition elements, or both, sufficient for detectable proteolysis at the scissile bond by FXIa under conditions suitable for FXIa protease activity. It is envisioned that any amino acid sequence cleaved by FXIa can be useful in aspects of the present specification. Although exceptions are known, a generalized consensus sequence for a FXIa cleavage site is $X_1X_2X_3$(R/K)*$X_4X_5X_6X_7$ (SEQ ID NO: 156), where $X_1$ is preferentially an acidic amino acid like D or E, a basic amino acid like K and R, or an aliphatic hydrophobic amino acid like, G, P, A, V, L, I, and M; $X_2$ is preferentially an acidic amino acid like D or E, an amidic amino acid like Q and N, a basic amino acid like K and R, an aromatic hydrophobic amino acid like F, W and Y, or an aliphatic hydrophobic amino acid like, G, P, A, V, L, I, and M; $X_3$ is preferentially H, an uncharged amino acid like C, S, and T, an aromatic hydrophobic amino acid like F, W and Y, or an aliphatic hydrophobic amino acid like, G, P, A, V, L, I, and M; $X_4$ is preferentially H, an uncharged amino acid like C, S, and T, or an aliphatic hydrophobic amino acid like, G, P, A, V, L, I, and M; $X_5$ is preferentially an acidic amino acid like D and E, or an aliphatic hydrophobic amino acid like, G, P, A, V, L, I, and M; $X_6$ is preferentially an amidic amino acid like Q and N, an uncharged amino acid like C, S, and T, an aromatic hydrophobic amino acid like F, W and Y, or an aliphatic hydrophobic amino acid like, G, P, A, V, L, I, and M; and $X_7$ is preferentially an uncharged amino acid like C, S, and T, or an aliphatic hydrophobic amino acid like, G, P, A, V, L, I, and M. Table 4 lists exemplary reference cleavage sites for FXIa (SEQ ID NO: 157-166). Additional FXIa cleavage sites are well known in the art or can be defined by routine methods. See, e.g., P. N. Walsh, *Coagulation Factor XIa*. In Handbook of Proteolytic Enzymes, pp. 1651-1655 (A. J. Barrett, N. D. Rawlings, and J. F. Woessner, eds; Elsevier, London, 2d, 2004); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Coagulation Factor XIa cleavage site. In an aspect of this embodiment, a Coagulation Factor XIa cleavage site comprises the consensus sequence SEQ ID NO: 156, where $X_1$ is an acidic amino acid like D or E, a basic amino acid like K and R, or an aliphatic hydrophobic amino acid like, G, P, A, V, L, I, and M; $X_2$ is an acidic amino acid like D or E, an amidic amino acid like Q and N, a basic amino acid like K and R, an aromatic hydrophobic amino acid like F, W and Y, or an aliphatic hydrophobic amino acid like, G, P, A, V, L, I, and M; $X_3$ is H, an uncharged amino acid like C, S, and T, an aromatic hydrophobic amino acid like F, W and Y, or an aliphatic hydrophobic amino acid like, G, P, A, V, L, I, and M; $X_4$ is H, an uncharged amino acid like C, S, and T, or an aliphatic hydrophobic amino acid like, G, P, A, V, L, I, and M; $X_5$ is an acidic amino acid like D and E, or an aliphatic hydrophobic amino acid like, G, P, A, V, L, I, and M; $X_6$ is an amidic amino acid like Q and N, an uncharged amino acid like C, S, and T, an aromatic hydrophobic amino acid like F, W and Y, or an aliphatic hydrophobic amino acid like, G, P, A, V, L, I, and M; and $X_7$ is an uncharged amino acid like C, S, and T, or an aliphatic hydrophobic amino acid like, G, P, A, V, L, I, and M. In another aspect of this embodiment, a Coagulation Factor XIa cleavage site comprises the consensus sequence SEQ ID NO: 156, where $X_1$ is an acidic amino acid like D or E, or a basic amino acid like K and R; $X_2$ is an aromatic hydrophobic amino acid like F, W and Y, or an aliphatic hydrophobic amino acid like, G, P, A, V, L, I, and M; $X_3$ is an uncharged amino acid like C, S, and T, or an aliphatic hydrophobic amino acid like, G, P, A, V, L, I, and M; $X_4$ is an aliphatic hydrophobic amino acid like, G, P, A, V, L, I, and M; $X_5$ is an acidic amino acid like D and E, or an aliphatic hydrophobic amino acid like, G, P, A, V, L, I, and M; $X_6$ is an uncharged amino acid like C, S, and T, or an aliphatic hydrophobic amino acid like, G, P, A, V, L, I, and M; and $X_7$ is an aliphatic hydrophobic amino acid like, G, P, A, V, L, I, and M. In another aspect of this embodiment, a Coagulation Factor XIa cleavage site comprises the consensus sequence SEQ ID NO: 156, where $X_1$ is D or K; $X_2$ is F or L; $X_3$ is T or P; $X_4$ is A or V; $X_5$ is E or V; $X_6$ is T or G; and $X_7$ is G or V. In other aspects of this embodiment, a Coagulation Factor XIa cleavage site comprises, e.g., SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, or SEQ ID NO: 166.

Aspects of the present specification disclose, in part, a Coagulation Factor XIIa cleavage site as an inactivation cleavage site. As used herein, the term "Coagulation Factor XIIa cleavage site" or "FXIIa cleavage site" refers to a scissile bond together with adjacent or non-adjacent recognition elements, or both, sufficient for detectable proteolysis at the scissile bond by FXIIa under conditions suitable for FXIIa protease activity. It is envisioned that any amino acid sequence cleaved by FXIIa can be useful in aspects of the present specification. Although exceptions are known, a generalized consensus sequence for a FXIIa cleavage site is $X_1X_2X_3(R/K)*X_4X_5X_6X_7$ (SEQ ID NO: 167), where $X_1$ is preferentially an uncharged amino acid like C, S, and T, or an aliphatic hydrophobic amino acid like, G, P, A, V, L, I, and M; $X_2$ is preferentially an acidic amino acid like D and E, a basic amino acid like K and R, an uncharged amino acid like C, S, and T, or an aliphatic hydrophobic amino acid like, G, P, A, V, L, I, and M; $X_3$ is preferentially a basic amino acid like K and R, an uncharged amino acid like C, S, and T, or an aliphatic hydrophobic amino acid like, G, P, A, V, L, I, and M; $X_4$ is preferentially an aliphatic hydrophobic amino acid like, G, P, A, V, L, I, and M; $X_5$ is preferentially an uncharged amino acid like C, S, and T, or an aliphatic hydrophobic amino acid like, G, P, A, V, L, I, and M; $X_6$ is preferentially an aliphatic hydrophobic amino acid like, G, P, A, V, L, I, and M; and $X_7$ is preferentially an aliphatic hydrophobic amino acid like, G, P, A, V, L, I, and M. Table 4 lists exemplary reference cleavage sites for FXIIa (SEQ ID NO: 168-172). Additional FXIIa cleavage sites are well known in the art or can be defined by routine methods. See, e.g., O. D. Ratnoff, *Coagulation Factor XIIa*. In Handbook of Proteolytic Enzymes, pp. 1642-1644 (A. J. Barrett, N. D. Rawlings, and J. F. Woessner, eds; Elsevier, London, 2d, 2004); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Coagulation Factor XIIa cleavage site. In an aspect of this embodiment, a Coagulation Factor XIIa cleavage site comprises the consensus sequence SEQ ID NO: 167, where $X_1$ is an uncharged amino acid like C, S, and T, or an aliphatic hydrophobic amino acid like, G, P, A, V, L, I, and M; $X_2$ is an acidic amino acid like D and E, a basic amino acid like K and R, an uncharged amino acid like C, S, and T, or an aliphatic hydrophobic amino acid like, G, P, A, V, L, I, and M; $X_3$ is a basic amino acid like K and R, an uncharged amino acid like C, S, and T, or an aliphatic hydrophobic amino acid like, G, P, A, V, L, I, and M; $X_4$ is an aliphatic hydrophobic amino acid like, G, P, A, V, L, I, and M; $X_5$ is an uncharged amino acid like C, S, and T, or an aliphatic hydrophobic amino acid like, G, P, A, V, L, I, and M; $X_6$ is an aliphatic hydrophobic amino acid like, G, P, A, V, L, I, and M; and $X_7$ is an aliphatic hydrophobic amino acid like, G, P, A, V, L, I, and M. In other aspect of this embodiment, a Coagulation Factor XIIa cleavage site comprises the consensus sequence SEQ ID NO: 167, where $X_1$ is S, T, P, or I; $X_2$ is Q, K, S, or M; $X_3$ is K, T, G, or P; $X_4$ is L, I, or V; $X_5$ is T or V; $X_6$ is G or L; and $X_7$ is G. In other aspects of this embodiment, a Coagulation Factor XIIa cleavage site comprises, e.g., SEQ ID NO: 168, SEQ ID NO: 169, SEQ ID NO: 170, SEQ ID NO: 171, or SEQ ID NO: 172.

Aspects of the present specification disclose, in part, a Kallikrein 1 cleavage site as an inactivation cleavage site. As used herein, the term "Kallikrein 1 cleavage site" refers to a scissile bond together with adjacent or non-adjacent recognition elements, or both, sufficient for detectable proteolysis at the scissile bond by Kallikrein 1 under conditions suitable for Kallikrein 1 protease activity. It is envisioned that any amino acid sequence cleaved by Kallikrein 1 can be useful in aspects of the present specification. Although exceptions are known, a generalized consensus sequence for a Kallikrein 1 cleavage site is $X_1X_2X_3X_4$*(R/K/S)$X_5X_6X_7$ (SEQ ID NO: 173), where $X_1$ is preferentially an acidic amino acid like D and E, an amidic amino acid like Q and N, an uncharged amino acid like C, S, and T, or an aliphatic hydrophobic amino acid like, G, P, A, V, L, I, and M; $X_2$ is any amino acid; $X_3$ is any amino acid; $X_4$ is preferentially a positive amino acid like H, K, and R, a large non-polar amino acid like F, I, L, M and V, or an aromatic hydrophobic amino acid like F, W and Y; $X_5$ is any amino acid; $X_6$ is any amino acid; and $X_7$ is any amino acid. Table 4 lists exemplary reference cleavage sites for Kallikrein 1 (SEQ ID NO: 174-198). Additional Kallikrein 1 cleavage sites are well known in the art or can be defined by routine methods. See, e.g., R. W. Colman, *Contact Activation Pathway: Inflammation, Fibrinolytic, Anticoagulant, Antiadhesive, and Antiangiogenic Activities*. In HEMOSTASIS AND THROMBOSIS, BASIC PRINCIPLES AND CLINICAL PRACTICE, pp. 103-104 (R. W. Colman, J. Hirsh, V. J. Marder, A. W Clowes, J. N. George, eds; Lippincott Williams & Wilkins, Philadelphia, Pa., 2d, 2001); J. Chao, *Human Kallikrein 1, Tissue Kallikrein*. In Handbook of Proteolytic Enzymes, pp. 1577-1580 (A. J. Barrett, N. D. Rawlings, and J. F. Woessner, eds; Elsevier, London, 2d, 2004); H. X. Li, et al., *Substrate Specificity of Human Kallikreins 1 and 6 Determined by Phage Display*, Protein Sci. 17: 664-672 (2008); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database, Nucleic Acids Res*. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Kallikrein 1 cleavage site. In an aspect of this embodiment, a Kallikrein 1 cleavage site comprises the consensus sequence SEQ ID NO: 173, where $X_1$ is an acidic amino acid like D and E, an amidic amino acid like Q and N, an uncharged amino acid like C, S, and T, or an aliphatic hydrophobic amino acid like, G, P, A, V, L, I, and M; $X_2$ is any amino acid; $X_3$ is any amino acid; $X_4$ is a positive amino acid like H, K, and R, a large non-polar amino acid like F, I, L, M and V, or an aromatic hydrophobic amino acid like F, W and Y; $X_5$ is any amino acid; $X_6$ is any amino acid; and $X_7$ is any amino acid. In another aspect of this embodiment, a Kallikrein 1 cleavage site comprises the consensus sequence SEQ ID NO: 173, where $X_1$ is D, S, T, or an aliphatic hydrophobic amino acid like, G, P, A, V, L, I, and M; $X_2$ is S, T, A, P, or V; $X_3$ is S, F, or L; $X_4$ is R or an aromatic hydrophobic amino acid like F, W and Y; $X_5$ is R, S, T, or A; $X_6$ is R, S, or G; and $X_7$ is R, G, or A. In other aspects of this embodiment, a Kallikrein 1 cleavage site comprises, e.g., SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, or SEQ ID NO: 198.

Aspects of the present specification disclose, in part, a Protein C cleavage site as an inactivation cleavage site. As used herein, the term "Protein C cleavage site" refers to a scissile bond together with adjacent or non-adjacent recognition elements, or both, sufficient for detectable proteolysis at the scissile bond by Protein C under conditions suitable for Protein C protease activity. It is envisioned that any amino acid sequence cleaved by Protein C can be useful in aspects of the present specification. Although exceptions are known, a generalized consensus sequence for a Protein C cleavage site is $X_1X_2X_3$(R/K)*$X_4X_5X_6X_7$ (SEQ ID NO: 199), where $X_1$ is preferentially a basic amino acid like K and R, or an aliphatic hydrophobic amino acid like, G, P, A, V, L, I, and M; $X_2$ is preferentially an acidic amino acid like D and E, an amidic amino acid like Q and N, a basic amino acid like K and R, or an aliphatic hydrophobic amino acid like, G, P, A, V, L, I, and M; $X_3$ is preferentially an amidic amino acid like Q and N, a basic amino acid like K and R, an uncharged amino acid like C, S, and T, or an aliphatic hydrophobic amino acid like, G, P, A, V, L, I, and M; $X_4$ is preferentially an amidic amino acid like Q and N, a basic amino acid like K and R, an uncharged amino acid like C, S, and T, or an aliphatic hydrophobic amino acid like, G, P, A, V, L, I, and M; $X_5$ is preferentially an amidic amino acid like Q and N, a basic amino acid like K and R, an aromatic hydrophobic amino acid like F, W and Y, or an aliphatic hydrophobic amino acid like, G, P, A, V, L, I, and M; $X_6$ is preferentially an amidic amino acid like Q and N, a positive amino acid like H, K, and R, an uncharged amino acid like C, S, and T, or an aromatic hydrophobic amino acid like F, W and Y; $X_7$ is preferentially an acidic amino acid like D and E, an amidic amino acid like Q and N, a basic amino acid like K and R, an uncharged amino acid like C, S, and T, or an aliphatic hydrophobic amino acid like, G, P, A, V, L, I, and M. Table 4 lists exemplary reference cleavage sites for Protein C (SEQ ID NO: 200-209). Additional Protein C cleavage sites are well known in the art or can be defined by routine methods. See, e.g., L. Shen and B. Dahiback, *Protein C*. In Handbook of Proteolytic Enzymes, pp. 1673-1677 (A. J. Barrett, N. D. Rawlings, and J. F. Woessner, eds; Elsevier, London, 2d, 2004); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Protein C cleavage site. In an aspect of this embodiment, a Protein C cleavage site comprises the consensus sequence SEQ ID NO: 199, where $X_1$ is a basic amino acid like K and R, or an aliphatic hydrophobic amino acid like, G, P, A, V, L, I, and M; $X_2$ is an acidic amino acid like D and E, an amidic amino acid like Q and N, a basic amino acid like K and R, or an aliphatic hydrophobic amino acid like, G, P, A, V, L, I, and M; $X_3$ and $X_4$ are independently an amidic amino acid like Q and N, a basic amino acid like K and R, an uncharged amino acid like C, S, and T, or an aliphatic hydrophobic amino acid like, G, P, A, V, L, I, and M; $X_5$ is an amidic amino acid like Q and N, a basic amino acid like K and R, an aromatic hydrophobic amino acid like F, W and Y, or an aliphatic hydrophobic amino acid like, G, P, A, V, L, I, and M; $X_6$ is an amidic amino acid like Q and N, a positive amino acid like H, K, and R, an uncharged amino acid like C, S, and T, or an aromatic hydrophobic amino acid like F, W and Y; $X_7$ is an acidic amino acid like D and E, an amidic amino acid like Q and N, a basic amino acid like K and R, an uncharged amino acid like C, S, and T, or an aliphatic hydrophobic amino acid like, G, P, A, V, L, I, and M. In another aspect of this embodiment, a Protein C cleavage site comprises the sequence SEQ ID NO: 199, where $X_1$ is K, R, or an aliphatic hydrophobic amino acid like, G, P, A, V, L, I, and M; $X_2$ is D, E, Q, N, or K; $X_3$ is P, L, T, Q, K, or R; $X_4$ is G, I, S, N, or K; $X_5$ is Q, N, K, F, or an aliphatic hydrophobic amino acid like, G, P, A, V, L, I, and M; $X_6$ is F, S, N, Q, K, or H; $X_7$ is L, I, T, K, D, E, Q, or N. In other aspects of this embodiment, a Protein C cleavage site comprises, e.g., SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, or SEQ ID NO: 209.

Aspects of the present specification disclose, in part, a Plasminogen cleavage site as an inactivation cleavage site. As used herein, the term "Plasminogen cleavage site" refers to a scissile bond together with adjacent or non-adjacent recognition elements, or both, sufficient for detectable proteolysis at the scissile bond by Plasminogen under conditions suitable for Plasminogen protease activity. It is envisioned that any amino acid sequence cleaved by Plasminogen can be useful in aspects of the present specification. Although exceptions are known, a generalized consensus sequence for a Plasminogen cleavage site is $X_1X_2X_3$(R/K)*$X_4X_5X_6X_7$ (SEQ ID NO: 210), where $X_1$ is preferentially a positive amino acid like H, K and R, an uncharged amino acid like C, S, and T, or an aliphatic hydrophobic amino acid like, G, P, A, V, L, I, and M; $X_2$ is preferentially an amidic amino acid like N and Q, a positive amino acid like H, K and R, an uncharged amino acid like C, S, and T, or an aliphatic hydrophobic amino acid like, G, P, A, V, L, I, and M; $X_3$ is preferentially an amidic amino acid like N and Q, an uncharged amino acid like C, S, and T, an aromatic amino acid like F, W and Y, or an aliphatic hydrophobic amino acid like, G, P, A, V, L, I, and M; $X_4$ is preferentially a positive amino acid like H, K and R, an uncharged amino acid like C, S, and T, or an aliphatic hydrophobic amino acid like, G, P, A, V, L, I, and M; $X_5$ is preferentially a positive amino acid like H, K and R, an uncharged amino acid like C, S, and T, or an aliphatic hydrophobic amino acid like, G, P, A, V, L, I, and M; $X_6$ is any amino acid; $X_7$ is preferentially H, F, Y, R, an uncharged amino acid like C, S, and T, an aliphatic hydrophobic amino acid like, G, P, A, V, L, I, and M. Table 4 lists exemplary reference cleavage sites for Plasminogen (SEQ ID NO: 211-240). Additional Plasminogen cleavage sites are well known in the art or can be defined by routine methods. See, e.g., O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Plasminogen cleavage site. In an aspect of this embodiment, a Plasminogen cleavage site comprises the consensus sequence SEQ ID NO: 211, where $X_1$ is a positive amino acid like H, K and R, an uncharged amino acid like C, S, and T, or an aliphatic hydrophobic amino acid like, G, P, A, V, L, I, and M; $X_2$ is an amidic amino acid like N and Q, a positive amino acid like H, K and R, an uncharged amino acid like C, S, and T, or an aliphatic hydrophobic amino acid like, G, P, A, V, L, I, and M; $X_3$ is an amidic amino acid like N and Q, an uncharged amino acid like C, S, and T, an aromatic amino acid like F, W and Y, or an aliphatic hydrophobic amino acid like, G, P, A, V, L, I, and M; $X_4$ is a positive amino acid like H, K and R, an uncharged amino acid like C, S, and T, or an aliphatic hydrophobic amino acid like, G, P, A, V, L, I, and M; $X_5$ is a positive amino acid like H, K and R, an uncharged amino acid like C, S, and T, or an aliphatic hydrophobic amino acid like, G, P, A, V, L, I, and M; $X_6$ is any amino acid; $X_7$ is H, F, Y, R, an uncharged amino acid like C, S, and T, an aliphatic hydrophobic amino acid like, G, P, A, V, L, I, and M. In another aspect of this embodiment, a Plasminogen cleavage site comprises the sequence SEQ ID NO: 211, where $X_1$ is K, R, S, T, A, G, L, or P; $X_2$ is D, E, Q, N, K, R, S, T, A, G, I or L; $X_3$ is N, Q, S, F, Y, A or L; $X_4$ is K, R, S, A, G, L, or V; $X_5$ is K, R, N, S, F, Y, A, I, L, P, or V; $X_6$ is K, R, N, S, F, Y, A, G, L, P or V; $X_7$ is R, S, T, F, Y, A, G, I, L, or P. In other aspects of this embodiment, a Plasminogen cleavage site comprises, e.g., SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, or SEQ ID NO: 240.

Aspects of the present specification disclose, in part, a Matrix Metalloproteinase-2 cleavage site as an inactivation cleavage site. As used herein, the term "Matrix Metalloproteinase-2 cleavage site" or "MMP-2 cleavage site" refers to a scissile bond together with adjacent or non-adjacent recognition elements, or both, sufficient for detectable proteolysis at the scissile bond by MMP-2 under conditions suitable for MMP-2 protease activity. It is envisioned that any amino acid sequence cleaved by MMP-2 can be useful in aspects of the present specification. Although exceptions are known, a generalized consensus sequence for a MMP-2 cleavage site is $X_1$(P/A/V/L/I)$X_2X_3$*(V/L/I/F/Q)$X_4X_5X_6$ (SEQ ID NO: 241), where $X_1$, $X_2$, $X_3$, $X_4$, $X_5$, and $X_6$ are any amino acid. Table 4 lists exemplary reference cleavage sites for MMP-2 (SEQ ID NO: 242-273). Additional MMP-2 cleavage sites are well known in the art or can be defined by routine methods. See, e.g., O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of*

*Peptidase Cleavages in the MEROPS Database*, Database in press (2010), each of which is incorporated by reference in its entirety.

Thus, in an embodiment, a Clostridial toxin or Clostridial toxin chimeric comprises a Matrix Metalloproteinase-2 cleavage site. In an aspect of this embodiment, a Matrix Metalloproteinase-2 cleavage site comprises the consensus sequence SEQ ID NO: 241, where $X_1$, $X_2$, $X_3$, $X_4$, $X_5$, and $X_6$ are any amino acid. In another aspect of this embodiment, a Matrix Metalloproteinase-2 cleavage site comprises the consensus sequence SEQ ID NO: 241, where $X_1$ is an acidic amino acid like D and E, an amidic amino acid like N and Q, an uncharged amino acid like C, S, and T, or an aliphatic hydrophobic amino acid like, G, P, A, V, L, I, and M; $X_2$ is an acidic amino acid like D and E, a basic amino acid like K and R, an amidic amino acid like N and Q, an uncharged amino acid like C, S, and T, or an aliphatic hydrophobic amino acid like, G, P, A, V, L, I, and M; $X_3$ is H, an acidic amino acid like D and E, an amidic amino acid like N and Q, an uncharged amino acid like C, S, and T, or an aliphatic hydrophobic amino acid like, G, P, A, V, L, I, and M; $X_4$ is a basic amino acid like K and R, an amidic amino acid like N and Q, an uncharged amino acid like C, S, and T, an aromatic amino acid like F, W, and Y, or an aliphatic hydrophobic amino acid like, G, P, A, V, L, I, and M; $X_5$ is an acidic amino acid like D and E, a basic amino acid like K and R, an amidic amino acid like N and Q, an uncharged amino acid like C, S, and T, or an aliphatic hydrophobic amino acid like, G, P, A, V, L, I, and M; $X_6$ is an acidic amino acid like D and E, a basic amino acid like K and R, an amidic amino acid like N and Q, an uncharged amino acid like C, S, and T, or an aliphatic hydrophobic amino acid like, G, P, A, V, L, I, and M. In another aspect of this embodiment, a Matrix Metalloproteinase-2 cleavage site comprises the sequence SEQ ID NO: 241, where $X_1$ is G, P, A, V, L, I, S, T, E, or Q; $X_2$ is G, A, L, S, N, Q, W, or K; $X_3$ is G, P, A, S, Q, D, E, or H; $X_4$ is G, A, V, L, I, F, S, T, Q, or K; $X_5$ is G, A, V, S, T, Q, or K; $X_6$ is G, P, A, V, L, I, S, T, D, E, K, N, or Q. In another aspect of this embodiment, a Matrix Metalloproteinase-2 cleavage site comprises the sequence SEQ ID NO: 241, where $X_1$ is G, A, or L, or Q; $X_2$ is G, A, or S; $X_3$ is G, A, S, or N; $X_4$ is A, V, L, I, or K; $X_5$ is G, A, or S; $X_6$ is G, P, A, V, L, or D. In other aspects of this embodiment, a Matrix Metalloproteinase-2 cleavage site comprises, e.g., SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, or SEQ ID NO: 273.

Aspects of the present specification disclose, in part, a Matrix Metalloproteinase-9 cleavage site as an inactivation cleavage site. As used herein, the term "Matrix Metalloproteinase-9 cleavage site" or "MMP-2 cleavage site" refers to a scissile bond together with adjacent or non-adjacent recognition elements, or both, sufficient for detectable proteolysis at the scissile bond by MMP-9 under conditions suitable for MMP-9 protease activity. It is envisioned that any amino acid sequence cleaved by MMP-9 can be useful in aspects of the present specification. Although exceptions are known, a generalized consensus sequence for a MMP-9 cleavage site is $X_1X_2X_3X_4{}^*X_5X_6X_7X_8$ (SEQ ID NO: 274), where $X_1$ is preferentially F, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; $X_2$ is preferentially F, Y, S, T, an acidic amino acid like D and E, an amidic amino acid like N and Q, a positive amino acid like H, K, and R, or an aliphatic hydrophobic amino acid like, G, P, A, V, L, I, and M; $X_3$ is preferentially F, Y, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; $X_4$ is any amino acid; $X_5$ is preferentially S, T, an acidic amino acid like D and E, an amidic amino acid like N and Q, a positive amino acid like H, K, and R, an aromatic hydrophobic amino acid like F, W, and Y, or an aliphatic hydrophobic amino acid like, G, P, A, V, L, I, and M; $X_6$ is any amino acid; $X_7$ is any amino acid; $X_8$ is preferentially F, Y, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M. Table 4 lists exemplary reference cleavage sites for MMP-9 (SEQ ID NO: 275-319). Additional MMP-9 cleavage sites are well known in the art or can be defined by routine methods. See, e.g., S. L. Kridel, et al., *Substrate Hydrolysis by Matrix Metalloproteinase-9*, J. Biol. Chem. 276: 20572-20578 (2001); E. Y. Zhen, et al., *Characterization of Metalloprotease Cleavage Products of Human Articular Cartilage*, Arthritis Rheum. 58: 2420-2431 (2008); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Matrix Metalloproteinase-9 cleavage site. In an aspect of this embodiment, a Matrix Metalloproteinase-9 cleavage site comprises the consensus sequence SEQ ID NO: 274, where $X_1$ is F, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; $X_2$ is F, Y, S, T, an acidic amino acid like D and E, an amidic amino acid like N and Q, a positive amino acid like H, K, and R, or an aliphatic hydrophobic amino acid like, G, P, A, V, L, I, and M; $X_3$ is F, Y, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; $X_4$ is any amino acid; $X_5$ is S, T, an acidic amino acid like D and E, an amidic amino acid like N and Q, a positive amino acid like H, K, and R, an aromatic hydrophobic amino acid like F, W, and Y, or an aliphatic hydrophobic amino acid like, G, P, A, V, L, I, and M; $X_6$ is any amino acid; $X_7$ is any amino acid; $X_8$ is F, Y, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M. In another aspect of this embodiment, a Matrix Metalloproteinase-9 cleavage site comprises the consensus sequence SEQ ID NO: 274, where $X_1$ is G, V, L, I, F, S, Q, K, or R; $X_2$ is P, A, V, L, I, or S; $X_3$ is G, P, A, V, L, S, Q, E, K, or R; $X_4$ is G, P, A, V, L, F, S, N, E, or K; $X_5$ is A, V, L, I, M, F, S, Q, or K; $X_6$ is P, A, V, L, I, S, T, Q, E, K, or R; $X_7$ is G, A, V, L, S, or T; X$_8$ is G, P, A, V, L, F, T, D, E, K, or R. In another aspect of this embodiment, a Matrix Metalloproteinase-9 cleavage site comprises the consensus sequence SEQ ID NO: 274, where X$_1$ is G or L; X$_2$ is P, A, or V; X$_3$ is P, A, R, K, or S; X$_4$ is G; X$_5$ is A, V, L, or I; X$_6$ is T, Q, K, or R; X$_7$ is G, A, or S; X$_8$ is G, P, A, V, or E. In other aspects of this embodiment, a Matrix Metalloproteinase-9 cleavage site comprises, e.g., SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, or SEQ ID NO: 319.

Aspects of the present specification disclose, in part, a Furin cleavage site as an inactivation cleavage site. As used herein, the term "Furin cleavage site" refers to a scissile bond together with adjacent or non-adjacent recognition elements, or both, sufficient for detectable proteolysis at the scissile bond by Furin under conditions suitable for Furin protease activity. It is envisioned that any amino acid sequence cleaved by Furin can be useful in aspects of the present specification. Although exceptions are known, a generalized consensus sequence for a Furin cleavage site is (R/I/A)X$_1$(R/K/A/P)R*X$_2$*X$_3$X$_4$X$_5$ (SEQ ID NO: 320), where X$_1$, X$_2$, X$_3$, X$_4$, and X$_5$ are any amino acid. Table 4 lists exemplary reference cleavage sites for Furin (SEQ ID NO: 321-346). Additional Furin cleavage sites are well known in the art or can be defined by routine methods. See, e.g., A. Basak, et al., *Implication of the Proprotein Convertases Furin, PC5 And PC7 in the Cleavage of Surface Glycoproteins of Hong Kong, Ebola and Respiratory Syncytial Viruses: A Comparative Analysis with Fluorogenic Peptides*, Biochem. J. 353: 537-545 (2001); O. Bader, et al., *Processing of Predicted Substrates of Fungal Kex2 Proteinases from Candida albicans, C. glabrata, Saccharomyces cerevisiae and Pichia pastoris*, BMC Microbiol. 8: 116 (2008); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Furin cleavage site. In an aspect of this embodiment, a Furin cleavage site comprises the consensus sequence SEQ ID NO: 320, where X$_1$, X$_2$, X$_3$, X$_4$, and X$_5$ are any amino acid. In another aspect of this embodiment, a Furin cleavage site comprises the consensus sequence SEQ ID NO: 320, where X$_1$ is F, S, T, an acidic amino acid like D and E, an amidic amino acid like N and Q, a positive amino acid like H, K, and R, or an aliphatic hydrophobic amino acid like, G, P, A, V, L, I, and M; X$_2$ is G, P, M, F, Y, an acidic amino acid like D and E, an amidic amino acid like N and Q, a positive amino acid like H, K, and R, or an uncharged amino acid like C, S, and T; X$_3$ is G, P, A, V, L, I, F, W, S, T, N, Q, D, H, K, or R; X$_4$ is F, Y, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; and X$_5$ is F, Y, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M. In another aspect of this embodiment, a Furin cleavage site comprises the consensus sequence SEQ ID NO: 320, where X$_1$ is K, R, S or T; X$_2$ is D, E, S, A or G; X$_3$ is A, V, L, or I; and X$_4$ is S, G, D, E or R; and X$_5$ is G, P, A, S, T, Q, D, or E. In other aspects of this embodiment, a Furin cleavage site comprises, e.g., SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, or SEQ ID NO: 346.

Aspects of the present specification disclose, in part, a u-Plasminogen Activator cleavage site as an inactivation cleavage site. As used herein, the term "u-Plasminogen Activator cleavage site" or "u-PA cleavage site" refers to a scissile bond together with adjacent or non-adjacent recognition elements, or both, sufficient for detectable proteolysis at the scissile bond by u-PA under conditions suitable for u-PA protease activity. It is envisioned that any amino acid sequence cleaved by u-Plasminogen Activator can be useful in aspects of the present specification. Although exceptions are known, a generalized consensus sequence for a u-PA cleavage site is X$_1$X$_2$X$_3$(R/K)*X$_4$*X$_5$X$_6$X$_7$ (SEQ ID NO: 347), where X$_1$ is any amino acid;, X$_2$ is preferentially an uncharged amino acid like C, S, and T, an aromatic amino acid like F, W, and Y, or an aliphatic hydrophobic amino acid like, G, P, A, V, L, I, and M; X$_3$ is preferentially an amidic amino acid like N and Q, an uncharged amino acid like C, S, and T, or an aliphatic hydrophobic amino acid like, G, P, A, V, L, I, and M; X$_4$ is any amino acid; X$_5$ is preferentially a basic amino acid like K and R, an aromatic amino acid like F, W, and Y, or an aliphatic hydrophobic amino acid like, G, P, A, V, L, I, and M; X$_6$ is preferentially an uncharged amino acid like C, S, and T, an aromatic amino acid like F, W, and Y, or an aliphatic hydrophobic amino acid like, G, P, A, V, L, I, and M; and X$_7$ is any amino acid. Table 4 lists exemplary reference cleavage sites for u-PA (SEQ ID NO: 347-368). Additional u-PA cleavage sites are well known in the art or can be defined by routine methods. See, e.g., V. Ellis, *u-Plasminogen Activator*. In Handbook of Proteolytic Enzymes, pp. 1677-1683 (A. J. Barrett, N. D. Rawlings, and J. F. Woessner, eds; Elsevier, London, 2d, 2004); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a u-Plasminogen Activator cleavage site. In an aspect of this embodiment, a u-Plasminogen Activator cleavage site comprises the consensus sequence SEQ ID NO: 347, where X$_1$ is any amino acid;, X$_2$ is an uncharged amino acid like C, S, and T, an aromatic amino acid like F, W, and Y, or an aliphatic hydrophobic amino acid like, G, P, A, V, L, I, and M; $X_3$ is an amidic amino acid like N and Q, an uncharged amino acid like C, S, and T, or an aliphatic hydrophobic amino acid like, G, P, A, V, L, I, and M; $X_4$ is any amino acid; $X_5$ is a basic amino acid like K and R, an aromatic amino acid like F, W, and Y, or an aliphatic hydrophobic amino acid like, G, P, A, V, L, I, and M; $X_6$ is an uncharged amino acid like C, S, and T, an aromatic amino acid like F, W, and Y, or an aliphatic hydrophobic amino acid like, G, P, A, V, L, I, and M; and $X_7$ is any amino acid. In another aspect of this embodiment, a u-Plasminogen Activator cleavage site comprises the consensus sequence SEQ ID NO: 347, where $X_1$ is P, A, L, S, T, C, N, or R; $X_2$ is G, P, L, Y, S, or T; $X_3$ is G, A, S, or N; and $X_4$ is G, A, V, I, Y, S, or R; $X_5$ is P, V, L, F, or R; $X_6$ is G, A, V, Y, S, or T; and $X_7$ is G, V, L, F, Y, N, or H. In another aspect of this embodiment, a u-Plasminogen Activator cleavage site comprises the consensus sequence SEQ ID NO: 347, where $X_1$ is P, A, L, S, T, C, N, or R; $X_2$ is G, Y, or S; $X_3$ is G or S; and $X_4$ is G, A, V, I, Y, S, or R; $X_5$ is V or R; $X_6$ is T or Y; and $X_7$ is G, V, L, F, Y, N, or H. In other aspects of this embodiment, a u-Plasminogen Activator cleavage site comprises, e.g., SEQ ID NO: 348, SEQ ID NO: 349, NO: 350, SEQ ID NO: 351, SEQ ID NO: 352, SEQ ID NO: 353, SEQ ID NO: 354, SEQ ID NO: 355, or SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, or SEQ ID NO: 368.

Aspects of the present specification disclose, in part, a t-Plasminogen Activator cleavage site as an inactivation cleavage site. As used herein, the term "t-Plasminogen Activator cleavage site" or "t-PA cleavage site" refers to a scissile bond together with adjacent or non-adjacent recognition elements, or both, sufficient for detectable proteolysis at the scissile bond by t-PA under conditions suitable for t-PA protease activity. It is envisioned that any amino acid sequence cleaved by t-PA can be useful in aspects of the present specification. Although exceptions are known, a generalized consensus sequence for a t-PA cleavage site is $X_1X_2X_3$(R/K)*$X_4$*$X_5X_6X_7$ (SEQ ID NO: 369), where $X_1$, $X_2$, $X_3$, $X_4$, $X_5$, $X_6$, and $X_7$ are any amino acid. Table 4 lists exemplary reference cleavage sites for t-PA (SEQ ID NO: 370-373). Additional t-PA cleavage sites are well known in the art or can be defined by routine methods. See, e.g., H. R. Lijnen and D. Collen, *t-Plasminogen Activator*. In Handbook of Proteolytic Enzymes, pp. 1684-1689 (A. J. Barrett, N. D. Rawlings, and J. F. Woessner, eds; Elsevier, London, 2d, 2004); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a t-Plasminogen Activator cleavage site. In an aspect of this embodiment, a t-Plasminogen Activator cleavage site comprises the consensus sequence SEQ ID NO: 369, where $X_1$, $X_2$, $X_3$, $X_4$, $X_5$, $X_6$, and $X_7$ are any amino acid. In another aspect of this embodiment, a t-Plasminogen Activator cleavage site comprises the consensus sequence SEQ ID NO: 369, where $X_1$ is an amidic amino acid like N and Q, an uncharged amino acid like C, S, and T, or an aliphatic hydrophobic amino acid like, G, P, A, V, L, I, and M; $X_2$ is an amidic amino acid like N and Q, or an aliphatic hydrophobic amino acid like, G, P, A, V, L, I, and M; $X_3$ is an amidic amino acid like N and Q, an aromatic hydrophobic amino acid like F, W and Y, or an aliphatic hydrophobic amino acid like, G, P, A, V, L, I, and M; $X_4$ is an aromatic hydrophobic amino acid like F, W and Y, or an aliphatic hydrophobic amino acid like, G, P, A, V, L, I, and M; $X_5$ is a basic amino acid like K and R, or an aliphatic hydrophobic amino acid like, G, P, A, V, L, I, and M; $X_6$ is an aliphatic hydrophobic amino acid like, G, P, A, V, L, I, and M; and $X_7$ is an acidic amino acid like D and E, or an aliphatic hydrophobic amino acid like, G, P, A, V, L, I, and M. In another aspect of this embodiment, a t-Plasminogen Activator cleavage site comprises the consensus sequence SEQ ID NO: 369, where $X_1$ is A, P, C, or N; $X_2$ is A, L, P, or Q; $X_3$ is G, L, S, or F; $X_4$ is I, V, M, or Y; $X_5$ is A, V, or K; $X_6$ is G, V, or P; and $X_7$ is G, L, or D. In other aspects of this embodiment, a t-Plasminogen Activator cleavage site comprises, e.g., SEQ ID NO: 370, SEQ ID NO: 371, SEQ ID NO: 372, or SEQ ID NO: 373.

Aspects of the present specification disclose, in part, a Tryptase-ε cleavage site as an inactivation cleavage site. As used herein, the term "Tryptase-ε cleavage site" or "Prosemin cleavage site" refers to a scissile bond together with adjacent or non-adjacent recognition elements, or both, sufficient for detectable proteolysis at the scissile bond by Tryptase-ε under conditions suitable for Tryptase-ε protease activity. It is envisioned that any amino acid sequence cleaved by Tryptase-ε can be useful in aspects of the present specification. Although exceptions are known, a generalized consensus sequence for a Tryptase-ε cleavage site is *(R/K)$X_1X_2X_3X_4$(D/E) (SEQ ID NO: 374), where $X_1$, $X_2$, $X_3$, and $X_4$, are independently an aliphatic hydrophobic amino acid like, G, P, A, V, L, I, and M. Table 4 lists exemplary reference cleavage sites for Tryptase-ε (SEQ ID NO: 375-386). Additional Tryptase-ε cleavage sites are well known in the art or can be defined by routine methods. See, e.g., O. Schilling and C. M. *Overall, Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Tryptase-E cleavage site. In an aspect of this embodiment, a Tryptase-ε cleavage site comprises the consensus sequence SEQ ID NO: 374, where $X_1$, $X_2$, $X_3$, and $X_4$, are independently an aliphatic hydrophobic amino acid like, G, P, A, V, L, I, and M. In another aspect of this embodiment, a Tryptase-ε cleavage site comprises the consensus sequence SEQ ID NO: 374, where $X_1$ is I or V; $X_2$ is I or V; $X_3$ is G or S; $X_4$ is G or S. In other aspects of this embodiment, a Tryptase-ε cleavage site comprises, e.g., SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, or SEQ ID NO: 386.

Aspects of the present specification disclose, in part, a Mouse Mast Cell Protease-7 cleavage site as an inactivation cleavage site. As used herein, the term "Mouse Mast Cell Protease-7 cleavage site" or "mMCP-7 cleavage site" refers to a scissile bond together with adjacent or non-adjacent recognition elements, or both, sufficient for detectable proteolysis at the scissile bond by mMCP-7 under conditions suitable for mMCP-7 protease activity. It is envisioned that any amino acid sequence cleaved by mMCP-7 can be useful in aspects of the present specification. Although exceptions are known, a generalized consensus sequence for a mMCP-7 cleavage site is $X_1X_2X_3(K/R)*X_4X_5X_6X_7$ (SEQ ID NO: 387), where $X_1$ is any amino acid; $X_2$ is preferentially an amidic amino acid like N or Q, or an aliphatic hydrophobic amino acid like, G, P, A, V, L, I, and M; $X_3$ is preferentially an aliphatic hydrophobic amino acid like, G, P, A, V, L, I, and M; and $X_4, X_5, X_6, X_7$ are any amino acid. Table 4 lists exemplary reference cleavage sites for mMMCP-7 (SEQ ID NO: 388-391). Additional mMMCP-7 cleavage sites are well known in the art or can be defined by routine methods. See, e.g., O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Mouse Mast Cell Protease-7 cleavage site. In an aspect of this embodiment, a Mouse Mast Cell Proteas-7 cleavage site comprises the consensus sequence SEQ ID NO: 387, where $X_1$ is any amino acid; $X_2$ is an amidic amino acid like N or Q, or an aliphatic hydrophobic amino acid like, G, P, A, V, L, I, and M; $X_3$ is an aliphatic hydrophobic amino acid like, G, P, A, V, L, I, and M; and $X_4, X_5, X_6, X_7$ are independently any amino acid. In another aspect of this embodiment, a Mouse Mast Cell Protease-7 cleavage site comprises the consensus sequence SEQ ID NO: 387, where $X_1$ is any amino acid; $X_2$ is G, S, or Q; $X_3$ is A, P or S; and $X_4, X_5, X_6, X_7$ are any amino acid. In other aspects of this embodiment, a Mouse Mast Cell Protease-7 cleavage site comprises, e.g., SEQ ID NO: 388, SEQ ID NO: 389, SEQ ID NO: 390, or SEQ ID NO: 391.

Aspects of the present specification disclose, in part, an Endothelin-Converting Enzyme-1 cleavage site as an inactivation cleavage site. As used herein, the term "Endothelin-Converting Enzyme-1 cleavage site" or "ECE-1 cleavage site" refers to a scissile bond together with adjacent or non-adjacent recognition elements, or both, sufficient for detectable proteolysis at the scissile bond by ECE-1 under conditions suitable for ECE-1 protease activity. It is envisioned that any amino acid sequence cleaved by ECE-1 can be useful in aspects of the present specification. Although exceptions are known, a generalized consensus sequence for an ECE-1 cleavage site is $X_1X_2X_3X_4*(F/L/I/V/Y)X_5X_6X_7$ (SEQ ID NO: 392), where $X_1, X_2, X_3, X_4, X_5, X_6$, and $X_7$ are any amino acid. Table 4 lists exemplary reference cleavage sites for ECE-1 (SEQ ID NO: 393-412). Additional ECE-1 cleavage sites are well known in the art or can be defined by routine methods. See, e.g., K. Ahn and G. D. Johnson, *Endothelin-Converting Enzyme*-1. In Handbook of Proteolytic Enzymes, pp. 429-434 (A. J. Barrett, N. D. Rawlings, and J. F. Woessner, eds; Elsevier, London, 2d, 2004); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises an Endothelin-Converting Enzyme-1 cleavage site. In an aspect of this embodiment, an Endothelin-Converting Enzyme-1 cleavage site comprises the consensus sequence SEQ ID NO: 392, where $X_1, X_2, X_3, X_4, X_5, X_6$, and $X_7$ are independently any amino acid. In another aspect of this embodiment, an Endothelin-Converting Enzyme-1 cleavage site comprises the consensus sequence SEQ ID NO: 392, where $X_1$ is G, P, Y, an acidic amino acid like D and E, an amidic amino acid like N and Q, a positive amino acid like H, K, and R, or an uncharged amino acid like C, S, and T; $X_2$ is F, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; $X_3$ is S, an acidic amino acid like D and E, an amidic amino acid like N and Q, a positive amino acid like H, K, and R, an aromatic hydrophobic amino acid like F, W and Y, or an aliphatic hydrophobic amino acid like, G, P, A, V, L, I, and M; $X_4$ is S, an acidic amino acid like D and E, an amidic amino acid like N and Q, a positive amino acid like H, K, and R, an aromatic hydrophobic amino acid like F, W and Y, or an aliphatic hydrophobic amino acid like, G, P, A, V, L, I, and M; $X_5$ is F, W, S, C, N, E, a positive amino acid like H, K, and R, or an aliphatic hydrophobic amino acid like, G, P, A, V, L, I, and M; $X_6$ is G, P, V, L, F, Y, an acidic amino acid like D and E, an amidic amino acid like N and Q, a positive amino acid like H, K, and R, or an uncharged amino acid like C, S, and T; and $X_7$ is P, A, V, L, M, F, Y, S, N, D, or K. In another aspect of this embodiment, an Endothelin-Converting Enzyme-1 cleavage site comprises the consensus sequence SEQ ID NO: 392, where $X_1$ is G, P, Y, C, D, K, R, or H; $X_2$ is P, L, I, F, S, C, Q, D, R, or H; $X_3$ is V, L, I, S, Q, K, or R; $X_4$ is G, P, L, F, Y, W, or R; $X_5$ is V, I, M, F, N, R, or H; $X_6$ is P, L, F, T, E, or H; and $X_7$ is P, V, L, F, S, N, D, or K. In another aspect of this embodiment, an Endothelin-Converting Enzyme-1 cleavage site comprises the consensus sequence SEQ ID NO: 392, where $X_1$ is G, D, or H; $X_2$ is I or F; $X_3$ is V, I, S, Q or K; $X_4$ is P, F, or W; $X_5$ is I, N, R, or H; $X_6$ is L, T, or H; and $X_7$ is P, S, or D. In other aspects of this embodiment, an Endothelin-Converting Enzyme-1 cleavage site comprises, e.g., SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, or SEQ ID NO: 412.

Aspects of the present specification disclose, in part, a Kell blood-group protein cleavage site as an inactivation cleavage site. As used herein, the term "Kell blood-group protein cleavage site" or KBGP cleavage site" refers to a scissile bond together with adjacent or non-adjacent recognition elements, or both, sufficient for detectable proteolysis at the scissile bond by KBGP under conditions suitable for KBGP protease activity. It is envisioned that any amino acid sequence cleaved by KBGP can be useful in aspects of the present specification. Although exceptions are known, a generalized consensus sequence for a KBGP cleavage site is $X_1X_2X_3X_4*X_5X_6X_7X_8$ (SEQ ID NO: 413), where $X_1$ is preferentially an acidic amino acid like D and E; $X_2$ is preferentially an aliphatic hydrophobic amino acid like, G, P, A, V, L, I, and M; $X_3$ is preferentially an aliphatic hydrophobic amino acid like, G, P, A, V, L, I, and M; $X_4$ is preferentially an aromatic amino acid like F, W, and Y; $X_5$ is preferentially an aliphatic hydrophobic amino acid like, G, P, A, V, L, I, and M; $X_6$ is preferentially an amidic amino acid like N and Q; $X_7$ is an uncharged amino acid like C, S, and T; $X_8$ is preferentially an aliphatic hydrophobic amino acid like, G, P, A, V, L, I, and M. Table 4 lists exemplary reference cleavage sites for KBGP (SEQ ID NO: 414-415). Additional KBGP cleavage sites are well known in the art or can be defined by routine methods. See, e.g., O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Kell blood-group protein cleavage site. In an aspect of this embodiment, a Kell blood-group protein cleavage site comprises the consensus sequence SEQ ID NO: 413, where $X_1$ is an acidic amino acid like D and E; $X_2$ is T or an aliphatic hydrophobic amino acid like, G, P, A, V, L, I, and M; $X_3$ is an aliphatic hydrophobic amino acid like, G, P, A, V, L, I, and M; $X_4$ is an aromatic amino acid like F, W, and Y; $X_5$ is T or an aliphatic hydrophobic amino acid like, G, P, A, V, L, I, and M; $X_6$ is an amidic amino acid like N and Q; $X_7$ is an uncharged amino acid like C, S, and T, or a C-beta branched amino acid like I, V, or T; $X_8$ is an aliphatic hydrophobic amino acid like, G, P, A, V, L, I, and M. In another aspect of this embodiment, a Kell blood-group protein cleavage site comprises the consensus sequence SEQ ID NO: 413, where $X_1$ is D; $X_2$ is I, V, or T; $X_3$ is I, V, or T; $X_4$ is W; $X_5$ is I, V, or T; $X_6$ is N; $X_7$ is T; $X_8$ is P. In other aspects of this embodiment, a Kell blood-group protein cleavage site comprises, e.g., SEQ ID NO: 414 or SEQ ID NO: 415.

Aspects of the present specification disclose, in part, a Cathepsin L cleavage site as an inactivation cleavage site. As used herein, the term "Cathepsin L cleavage site" refers to a scissile bond together with adjacent or non-adjacent recognition elements, or both, sufficient for detectable proteolysis at the scissile bond by Cathepsin L under conditions suitable for Cathepsin L protease activity. It is envisioned that any amino acid sequence cleaved by Cathepsin L can be useful in aspects of the present specification. Although exceptions are known, a generalized consensus sequence for a Cathepsin L cleavage site is $X_1X_2X_3X_4*X_5X_6X_7X_8$ (SEQ ID NO: 416), where $X_1$ is preferentially W, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; $X_2$ is any amino acid; $X_3$ is preferentially L, V, F or Y; and $X_4$, $X_5$, $X_6$, $X_7$, and $X_8$ are any amino acid. Table 4 lists exemplary reference cleavage sites for Cathepsin L (SEQ ID NO: 417-443). Additional Cathepsin L cleavage sites are well known in the art or can be defined by routine methods. See, e.g., J. C. Kelly, et al., *Profiling of Calpain Activity with a Series of FRET-Based Substrates*, Biochim. Biophys. Acta 1794: 1505-1509 (2009); O. Schilling and C. M. Overall, *Proteome-Derived, Database-Searchable Peptide Libraries for Identifying Protease Cleavage Sites*, Nat. Biotechnol. 26: 685-694 (2008); Neil D. Rawlings, et al., *MEROPS: The Peptidase Database*, Nucleic Acids Res. 36(Database issue): D320-D325 (2008); Neil D. Rawlings, et al., *MEROPS: The Peptidase Database*, Nucleic Acids Res. 38(Database issue): D227-D233 (2010); Neil D. Rawlings, et al., *A Large and Accurate Collection of Peptidase Cleavages in the MEROPS Database*, Database in press (2010), each of which is incorporated by reference in its entirety.

Thus, in an embodiment, a Clostridial toxin or Clostridial toxin chimeric comprises a Cathepsin L cleavage site. In an aspect of this embodiment, a Cathepsin L cleavage site comprises the consensus sequence SEQ ID NO: 416, where $X_1$ is W, an acidic amino acid like D and E, an amidic amino acid like N and Q, a positive amino acid like H, K, and R, an uncharged amino acid like C, S, and T, or an aliphatic hydrophobic amino acid like, G, P, A, V, L, I, and M; $X_2$ is any amino acid; $X_3$ is L, V, F or Y; and $X_4$, $X_5$, $X_6$, $X_7$, and $X_8$ are any amino acid. In another aspect of this embodiment, a Cathepsin L cleavage site comprises the consensus sequence SEQ ID NO: 416, where $X_1$ is G, P, A, L, Q, E, or K; $X_2$ is an aromatic amino acid like F, W, and Y, or an aliphatic hydrophobic amino acid like, G, P, A, V, L, I, and M; $X_3$ is L, V, F or Y; $X_4$ is G, A, F, T, Q, E, K, or R; $X_5$ is G, A, S, an acidic amino acid like D and E, an amidic amino acid like N and Q, or a positive amino acid like H, K, and R; $X_6$ is P, A, L, I, S, Q, an acidic amino acid like D and E, or a positive amino acid like H, K, and R; $X_7$ is a positive amino acid like H, K, and R, or an aliphatic hydrophobic amino acid like, G, P, A, V, L, I, and M; and $X_8$ is P, L, S, T, an acidic amino acid like D and E, an amidic amino acid like N and Q, or a basic amino acid like K, and R. In another aspect of this embodiment, a Cathepsin L cleavage site comprises the consensus sequence SEQ ID NO: 416, where $X_1$ is G, A, Q, E, or K; $X_2$ is G, P, L, or F; $X_3$ is L, V, F or Y; $X_4$ is G, A, F, T, Q, E, K, or R; $X_5$ is A, S, Q, E, K, or R; $X_6$ is P, A, L, I, S, or E; $X_7$, P, L, or R; and $X_8$ is P, L, S, or K. In other aspects of this embodiment, a Cathepsin L cleavage site comprises, e.g., SEQ ID NO: 417, SEQ ID NO: 418, SEQ ID NO: 419, SEQ ID NO: 420, SEQ ID NO: 421, SEQ ID NO: 422, SEQ ID NO: 423, SEQ ID NO: 424, SEQ ID NO: 425, SEQ ID NO: 426, SEQ ID NO: 427, SEQ ID NO: 428, SEQ ID NO: 429, SEQ ID NO: 430, SEQ ID NO: 431, SEQ ID NO: 432, SEQ ID NO: 433, SEQ ID NO: 434, SEQ ID NO: 435, SEQ ID NO: 436, SEQ ID NO: 437, SEQ ID NO: 438, SEQ ID NO: 439, SEQ ID NO: 440, SEQ ID NO: 441, SEQ ID NO: 442, or SEQ ID NO: 443.

Aspects of the present specification disclose, in part, a PAR1 cleavage site as an inactivation cleavage site. As used herein, the term "PAR1 cleavage site" refers to a scissile bond together with adjacent or non-adjacent recognition elements, or both, sufficient for detectable proteolysis at the scissile bond by PAR1 under conditions suitable for PAR1 protease activity. It is envisioned that any amino acid sequence cleaved by PAR1 can be useful in aspects of the present specification. Although exceptions are known, a generalized consensus sequence for a PAR1 cleavage site is $X_1X_2X_3X_4(K/R)X_5$ (SEQ ID NO: 444), where $X_1$ is preferentially a small non-polar amino acid like A, C G, S, and T; $X_2$ is preferentially a large non-polar amino acid like F, I, L, M, V, or an aromatic amino acid like F, H, W, or Y; $X_3$ is preferentially a large non-polar amino acid like F, I, L, M, V, or an aromatic amino acid like F, H, W, or Y; $X_4$ is preferentially an aliphatic hydrophobic amino acid like, G, P, A, V, L, I, and M; and $X_5$ is preferentially an amidic amino acid like N and Q, or an aromatic hydrophobic amino acid like F, W, or Y. Table 4 lists exemplary reference cleavage sites for PAR1 (SEQ ID NO: 445-452). Additional PAR1 cleavage sites are well known in the art or can be defined by routine methods.

Thus, in an embodiment, a Clostridial toxin or Clostridial toxin chimeric comprises a PAR1 cleavage site. In an aspect of this embodiment, a PAR1 cleavage site comprises the consensus sequence SEQ ID NO: 444, where $X_1$ is a small non-polar amino acid like A, C G, S, and T; $X_2$ is a large non-polar amino acid like F, I, L, M, V, or an aromatic amino acid like F, H, W, or Y; $X_3$ is a large non-polar amino acid like F, I, L, M, V, or an aromatic amino acid like F, H, W, or Y; $X_4$ is an aliphatic hydrophobic amino acid like, G, P, A, V, L, I, and M; and $X_5$ is an amidic amino acid like N and Q, or an aromatic hydrophobic amino acid like F, W, or Y. In another aspect of this embodiment, a PAR1 cleavage site comprises the consensus sequence SEQ ID NO: 444, where $X_1$ is S, T, or G; $X_2$ is F or Y; $X_3$ is L, P, or F; $X_4$ is A, G, I, or L; and $X_5$ is F or N. In other aspects of this embodiment, a PAR1 cleavage site comprises, e.g., SEQ ID NO: 445, SEQ ID NO: 446, SEQ ID NO: 447, SEQ ID NO: 448, SEQ ID NO: 449, SEQ ID NO: 450, SEQ ID NO: 451, or SEQ ID NO: 452.

Aspects of the present specification disclose, in part, a PAR2 cleavage site as an inactivation cleavage site. As used herein, the term "PAR2 cleavage site" refers to a scissile bond together with adjacent or non-adjacent recognition elements, or both, sufficient for detectable proteolysis at the scissile bond by PAR2 under conditions suitable for PAR2 protease activity. It is envisioned that any amino acid sequence cleaved by PAR2 can be useful in aspects of the present specification. Although exceptions are known, a generalized consensus sequence for a PAR2 cleavage site is $X_1X_2X_3X_4(K/R)X_5$ (SEQ ID NO: 453), where $X_1$ is preferentially a small non-polar amino acid like A, C G, S, and T; $X_2$ is preferentially a large non-polar amino acid like F, I, L, M, V; $X_3$ is preferentially a large non-polar amino acid like F, I, L, M, V; $X_4$ is preferentially an aliphatic hydrophobic amino acid like, G, P, A, V, L, I, and M; and $X_5$ is preferentially a large non-polar amino acid like F, I, L, M, V. Table 4 lists exemplary reference cleavage sites for PAR2 (SEQ ID NO: 454-455). Additional PAR2 cleavage sites are well known in the art or can be defined by routine methods.

Thus, in an embodiment, a Clostridial toxin or Clostridial toxin chimeric comprises a PAR2 cleavage site. In an aspect of this embodiment, a PAR2 cleavage site comprises the consensus sequence SEQ ID NO: 453, where $X_1$ is a small non-polar amino acid like A, C G, S, and T; $X_2$ is a large non-polar amino acid like F, I, L, M, V; $X_3$ is a large non-polar amino acid like F, I, L, M, V; $X_4$ is an aliphatic hydrophobic amino acid like, G, P, A, V, L, I, and M; and $X_5$ is a large non-polar amino acid like F, I, L, M, V. In another aspect of this embodiment, a PAR2 cleavage site comprises the consensus sequence SEQ ID NO: 453, where $X_1$ is S; $X_2$ is I or L; $X_3$ is I or L; $X_4$ is A or G; $X_5$ is L or V. In other aspects of this embodiment, a PAR2 cleavage site comprises, e.g., SEQ ID NO: 454 or SEQ ID NO: 455.

Aspects of the present specification disclose, in part, a PAR3 cleavage site as an inactivation cleavage site. As used herein, the term "PAR3 cleavage site" refers to a scissile bond together with adjacent or non-adjacent recognition elements, or both, sufficient for detectable proteolysis at the scissile bond by PAR3 under conditions suitable for PAR3 protease activity. It is envisioned that any amino acid sequence cleaved by PAR3 can be useful in aspects of the present specification. Although exceptions are known, a generalized consensus sequence for a PAR3 cleavage site is $X_1X_2X_3X_4X_5X_6$ (SEQ ID NO: 456), where $X_1$ is preferentially a small non-polar amino acid like A, C G, S, and T; $X_2$ is preferentially a large non-polar amino acid like F, I, L, M, V; $X_3$ is preferentially an amidic amino acid like N and Q, or a basic amino acid like K and R; $X_4$ is preferentially a small non-polar amino acid like A, C G, S, and T; $X_5$ is preferentially a small non-polar amino acid like A, C G, S, and T, or a small polar amino acid like D, N, or P; and $X_6$ is preferentially an acidic amino acid like D and E, or a small polar amino acid like D, N, or P. Table 4 lists exemplary reference cleavage sites for PAR3 (SEQ ID NO: 457-459). Additional PAR3 cleavage sites are well known in the art or can be defined by routine methods.

Thus, in an embodiment, a Clostridial toxin or Clostridial toxin chimeric comprises a PAR3 cleavage site. In an aspect of this embodiment, a PAR3 cleavage site comprises the consensus sequence SEQ ID NO: 456, where $X_1$ is a small non-polar amino acid like A, C G, S, and T; $X_2$ is a large non-polar amino acid like F, I, L, M, V; $X_3$ is an amidic amino acid like N and Q, or a basic amino acid like K and R; $X_4$ is a small non-polar amino acid like A, C G, S, and T; $X_5$ is a small non-polar amino acid like A, C G, S, and T, or a small polar amino acid like D, N, or P; and $X_6$ is an acidic amino acid like D and E, or a small polar amino acid like D, N, or P. In another aspect of this embodiment, a PAR3 cleavage site comprises the consensus sequence SEQ ID NO: 456, where $X_1$ is S or T; $X_2$ is F; $X_3$ is N or R; $X_4$ is A or G; $X_5$ is A, G, or N and $X_6$ is P or E. In other aspects of this embodiment, a PAR3 cleavage site comprises, e.g., SEQ ID NO: 457, SEQ ID NO: 458, or SEQ ID NO: 459.

Aspects of the present specification disclose, in part, a PAR4 cleavage site as an inactivation cleavage site. As used herein, the term "PAR4 cleavage site" refers to a scissile bond together with adjacent or non-adjacent recognition elements, or both, sufficient for detectable proteolysis at the scissile bond by PAR4 under conditions suitable for PAR4 protease activity. It is envisioned that any amino acid sequence cleaved by PAR4 can be useful in aspects of the present specification. Although exceptions are known, a generalized consensus sequence for a PAR4 cleavage site is $X_1X_2X_3X_4(K/R/Q/F)X_5$ (SEQ ID NO: 460), where $X_1$ is preferentially a small non-polar amino acid like A, C G, S, and T; $X_2$ is preferentially a large non-polar amino acid like F, I, L, M, V, or an aromatic amino acid like F, H, W, or Y; $X_3$ is preferentially an aliphatic hydrophobic amino acid like, G, P, A, V, L, I, and M; $X_4$ is preferentially an aliphatic hydrophobic amino acid like, G, P, A, V, L, I, and M; and $X_5$ is preferentially a basic amino acid like K and R, an aromatic hydrophobic amino acid like F, W, or Y, or an aliphatic hydrophobic amino acid like, G, P, A, V, L, I, and M. Table 4 lists exemplary reference cleavage sites for PAR4 (SEQ ID NO: 461-478). Additional PAR4 cleavage sites are well known in the art or can be defined by routine methods. Thus, in an embodiment, a Clostridial toxin or Clostridial toxin chimeric comprises a PAR4 cleavage site. In an aspect of this embodiment, a PAR4 cleavage site comprises the consensus sequence SEQ ID NO: 460, where $X_1$ is a small non-polar amino acid like A, C G, S, and T; $X_2$ is a large non-polar amino acid like F, I, L, M, V, or an aromatic amino acid like F, H, W, or Y; $X_3$ is an aliphatic hydrophobic amino acid like, G, P, A, V, L, I, and M; $X_4$ is an aliphatic hydrophobic amino acid like, G, P, A, V, L, I, and M; and $X_5$ is a basic amino acid like K and R, an aromatic hydrophobic amino acid like F, W, or Y, or an aliphatic hydrophobic amino acid like, G, P, A, V, L, I, and M. In another aspect of this embodiment, a PAR4 cleavage site comprises the consensus sequence SEQ ID NO: 460, where $X_1$ is A, G, S, or T; $X_2$ is F or Y; $X_3$ is A or P; $X_4$ is A or G; and $X_5$ is A, V, P, F, W, Y, or K. In other aspects of this embodiment, a PAR4 cleavage site comprises, e.g., SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, SEQ ID NO: 472, SEQ ID NO: 473, SEQ ID NO: 474, SEQ ID NO: 475, SEQ ID NO: 476, SEQ ID NO: 477, or SEQ ID NO: 478.

The location of an inactivation cleavage site is a critical aspect that is governed by several criteria. First, the placement of the inactivation cleavage site should not substantially affect the ability of a Clostridial toxin or Clostridial toxin chimeric to intoxicate its target cell. As used herein, the term "not substantially affect," with regards to intoxication, refers to a Clostridial toxin or Clostridial toxin chimeric disclosed in the present specification that can still execute the overall intoxication mechanism whereby a Clostridial toxin or Clostridial toxin chimeric enters a target cell and proteolytically cleaves a target substrate and encompasses the binding of a Clostridial toxin or Clostridial toxin chimeric to a low or high affinity receptor complex, the internalization of the toxin/receptor complex, the translocation of the light chain into the cytoplasm and the enzymatic modification of a target substrate.

In an aspect of this embodiment, a Clostridial toxin or Clostridial toxin chimeric comprising an inactivation cleavage site can intoxicate a target cell to the same extent as the same or similar Clostridial toxin or Clostridial toxin chimeric, but without the inactivation cleavage site modification. In other aspects of this embodiment, a Clostridial toxin or Clostridial toxin chimeric comprising an inactivation cleavage site can intoxicate a target cell by, e.g., at least 50%, 60%, 70%, 80%, 90% or 95% the extent as the same or similar Clostridial toxin or Clostridial toxin chimeric, but without the inactivation cleavage site modification. In other aspects of this embodiment, a Clostridial toxin or Clostridial toxin chimeric comprising an inactivation cleavage site can intoxicate a target cell by, e.g., at most 50%, 60%, 70%, 80%, 90% or 95% the extent as the same or similar Clostridial toxin or Clostridial toxin chimeric, but without the inactivation cleavage site modification.

Second, the placement of an inactivation cleavage site should be at a surface exposed region of the toxin or Clostridial toxin chimeric and not buried internally within the protein or masked by secondary structure elements. Proper surface exposure of the inactivation cleavage site facilitates proper access of the site to its corresponding protease, thereby enabling proteolytic cleavage. Proteolytic cleavage of the inactivation cleavage site by its corresponding protease substantially inactivates the ability of the Clostridial toxin or Clostridial toxin chimeric to intoxicate the cell. As used herein, the term "substantially inactivates," with regards to intoxication, refers to a Clostridial toxin or Clostridial toxin chimeric disclosed in the present specification that, after cleavage at an inactivation cleavage site, has a reduced ability to execute the overall intoxication mechanism whereby a Clostridial toxin or Clostridial toxin chimeric enters a target cell and proteolytically cleaves a target substrate and encompasses the binding of a Clostridial toxin or Clostridial toxin chimeric to a low or high affinity receptor complex, the internalization of the toxin/receptor complex, the translocation of the light chain into the cytoplasm and the enzymatic modification of a target substrate.

In one aspect of this embodiment, proteolytic cleavage of a Clostridial toxin or Clostridial toxin chimeric disclosed in the present specification at an inactivation cleavage site results in complete inability of the toxin to intoxicate a target cell as compared to the same or similar Clostridial toxin or Clostridial toxin chimeric, but in a proteolytic uncleaved state (i.e., the intoxication cleavage site is intact or uncleaved). In other aspects of this embodiment, proteolytic cleavage of a Clostridial toxin or Clostridial toxin chimeric disclosed in the present specification at an inactivation cleavage site results in, e.g., at least a 10%, 20%, 30%, 40%, 50%, 60%, 70%, 80%, 90% or 95% decreased ability to intoxicate a target cell as compared to the same or similar Clostridial toxin or Clostridial toxin chimeric, but in a proteolytic uncleaved state. In other aspects of this embodiment, proteolytic cleavage of a Clostridial toxin or Clostridial toxin chimeric disclosed in the present specification at an inactivation cleavage site results in, e.g., at most a 10%, 20%, 30%, 40%, 50%, 60%, 70%, 80%, 90% or 95% decreased ability to intoxicate a target cell as compared to the same or similar Clostridial toxin or Clostridial toxin chimeric, but in a proteolytic uncleaved state.

In an aspect of the present specification, an inactivation cleavage site is located within an inactivation cleavage site region. As used herein, the term "inactivation cleavage site region" refers to an amino acid sequence of a Clostridial toxin or Clostridial toxin chimeric that can be modified to contain an inactivation cleavage site because such modification will not substantially disrupt the ability of the protein to intoxicate a target cell; and upon exposure to its cognate protease, the inactivation cleavage site will be cleaved and substantially inactivate the Clostridial toxin or Clostridial toxin chimeric. The location of an inactivation cleavage site can be anywhere within the inactivation cleavage site region, with the proviso that such location will not substantially affect the ability of the Clostridial toxin or Clostridial toxin chimeric to intoxicate a target cell; and upon exposure to its cognate protease, cleavage of the inactivation cleavage site will substantially inactivate the Clostridial toxin or Clostridial toxin chimeric. Table 5 lists exemplary inactivation cleavage site regions suitable for use with a Clostridial toxin or Clostridial toxin chimeric disclosed in the present specification.

Thus, in an embodiment, a Clostridial toxin or Clostridial toxin chimeric disclosed in the present specification comprises an inactivation cleavage site located within inactivation cleavage site region. In aspects of this embodiment, a Clostridial toxin or Clostridial toxin chimeric disclosed in the present specification comprises an inactivation cleavage site located within inactivation cleavage site region from the translocation domain or the $H_{CN}$ subdomain.

In other aspects of this embodiment, a Clostridial toxin or Clostridial toxin chimeric disclosed in the present specification comprises an inactivation cleavage site is located within an inactivation cleavage site region comprising amino acids 462-496 of SEQ ID NO: 1, SEQ ID NO: 2, SEQ ID NO: 4 or SEQ ID NO: 5; amino acids 458-492 of SEQ ID NO: 3; amino acids 464-487 of SEQ ID NO: 6, SEQ ID NO: 7, SEQ ID NO: 8, SEQ ID NO: 9, or SEQ ID NO: 10; amino acids 463-496 of SEQ ID NO: 11 or SEQ ID NO: 12; amino acids 458-491 of SEQ ID NO: 13 or SEQ ID NO: 14; amino acids 434-467 of SEQ ID NO: 15, SEQ ID NO: 16, or SEQ ID NO: 17; amino acids 453-486 of SEQ ID NO: 18, SEQ ID NO: 19, or SEQ ID NO: 20; amino acids 458-491 of SEQ ID NO: 21; amino acids 475-508 of SEQ ID NO: 22; amino acids 443-476 of SEQ ID NO: 23; or amino acids 434-467 of SEQ ID NO: 24 or SEQ ID NO: 25.

In yet other aspects of this embodiment, a Clostridial toxin or Clostridial toxin chimeric disclosed in the present specification comprises an inactivation cleavage site is located within an inactivation cleavage site region comprising amino acids 618-634 of SEQ ID NO: 1, SEQ ID NO: 2, SEQ ID NO: 4 or SEQ ID NO: 5; amino acids 614-630 of SEQ ID NO: 3; amino acids 605-621 of SEQ ID NO: 6, SEQ ID NO: 7, SEQ ID NO: 8, SEQ ID NO: 9, or SEQ ID NO: 10; amino acids 613-629 of SEQ ID NO: 11 or SEQ ID NO: 12; amino acids 609-625 of SEQ ID NO: 13 or SEQ ID NO: 14; amino acids 587-603 of SEQ ID NO: 15, SEQ ID NO: 16, or SEQ ID NO: 17; amino acids 604-620 of SEQ ID NO: 18; amino acids 605-621 of SEQ ID NO: 19 or SEQ ID NO: 20; amino acids 610-626 of SEQ ID NO: 21; amino acids 627-643 of SEQ ID NO: 22; amino acids 596-612 of SEQ ID NO: 23; or amino acids 587-603 of SEQ ID NO: 24 or SEQ ID NO: 25.

TABLE 5

Inactivation Cleavage Site Regions of Clostridial Toxins

| Toxin | SEQ ID NO: | Inactivation Cleavage Site Regions | | | | | | | |
|---|---|---|---|---|---|---|---|---|---|
| | | 1 | 2 | 3 | 4 | 5 | 6 | 7 | 8 |
| BoNT/A | 1 | L462-L496 | T618-I634 | G638-D651 | L665-N687 | N752-N765 | N826-D835 | T844-L863 | K871-A895 |
| BoNT/B | 2 | L464-P487 | A605-V621 | G625-N638 | L652-N674 | N739-D752 | N813-A824 | Y831-I850 | S858-G882 |
| BoNT/C1 | 3 | L463-S496 | I613-I629 | G633-N646 | L660-E682 | K747-Q760 | H821-D830 | S839-K858 | N866-N890 |
| BoNT/D | 4 | L458-S491 | I609-I625 | G629-N642 | L656-E678 | K743-Q756 | H817-D826 | S835-K854 | N862-N886 |
| BoNT/E | 5 | L434-D467 | A587-V603 | G607-N620 | L634-N659 | N724-D739 | H800-Q809 | T818-I837 | K845-D869 |
| BoNT/F | 6 | L453-N486 | A605-V621 | G625-N638 | L652-N677 | N742-N757 | H818-N827 | T836-I855 | K863-G887 |
| BoNT/G | 7 | L458-S491 | S610-I626 | G630-N643 | M657-N679 | N744-D757 | N818-N827 | H836-I855 | S863-G887 |
| TeNT | 8 | L475-S508 | S627-V643 | G647-N660 | L674-Q696 | K761-E774 | N835-K844 | V854-V871 | V879-N903 |
| BaNT | 9 | L443-N476 | A596-V612 | G616-N629 | L643-S668 | N733-N748 | N809-P819 | T828-I847 | K855-G879 |
| BuNT | 10 | L434-D467 | A587-V603 | G607-N620 | L634-S659 | N724-D739 | H800-Q809 | T818-I837 | K845-D869 |

In still other aspects of this embodiment, a Clostridial toxin or Clostridial toxin chimeric disclosed in the present specification comprises an inactivation cleavage site is located within an inactivation cleavage site region comprising amino acids 638-651 of SEQ ID NO: 1, SEQ ID NO: 2, SEQ ID NO: 4 or SEQ ID NO: 5; amino acids 634-647 of SEQ ID NO: 3; amino acids 625-638 of SEQ ID NO: 6, SEQ ID NO: 7, SEQ ID NO: 8, SEQ ID NO: 9, or SEQ ID NO: 10; amino acids 633-646 of SEQ ID NO: 11 or SEQ ID NO: 12; amino acids 629-642 of SEQ ID NO: 13 or SEQ ID NO: 14; amino acids 607-620 of SEQ ID NO: 15, SEQ ID NO: 16, or SEQ ID NO: 17; amino acids 624-637 of SEQ ID NO: 18; amino acids 625-638 of SEQ ID NO: 19 or SEQ ID NO: 20; amino acids 630-643 of SEQ ID NO: 21; amino acids 647-660 of SEQ ID NO: 22; amino acids 616-629 of SEQ ID NO: 23; or amino acids 607-620 of SEQ ID NO: 24 or SEQ ID NO: 25.

In further aspects of this embodiment, a Clostridial toxin or Clostridial toxin chimeric disclosed in the present specification comprises an inactivation cleavage site is located within an inactivation cleavage site region comprising amino acids 665-687 of SEQ ID NO: 1, SEQ ID NO: 2, SEQ ID NO: 4 or SEQ ID NO: 5; amino acids 661-683 of SEQ ID NO: 3; amino acids 652-674 of SEQ ID NO: 6, SEQ ID NO: 7, SEQ ID NO: 8, SEQ ID NO: 9, or SEQ ID NO: 10; amino acids 660-682 of SEQ ID NO: 11 or SEQ ID NO: 12; amino acids 656-678 of SEQ ID NO: 13 or SEQ ID NO: 14; amino acids 634-659 of SEQ ID NO: 15, SEQ ID NO: 16, or SEQ ID NO: 17; amino acids 651-676 of SEQ ID NO: 18; amino acids 652-677 of SEQ ID NO: 19 or SEQ ID NO: 20; amino acids 657-679 of SEQ ID NO: 21; amino acids 674-696 of SEQ ID NO: 22; amino acids 643-668 of SEQ ID NO: 23; or amino acids 634-659 of SEQ ID NO: 24 or SEQ ID NO: 25.

In other aspects of this embodiment, a Clostridial toxin or Clostridial toxin chimeric disclosed in the present specification comprises an inactivation cleavage site is located within an inactivation cleavage site region comprising amino acids 752-765 of SEQ ID NO: 1, SEQ ID NO: 2, SEQ ID NO: 4 or SEQ ID NO: 5; amino acids 748-761 of SEQ ID NO: 3; amino acids 739-752 of SEQ ID NO: 6, SEQ ID NO: 7, SEQ ID NO: 8, SEQ ID NO: 9, or SEQ ID NO: 10; amino acids 747-760 of SEQ ID NO: 11 or SEQ ID NO: 12; amino acids 743-756 of SEQ ID NO: 13 or SEQ ID NO: 14; amino acids 724-739 of SEQ ID NO: 15, SEQ ID NO: 16, or SEQ ID NO: 17; amino acids 741-756 of SEQ ID NO: 18; amino acids 742-757 of SEQ ID NO: 19 or SEQ ID NO: 20; amino acids 744-757 of SEQ ID NO: 21; amino acids 761-774 of SEQ ID NO: 22; amino acids 733-748 of SEQ ID NO: 23; or amino acids 724-739 of SEQ ID NO: 24 or SEQ ID NO: 25.

In yet other aspects of this embodiment, a Clostridial toxin or Clostridial toxin chimeric disclosed in the present specification comprises an inactivation cleavage site is located within an inactivation cleavage site region comprising amino acids 826-835 of SEQ ID NO: 1, SEQ ID NO: 2, SEQ ID NO: 4 or SEQ ID NO: 5; amino acids 824-831 of SEQ ID NO: 3; amino acids 813-824 of SEQ ID NO: 6, SEQ ID NO: 7, SEQ ID NO: 8, SEQ ID NO: 9, or SEQ ID NO: 10; amino acids 821-830 of SEQ ID NO: 11 or SEQ ID NO: 12; amino acids 817-826 of SEQ ID NO: 13 or SEQ ID NO: 14; amino acids 800-809 of SEQ ID NO: 15, SEQ ID NO: 16, or SEQ ID NO: 17; amino acids 817-826 of SEQ ID NO: 18; amino acids 818-827 of SEQ ID NO: 19 or SEQ ID NO: 20; amino acids 818-827 of SEQ ID NO: 21; amino acids 835-844 of SEQ ID NO: 22; amino acids 809-819 of SEQ ID NO: 23; or amino acids 800-809 of SEQ ID NO: 24 or SEQ ID NO: 25.

In still other aspects of this embodiment, a Clostridial toxin or Clostridial toxin chimeric disclosed in the present specification comprises an inactivation cleavage site is located within an inactivation cleavage site region comprising amino acids 844-863 of SEQ ID NO: 1, SEQ ID NO: 2, SEQ ID NO: 4 or SEQ ID NO: 5; amino acids 840-859 of SEQ ID NO: 3;; amino acids 831-850 of SEQ ID NO: 6, SEQ ID NO: 7, SEQ ID NO: 8, SEQ ID NO: 9, or SEQ ID NO: 10; amino acids 839-858 of SEQ ID NO: 11 or SEQ ID NO: 12; amino acids 835-854 of SEQ ID NO: 13 or SEQ ID NO: 14; amino acids 818-837 of SEQ ID NO: 15, SEQ ID NO: 16, or SEQ ID NO: 17; amino acids 835-854 of SEQ ID NO: 18; amino acids 836-855 of SEQ ID NO: 19 or SEQ ID NO: 20; amino acids 836-855 of SEQ ID NO: 21; amino acids 854-871 of SEQ ID NO: 22; amino acids 828-847 of SEQ ID NO: 23; or amino acids 818-837 of SEQ ID NO: 24 or SEQ ID NO: 25.

In further aspects of this embodiment, a Clostridial toxin or Clostridial toxin chimeric disclosed in the present specification comprises an inactivation cleavage site is located within an inactivation cleavage site region comprising amino acids 871-895 of SEQ ID NO: 1, SEQ ID NO: 2, SEQ ID NO: 4 or SEQ ID NO: 5; amino acids 867-891 of SEQ ID NO: 3; amino acids 858-882 of SEQ ID NO: 6, SEQ ID NO: 7, SEQ ID NO: 8, SEQ ID NO: 9, or SEQ ID NO: 10; amino acids 866-890 of SEQ ID NO: 11 or SEQ ID NO: 12; amino acids 862-886 of SEQ ID NO: 13 or SEQ ID NO: 14; amino acids 845-869 of SEQ ID NO: 15, SEQ ID NO: 16, or SEQ ID NO: 17; amino acids 862-886 of SEQ ID NO: 18; amino acids 863-887 of SEQ ID NO: 19 or SEQ ID NO: 20; amino acids 863-887 of SEQ ID NO: 21; amino acids 879-903 of SEQ ID NO: 22; amino acids 855-879 of SEQ ID NO: 23; or amino acids 845-869 of SEQ ID NO: 24 or SEQ ID NO: 25.

In another aspect of this embodiment, a BoNT/A or BoNT/A chimeric disclosed in the present specification comprises an inactivation cleavage site is located within an inactivation cleavage site region from the translocation domain or the H$_{CN}$ subdomain. In other aspects of this embodiment, a BoNT/A or BoNT/A chimeric disclosed in the present specification comprises an inactivation cleavage site is located within an inactivation cleavage site region comprising amino acids 462-496, 618-634, 638-651, 665-687, 752-765, 826-835, 844-863, or 871-895 of SEQ ID NO: 1, SEQ ID NO: 2, SEQ ID NO: 4 or SEQ ID NO: 5; or comprising amino acids 458-492, 614-630, 634-647, 665-687, 748-761, 822-831, 840-859, or 867-891 of SEQ ID NO: 3. In yet other aspects of this embodiment, a BoNT/A comprising an inactivation cleavage site located within inactivation cleavage site region is encoded by SEQ ID NO: 530, SEQ ID NO: 532, SEQ ID NO: 534, or SEQ ID NO: 536. In still other aspects of this embodiment, a BoNT/A comprising an inactivation cleavage site located within inactivation cleavage site region comprises SEQ ID NO: 531, SEQ ID NO: 533, SEQ ID NO: 535, or SEQ ID NO: 537.

In yet another aspect of this embodiment, a BoNT/B or BoNT/B chimeric disclosed in the present specification comprises an inactivation cleavage site is located within an inactivation cleavage site region from the translocation domain or the H$_{CN}$ subdomain. In other aspects of this embodiment, a BoNT/B or BoNT/B chimeric disclosed in the present specification comprises an inactivation cleavage site is located within an inactivation cleavage site region comprising amino acids 464-487, 605-621, 625-638, 652-674, 739-752, 813-824, 831-850, or 858-882 of SEQ ID NO: 6, SEQ ID NO: 7, SEQ ID NO: 8, SEQ ID NO: 9, or SEQ ID NO: 10.

In still another aspect of this embodiment, a BoNT/C1 or BoNT/C1 chimeric disclosed in the present specification comprises an inactivation cleavage site is located within an inactivation cleavage site region from the translocation domain or the H$_{CN}$ subdomain. In other aspects of this embodiment, a BoNT/C1 or BoNT/C1 chimeric disclosed in the present specification comprises an inactivation cleavage site is located within an inactivation cleavage site region comprising amino acids 463-496, 613-629, 633-646, 660-682, 747-760, 821-830, 839-858, or 866-890 of SEQ ID NO: 11 or SEQ ID NO: 12.

In a further aspect of this embodiment, a BoNT/D or BoNT/D chimeric disclosed in the present specification comprises an inactivation cleavage site is located within an inactivation cleavage site region from the translocation domain or the H$_{CN}$ subdomain. In other aspects of this embodiment, a BoNT/D or BoNT/D chimeric disclosed in the present specification comprises an inactivation cleavage site is located within an inactivation cleavage site region comprising amino acids 458-491, 609-625, 629-642, 656-678, 743-756, 817-826, 835-854, or 862-886 of SEQ ID NO: 13 or SEQ ID NO: 14.

In another aspect of this embodiment, a BoNT/E or BoNT/E chimeric disclosed in the present specification comprises an inactivation cleavage site is located within an inactivation cleavage site region from the translocation domain or the H$_{CN}$ subdomain. In other aspects of this embodiment, a BoNT/E or BoNT/E chimeric disclosed in the present specification comprises an inactivation cleavage site is located within an inactivation cleavage site region comprising amino acids 434-467, 587-603, 607-620, 634-659, 724-739, 800-809, 818-837, or 845-869 of SEQ ID NO: 15, SEQ ID NO: 16, or SEQ ID NO: 17.

In still another aspect of this embodiment, a BoNT/F or BoNT/F chimeric disclosed in the present specification comprises an inactivation cleavage site is located within an inactivation cleavage site region from the translocation domain or the H$_{CN}$ subdomain. In other aspects of this embodiment, a BoNT/F or BoNT/F chimeric disclosed in the present specification comprises an inactivation cleavage site is located within an inactivation cleavage site region comprising amino acids 453-486, 604-620, 624-637, 651-676, 741-756, 817-826, 835-854, or 862-886 of SEQ ID NO: 18; or comprising amino acids 453-486, 605-621, 625-638, 652-677, 742-757, 818-827, 836-855, or 863-887 of SEQ ID NO: 19 or SEQ ID NO: 20.

In a further aspect of this embodiment, a BoNT/G or BoNT/G chimeric disclosed in the present specification comprises an inactivation cleavage site is located within an inactivation cleavage site region from the translocation domain or the H$_{CN}$ subdomain. In other aspects of this embodiment, a BoNT/G or BoNT/G chimeric disclosed in the present specification comprises an inactivation cleavage site is located within an inactivation cleavage site region comprising amino acids 458-491, 610-626, 630-643, 657-679, 744-757, 818-827, 836-855, or 863-887 of SEQ ID NO: 21.

In another aspect of this embodiment, a TeNT or TeNT chimeric disclosed in the present specification comprises an inactivation cleavage site is located within an inactivation cleavage site region from the translocation domain or the H$_{CN}$ subdomain. In other aspects of this embodiment, a TeNT or TeNT chimeric disclosed in the present specification comprises an inactivation cleavage site is located within an inactivation cleavage site region comprising amino acids 475-508, 627-643, 647-660, 674-696, 761-774, 835-844, 854-871, or 879-903 of SEQ ID NO: 22.

In yet another aspect of this embodiment, a BaNT or BaNT chimeric disclosed in the present specification comprises an inactivation cleavage site is located within an inactivation cleavage site region from the translocation domain or the H$_{CN}$ subdomain. In other aspects of this embodiment, a BaNT or BaNT chimeric disclosed in the present specification comprises an inactivation cleavage site is located within an inactivation cleavage site region comprising amino acids 443-476, 596-612, 616-629, 643-668, 733-748, 809-819, 828-847, or 855-879 of SEQ ID NO: 23.

In still another aspect of this embodiment, a BuNT or BuNT chimeric disclosed in the present specification comprises an inactivation cleavage site is located within an inactivation cleavage site region from the translocation domain or the H$_{CN}$ subdomain. In other aspects of this embodiment, a BuNT or BuNT chimeric disclosed in the present specification comprises an inactivation cleavage site is located within an inactivation cleavage site region comprising amino acids 434-467, 587-603, 607-620, 634-659, 724-739, 800-809, 818-837, or 845-869 of SEQ ID NO: 24 or SEQ ID NO: 25.

In an aspect of the present specification, a Clostridial toxin or Clostridial toxin chimeric comprising an inactivation cleavage site has a safety margin greater than the safety margin for the same or similar Clostridial toxin or Clostridial toxin chimeric, but without the inactivation cleavage site. In other words, the addition of an inactivation cleavage site increases the safety margin of the Clostridial toxin or Clostridial toxin chimeric relative to the same or similar Clostridial toxin or Clostridial toxin chimeric, but without the additional inactivation cleavage site.

Thus, in an embodiment, a Clostridial toxin or Clostridial toxin chimeric comprising an inactivation cleavage site has a safety margin that is greater relative to the same or similar Clostridial toxin or Clostridial toxin chimeric, but without the inactivation cleavage site. In aspects of this embodiment, a Clostridial toxin or Clostridial toxin chimeric comprising an inactivation cleavage site has a safety margin that is greater than, e.g., at least 10%, at least 20%, at least 30%, at least 40%, at least 50%, at least 60%, at least 70%, at least 80%, at least 90%, at least 100%, 110%, at least 120%, at least 130%, at least 140%, at least 150%, at least 160%, at least 170%, at least 180%, at least 190%, at least 200%, 210%, at least 220%, at least 230%, at least 240%, at least 250%, at least 260%, at least 270%, at least 280%, at least 290%, or at least 300%, relative to the same or similar Clostridial toxin or Clostridial toxin chimeric, but without the inactivation cleavage site. In other aspects of this embodiment, a Clostridial toxin or Clostridial toxin chimeric comprising an inactivation cleavage site has a safety margin that is greater than, e.g., at most 10%, at most 20%, at most 30%, at most 40%, at most 50%, at most 60%, at most 70%, at most 80%, at most 90%, at most 100%, 110%, at most 120%, at most 130%, at most 140%, at most 150%, at most 160%, at most 170%, at most 180%, at most 190%, at most 200%, 210%, at most 220%, at most 230%, at most 240%, at most 250%, at most 260%, at most 270%, at most 280%, at most 290%, or at most 300%, relative to the same or similar Clostridial toxin or Clostridial toxin chimeric, but without the inactivation cleavage site. In yet other aspects of this embodiment, a Clostridial toxin or Clostridial toxin chimeric comprising an inactivation cleavage site has a safety margin that is greater by, e.g., about 10% to about 300%, about 20% to about 300%, about 30% to about 300%, about 40% to about 300%, about 50% to about 300%, about 60% to about 300%, about 70% to about 300%, about 80% to about 300%, about 90% to about 300%, or about 100% to about 300%, relative to the same or similar Clostridial toxin or Clostridial toxin chimeric, but without the inactivation cleavage site.

In other aspects embodiment, a Clostridial toxin or Clostridial toxin chimeric comprising an inactivation cleavage site has a safety margin that is greater than, e.g., at least 1-fold, at least 1-fold, at least 3-fold, at least 4-fold, at least 5-fold, at least 6-fold, at least 7-fold, at least 8-fold, at least 9-fold, or at least 10-fold, relative to the same or similar Clostridial toxin or Clostridial toxin chimeric, but without the inactivation cleavage site. In yet other aspects embodiment, a Clostridial toxin or Clostridial toxin chimeric comprising an inactivation cleavage site has a safety margin that is greater than, e.g., at least 1-fold, at most 1-fold, at most 3-fold, at most 4-fold, at most 5-fold, at most 6-fold, at most 7-fold, at most 8-fold, at most 9-fold, or at most 10-fold, relative to the same or similar Clostridial toxin or Clostridial toxin chimeric, but without the inactivation cleavage site. In still other aspects of this embodiment, a Clostridial toxin or Clostridial toxin chimeric comprising an inactivation cleavage site has a safety margin that is greater by, e.g., about 1-fold to about 10-fold, about 1-fold to about 9-fold, about 1-fold to about 8-fold, about 1-fold to about 7-fold, about 1-fold to about 6-fold, about 1-fold to about 5-fold, about 2-fold to about 10-fold, about 2-fold to about 9-fold, about 2-fold to about 8-fold, about 2-fold to about 7-fold, about 2-fold to about 6-fold, or about 2-fold to about 5-fold.

In another embodiment, a Clostridial toxin or Clostridial toxin chimeric comprises the addition of an inactivation cleavage site that increases the safety margin of the Clostridial toxin or Clostridial toxin chimeric relative to the same or similar Clostridial toxin or Clostridial toxin chimeric, but without the additional inactivation cleavage site. In aspects of this embodiment, a Clostridial toxin or Clostridial toxin chimeric comprises the addition of an inactivation cleavage site that increases the safety margin of the Clostridial toxin or Clostridial toxin chimeric relative to the same or similar Clostridial toxin or Clostridial toxin chimeric, but without the additional inactivation cleavage site by, e.g., at least 10%, at least 20%, at least 30%, at least 40%, at least 50%, at least 60%, at least 70%, at least 80%, at least 90%, at least 100%, 110%, at least 120%, at least 130%, at least 140%, at least 150%, at least 160%, at least 170%, at least 180%, at least 190%, at least 200%, 210%, at least 220%, at least 230%, at least 240%, at least 250%, at least 260%, at least 270%, at least 280%, at least 290%, or at least 300%. In other aspects of this embodiment, a Clostridial toxin or Clostridial toxin chimeric comprises the addition of an inactivation cleavage site that increases the safety margin of the Clostridial toxin or Clostridial toxin chimeric relative to the same or similar Clostridial toxin or Clostridial toxin chimeric, but without the additional inactivation cleavage site by, e.g., at most 10%, at most 20%, at most 30%, at most 40%, at most 50%, at most 60%, at most 70%, at most 80%, at most 90%, at most 100%, 110%, at most 120%, at most 130%, at most 140%, at most 150%, at most 160%, at most 170%, at most 180%, at most 190%, at most 200%, 210%, at most 220%, at most 230%, at most 240%, at most 250%, at most 260%, at most 270%, at most 280%, at most 290%, or at most 300%. In yet other aspects of this embodiment, a Clostridial toxin or Clostridial toxin chimeric comprises the addition of an inactivation cleavage site that increases the safety margin of the Clostridial toxin or Clostridial toxin chimeric relative to the same or similar Clostridial toxin or Clostridial toxin chimeric, but without the additional inactivation cleavage site by, e.g., about 10% to about 300%, about 20% to about 300%, about 30% to about 300%, about 40% to about 300%, about 50% to about 300%, about 60% to about 300%, about 70% to about 300%, about 80% to about 300%, about 90% to about 300%, or about 100% to about 300%.

In other aspects of this embodiment, a Clostridial toxin or Clostridial toxin chimeric comprises the addition of an inactivation cleavage site that increases the safety margin of the Clostridial toxin or Clostridial toxin chimeric relative to the same or similar Clostridial toxin or Clostridial toxin chimeric, but without the additional inactivation cleavage site by, e.g., at least 1-fold, at least 1-fold, at least 3-fold, at least 4-fold, at least 5-fold, at least 6-fold, at least 7-fold, at least 8-fold, at least 9-fold, or at least 10-fold. In yet other aspects of this embodiment, a Clostridial toxin or Clostridial toxin chimeric comprises the addition of an inactivation cleavage site that increases the safety margin of the Clostridial toxin or Clostridial toxin chimeric relative to the same or similar Clostridial toxin or Clostridial toxin chimeric, but without the additional inactivation cleavage site by, e.g., at most 1-fold, at most 3-fold, at most 4-fold, at most 5-fold, at most 6-fold, at most 7-fold, at most 8-fold, at most 9-fold, or at most 10-fold. In still other aspects of this embodiment, a Clostridial toxin or Clostridial toxin chimeric comprises the addition of an inactivation cleavage site that increases the safety margin of the Clostridial toxin or Clostridial toxin chimeric relative to the same or similar Clostridial toxin or Clostridial toxin chimeric, but without the additional inactivation cleavage site by, e.g., about 1-fold to about 10-fold, about 1-fold to about 9-fold, about 1-fold to about 8-fold, about 1-fold to about 7-fold, about 1-fold to about 6-fold, about 1-fold to about 5-fold, about 2-fold to about 10-fold, about 2-fold to about 9-fold, about 2-fold to about 8-fold, about 2-fold to about 7-fold, about 2-fold to about 6-fold, or about 2-fold to about 5-fold.

In another embodiment, an inactivation cleavage site region can be modified to include a single inactivation cleavage site. In yet another embodiment, an inactivation cleavage site region can be modified to include a plurality inactivation cleavage site cleavage sites. In aspects of this embodiment, an inactivation cleavage site cleavage site region can comprise, e.g., at least 1, 2, 3, 4, 5, 6, 7, 8, 9, or 10 inactivation cleavage sites. In other aspects of this embodiment, an inactivation cleavage site cleavage site region can comprise, e.g., at most 1, 2, 3, 4, 5, 6, 7, 8, 9, or 10 inactivation cleavage sites. In yet other aspects of this embodiment, an inactivation cleavage site cleavage site region can comprise, e.g., 2-10 inactivation cleavage sites, 2-8 inactivation cleavage sites, 2-6 inactivation cleavage sites, 2-4 inactivation cleavage sites, 2-3 inactivation cleavage sites, 3-9 inactivation cleavage sites, 3-7 inactivation cleavage sites, 3-5 inactivation cleavage sites, or 3-4 inactivation cleavage sites.

In another embodiment, an inactivation cleavage site region can be modified to include only one type of inactivation cleavage site, such as, e.g., a thrombin cleavage site. In still another embodiment, an inactivation cleavage site region can be modified to include a plurality of different types of inactivation cleavage sites, such as, e.g., a thrombin cleavage site, a Factor Xa cleavage site, MMP-2 cleavage site, and a MMP-9 cleavage site. In aspects of this embodiment, an inactivation cleavage site region can comprise, e.g., at least 2, 3, 4, or 5 different types of inactivation cleavage sites. In other aspects of this embodiment, an inactivation cleavage site region can comprise, e.g., at most 2, 3, 4, or 5 different types of inactivation cleavage sites. In other aspects of this embodiment, an inactivation cleavage site region can comprise, e.g., 2-5 different types of inactivation cleavage sites, 2-4 different types of inactivation cleavage sites, 2-3 different types of inactivation cleavage sites, 3-5 different types of inactivation cleavage sites, or 3-4 different types of inactivation cleavage sites.

Modification of an inactivation cleavage site region to include a inactivation cleavage site can be accomplished by altering at least one of the amino acids within the inactivation cleavage site region. Non-limiting examples of an amino acid alteration include a deletion of an amino acid, an addition of an amino acid, or a substitution of an original amino acid with a different amino acid. In aspects of this embodiment, an inactivation cleavage site region is modified to include an inactivation cleavage site by altering, e.g., at least 1, 2, 3, 4, or 5 amino acids within the inactivation cleavage site region. In other aspects of this embodiment, an inactivation cleavage site region is modified to include an inactivation cleavage site by altering, e.g., at most 1, 2, 3, 4, or 5 amino acids within the inactivation cleavage site region. In yet aspects of this embodiment, an inactivation cleavage site region is modified to include an inactivation cleavage site by altering, e.g., 1-5 amino acids within the inactivation cleavage site region, 1-4 amino acids within the inactivation cleavage site region, 1-3 amino acids within the inactivation cleavage site region, 1-2 amino acids within the inactivation cleavage site region, 2-5 amino acids within the inactivation cleavage site region, 2-4 amino acids within the inactivation cleavage site region, 2-3 amino acids within the inactivation cleavage site region, 3-5 amino acids within the inactivation cleavage site region, or 4-5 amino acids within the inactivation cleavage site region.

In aspects of this embodiment, an inactivation cleavage site region is modified to include an inactivation cleavage site by deleting, adding, substituting, or any combination thereof, e.g., at least 1, 2, 3, 4, or 5 amino acids within the inactivation cleavage site region. In other aspects of this embodiment, an inactivation cleavage site region is modified to include an inactivation cleavage site by deleting, adding, substituting, or any combination thereof, e.g., at most 1, 2, 3, 4, or 5 amino acids within the inactivation cleavage site region. In yet aspects of this embodiment, an inactivation cleavage site region is modified to include an inactivation cleavage site by deleting, adding, substituting, or any combination thereof, e.g., 1-5 amino acids within the inactivation cleavage site region, 1-4 amino acids within the inactivation cleavage site region, 1-3 amino acids within the inactivation cleavage site region, 1-2 amino acids within the inactivation cleavage site region, 2-5 amino acids within the inactivation cleavage site region, 2-4 amino acids within the inactivation cleavage site region, 2-3 amino acids within the inactivation cleavage site region, 3-5 amino acids within the inactivation cleavage site region, or 4-5 amino acids within the inactivation cleavage site region.

Modification of an inactivation cleavage site region to include an inactivation cleavage site can be achieved using standard mutagenesis procedures known to a person skilled in the art. Non-limiting examples of mutagenesis procedures, as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures within the scope of one skilled in the art and from the teaching herein.

As mentioned above, Clostridial toxins and Clostridial toxin chimeras disclosed in the present specification are translated as single-chain polypeptides that are subsequently cleaved by proteolytic scission within a disulfide loop region. This posttranslational processing yields a di-chain molecule held together by a single disulphide bond and noncovalent interactions. The proteolytic scission within a disulfide loop region can be achieved by using the endogenous protease cleavage sites naturally-occurring within the di-chain loop region, or by engineering the di-chain loop region to comprise an exogenous protease cleavage site.

Aspects of the present specification disclose, in part, a di-chain loop region. As used herein, the term "di-chain loop region" refers to an amino acid sequence of a Clostridial toxin or Clostridial toxin chimeric flanked by cysteine amino acids and containing a protease cleavage site used to convert the single-chain form of a Clostridial toxin or Clostridial toxin chimeric into its di-chain form (Table 6). Non-limiting examples of a di-chain loop region, include, a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; and a di-chain loop region of TeNT comprising amino acids 439-467 of SEQ ID NO: 8 (Table 6).

TABLE 6

Di-chain Loop Region

| Toxin | Di-chain Loop Region Containing the Naturally-occurring Protease Cleavage Site |
|---|---|
| BoNT/A | CVRGIITSKTKSLDKGYNK*----ALNDLC |
| BoNT/B | CKSVK*------------------APGIC |
| BoNT/C1 | CHKAIDGRSLYNK*------------TLDC |
| BoNT/D | CLRLTKNSR*--------------DDSTC |
| BoNT/E | CKNIVSVKGIR*-------------KSIC |

TABLE 6-continued

Di-chain Loop Region

| Toxin | Di-chain Loop Region Containing the Naturally-occurring Protease Cleavage Site |
|---|---|
| BoNT/F | CKSVIPRKGTK*------------APPRLC |
| BoNT/G | CKPVMYKNTGK*--------------SEQC |
| TeNT | CKKIIPPTNIRENLYNRTA*SLTDLGGELC |
| BaNT | CKS-IVSKKGTK*------------NSLC |
| BuNT | CKN-IVSVKGIR*--------------KSIC |

The amino acid sequence displayed are as follows: BoNT/A, residues 430-454 of SEQ ID NO: 1; BoNT/B, residues 437-446 of SEQ ID NO: 2; BoNT/C1, residues 437-453 of SEQ ID NO: 3; BoNT/D, residues 437-450 of SEQ ID NO: 4; BoNT/E, residues 412-426 of SEQ ID NO: 5; BoNT/F, residues 429-445 of SEQ ID NO: 6; BoNT/G, residues 436-450 of SEQ ID NO: 7; TeNT, residues 439-467 of SEQ ID NO: 8; BaNT, residues 421-435 of SEQ ID NO: 9; and BuNT, residues 412-426 of SEQ ID NO: 10. An asterisks (*) indicates the peptide bond that is cleaved by a Clostridial toxin protease.

Thus, in an embodiment, a di-chain loop region comprises a Clostridial toxin di-chain loop region. In aspects of this embodiment, a di-chain loop region comprises, e.g., a BoNT/A di-chain loop region, a BoNT/B di-chain loop region, a BoNT/C1 di-chain loop region, a BoNT/D di-chain loop region, a BoNT/E di-chain loop region, a BoNT/F di-chain loop region, a BoNT/G di-chain loop region, a TeNT di-chain loop region, a BaNT di-chain loop region, or a BuNT di-chain loop region. In other aspects of this embodiment, a di-chain loop region comprises, e.g., a BoNT/A di-chain loop region comprising amino acids 430-454 of SEQ ID NO: 1; a BoNT/B di-chain loop region comprising amino acids 437-446 of SEQ ID NO: 2; a BoNT/C1 di-chain loop region comprising amino acids 437-453 of SEQ ID NO: 3; a BoNT/D di-chain loop region comprising amino acids 437-450 of SEQ ID NO: 4; a BoNT/E di-chain loop region comprising amino acids 412-426 of SEQ ID NO: 5; a BoNT/F di-chain loop region comprising amino acids 429-445 of SEQ ID NO: 6; a BoNT/G di-chain loop region comprising amino acids 436-450 of SEQ ID NO: 7; or a TeNT di-chain loop region comprising amino acids 439-467 of SEQ ID NO: 8. a BaNT di-chain loop region comprising amino acids 421-435 of SEQ ID NO: 9; or a BuNT di-chain loop region comprising amino acids 412-426 of SEQ ID NO: 10.

Aspects of the present specification disclose, in part, an endogenous di-chain loop protease cleavage site. As used herein, the term "endogenous di-chain loop protease cleavage site" is synonymous with a "naturally occurring di-chain loop protease cleavage site" and refers to a naturally occurring protease cleavage site found within the di-chain loop region of a naturally occurring Clostridial toxin or Clostridial toxin chimeric and includes, without limitation, naturally occurring Clostridial toxin di-chain loop protease cleavage site variants, such as, e.g., Clostridial toxin di-chain loop protease cleavage site isoforms and Clostridial toxin di-chain loop protease cleavage site subtypes. Non-limiting examples of an endogenous protease cleavage site, include, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

While the identity of the protease is currently unknown, the di-chain loop protease cleavage site for many Clostridial toxins has been determined. In BoNTs, cleavage at K448-A449 converts the single polypeptide form of BoNT/A into the di-chain form; cleavage at K441-A442 converts the single polypeptide form of BoNT/B into the di-chain form; cleavage at K449-T450 converts the single polypeptide form of BoNT/C1 into the di-chain form; cleavage at R445-D446 converts the single polypeptide form of BoNT/D into the di-chain form; cleavage at R422-K423 converts the single polypeptide form of BoNT/E into the di-chain form; cleavage at K439-A440 converts the single polypeptide form of BoNT/F into the di-chain form; and cleavage at K446-5447 converts the single polypeptide form of BoNT/G into the di-chain form. Proteolytic cleavage of the single polypeptide form of TeNT at A457-5458 results in the di-chain form. Proteolytic cleavage of the single polypeptide form of BaNT at K431-N432 results in the di-chain form. Proteolytic cleavage of the single polypeptide form of BuNT at R422—K423 results in the di-chain form. Such a di-chain loop protease cleavage site is operably-linked to a Clostridial toxin or Clostridial toxin chimeric as a fusion protein. However, it should also be noted that additional cleavage sites within the di-chain loop also appear to be cleaved resulting in the generation of a small peptide fragment being lost. As a non-limiting example, BoNT/A single-chain polypeptide cleave ultimately results in the loss of a ten amino acid fragment within the di-chain loop.

Thus, in an embodiment, a Clostridial toxin or Clostridial toxin chimeric disclosed in the present specification comprises a di-chain loop region including an endogenous di-chain loop protease cleavage site. In aspects of this embodiment, an endogenous di-chain loop protease cleavage site located within the di-chain loop region comprises, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site, a TeNT di-chain loop protease cleavage site, a BaNT di-chain loop protease cleavage site, or a BuNT di-chain loop protease cleavage site. In other aspects of this embodiment, an endogenous di-chain loop protease cleavage site located within the di-chain loop region comprises, e.g., a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; or a di-chain loop region of TeNT comprising amino acids 439-467 of SEQ ID NO: 8. a di-chain loop region of BaNT comprising amino acids 421-435 of SEQ ID NO: 9; or a di-chain loop region of BuNT comprising amino acids 412-426 of SEQ ID NO: 10.

Aspects of the present specification disclose, in part, an exogenous protease cleavage site. As used herein, the term "exogenous protease cleavage site" is synonymous with "engineered protease cleavage site", "non-naturally occurring protease cleavage site", or "non-native protease cleavage site" and refers to a protease cleavage site that is not normally present in a di-chain loop region from a naturally occurring Clostridial toxin. Such engineered or exogenous protease cleavage sites within the di-chain loop region are used to convert the single-chain polypeptide form of a Clostridial toxin of Clostridial toxin chimeric disclosed in the present specification into its di-chain form. It is envisioned that any and all exogenous protease cleavage sites can be used to convert the single-chain polypeptide form of a Clostridial toxin or Clostridial toxin chimeric into its active di-chain form are useful to practice aspects of the present specification. Non-limiting examples of exogenous protease cleavage sites include, e.g., a plant papain cleavage site, an insect papain cleavage site, a crustacean papain cleavage site, an enterokinase cleavage site, a human rhinovirus 3C protease cleavage site, a human enterovirus 3C protease cleavage site, a tobacco etch virus (TEV) protease cleavage site, a Tobacco Vein Mottling Virus (TVMV) cleavage site, a subtilisin cleavage site, a hydroxylamine cleavage site, or a Caspase 3 cleavage site. Engineered protease cleavage sites located within the di-chain loop are described in, e.g., Dolly, et al., Activatable Recombinant Neurotoxins, U.S. Pat. No. 7,419,676, Dolly, et al., Activatable Recombinant Neurotoxins, U.S. Pat. No. 7,422,877, Steward, et al., Activatable Recombinant Neurotoxins, U.S. Patent Publication 2009/0069238, Steward, et al., Activatable Recombinant Neurotoxins, U.S. Patent Publication 2008/0032930, Steward, et al., Activatable Recombinant Neurotoxins, U.S. Patent Publication 2009/0018081, Steward, et al., Activatable Recombinant Neurotoxins, U.S. Patent Publication 2009/0005313, Steward, et al., Activatable Recombinant Neurotoxins, U.S. Patent Publication 2009/0004224; each of which is hereby incorporated by reference in its entirety.

It is envisioned that an exogenous protease cleavage site of any and all lengths can be useful in aspects of the present specification with the proviso that the exogenous protease cleavage site can be cleaved by its respective protease. Thus, in aspects of this embodiment, an exogenous protease cleavage site can have a length of, e.g., at least 6, 7, 8, 9, 10, 15, 20, 25, 30, 40, 50, or at least 60 amino acids; or at most 6, 7, 8, 9, 10, 15, 20, 25, 30, 40, 50, or at least 60 amino acids.

In an embodiment, a Clostridial toxin or Clostridial toxin chimeric disclosed in the present specification comprises a di-chain loop region including an exogenous protease cleavage site. In aspects of this embodiment, an exogenous protease cleavage site located within the di-chain loop region comprises, e.g., a plant papain cleavage site, an insect papain cleavage site, a crustacean papain cleavage site, a non-human enterokinase protease cleavage site, a Tobacco Etch Virus protease cleavage site, a Tobacco Vein Mottling Virus protease cleavage site, a human rhinovirus 3C protease cleavage site, a human enterovirus 3C protease cleavage site, a subtilisin cleavage site, a hydroxylamine cleavage site, a SUMO/ULP-1 protease cleavage site, and a non-human Caspase 3 cleavage site.

In an aspect of this embodiment, an exogenous protease cleavage site located within the di-chain loop region comprises, e.g., a non-human enterokinase cleavage site. In another aspect of the embodiment, an exogenous protease cleavage site located within the di-chain loop region comprises, e.g., a bovine enterokinase protease cleavage site. In yet another aspect of the embodiment, an exogenous protease cleavage site located within the di-chain loop region comprises, e.g., SEQ ID NO: 480.

In another aspect of this embodiment, an exogenous protease cleavage site located within the di-chain loop region comprises, e.g., a Tobacco Etch Virus protease cleavage. In other aspects of the embodiment, an exogenous protease cleavage site located within the di-chain loop region comprises, e.g., the consensus sequence $EX_1X_2YX_3Q*G$ (SEQ ID NO: 481) or $EX_1X_2YX_3Q*S$ (SEQ ID NO: 482), where $X_1$, $X_2$ and $X_3$ is any amino acid. In other aspects of the embodiment, an exogenous protease cleavage site located within the di-chain loop region comprises, e.g., SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, or SEQ ID NO: 492.

In another aspect of this embodiment, an exogenous protease cleavage site located within the di-chain loop region comprises, e.g., a Tobacco Vein Mottling Virus protease cleavage site. In other aspects of the embodiment, an exogenous protease cleavage site located within the di-chain loop region comprises, e.g., the consensus sequence $X_1X_2VRFQ*G$ (SEQ ID NO: 493) or $X_1X_2VRFQ*S$ (SEQ ID NO: 494), where $X_1$ and $X_2$ are independently any amino acid. In other aspects of the embodiment, an exogenous protease cleavage site located within the di-chain loop region comprises, e.g., SEQ ID NO: 495, SEQ ID NO: 496, SEQ ID NO: 497, or SEQ ID NO: 498.

In still another aspect of this embodiment, an exogenous protease cleavage site located within the di-chain loop region comprises, e.g., a human rhinovirus 3C protease cleavage site. In another aspect of the embodiment, an exogenous protease cleavage site located within the di-chain loop region comprises, e.g., the consensus sequence $X_1X_2LFQ*GP$ (SEQ ID NO: 499), where $X_1$ is any amino acid with an acidic amino acid like D or E preferred; and $X_2$ is preferentially S, T, and an aliphatic hydrophobic amino acid like G, P, A, V, L, I, and M. In other aspects of the embodiment, an exogenous protease cleavage site located within the di-chain loop region comprises, e.g., SEQ ID NO: 500, SEQ ID NO: 501, SEQ ID NO: 502, SEQ ID NO: 503, SEQ ID NO: 504, or SEQ ID NO: 505. In another aspect of the embodiment, an exogenous protease cleavage site located within the di-chain loop region comprises, e.g., a human rhinovirus 3C protease cleaved by PRESCISSION®.

In yet another aspect of this embodiment, an exogenous protease cleavage site located within the di-chain loop region comprises, e.g., a subtilisin cleavage site. In other aspects of the embodiment, an exogenous protease cleavage site located within the di-chain loop region comprises, e.g., the consensus sequence $X_1X_2X_3X_4WY$ (SEQ ID NO: 506) or $X_1X_2X_3X_4YH*$ (SEQ ID NO: 507), where $X_1$, $X_2$, $X_3$, and $X_4$ are independently any amino acid. In other aspects of the embodiment, an exogenous protease cleavage site located within the di-chain loop region comprises, e.g., SEQ ID NO: 508, SEQ ID NO: 509, or SEQ ID NO: 510. In other aspects of the embodiment, an exogenous protease cleavage site located within the di-chain loop region comprises, e.g., a subtilisin cleavage site cleaved by GENENASE®.

In yet another aspect of this embodiment, an exogenous protease cleavage site located within the di-chain loop region comprises, e.g., a hydroxylamine cleavage site. In other aspects of the embodiment, an exogenous protease cleavage site located within the di-chain loop region comprises, e.g., the dipeptide N*G. In other aspects of the embodiment, an exogenous protease cleavage site located within the di-chain loop region comprises, e.g., SEQ ID NO: 511 or SEQ ID NO: 512.

In yet another aspect of this embodiment, an exogenous protease cleavage site located within the di-chain loop region comprises, e.g., a SUMO/ULP-1 protease cleavage site. In other aspects of the embodiment, an exogenous protease cleavage site located within the di-chain loop region comprises, e.g., the consensus sequence GG*$X_1X_2X_3$ (SEQ ID NO: 513), where $X_1$, $X_2$, and $X_3$ are independently any amino acid. In other aspects of the embodiment, an exogenous protease cleavage site located within the di-chain loop region comprises, e.g., SEQ ID NO: 514.

In an aspect of this embodiment, an exogenous protease cleavage site located within the di-chain loop region comprises, e.g., a Caspase 3 cleavage site. In other aspects of the embodiment, an exogenous protease cleavage site located within the di-chain loop region comprises, e.g., a non-human Caspase 3 protease cleavage site. In other aspects of the embodiment, an exogenous protease cleavage site located within the di-chain loop region comprises, e.g., the consensus sequence $DX_1X_2D*X_3$ (SEQ ID NO: 515), where $X_1$ is any amino acid, with an acidic amino acid like D and E preferred, $X_2$ is any amino acid and $X_3$ is amino acid, with a small non-polar amino acid like A, C, G, S, and T preferred. In other aspects of the embodiment, an exogenous protease cleavage site located within the di-chain loop region comprises, e.g., SEQ ID NO: 516, SEQ ID NO: 517, SEQ ID NO: 518, SEQ ID NO: 519, SEQ ID NO: 520, or SEQ ID NO: 521.

A di-chain loop region can be modified so that a naturally-occurring di-chain loop protease cleavage site is replaced by an exogenous protease cleavage site. In this modification, the naturally-occurring di-chain loop protease cleavage site is made inoperable and thus cannot be cleaved by its protease. Only the exogenous protease cleavage site can be cleaved by its corresponding exogenous protease. In this type of modification, the exogenous protease site is operably-linked to a Clostridial toxin or Clostridial toxin chimeric as a fusion protein and the site can be cleaved by its respective exogenous protease. Replacement of an endogenous di-chain loop protease cleavage site with an exogenous protease cleavage site can be a substitution of the sites where the exogenous site is engineered at the position approximating the cleavage site location of the endogenous site. Replacement of an endogenous di-chain loop protease cleavage site with an exogenous protease cleavage site can be an addition of an exogenous site where the exogenous site is engineered at the position different from the cleavage site location of the endogenous site, the endogenous site being engineered to be inoperable. The location and kind of protease cleavage site may be critical because certain binding domains require a free amino-terminal or carboxyl-terminal amino acid. For example, when a peptide binding domain is placed between two other domains, e.g., see FIG. 4, a criterion for selection of a protease cleavage site could be whether the protease that cleaves its site leaves a flush cut, exposing the free amino-terminal or carboxyl-terminal of the binding domain necessary for selective binding of the binding domain to its receptor.

A naturally-occurring protease cleavage site can be made inoperable by altering at least one of the two amino acids flanking the peptide bond cleaved by the naturally-occurring di-chain loop protease. More extensive alterations can be made, with the proviso that the two cysteine residues of the di-chain loop region remain intact and the region can still form the disulfide bridge. Non-limiting examples of an amino acid alteration include deletion of an amino acid or replacement of the original amino acid with a different amino acid. Thus, in one embodiment, a naturally-occurring protease cleavage site is made inoperable by altering at least 1, 2, 3, 4, 5, 6, 7, 8, 9, 10, 15, 20 amino acids including at least one of the two amino acids flanking the peptide bond cleaved by a naturally-occurring protease. In another embodiment, a naturally-occurring protease cleavage site is made inoperable by altering at most 1, 2, 3, 4, 5, 6, 7, 8, 9, 10, 15, 20 amino acids including at least one of the two amino acids flanking the peptide bond cleaved by a naturally-occurring protease.

It is understood that a modified Clostridial toxin disclosed in the present specification can optionally further comprise a flexible region comprising a flexible spacer. A flexible region comprising flexible spacers can be used to adjust the length of a polypeptide region in order to optimize a characteristic, attribute or property of a polypeptide. As a non-limiting example, a polypeptide region comprising one or more flexible spacers in tandem can be used to better expose a protease cleavage site thereby facilitating cleavage of that site by a protease. As another non-limiting example, a polypeptide region comprising one or more flexible spacers in tandem can be used to better present a peptide binding domain, thereby facilitating the binding of that binding domain to its receptor.

A flexible space comprising a peptide is at least one amino acid in length and comprises non-charged amino acids with small side-chain R groups, such as, e.g., small non-polar amino acids like A, C, G, S, and T. Thus, in an embodiment a flexible spacer can have a length of, e.g., at least 1, 2, 3, 4, 5, 6, 7, 8, 9, or 10 amino acids; or at most 1, 2, 3, 4, 5, 6, 7, 8, 9, or 10 amino acids. In still another embodiment, a flexible spacer can be, e.g., between 1-3 amino acids, between 2-4 amino acids, between 3-5 amino acids, between 4-6 amino acids, or between 5-7 amino acids. Non-limiting examples of a flexible spacer include, e.g., a G-spacers such as GGG, GGGG (SEQ ID NO: 522), and GGGGS (SEQ ID NO: 523) or an A-spacers such as AAA, AAAA (SEQ ID NO: 524) and AAAAT (SEQ ID NO: 525). Such a flexible region is operably-linked in-frame to the modified Clostridial toxin as a fusion protein.

Thus, in an embodiment, a Clostridial toxin or Clostridial toxin chimeric disclosed in the present specification can further comprise a flexible region comprising a flexible spacer. In another embodiment, a Clostridial toxin or Clostridial toxin chimeric disclosed in the present specification can further comprise flexible region comprising a plurality of flexible spacers in tandem. In aspects of this embodiment, a flexible region can comprise in tandem, e.g., at least 1, 2, 3, 4, or 5 G-spacers; or at most 1, 2, 3, 4, or 5 G-spacers. In still other aspects of this embodiment, a flexible region can comprise in tandem, e.g., at least 1, 2, 3, 4, or 5 A-spacers; or at most 1, 2, 3, 4, or 5 A-spacers. In another aspect of this embodiment, a Clostridial toxin or Clostridial toxin chimeric can comprise a flexible region comprising one or more copies of the same flexible spacers, one or more copies of different flexible-spacer regions, or any combination thereof.

It is envisioned that a Clostridial toxin or Clostridial toxin chimeric disclosed in the present specification can comprise a flexible spacer in any and all locations with the proviso that the Clostridial toxin or Clostridial toxin chimeric is capable of performing the overall intoxication process. In aspects of this embodiment, a flexible spacer is positioned between, e.g., an enzymatic domain and a translocation domain, an enzymatic domain and a binding domain, an enzymatic domain and an exogenous protease cleavage site. In other aspects of this embodiment, a flexible spacer is positioned between, e.g., a binding domain and a translocation domain, a binding domain and an enzymatic domain, a binding domain and an exogenous protease cleavage site. In yet other aspects of this embodiment, a flexible spacer is positioned between, e.g., a translocation domain and an enzymatic domain, a translocation domain and a binding domain, a translocation domain and an exogenous protease cleavage site.

As another non-limiting example of an optional component, a Clostridial toxin or Clostridial toxin chimeric can further comprise an epitope-binding region. An epitope-binding region can be used in a wide variety of procedures involving, e.g., protein purification and protein visualization. Such an epitope-binding region is operably-linked in-frame to a modified Clostridial toxin as a fusion protein. Non-limiting examples of an epitope-binding region include, e.g., FLAG, Express™, human Influenza virus hemagglutinin (HA), human p62$^{c\text{-}Myc}$ protein (c-MYC), Vesicular Stomatitis Virus Glycoprotein (VSV-G), glycoprotein-D precursor of Herpes simplex virus (HSV), V5, AU1, and AU5; affinity-binding, such as. e.g., polyhistidine (HIS), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein. Non-limiting examples of specific protocols for selecting, making and using an appropriate binding peptide are described in, e.g., Epitope Tagging, pp. 17.90-17.93 (Sambrook and Russell, eds., MOLECULAR CLONING A LABORATORY MANUAL, Vol. 3, 3$^{rd}$ ed. 2001); ANTIBODIES: A LABORATORY MANUAL (Edward Harlow & David Lane, eds., Cold Spring Harbor Laboratory Press, 2$^{nd}$ ed. 1998); and USING ANTIBODIES: A LABORATORY MANUAL: PORTABLE PROTOCOL NO. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Thus, in an embodiment, a Clostridial toxin or Clostridial toxin chimeric disclosed in the present specification can further comprise an epitope-binding region. In another embodiment, a Clostridial toxin or Clostridial toxin chimeric disclosed in the present specification can further comprises a plurality of epitope-binding regions. In aspects of this embodiment, a Clostridial toxin or Clostridial toxin chimeric can comprise, e.g., at least 1, 2, 3, 4, or 5 epitope-binding regions. In other aspects of this embodiment, a Clostridial toxin or Clostridial toxin chimeric can comprise, e.g., at most 1, 2, 3, 4, or 5 epitope-binding regions. In another aspect of this embodiment, a modified Clostridial toxin can comprise one or more copies of the same epitope-binding region, one or more copies of different epitope-binding regions, or any combination thereof.

The location of an epitope-binding region can be in various positions, including, without limitation, at the amino terminus, within, or at the carboxyl terminus of a Clostridial toxin or Clostridial toxin chimeric. Thus, in an embodiment, an epitope-binding region is located at the amino-terminus of a Clostridial toxin or Clostridial toxin chimeric. In another embodiment, an epitope-binding region is located at the carboxyl-terminus of a modified Clostridial toxin.

Aspects of the present specification provide, in part, polynucleotide molecules. As used herein, the term "polynucleotide molecule" is synonymous with "nucleic acid molecule" and refers to a polymeric form of nucleotides, such as, e.g., ribonucleotides and deoxyribonucleotides. It is envisioned that any and all polynucleotide molecules that can encode a Clostridial toxin or Clostridial toxin chimeric disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagemid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Well-established molecular biology techniques that may be necessary to make a polynucleotide molecule encoding a Clostridial toxin or Clostridial toxin chimeric disclosed in the present specification including, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques are routine procedures well within the scope of one skilled in the art and from the teaching herein. Non-limiting examples of specific protocols necessary to make a polynucleotide molecule encoding a modified Clostridial toxin are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). Additionally, a variety of commercially available products useful for making a polynucleotide molecule encoding a Clostridial toxin or Clostridial toxin chimeric disclosed in the present specification are widely available. These protocols are routine procedures well within the scope of one skilled in the art and from the teaching herein.

Thus, in an embodiment, a polynucleotide molecule encodes a Clostridial toxin or Clostridial toxin chimeric disclosed in the present specification.

Another aspect of the present specification provides, in part, a method of producing a Clostridial toxin or Clostridial toxin chimeric disclosed in the present specification, such method comprising the step of expressing a polynucleotide molecule encoding a Clostridial toxin or Clostridial toxin chimeric in a cell. Another aspect of the present specification provides a method of producing a Clostridial toxin or Clostridial toxin chimeric disclosed in the present specification, such method comprising the steps of introducing an expression construct comprising a polynucleotide molecule encoding a Clostridial toxin or Clostridial toxin chimeric into a cell and expressing the expression construct in the cell.

The methods disclosed in the present specification include, in part, a Clostridial toxin or Clostridial toxin chimeric. It is envisioned that any and all Clostridial toxins or Clostridial toxin chimeras disclosed in the present specification can be produced using the methods disclosed in the present specification. It is also envisioned that any and all polynucleotide molecules encoding a Clostridial toxin or Clostridial toxin chimeric disclosed in the present specification can be useful in producing a Clostridial toxin or Clostridial toxin chimeric disclosed in the present specification using the methods disclosed in the present specification.

The methods disclosed in the present specification include, in part, an expression construct. An expression construct comprises a polynucleotide molecule disclosed in the present specification operably-linked to an expression vector useful for expressing the polynucleotide molecule in a cell or cell-free extract. A wide variety of expression vectors can be employed for expressing a polynucleotide molecule encoding a Clostridial toxin or Clostridial toxin chimeric disclosed in the present specification, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express a Clostridial toxin or Clostridial toxin chimeric under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

Thus, in aspects of this embodiment, a polynucleotide molecule encoding a Clostridial toxin or Clostridial toxin chimeric disclosed in the present specification operably-linked to an expression vector. In aspects of this embodiment, the expression vector is, e.g., a viral expression vector, a prokaryotic expression vector, a yeast expression vector, an insect expression vector, or a mammalian expression vector. On other aspects of this embodiment, a polynucleotide molecule encoding a Clostridial toxin or Clostridial toxin chimeric disclosed in the present specification operably-linked to a cell-free extract expression vector.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacteria cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria mengirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, $4^{th}$ ed. 2000); ANIMAL CELL CULTURE: A PRACTICAL APPROACH (John R. W. Masters ed., Oxford University Press, $3^{rd}$ ed. 2000); MOLECULAR CLONING A LABORATORY MANUAL, supra, (2001); BASIC CELL CULTURE: A PRACTICAL APPROACH (John M. Davis, Oxford Press, $2^{nd}$ ed. 2002); and CURRENT PROTOCOLS IN MOLECULAR BIOLOGY, supra, (2004). These protocols are routine procedures within the scope of one skilled in the art and from the teaching herein.

The methods disclosed in the present specification include, in part, introducing into a cell a polynucleotide molecule. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously. It is envisioned that any and all methods for introducing a polynucleotide molecule disclosed in the present specification into a cell can be used. Methods useful for introducing a polynucleotide molecule into a cell include, without limitation, chemical-mediated transfection or transformation such as, e.g., calcium chloride-mediated, calcium phosphate-mediated, diethyl-aminoethyl (DEAE) dextran-mediated, lipid-mediated, polyethyleneimine (PEI)-mediated, polylysine-mediated and polybrene-mediated; physical-mediated transfection or transformation, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce into a cell a polynucleotide molecule encoding a Clostridial toxin or Clostridial toxin chimeric disclosed in the present specification. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, *Transfection of adherent and suspended cells by calcium phosphate*, 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., *Polyethylenimine strategies for plasmid delivery to brain-derived cells*, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); LIPOFECTAMINE™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce into a cell a polynucleotide molecule encoding a Clostridial toxin or Clostridial toxin chimeric disclosed in the present specification. Physical techniques include, without limitation, electroporation, biolistic and microinjection. Biolistics and microinjection techniques perforate the cell wall in order to introduce the nucleic acid molecule into the cell, see, e.g., Jeike E. Biewenga et al., *Plasmid-mediated gene transfer in neurons* using the biolistics technique, 71(1) J. Neurosci. Methods 67-75 (1997); and John O'Brien & Sarah C. R. Lummis, Biolistic and diolistic transfection: using the gene gun to deliver DNA and lipophilic dyes into mammalian cells, 33(2) Methods 121-125 (2004). Electroporation, also termed electropermeabilization, uses brief, high-voltage, electrical pulses to create transient pores in the membrane through which the nucleic acid molecules enter and can be used effectively for stable and transient transfections of all cell types, see, e.g., M. Golzio et al., *In vitro and in vivo electric field-mediated permeabilization, gene transfer, and expression,* 33(2) Methods 126-135 (2004); and Oliver Gresch et al., *New non-viral method for gene transfer into primary cells,* 33(2) Methods 151-163 (2004).

In another aspect of this embodiment, a viral-mediated method, termed transduction, is used to introduce into a cell a polynucleotide molecule encoding a Clostridial toxin or Clostridial toxin chimeric disclosed in the present specification. In viral-mediated methods of transient transduction, the process by which viral particles infect and replicate in a host cell has been manipulated in order to use this mechanism to introduce a polynucleotide molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, *Lentiviral and MLV based retroviral vectors for ex vivo and in vivo gene transfer,* 33(2) Methods 164-172 (2004); and Maurizio Federico, *From lentiviruses to lentivirus vectors,* 229 Methods Mol. Biol. 3-15 (2003); E. M. Poeschla, *Non-primate lentiviral vectors,* 5(5) Curr. Opin. Mol. Ther. 529-540 (2003); Karim Benihoud et al, *Adenovirus vectors for gene delivery,* 10(5) Curr. Opin. Biotechnol. 440-447 (1999); H. Bueler, *Adeno-associated viral vectors for gene transfer and gene therapy,* 380(6) Biol. Chem. 613-622 (1999); Chooi M. Lai et al., *Adenovirus and adeno-associated virus vectors,* 21(12) DNA Cell Biol. 895-913 (2002); Edward A. Burton et al., *Gene delivery using herpes simplex virus vectors,* 21(12) DNA Cell Biol. 915-936 (2002); Paola Grandi et al., *Targeting HSV amplicon vectors,* 33(2) Methods 179-186 (2004); Ilya Frolov et al., *Alphavirus-based expression vectors: strategies and applications,* 93(21) Proc. Natl. Acad. Sci. U.S.A. 11371-11377 (1996); Markus U. Ehrengruber, *Alphaviral gene transfer in neurobiology,* 59(1) Brain Res. Bull. 13-22 (2002); Thomas A. Kost & J. Patrick Condreay, *Recombinant baculoviruses as mammalian cell gene-delivery vectors,* 20(4) Trends Biotechnol. 173-180 (2002); and A. Huser & C. Hofmann, *Baculovirus vectors: novel mammalian cell gene-delivery vehicles and their applications,* 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Wim T. J. M. C. Hermens et al., *Transient gene transfer to neurons and glia: analysis of adenoviral vector performance in the CNS and PNS,* 71(1) J. Neurosci. Methods 85-98 (1997); and Hiroyuki Mizuguchi et al., *Approaches for generating recombinant adenovirus vectors,* 52(3) Adv. Drug Deliv. Rev. 165-176 (2001). Transduction using adenoviral-based system do not support prolonged protein expression because the nucleic acid molecule is carried by an episome in the cell nucleus, rather than being integrated into the host cell chromosome. Adenoviral vector systems and specific protocols for how to use such vectors are disclosed in, e.g., VIRAPOWER™ Adenoviral Expression System (Invitrogen, Inc., Carlsbad, Calif.) and VIRAPOWER™ Adenoviral Expression System Instruction Manual 25-0543 version A, Invitrogen, Inc., (Jul. 15, 2002); and ADEASY™ Adenoviral Vector System (Stratagene, Inc., La Jolla, Calif.) and ADEASY™ Adenoviral Vector System Instruction Manual 064004f, Stratagene, Inc.

Polynucleotide molecule delivery can also use single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., *Transient production of retroviral-and lentiviral-based vectors for the transduction of Mammalian cells,* 285 Methods Mol. Biol. 141-148 (2004); Armin Blesch, Lentiviral and MLV based retroviral vectors for ex vivo and in vivo gene transfer, 33(2) Methods 164-172 (2004); Félix Recillas-Targa, *Gene transfer and expression in mammalian cell lines and transgenic animals,* 267 Methods Mol. Biol. 417-433 (2004); and Roland Wolkowicz et al., *Lentiviral vectors for the delivery of DNA into mammalian cells,* 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., *In vivo gene delivery and stable transduction of non-dividing cells by a lentiviral vector,* 272 (5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., Manfred Gossen & Hermann Bujard, Tight control of gene expression in eukaryotic cells by tetracycline-responsive promoters, U.S. Pat. No.

5,464,758 (Nov. 7, 1995) and Hermann Bujard & Manfred Gossen, Methods for regulating gene expression, U.S. Pat. No. 5,814,618 (Sep. 29, 1998) David S. Hogness, Polynucleotides encoding insect steroid hormone receptor polypeptides and cells transformed with same, U.S. Pat. No. 5,514,578 (May 7, 1996) and David S. Hogness, Polynucleotide encoding insect ecdysone receptor, U.S. Pat. No. 6,245,531 (Jun. 12, 2001); Elisabetta Vegeto et al., Progesterone receptor having C. terminal hormone binding domain truncations, U.S. Pat. No. 5,364,791 (Nov. 15, 1994), Elisabetta Vegeto et al., Mutated steroid hormone receptors, methods for their use and molecular switch for gene therapy, U.S. Pat. No. 5,874,534 (Feb. 23, 1999) and Elisabetta Vegeto et al., Mutated steroid hormone receptors, methods for their use and molecular switch for gene therapy, U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems (BD Biosciences-Clontech, Palo Alto, Calif.) and BD™ Tet-Off and Tet-On Gene Expression Systems User Manual, PT3001-1, BD Biosciences Clontech, (Mar. 14, 2003), GENESWITCH™ System (Invitrogen, Inc., Carlsbad, Calif.) and GENESWITCH™ System A Mifepristone-Regulated Expression System for Mammalian Cells version D, 25-0313, Invitrogen, Inc., (Nov. 4, 2002); VIRAPOWER™ Lentiviral Expression System (Invitrogen, Inc., Carlsbad, Calif.) and VIRAPOWER™ Lentiviral Expression System Instruction Manual 25-0501 version E, Invitrogen, Inc., (Dec. 8, 2003); and COMPLETE CONTROL® Retroviral Inducible Mammalian Expression System (Stratagene, La Jolla, Calif.) and COMPLETE CONTROL® Retroviral Inducible Mammalian Expression System Instruction Manual, 064005e.

The methods disclosed in the present specification include, in part, expressing from a polynucleotide molecule a Clostridial toxin or Clostridial toxin chimeric disclosed in the present specification. It is envisioned that any of a variety of expression systems may be useful for expressing from a polynucleotide molecule a Clostridial toxin or Clostridial toxin chimeric disclosed in the present specification, including, without limitation, cell-based systems and cell-free expression systems. Cell-based systems include, without limitation, viral expression systems, prokaryotic expression systems, yeast expression systems, baculoviral expression systems, insect expression systems, and mammalian expression systems. Cell-free systems include, without limitation, wheat germ extracts, rabbit reticulocyte extracts, and E. coli extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins*, 80(9) CURRENT SCIENCE 1121-1128, (2001). These protocols are routine procedures well within the scope of one skilled in the art and from the teaching herein.

A variety of cell-based expression procedures are useful for expressing a polynucleotide molecule encoding a Clostridial toxin or Clostridial toxin chimeric disclosed in the present specification. Examples included, without limitation, viral expression systems, prokaryotic expression systems, yeast expression systems, baculoviral expression systems, insect expression systems, and mammalian expression systems. Viral expression systems include, without limitation, the VIRAPOWER™ Lentiviral (Invitrogen, Inc., Carlsbad, Calif.), the Adenoviral Expression Systems (Invitrogen, Inc., Carlsbad, Calif.), the ADEASY™ XL Adenoviral Vector System (Stratagene, La Jolla, Calif.) and the VIRAPORT® Retroviral Gene Expression System (Stratagene, La Jolla, Calif.). Non-limiting examples of prokaryotic expression systems include the CHAMPION™ pET Expression System (EMD Biosciences-Novagen, Madison, Wis.), the TRIEX™ Bacterial Expression System (EMD Biosciences-Novagen, Madison, Wis.), the QIAEXPRESS® Expression System (QIAGEN, Inc.), and the AFFINITY® Protein Expression and Purification System (Stratagene, La Jolla, Calif.). Yeast expression systems include, without limitation, the EASY-SELECT™ *Pichia* Expression Kit (Invitrogen, Inc., Carlsbad, Calif.), the YES-ECHO™ Expression Vector Kits (Invitrogen, Inc., Carlsbad, Calif.) and the SPECTRA™ *S. pombe* Expression System (Invitrogen, Inc., Carlsbad, Calif.). Non-limiting examples of baculoviral expression systems include the BACULODIRECT™ (Invitrogen, Inc., Carlsbad, Calif.), the BAC-TO-BAC® (Invitrogen, Inc., Carlsbad, Calif.), and the BD BACULOGOLD™ (BD Biosciences-Pharmingen, San Diego, Calif.). Insect expression systems include, without limitation, the *Drosophila* Expression System (DES®) (Invitrogen, Inc., Carlsbad, Calif.), INSECTSELECT™ System (Invitrogen, Inc., Carlsbad, Calif.) and INSECTDIRECT™ System (EMD Biosciences-Novagen, Madison, Wis.). Non-limiting examples of mammalian expression systems include the T-REX™ (Tetracycline-Regulated Expression) System (Invitrogen, Inc., Carlsbad, Calif.), the FLP-IN™ T-REX™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the EXCHANGER® System, INTERPLAY™ Mammalian TAP System (Stratagene, La Jolla, Calif.), COMPLETE CONTROL® Inducible Mammalian Expression System (Stratagene, La Jolla, Calif.) and LACSWITCH® II Inducible Mammalian Expression System (Stratagene, La Jolla, Calif.).

Another procedure of expressing a polynucleotide molecule encoding a Clostridial toxin or Clostridial toxin chimeric disclosed in the present specification employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ActivePro In Vitro Translation Kit (Ambion, Inc., Austin, Tex.), the ECOPRO™ System (EMD Biosciences-Novagen, Madison, Wis.) and the EXPRESSWAY™ Plus Expression System (Invitrogen, Inc., Carlsbad, Calif.). Eukaryotic cell extract include, without limitation, the RTS 100 Wheat Germ CECF Kit (Roche Applied Science, Indianapolis, Ind.), the TNT® Coupled Wheat Germ Extract Systems (Promega Corp., Madison, Wis.), the Wheat Germ IVT™ Kit (Ambion, Inc., Austin, Tex.), the Retic Lysate IVT™ Kit (Ambion, Inc., Austin, Tex.), the PROTEINSCRIPT® II System (Ambion, Inc., Austin, Tex.) and the TNT® Coupled Reticulocyte Lysate Systems (Promega Corp., Madison, Wis.).

The Clostridial toxin or Clostridial toxin chimeric disclosed in the present specification disclosed in the present specification are produced by the cell in a single-chain form. In order to achieve full activity, this single-chain form has to be converted into its di-chain form. As discussed above, this conversion process is achieved by cleaving a protease cleavage site located within the di-chain loop region of the Clostridial toxin or Clostridial toxin chimeric disclosed in the present specification. This conversion process can be performed using a standard in vitro proteolytic cleavage assay or in a cell-based proteolytic cleavage system as described in patent application Ghanshani, et al., Methods of Intracellular Conversion of Single-Chain Proteins into their Di-chain Form, U.S. Pat. No. 8,546,108, which is hereby incorporated by reference in its entirety.

Aspects of the present specification disclose, in part, a composition comprising a Clostridial toxin or Clostridial toxin chimeric disclosed in the present specification. In a further aspect, the composition is a pharmaceutical acceptable composition. As used herein, the term "pharmaceutically acceptable" refers to any molecular entity or composition that does not produce an adverse, allergic, or other untoward or unwanted reaction when administered to an individual. As used herein, the term "pharmaceutically acceptable composition" is synonymous with "pharmaceutical composition" and refers to a therapeutically effective concentration of an active ingredient, such as, e.g., any of the Clostridial toxins or Clostridial toxin chimeras disclosed in the present specification. A pharmaceutical composition comprising a Clostridial toxin or Clostridial toxin chimeric is useful for medical and veterinary applications. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition comprising a Clostridial toxin or Clostridial toxin chimeric disclosed in the present specification can optionally include a pharmaceutically acceptable carriers that facilitate processing of an active ingredient into pharmaceutically acceptable compositions. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or is permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7$^{th}$ ed. 1999); REMINGTON: THE SCIENCE AND PRACTICE OF PHARMACY (Alfonso R. Gennaro ed., Lippincott, Williams & Wilkins, 20$^{th}$ ed. 2000); GOODMAN & GILMAN'S THE PHARMACOLOGICAL BASIS OF THERAPEUTICS (Joel G. Hardman et al., eds., McGraw-Hill Professional, 10$^{th}$ ed. 2001); and HANDBOOK OF PHARMACEUTICAL EXCIPIENTS (Raymond C. Rowe et al., APhA Publications, 4$^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and refers to for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many different acids, including, but not limited to, hydrochloric, sulfuric, acetic, lactic, tartaric, malic, and succinic. Salts tend to be more soluble in aqueous or other protonic solvents than are the corresponding free base forms. It is understood that these and other substances known in the art of pharmacology can be included in a pharmaceutical composition useful in the specification.

In an embodiment, a composition comprises a Clostridial toxin or Clostridial toxin chimeric disclosed in the present specification. In an aspect of this embodiment, the composition is a pharmaceutical composition comprising a Clostridial toxin or Clostridial toxin chimeric disclosed in the present specification. In aspects of this embodiment, a pharmaceutical composition comprising Clostridial toxin or Clostridial toxin chimeric disclosed in the present specification further comprises a pharmacological carrier, a pharmaceutical component, or both a pharmacological carrier and a pharmaceutical component. In other aspects of this embodiment, a pharmaceutical composition comprising a Clostridial toxin or Clostridial toxin chimeric disclosed in the present specifica- Aspects of the present specification can also be described as follows:
1. A Clostridial toxin comprising at least one inactivation cleavage site located within an inactivation cleavage site region, wherein the inactivation cleavage site region is located in the translocation domain and/or the H$_{CN}$ binding subdomain, wherein the at least one inactivation cleavage site comprises a dual Thrombin-Thrombin site, a Factor Xa site, a dual Factor Xa-Thrombin site, and/or a MMP-9 site.
2. A Clostridial toxin comprising a Clostridial toxin enzymatic domain, a Clostridial toxin translocation domain, a Clostridial toxin binding domain, a di-chain loop region, an exogenous protease cleavage site, and at least two inactivation cleavage sites located within an inactivation cleavage site region; wherein the exogenous protease cleavage site located within the di-chain loop region.
3. A Clostridial toxin of aspect 2, wherein the inactivation cleavage sites comprise a dual Thrombin-Thrombin site and/or a dual Factor Xa-Thrombin site.
4. A Clostridial toxin chimeric comprising a Clostridial toxin enzymatic domain, a Clostridial toxin translocation domain, a non-Clostridial toxin binding domain, and an inactivation cleavage located within an inactivation cleavage site region, wherein the inactivation cleavage site region is located in the translocation domain and/or the H$_{CN}$ binding subdomain.
5. The Clostridial toxin and/or Clostridial toxin chimeric of aspects 1-4, wherein the inactivation cleavage site region comprises amino acids 462-496 of SEQ ID NO: 1, SEQ ID NO: 2, SEQ ID NO: 4 and/or SEQ ID NO: 5; amino acids 458-492 of SEQ ID NO: 3; amino acids 464-487 of SEQ ID NO: 6, SEQ ID NO: 7, SEQ ID NO: 8, SEQ ID NO: 9, and/or SEQ ID NO: 10; amino acids 463-496 of SEQ ID NO: 11 and/or SEQ ID NO: 12; amino acids 458-491 of SEQ ID NO: 13 and/or SEQ ID NO: 14; amino acids 434-467 of SEQ ID NO: 15, SEQ ID NO: 16, and/or SEQ ID NO: 17; amino acids 453-486 of SEQ ID NO: 18, SEQ ID NO: 19, and/or SEQ ID NO: 20; amino acids 458-491 of SEQ ID NO: 21; amino acids 443-476 of SEQ ID NO: 23; and/or amino acids 434-467 of SEQ ID NO: 24 and/or SEQ ID NO: 25.
6. The Clostridial toxin and/or Clostridial toxin chimeric of aspects 1-4, wherein the inactivation cleavage site region comprises amino acids 618-634 of SEQ ID NO: 1, SEQ ID NO: 2, SEQ ID NO: 4 and/or SEQ ID NO: 5; amino acids 614-630 of SEQ ID NO: 3; amino acids 605-621 of SEQ ID NO: 6, SEQ ID NO: 7, SEQ ID NO: 8, SEQ ID NO: 9, and/or SEQ ID NO: 10; amino acids 613-629 of SEQ ID NO: 11 and/or SEQ ID NO: 12; amino acids 609-625 of SEQ ID NO: 13 and/or SEQ ID NO: 14; amino acids 587-603 of SEQ ID NO: 15, SEQ ID NO: 16, and/or SEQ ID NO: 17; amino acids 604-620 of SEQ ID NO: 18; amino acids 605-621 of SEQ ID NO: 19 and/or SEQ ID NO: 20; amino acids 610-626 of SEQ ID NO: 21; amino acids 596-612 of SEQ ID NO: 23; and/or amino acids 587-603 of SEQ ID NO: 24 and/or SEQ ID NO: 25.
7. The Clostridial toxin and/or Clostridial toxin chimeric of aspects 1-4, wherein the inactivation cleavage site region comprises amino acids 638-651 of SEQ ID NO: 1, SEQ ID NO: 2, SEQ ID NO: 4 and/or SEQ ID NO: 5; amino acids 634-647 of SEQ ID NO: 3; amino acids 625-638 of SEQ ID NO: 6, SEQ ID NO: 7, SEQ ID NO: 8, SEQ ID NO: 9, and/or SEQ ID NO: 10; amino acids 633-646 of SEQ ID NO: 11 and/or SEQ ID NO: 12; amino acids 629-642 of SEQ ID NO: 13 and/or SEQ ID NO: 14; amino acids 607-620 of SEQ ID NO: 15, SEQ ID NO: 16, and/or SEQ ID NO: 17; amino acids 624-637 of SEQ ID NO: 18; amino acids 625-638 of SEQ ID NO: 19 and/or SEQ ID NO: 20; amino acids 630-643 of SEQ ID NO: 21; amino acids 616-629 of SEQ ID NO: 23; and/or amino acids 607-620 of SEQ ID NO: 24 and/or SEQ ID NO: 25.
8. The Clostridial toxin and/or Clostridial toxin chimeric of aspects 1-4, wherein the inactivation cleavage site region comprises amino acids 665-687 of SEQ ID NO: 1, SEQ ID NO: 2, SEQ ID NO: 4 and/or SEQ ID NO: 5; amino acids 661-683 of SEQ ID NO: 3; amino acids 652-674 of SEQ ID NO: 6, SEQ ID NO: 7, SEQ ID NO: 8, SEQ ID NO: 9, and/or SEQ ID NO: 10; amino acids 660-682 of SEQ ID NO: 11 and/or SEQ ID NO: 12; amino acids 656-678 of SEQ ID NO: 13 and/or SEQ ID NO: 14; amino acids 634-659 of SEQ ID NO: 15, SEQ ID NO: 16, and/or SEQ ID NO: 17; amino acids 651-676 of SEQ ID NO: 18; amino acids 652-677 of SEQ ID NO: 19 and/or SEQ ID NO: 20; amino acids 657-679 of SEQ ID NO: 21; amino acids 643-668 of SEQ ID NO: 23; and/or amino acids 634-659 of SEQ ID NO: 24 and/or SEQ ID NO: 25.
9. The Clostridial toxin and/or Clostridial toxin chimeric of aspects 1-4, wherein the inactivation cleavage site region comprises amino acids 752-765 of SEQ ID NO: 1, SEQ ID NO: 2, SEQ ID NO: 4 and/or SEQ ID NO: 5; amino acids 748-761 of SEQ ID NO: 3; amino acids 739-752 of SEQ ID NO: 6, SEQ ID NO: 7, SEQ ID NO: 8, SEQ ID NO: 9, and/or SEQ ID NO: 10; amino acids 747-760 of SEQ ID NO: 11 and/or SEQ ID NO: 12; amino acids 743-756 of SEQ ID NO: 13 and/or SEQ ID NO: 14; amino acids 724-739 of SEQ ID NO: 15, SEQ ID NO: 16, and/or SEQ ID NO: 17; amino acids 741-756 of SEQ ID NO: 18; amino acids 742-757 of SEQ ID NO: 19 and/or SEQ ID NO: 20; amino acids 744-757 of SEQ ID NO: 21; amino acids 733-748 of SEQ ID NO: 23; and/or amino acids 724-739 of SEQ ID NO: 24 and/or SEQ ID NO: 25.
10. The Clostridial toxin and/or Clostridial toxin chimeric of aspects 1-4, wherein the inactivation cleavage site region comprises amino acids 826-835 of SEQ ID NO: 1, SEQ ID NO: 2, SEQ ID NO: 4 and/or SEQ ID NO: 5; amino acids 824-831 of SEQ ID NO: 3; amino acids 813-824 of SEQ ID NO: 6, SEQ ID NO: 7, SEQ ID NO: 8, SEQ ID NO: 9, and/or SEQ ID NO: 10; amino acids 821-830 of SEQ ID NO: 11 and/or SEQ ID NO: 12; amino acids 817-826 of SEQ ID NO: 13 and/or SEQ ID NO: 14; amino acids 800-809 of SEQ ID NO: 15, SEQ ID NO: 16, and/or SEQ ID NO: 17; amino acids 817-826 of SEQ ID NO: 18; amino acids 818-827 of SEQ ID NO: 19 and/or SEQ ID NO: 20; amino acids 818-827 of SEQ ID NO: 21; amino acids 809-819 of SEQ ID NO: 23; and/or amino acids 800-809 of SEQ ID NO: 24 and/or SEQ ID NO: 25.
11. The Clostridial toxin and/or Clostridial toxin chimeric of aspects 1-4, wherein the inactivation cleavage site region comprises amino acids 844-863 of SEQ ID NO: 1, SEQ ID NO: 2, SEQ ID NO: 4 and/or SEQ ID NO: 5; amino acids 840-859 of SEQ ID NO: 3;; amino acids 831-850 of SEQ ID NO: 6, SEQ ID NO: 7, SEQ ID NO: 8, SEQ ID NO: 9, and/or SEQ ID NO: 10; amino acids 839-858 of SEQ ID NO: 11 and/or SEQ ID NO: 12; amino acids 835-854 of SEQ ID NO: 13 and/or SEQ ID NO: 14; amino acids 818-837 of SEQ ID NO: 15, SEQ ID NO: 16, and/or SEQ ID NO: 17; amino acids 835-854 of SEQ ID NO: 18; amino acids 836-855 of SEQ ID NO: 19 and/or SEQ ID NO: 20; amino acids 836-855 of SEQ ID NO: 21; amino acids 828-847 of SEQ ID NO: 23; and/or amino acids 818-837 of SEQ ID NO: 24 and/or SEQ ID NO: 25.

12. The Clostridial toxin and/or Clostridial toxin chimeric of aspects 1-4, wherein the inactivation cleavage site region comprises amino acids 871-895 of SEQ ID NO: 1, SEQ ID NO: 2, SEQ ID NO: 4 and/or SEQ ID NO: 5; amino acids 867-891 of SEQ ID NO: 3; amino acids 858-882 of SEQ ID NO: 6, SEQ ID NO: 7, SEQ ID NO: 8, SEQ ID NO: 9, and/or SEQ ID NO: 10; amino acids 866-890 of SEQ ID NO: 11 and/or SEQ ID NO: 12; amino acids 862-886 of SEQ ID NO: 13 and/or SEQ ID NO: 14; amino acids 845-869 of SEQ ID NO: 15, SEQ ID NO: 16, and/or SEQ ID NO: 17; amino acids 862-886 of SEQ ID NO: 18; amino acids 863-887 of SEQ ID NO: 19 and/or SEQ ID NO: 20; amino acids 863-887 of SEQ ID NO: 21; amino acids 855-879 of SEQ ID NO: 23; and/or amino acids 845-869 of SEQ ID NO: 24 and/or SEQ ID NO: 25.

13. The Clostridial toxin and/or Clostridial toxin chimeric of aspects 1-12, wherein the Clostridial toxin enzymatic domain comprises a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a BaNT enzymatic domain, and/or a BuNT enzymatic domain.

14. The Clostridial toxin and/or Clostridial toxin chimeric of aspects 1-13, wherein the inactivation cleavage site comprises Thrombin cleavage sites, Plasmin cleavage sites, Coagulation Factor VIIa cleavage sites, Coagulation Factor IXa cleavage sites, Coagulation Factor Xa cleavage sites, Coagulation Factor XIa cleavage sites, Coagulation Factor XIIa cleavage sites, plasma kallikrein cleavage sites, protease-activated G protein-coupled receptor-1 (PAR1) cleavage sites, PAR2 cleavage sites, PAR3 cleavage sites, PAR4 cleavage sites, Matrix Metalloproteinase-2 (MMP-2) cleavage sites, Matrix Metalloproteinase-9 (MMP-9) cleavage sites, Furin cleavage sites, urokinase-type Plasminogen activator (uPA) cleavage sites, tissue-type Plasminogen activator (tPA) cleavage sites, Tryptase-ε cleavage sites, Mouse mast cell protease-7 (mMCP-7) cleavage sites, endothelin-converting enzyme-1 (ECE-1) cleavage sites, Kell blood group cleavage sites, DPPIV cleavage sites, ADAM metallopeptidase with thrombospondin type 1 motif-13 (ADAMTS13) cleavage sites, and/or Cathepsin L cleavage sites.

15. The Clostridial toxin and/or Clostridial toxin chimeric of aspects 1-14, wherein the Clostridial toxin translocation domain comprises a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, and/or a BuNT translocation domain.

16. The Clostridial toxin and/or Clostridial toxin chimeric of aspects 1-15, wherein the inactivation cleavage site comprises a dual Thrombin-Thrombin site, a Factor Xa site, a dual Factor Xa-Thrombin site, and/or a MMP-9 site.

17. The Clostridial toxin and/or Clostridial toxin chimeric of aspects 1-16, wherein the, a non-Clostridial toxin binding domain, comprises a opioid binding domain, a tachykinin binding domain, a melanocortin binding domain, a galanin binding domain, a granin binding domain, a Neuropeptide Y related peptide binding domain, a neurohormone binding domain, a neuroregulatory cytokine binding domain, a kinin peptide binding domain, a growth factor binding domain, and/or a glucagon like hormone binding domain.

18. A BoNT/A comprising an inactivation cleavage site located within an inactivation cleavage site region, wherein the inactivation cleavage site region is located in the translocation domain and/or the $H_{CN}$ binding subdomain.

19. A Clostridial toxin comprising a BoNT/A enzymatic domain, a BoNT/A translocation domain, a BoNT/A binding domain, and an inactivation cleavage site located within an inactivation cleavage site region, wherein the inactivation cleavage site region is located in the translocation domain and/or the $H_{CN}$ binding subdomain.

20. A Clostridial toxin comprising a BoNT/A enzymatic domain, a BoNT/A translocation domain, a BoNT/A binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

21. A Clostridial toxin comprising a BoNT/A enzymatic domain, a BoNT/A translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.

22. A Clostridial toxin comprising a BoNT/A enzymatic domain, a BoNT/A translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

23. The toxin and/or chimeric of aspects 18-22, wherein the inactivation cleavage site region comprises amino acids 462-496, 618-634, 638-651, 665-687, 752-765, 826-835, 844-863, and/or 871-895 of SEQ ID NO: 1, SEQ ID NO: 2, SEQ ID NO: 4 and/or SEQ ID NO: 5, and/or amino acids 458-492, 614-630, 634-647, 665-687, 748-761, 822-831, 840-859, and/or 867-891 of SEQ ID NO: 3.

24. A BoNT/B comprising an inactivation cleavage site located within an inactivation cleavage site region, wherein the inactivation cleavage site region is located in the translocation domain and/or the $H_{CN}$ binding subdomain.

25. A Clostridial toxin comprising a BoNT/B enzymatic domain, a BoNT/B translocation domain, a BoNT/B binding domain, and an inactivation cleavage site located within an inactivation cleavage site region, wherein the inactivation cleavage site region is located in the translocation domain and/or the $H_{CN}$ binding subdomain.

26. A Clostridial toxin comprising a BoNT/B enzymatic domain, a BoNT/B translocation domain, a BoNT/B binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

27. A Clostridial toxin comprising a BoNT/B enzymatic domain, a BoNT/B translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.

28. A Clostridial toxin comprising a BoNT/B enzymatic domain, a BoNT/B translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.
29. The toxin and/or chimeric of aspects 24-28, wherein the inactivation cleavage site region comprises amino acids 464-487, 605-621, 625-638, 652-674, 739-752, 813-824, 831-850, and/or 858-882 of SEQ ID NO: 6, SEQ ID NO: 7, SEQ ID NO: 8, SEQ ID NO: 9, and/or SEQ ID NO: 10.
30. A BoNT/C1 comprising an inactivation cleavage site located within an inactivation cleavage site region, wherein the inactivation cleavage site region is located in the translocation domain and/or the $H_{CN}$ binding subdomain.
31. A Clostridial toxin comprising a BoNT/C1 enzymatic domain, a BoNT/C1 translocation domain, a BoNT/C1 binding domain, and an inactivation cleavage site located within an inactivation cleavage site region, wherein the inactivation cleavage site region is located in the translocation domain and/or the $H_{CN}$ binding subdomain.
32. A Clostridial toxin comprising a BoNT/C1 enzymatic domain, a BoNT/C1 translocation domain, a BoNT/C1 binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.
33. A Clostridial toxin comprising a BoNT/C1 enzymatic domain, a BoNT/C1 translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.
34. A Clostridial toxin comprising a BoNT/C1 enzymatic domain, a BoNT/C1 translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.
35. The toxin and/or chimeric of aspects 30-34, wherein the inactivation cleavage site region comprises amino acids 463-496, 613-629, 633-646, 660-682, 747-760, 821-830, 839-858, and/or 866-890 of SEQ ID NO: 11 and/or SEQ ID NO: 12.
36. A BoNT/D comprising an inactivation cleavage site located within an inactivation cleavage site region, wherein the inactivation cleavage site region is located in the translocation domain and/or the $H_{CN}$ binding subdomain.
37. A Clostridial toxin comprising a BoNT/D enzymatic domain, a BoNT/D translocation domain, a BoNT/D binding domain, and an inactivation cleavage site located within an inactivation cleavage site region, wherein the inactivation cleavage site region is located in the translocation domain and/or the $H_{CN}$ binding subdomain.
38. A Clostridial toxin comprising a BoNT/D enzymatic domain, a BoNT/D translocation domain, a BoNT/D binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.
39. A Clostridial toxin comprising a BoNT/D enzymatic domain, a BoNT/D translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.
40. A Clostridial toxin comprising a BoNT/D enzymatic domain, a BoNT/D translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.
41. The toxin and/or chimeric of aspects 36-40, wherein the inactivation cleavage site region comprises amino acids 458-491, 609-625, 629-642, 656-678, 743-756, 817-826, 835-854, and/or 862-886 of SEQ ID NO: 13 and/or SEQ ID NO: 14.
42. A BoNT/E comprising an inactivation cleavage site located within an inactivation cleavage site region, wherein the inactivation cleavage site region is located in the translocation domain and/or the $H_{CN}$ binding subdomain.
43. A Clostridial toxin comprising a BoNT/E enzymatic domain, a BoNT/E translocation domain, a BoNT/E binding domain, and an inactivation cleavage site located within an inactivation cleavage site region, wherein the inactivation cleavage site region is located in the translocation domain and/or the $H_{CN}$ binding subdomain.
44. A Clostridial toxin comprising a BoNT/E enzymatic domain, a BoNT/E translocation domain, a BoNT/E binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.
45. A Clostridial toxin comprising a BoNT/E enzymatic domain, a BoNT/E translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.
46. A Clostridial toxin comprising a BoNT/E enzymatic domain, a BoNT/E translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.
47. The toxin and/or chimeric of aspects 42-46, wherein the inactivation cleavage site region comprises amino acids 434-467, 587-603, 607-620, 634-659, 724-739, 800-809, 818-837, and/or 845-869 of SEQ ID NO: 15, SEQ ID NO: 16, and/or SEQ ID NO: 17.
48. A BoNT/F comprising an inactivation cleavage site located within an inactivation cleavage site region, wherein the inactivation cleavage site region is located in the translocation domain and/or the $H_{CN}$ binding subdomain.

49. A Clostridial toxin comprising a BoNT/F enzymatic domain, a BoNT/F translocation domain, a BoNT/F binding domain, and an inactivation cleavage site located within an inactivation cleavage site region, wherein the inactivation cleavage site region is located in the translocation domain and/or the $H_{CN}$ binding subdomain.

50. A Clostridial toxin comprising a BoNT/F enzymatic domain, a BoNT/F translocation domain, a BoNT/F binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

51. A Clostridial toxin comprising a BoNT/F enzymatic domain, a BoNT/F translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.

52. A Clostridial toxin comprising a BoNT/F enzymatic domain, a BoNT/F translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

53. The toxin and/or chimeric of aspects 48-52, wherein the inactivation cleavage site region comprises amino acids 453-486, 604-620, 624-637, 651-676, 741-756, 817-826, 835-854, and/or 862-886 of SEQ ID NO: 18; and/or amino acids 453-486, 605-621, 625-638, 652-677, 742-757, 818-827, 836-855, and/or 863-887 of SEQ ID NO: 19 and/or SEQ ID NO: 20.

54. A BoNT/G comprising an inactivation cleavage site located within an inactivation cleavage site region, wherein the inactivation cleavage site region is located in the translocation domain and/or the $H_{CN}$ binding subdomain.

55. A Clostridial toxin comprising a BoNT/G enzymatic domain, a BoNT/G translocation domain, a BoNT/G binding domain, and an inactivation cleavage site located within an inactivation cleavage site region, wherein the inactivation cleavage site region is located in the translocation domain and/or the $H_{CN}$ binding subdomain.

56. A Clostridial toxin comprising a BoNT/G enzymatic domain, a BoNT/G translocation domain, a BoNT/G binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

57. A Clostridial toxin comprising a BoNT/G enzymatic domain, a BoNT/G translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.

58. A Clostridial toxin comprising a BoNT/G enzymatic domain, a BoNT/G translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

59. The toxin and/or chimeric of aspects 54-58, wherein the inactivation cleavage site region comprises amino acids 458-491, 610-626, 630-643, 657-679, 744-757, 818-827, 836-855, and/or 863-887 of SEQ ID NO: 21.

60. A BaNT comprising an inactivation cleavage site located within an inactivation cleavage site region, wherein the inactivation cleavage site region is located in the translocation domain and/or the $H_{CN}$ binding subdomain.

61. A Clostridial toxin comprising a BaNT enzymatic domain, a BaNT translocation domain, a BaNT binding domain, and an inactivation cleavage site located within an inactivation cleavage site region, wherein the inactivation cleavage site region is located in the translocation domain and/or the $H_{CN}$ binding subdomain.

62. A Clostridial toxin comprising a BaNT enzymatic domain, a BaNT translocation domain, a BaNT binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

63. A Clostridial toxin comprising a BaNT enzymatic domain, a BaNT translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.

64. A Clostridial toxin comprising a BaNT enzymatic domain, a BaNT translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

65. The toxin and/or chimeric of aspects 60-64, wherein the inactivation cleavage site region comprises amino acids 443-476, 596-612, 616-629, 643-668, 733-748, 809-819, 828-847, and/or 855-879 of SEQ ID NO: 23.

66. A BuNT comprising an inactivation cleavage site located within an inactivation cleavage site region, wherein the inactivation cleavage site region is located in the translocation domain and/or the $H_{CN}$ binding subdomain.

67. A Clostridial toxin comprising a BuNT enzymatic domain, a BuNT translocation domain, a BuNT binding domain, and an inactivation cleavage site located within an inactivation cleavage site region, wherein the inactivation cleavage site region is located in the translocation domain and/or the $H_{CN}$ binding subdomain.

68. A Clostridial toxin comprising a BuNT enzymatic domain, a BuNT translocation domain, a BuNT binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

69. A Clostridial toxin comprising a BuNT enzymatic domain, a BuNT translocation domain, a non-Clostridial toxin binding domain, and an inactivation cleavage site located within an inactivation cleavage site region, wherein the inactivation cleavage site region is located in the translocation domain and/or the $H_{CN}$ binding subdomain.

70. A Clostridial toxin comprising a BuNT enzymatic domain, a BuNT translocation domain, a non-Clostridial toxin binding domain, an exogenous protease cleavage site, a di-chain loop region, and an inactivation cleavage site located within an inactivation cleavage site region, wherein the exogenous protease cleavage site is located within the di-chain loop region; the wherein inactivation cleavage site region is located in the translocation domain and/or the $H_{CN}$ binding subdomain.

71. The toxin and/or chimeric of aspects 66-70, wherein the inactivation cleavage site region comprises amino acids 434-467, 587-603, 607-620, 634-659, 724-739, 800-809, 818-837, and/or 845-869 of SEQ ID NO: 24 and/or SEQ ID NO: 25.

72. The toxin and/or chimeric of aspects 1-71, wherein the Clostridial toxin and/or Clostridial toxin chimeric comprising an inactivation cleavage site has a safety margin that is greater relative to the same and/or similar to the Clostridial toxin and/or Clostridial toxin chimeric, but without the inactivation cleavage site.

73. The toxin and/or chimeric of aspect 72, wherein the Clostridial toxin and/or Clostridial toxin chimeric comprising an inactivation cleavage site has a safety margin that is greater than at least 10%, at least 20%, at least 30%, at least 40%, at least 50%, at least 60%, at least 70%, at least 80%, at least 90%, at least 100%, 110%, at least 120%, at least 130%, at least 140%, at least 150%, at least 160%, at least 170%, at least 180%, at least 190%, at least 200%, 210%, at least 220%, at least 230%, at least 240%, at least 250%, at least 260%, at least 270%, at least 280%, at least 290%, and/or at least 300%, relative to the same and/or similar Clostridial toxin and/or Clostridial toxin chimeric, but without the inactivation cleavage site, and/or wherein Clostridial toxin and/or Clostridial toxin chimeric comprising an inactivation cleavage site has a safety margin that is greater than at most 10%, at most 20%, at most 30%, at most 40%, at most 50%, at most 60%, at most 70%, at most 80%, at most 90%, at most 100%, 110%, at most 120%, at most 130%, at most 140%, at most 150%, at most 160%, at most 170%, at most 180%, at most 190%, at most 200%, 210%, at most 220%, at most 230%, at most 240%, at most 250%, at most 260%, at most 270%, at most 280%, at most 290%, and/or at most 300%, relative to the same and/or similar Clostridial toxin and/or Clostridial toxin chimeric, but without the inactivation cleavage site, and/or wherein the Clostridial toxin and/or Clostridial toxin chimeric comprising an inactivation cleavage site has a safety margin that is greater by about 10% to about 300%, about 20% to about 300%, about 30% to about 300%, about 40% to about 300%, about 50% to about 300%, about 60% to about 300%, about 70% to about 300%, about 80% to about 300%, about 90% to about 300%, and/or about 100% to about 300%, relative to the same and/or similar Clostridial toxin and/or Clostridial toxin chimeric, but without the inactivation cleavage site, or wherein the Clostridial toxin and/or Clostridial toxin chimeric comprising an inactivation cleavage site has a safety margin that is greater than at least 1-fold, at least 1-fold, at least 3-fold, at least 4-fold, at least 5-fold, at least 6-fold, at least 7-fold, at least 8-fold, at least 9-fold, and/or at least 10-fold, relative to the same and/or similar Clostridial toxin and/or Clostridial toxin chimeric, but without the inactivation cleavage site, and/or wherein the Clostridial toxin and/or Clostridial toxin chimeric comprising an inactivation cleavage site has a safety margin that is greater than at least 1-fold, at most 1-fold, at most 3-fold, at most 4-fold, at most 5-fold, at most 6-fold, at most 7-fold, at most 8-fold, at most 9-fold, and/or at most 10-fold, relative to the same and/or similar Clostridial toxin and/or Clostridial toxin chimeric, but without the inactivation cleavage site, and/or wherein the Clostridial toxin and/or Clostridial toxin chimeric comprising an inactivation cleavage site has a safety margin that is greater by about 1-fold to about 10-fold, about 1-fold to about 9-fold, about 1-fold to about 8-fold, about 1-fold to about 7-fold, about 1-fold to about 6-fold, about 1-fold to about 5-fold, about 2-fold to about 10-fold, about 2-fold to about 9-fold, about 2-fold to about 8-fold, about 2-fold to about 7-fold, about 2-fold to about 6-fold, and/or about 2-fold to about 5-fold.

74. The toxin and/or chimeric of aspects 1-73, wherein the addition of the inactivation cleavage site increases the safety margin of the Clostridial toxin and/or Clostridial toxin chimeric relative to the same and/or similar Clostridial toxin and/or Clostridial toxin chimeric, but without the additional inactivation cleavage site.

75. The toxin and/or chimeric of aspect 74, wherein the Clostridial toxin and/or Clostridial toxin chimeric comprises the addition of an inactivation cleavage site that increases the safety margin of the Clostridial toxin and/or Clostridial toxin chimeric relative to the same and/or similar Clostridial toxin and/or Clostridial toxin chimeric, but without the additional inactivation cleavage site by at least 10%, at least 20%, at least 30%, at least 40%, at least 50%, at least 60%, at least 70%, at least 80%, at least 90%, at least 100%, 110%, at least 120%, at least 130%, at least 140%, at least 150%, at least 160%, at least 170%, at least 180%, at least 190%, at least 200%, 210%, at least 220%, at least 230%, at least 240%, at least 250%, at least 260%, at least 270%, at least 280%, at least 290%, and/or at least 300%, or wherein the Clostridial toxin and/or Clostridial toxin chimeric comprises the addition of an inactivation cleavage site that increases the safety margin of the Clostridial toxin and/or Clostridial toxin chimeric relative to the same and/or similar Clostridial toxin and/or Clostridial toxin chimeric, but without the additional inactivation cleavage site by at most 10%, at most 20%, at most 30%, at most 40%, at most 50%, at most 60%, at most 70%, at most 80%, at most 90%, at most 100%, 110%, at most 120%, at most 130%, at most 140%, at most 150%, at most 160%, at most 170%, at most 180%, at most 190%, at most 200%, 210%, at most 220%, at most 230%, at most 240%, at most 250%, at most 260%, at most 270%, at most 280%, at most 290%, and/or at most 300%, or wherein the Clostridial toxin and/or Clostridial toxin chimeric comprises the addition of an inactivation cleavage site that increases the safety margin of the Clostridial toxin and/or Clostridial toxin chimeric relative to the same and/or similar Clostridial toxin and/or Clostridial toxin chimeric, but without the additional inactivation cleavage site by about 10% to about 300%, about 20% to about 300%, about 30% to about 300%, about 40% to about 300%, about 50% to about 300%, about 60% to about 300%, about 70% to about 300%, about 80% to about 300%, about 90% to about 300%, and/or about 100% to about 300%, or wherein the Clostridial toxin and/or Clostridial toxin chimeric comprises the addition of an inactivation cleavage site that increases the safety margin of the Clostridial toxin and/or Clostridial toxin chimeric relative to the same and/or similar Clostridial toxin and/or Clostridial toxin chimeric, but without the additional inactivation cleavage site by at least 1-fold, at least 1-fold, at least 3-fold, at least 4-fold, at least 5-fold, at least 6-fold, at least 7-fold, at least 8-fold, at least 9-fold, and/or at least 10-fold, and/or wherein the Clostridial toxin and/or Clostridial toxin chimeric comprises the addition of an inactivation cleavage site that increases the safety margin of the Clostridial toxin and/or Clostridial toxin chimeric relative to the same and/or similar Clostridial toxin and/or Clostridial toxin chimeric, but without the additional inactivation cleavage site by, e.g., at most 1-fold, at most 3-fold, at most 4-fold, at most 5-fold, at most 6-fold, at most 7-fold, at most 8-fold, at most 9-fold, and/or at most 10-fold, and/or wherein the Clostridial toxin and/or Clostridial toxin chimeric comprises the addition of an inactivation cleavage site that increases the safety margin of the Clostridial toxin and/or Clostridial toxin chimeric relative to the same and/or similar Clostridial toxin and/or Clostridial toxin chimeric, but without the additional inactivation cleavage site by about 1-fold to about 10-fold, about 1-fold to about 9-fold, about 1-fold to about 8-fold, about 1-fold to about 7-fold, about 1-fold to about 6-fold, about 1-fold to about 5-fold, about 2-fold to about 10-fold, about 2-fold to about 9-fold, about 2-fold to about 8-fold, about 2-fold to about 7-fold, about 2-fold to about 6-fold, and/or about 2-fold to about 5-fold.

76. A polynucleotide molecule encoding a toxin and/or chimeric according to any one of aspects 1-75.

77. The polynucleotide molecule, wherein the molecule comprises SEQ ID NO: 530, SEQ ID NO: 532, SEQ ID NO: 534, and/or SEQ ID NO: 536.

78. A method of producing a Clostridial toxin and/or Clostridial toxin chimeric comprising the step of expressing in a cell a polynucleotide molecule according to aspect 76 and/or 77, wherein expression from the polynucleotide molecule produces the encoded Clostridial toxin and/or Clostridial toxin chimeric.

79. A method of producing a modified Clostridial toxin comprising the steps of:
  a. introducing into a cell a polynucleotide molecule according to aspect 76 and/or 77; and
  b. expressing the polynucleotide molecule, wherein expression from the polynucleotide molecule produces the encoded Clostridial toxin and/or Clostridial toxin chimeric.

80. A Clostridial toxin comprising SEQ ID NO: 531, SEQ ID NO: 533, SEQ ID NO: 535, and/or SEQ ID NO: 537.

81. A Clostridial toxin comprising SEQ ID NO: 531.

82. A Clostridial toxin comprising SEQ ID NO: 533.

83. A Clostridial toxin comprising SEQ ID NO: 535.

84. A Clostridial toxin comprising SEQ ID NO: 537.

EXAMPLES

The following non-limiting examples are provided for illustrative purposes only in order to facilitate a more complete understanding of disclosed embodiments and are in no way intended to limit any of the embodiments disclosed in the present specification.

Example 1

Identification of Inactivation Cleavage Site Regions

This example illustrates how to identify regions within a Clostridial toxin or Clostridial toxin chimeric suitable for modifying the toxin to comprise an inactivation cleavage site and how to make a Clostridial toxin or Clostridial toxin chimeric comprising an inactivation cleavage site.

To identify a location or locations in the protein structure suitable as a potential inactivation cleavage site region, the three-dimensional structure of a BoNT/A was initially analyzed by computer software to identify surface exposed loops or extended regions that would be more accessible to a protease. Of the regions predicted to be accessible, eight were selected for further analysis: amino acids 462-496 of SEQ ID NO: 1, amino acids 618-634 of SEQ ID NO: 1, amino acids 638-651 of SEQ ID NO: 1, amino acids 665-687 of SEQ ID NO: 1, amino acids 752-765 of SEQ ID NO: 1, and amino acids 826-835 of SEQ ID NO: 1, amino acids 844-863 of SEQ ID NO: 1, and amino acids 871-895 of SEQ ID NO: 1.

To determine whether a region identified by computer analysis could function as an inactivation cleavage site region, thrombin cleavage sites were genetically engineered into these regions using multi-primer mutagenesis and assayed for its ability to be cleaved by thrombin. A 50 μL reaction was assembled comprising a primer pool of unidirectional oligonucleotide primers each containing the desired modification (125 ng of each primer) mixed in different ratios with a DNA template comprising an expression construct encoding a BoNT/A, such as, e.g., an expression construct comprising SEQ ID NO: 526 encoding SEQ ID NO: 527, or an expression construct comprising SEQ ID NO: 528 encoding SEQ ID NO: 529, that was hypermethylated with dam methylase. To this mixture was added 5 μL of 10×PCR Buffer, 1 μL of deoxyribonucleotides (dNTPs), 1 μL of 2.5 units/EL PFUULTRA™ High Fidelity DNA polymerase (Stratagene, La Jolla, Calif.), Pfu DNA ligase, ATP, and nuclease-free water to a final volume of 50 μL. The thermocycler conditions were: 30 cycles of 96° C. for 1 minute, 60° C. for 30 seconds, and 68° C. for 20 minutes. Following thermocycling, 1 μL of DpnI restriction enzyme (Stratagene, La Jolla, Calif.) was added to the reaction and incubated for 1 hour at 37° C. to digest the template DNA and reduce the recovery of wild-type clones. The digested reaction mixture was transformed into electro-competent E. coli BL21(DE3) Acella cells (Edge BioSystems, Gaithersburg, Md.) by electroporation, plated on 1.5% Luria-Bertani agar plates (pH 7.0) containing 50 μg/mL of kanamycin, and placed in a 37° C. incubator for overnight growth. Bacteria containing expression constructs were identified as kanamycin resistant colonies. Candidate constructs were isolated using an alkaline lysis plasmid mini-preparation procedure and analyzed by sequencing to determine the frequency and identity of the mutations incorporated. Table 7 lists each BoNT/A comprising a Thrombin cleavage site (BoNT/A-TCS) made and tested in this thrombin scanning analysis.

TABLE 7

Thrombin Scanning Analysis

| Region | Modification | Expression | Thrombin Sensitivity | BoNT/A Potency |
|---|---|---|---|---|
| 462-496 | T482insLVPRGS | + | ND | ND |
| 462-496 | A489insLVPRGS | ++ | ++ | ND |
| 618-634 | E620insLVPRGS | + | ND | ND |
| 638-651 | M646insLVPRGS | −/+ | ND | ND |
| 665-687 | I673insLVPRGS | + | ND | ND |
| 752-765 | E758insLVPRGS | − | ND | ND |
| 826-835 | delR827GT-insLVPRGS | −/+ | ND | ND |
| 844-863 | T844insLVPRGS | +++ | + | ND |
| 844-863 | D848insLVPRGS | +++ | + | ND |
| 844-863 | Q852insLVPRGS | −/+ | ND | ND |
| 844-863 | L862insLVPRGS | +++ | ++ | ND |
| 871-895 | E868insLVPRGS | | | ND |
| 871-895 | delE868YIKNI-insLVPRGS | | | ND |
| 871-895 | K871insLVPRGS | +++ | +++ | ND |
| 871-895 | I873insLVPRGS | +++ | ++++ | ND |
| 871-895 | delN872IINTS-insLVPRGS | | | ND |
| 871-895 | T876insLVPRGS | | | ND |
| 871-895 | L879insVPRGS | | | ND |
| 871-895 | delL879NLRYE-insLVPRGS | | | ND |
| 871-895 | N880insLVPRGS | +++ | ++++ | 4.05 |
| 871-895 | L881insVPRGS | | | ND |
| 871-895 | delL881RYESN-insLVPRGS | | | ND |
| 871-895 | Y883insLVPRGS | | | ND |
| 871-895 | E884insLVPRGS | +++ | +++ | >50 |
| 871-895 | S885insLVPRGS | | | ND |
| 871-895 | delH887LIDLS-insLVPRGS | | | ND |
| 871-895 | L888insVPRGS | | | ND |
| 871-895 | D890insLVPRGS | ++ | ++++ | 3.15 |
| 871-895 | L891insVPRG | | | ND |
| 871-895 | delS892RYA-insVPRG | | | ND |
| 467-496 | T482insLVPRGS A489insLVPRGS | + | ND | ND |
| 618-634 665-687 | E620insLVPRGS I673insLVPRGS | + | ND | ND |
| 638-651 665-687 | M646insLVPRGS I673insLVPRGS | + | ND | ND |
| 825-832 | delR827GT-insLVPRGS | + | +++ | ND |
| 871-895 | K871insLVPRGS | | | |
| 844-863 | T844insLVPRGS Q852insLVPRGS | −/+ | ND | ND |
| 844-863 | Q852insLVPRGS L862insLVPRGS | − | ND | ND |
| 825-832 | delR827GT-insLVPRGS | + | ND | ND |
| 871-895 | K871insLVPRGS | | | |
| 825-832 | delR827GT-insLVPRGS | − | ND | ND |
| 871-895 | K880insLVPRGS | | | |
| 871-895 | E868insLVPRGS I873insLVPRGS | | | 1.32 |
| 871-895 | delE868YIKNI-insLVPRGS delL881RYESN-insLVPRGS | | | 0.86 |
| 871-895 | I873insLVPRGS E884insLVPRGS | | | 1.32 |
| 871-895 | L881insVPRGS L891insVPRG | +++ | ++++ | 4.20 |
| Control | Backbone | +++ | − | Yes |

Protease sensitivity: +, less than 25% of toxin proteolyzed within about 1 to about 4 hours; ++, from 25% to 50% of toxin proteolyzed within about 1 to about 4 hours; +++, from 51% to 75% of toxin proteolyzed within about 1 to about 4 hours; +++, more than 75% of toxin proteolyzed within about 1 to about 4 hours.
BoNT/A potency is calculated by dividing the $EC_{50}$ value of the toxin into the $EC_{50}$ value of the backbone control.
ND is not determined.

To determine the expression level of soluble protein for each BoNT/A-TCS, an expression construct comprising each BoNT/A-TCS was expressed, purified by immobilized metal affinity chromatography and analyzed by SDS-PAGE analysis. First, using a 96-well plate, 100 μL of PA-0.5G media containing 50 μg/mL Kanamycin was inoculated with a single colony of BL21(DE3) cells harboring the appropriate expression construct and grown at 37° C. with shaking overnight. A 5 μL aliquot from this starter culture was used to inoculate 1 mL of ZYP-5052 containing 50 μg/mL kanamycin and grown at 37° C. with shaking for 3.5 hours and then 22° C. for 16 hours. A 110 μL aliquot of Protein Extraction Reagent comprising 10× FASTBREAK™ Cell Lysis Reagent (Promega Corp., Madison, Wis.), 250 U/mL Benzonase nuclease (EMD Biosciences-Novagen, Madison, Wis.), and 10× Protease Inhibitor Cocktail III (EMD Biosciences-Calbiochem, Gibbstown, N.J.) was added to each 1 mL expression culture in a 96-well plate. 75 μL of HISLINK™ resin (Promega Corp., Madison, Wis.) was next transferred to each well and the mixture was alternately mixed by pipetting and by shaking at 900 rpm for 30 minutes. The lysates were transferred to a filter plate with a 25 μm pore size (Promega Corp., Madison, Wis.), with membranes pre-wetted with water, and the liquid was removed by vacuum filtration. The resin was washed three times with 200 μL Wash Buffer comprising 100 mM HEPES (pH 7.5), 10 mM imidazole. The protein was eluted by adding 200 μL Elution Buffer comprising 100 mM HEPES (pH 7.5), 500 mM imidazole, incubating for 5 minutes and the elute collected by vacuum filtration into a 96-well plate.

To perform SDS-PAGE, an equal volume of 2× Laemmli Sample Buffer was added to the IMAC purified BoNT/A comprising a thrombin cleavage site, and the mixture incubated at 95° C. for 5 minutes. A 15 μL aliquot was loaded and separated by MOPS polyacrylamide gel electrophoresis using NUPAGE® Novex 4-12% Bis-Tris precast polyacrylamide gels (Invitrogen, Inc, Carlsbad, Calif.) under denaturing, reducing conditions. The gel was washed and fixed in 10% methanol and 7% acetic acid for 30 minutes. The wash solution was removed and the gel incubated in SYPRO Ruby protein gel stain solution for 3 hours to overnight at room temperature. The stained gel was destained in 10% methanol and 7% acetic acid for 30 minutes. The destained gel was visualized with a Fluoro-S-Max digital imager (Bio-Rad).

The results of the expression analysis are given in Table 7. In general, toxins harboring an inserted thrombin cleavage site in the inactivation regions comprising amino acids 462-496 of SEQ ID NO: 1, amino acids 844-863, or amino acids 871-895 of SEQ ID NO: 1 were expressed well. For example, toxins comprising A489insLVPRGS was expressed at about 50% that of a wild-type control construct and toxins comprising D848insLVPRGS or N880insLVPRGS were expressed at, or near, control levels (Table 7). These results reveal that inactivation cleavage site regions located within the translocation domain and/or the $H_{CN}$ binding subdomain tolerated the modification of regions to include a protease cleavage site.

To further explore the extent to which the inactivation cleavage site regions identified could tolerate modifications that introduce a protease cleavage site, toxins were modified to include thrombin cleavage sites throughout the region. For example, toxins comprising T884insLVPRGS or L862insLVPRGS were made to examine the inactivation cleavage site region comprising 844-863 of SEQ ID NO: 1. Similarly, toxins comprising E868insLVPRGS, delE868YIKNI-insLVPRGS, deIN87211NTS-insLVPRGS, T876insLVPRGS, L879insVPRGS, delL879NLRYE-insLVPRGS, L881 insVPRGS, delL881 RYESN-insLVPRGS, Y883insLVPRGS, E884insLVPRGS, S885insLVPRGS, deIH887LIDLS-insLVPRGS, L888insLVPRGS, L891 insVPRG, and deIS892RYA-insVPRG were made to examine the inactivation cleavage site region comprising 871-895 of SEQ ID NO: 1. Both insertion and substitution modifications were made to examine whether the type of modification had any affect. In general, all toxins harboring an inserted thrombin cleavage site in these inactivation regions were expressed at, or near, the levels of a wild-type control construct. These results reveal that inactivation cleavage site regions within the translocation domain and/or the $H_{CN}$ binding subdomain can tolerate modifications placed anywhere within an inactivation site region.

Lastly, the ability of an inactivation site region to tolerate the presence of two or more protease cleavage sites was examined (Table 7). These results indicate that inactivation cleavage site regions within the translocation domain and/or the $H_{CN}$ binding subdomain can tolerate modifications placing two or more protease cleavage sites within an inactivation site region.

To determine whether a BoNT/A comprising a thrombin cleavage site could be cleaved by thrombin, an in vitro thrombin cleavage assay was performed. 5 µg of each purified BoNT/A-TCS was incubated with 1 U of Thrombin (Novagen) at 23° C. for 1 hour, 3 hours, and 18.5 hours. A zero-enzyme control was also set up in parallel for each BoNT/A-TCS. Samples were taken at each time point and quenched with SDS-Loading Buffer including DTT and analyzed by SDS-PAGE as described above.

The results of the expression analysis are given in Table 7. In general, modification of an inactivation cleavage site region comprising amino acids 467-496, 844-863, or 871-895 of SEQ ID NO: 1 to include a protease cleavage site resulted in a toxin that was susceptible to proteolytic cleavage by the appropriate protease.

To determine whether a BoNT/A comprising a thrombin cleavage site maintained its potency, a BoNT/A activity assay was performed using a cell-based activity assay. To conduct a cell-based activity assay, about $1.2 \times 10^6$ Neuro-2a or SiMa cells were plated into the wells of 24-well tissue culture plates containing 1 mL of serum-free medium containing Minimum Essential Medium, 2 mM GLUTAMAX™ I with Earle's salts, 1×B27 supplement, 1×N2 supplement, 0.1 mM Non-Essential Amino Acids, 10 mM HEPES and 25 µg/mL GT1b. The cells were incubated in a 37° C. incubator under 5% carbon dioxide until the cells differentiated, as assessed by standard and routine morphological criteria, such as growth arrest and neurite extension (approximately 3 days). The media was aspirated from each well and replaced with either 1) fresh media containing no toxin (untreated cell line) or 2) fresh media containing 1 nM of a BoNT/A complex (treated cell line). After an overnight incubation, the cells were washed by aspirating the media and rinsing each well with 200 µL of 1×PBS. To harvest the cells, the 1×PBS was aspirated, the cells were lysed by adding 50 µl of 2×SDS Loading Buffer, the lysate was transferred to a clean test tube and the sample was heated to 95° C. for 5 minutes.

To detect for the presence of cleaved SNAP-25 products, an aliquot from each harvested sample was analyzed by Western blot. In this analysis, a 12 µl aliquot of the harvested sample was separated by MOPS polyacrylamide gel electrophoresis using NUPAGE® Novex 12% Bis-Tris precast polyacrylamide gels (Invitrogen Inc., Carlsbad, Calif.) under denaturing, reducing conditions. Separated peptides were transferred from the gel onto polyvinylidene fluoride (PVDF) membranes (Invitrogen Inc., Carlsbad, Calif.) by Western blotting using a TRANS-BLOT® SD semi-dry electrophoretic transfer cell apparatus (Bio-Rad Laboratories, Hercules, Calif.). PVDF membranes were blocked by incubating at room temperature for 2 hours in a solution containing Tris-Buffered Saline (TBS) (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20® (polyoxyethylene (20) sorbitan monolaurate), 2% Bovine Serum Albumin (BSA), 5% nonfat dry milk. Blocked membranes were incubated at 4° C. for overnight in TBS, 0.1% TWEEN-20® (polyoxyethylene (20) sorbitan monolaurate), 2% BSA, and 5% nonfat dry milk containing either 1) a 1:5,000 dilution of an α-SNAP-25 mouse monoclonal antibody as the primary antibody (SMI-81; Sternberger Monoclonals Inc., Lutherville, Md.); or 2) a 1:5,000 dilution of S9684 α-SNAP-25 rabbit polyclonal antiserum as the primary antibody (Sigma, St. Louis, Mo.). Both α-SNAP-25 mouse monoclonal and rabbit polyclonal antibodies can detect both the uncleaved SNAP-25 substrate and the SNAP-25 cleavage product, allowing for the assessment of overall SNAP-25 expression in each cell line and the percent of SNAP-25 cleaved after BoNT/A treatment as a parameter to assess the amount of BoNT/A uptake. Primary antibody probed blots were washed three times for 15 minutes each time in TBS, TWEEN-20® (polyoxyethylene (20) sorbitan monolaurate). Washed membranes were incubated at room temperature for 2 hours in TBS, 0.1% TWEEN-20® (polyoxyethylene (20) sorbitan monolaurate), 2% BSA, and 5% nonfat dry milk containing either 1) a 1:10,000 dilution of goat polyclonal anti-mouse immunoglobulin G, heavy and light chains (IgG, H+L) antibody conjugated to horseradish peroxidase (Zymed, South San Francisco, Calif.) as a secondary antibody; or 2) a 1:10,000 dilution of goat polyclonal anti-rabbit immunoglobulin G, heavy and light chains (IgG, H+L) antibody conjugated to horseradish peroxidase (Zymed, South San Francisco, Calif.) as a secondary antibody. Secondary antibody-probed blots were washed three times for 15 minutes each time in TBS, 0.1% TWEEN-20® (polyoxyethylene (20) sorbitan monolaurate). Signal detection of the labeled SNAP-25 products were visualized using the ECL Plus™ Western Blot Detection System (GE Healthcare, Amersham Biosciences, Piscataway, N.J.) and the membrane was imaged and the percent of cleaved quantified with a Typhoon 9410 Variable Mode Imager and Imager Analysis software (GE Healthcare, Amersham Biosciences, Piscataway, N.J.). The choice of pixel size (100 to 200 pixels) and PMT voltage settings (350 to 600, normally 400) depended on the individual blot.

The results of the expression analysis are given in Table 7. In general, modification of an inactivation cleavage site region comprising amino acids 467-496, 844-863, or 871-895 of SEQ ID NO: 1 to include a protease cleavage site resulted in a potent toxin that was able to execute the overall intoxication process.

Taken together, these results indicate that although eight different inactivation cleavage regions were identified, not all were able to support the insertion of a functional thrombin cleavage site. In general, modification of the inactivation cleavage site regions comprising amino acids 467-496, 844-863 and 871-895 of SEQ ID NO: 1 to include a protease cleavage site resulted in a stably produced toxin that was able to execute the overall intoxication process and was sensitive to proteolytic cleavage by the appropriate protease.

Because the three-dimensional structure of all Clostridial toxins are similar, the corresponding locations in BoNT/B, BoNT/C1, BoNT/D, BoNT/E, BoNT/F, BoNT/G, TeNT, BaNT, and BuNT are also suitable as inactivation cleavage site regions. Table 5 lists these regions.

Example 2

Protease Cleavage Site Analysis

This example illustrates how to make a Clostridial toxin or Clostridial toxin chimeric comprising an inactivation cleavage site.

To explore whether protease cleavage sites other than thrombin could be useful as an inactivation site, toxins comprising many different protease cleavage sites were examined.

To make a Clostridial toxin or Clostridial toxin chimeric comprising an inactivation cleavage site, protease cleavage sites were genetically engineered into inactivation cleavage site regions using multi-primer mutagenesis as described in Example 1. Table 8 lists the expression constructs modified to contain a protease cleavage site.

To determine whether a BoNT/A comprising a protease cleavage site could be cleaved by its cognate protease, in vitro protease cleavage assays was performed essentially as described above, but using the appropriate protease instead of thrombin. Samples were taken at each time point and quenched with SDS-Loading Buffer including DTT, and analyzed by SDS-PAGE as described in Example 1.

The results of the expression analysis are given in Table 7. In general, modification of an inactivation cleavage site region comprising amino acids 467-496, 844-863, or 871-895 of SEQ ID NO: 1 to include a protease cleavage site resulted in a toxin that was susceptible to proteolytic cleavage by the appropriate protease.

TABLE 8

Protease Cleavage Site Analysis

| Protease Cleavage Site | Region | Modification | Protease Sensitivity | BoNT/A Potency |
|---|---|---|---|---|
| Factor Xa | 535 | E535insG | + | 2.70 |
| Factor Xa | 844-863 | L863insIEGR | + | >50 |
| Factor Xa | 871-895 | K871insIEGR | ++ | 6.15 |
| Factor Xa | 871-895 | I873insEGR | + | 3.97 |
| Factor Xa | 871-895 | L881insIEG | ND | ND |
| Factor Xa | 871-895 | E884insIEGR | + | 2.95 |
| Factor Xa | 871-895 | L891insIEGR | ++ | ND |
| Factor Xa | 1272 | E1272insG | + | ND |
| Factor Xa × 2 | 535 1272 | E535insG E1272insG | + | ND |
| Factor Xa × 2 | 871-895 | K871insIEGR L891insIEGR | ++ | 4.35 |
| Factor Xa × 2 | 871-895 | I873insEGR L891insIEGR | + | 7.63 |
| Factor Xa × 2 | 871-895 | L881insIEG L891insIEGR | ++ | >50 |
| Factor Xa tPA | 871-895 | I873insEGR delS885NHLIDL-insPQRGRSA | ND | ND |
| Factor Xa Thrombin | 871-895 | I873insEGR E884insLVPRG | + ++++ | 3.29 |
| MMP-2 | 871-895 | S885insGPLGMLSQ | + | 6.55 |
| MMP-2 | 871-895 | delK871NIINTSI-insGPLGMLSQ | ++ | 5.27 |
| MMP-2 | 871-895 | delS885NHLIDLS-insGPLGMLSQ | ++ | 4.76 |
| MMP-9 | 871-895 | K871insGPLGLWAQ | ND | ND |
| MMP-9 | 871-895 | delK871NIINTSI-insGPLGLWAQ | + | 3.36 |
| MMP-9 | 871-895 | I873insGPLGLWAQ | | 22.8 |
| MMP-9 | 871-895 | delI874NTSILNL-insGPLGLWAQ | | 37.7 |
| MMP-9 | 871-895 | delL881RYESNHL-insGPLGLWAQ | ND | ND |
| MMP-9 | 871-895 | E884insGPLGLWAQ | ND | ND |
| MMP-9 | 871-895 | delS885NHLIDLS-insGPLGLWAQ | + | 4.38 |
| MMP-9 | 871-895 | S885insGPLGLWAQ | | 3.38 |
| MMP-9 | 871-895 | L891insGPLGLWAQ | | 20.61 |
| MMP-9 Thrombin | 871-895 | delK871NIINTSI-insGPLGLWAQ E884insLVPRG | ND | ND |
| MMP-9 Factor Xa | 871-895 | delK871NIINTSI-insGPLGLWAQ E884insIEGR | | 19.62 |
| u-PA | 871-895 | delN872IINTSI-insPGSGKSA | + | ND |
| u-PA | 871-895 | S885insPGSGKSA | ++ | 3.00 |
| u-PA | 871-895 | delN886HLIDL-insPGSGKSA | ++ | 4.90 |
| t-PA | 871-895 | delN872IINTSI-insPQRGRSA | ++ | 3.65 |
| t-PA | 871-895 | S885insPQRGRSA | +++ | 3.30 |
| t-PA | 871-895 | delS885NHLIDL-insPQRGRSA | ++ | 4.80 |
| Thrombin tPA | 871-895 | I873LVPRGS delS885NHLIDL-insPQRGRSA | ND | ND |
| Furin | 871-895 | I870insRKKR | +++ | 6.70 |
| Furin | 871-895 | delK871NII-insRKKR | + | 3.50 |
| Furin | 871-895 | L881insRKK | + | 7.20 |
| Furin | 871-895 | delY883ES-insKKR | + | 12.1 |
| Furin | 871-895 | S892RKK | + | 15.2 |
| Furin × 2 | 871-895 | delK871NII-insRKKR delY883ES-insKKR | + | 12.6 |
| Furin × 2 | 871-895 | delK871NII-insRKKR S892RKK | ++ | 6.00 |
| Furin × 3 | 871-895 | delK871NII-insRKKR delY883ES-insKKR S892RKK | ND | ND |
| Kell | 871-895 | L891insAAF | + | 10.8 |
| Kell | 871-895 | delI889DL-insAAF | + | 4.80 |
| Tryptase ε | 871-895 | K871insIVGGE | + | 9.45 |
| Tryptase ε | 871-895 | K871insRIVGGE | + | 6.48 |
| Tryptase ε | 871-895 | delN886HLIDL-insRIVGGE | | 5.50 |
| Tryptase ε | 871-895 | delN886HLIDL-insKIVGGE | ND | ND |
| mMMCP-7 | 871-895 | K871insSLSSRQSP | | 3.90 |
| mMMCP-7 | 871-895 | delN886HLIDLS-insLSSRQSP | | 4.80 |
| ECE-1 | 871-895 | I870insRPPGFSAF | + | 5.70 |
| ECE-1 | 871-895 | K871insAFA | + | 3.85 |
| ECE-1 | 871-895 | K871insDIIWVNT-PEHVVPYGLGS | + | >50 |
| ECE-1 | 871-895 | K871insRPKPQQFFGLM | ND | ND |
| ECE-1 | 871-895 | delYES885NHLIDLS-insPKPQQFFGLM | + | 9.20 |
| ECE-1 | 871-895 | E884insKAFA | + | 2.95 |
| ECE-1 | 871-895 | delS885NHLIDLS-insRPPGFSAF | + | 3.70 |
| Cathespin L | 871-895 | I870insRGFFYTPK | ++++ | 10.3 |
| Cathespin L | 871-895 | K871insLR | ++++ | 2.25 |
| Cathespin L | 871-895 | K871insFR | ++++ | 3.05 |
| Cathespin L Thrombin | 871-895 | K871insLR L891insLVPRGS | | 12.6 |
| PolyArg | 844-863 | R861insRR | ND | ND |
| PolyArg | 871-895 | R882insRRR | | Yes |
| PolyArg | 871-895 | S885insRRR | | 2.22 |
| PolyArg | 871-895 | S892insRRR | | 3.02 |
| PolyArg × 2 | 844-863 871-895 | R861insRR K871insRKR | ND | ND |
| PolyArg × 2 | 844-863 871-895 | R861insRR I873insRRRR | ND | ND |

TABLE 8-continued

| Protease Cleavage Site Analysis | | | | |
|---|---|---|---|---|
| Protease Cleavage Site | Region | Modification | Protease Sensitivity | BoNT/A Potency |
| PolyArg × 2 | 844-863<br>871-895 | R861insRR<br>R882insRRR | ND | ND |
| PolyArg × 2 | 871-895 | K871insRKR<br>S885insRRR | | 1.92 |
| PolyArg × 2 | 871-895 | R882insRRR<br>S892insRRR | ND | ND |

Protease sensitivity: +, less than 25% of toxin proteolysed within about 1 to about 4 hours; ++, from 25% to 50% of toxin proteolyzed within about 1 to about 4 hours; +++, from 51% to 75% of toxin proteolyzed within about 1 to about 4 hours; ++++, more than 75% of toxin proteolyzed within about 1 to about 4 hours.
BoNT/A potency is calculated by dividing the $EC_{50}$ value of the toxin into the $EC_{50}$ value of the backbone control.
ND is not determined.

To determine whether a BoNT/A comprising a protease cleavage site maintained its potency, the cell-based activity assay described above was performed (Table 8). In general, toxins comprising a protease cleavage site that exhibited an $EC_{50}$ of about 20 or less were deemed to retain enough potency to warranted evaluation using an animal-based assay.

Example 3

In Vivo Analysis

This example illustrates how to evaluate a Clostridial toxin or Clostridial toxin chimeric comprising an inactivation cleavage site using an animal-based assay analysis.

Although the cell-based activity assay is a good assessment of whether a Clostridial toxin or Clostridial toxin chimeric comprising an inactivation cleavage site can be cleaved by its cognate protease, certain candidates were selected for evaluation in an animal-based assay.

To test the activity of a Clostridial toxin or Clostridial toxin chimeric comprising an inactivation cleavage site using an animal-based assay, an in vivo Digit Abduction Score (DAS) assay was initially performed. CD-1 Fe mice were weighed and placed into subsets of 10 animals for each discrete DAS assay. Mice were included into a particular subset based on the following criteria: 1) good health; 2) robust baseline DAS response of 0; 3) inclusion in a median weight range of X±2g established for the selected subset and 4) weight greater than 17.0 g.

Each mouse was injected using a 30-gauge needle in the gastrocnemius muscle of the right hind limb with either 1) 5 μL of 10.0 nM BoNT/A comprising an inactivation cleavage site (single-dose DAS study); or 2) 5 μL of one of seven different doses of BoNT/A comprising an inactivation cleavage site (0.01 nM, 0.04 nM, 0.12 nM, 0.37 nM, 1.11 nM, 3.33 nM and 10.0 nM; Full-Dosing DAS study). As a control, the gastrocnemius muscle of the left hind limb was injected with 5 μL of a solution not containing any toxin. Mice were observed for the DAS response consecutively for the first 4 days. The DAS was read by lifting each mouse by the tail and precisely observing the injected hind limbs. The abduction or no abduction of the hind digits reveals the effect of paralysis due to the test toxin injected in the muscle. The digit abduction of the injected hind limb was compared with that of the non-injected hind limb and scored accordingly. DAS data was analyzed by calculating the $ED_{50}$ dose based on peak mean DAS score and AUC (area under the curve) in terms of u/Kg and/or ng/Kg. This was accomplished as follows: 1) the mean peak DAS score for each dose was calculated in each study; 2) any dose that elicited more than five deaths in any study was eliminated from consideration; 3) the highest dose used in a given individual study was the lowest dose which elicited an average peak of 4.0; 4) the lowest dose used in a given individual study was the highest dose which elicited an average peak of 0; 5) curves were constructed for each individual study of average peak DAS vs. log (dose); 6) an AUC value was calculated for each group of 10 mice of the multiple groups in some studies; 7) curves were constructed for each individual study of average AUC vs. log (dose); 8) an x, y replicate response curve was constructed for each set of multiple identical studies; for each test toxin; 9) dose-response data were analyzed by non-linear regression (non-weighted) using a three-parameter logistic equation (Sigma Plot v 8.0; SPSS Science, Chicago, Ill.) using the following equation:

$$y=a/(1+(x/x0)^b)$$

where y is the response, a is the asymptotic $y_{max}$, b is the slope, x is the dose, and 0 is the $ED_{50}$ dose, For peak $ED_{50}$ determinations, $Y_{max}$ was set to 4 (maximum DAS reading on scale). Mean (peak and/or AUC) $ED_{50}$ values were computed for each eight-dose study performed.

The results indicate that (Table 9). In general, toxins comprising an inactivation cleavage site that exhibited a relative potency of about 10 or above were deemed to retain enough potency to warranted evaluation of its safety margin.

To determine the safety margin of a Clostridial toxin or Clostridial toxin chimeric comprising an inactivation cleavage site, a mouse lethality assay was performed.

To calculate the safety margin of a Clostridial toxin or Clostridial toxin chimeric comprising an inactivation cleavage site, the $LD_{50}$ value obtained from the mouse lethality assay was divided by the $EC_{50}$ value obtained from a full-dosing DAS study. A toxin comprising an inactivation cleavage site was deemed to possess enough activity at the inactivation cleavage site if it exhibited a safety margin value of about 15 or more.

TABLE 9

| Animal-based Assay Analysis | | | | | | | | |
|---|---|---|---|---|---|---|---|---|
| Protease Cleavage | | | Single-Dose DAS | | Full-Dosing DAS | | Lethality Assay | Safety Margin |
| Site | Region | Modification | $EC_{50}$ | Relative | $EC_{50}$ | Relative | $LD_{50}$ | $LD_{50}$/DAS $ED_{50}$ |
| Thrombin | 871-895 | I873insLVPGRS | 1.08 | 30.5 | ND | ND | ND | ND |
| Thrombin | 871-895 | L881insVPRGS | 0.37 | 7.38 | ND | ND | ND | ND |
| Thrombin | 871-895 | E884insLVPRGS | 0.16 | 25.3 | 0.15 | 46.7 | 1.90 | 12.5 |
| Thrombin | 871-895 | L891insVPRG | 0.12 | 23.3 | 0.19 | 36.8 | 2.74 | 14.8 |
| Thrombin × 2 | 871-895 | L881insVPRGS<br>L891insVPRG | 0.25 | 11.0 | 0.15 | 34.5 | 4.20 | 26.9 |
| Factor Xa | 871-895 | I873insEGR | 0.11 | 46.3 | 0.10 | 70.0 | 2.39 | 23.0 |
| Factor Xa | 871-895 | I873insEGR | 0.09 | 37.2 | 0.26 | 15.3 | 6.69 | 26.9 |

TABLE 9-continued

Animal-based Assay Analysis

| Protease Cleavage Site | Region | Modification | Single-Dose DAS EC$_{50}$ | Single-Dose DAS Relative | Full-Dosing DAS EC$_{50}$ | Full-Dosing DAS Relative | Lethality Assay LD$_{50}$ | Safety Margin LD$_{50}$/DAS ED$_{50}$ |
|---|---|---|---|---|---|---|---|---|
| Thrombin | | E884insLVPRG | | | | | | |
| MMP-2 | 871-895 | delK871NIINTSI-insGPLGMLSQ | 0.33 | 10.0 | ND | ND | ND | ND |
| MMP-2 | 871-895 | delS885NHLIDLS-insGPLGMLSQ | 0.10 | 34.5 | ND | ND | ND | ND |
| MMP-9 | 871-895 | delK871NIINTSI-insGPLGLWAQ | 0.11 | 29.1 | 0.16 | 27.7 | 5.04 | 23.9 |
| MMP-9 | 871-895 | delS885NHLIDLS-insGPLGLWAQ | 0.08 | 40.8 | ND | ND | ND | ND |
| u-PA | 871-895 | S885insPGSGKSA | 0.03 | 36.6 | ND | ND | ND | ND |
| u-PA | 871-895 | delN886HLIDL-insPGSGKSA | 0.35 | 3.52 | ND | ND | ND | ND |
| t-PA | 871-895 | delN872IINTSI-insPQRGRSA | 0.04 | 30.0 | ND | ND | ND | ND |
| t-PA | 871-895 | S885insPQRGRSA | 0.12 | 10.1 | ND | ND | ND | ND |
| t-PA | 871-895 | delS885NHLIDL-insPQRGRSA | 0.08 | 16.0 | 0.27 | 25.9 | 4.46 | 17.2 |
| Furin | 871-895 | I870insRKKR | 0.80 | 2.68 | ND | ND | ND | ND |
| Furin × 2 | 871-895 | delK871NII-insRKKR delY883ES-insKKR | 0.24 | 8.93 | ND | ND | ND | ND |
| Furin × 2 | 871-895 | delK871NII-insRKKR S892RKK | 0.34 | 6.25 | ND | ND | ND | ND |
| Tryptase ε | 871-895 | K871insIVGGE | 0.14 | 37.3 | ND | ND | ND | ND |
| Tryptase ε | 871-895 | K871insRIVGGE | 0.21 | 10.4 | ND | ND | ND | ND |
| Tryptase ε | 871-895 | delN886HLIDL-insRIVGGE | 0.13 | 17.2 | ND | ND | ND | ND |
| ECE-1 | 871-895 | E884insKAFA | 0.05 | 43.1 | ND | ND | ND | ND |
| Cathespin L | 871-895 | K871insLR | 0.10 | 34.3 | ND | ND | ND | ND |
| Cathespin L | 871-895 | K871insFR | 0.27 | 13.0 | ND | ND | ND | ND |
| Control | — | WT | 0.05 | 57.0 | 0.07 | 32.4 | 0.88 | 14.2 |

ND is not determined.

After the DAS analysis, a Clostridial toxin or Clostridial toxin chimeric comprising an inactivation cleavage site was evaluated using a mouse lethality assay in order to determine the safety margin by comparing the ED$_{50}$ with the LD$_{50}$.

Although aspects of the present specification have been described with reference to the disclosed embodiments, one skilled in the art will readily appreciate that the specific examples disclosed are only illustrative of these aspects and in no way limit the present specification. Various modifications can be made without departing from the spirit of the present specification.

The invention claimed is:

1. An isolated Clostridial toxin comprising SEQ ID NO: 533.

* * * * *